United States Patent
Heo et al.

(10) Patent No.: US 11,849,636 B2
(45) Date of Patent: *Dec. 19, 2023

(54) HETEROCYCLIC COMPOUND AND ORGANIC LIGHT EMITTING ELEMENT COMPRISING SAME

(71) Applicant: LG Chem, Ltd., Seoul (KR)

(72) Inventors: Dong Uk Heo, Daejeon (KR); Dong Hoon Lee, Daejeon (KR); Jungoh Huh, Daejeon (KR); Boonjae Jang, Daejeon (KR); Yongbum Cha, Daejeon (KR); Minyoung Kang, Daejeon (KR); Miyeon Han, Daejeon (KR); Min Woo Jung, Daejeon (KR)

(73) Assignee: LG Chem, Ltd.

(*) Notice: Subject to any disclaimer, the term of this patent is extended or adjusted under 35 U.S.C. 154(b) by 237 days.

This patent is subject to a terminal disclaimer.

(21) Appl. No.: 17/331,943

(22) Filed: May 27, 2021

(65) Prior Publication Data

US 2021/0288264 A1 Sep. 16, 2021

Related U.S. Application Data

(62) Division of application No. 15/777,811, filed as application No. PCT/KR2017/001956 on Feb. 22, 2017, now Pat. No. 11,094,889.

(30) Foreign Application Priority Data

Feb. 23, 2016 (KR) .................. 10-2016-0021358

(51) Int. Cl.
*H10K 85/60* (2023.01)
*C07D 405/10* (2006.01)
(Continued)

(52) U.S. Cl.
CPC ........ *H10K 85/654* (2023.02); *C07D 251/24* (2013.01); *C07D 307/91* (2013.01); *C07D 311/78* (2013.01); *C07D 311/96* (2013.01); *C07D 333/76* (2013.01); *C07D 405/10* (2013.01); *C07D 405/14* (2013.01);
(Continued)

(58) Field of Classification Search
None
See application file for complete search history.

(56) References Cited

U.S. PATENT DOCUMENTS

2004/0219386 A1 11/2004 Thoms
2004/0251816 A1 12/2004 Leo et al.
(Continued)

FOREIGN PATENT DOCUMENTS

CN 102786508 A * 11/2012
CN 102786508 A 11/2012
(Continued)

OTHER PUBLICATIONS

English language machine translation of CN-102786508-A obtained on Mar. 14, 2023. (Year: 2023).*
(Continued)

*Primary Examiner* — Eli S Mekhlin
(74) *Attorney, Agent, or Firm* — Lerner David LLP

(57) ABSTRACT

The present specification relates to a hetero-cyclic compound and an organic light emitting device comprising the same.

7 Claims, 7 Drawing Sheets

(51) Int. Cl.

| | | |
|---|---|---|
| C07D 333/76 | (2006.01) | |
| C07D 307/91 | (2006.01) | |
| C07D 311/96 | (2006.01) | |
| C07D 311/78 | (2006.01) | |
| C07D 251/24 | (2006.01) | |
| H05B 33/14 | (2006.01) | |
| C07D 417/10 | (2006.01) | |
| C07D 413/10 | (2006.01) | |
| H10K 50/00 | (2023.01) | |
| H10K 50/11 | (2023.01) | |
| H10K 99/00 | (2023.01) | |
| C07D 405/14 | (2006.01) | |
| C07D 471/04 | (2006.01) | |
| H10K 50/15 | (2023.01) | |
| H10K 50/16 | (2023.01) | |
| H10K 50/17 | (2023.01) | |
| H10K 50/18 | (2023.01) | |
| H10K 71/00 | (2023.01) | |
| H10K 71/16 | (2023.01) | |
| H10K 101/40 | (2023.01) | |
| H10K 101/30 | (2023.01) | |
| H10K 102/00 | (2023.01) | |

(52) U.S. Cl.
CPC ......... *C07D 413/10* (2013.01); *C07D 417/10* (2013.01); *C07D 471/04* (2013.01); *H05B 33/14* (2013.01); *H10K 50/00* (2023.02); *H10K 50/11* (2023.02); *H10K 85/6572* (2023.02); *H10K 85/6574* (2023.02); *H10K 99/00* (2023.02); *H10K 50/15* (2023.02); *H10K 50/16* (2023.02); *H10K 50/17* (2023.02); *H10K 50/171* (2023.02); *H10K 50/18* (2023.02); *H10K 71/00* (2023.02); *H10K 71/164* (2023.02); *H10K 2101/30* (2023.02); *H10K 2101/40* (2023.02); *H10K 2102/351* (2023.02)

(56) References Cited

U.S. PATENT DOCUMENTS

| | | | |
|---|---|---|---|
| 2015/0295181 A1 | 10/2015 | Mujica-Fernaud et al. | |
| 2016/0049613 A1 | 2/2016 | Kang et al. | |
| 2016/0118599 A1* | 4/2016 | Jeong | H10K 85/6572 |
| | | | 546/276.7 |
| 2017/0222157 A1* | 8/2017 | Jatsch | C07D 405/14 |

FOREIGN PATENT DOCUMENTS

| | | |
|---|---|---|
| JP | 2003096072 A | 4/2003 |
| KR | 20100125558 A | 12/2010 |
| KR | 20130140303 A | 12/2013 |
| KR | 20150106501 A | 9/2015 |
| KR | 20160021358 A | 2/2016 |
| KR | 20160079514 A | 7/2016 |
| WO | 2014072017 A1 | 5/2014 |
| WO | 2016023458 A1 | 2/2016 |

OTHER PUBLICATIONS

Clarkson, et al., Spirans With Four Aromatic Radicals on the Spiro Carbon Atom, Journal of the American Chemical Society, Jul. 1930, pp. 2881-2891, vol. 52.
Extended European Search Report including Written Opinion for Application No. EP17756804.4 dated Nov. 12, 2018.
Search report from International Application No. PCT/KR2017/001956, dated May 31, 2017.
Xie et al., Unexpected One-Pot Method to Synthesize Spiro(Fluorene-9,9,9'—xanthene] Building Blocks for Blue-light-Emitting Materials 2006, 8, 13 2787-2790. (Year: 2006).

* cited by examiner

[FIG. 1]
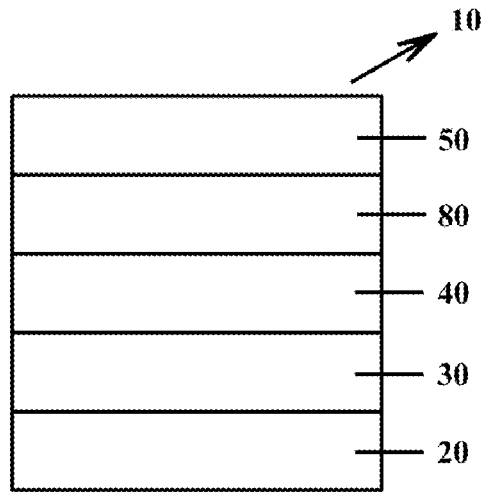
[FIG. 2]
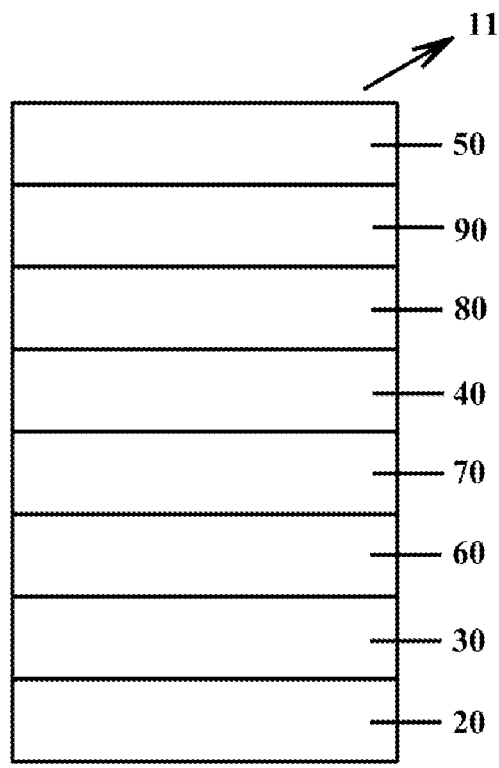

[FIG. 3]
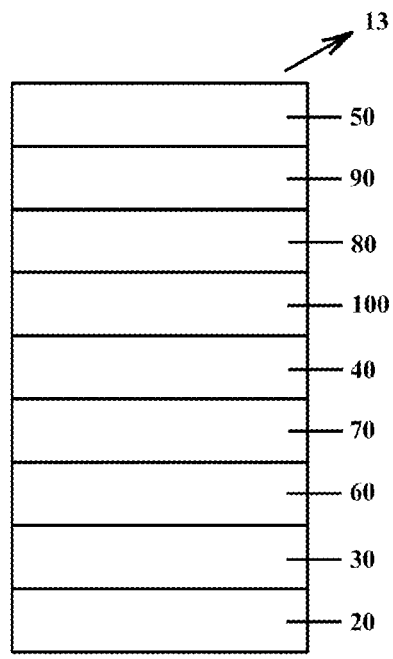
[FIG. 4]
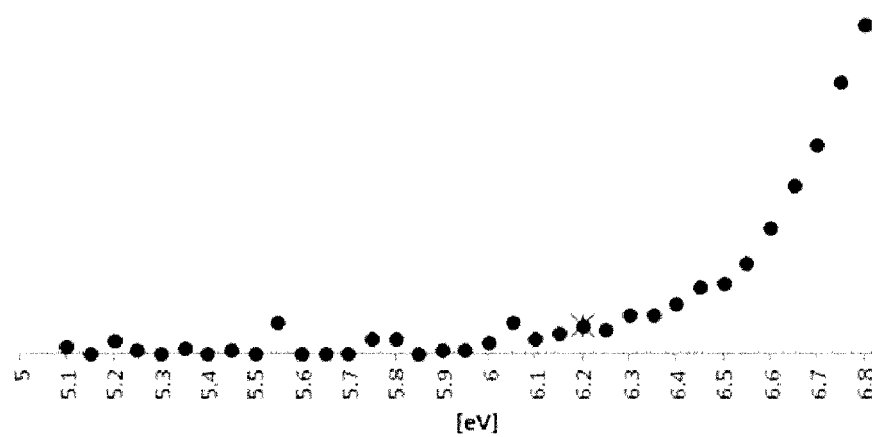

[FIG. 5]
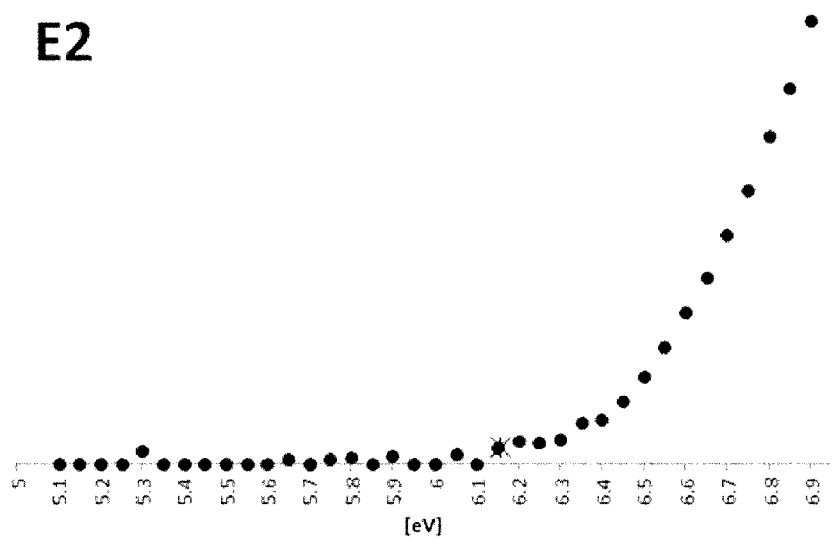
[FIG. 6]
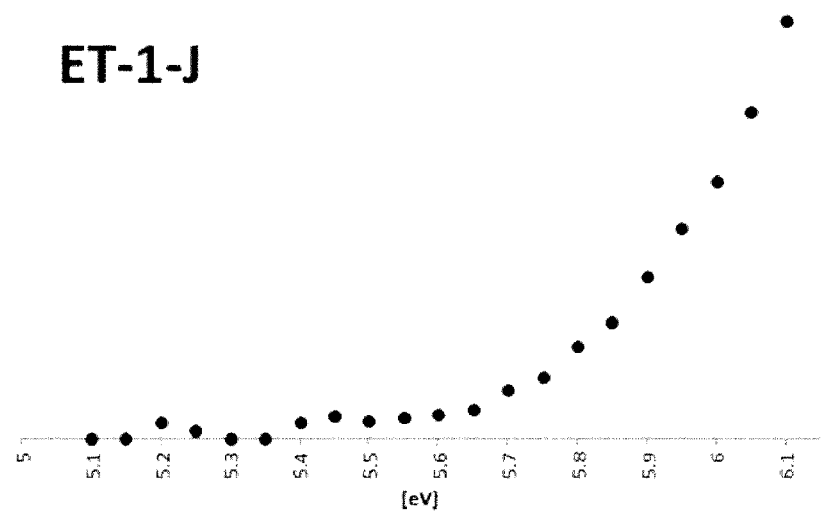

[FIG. 7]
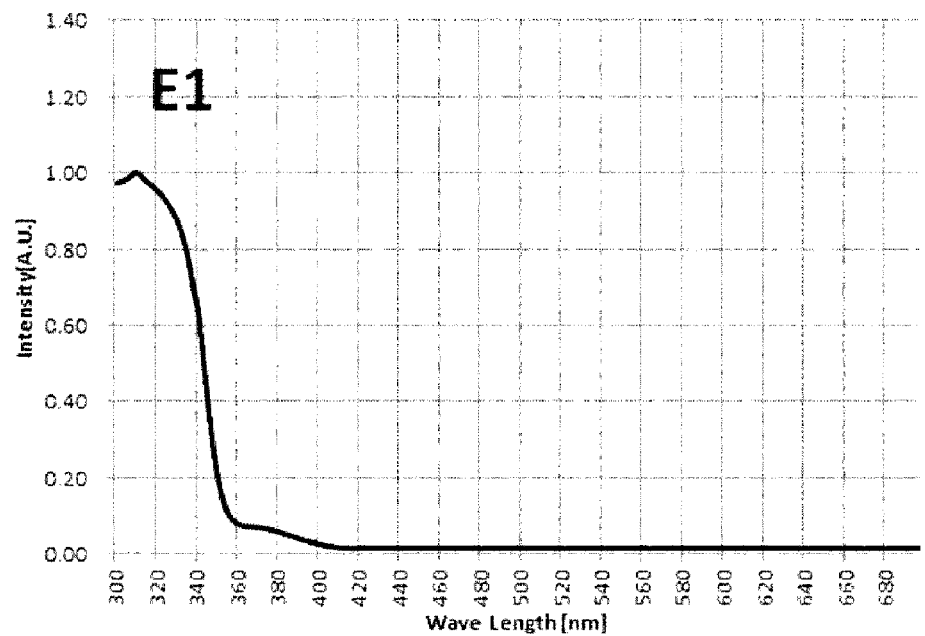
[FIG. 8]
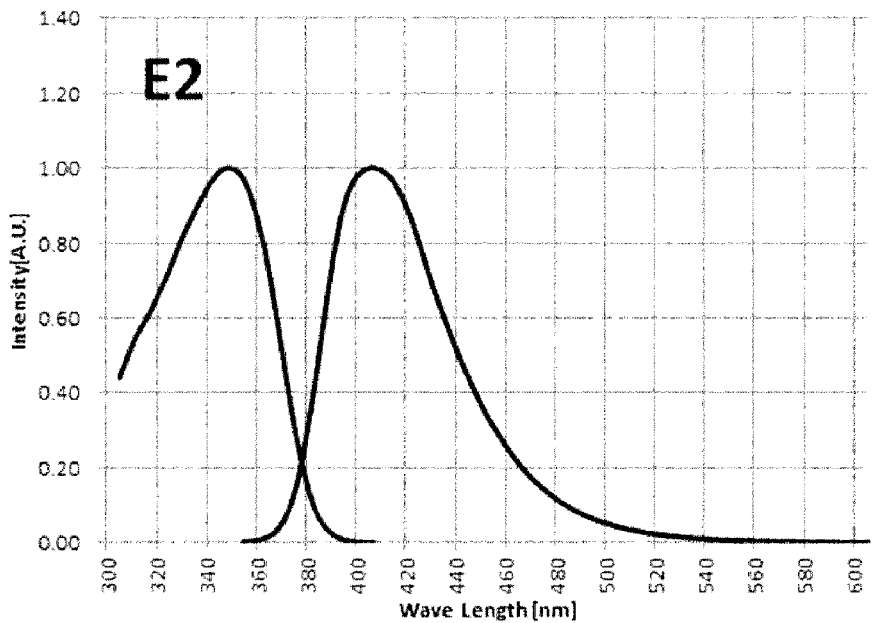

[FIG. 9]
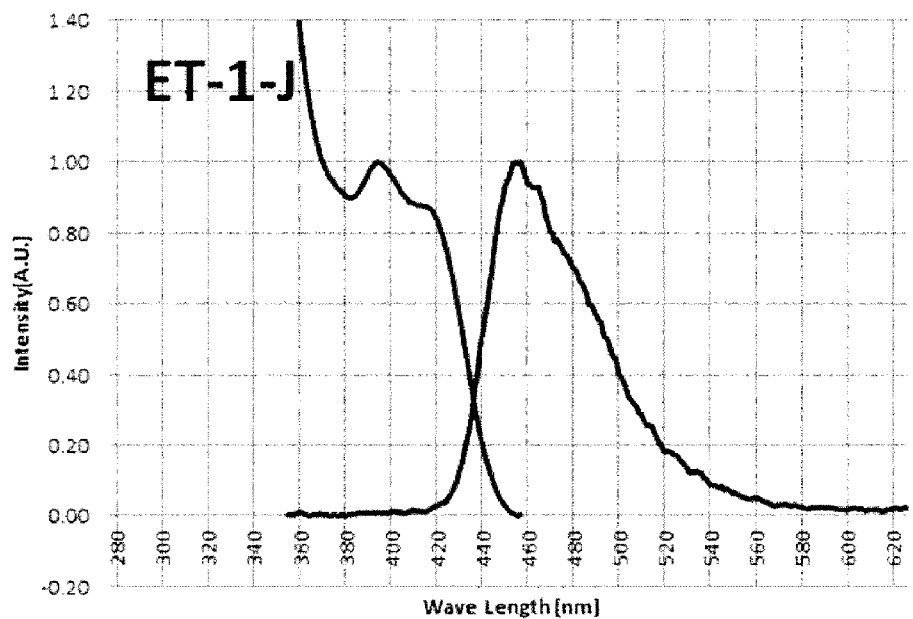
[FIG. 10]
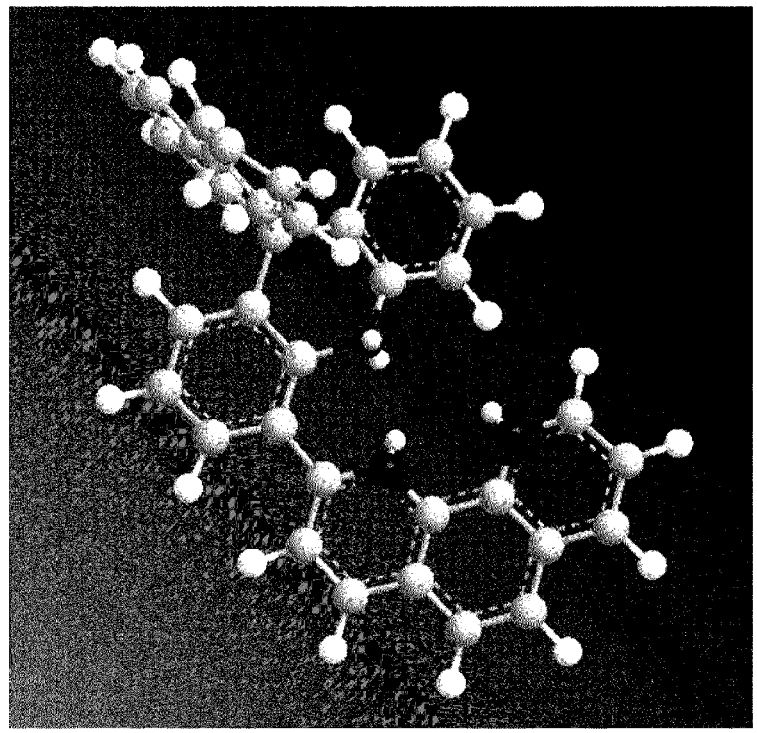

【FIG. 11】
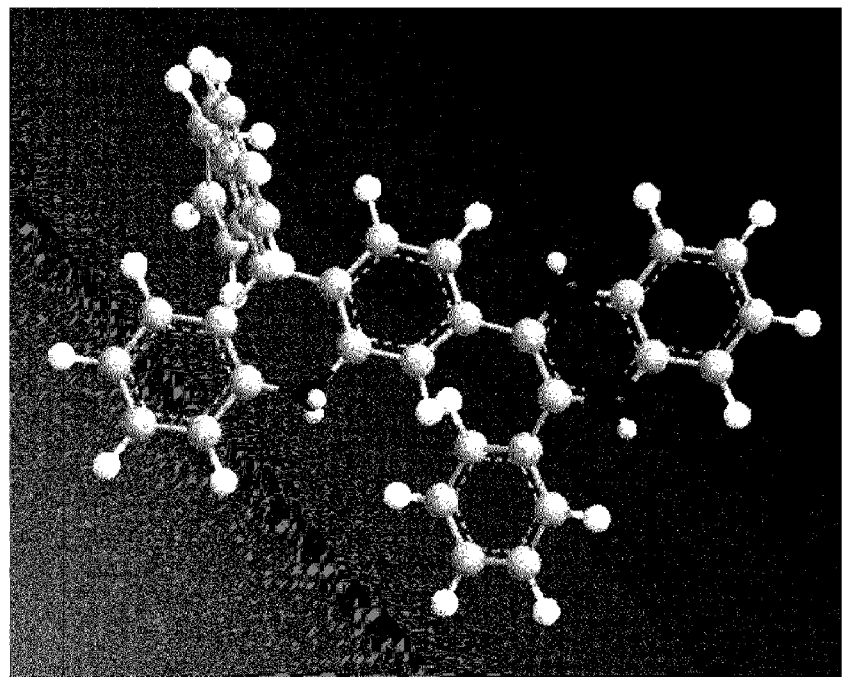
【FIG. 12】
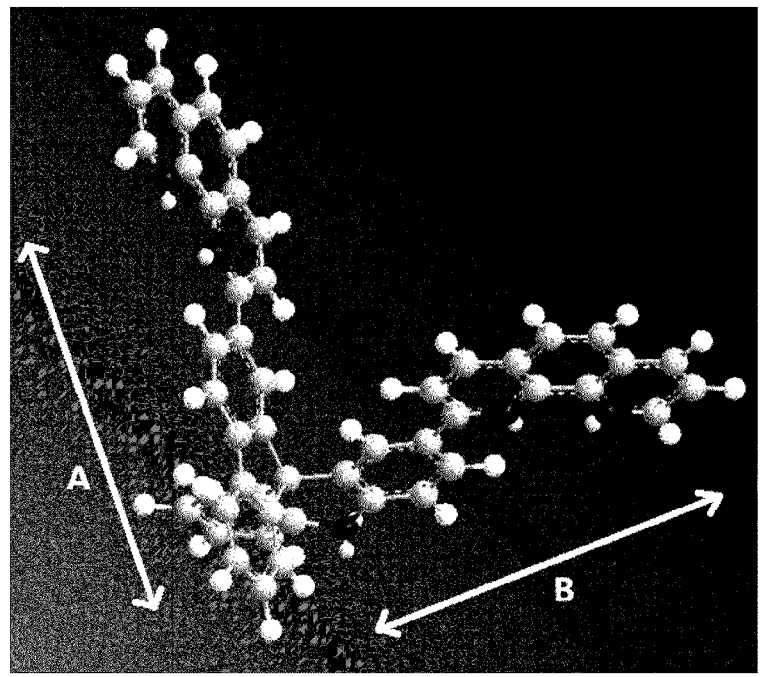

【FIG. 13】
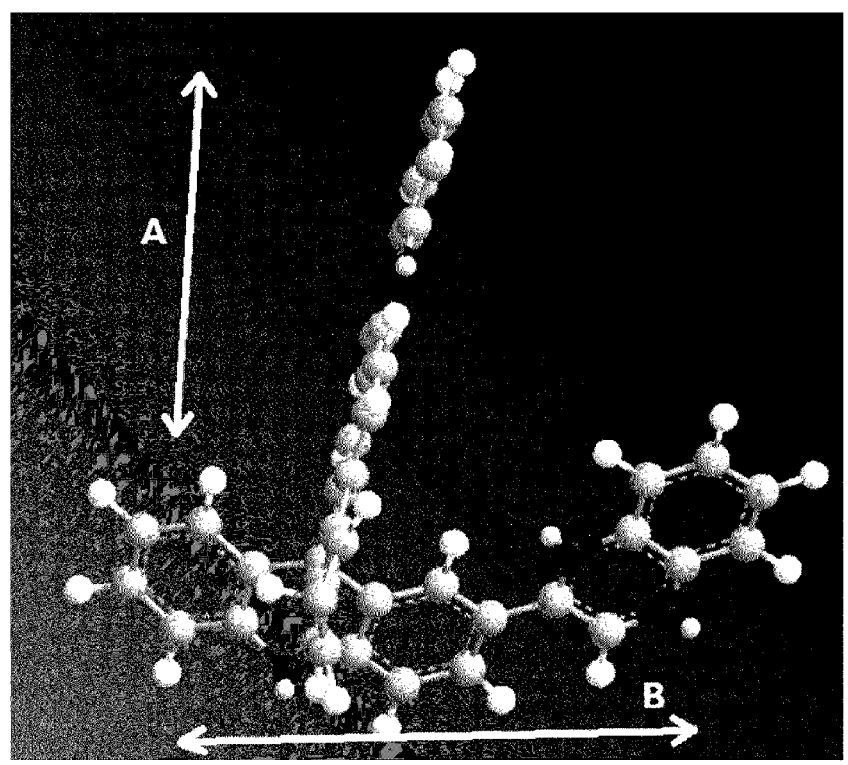

HETEROCYCLIC COMPOUND AND ORGANIC LIGHT EMITTING ELEMENT COMPRISING SAME

CROSS-REFERENCE TO RELATED APPLICATIONS

The present application is a divisional application of U.S. application Ser. No. 15/777,811 filed May 21, 2018 and issued as U.S. Pat. No. 11,094,889 on Aug. 17, 2021, a national phase entry under 35 U.S.C. § 371 of International Application No. PCT/KR2017/001956 filed Feb. 22, 2017, which claims priority from Korean Patent Application No. 10-2016-0021358 filed Feb. 23, 2016, all of which are incorporated herein by reference.

TECHNICAL FIELD

The present specification relates to a hetero-cyclic compound and an organic light emitting device comprising the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification provides a hetero-cyclic compound and an organic light emitting device comprising the same.

Technical Solution

One embodiment of present specification provides a hetero-cyclic compound represented by the following Chemical Formula 1.

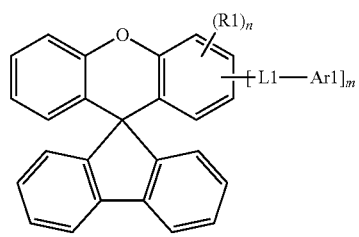

[Chemical Formula 1]

wherein, in Chemical Formula 1,

R1 is hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, L1 is a direct bond; a substituted or unsubstituted arylene group; or a substituted or unsubstituted heteroarylene group, Ar1 is hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; a substituted or unsubstituted monocyclic hetero-cyclic group; a substituted or unsubstituted tricyclic or higher hetero-cyclic group; a substituted or unsubstituted dicyclic hetero-cyclic group comprising two or more Ns; a substituted or unsubstituted isoquinolyl group; or a structure represented by the following Chemical Formula 2, m is an integer of 1 to 4, n is an integer of 0 to 3, 1≤n+m≤4, and when m and n are each 2 or greater, structures in the two or more parentheses are the same as or different from each other.

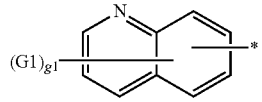

[Chemical Formula 2]

In Chemical Formula 2,

G1 is hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, g1 is an integer of 1 to 6, when g1 is 2 or greater, G1s are the same as or different from each other, and

* is a site bonding to L1 of Chemical Formula 1.

Another embodiment of the present specification provides an organic light emitting device comprising a first electrode; a second electrode provided opposite to the first electrode; and one or more organic material layers provided between the first electrode and the second electrode, wherein one or more layers of the organic material layers comprise the hetero-cyclic compound represented by Chemical Formula 1.

Advantageous Effects

A hetero-cyclic compound according to one embodiment of the present specification can be used as a material of an organic material layer of an organic light emitting device, and by using the hetero-cyclic compound, efficiency enhancement, low driving voltage and/or lifespan property enhancement can be obtained in the organic light emitting device.

DESCRIPTION OF DRAWINGS

FIG. 1 illustrates an organic light emitting device (10) according to one embodiment of the present specification.

FIG. 2 illustrates an organic light emitting device (11) according to another embodiment of the present specification.

FIG. 3 illustrates an organic light emitting device (12) according to still another embodiment of the present specification.

FIG. 4 shows a HOMO energy level measured using a photoelectron spectrometer for a compound of Chemical Formula E1 of Preparation Example 1 according to one embodiment of the present specification.

FIG. 5 shows a HOMO energy level measured using a photoelectron spectrometer for a compound of Chemical Formula E2 of Preparation Example 2 according to one embodiment of the present specification.

FIG. 6 shows a HOMO energy level measured using a photoelectron spectrometer for Compound [ET-1-J].

FIG. 7 shows a LUMO energy level calculated as a wavelength value measured through photoluminescence (PL) for a compound of Chemical Formula E1 of Preparation Example 1 according to one embodiment of the present specification.

FIG. 8 shows a LUMO energy level calculated as a wavelength value measured through photoluminescence (PL) for a compound of Chemical Formula E2 of Preparation Example 2 according to one embodiment of the present specification.

FIG. 9 shows a LUMO energy level calculated as a wavelength value measured through photoluminescence (PL) for Compound [ET-1-J].

FIG. 10 shows a molecular 3D structure obtained using Chem 3D Pro for a compound of Chemical Formula E9 of Preparation Example 9 according to one embodiment of the present specification.

FIG. 11 shows a molecular 3D structure obtained using Chem 3D Pro for a compound of Chemical Formula E18 of Preparation Example 18 according to one embodiment of the present specification.

FIG. 12 shows a molecular 3D structure obtained using Chem 3D Pro for Compound [ET-1-E].

FIG. 13 shows a molecular 3D structure obtained using Chem 3D Pro for Compound [ET-1-I].

REFERENCE NUMERAL 10, 11: Organic Light Emitting Device
20: Substrate
30: First Electrode
40: Light Emitting Layer
50: Second Electrode
60: Hole Injection Layer
70: Hole Transfer Layer
80: Electron Transfer Layer
90: Electron Injection Layer
100: Electron Control Layer

MODE FOR DISCLOSURE

Hereinafter, the present specification will be described in more detail.

One embodiment of the present specification provides a hetero-cyclic compound represented by Chemical Formula 1.

The hetero-cyclic compound according to one embodiment of the present specification has a nonlinear structure, and efficiency enhancement, low driving voltage, lifespan property enhancement and the like are capable of being obtained in an organic light emitting device. In addition, by the substituent Ar1 having an electron depleted-structured substituent in the structure of the hetero-cyclic compound represented by Chemical Formula 1, a dipole moment of the molecule may be designed close to nonpolar, and therefore, an amorphous layer may be formed when manufacturing an organic light emitting device comprising the hetero-cyclic compound represented by Chemical Formula 1. Accordingly, in an organic light emitting device comprising the hetero-cyclic compound according to one embodiment of the present specification, efficiency enhancement, low driving voltage, lifespan property enhancement and the like are capable of being obtained.

Particularly, the compound of Chemical Formula 1 has a substituent in only one benzene in the core structure, and, particularly when n=0 and m=1, has a three-dimensionally horizontal structure as well has the electronic properties described above, and therefore, electron mobility is strengthened when forming an organic material layer using such a material.

When two or more benzene rings are substituted in the core structure of Chemical Formula 1, such a horizontal structure is not obtained, and therefore, electron mobility is low compared to the compound of the present disclosure.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; a nitro group; an imide group; an amide group; a carbonyl group; an ester group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification,

means a site bonding to other substituents or bonding sites.

In the present specification, the halogen group may include fluorine, chlorine, bromine or iodine.

In the present specification, the number of carbon atoms of the imide group is not particularly limited, but is preferably from 1 to 30. Specifically, compounds having structures as below may be included, but the imide group is not limited thereto.

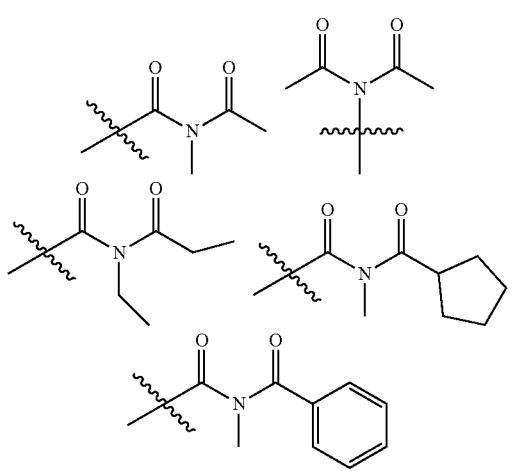

In the present specification, in the amide group, the nitrogen of the amide group may be substituted with a linear, branched or cyclic alkyl group having 1 to 30 carbon atoms or an aryl group having 6 to 30 carbon atoms. Specifically, compounds having the following structural formulae may be included, but the amide group is not limited thereto.

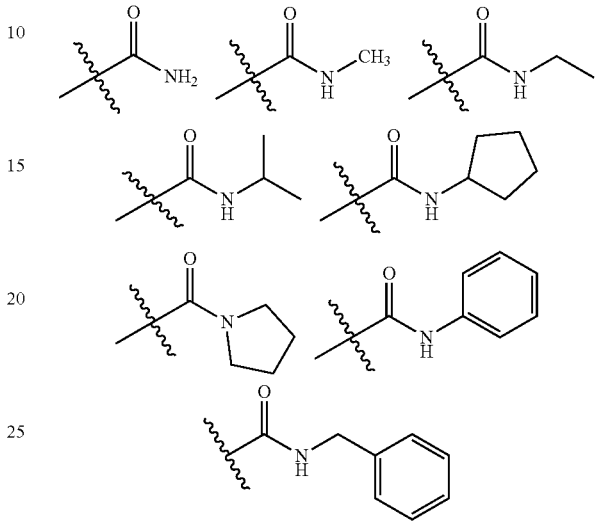

In the present specification, the number of carbon atoms of the carbonyl group is not particularly limited, but is preferably from 1 to 30. Specifically, compounds having structures as below may be included, but the carbonyl group is not limited thereto.

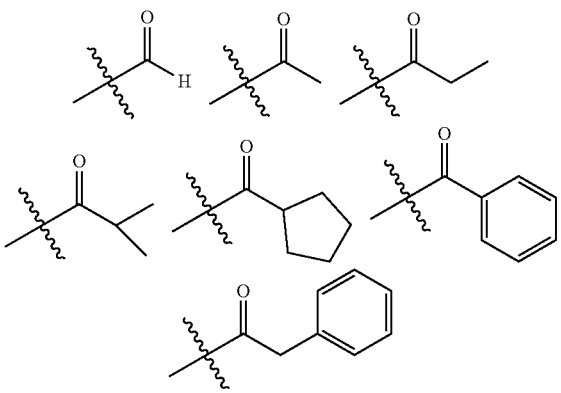

In the present specification, in the ester group, the oxygen of the ester group may be substituted with a linear, branched or cyclic alkyl group having 1 to 25 carbon atoms or an aryl group having 6 to 30 carbon atoms. Specifically, compounds having the following structural formulae may be included, but the ester group is not limited thereto.

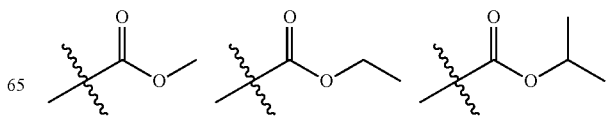

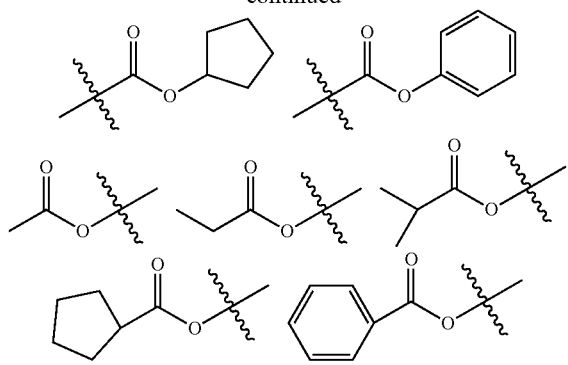

In the present specification, the alkyl group may be linear or branched, and the number of carbon atoms is not particularly limited, but is preferably from 1 to 30. Specifically, the number of carbon atoms is preferably from 1 to 20. More specifically, the number of carbon atoms is preferably from 1 to 10. Specific examples thereof may include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms, and more preferably has 3 to 20 carbon atoms. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 30. Specifically, the number of carbon atoms is preferably from 1 to 20. More specifically, the number of carbon atoms is preferably from 1 to 10. Specific examples thereof may include methoxy, ethoxy, n-propoxy, isopropoxy, propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the amine group may be selected from the group consisting of —NH$_2$; an alkylamine group; an N-alkylarylamine group; an arylamine group; an N-arylheteroarylamine group; an N-alkylheteroarylamine group and a heteroarylamine group, and the number of carbon atoms is, although not particularly limited thereto, preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methylanthracenylamine group, a diphenylamine group, an N-phenylnaphthylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the alkylamine group, the N-arylalkylamine group, the alkylthioxy group, the alkylsulfoxy group and the N-alkylheteroarylamine group is the same as the examples of the alkyl group described above. Specifically, the alkylthioxy group may include a methylthioxy group, an ethylthioxy group, a tert-butylthioxy group, a hexylthioxy group, an octylthioxy group and the like, and the alkylsulfoxy group may include mesyl, an ethylsulfoxy group, a propylsulfoxy group, a butylsulfoxy group and the like, however, the alkylthioxy group and the alkylsulfoxy group are not limited thereto.

In the present specification, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be —BR$_{100}$R$_{101}$, and herein, R$_{100}$ and R$_{101}$ are the same as or different from each other, and may be each independently selected from the group consisting of hydrogen; deuterium; halogen; a nitrile group; a substituted or unsubstituted monocyclic or multicyclic cycloalkyl group having 3 to 30 carbon atoms; a substituted or unsubstituted linear or branched alkyl group having 1 to 30 carbon atoms; a substituted or unsubstituted monocyclic or multicyclic aryl group having 6 to 30 carbon atoms; and a substituted or unsubstituted monocyclic or multicyclic heteroaryl group having 2 to 30 carbon atoms.

In the present specification, specific examples of the phosphine oxide group may include a diphenylphosphine oxide group, a dinaphthylphosphine oxide group and the like, but are not limited thereto.

In the present specification, the aryl group is not particularly limited, but preferably has 6 to 30 carbon atoms, and more preferably has 6 to 20 carbon atoms. The aryl group may be monocyclic or multicyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a multicyclic aryl group, the number of carbon atoms is not particularly limited, but is preferably from 10 to 30. Specific examples of the multicyclic aryl group may include a naphthyl group, an anthracenyl group, a phenanthryl group, a triphenyl group, a pyrenyl group, a phenalenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

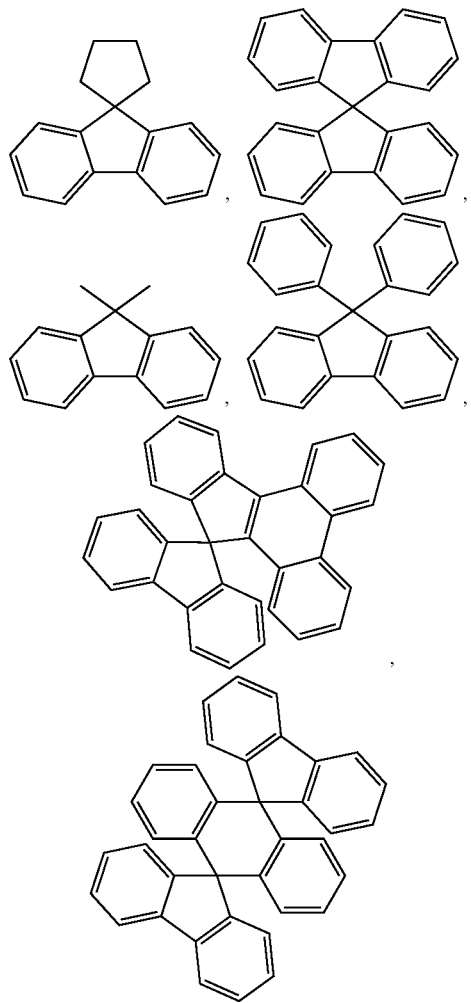

and the like may be included. However, the compound is not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the aryl group in the aryloxy group, the arylthioxy group, the arylsulfoxy group, the N-arylalkylamine group, the N-arylheteroarylamine group and the arylphosphine group is the same as the examples of the aryl group described above. Specific examples of the aryloxy group may include a phenoxy group, a p-tolyloxy group, an m-tolyloxy group, a 3,5-dimethylphenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like, and specific examples of the arylthioxy group may include a phenylthioxy group, a 2-methylphenylthioxy group, a 4-tert-butylphenylthioxy group and the like, and specific examples of the arylsulfoxy group may include a benzenesulfoxy group, a p-toluenesulfoxy group and the like, however, the aryloxy group, the arylthioxy group and the arylsulfonyl group are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups. For example, the aryl group in the arylamine group may be selected from among the examples of the aryl group described above.

In the present specification, the heteroaryl group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30 and more preferably from 2 to 20, and the heteroaryl group may be monocyclic or multicyclic. Examples of the heteroaryl group may include a thiophene group, a furanyl group, a pyrrole group, an imidazolyl group, a triazolyl group, an oxazolyl group, an oxadiazolyl group, a pyridyl group, a bipyridyl group, a pyrimidyl group, triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, a dibenzofuranyl group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include monocyclic heteroaryl groups, multicyclic heteroaryl groups, or both monocyclic heteroaryl groups and multicyclic heteroaryl groups. For example, the heteroaryl group in the heteroarylamine group may be selected from among the examples of the heteroaryl group described above.

In the present specification, examples of the heteroaryl group in the N-arylheteroarylamine group and the N-alkylheteroarylamine group are the same as the examples of the heteroaryl group described above.

In the present specification, the arylene group means an aryl group having two bonding sites, that is, a divalent group. Descriptions on the aryl group provided above may be applied thereto except for each being a divalent group.

In the present specification, the heteroarylene group means a heteroaryl group having two bonding sites, that is, a divalent group. Descriptions on the heteroaryl group provided above may be applied thereto except for each being a divalent group.

In the present specification, the hetero-cyclic group may be monocyclic or multicyclic, and aromatic, aliphatic or a fused ring of aromatic and aliphatic, and may be selected from among the examples of the heteroaryl group. In addition thereto, examples of the hetero-cyclic group may include a hydroacridyl group (for example,

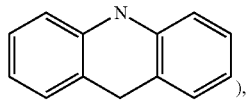 [SMILES: c1ccc2c(c1)Cc1ccccc1N2]), and a heteroring structure including a sulfonyl group such as

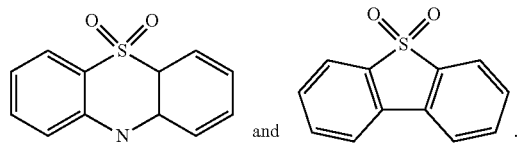 [SMILES: O=S1(=O)c2ccccc2NC2C=CC=CC21 ; O=S1(=O)c2ccccc2-c2ccccc21].

In the present specification, the "ring" in the substituted or unsubstituted ring formed by adjacent groups bonding to each other means a substituted or unsubstituted hydrocarbon ring; or a substituted or unsubstituted heteroring.

In the present specification, the hydrocarbon ring may be aromatic, aliphatic or a fused ring of aromatic and aliphatic, and may be selected from among the examples of the cycloalkyl group or the aryl group except for those that are not monovalent.

In the present specification, the aromatic ring may be monocyclic or multicyclic, and may be selected from among the examples of the aryl group except for those that are not monovalent.

In the present specification, the heteroring is a group including one or more atoms that are not carbon, that is, heteroatoms, and specifically, the heteroatom may include one or more atoms selected from the group consisting of O, N, Se, S and the like. The heteroring may be monocyclic or multicyclic, may be aromatic, aliphatic or a fused ring of aromatic and aliphatic, and may be selected from among the examples of the heteroaryl group except for those that are not monovalent.

According to one embodiment of the present specification, in Chemical Formula 1, L1 is a direct bond; or a substituted or unsubstituted arylene group.

According to one embodiment of the present specification, in Chemical Formula 1, L1 is a direct bond; an arylene group; or a heteroarylene group.

According to one embodiment of the present specification, in Chemical Formula 1, L1 is a direct bond; a phenylene group; a biphenylylene group; a naphthylene group; a terphenylylene group; a pyrimidylene group; a divalent furan group; or a divalent thiophene group.

According to one embodiment of the present specification, in Chemical Formula 1, Ar1 is a nitrile group; a substituted or unsubstituted alkoxy group; a substituted or unsubstituted phosphine oxide group; a substituted or unsubstituted silyl group; a substituted or unsubstituted monocyclic hetero-cyclic group; a substituted or unsubstituted tricyclic or higher hetero-cyclic group; a substituted or unsubstituted dicyclic hetero-cyclic group comprising two or more Ns; a substituted or unsubstituted isoquinolyl group; or a structure represented by Chemical Formula 2.

According to one embodiment of the present specification, in Chemical Formula 1, Ar1 is a nitrile group; an alkoxy group substituted with a halogen group; a phosphine oxide group substituted with an aryl group; or a silyl group substituted with an aryl group.

According to one embodiment of the present specification, in Chemical Formula 1, Ar1 is a nitrile group; a methoxy group substituted with a fluoro group; a phosphine oxide group substituted with a phenyl group; or a silyl group substituted with a phenyl group.

According to one embodiment of the present specification, in Chemical Formula 1, Ar1 may be represented by the following Chemical Formula 1a.

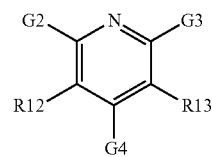

[Chemical Formula 1a]

In Chemical Formula 1a, any one of G2 to G4, R12 and R13 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

According to one embodiment of the present specification, in Chemical Formula 1, Ar1 is represented by any one of Chemical Formula 2 and the following Chemical Formulae 3 to 8, 10 and 11.

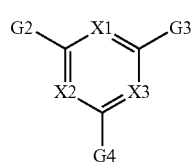

[Chemical Formula 3]

In Chemical Formula 3,

X1 is N or CR11, X2 is N or CR12 and X3 is N or CR13, at least two of X1 to X3 are N, any one of G2 to G4 and R11 to R13 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 4]

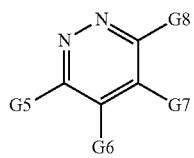

in Chemical Formula 4, any one of G5 to G8 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 5]

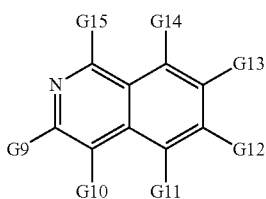

in Chemical Formula 5, any one of G9 to G15 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 6]

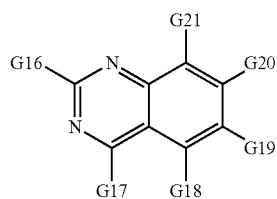

in Chemical Formula 6, any one of G16 to G21 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 7]

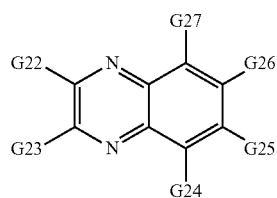

in Chemical Formula 7, any one of G22 to G27 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

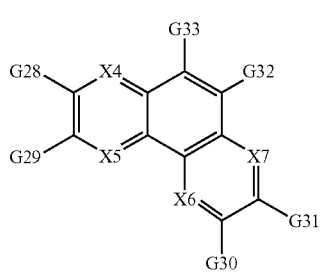

[Chemical Formula 8]

in Chemical Formula 8,

X4 is N or CR14, X5 is N or CR15, X6 is N or CR16 and X7 is N or CR17, at least one of X4 to X7 is N, any one of G28 to G33 and R14 to R17 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

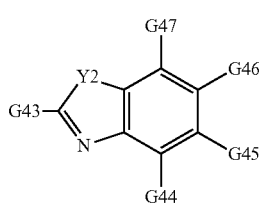

[Chemical Formula 10]

in Chemical Formula 10,

Y2 is O, S, NQ4 or CQ5Q6, any one of G43 to G47 is a site bonding to L1 of Chemical Formula 1, and the rest and Q4 to Q6 are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted ring,

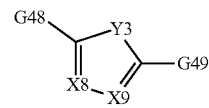

[Chemical Formula 11]

in Chemical Formula 11,

Y3 is O, S or NQ7,

X8 is N or CR18 and X9 is N or CR19, and any one of G48, G49, R18 and R19 is a site bonding to L1 of Chemical Formula 1, and the rest and Q7 are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

According to another embodiment of the present specification, in Chemical Formula 2, G1 is hydrogen; or an aryl group.

According to another embodiment of the present specification, in Chemical Formula 2, G1 is hydrogen; or a phenyl group.

According to another embodiment of the present specification, Chemical Formula 2 is represented by any one of the following structures.

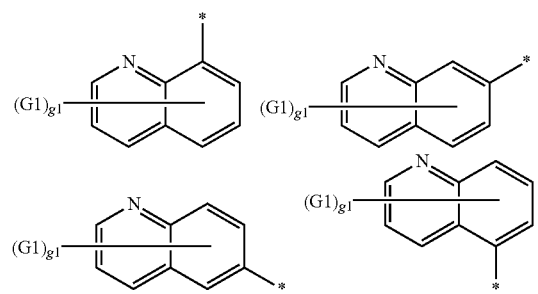

In the structures, definitions of G1 and g1 are the same as in Chemical Formula 2, and * is a site bonding to L1 of Chemical Formula 1.

According to another embodiment of the present specification, in Chemical Formula 3, any one of G2 to G4 and R11 to R13 is a site bonding to L1 of Chemical Formula 1, and the rest are the same as or different from each other and each independently hydrogen; a substituted or unsubstituted aryl group; or a substituted or unsubstituted heteroaryl group.

According to another embodiment of the present specification, in Chemical Formula 3, any one of G2 to G4 and R11 to R13 is a site bonding to L1 of Chemical Formula 1, and the rest are the same as or different from each other and each independently hydrogen; an aryl group unsubstituted or substituted with a nitrile group, an aryl group, a hetero-cyclic group substituted with an alkyl group, or a hetero-cyclic group unsubstituted or substituted with an aryl group; or a heteroaryl group.

According to another embodiment of the present specification, in Chemical Formula 3, any one of G2 to G4 and R11 to R13 is a site bonding to L1 of Chemical Formula 1, and the rest are the same as or different from each other and each independently hydrogen; a phenyl group unsubstituted or substituted with an aryl group, a hetero-cyclic group substituted with an alkyl group, or a hetero-cyclic group unsubstituted or substituted with an aryl group; a biphenyl group unsubstituted or substituted with a nitrile group or a hetero-cyclic group; a terphenyl group; a naphthyl group unsubstituted or substituted with an aryl group or a heteroaryl group; a fluorenyl group unsubstituted or substituted with an alkyl group; a triphenylenyl group; a phenanthrenyl group; a phenalenyl group; a pyridyl group; a dibenzofuranyl group; or a dibenzothiophene group.

According to another embodiment of the present specification, in Chemical Formula 3, any one of G2 to G4 and R11 to R13 is a site bonding to L1 of Chemical Formula 1, and the rest are the same as or different from each other and each independently hydrogen; a phenyl group unsubstituted or substituted with a phenyl group, a terphenyl group, a carbazolyl group, a quinolyl group, a phenoxazinyl group, a phenothiazinyl group, a triphenylenyl group, a fluoranthenyl group, a pyridyl group, a dibenzothiophene group, a dibenzofuranyl group, a benzocarbazolyl group, a dihydrophenazinyl group substituted with a phenyl group, or a dihydroacridine group substituted with a methyl group; a nitrile group; or a biphenyl group unsubstituted or substituted with a carbazolyl group; a terphenyl group; a naphthyl group unsubstituted or substituted with a phenyl group, a pyridyl group or a dibenzofuranyl group; a fluorenyl group unsubstituted or substituted with a methyl group; a triphenylenyl group; a phenanthrenyl group; a phenalenyl group; a pyridyl group; a dibenzofuranyl group; or a dibenzothiophene group.

According to another embodiment of the present specification, Chemical Formula 3 may be represented by the following Chemical Formula 3a or 3b.

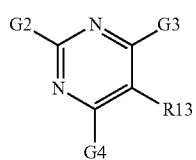

[Chemical Formula 3a]

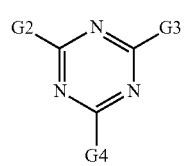

[Chemical Formula 3b]

In Chemical Formulae 3a and 3b, definitions of G2 to G4 and R13 are the same as in Chemical Formula 3.

According to one embodiment of the present specification, when at least two of X1 to X3 are N in Chemical Formula 3, HOMO energy is deep with 6.1 eV or higher, and electron mobility is high while smoothly performing a role of a hole blocking layer, and therefore, when used in an organic light emitting device, a device having low driving voltage, high efficiency and long lifespan is obtained. Specifically, the above-mentioned effects are maximized when Ar1 is represented by Chemical Formula 3a or Chemical Formula 3b.

Particularly, when Ar1 is a triazine group that is Chemical Formula 3b, HOMO energy is deep with 6.1 eV or higher, and electron mobility is high while smoothly performing a role of a hole blocking layer, and therefore, when used in an organic light emitting device, a device having low driving voltage, high efficiency and long lifespan is obtained.

When Ar1 is Chemical Formula 3b in the hetero-cyclic compound represented by Chemical Formula 1 described in FIG. 4 and FIG. 5, HOMO energy is identified to have a deep value of 6.1 eV of higher, and as a result, properties of low driving voltage, high efficiency and long lifespan are obtained in an organic light emitting device.

According to another embodiment of the present specification, in Chemical Formula 4, any one of G5 to G8 is a site bonding to L1 of Chemical Formula 1, and the rest are the same as or different from each other and each independently hydrogen; or a substituted or unsubstituted aryl group.

According to another embodiment of the present specification, in Chemical Formula 4, any one of G5 to G8 is a site bonding to L1 of Chemical Formula 1, and the rest are the same as or different from each other and each independently hydrogen; or an aryl group.

According to another embodiment of the present specification, in Chemical Formula 4, any one of G5 to G8 is a site bonding to L1 of Chemical Formula 1, and the rest are the same as or different from each other and each independently hydrogen; a phenyl group; or a naphthyl group.

According to another embodiment of the present specification, in Chemical Formula 5, any one of G9 to G15 is a site bonding to L1 of Chemical Formula 1, and the rest are the same as or different from each other and each independently hydrogen; or a substituted or unsubstituted aryl group.

According to another embodiment of the present specification, in Chemical Formula 5, any one of G9 to G15 is a site bonding to L1 of Chemical Formula 1, and the rest are the same as or different from each other and each independently hydrogen; or an aryl group.

According to another embodiment of the present specification, in Chemical Formula 5, any one of G9 to G15 is a site bonding to L1 of Chemical Formula 1, and the rest are the same as or different from each other and each independently hydrogen; or a phenyl group.

According to another embodiment of the present specification, in Chemical Formula 6, any one of G16 to G21 is a site bonding to L1 of Chemical Formula 1, and the rest are the same as or different from each other and each independently hydrogen; or a substituted or unsubstituted aryl group.

According to another embodiment of the present specification, in Chemical Formula 6, any one of G16 to G21 is a site bonding to L1 of Chemical Formula 1, and the rest are the same as or different from each other and each independently hydrogen; or an aryl group.

According to another embodiment of the present specification, in Chemical Formula 6, any one of G16 to G21 is a site bonding to L1 of Chemical Formula 1, and the rest are the same as or different from each other and each independently hydrogen; a phenyl group; a biphenyl group; or a naphthyl group.

According to another embodiment of the present specification, in Chemical Formula 7, any one of G22 to G27 is a site bonding to L1 of Chemical Formula 1, and the rest are the same as or different from each other and each independently hydrogen; or an aryl group.

According to another embodiment of the present specification, in Chemical Formula 7, any one of G22 to G27 is a site bonding to L1 of Chemical Formula 1, and the rest are the same as or different from each other and each independently hydrogen; or a phenyl group.

According to another embodiment of the present specification, in Chemical Formula 8, any one of G28 to G33 and R14 to R17 is a site bonding to L1 of Chemical Formula 1, and the rest are the same as or different from each other and each independently hydrogen.

According to another embodiment of the present specification, the Chemical Formula 8 is represented by any one of the following structures.

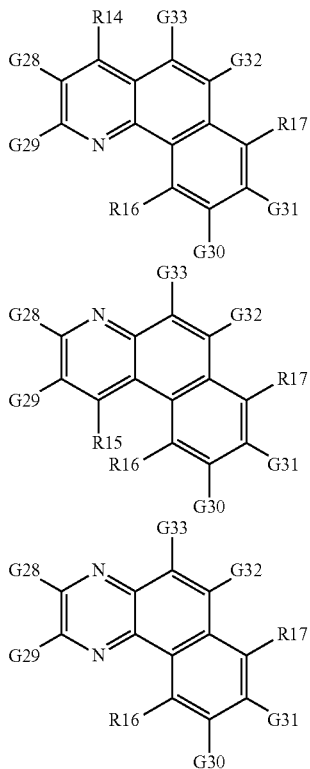

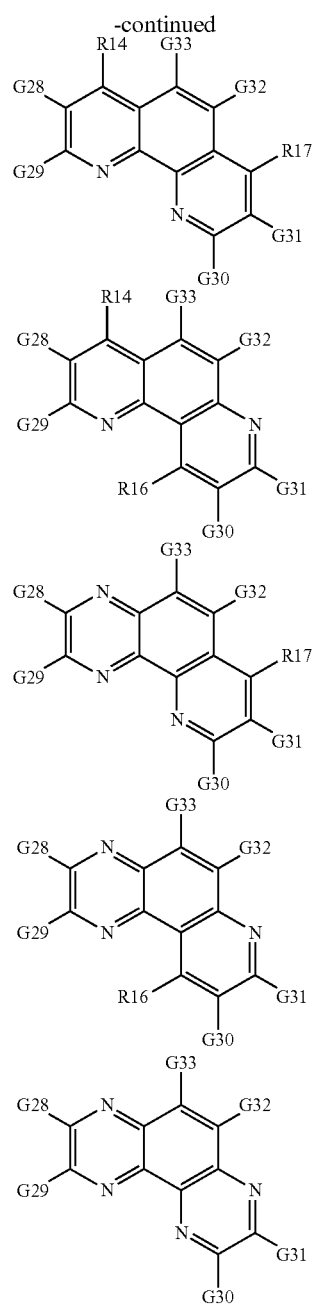

In the structures, definitions of G28 to G33 and R14 to R17 are the same as in Chemical Formula 8.

According to another embodiment of the present specification, in Chemical Formula 10, any one of G43 to G47 is a site bonding to L1 of Chemical Formula 1, and the rest and Q4 to Q6 are the same as or different from each other and each independently hydrogen; a substituted or unsubstituted alkyl group; or a substituted or unsubstituted aryl group.

According to another embodiment of the present specification, in Chemical Formula 10, any one of G43 to G47 is a site bonding to L1 of Chemical Formula 1, and the rest and Q4 to Q6 are the same as or different from each other and each independently hydrogen; an alkyl group; or an aryl group.

According to another embodiment of the present specification, in Chemical Formula 10, any one of G43 to G47 is a site bonding to L1 of Chemical Formula 1, and the rest and Q4 to Q6 are the same as or different from each other and each independently hydrogen; a methyl group; or a phenyl group.

According to another embodiment of the present specification, in Chemical Formula 10, when Y2 is NQ4, G43 and Q4 bond to each other to form a substituted or unsubstituted ring.

According to another embodiment of the present specification, in Chemical Formula 10, when Y2 is NQ4, G43 and Q4 bond to each other to form a substituted or unsubstituted heteroring.

According to another embodiment of the present specification, in Chemical Formula 10, when Y2 is NQ4, G43 and Q4 bond to each other to form a benzoisoquinol ring.

According to another embodiment of the present specification, Chemical Formula 10 is represented by any one of the following structures.

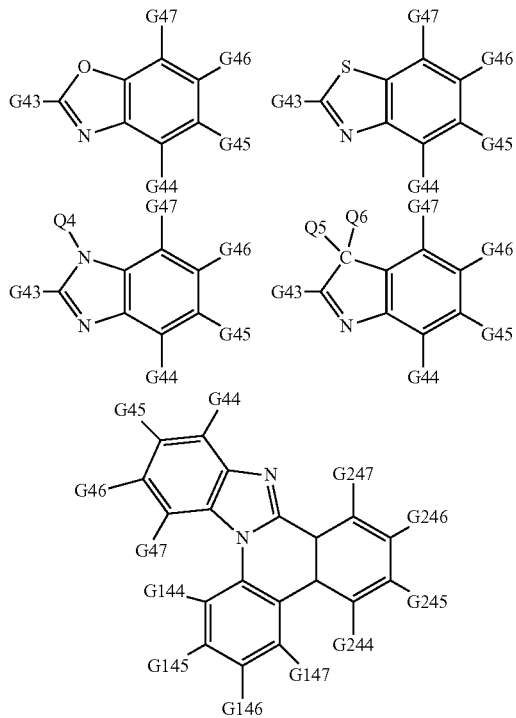

In the structures, any one of G43 to G47, G144 to G147 and G244 to G247 is a site bonding to L1 of Chemical Formula 1, and the rest and Q4 to Q6 are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted ring.

According to another embodiment of the present specification, Chemical Formula 10 is represented by any one of the following structures.

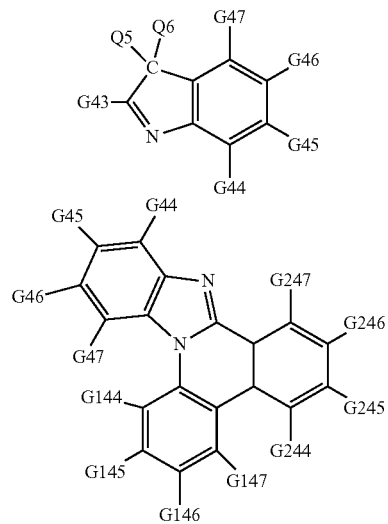

In the structures, any one of G43 to G47, G144 to G147 and G244 to G247 is a site bonding to L1 of Chemical Formula 1, and the rest and Q5 and Q6 are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted ring.

According to another embodiment of the present specification, in Chemical Formula 11, any one of G48, G49, R18 and R19 is a site bonding to L1 of Chemical Formula 1, and the rest and Q7 are the same as or different from each other and each independently hydrogen; or a substituted or unsubstituted aryl group.

According to another embodiment of the present specification, in Chemical Formula 11, any one of G48, G49, R18 and R19 is a site bonding to L1 of Chemical Formula 1, and the rest and Q7 are the same as or different from each other and each independently hydrogen; or an aryl group.

According to another embodiment of the present specification, in Chemical Formula 11, any one of G48, G49, R18 and R19 is a site bonding to L1 of Chemical Formula 1, and the rest and Q7 are the same as or different from each other and each independently hydrogen; or a phenyl group.

According to another embodiment of the present specification, Chemical Formula 11 is represented by any one of the following structures.

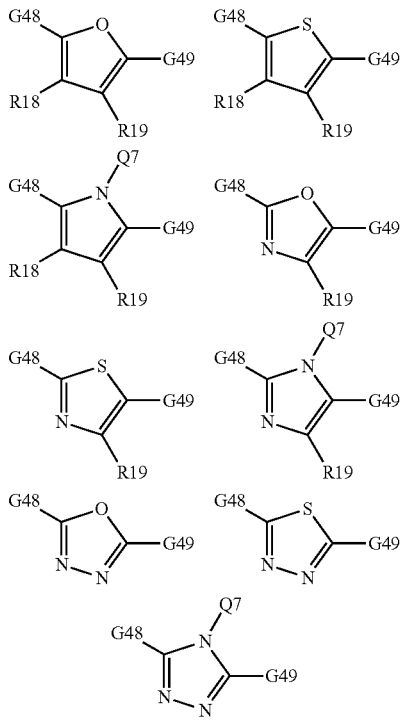

In the structures, definitions of G48, G49, R18, R19 and Q7 are the same as in Chemical Formula 11.

According to another embodiment of the present specification, Chemical Formula 11 is represented by any one of the following structures.

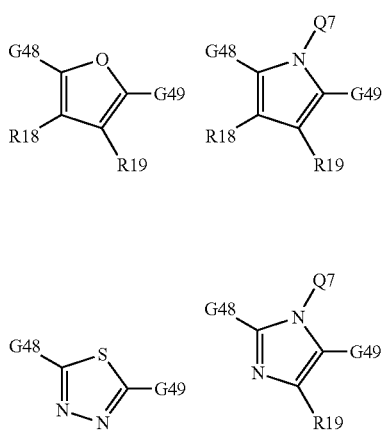

In the structures, definitions of G48, G49, R18, R19 and Q7 are the same as in Chemical Formula 11.

According to one embodiment of the present specification, m is an integer of 1.

According to one embodiment of the present specification, Chemical Formula 1 is represented by any one of the following Chemical Formulae 1-1 to 1-4.

[Chemical Formula 1-1]

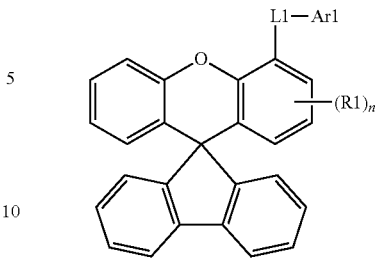

[Chemical Formula 1-2]

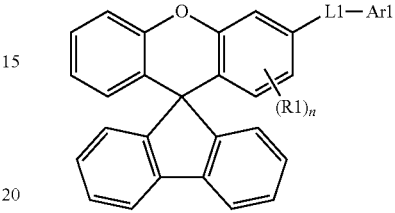

[Chemical Formula 1-3]

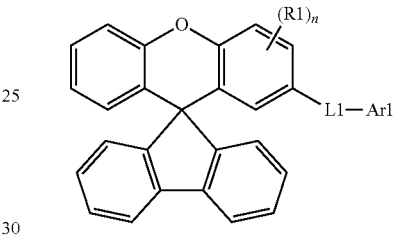

[Chemical Formula 1-4]

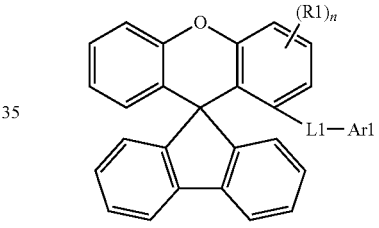

In Chemical Formulae 1-1 to 1-4, definitions of L1, Ar1, R1 and n are the same as in Chemical Formula 1.

According to one embodiment of the present specification, R1 is hydrogen.

Electron mobility of a compound generally varies depending on orientation in a molecular 3D structure, and electron mobility is strengthened in a more horizontal structure. The hetero-cyclic compound represented by Chemical Formula 1 in which one -L1-Ar1 is substituted according to one embodiment of the present specification has a strong tendency toward a horizontal structure of a molecule compared to compounds in which two -L1-Ar1s are substituted, and has an advantage of enhancing electron mobility. Accordingly, when using the hetero-cyclic compound represented by Chemical Formula 1 in an organic light emitting device, effects of low driving voltage, high efficiency and long lifespan are obtained. (refer to APPLIED PHYSICS LETTERS 95, 243303 (2009))

When referring to FIG. 10 and FIG. 11 showing 3D structures of Compounds E9 and E18 according to one embodiment of the present specification, the molecules of the compounds are identified to have a horizontal structure, and when referring to FIG. 12 and FIG. 13 showing 3D structures of Compounds ET-1-E and ET-1-I used as comparative example compounds of the present specification, the A axis and the B axis are almost perpendicular to each other in each compound identifying that the molecule is very out of a horizontal structure. As a result, Compounds E9 and E18 according to one embodiment of the present specification have a horizontal structure compared to Compounds ET-1-E and ET-1-I due to a difference in the orientation in the molecular 3 D structure, and as a result, it is seen that excellent effects in terms of driving voltage, efficiency and lifespan are obtained when using the hetero-cyclic compound represented by Chemical Formula 1 in an organic light emitting device.

According to one embodiment of the present specification, Chemical Formula 1 is selected from among the following compounds.

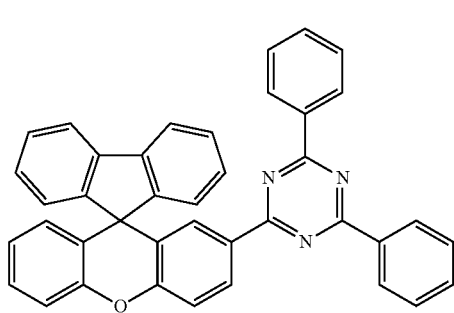
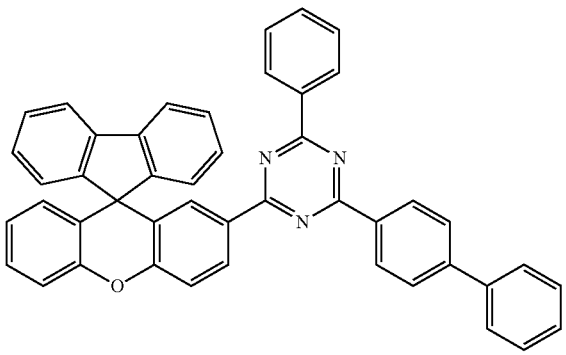
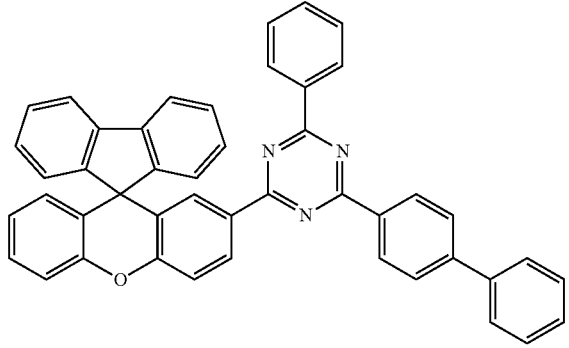
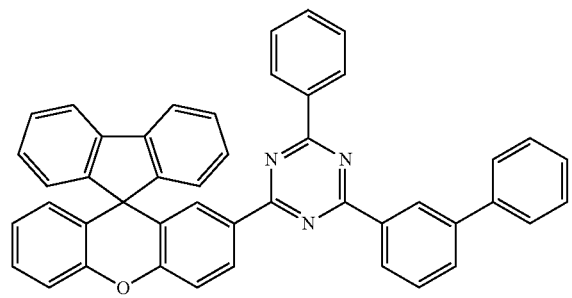
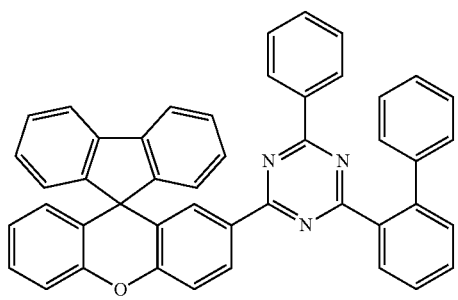
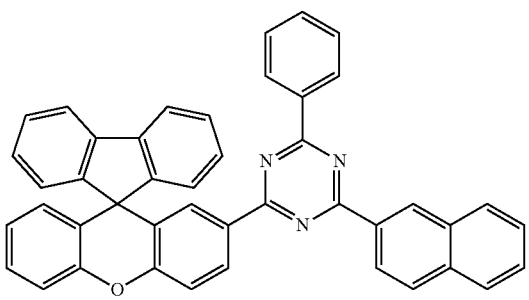
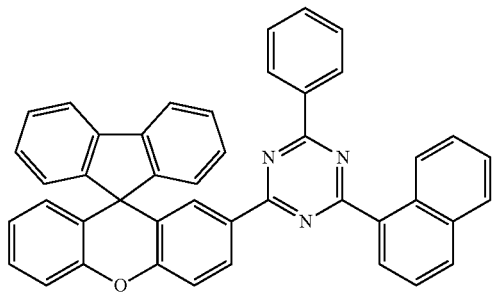
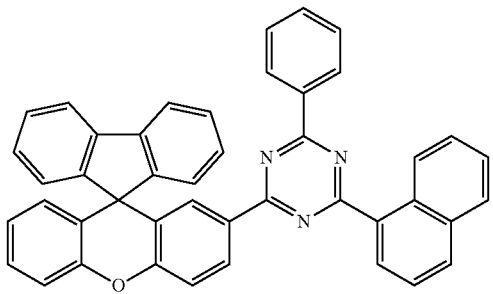

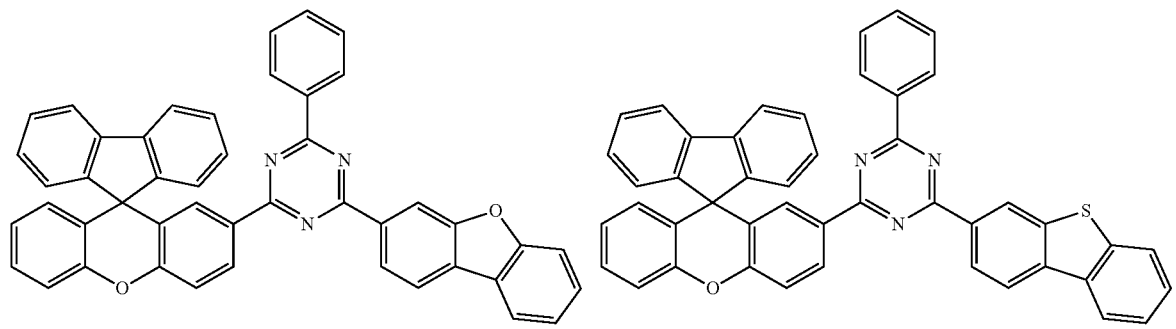
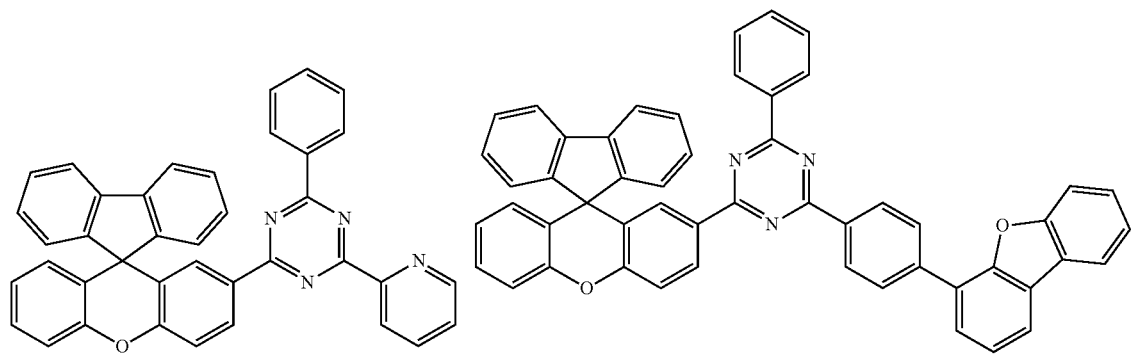
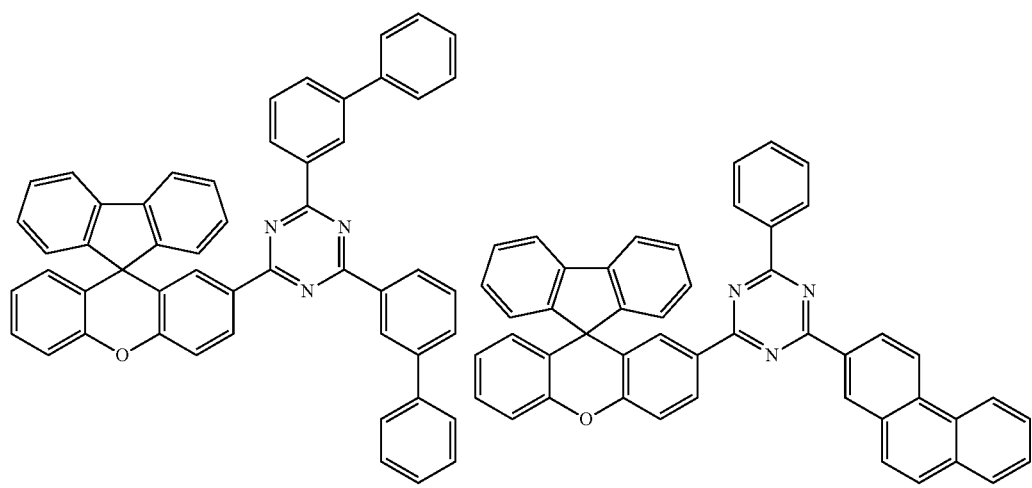
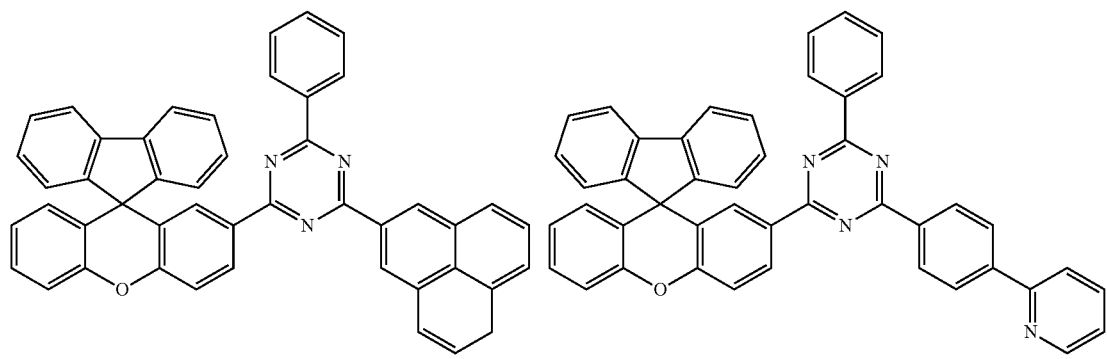

-continued
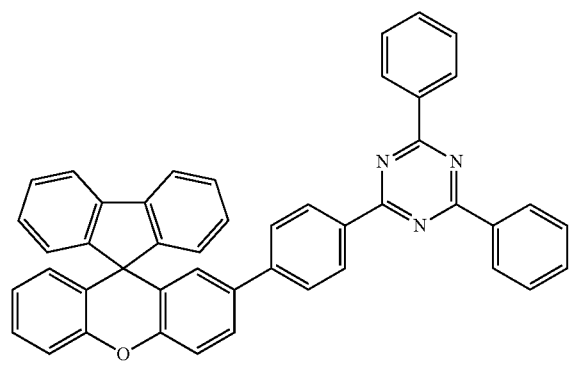
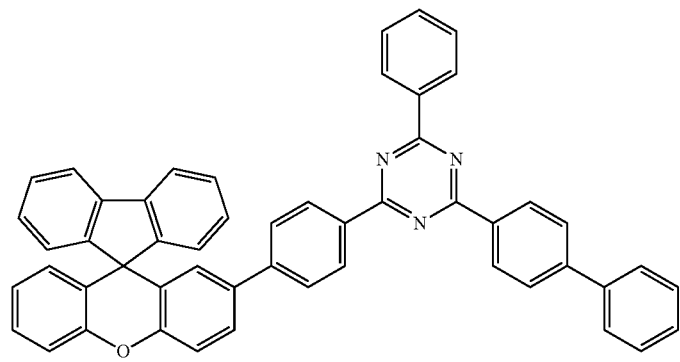
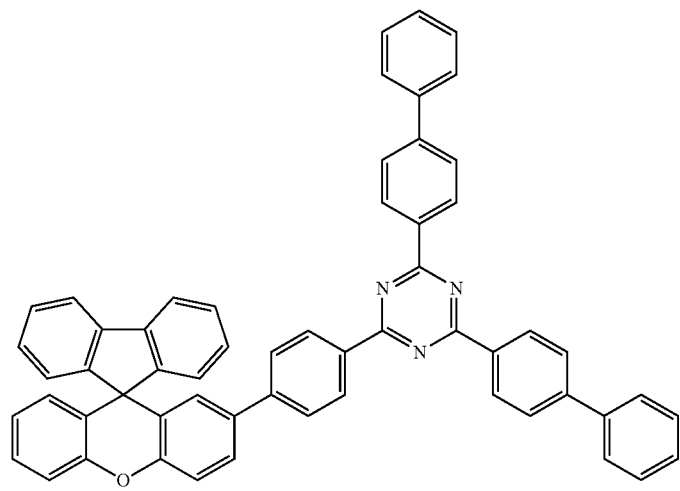
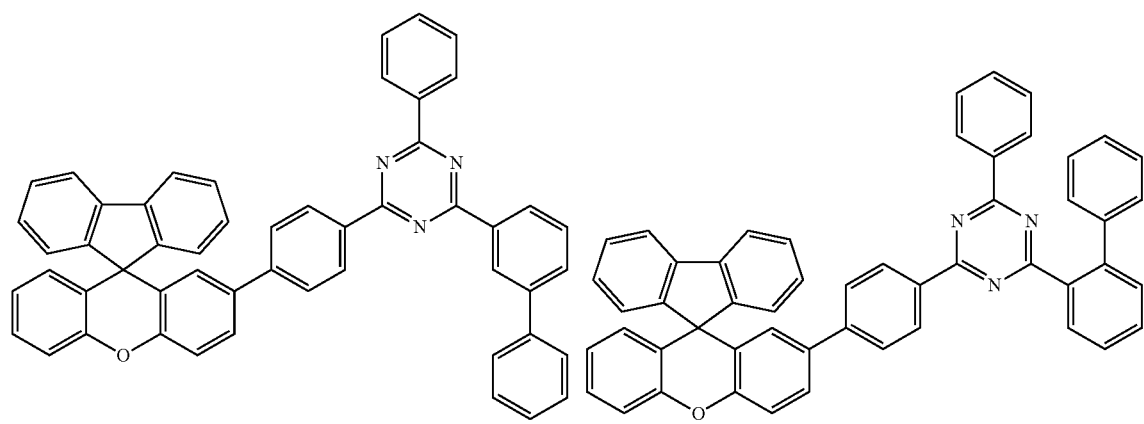

-continued
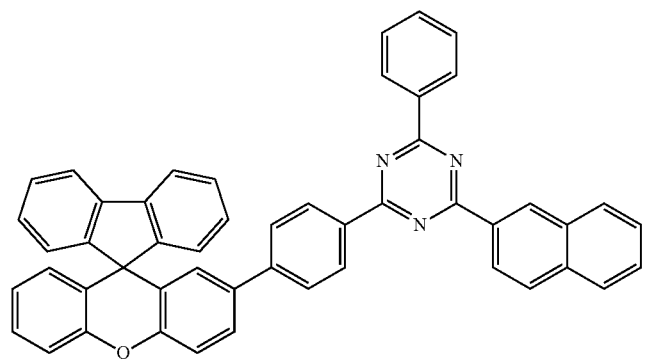
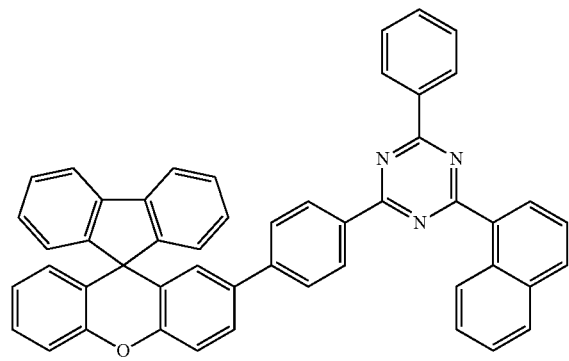
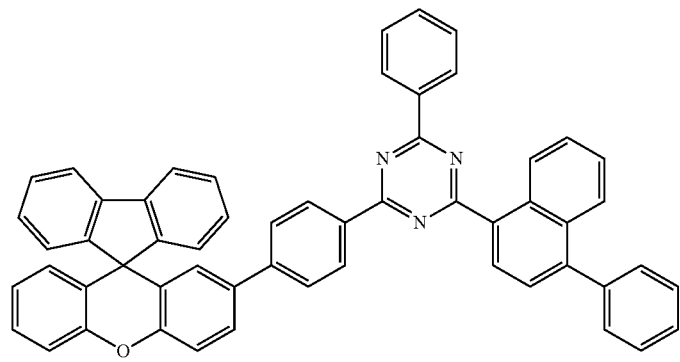
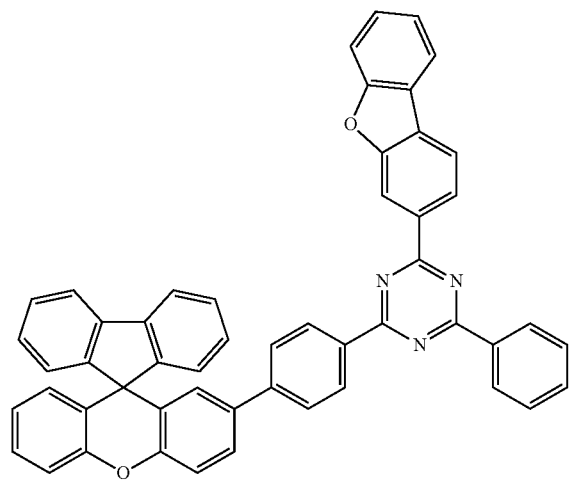

-continued
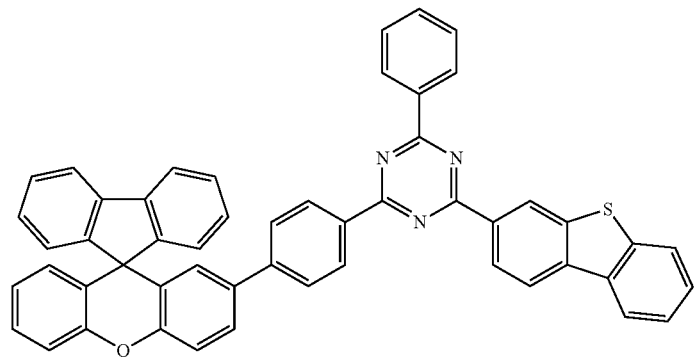
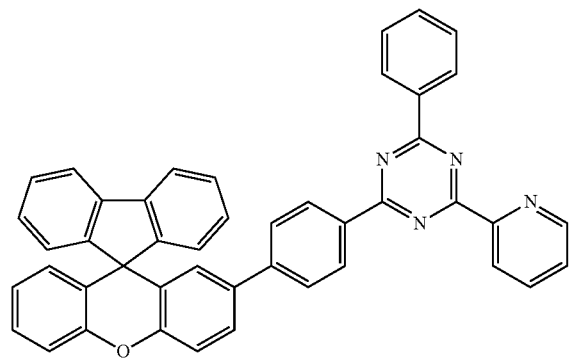
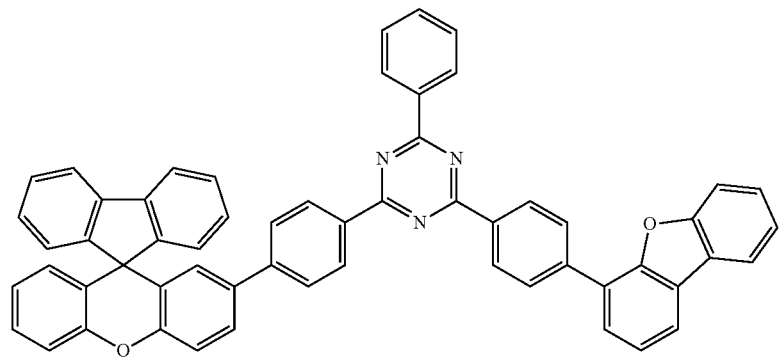
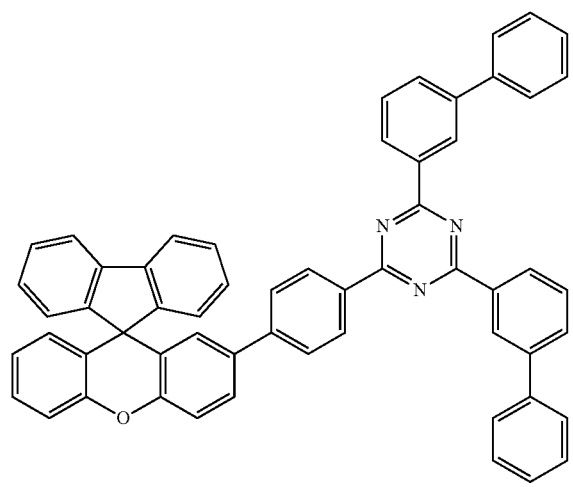

-continued
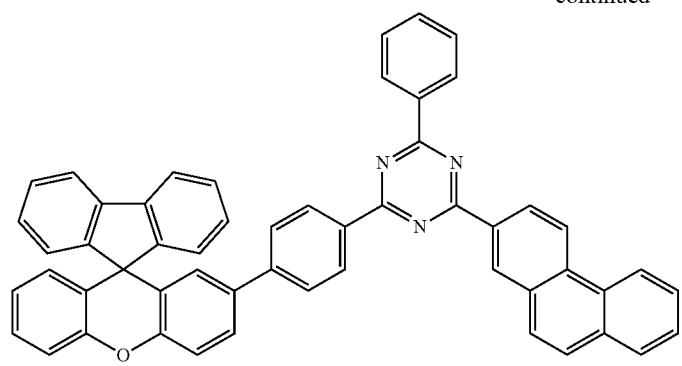
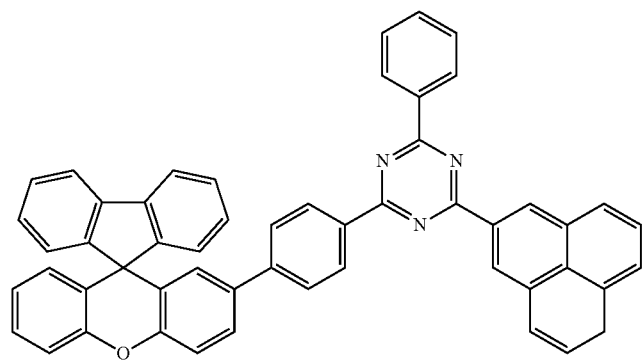
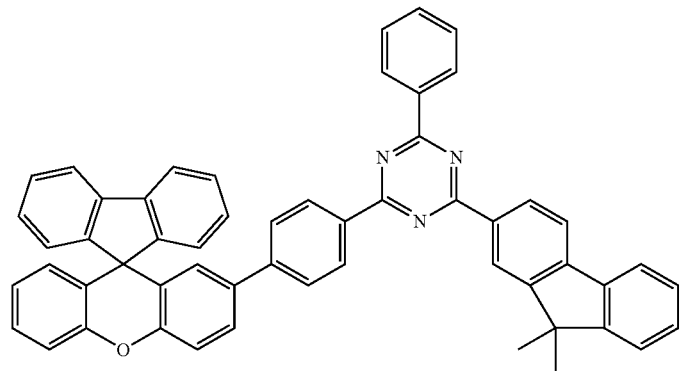
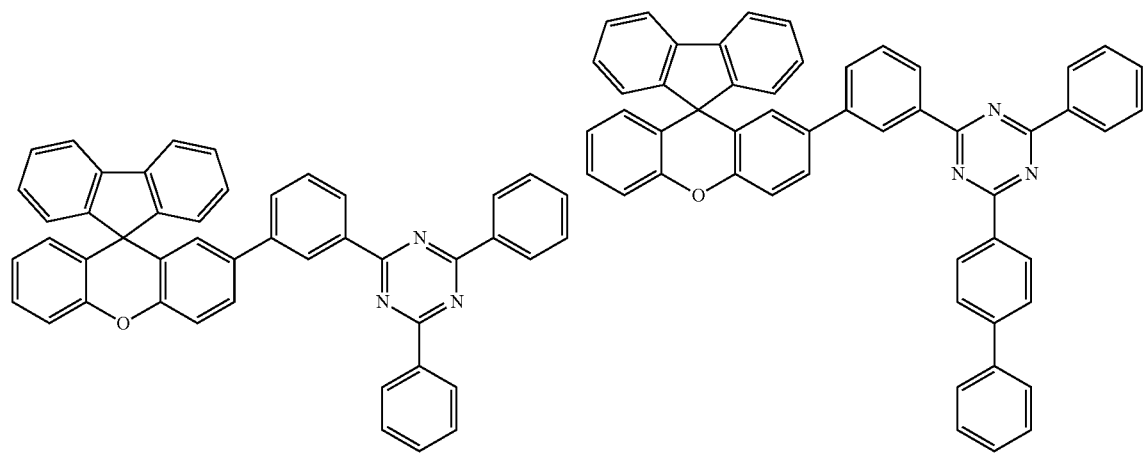

-continued
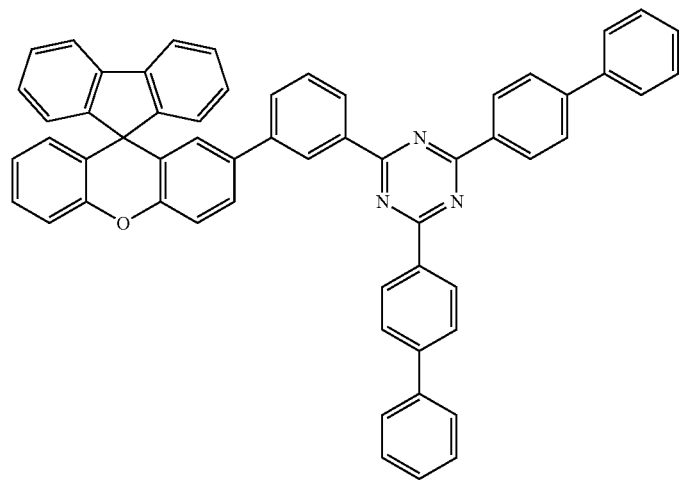
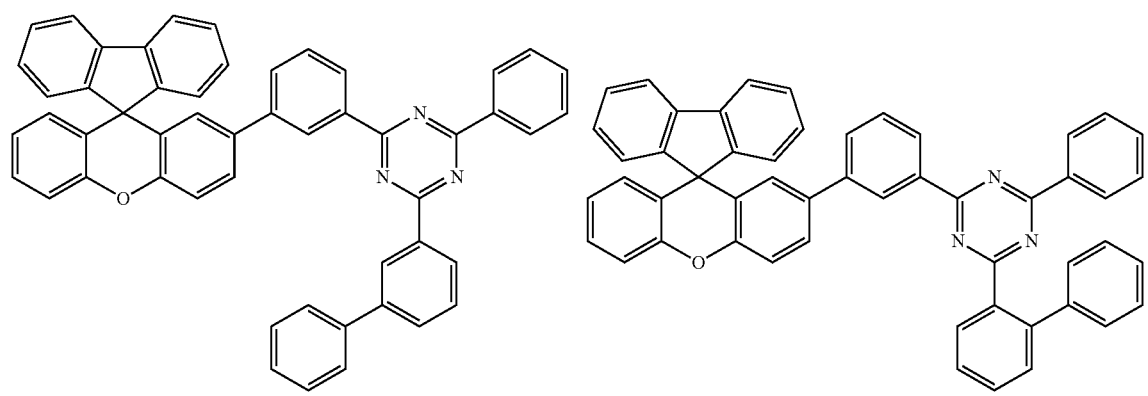
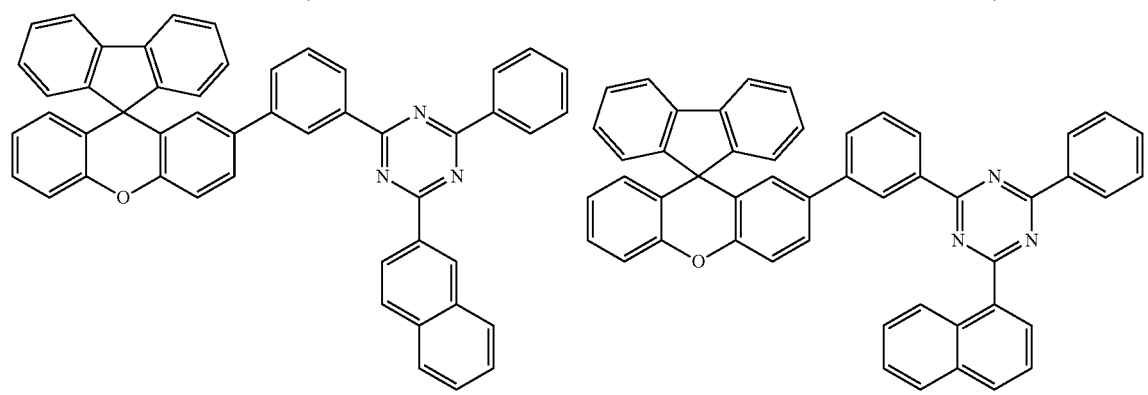
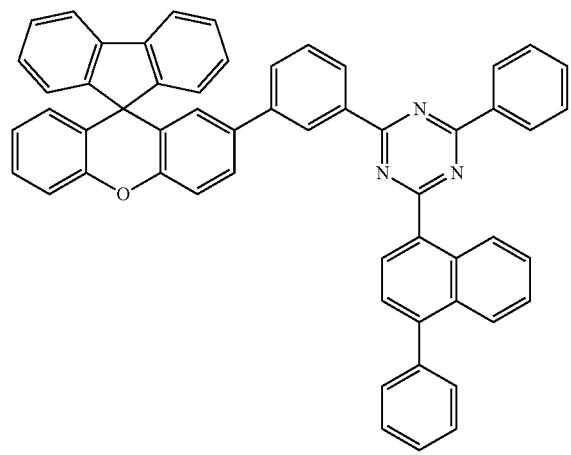

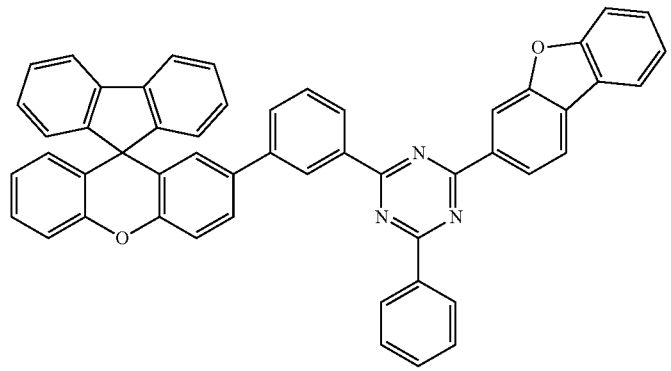
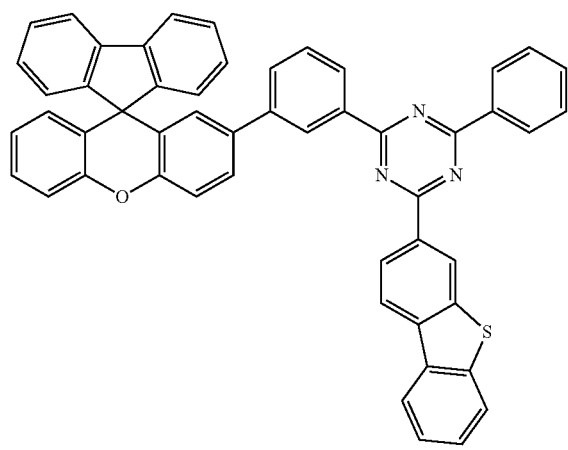
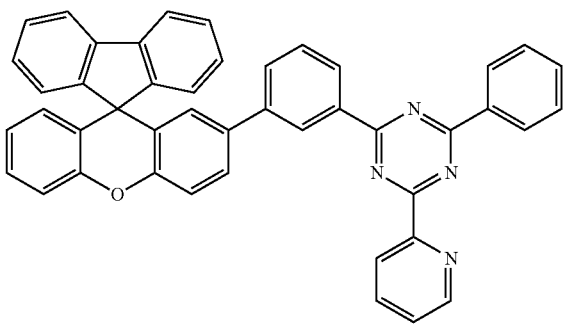
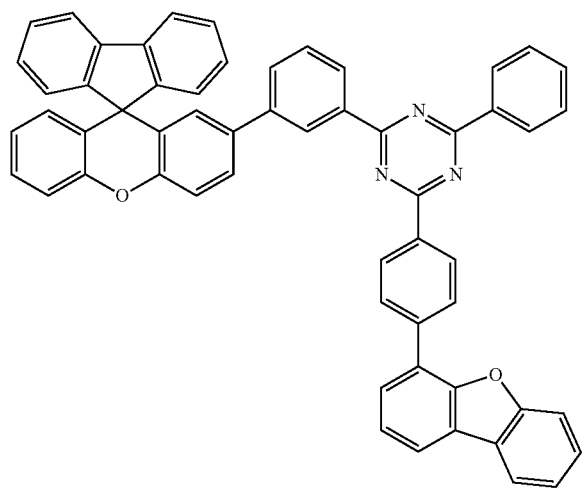
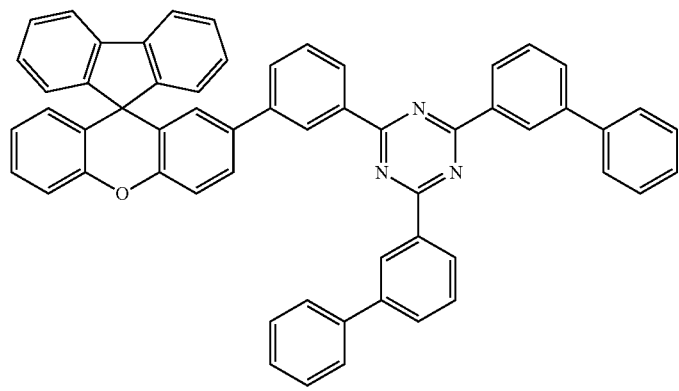

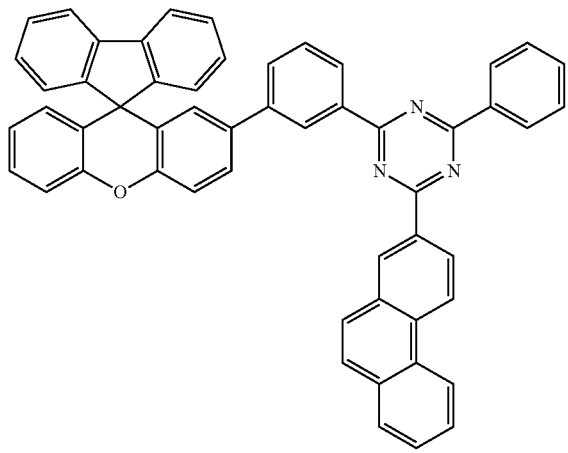
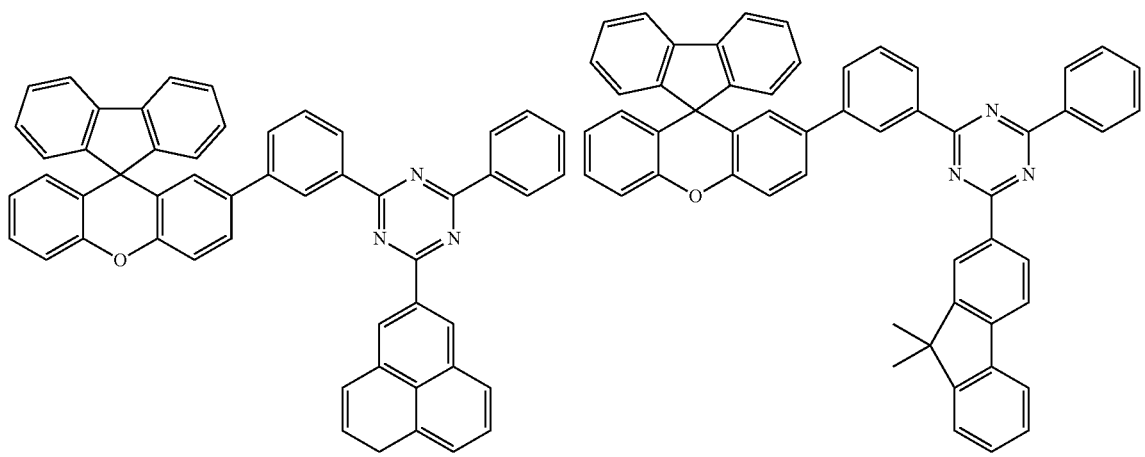
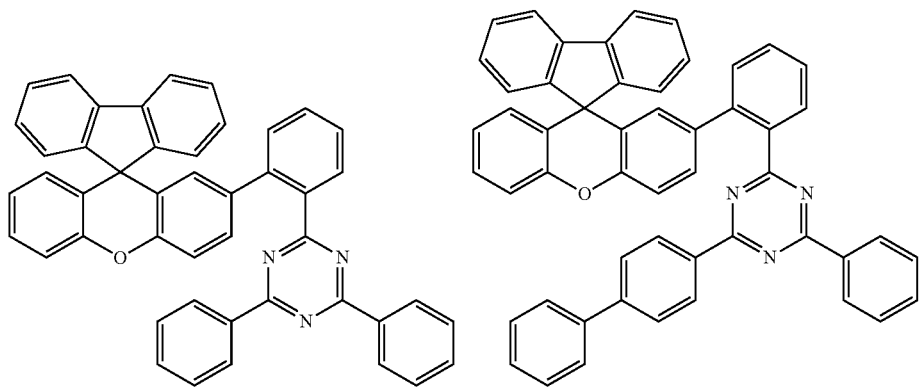
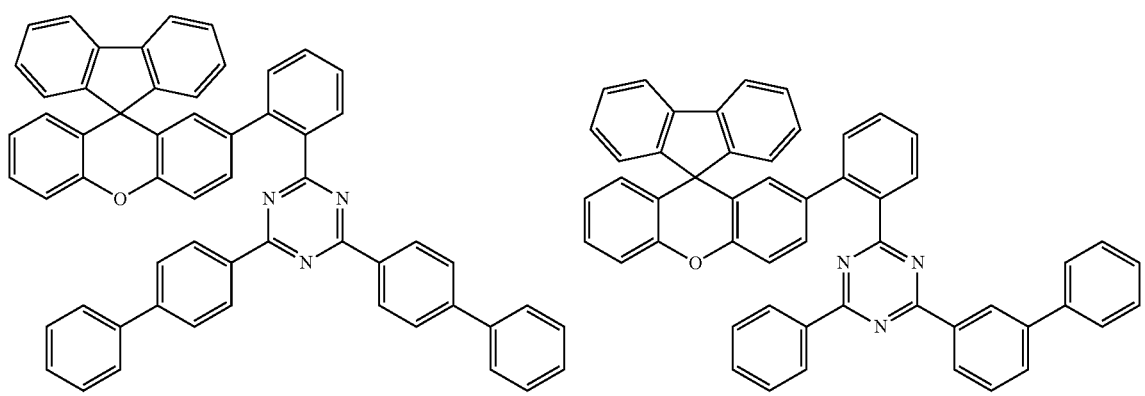

-continued
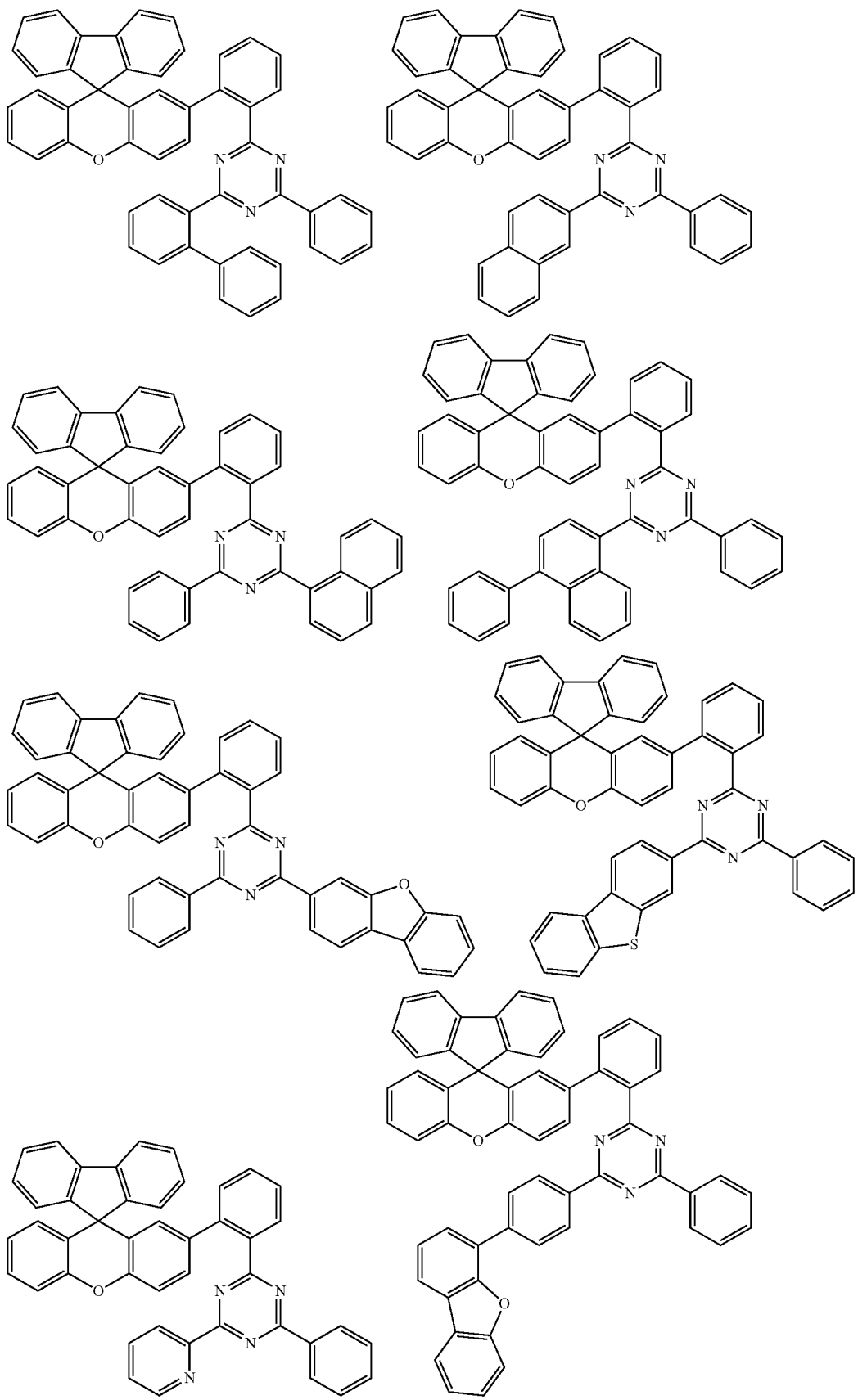

-continued
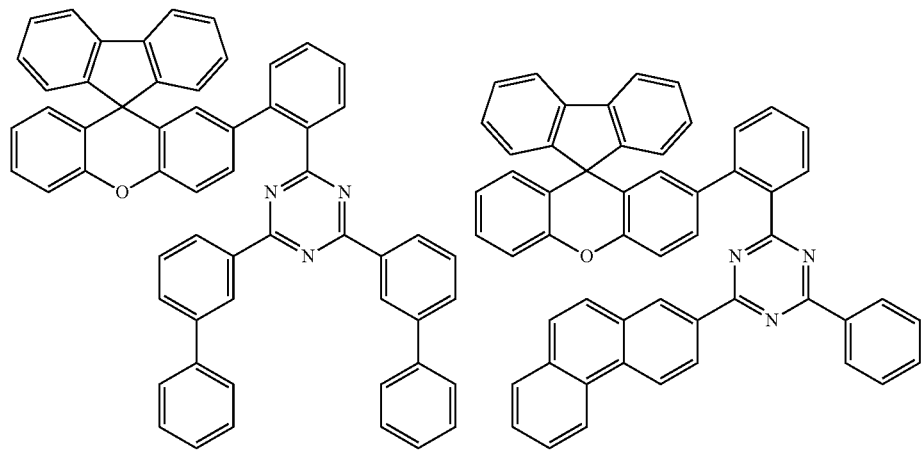
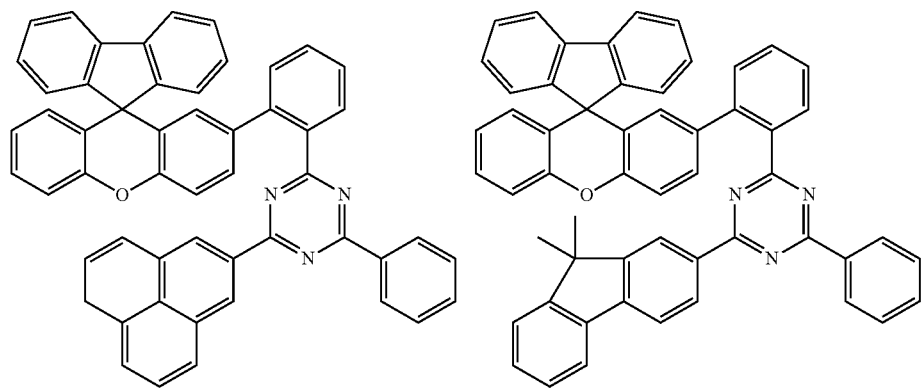
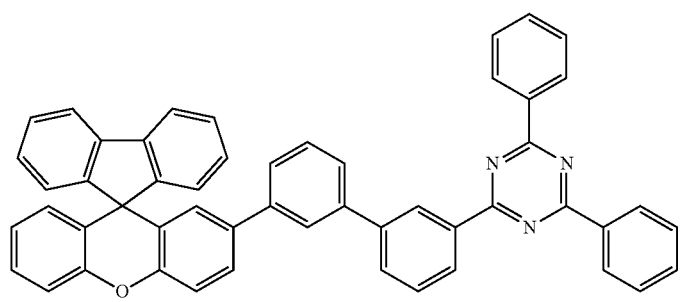
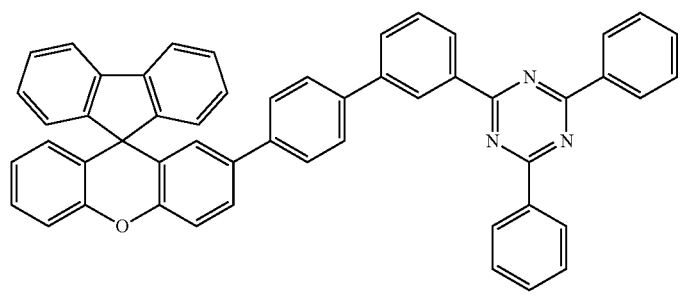

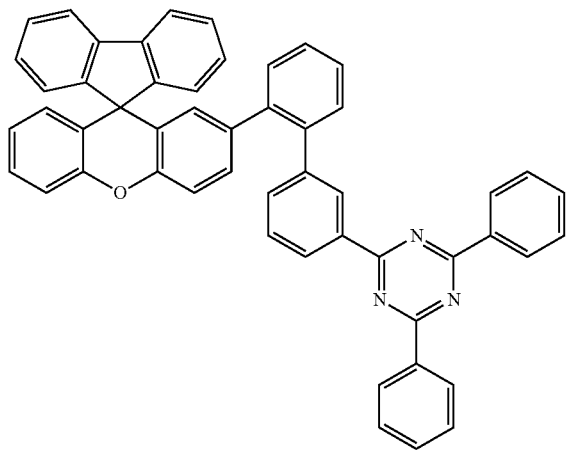
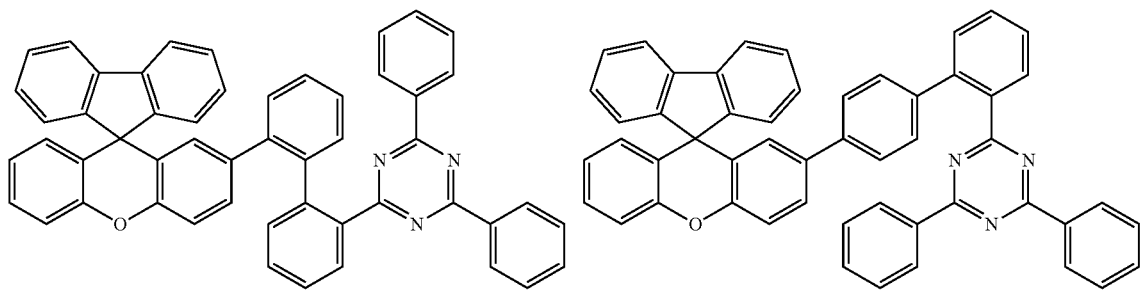
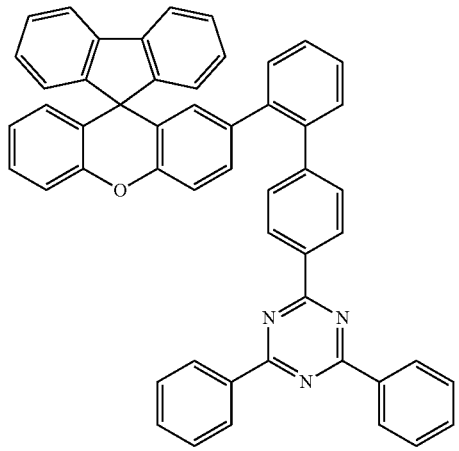
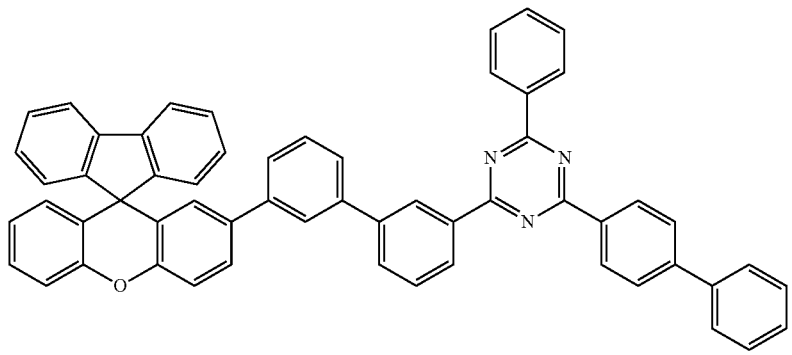

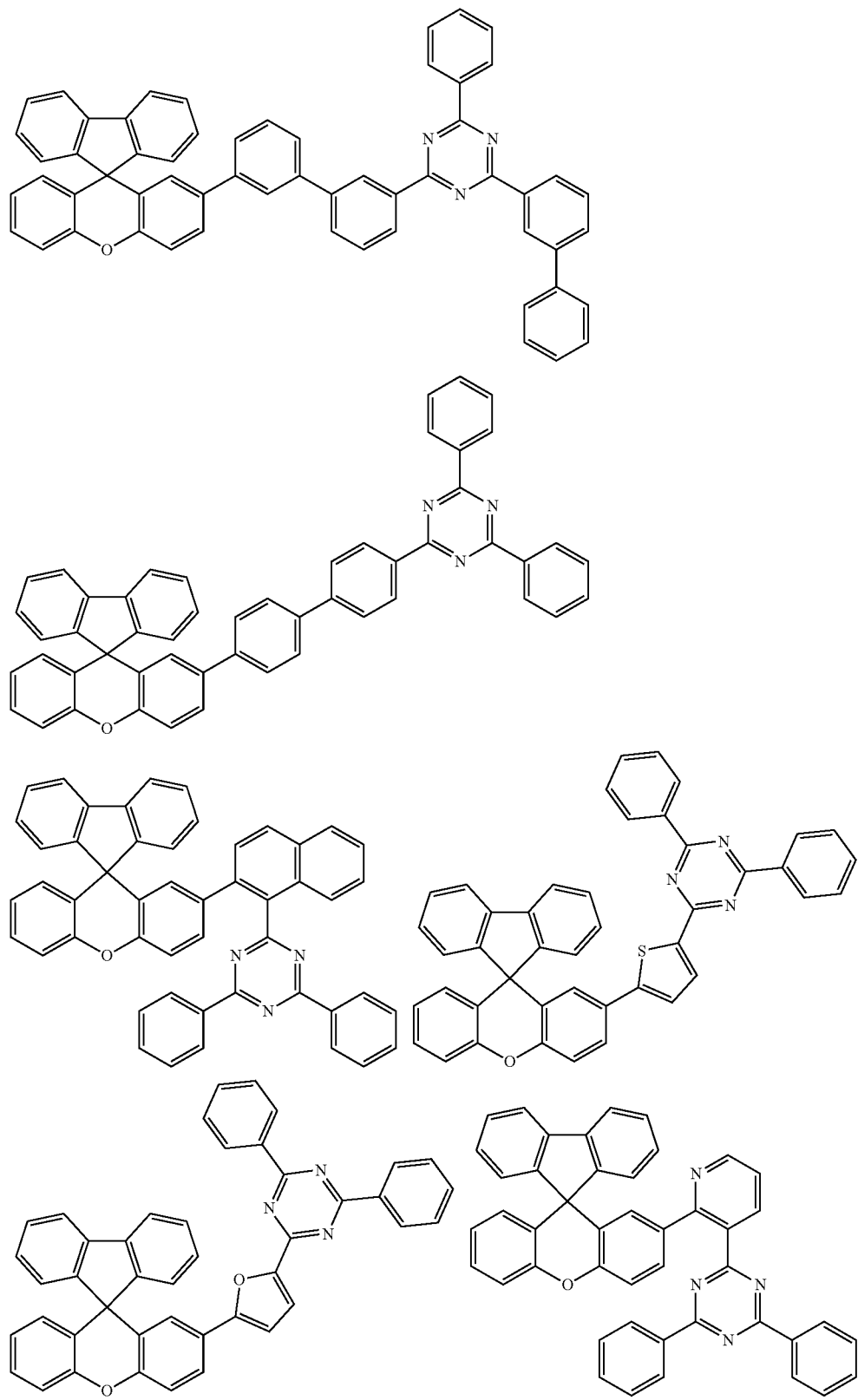

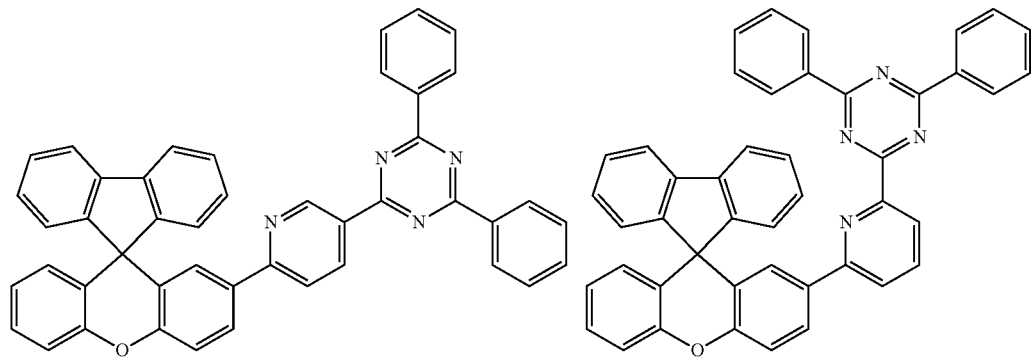
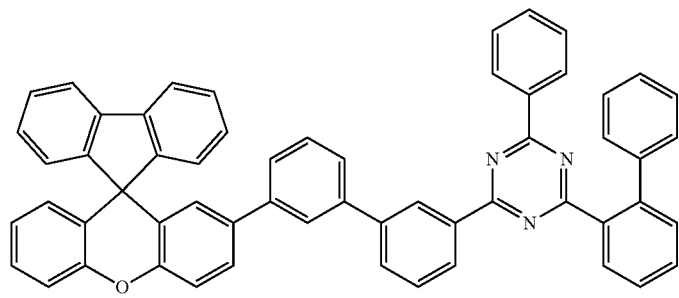
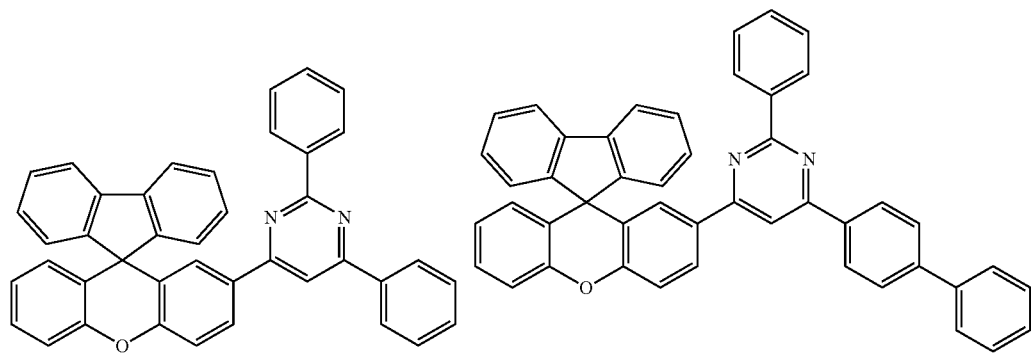
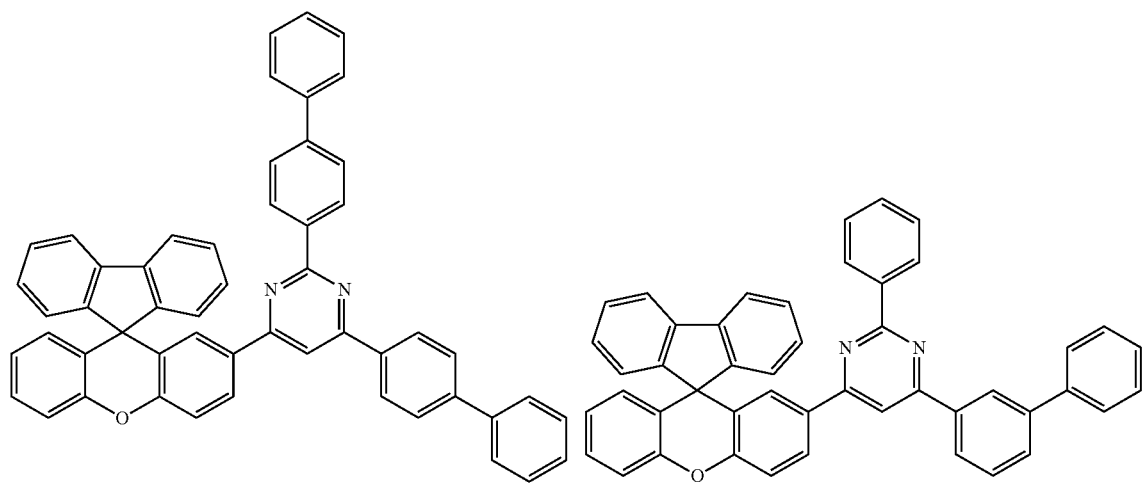

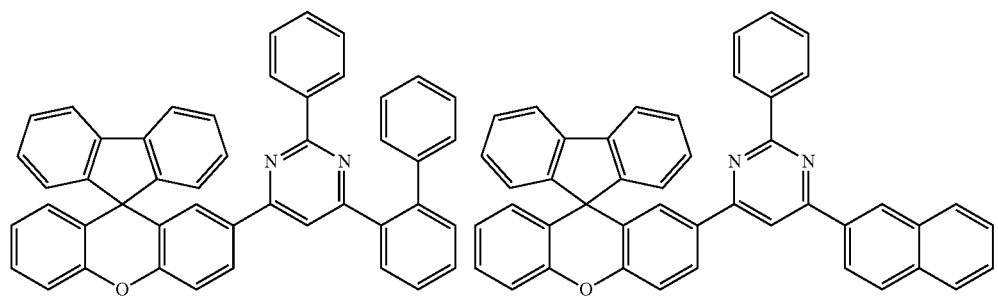
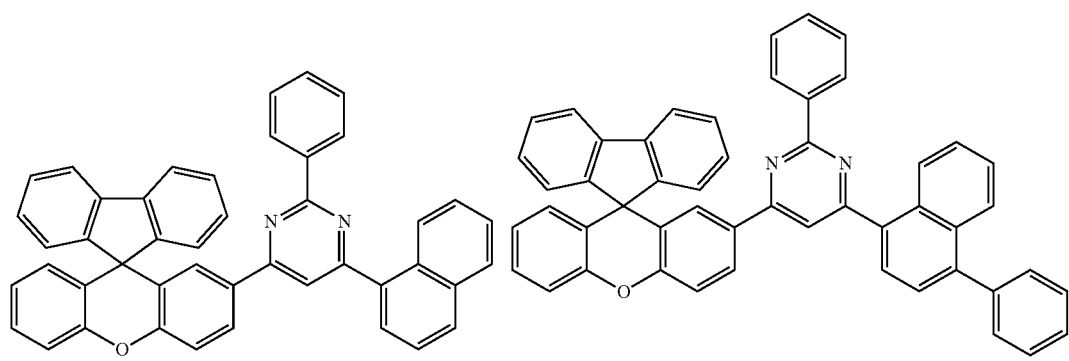
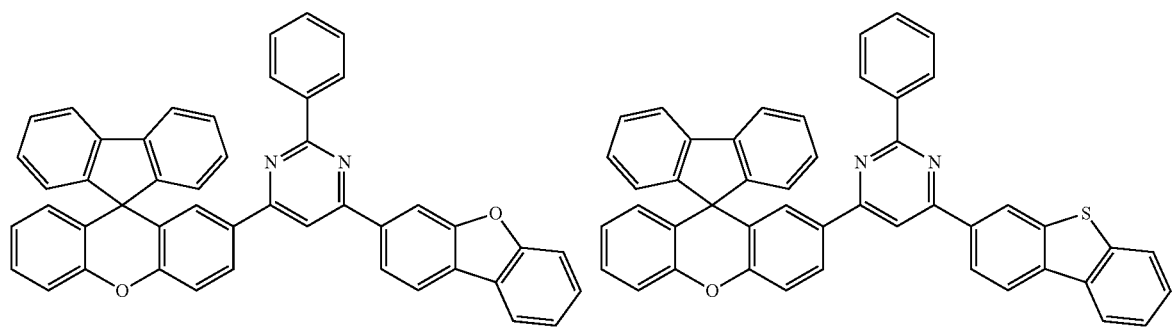
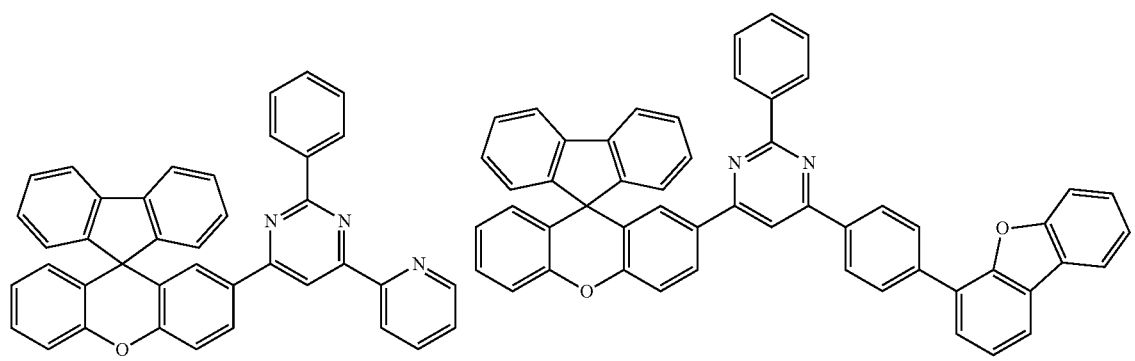

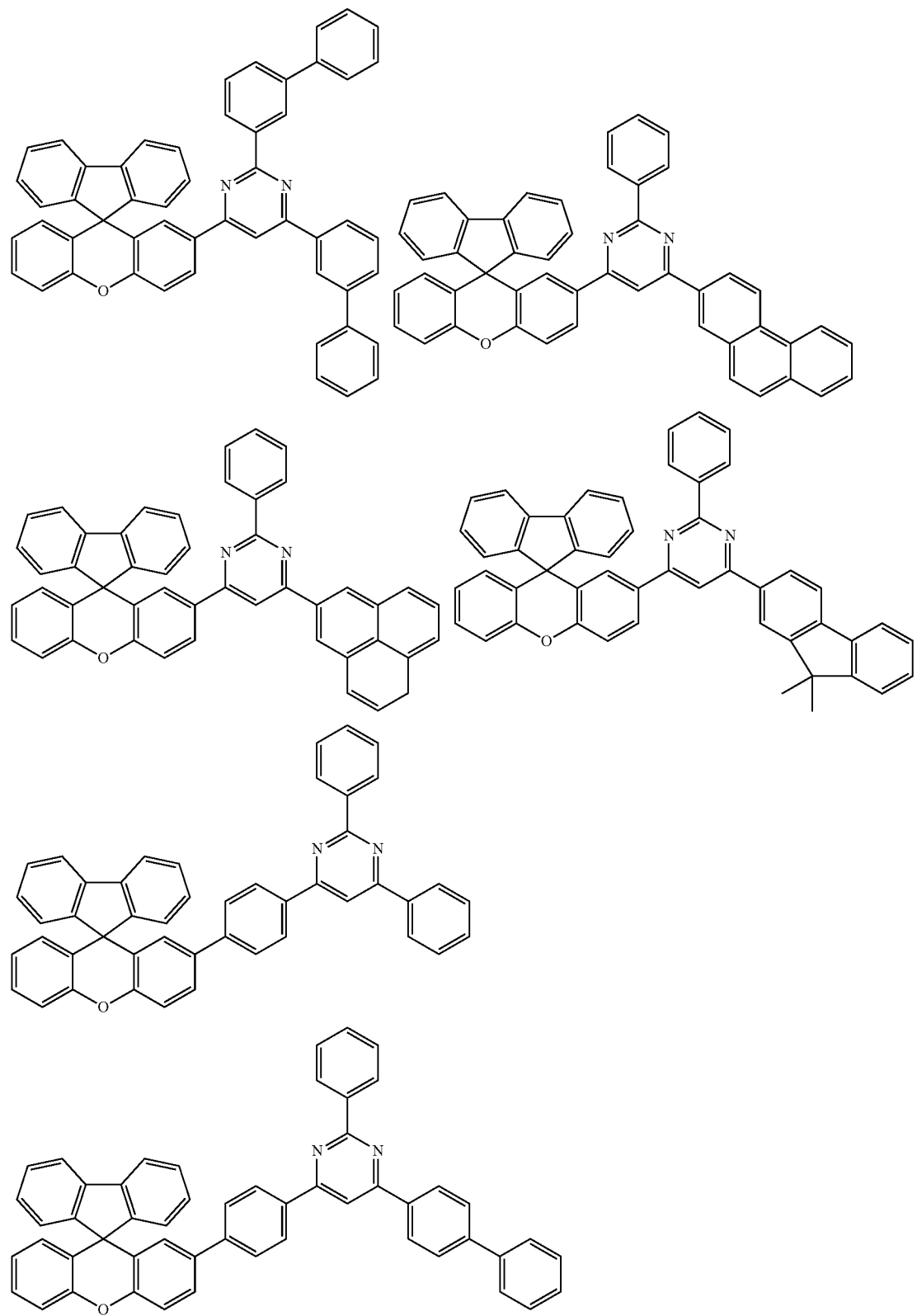

-continued
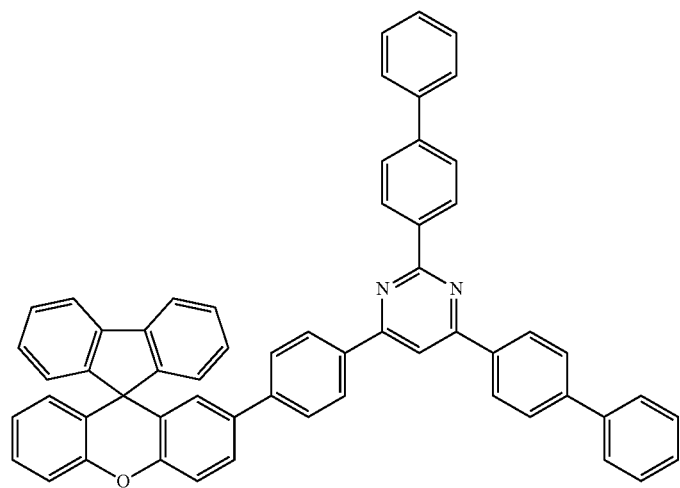
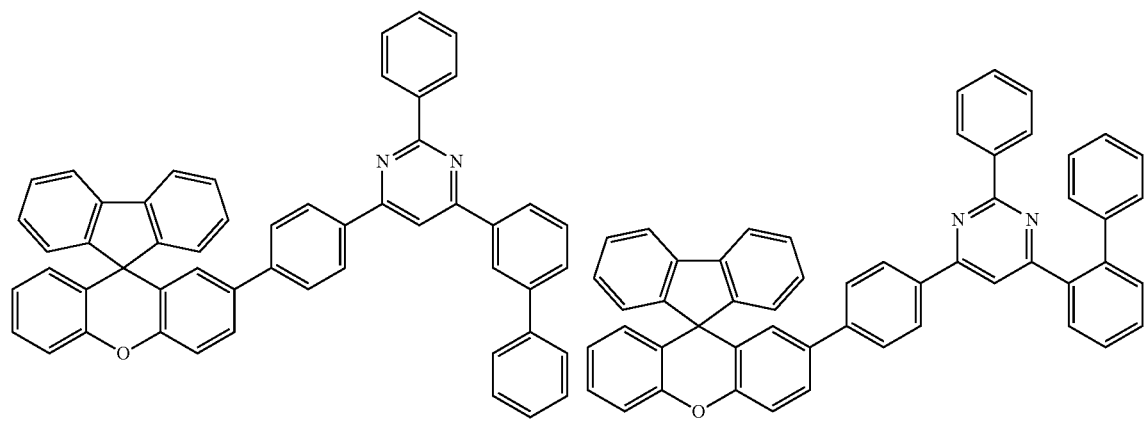
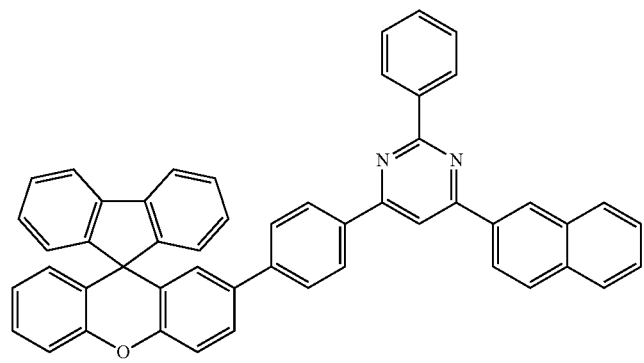
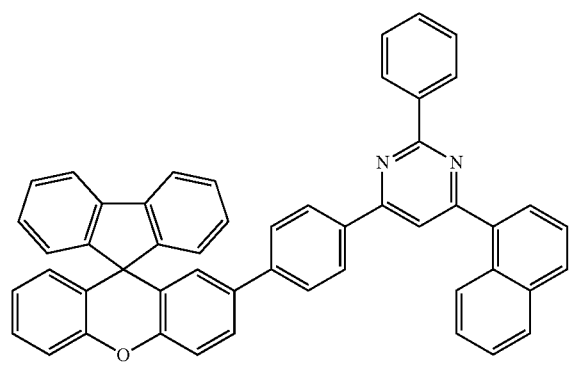

-continued
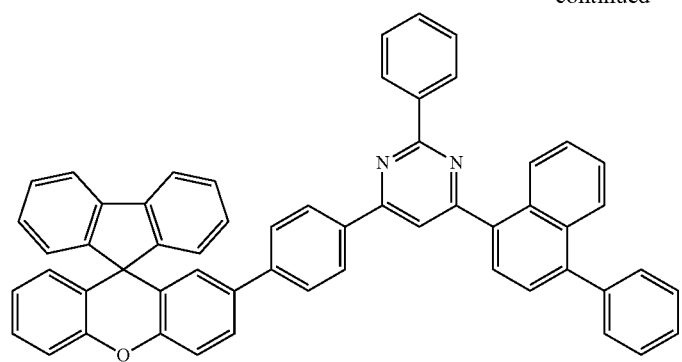
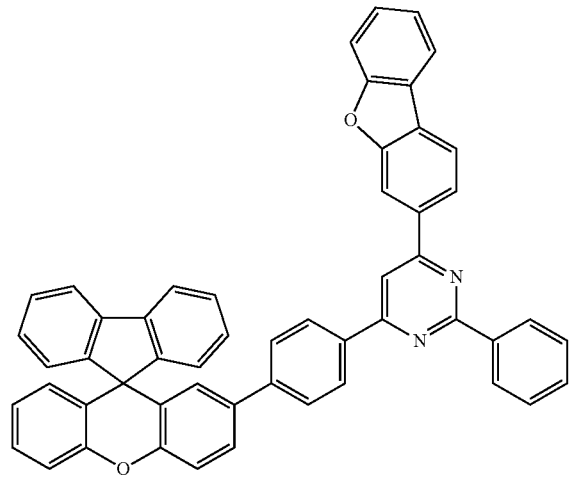
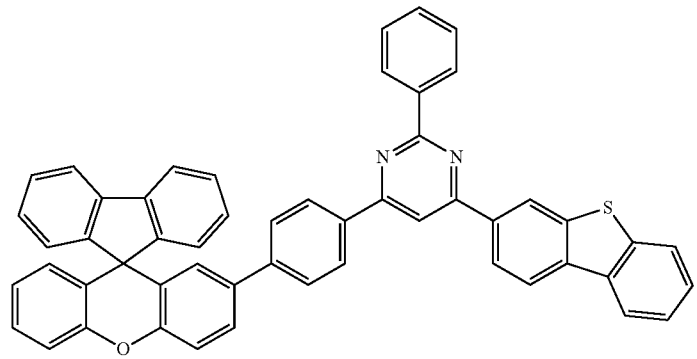
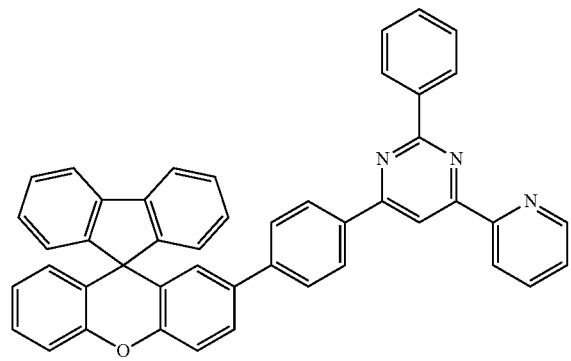

-continued
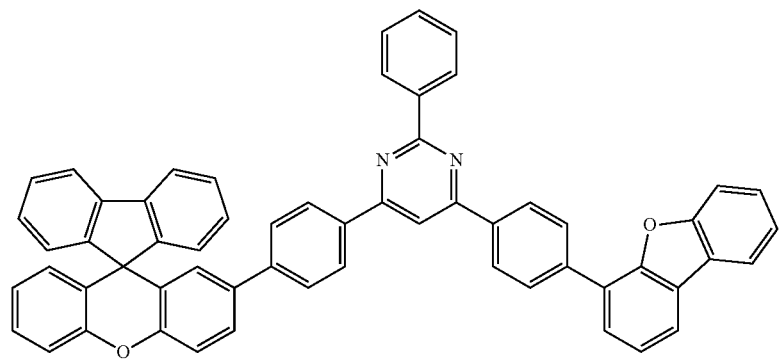
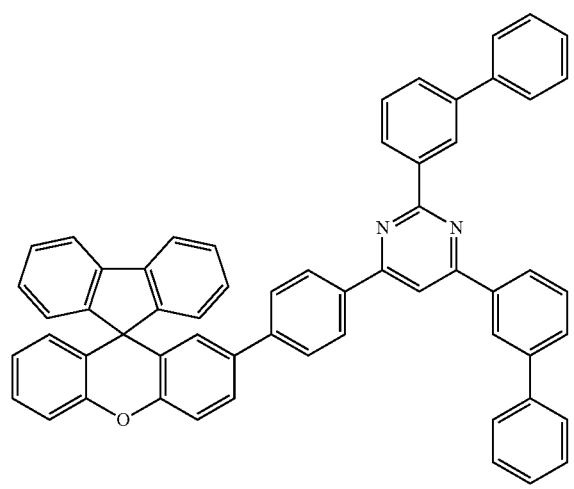
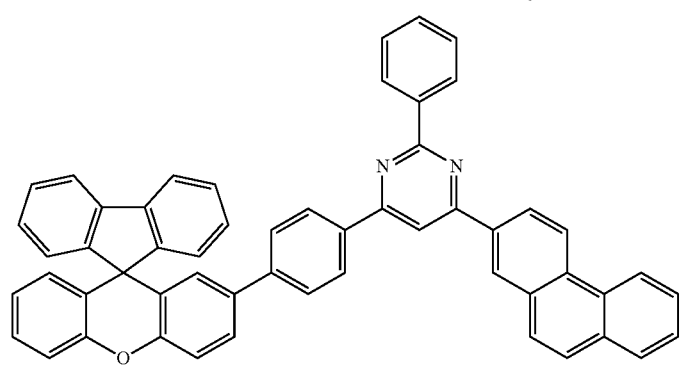
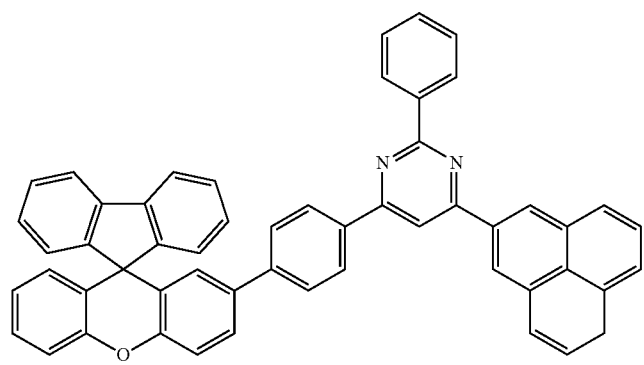

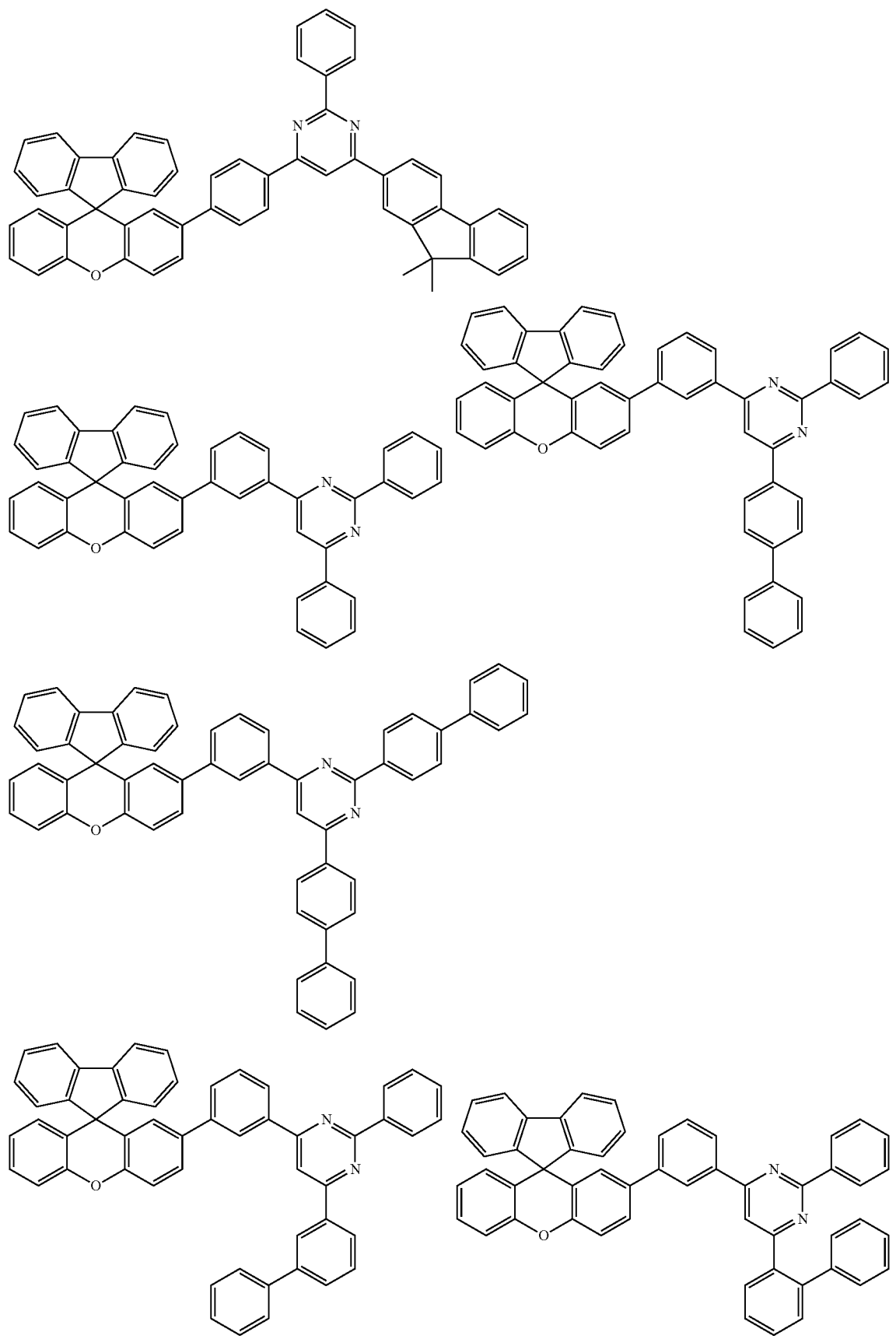

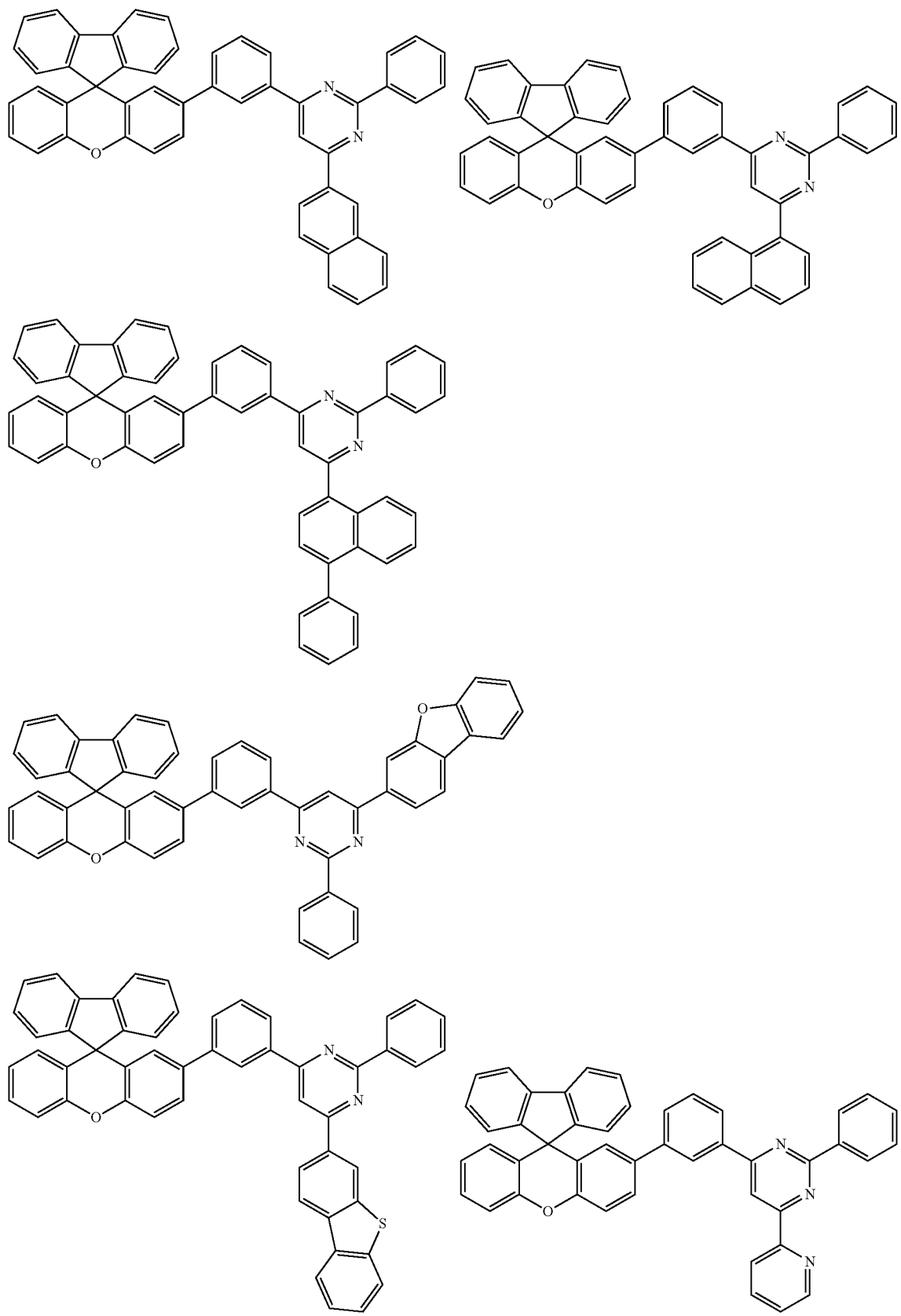

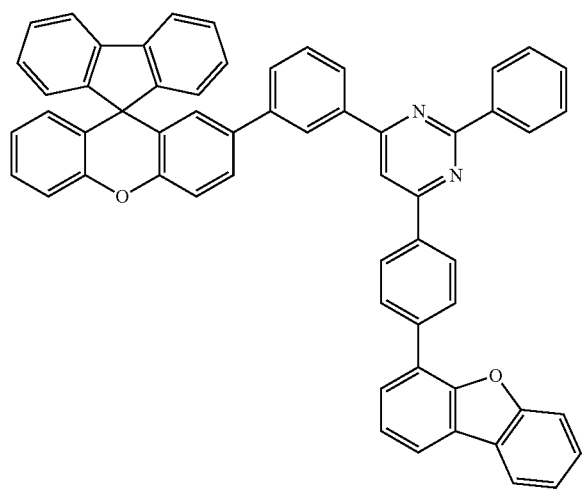
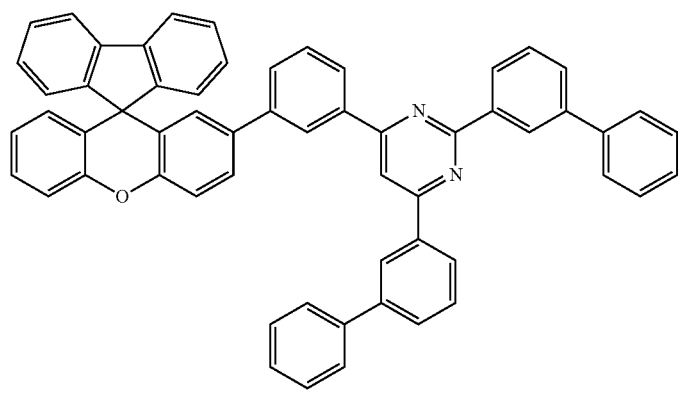
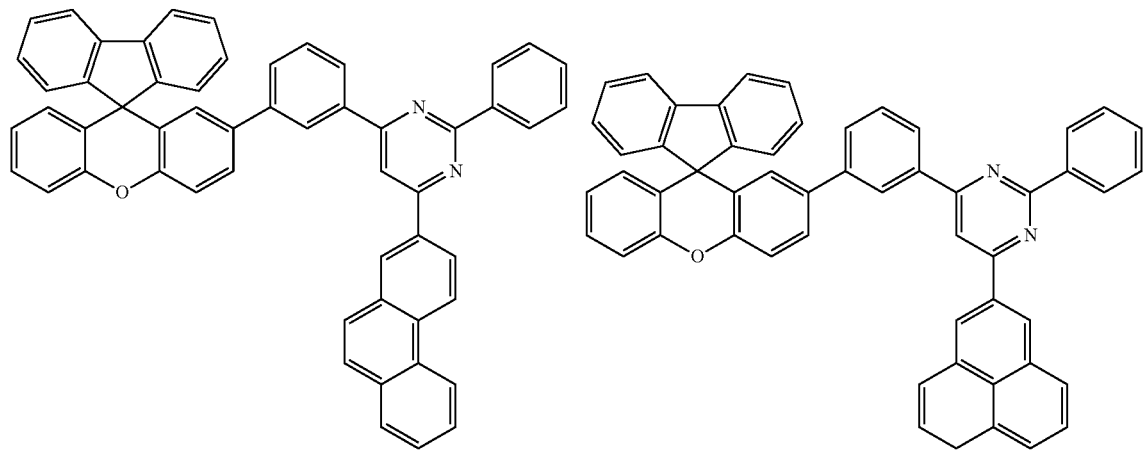

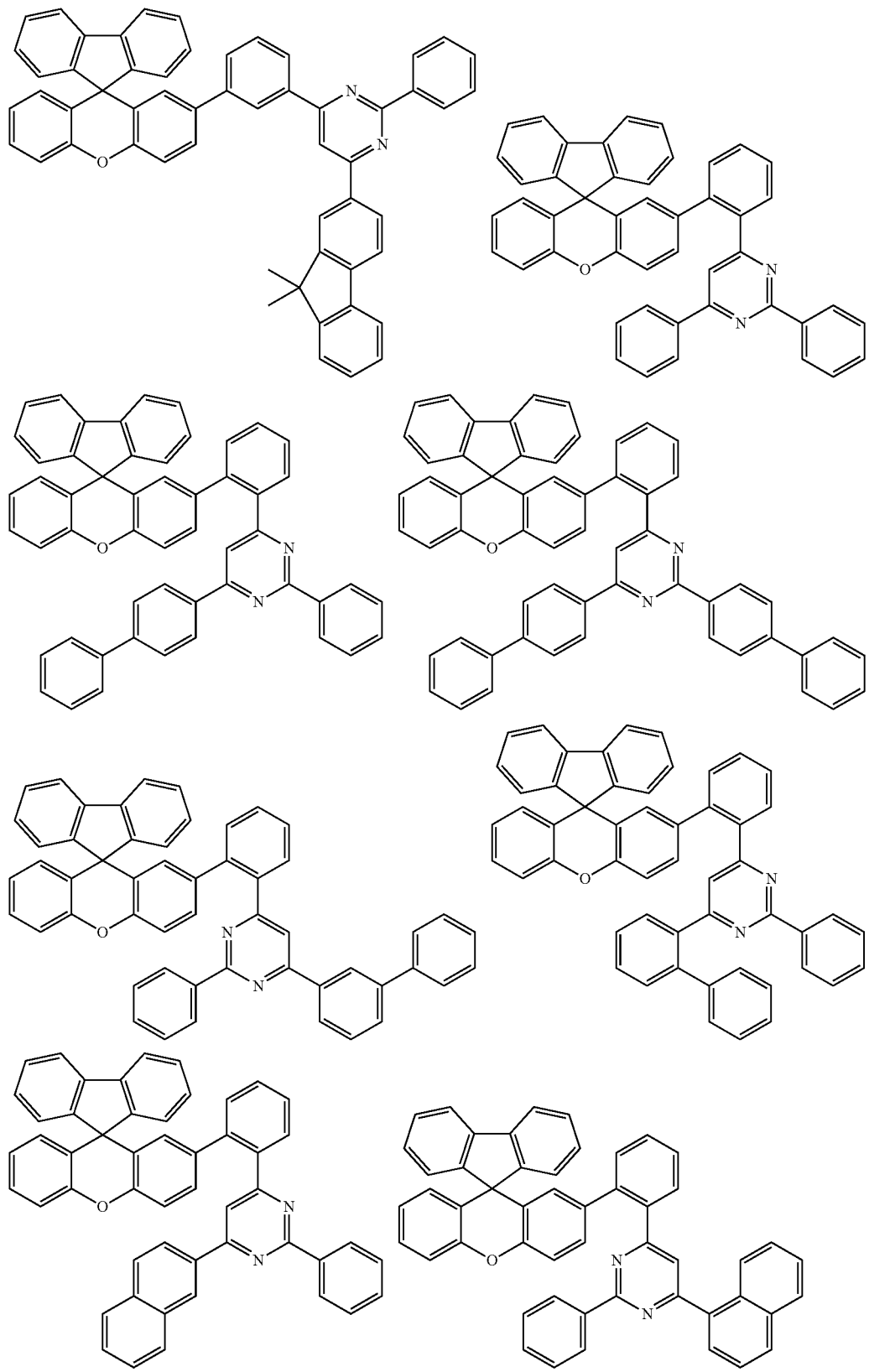

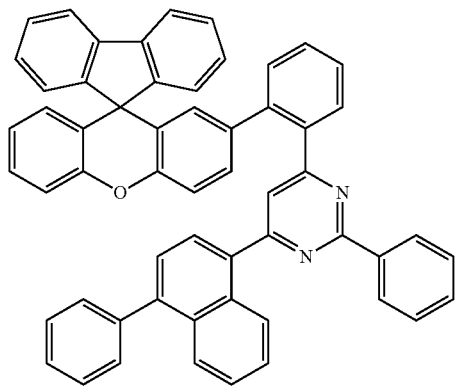
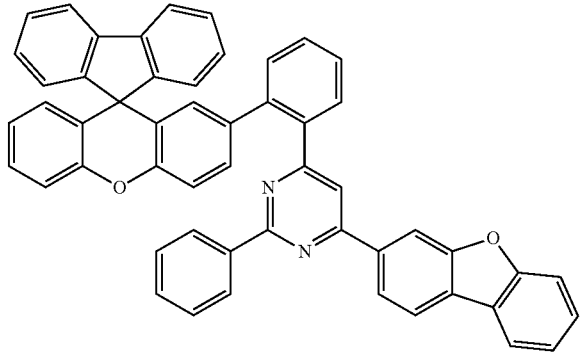
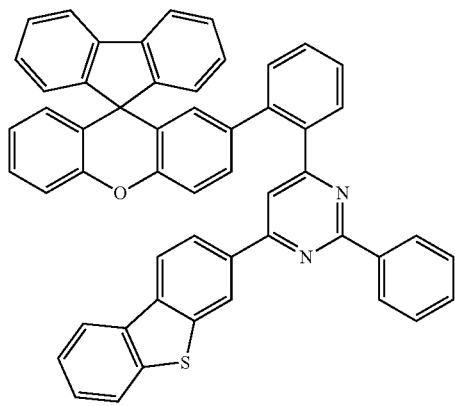
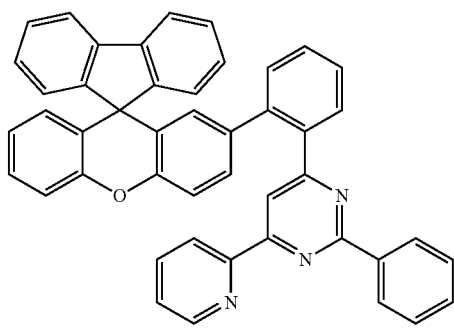
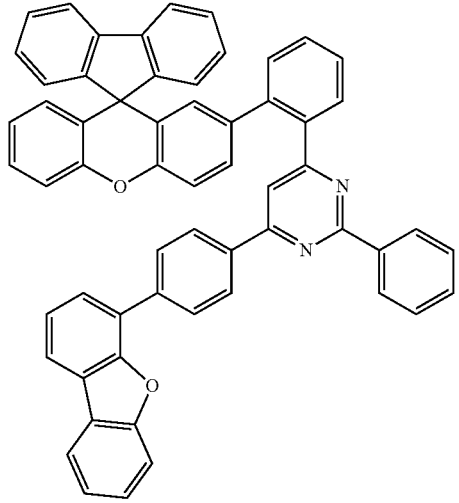
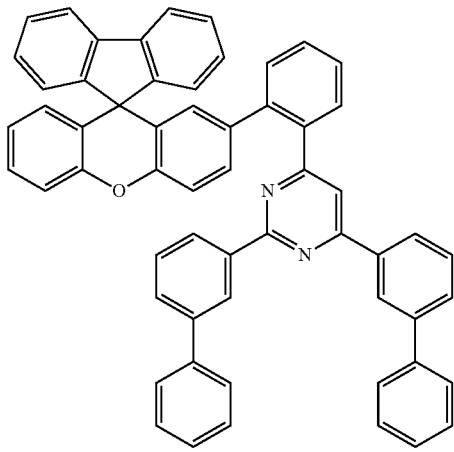
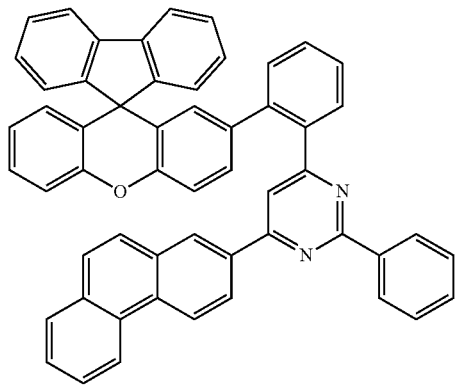
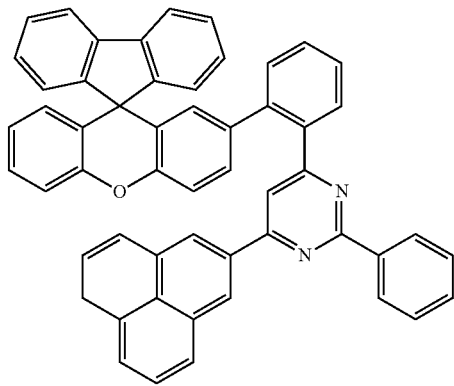

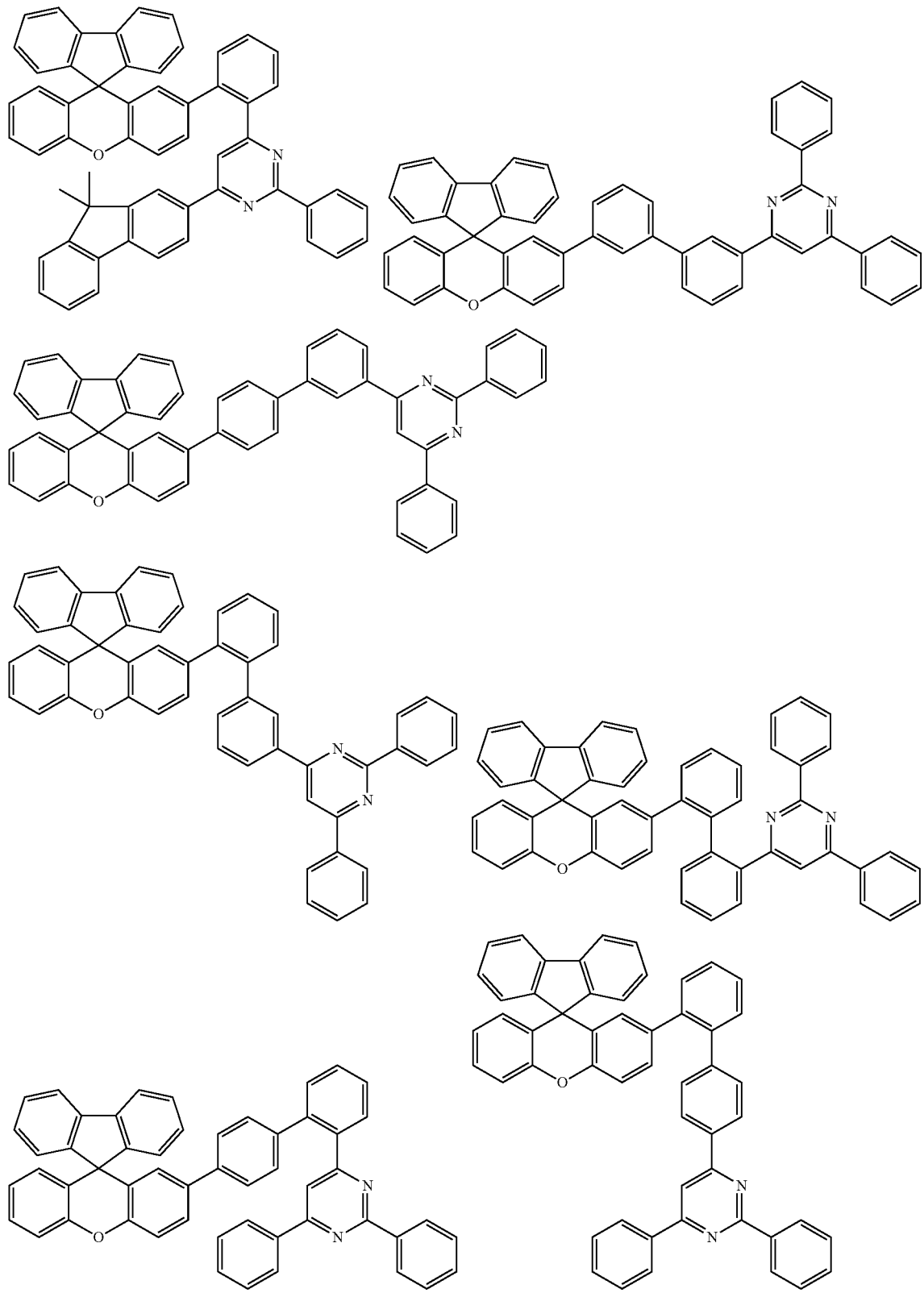

-continued
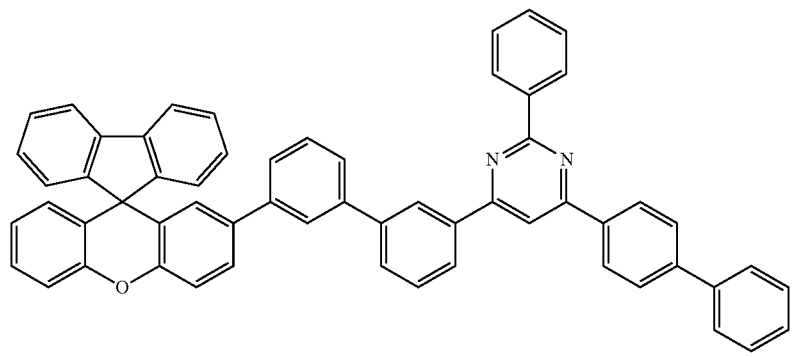
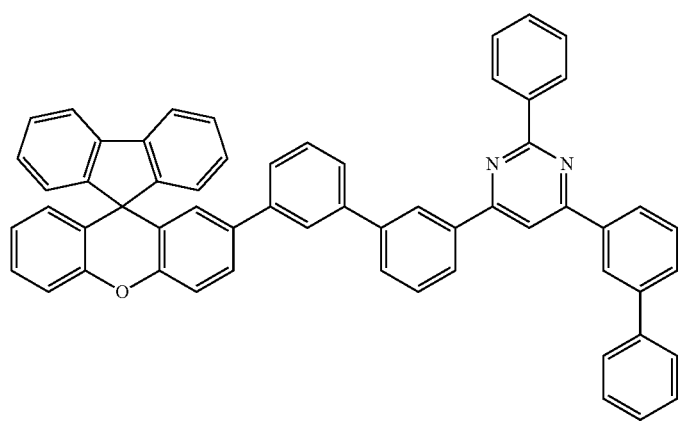
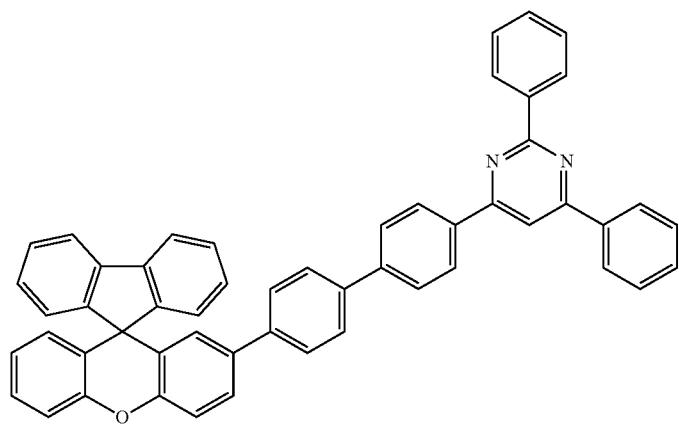
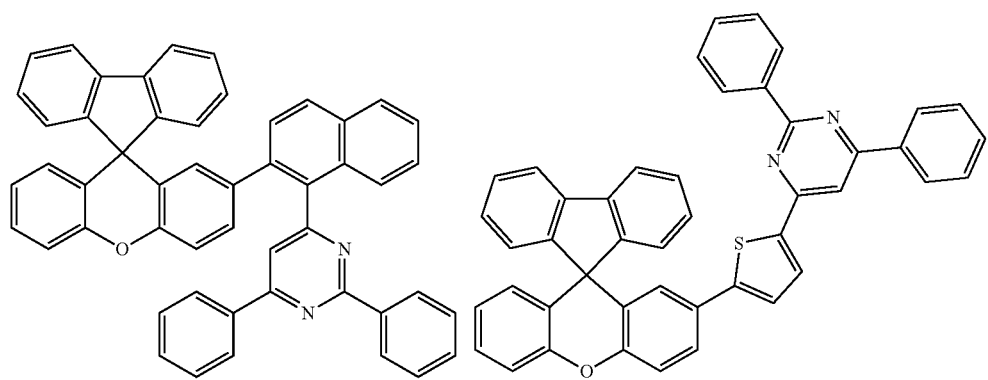

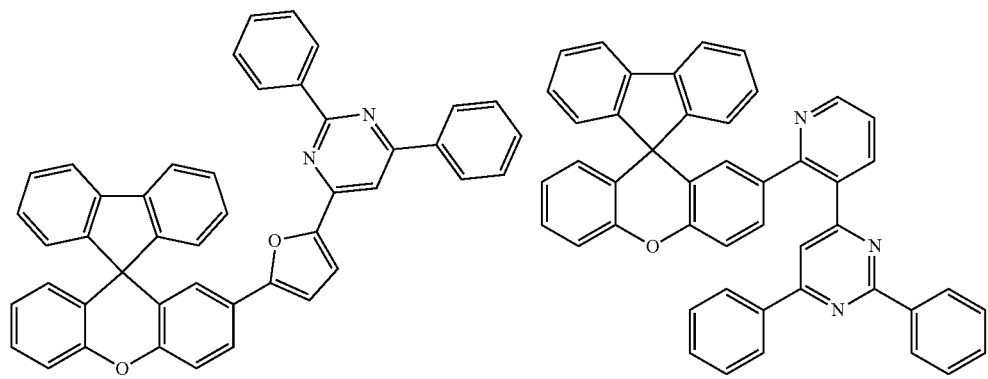
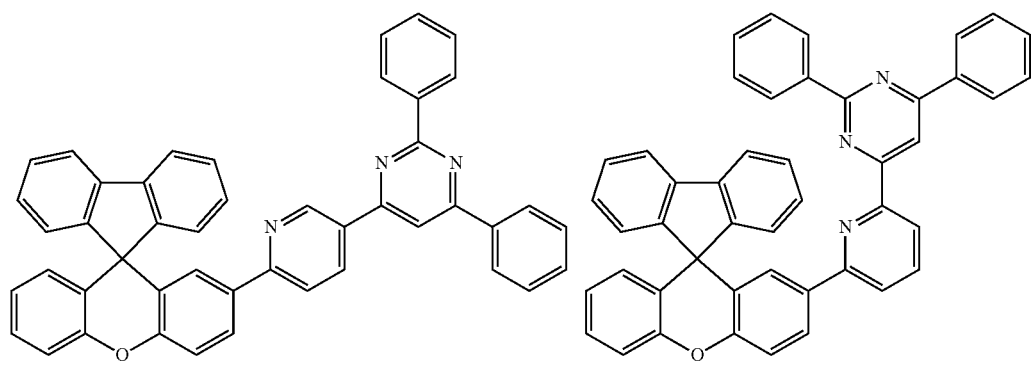
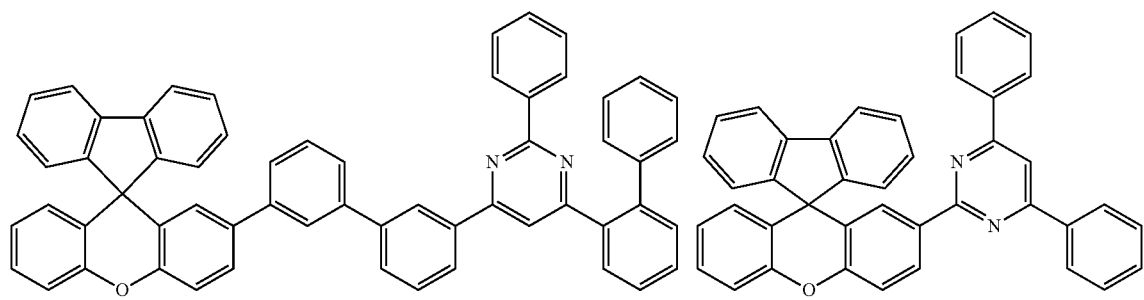
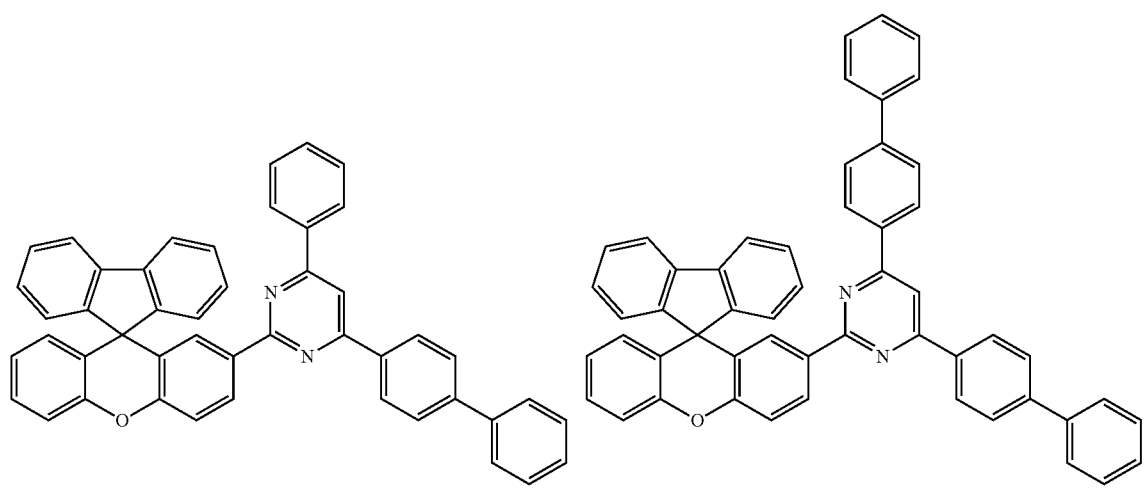

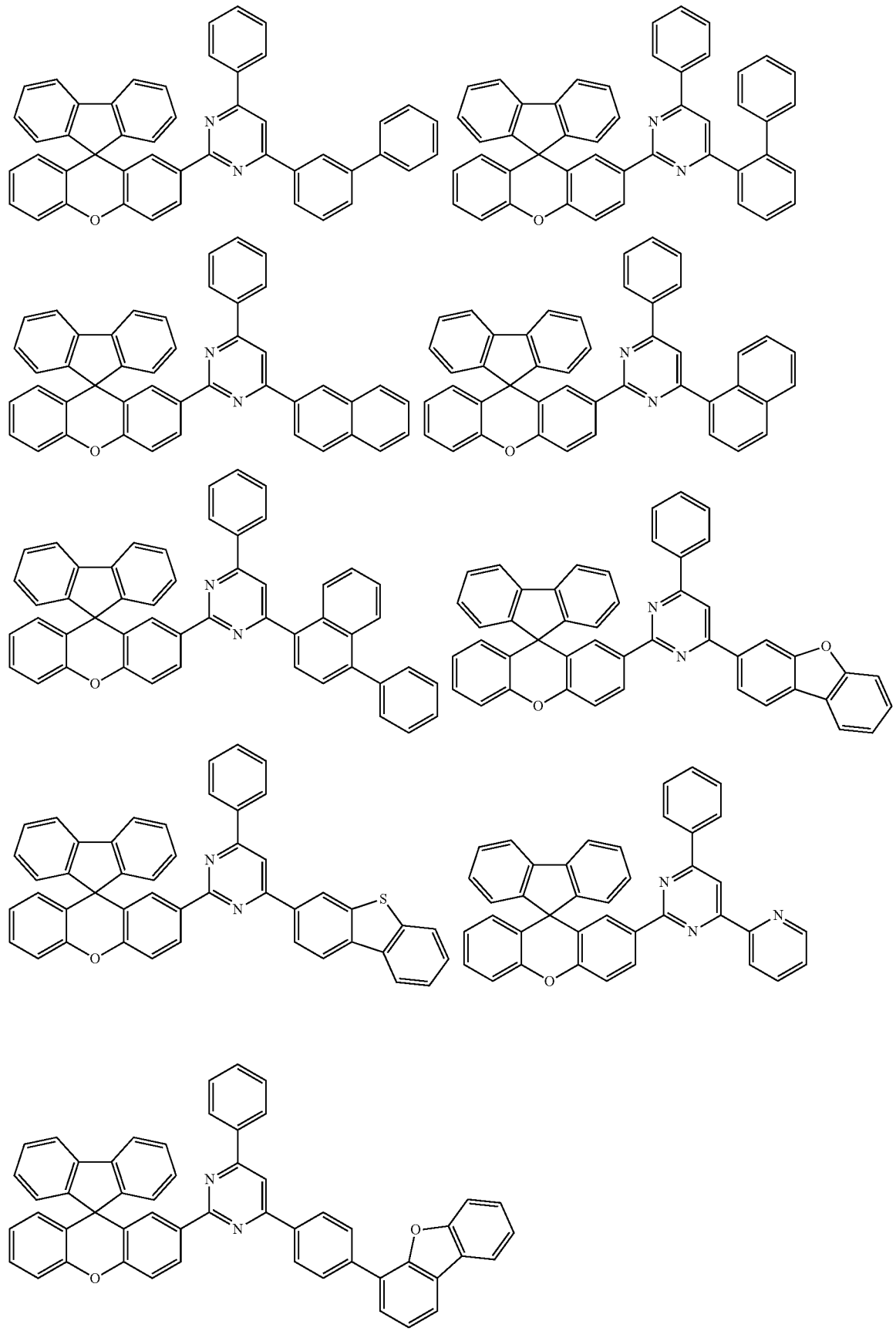

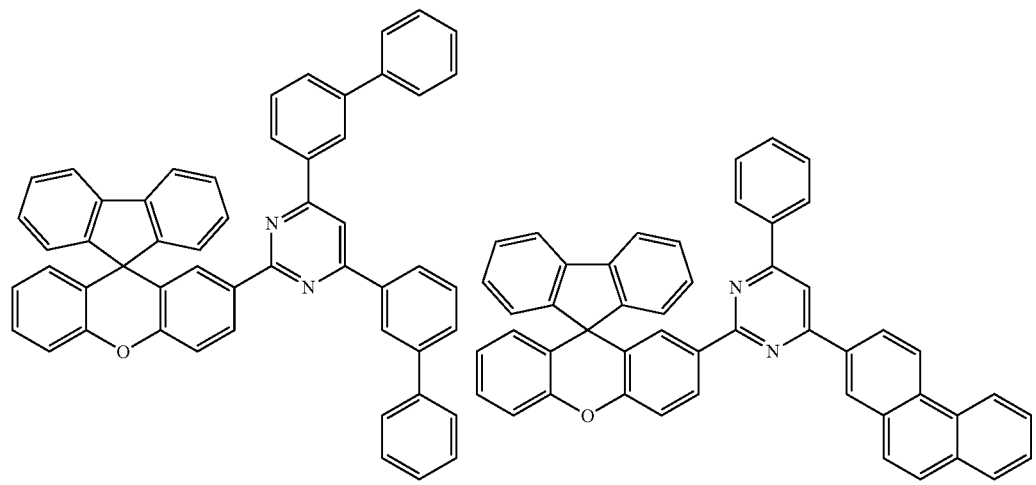
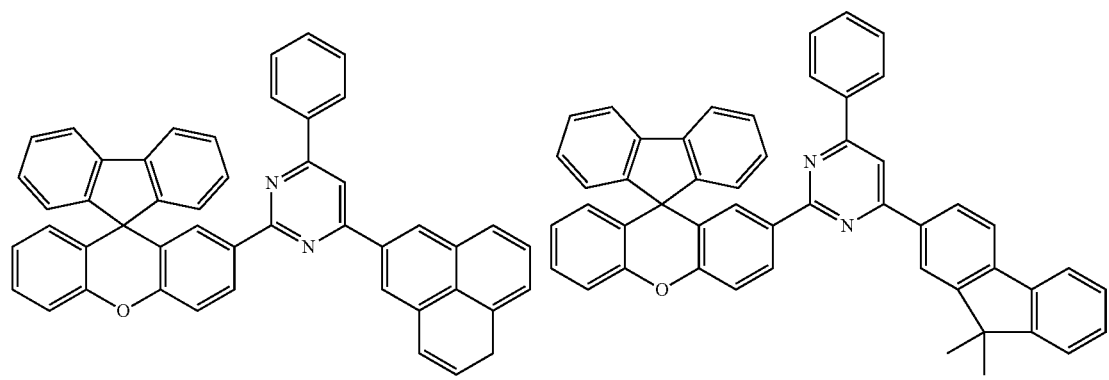
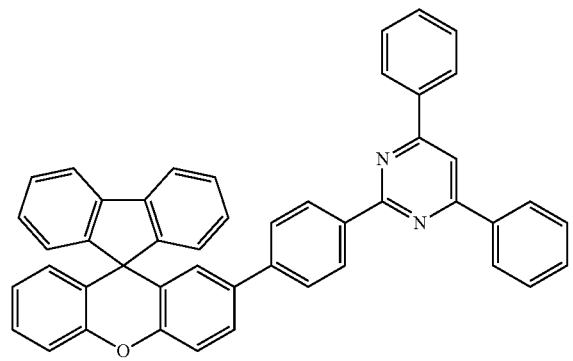
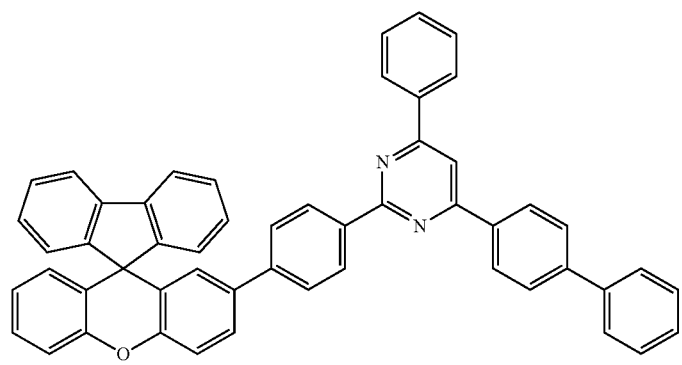

-continued
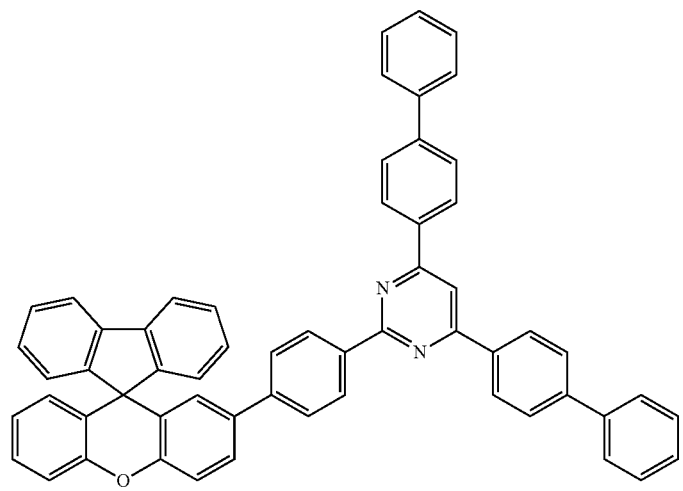
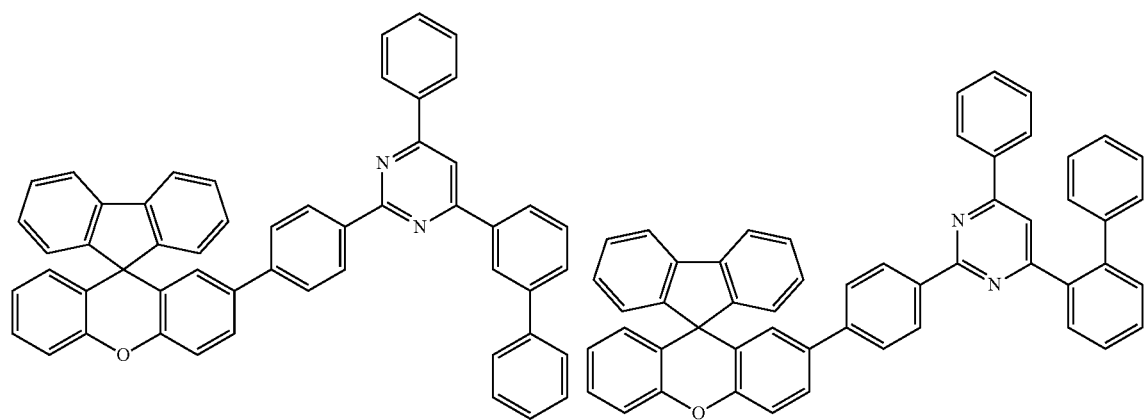
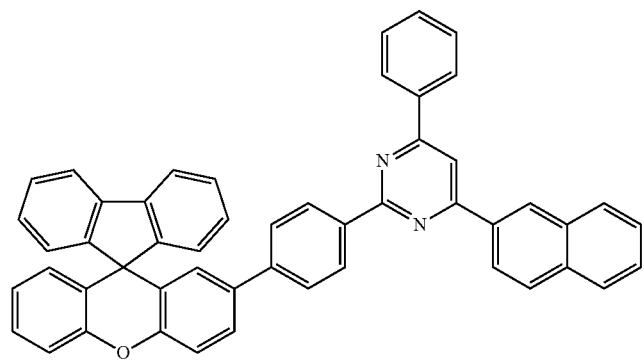
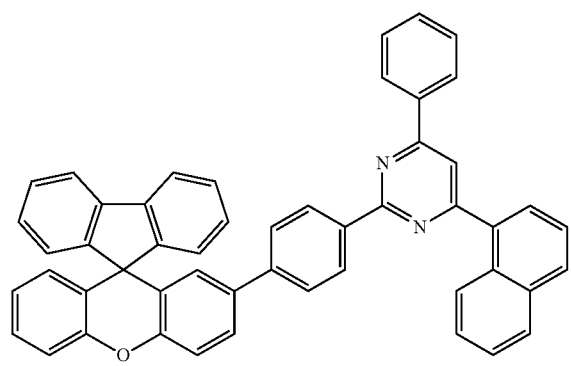

-continued
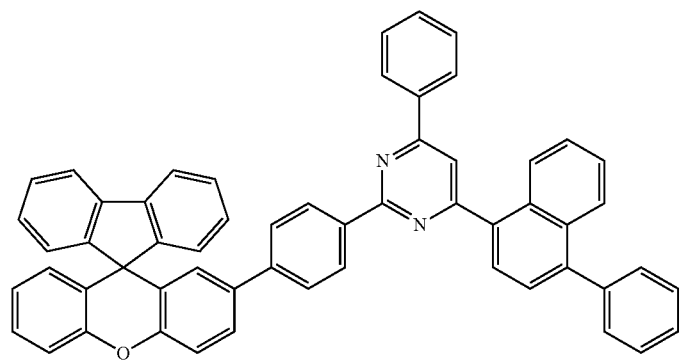
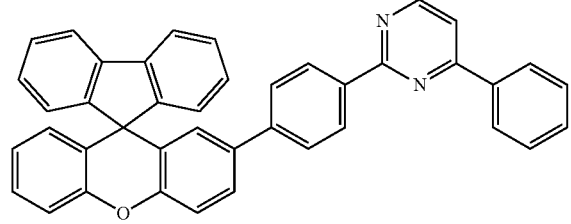
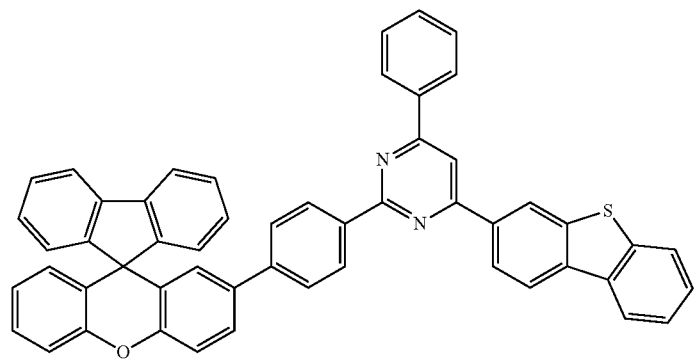
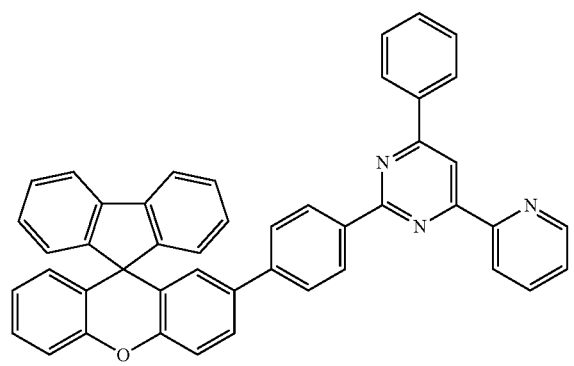

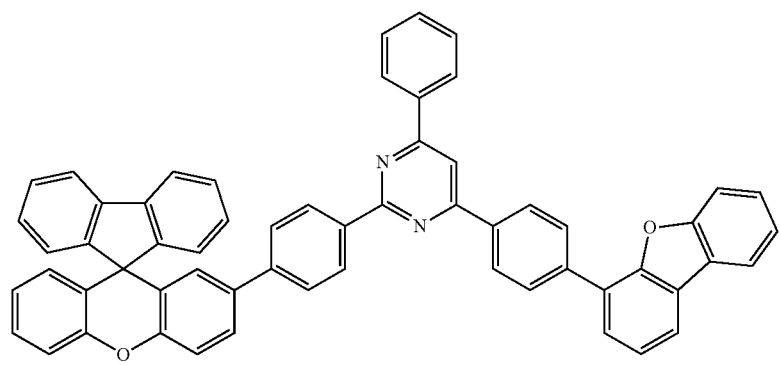
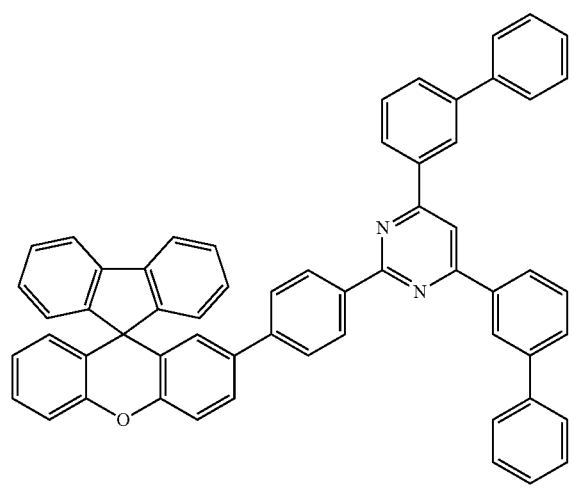
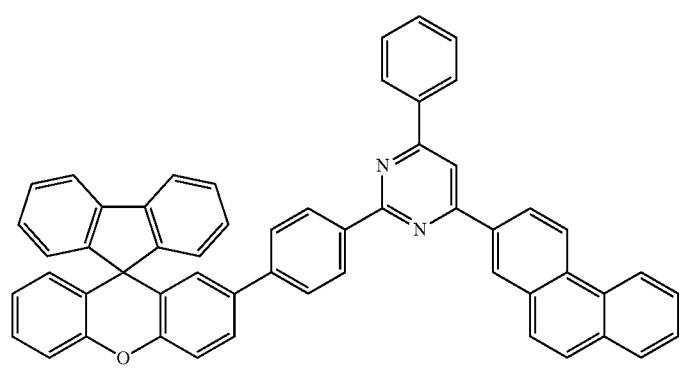
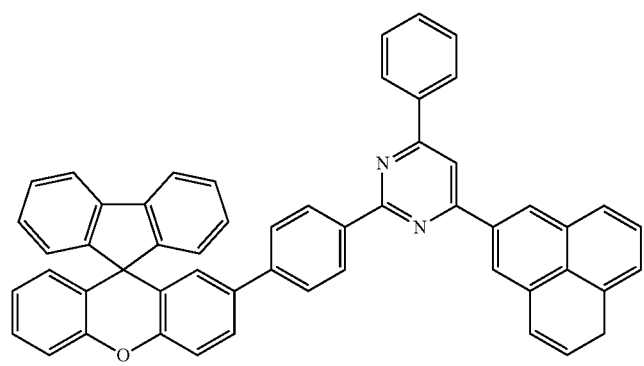

-continued
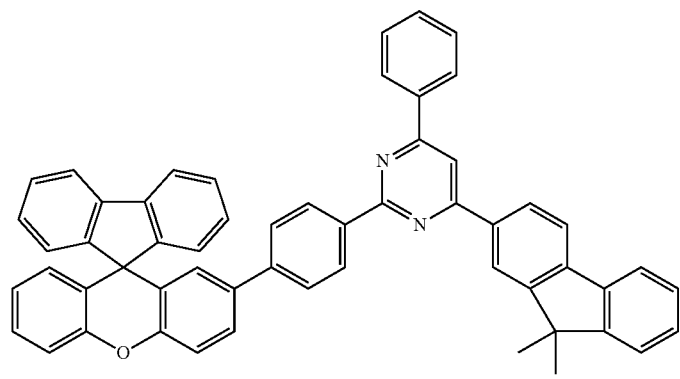
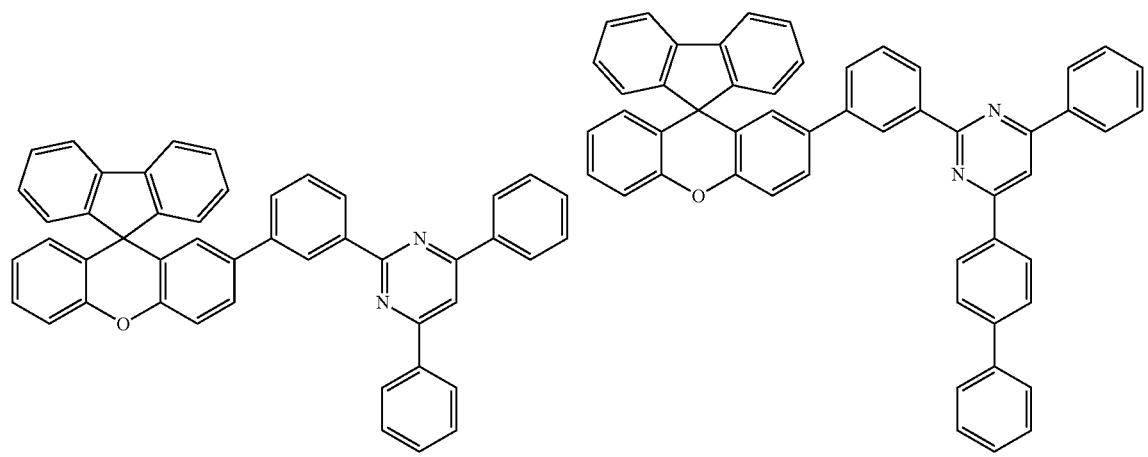
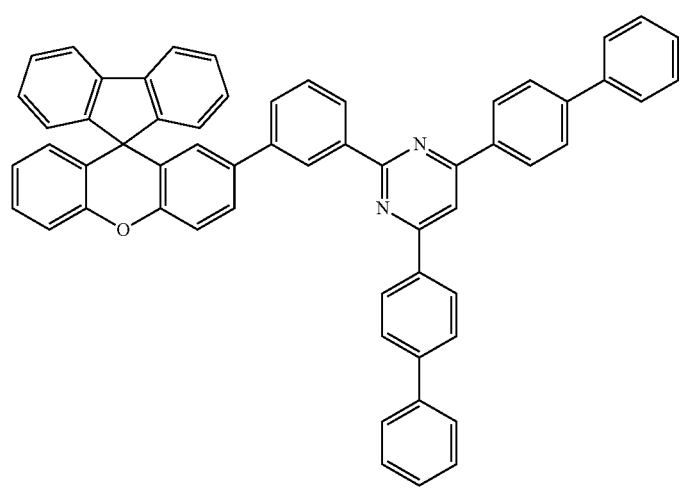
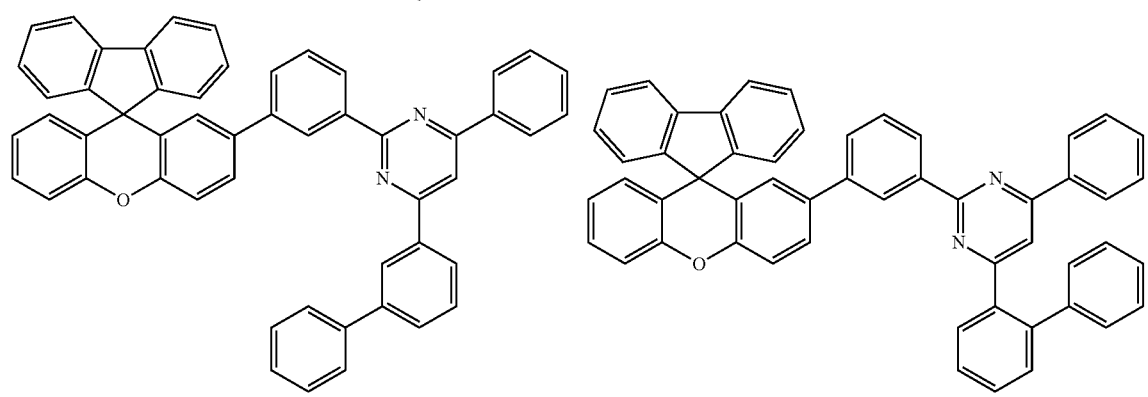

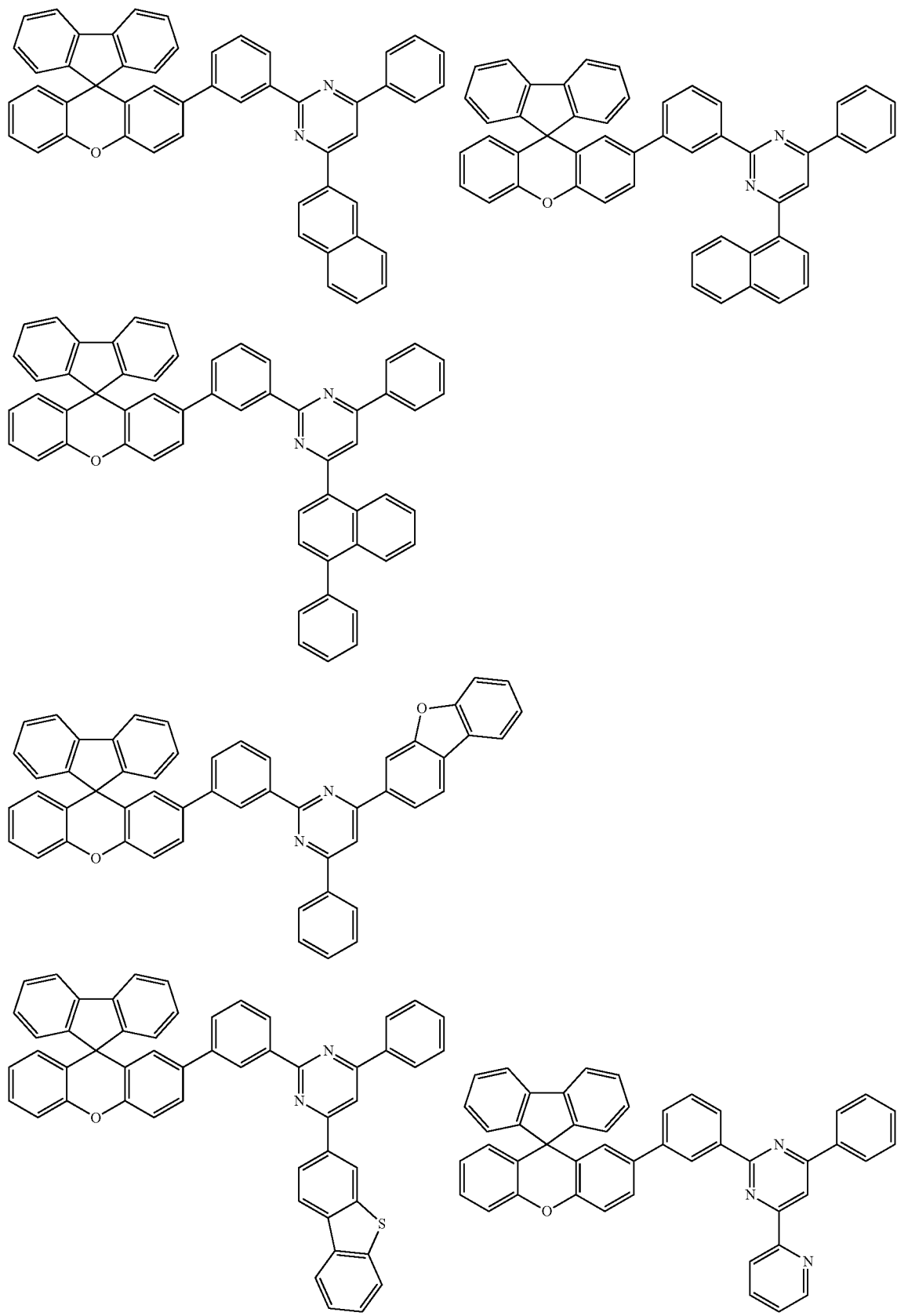

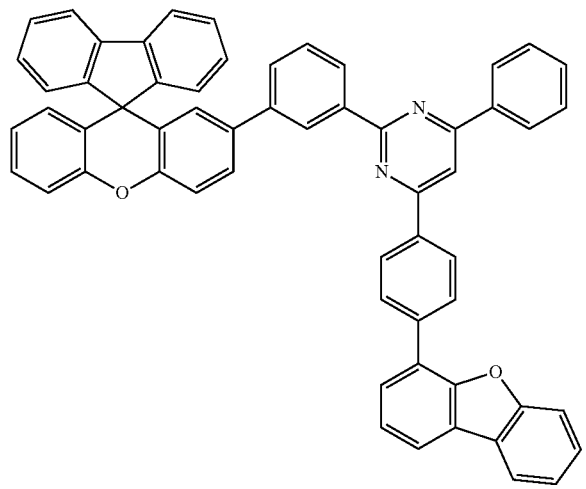
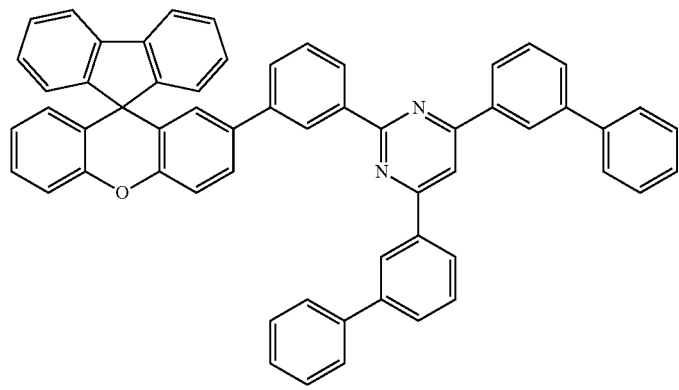
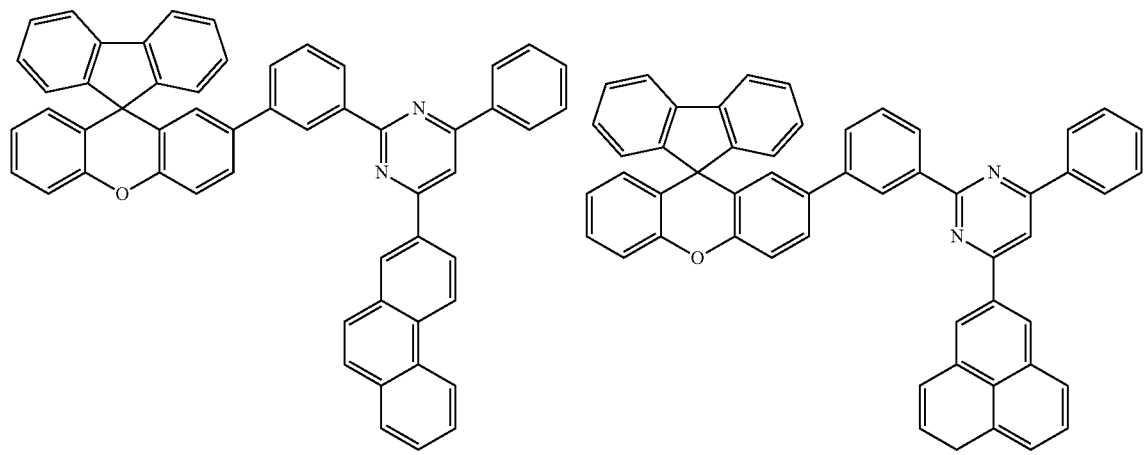

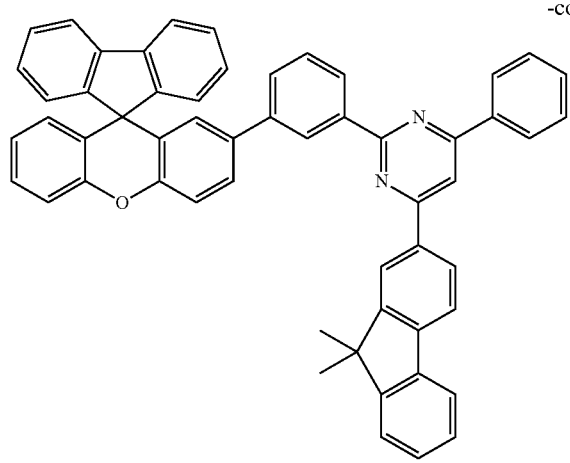
-continued
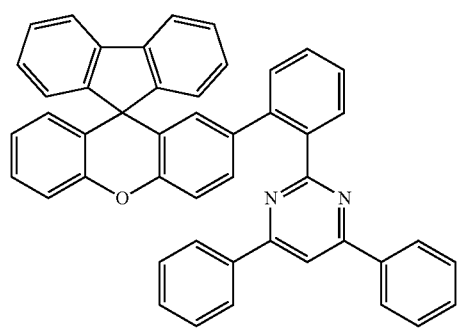
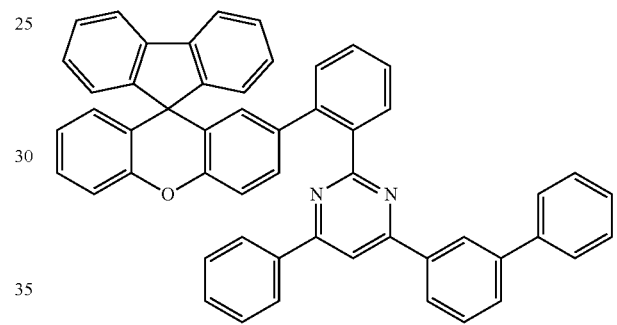
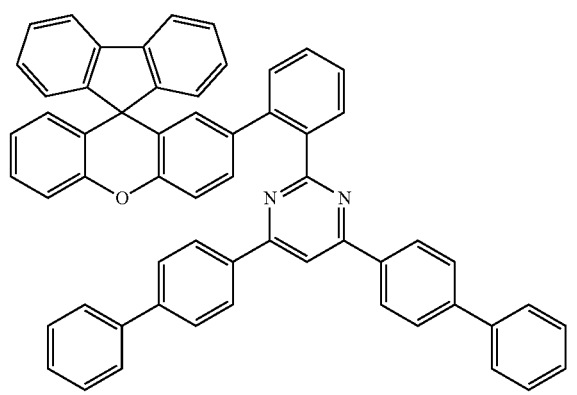

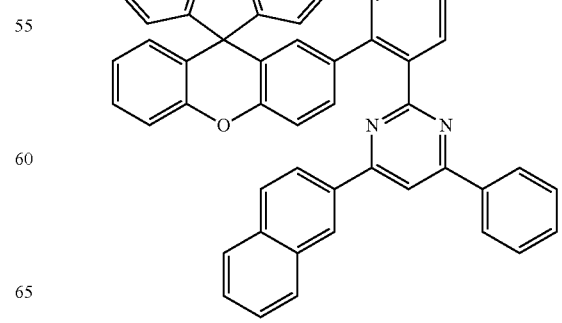

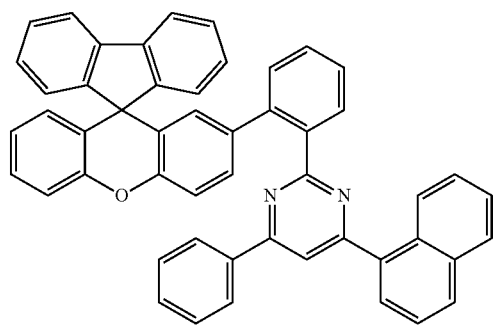
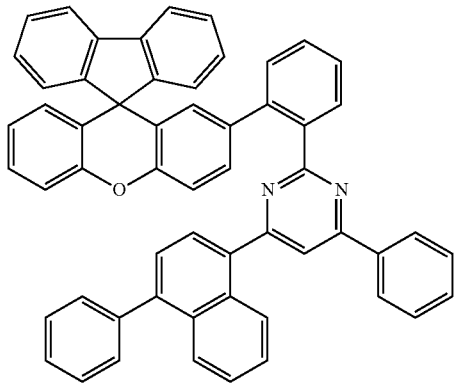
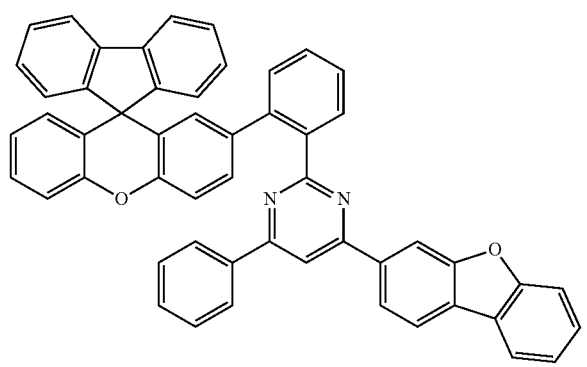
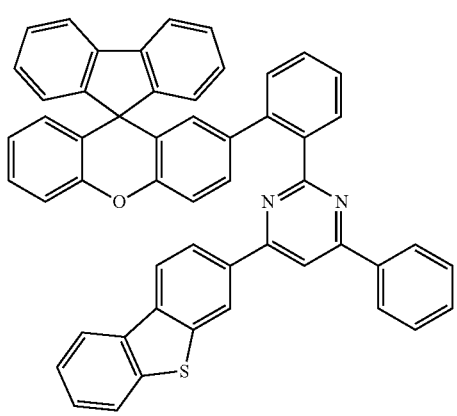
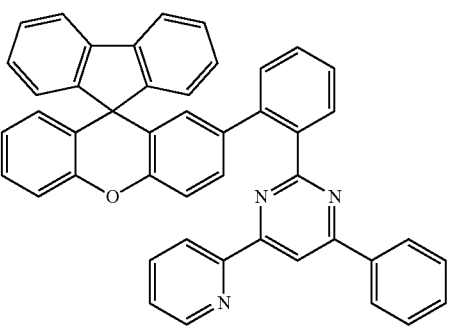
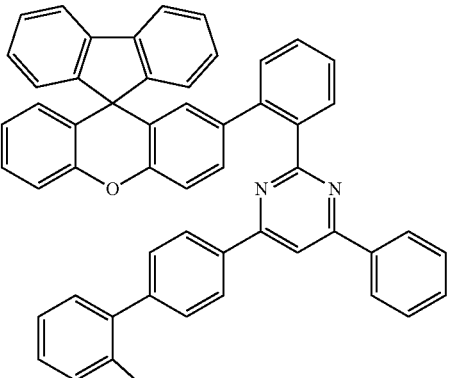
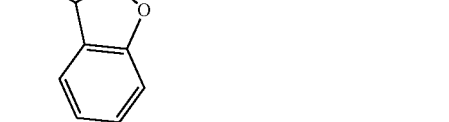
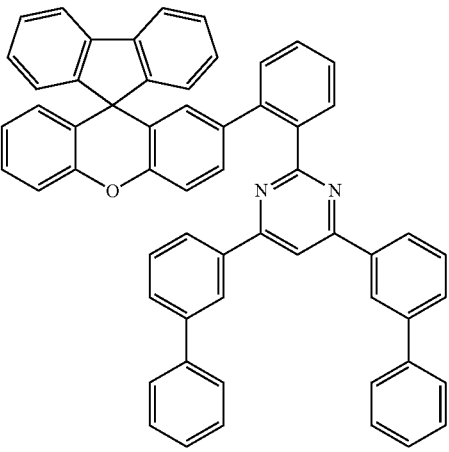
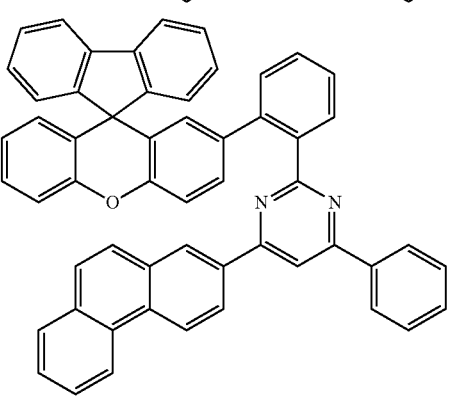

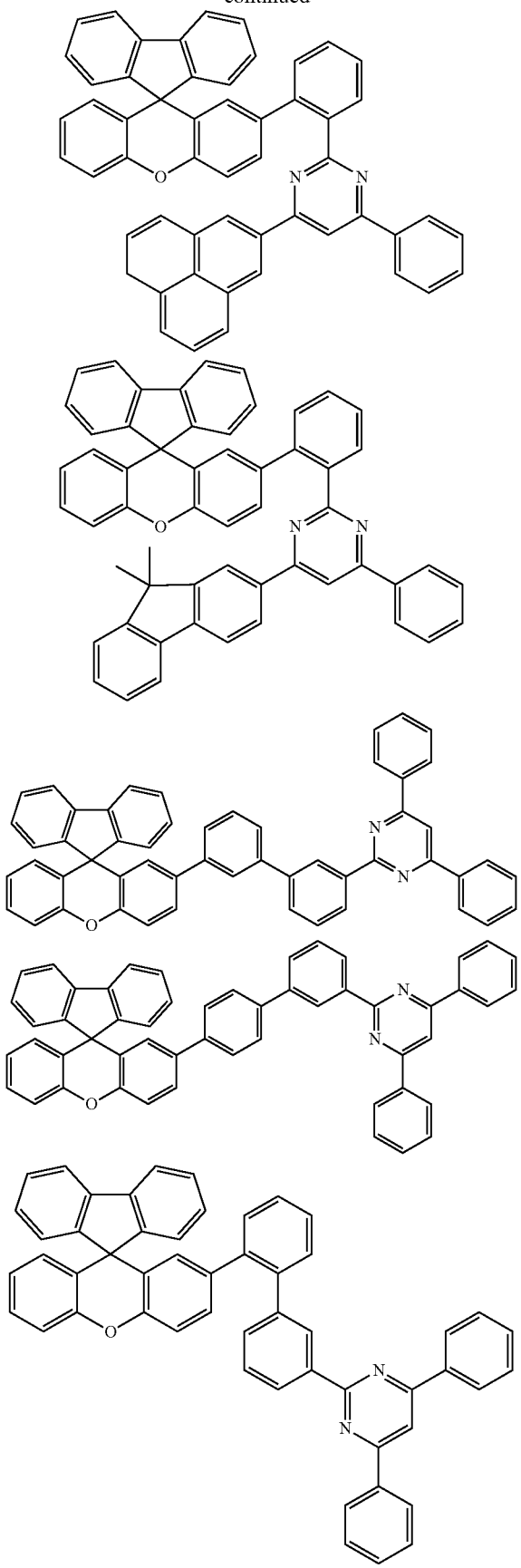

101
-continued
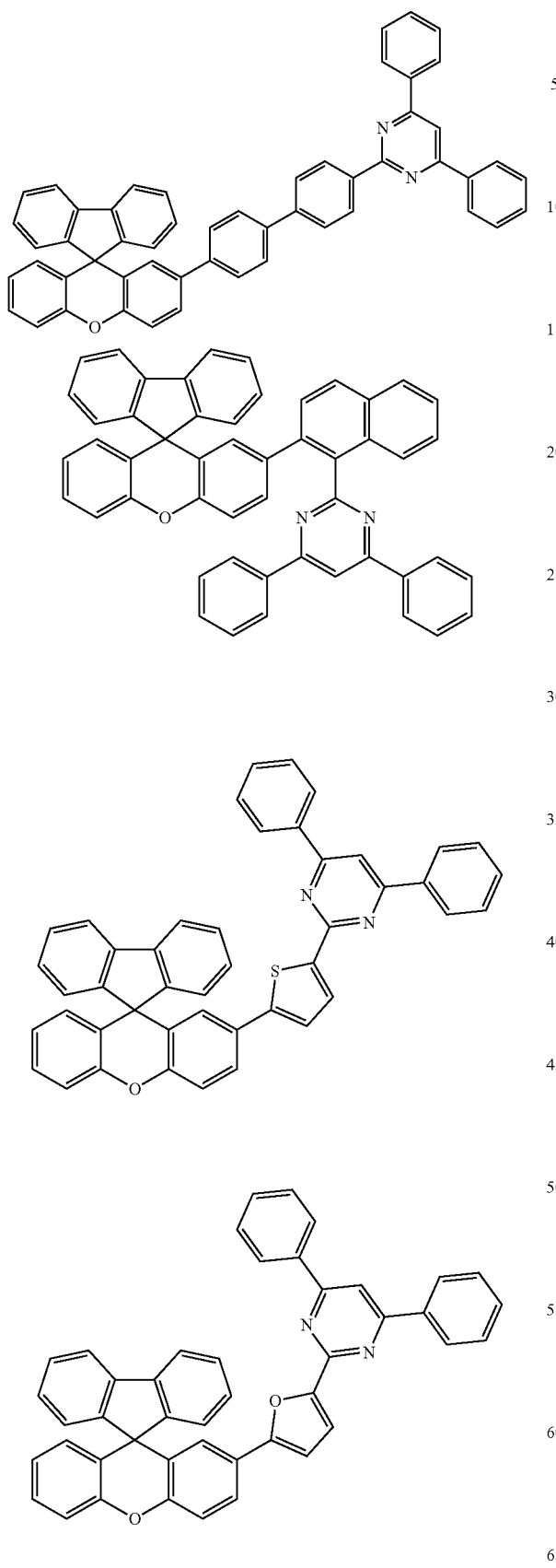
102
-continued
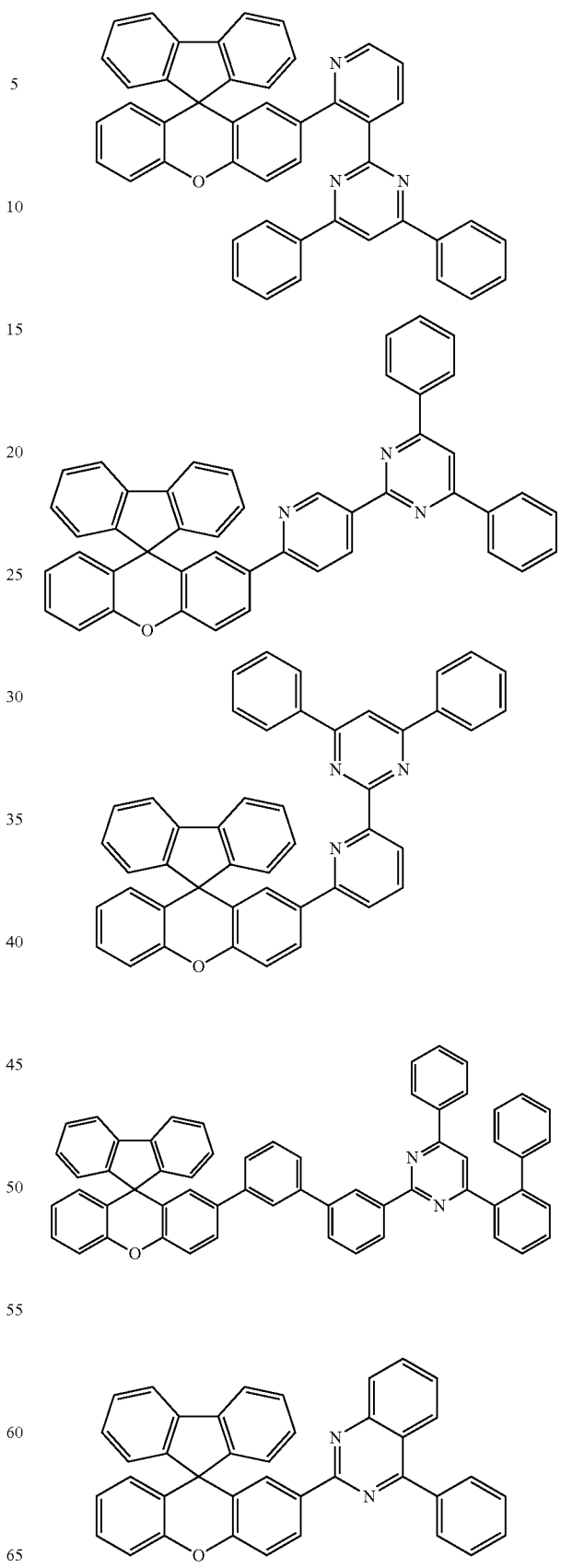

-continued
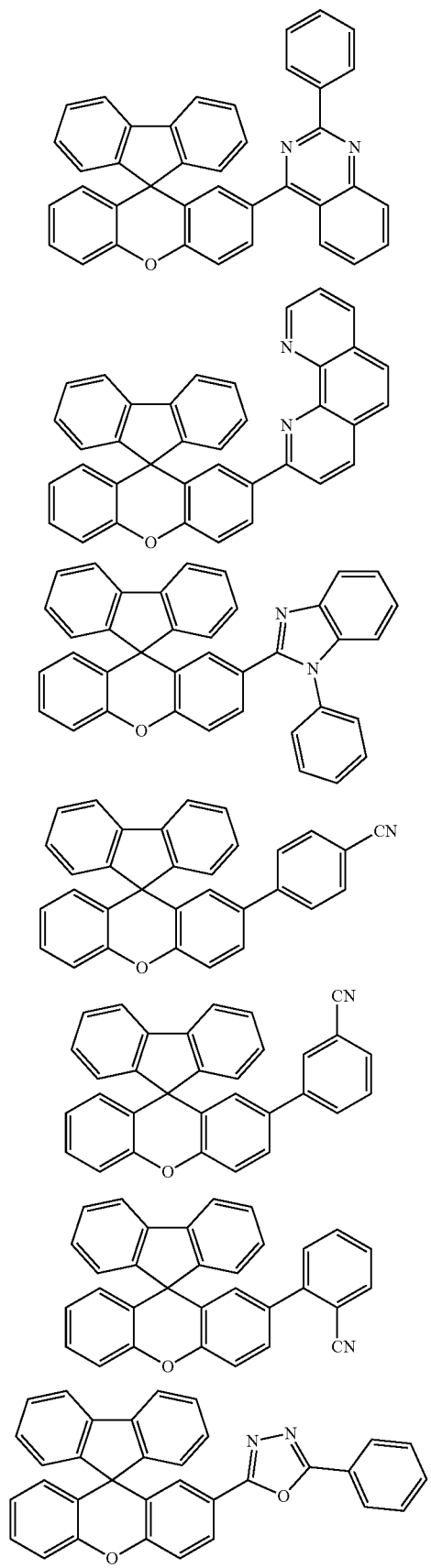
-continued
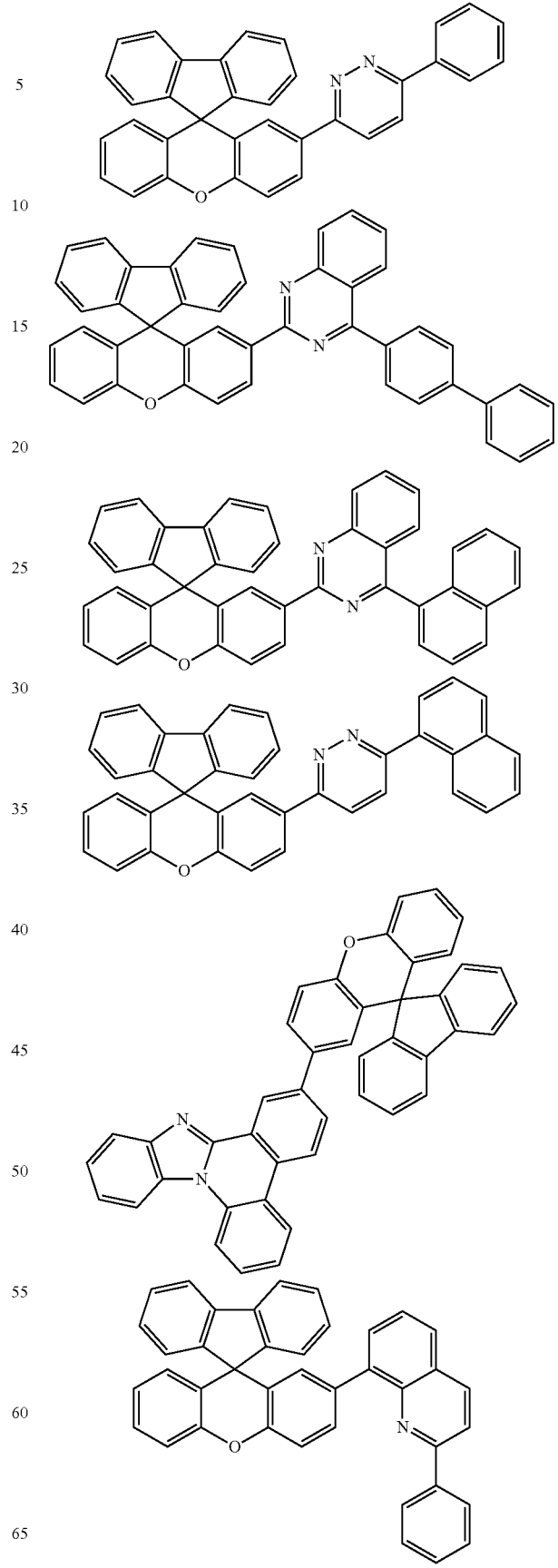

105
-continued
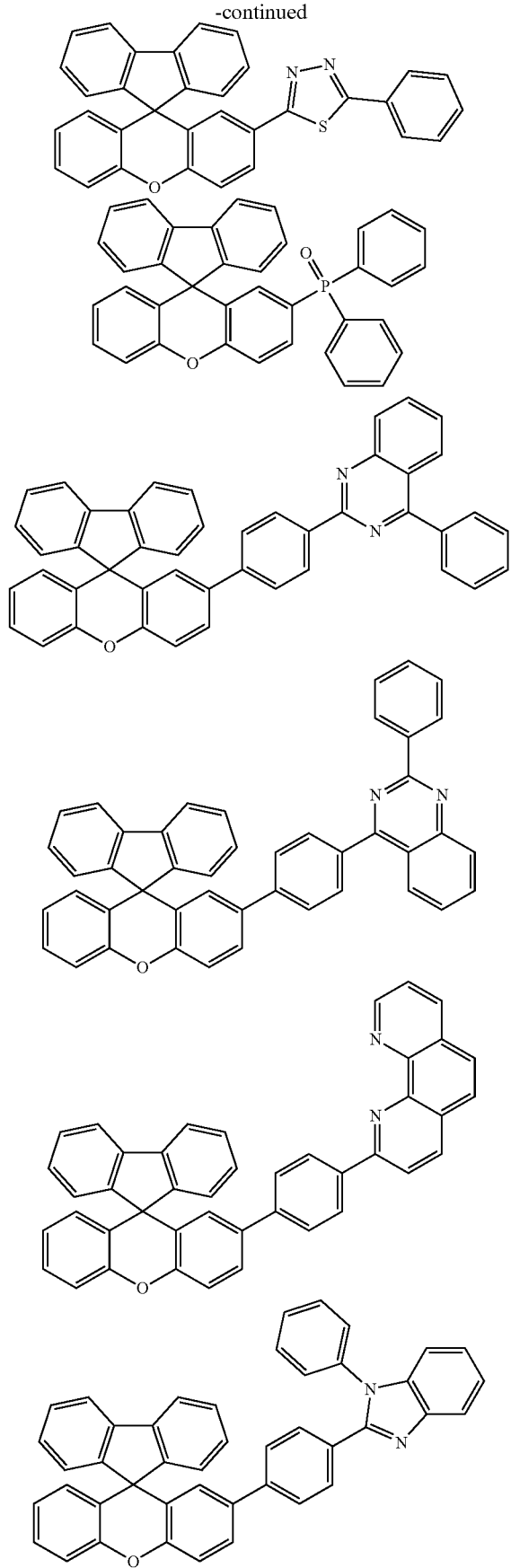
106
-continued
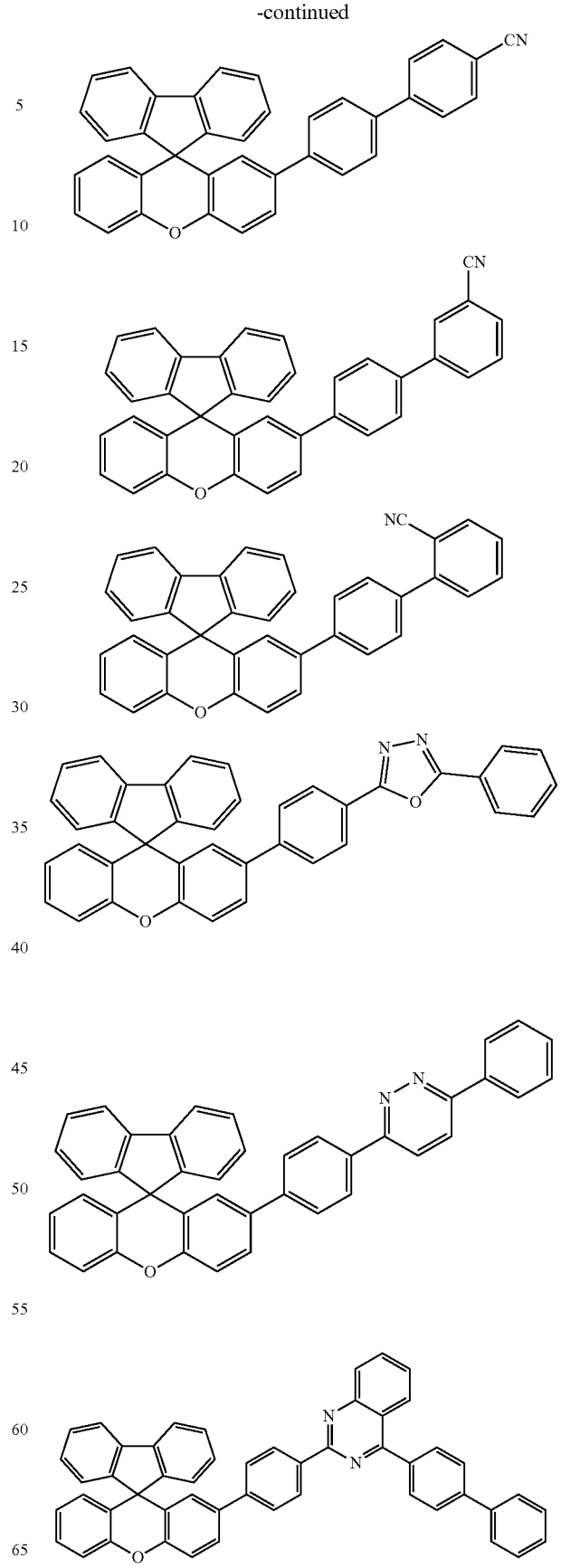

107
-continued
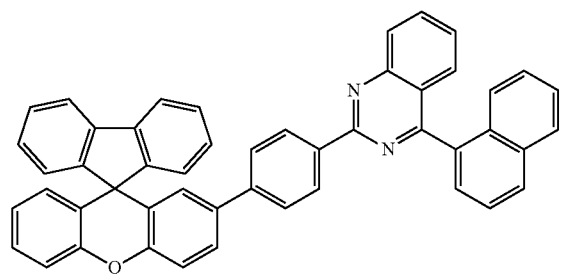
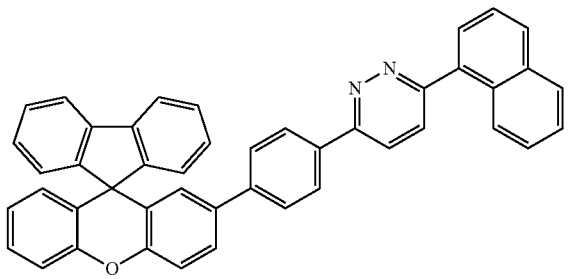
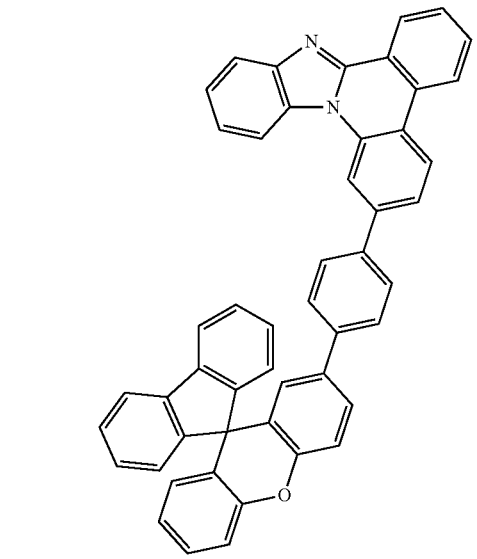
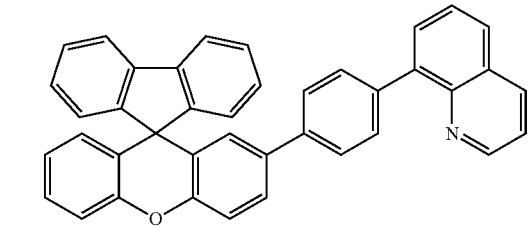
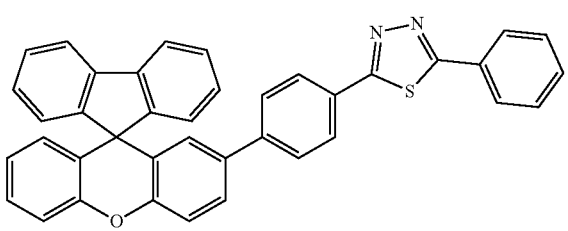
108
-continued
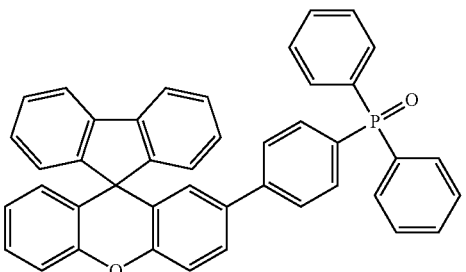
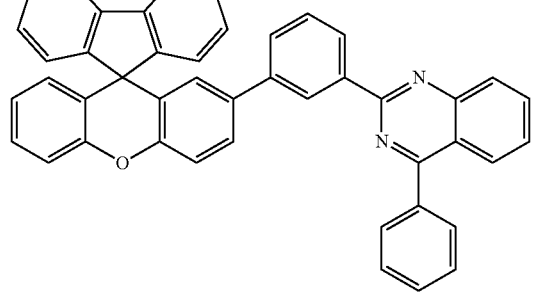
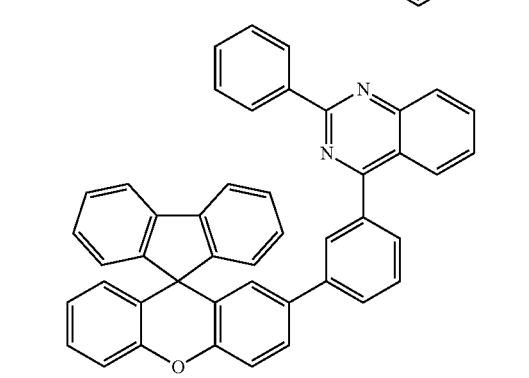
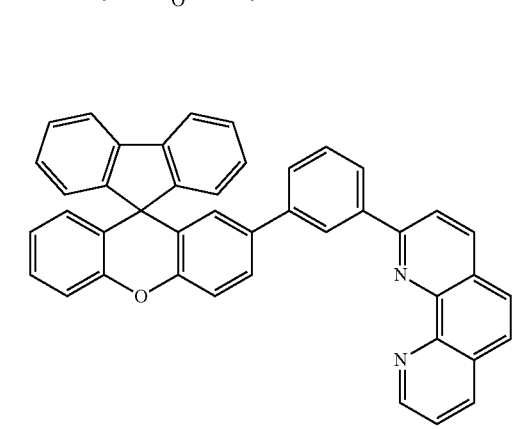
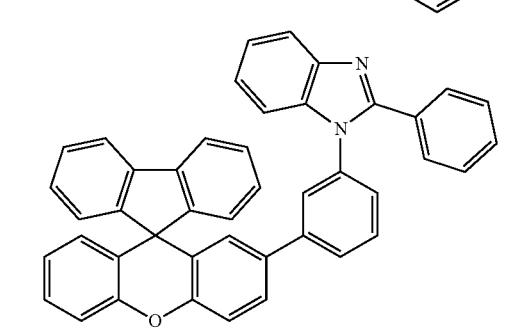

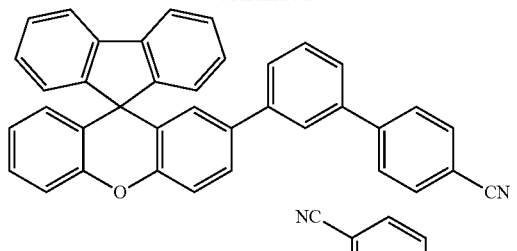
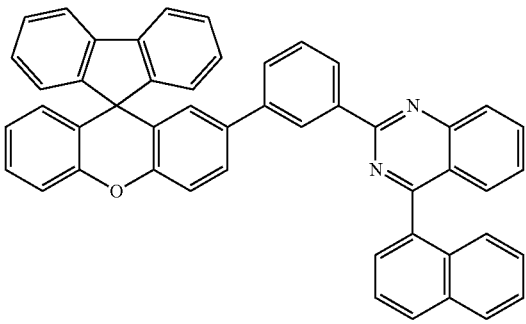
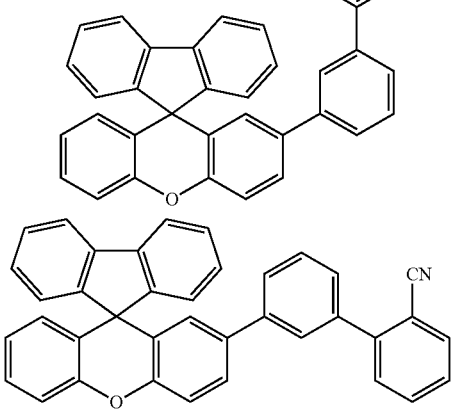
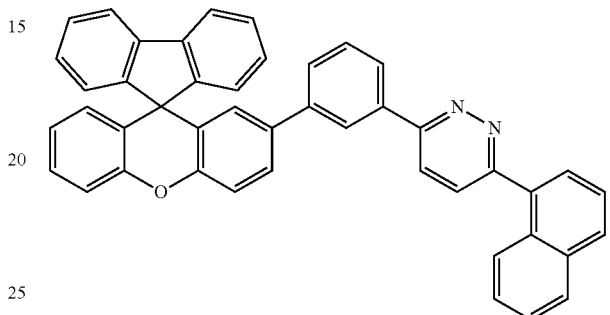
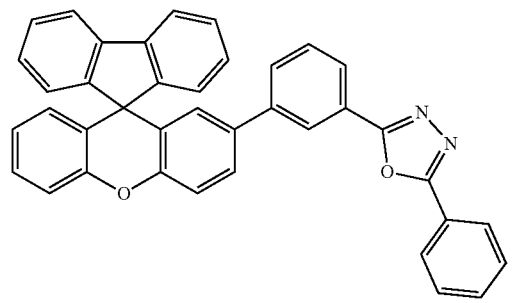
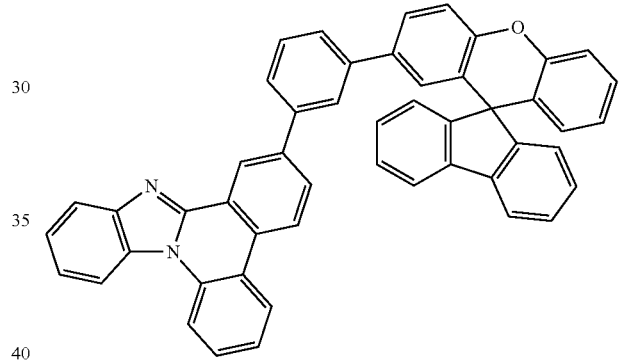
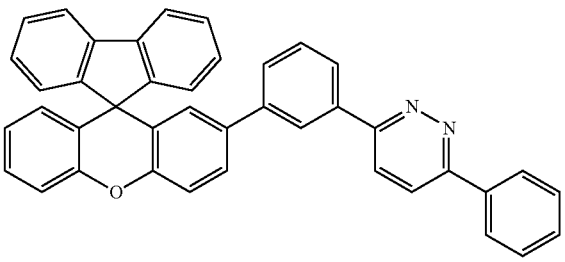
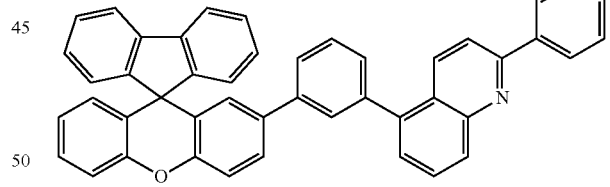
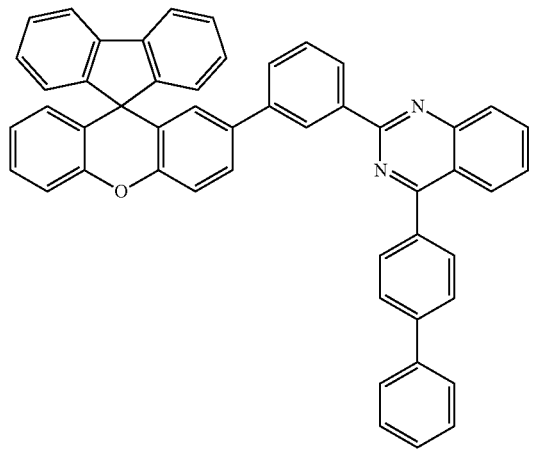
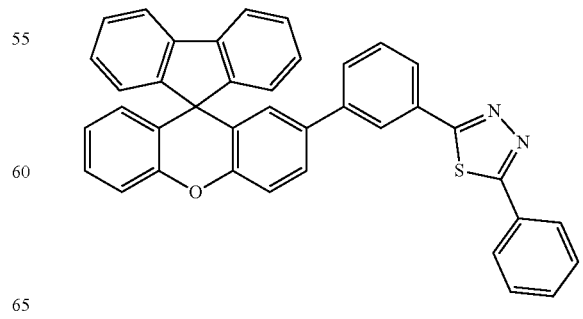

111
-continued
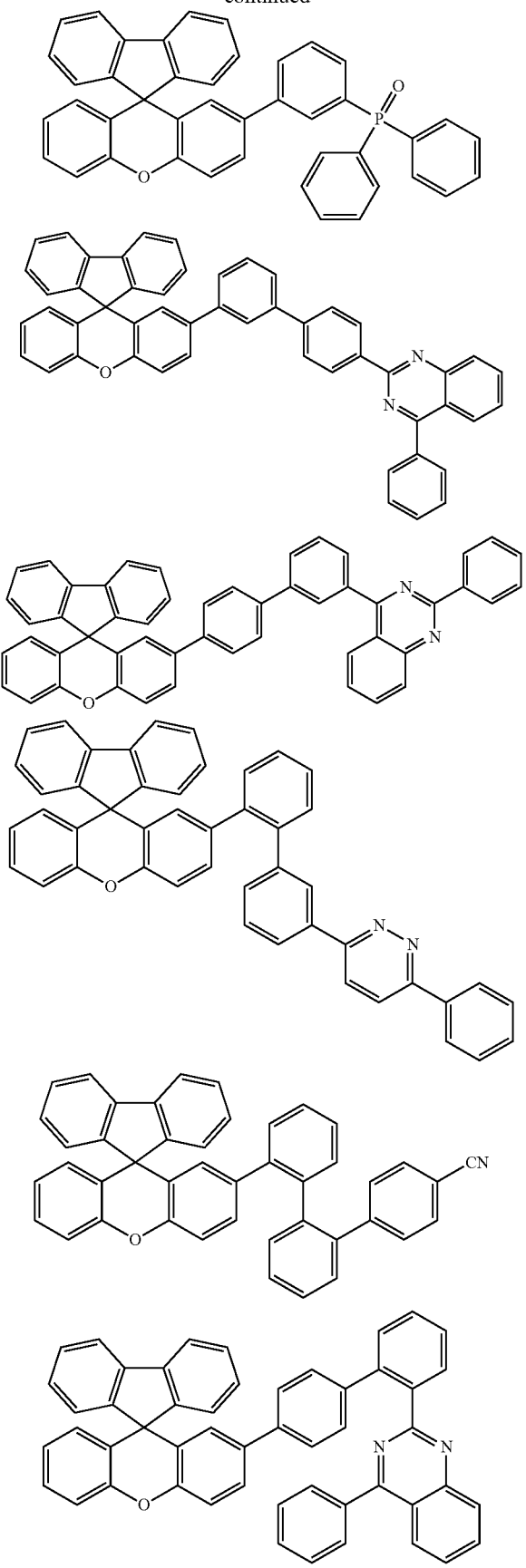
112
-continued
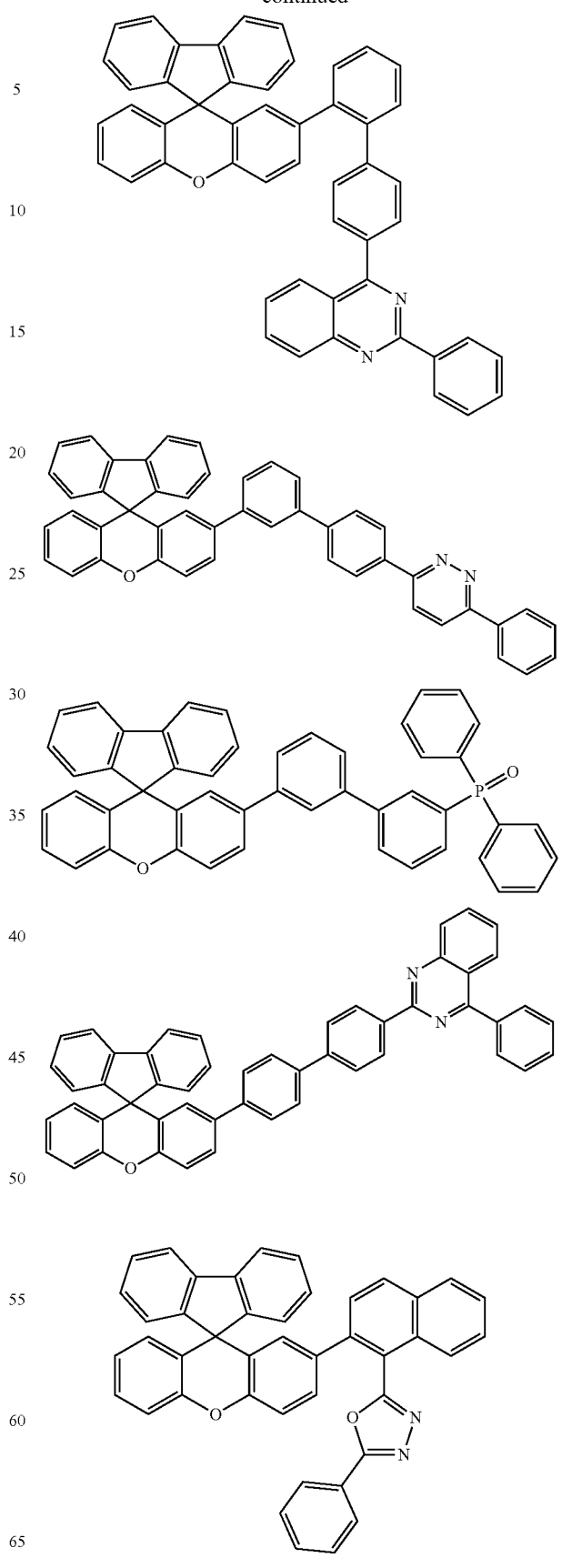

113
-continued
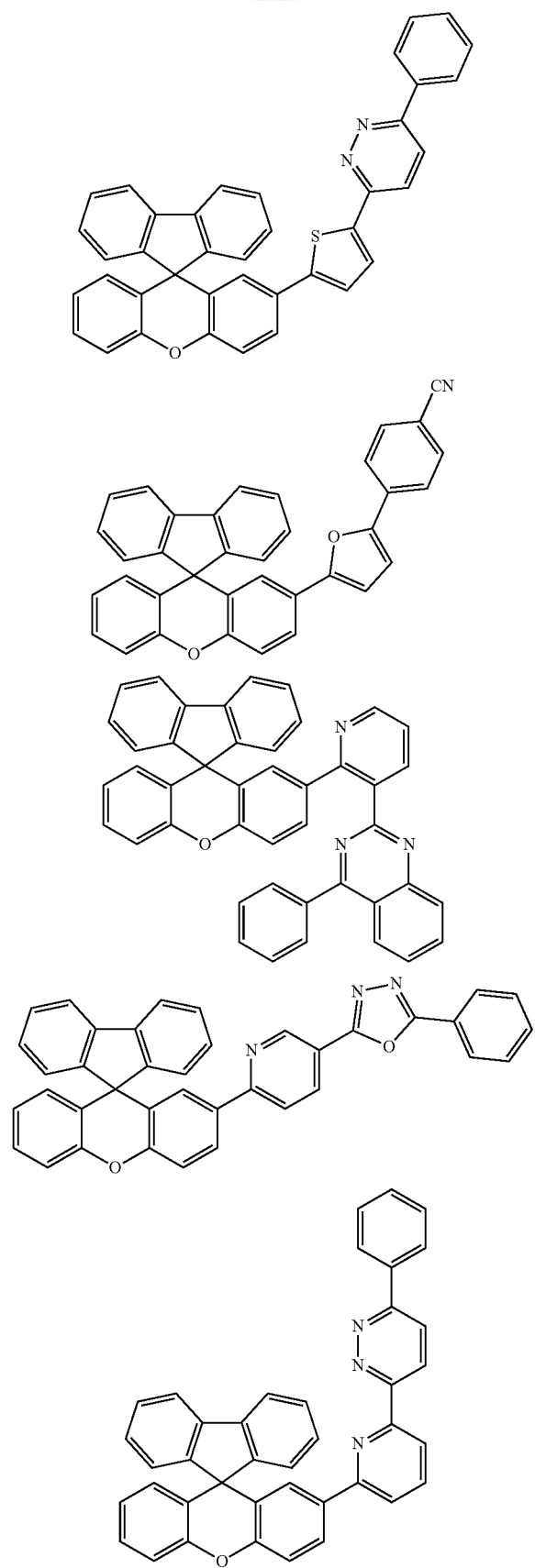
114
-continued
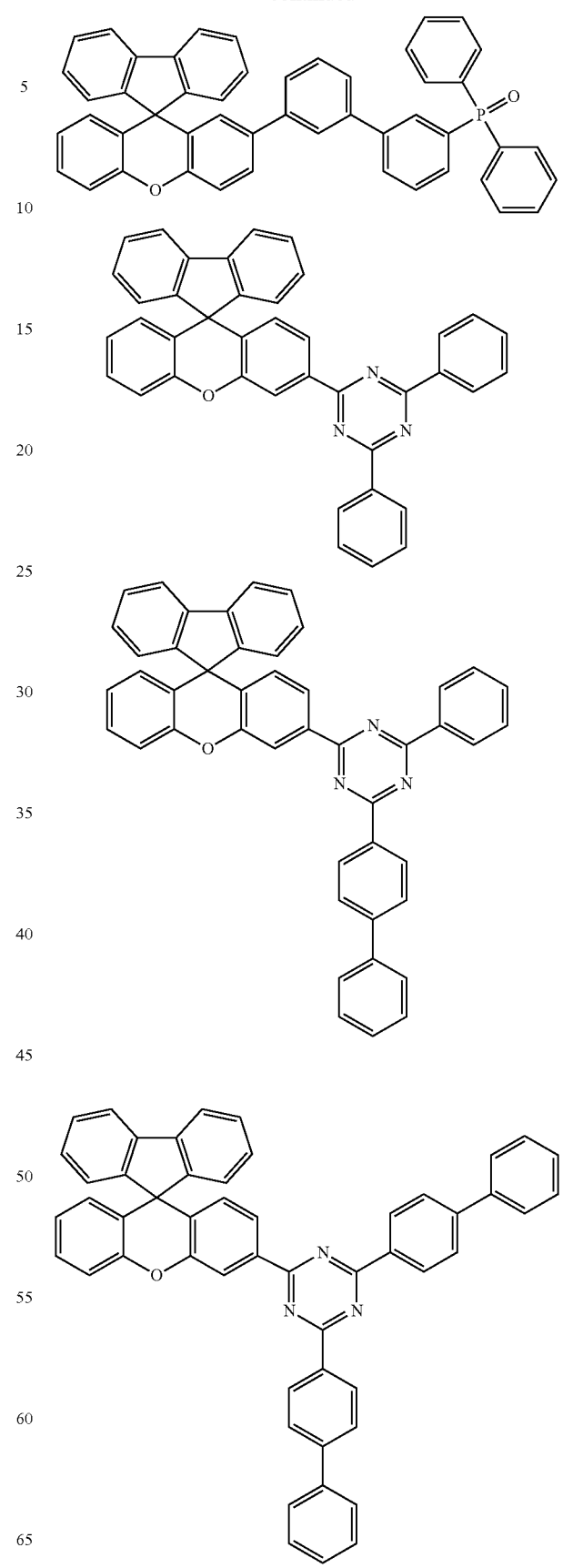

115
-continued
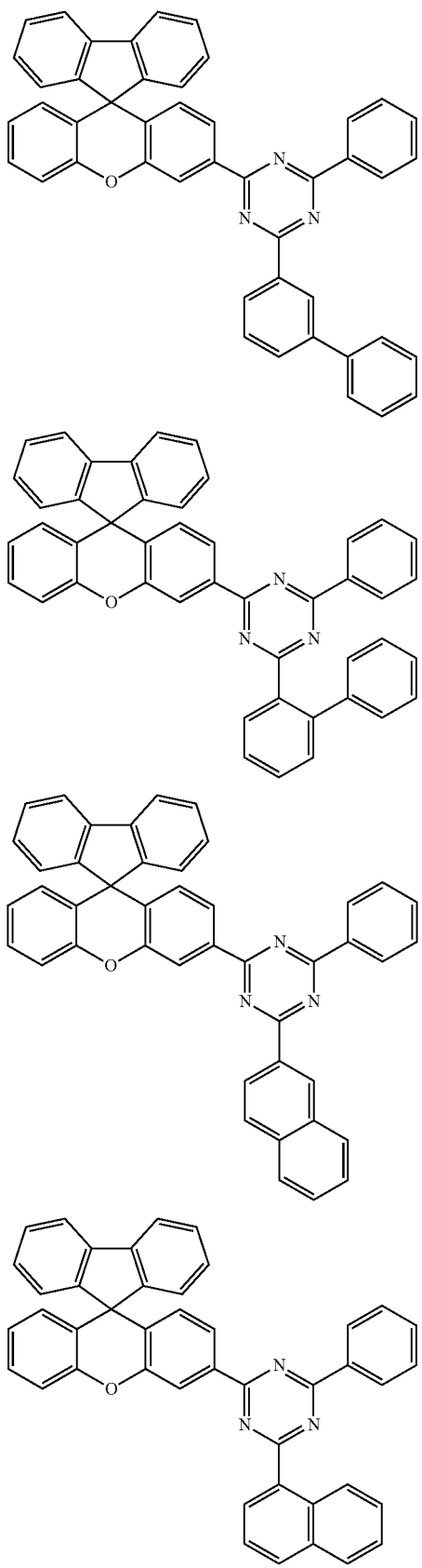
116
-continued
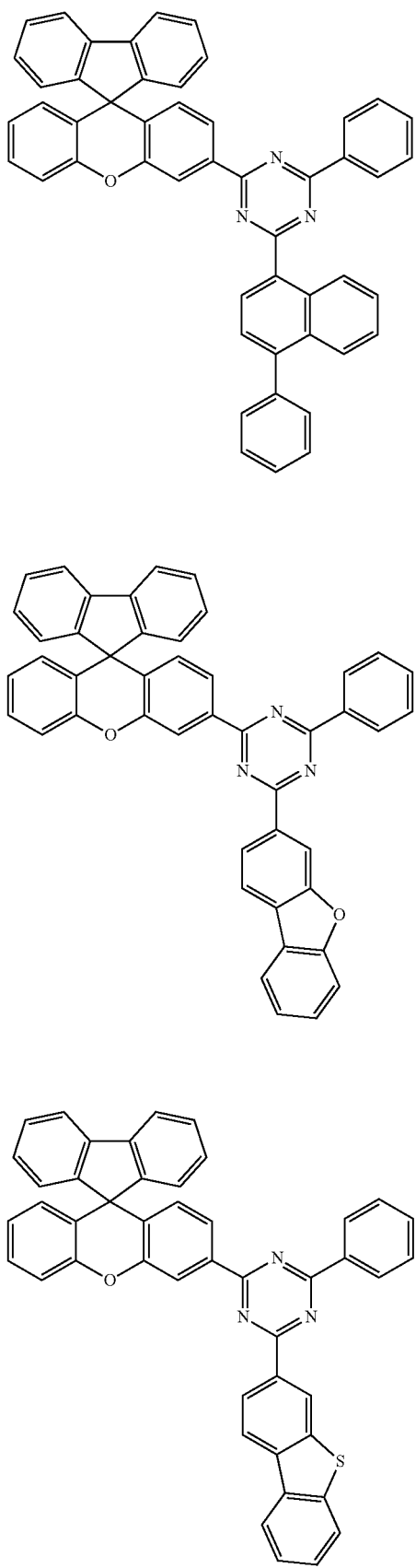

117
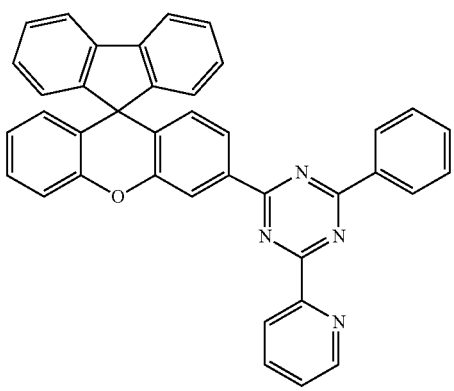
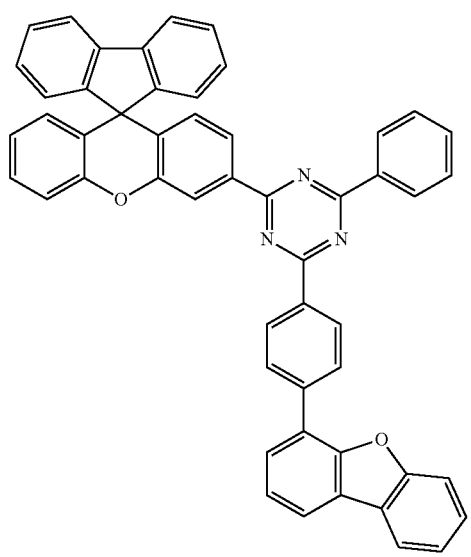
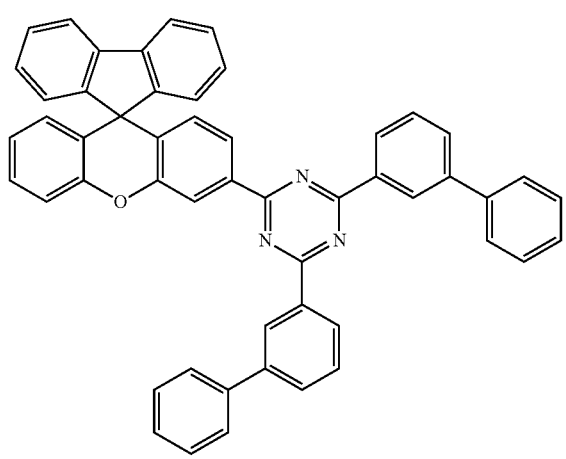
118
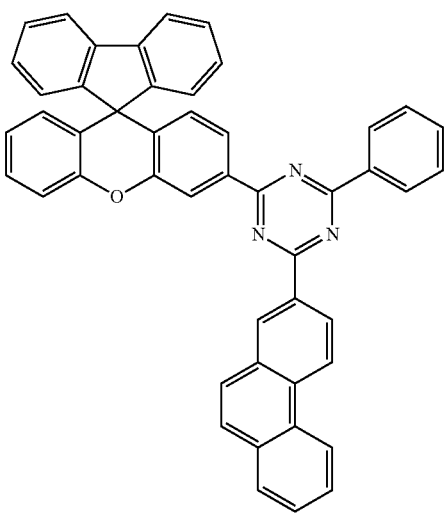
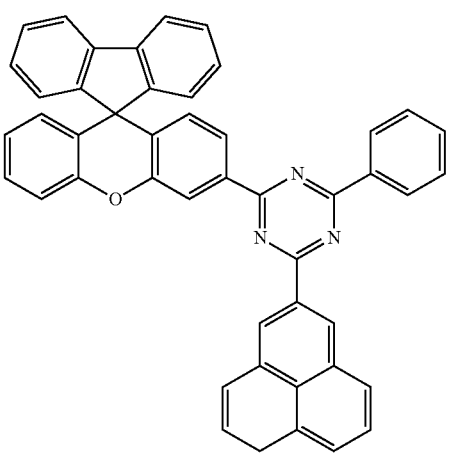
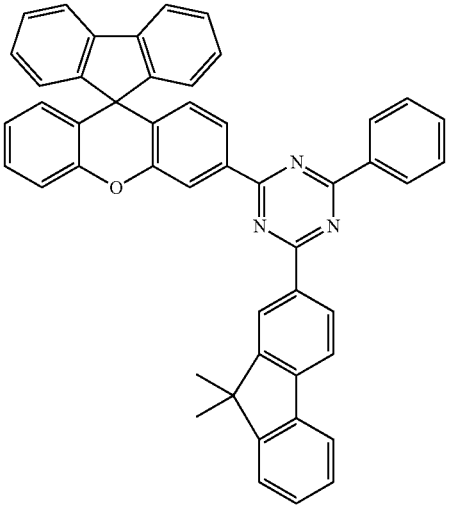

119
-continued
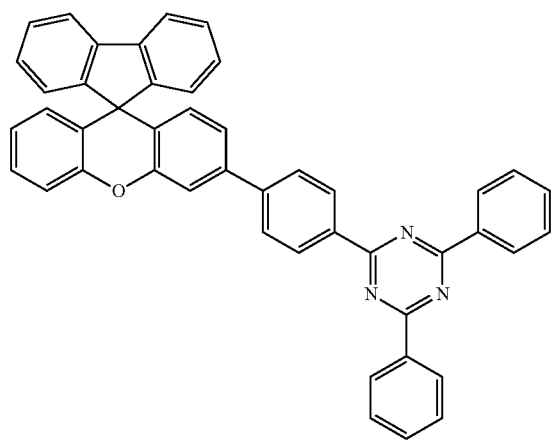
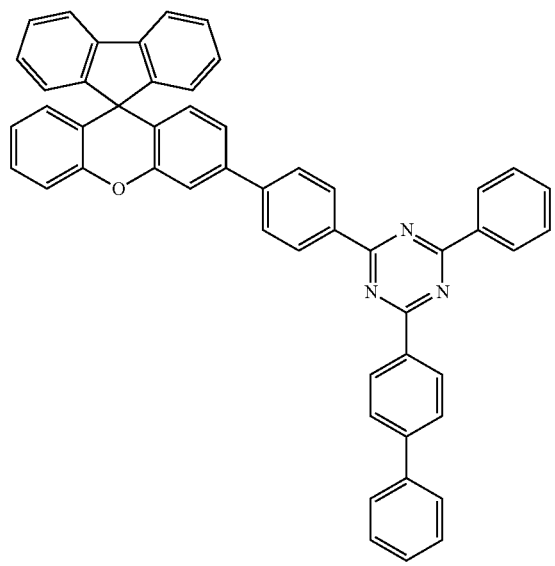 [SMILES: CC1(C)c2ccccc2-c2ccc(-c3cc(-c4ccc(-c5ccc6c(c5)Oc5ccccc5C65c6ccccc6-c6ccccc65)cc4)nc(-c4ccccc4)n3)cc21]
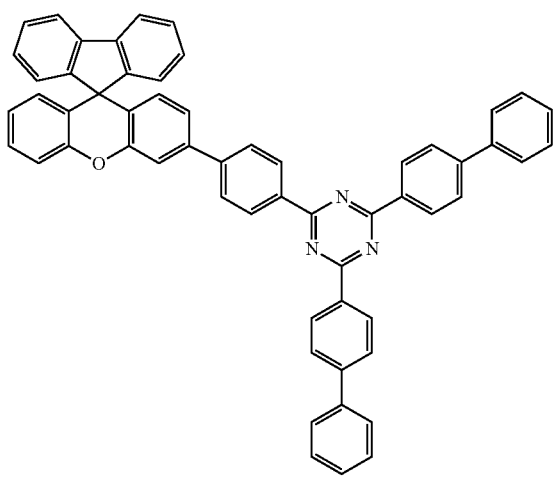
120
-continued
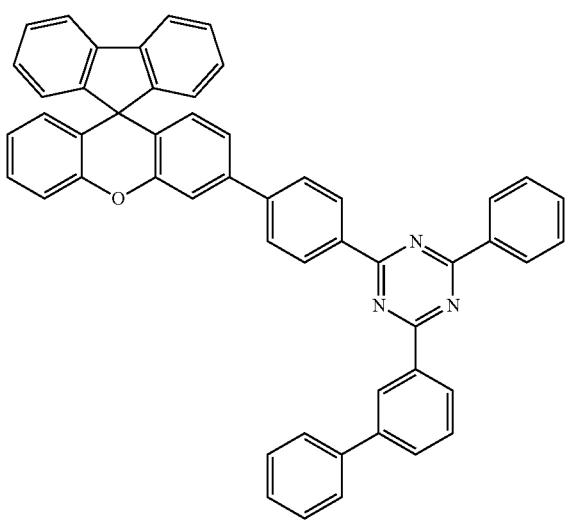
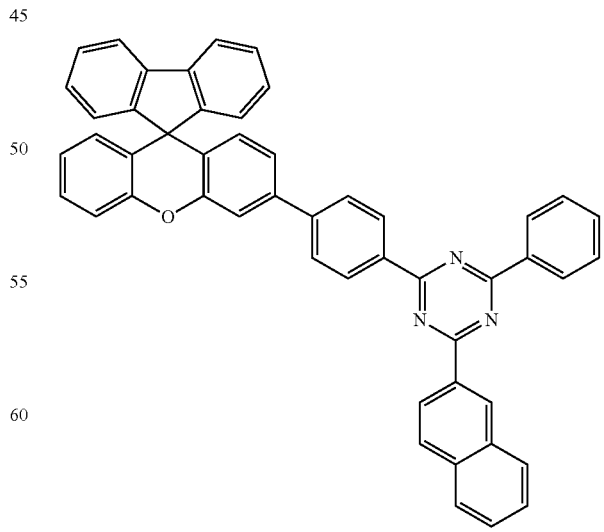

121
-continued
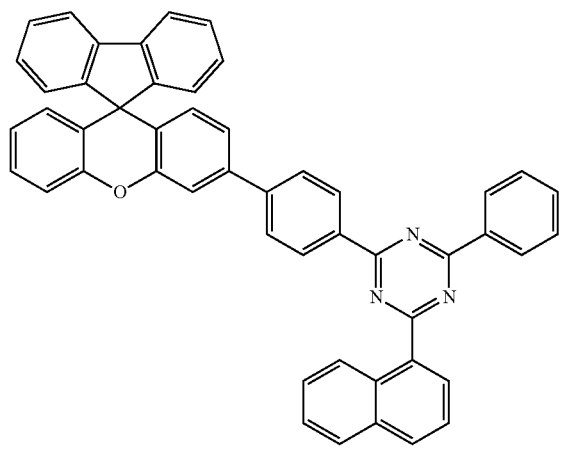
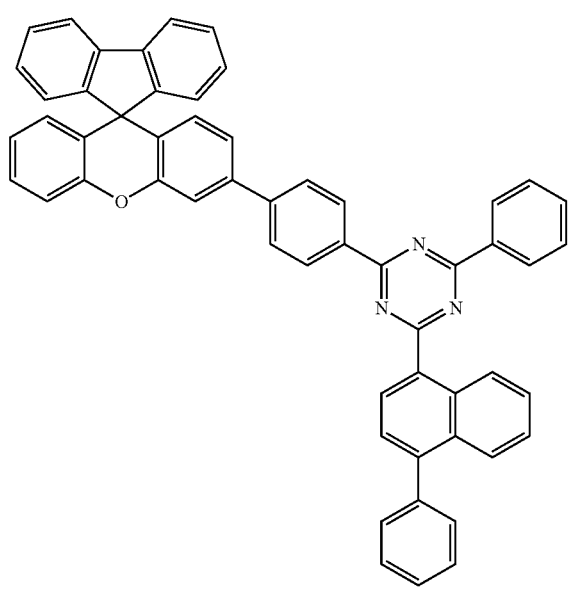
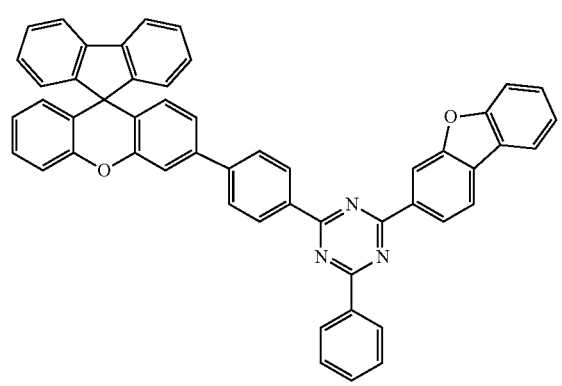
122
-continued
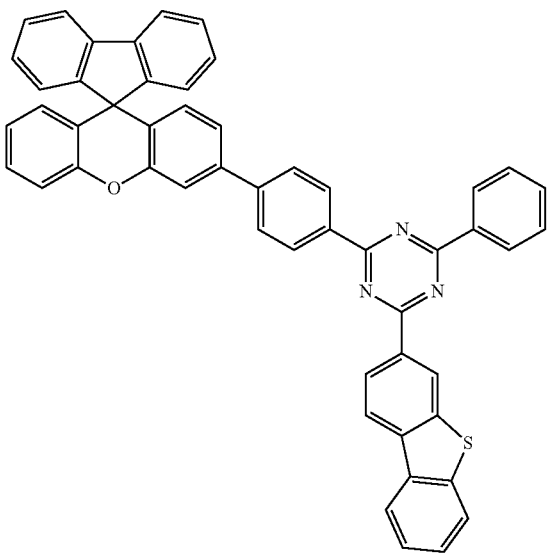
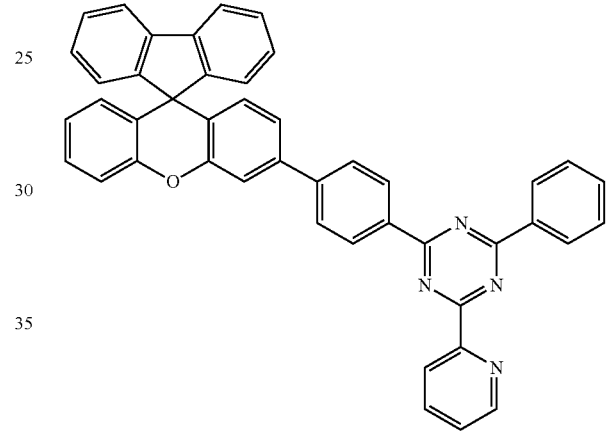
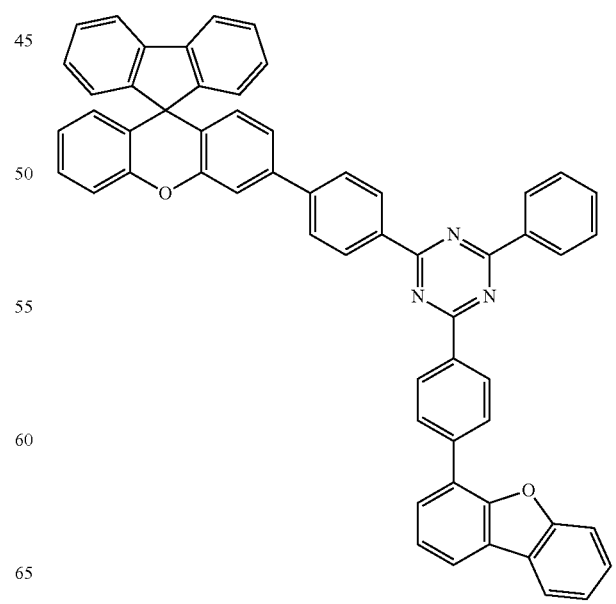

123
-continued
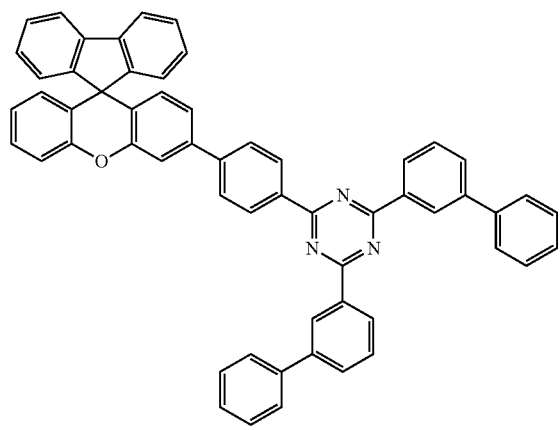
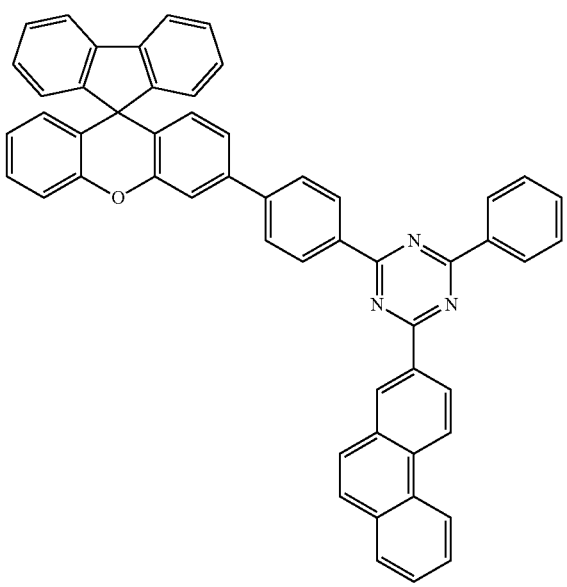
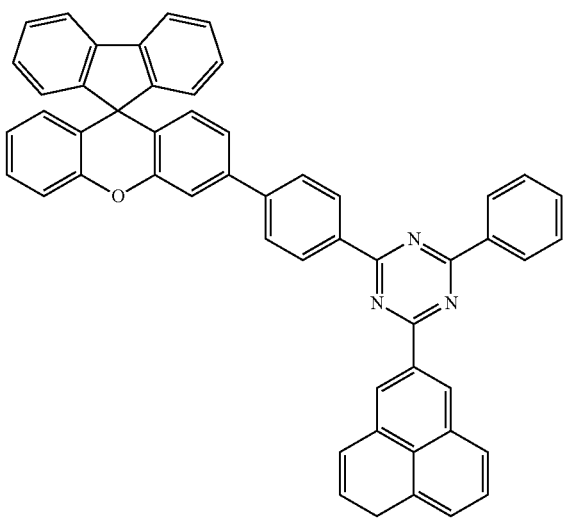
124
-continued
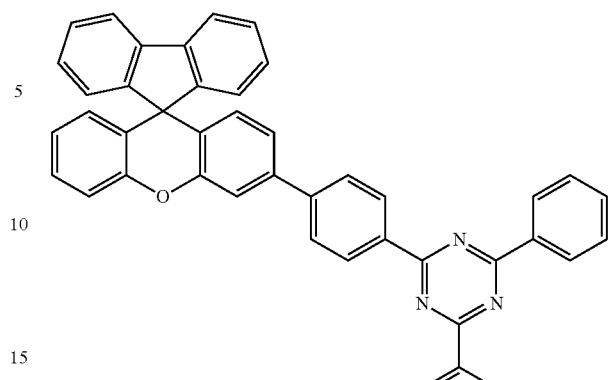
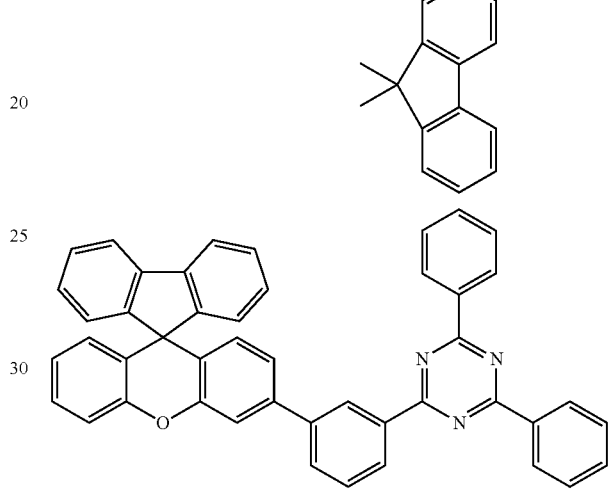
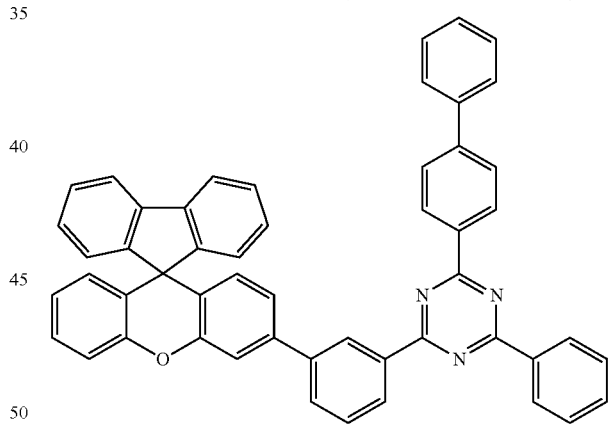
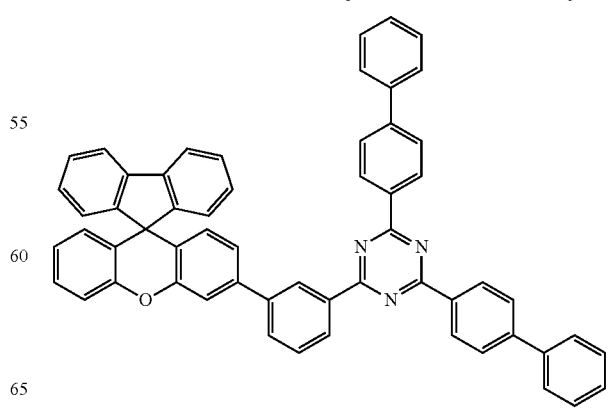

125
-continued
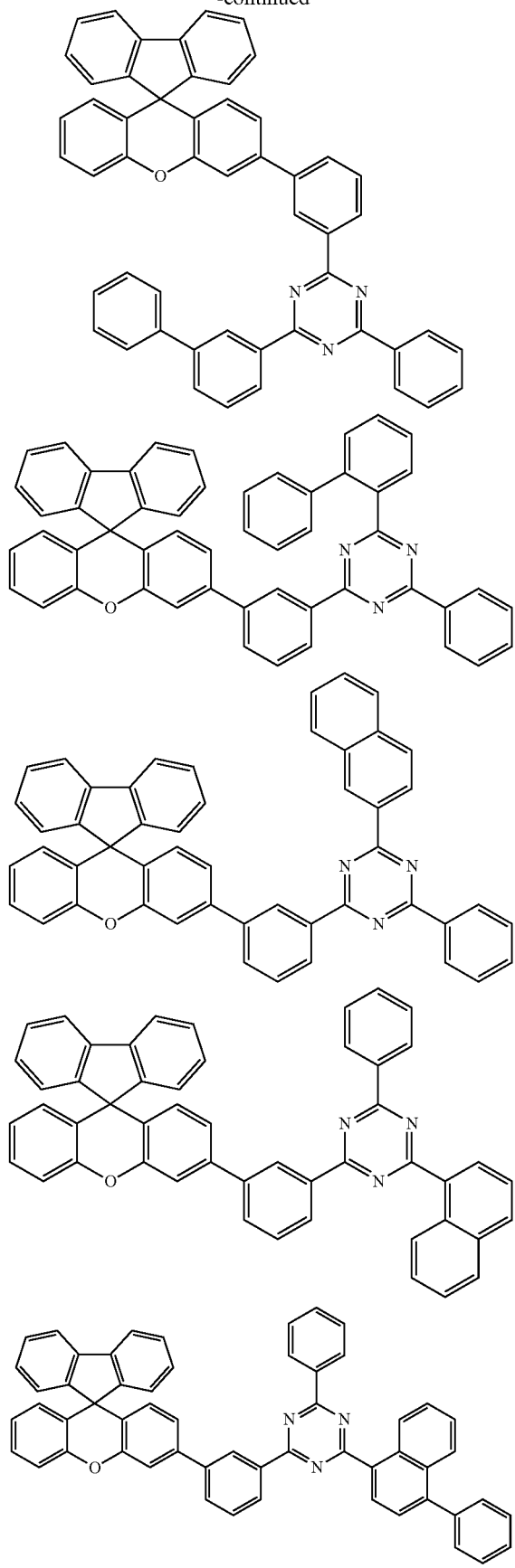
126
-continued
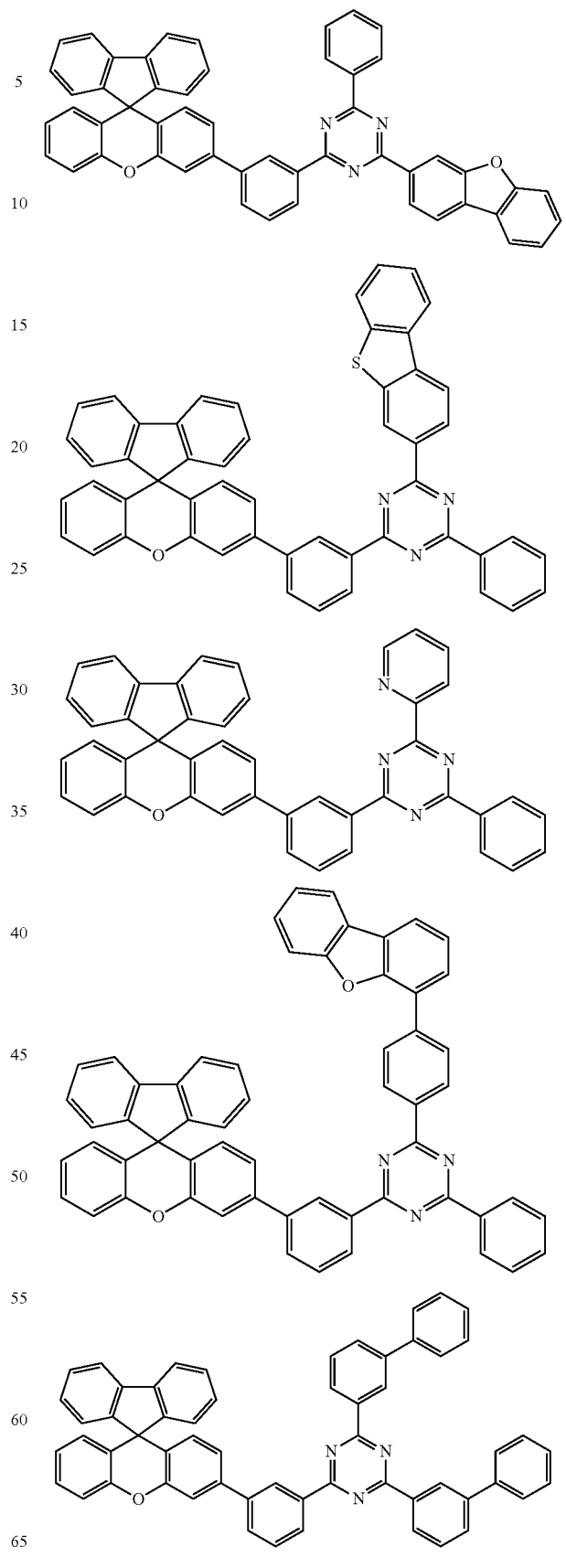

127
-continued
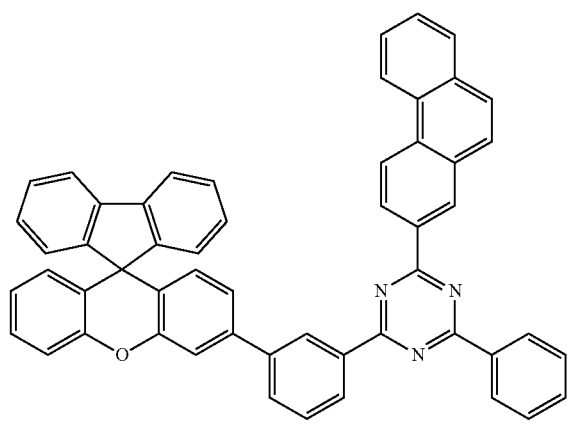
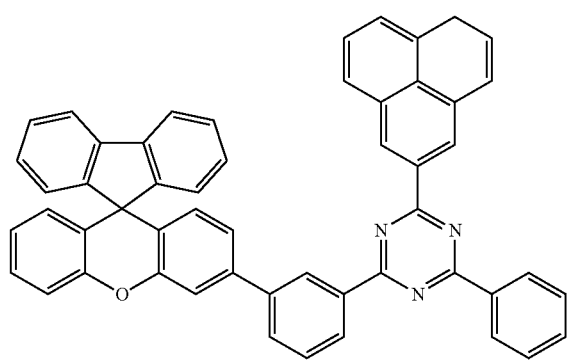
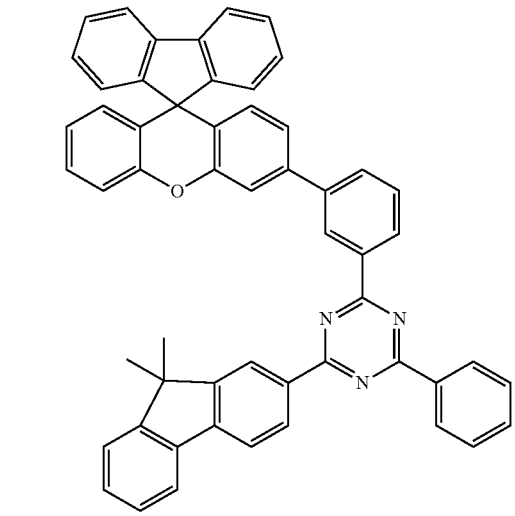
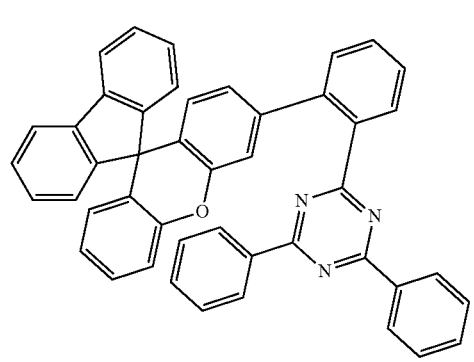
128
-continued
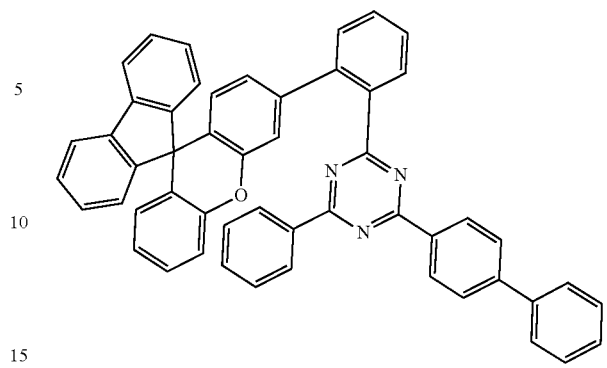
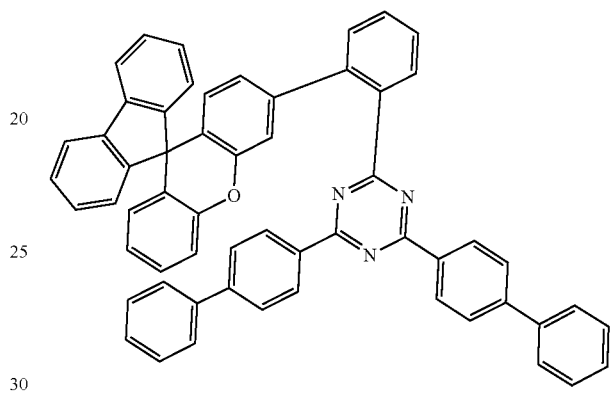
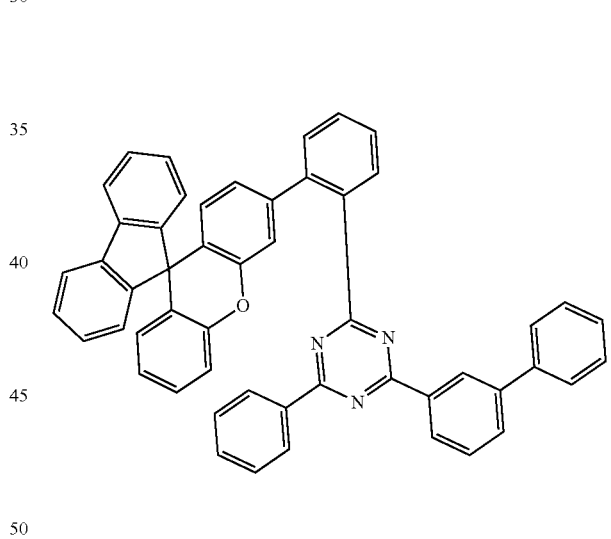
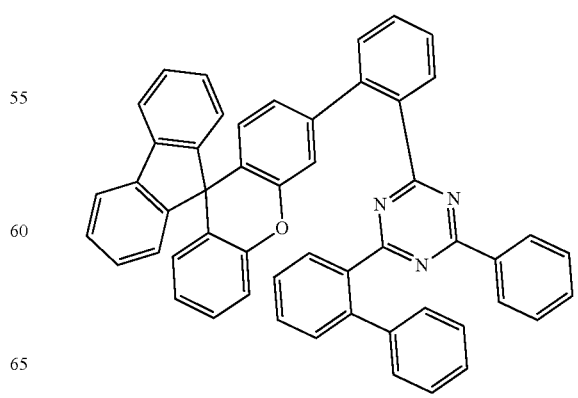

129
-continued
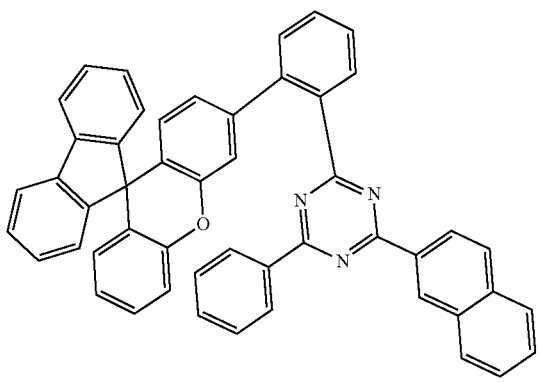
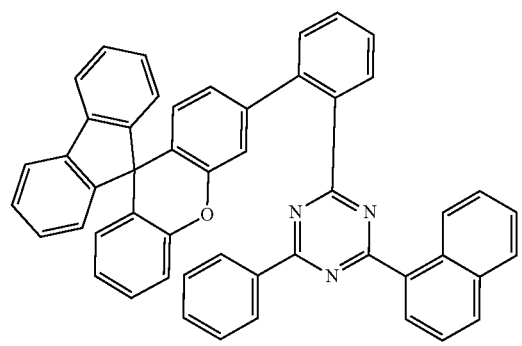
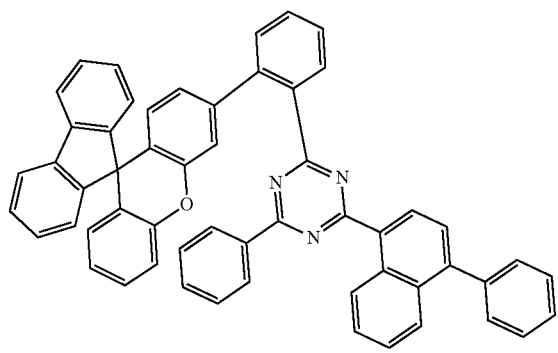
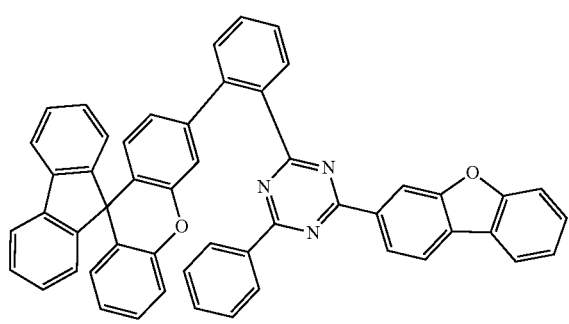
130
-continued
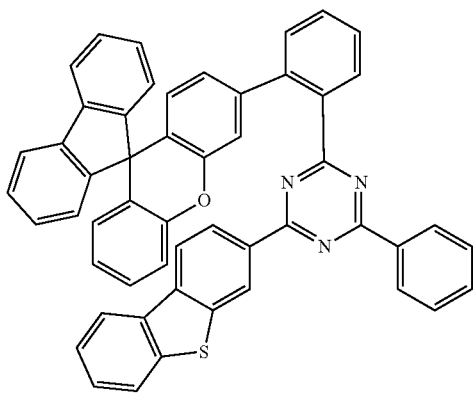
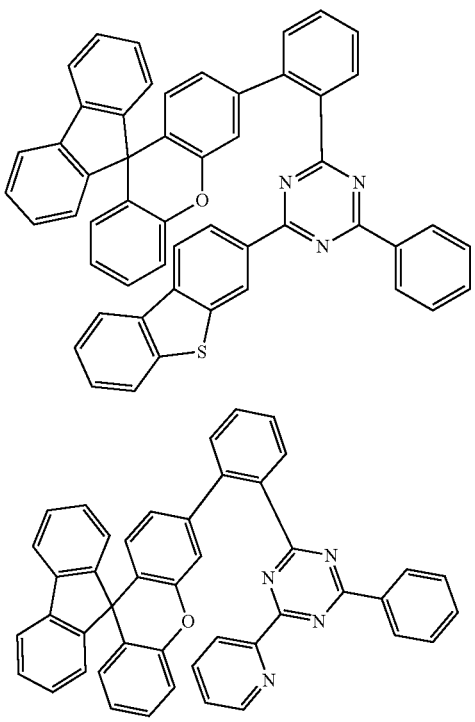
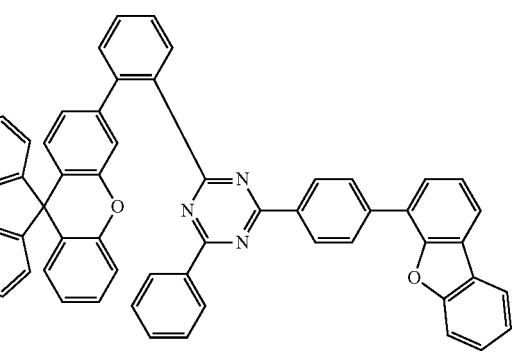
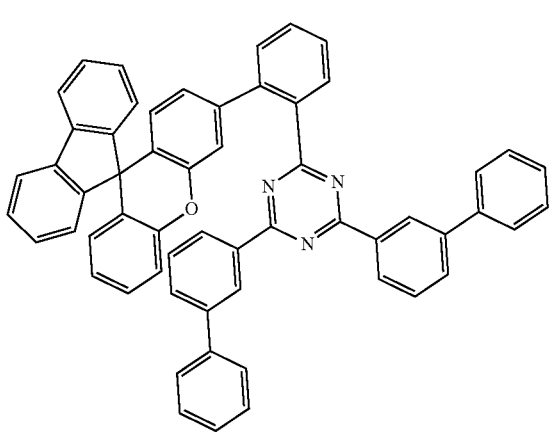

131
-continued
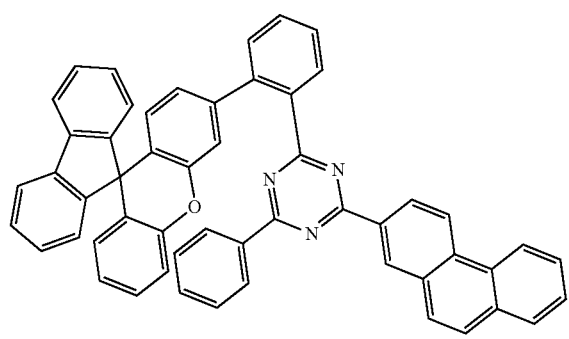
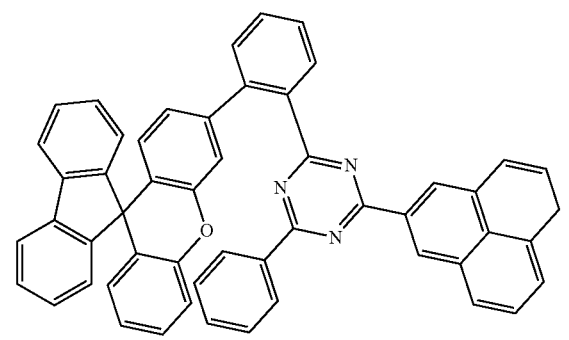
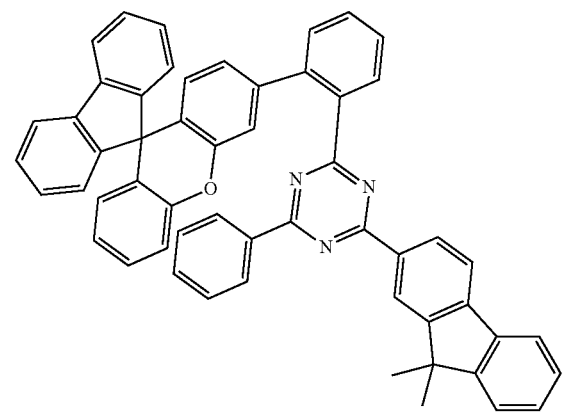
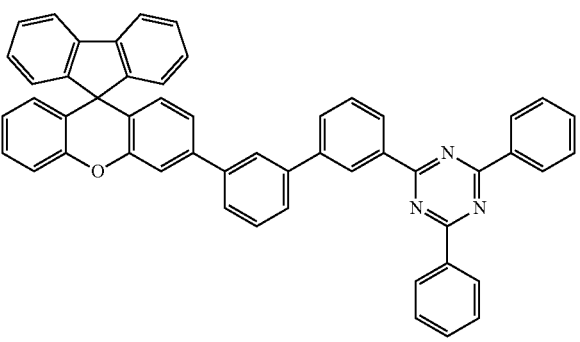
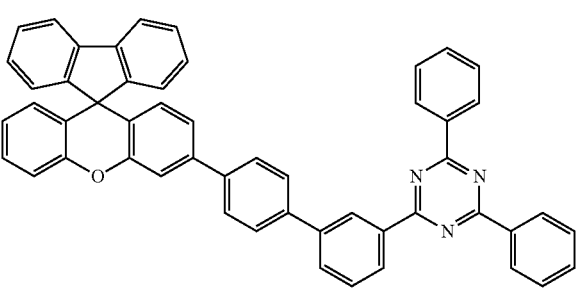
132
-continued
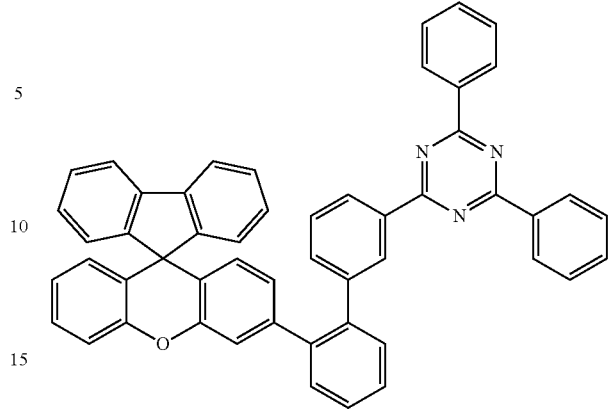
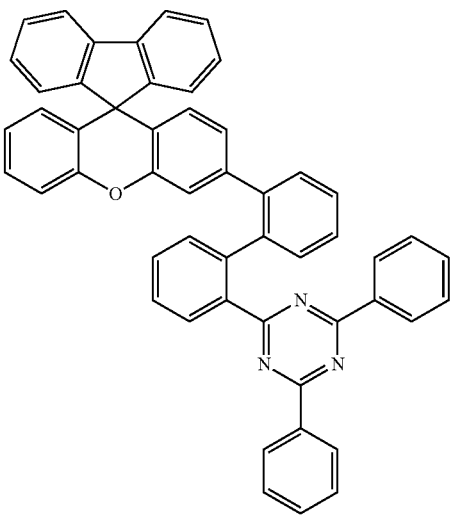
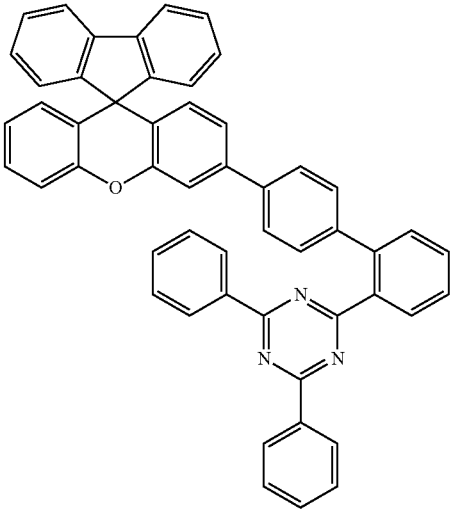

133
-continued
134
-continued
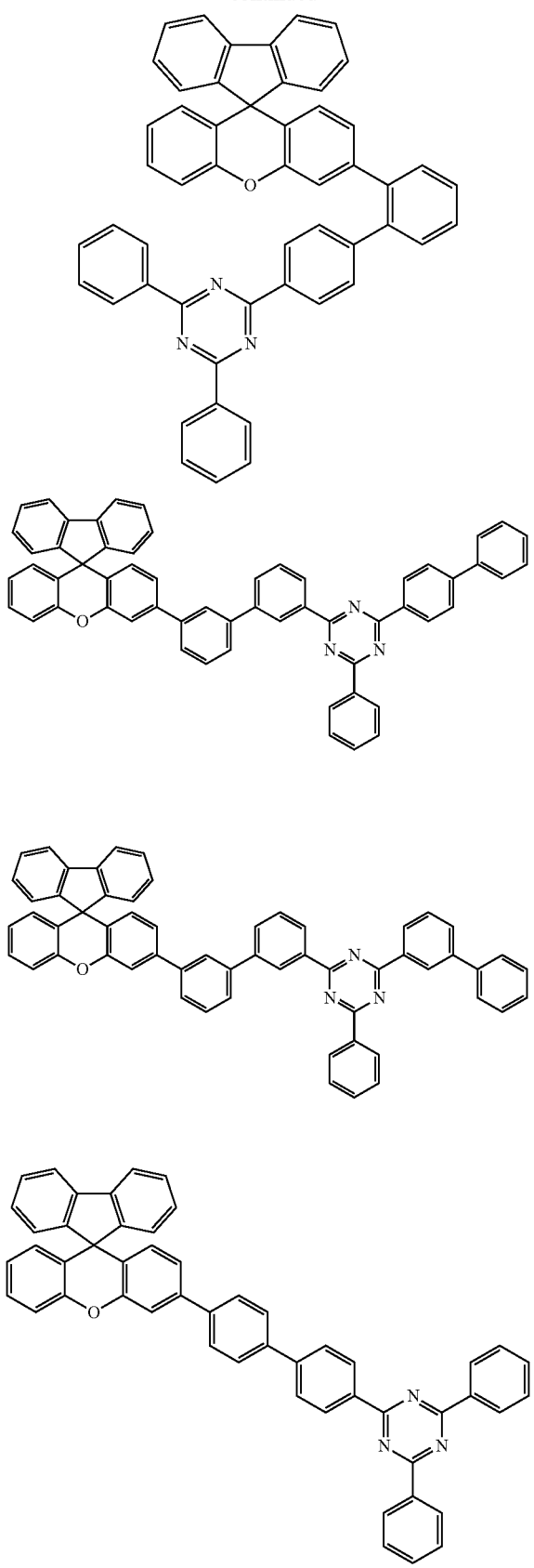
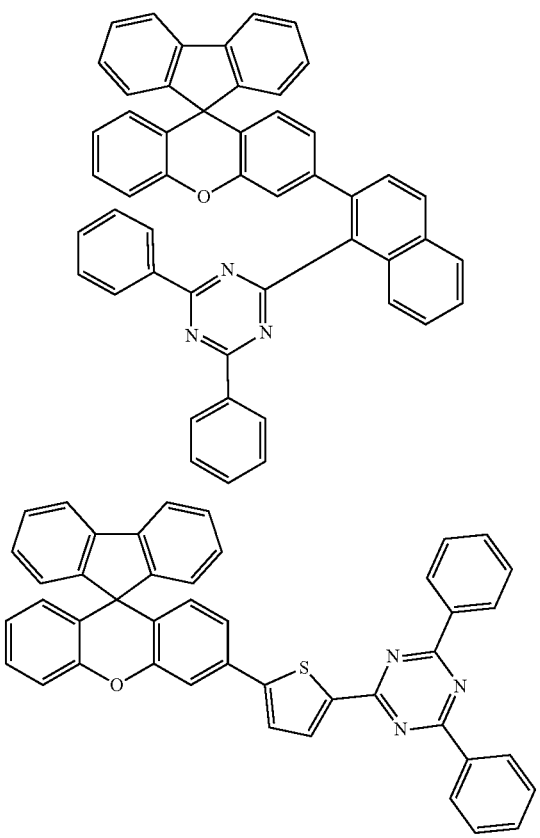

135
-continued
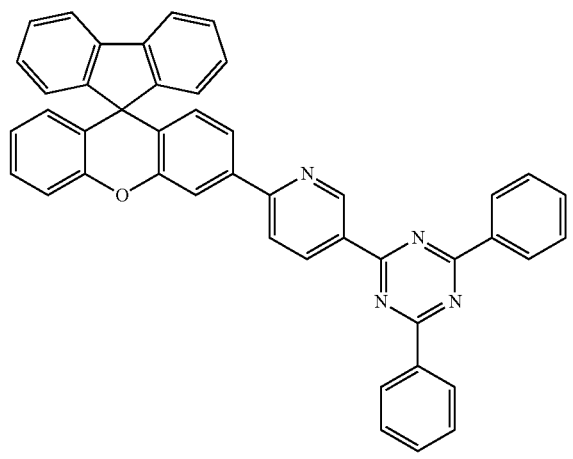
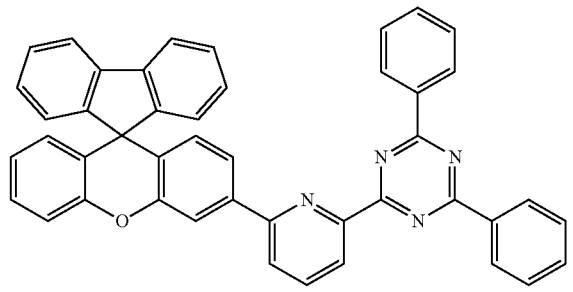
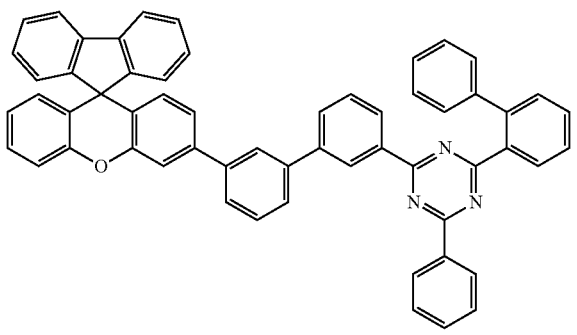
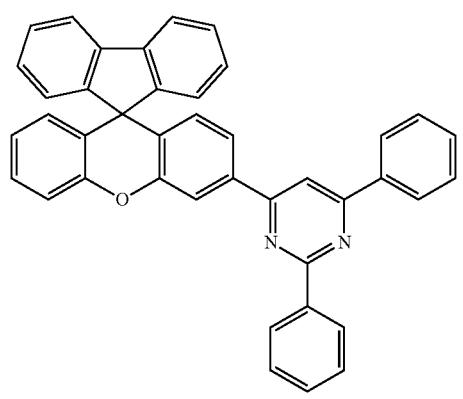
136
-continued
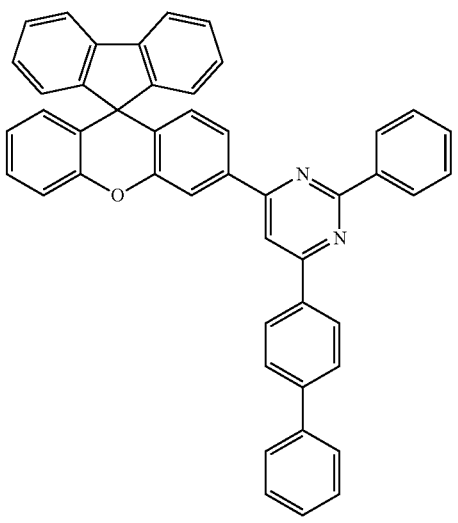
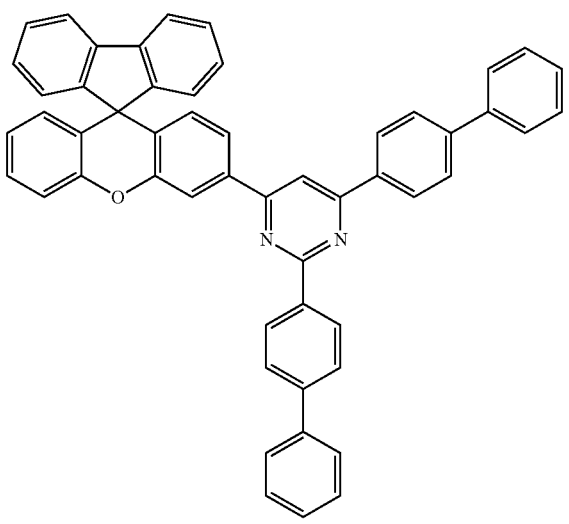
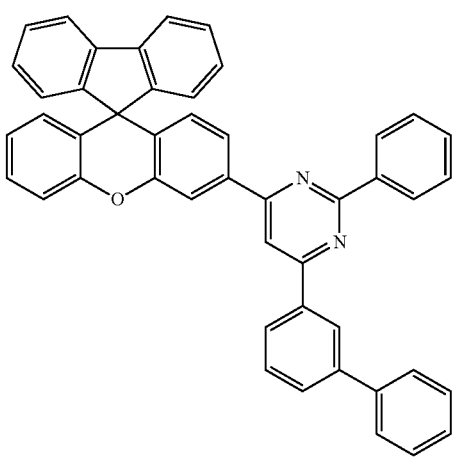

137
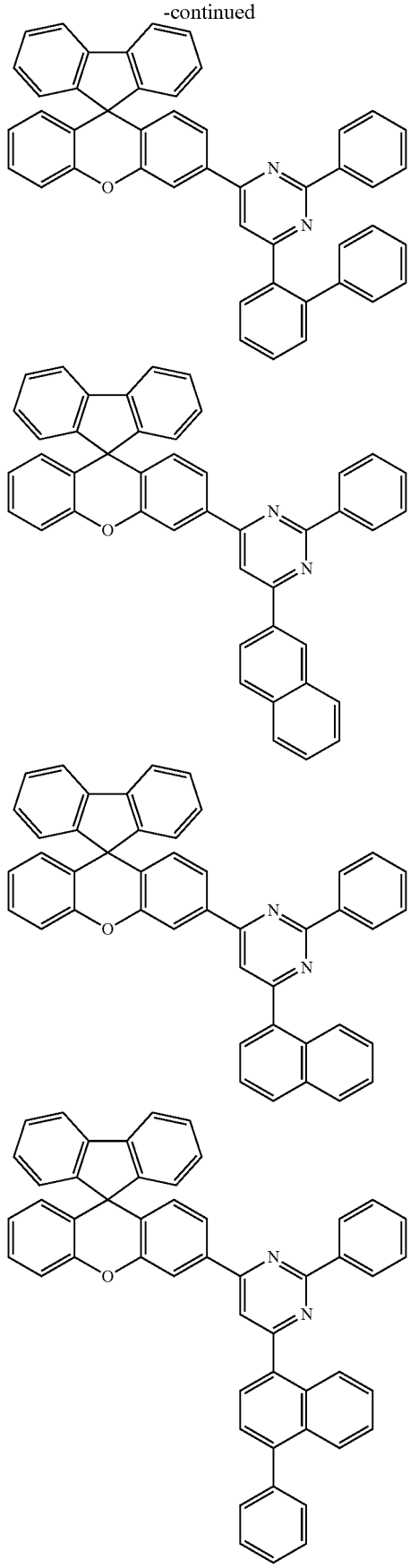
138
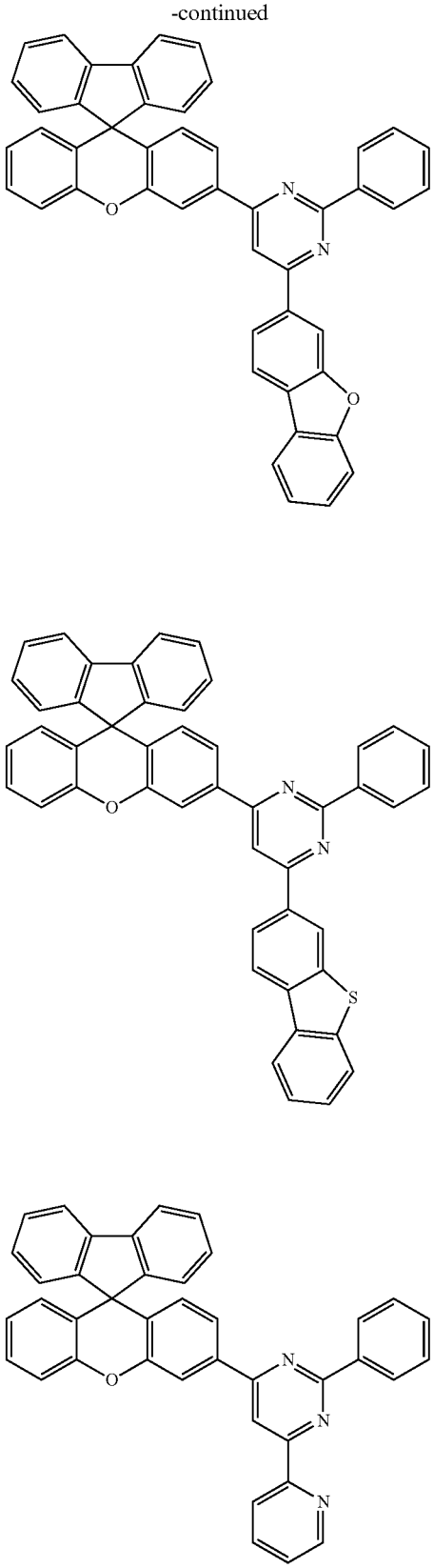

139
-continued
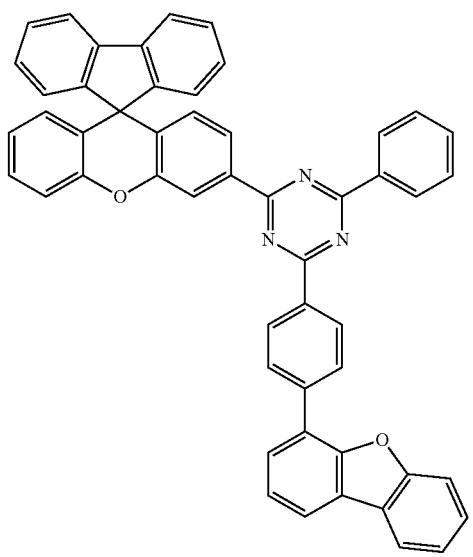
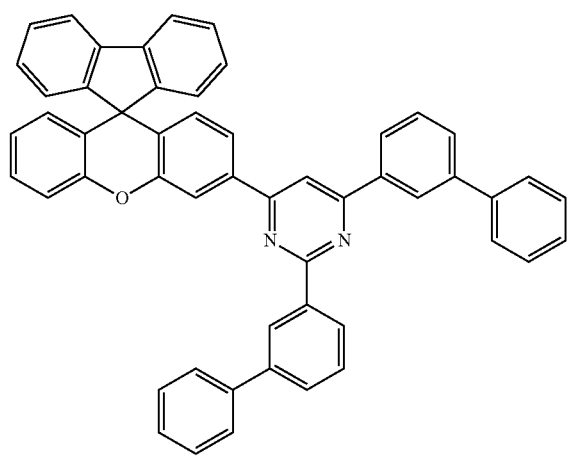
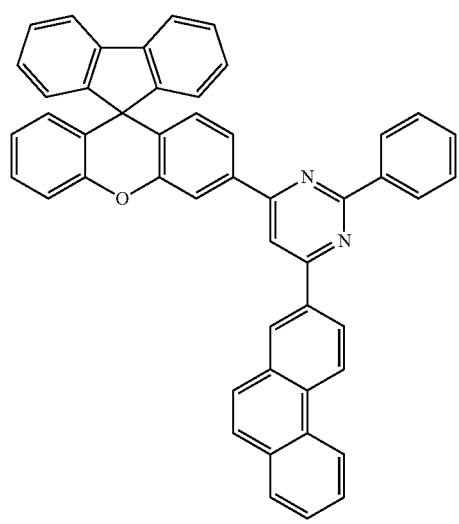
140
-continued
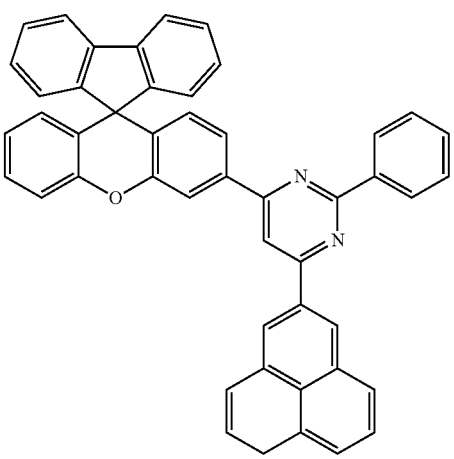
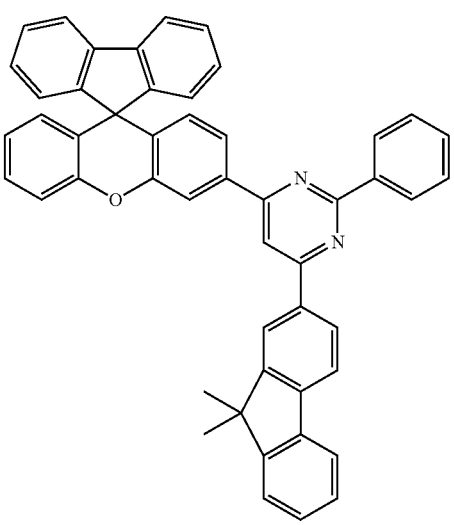
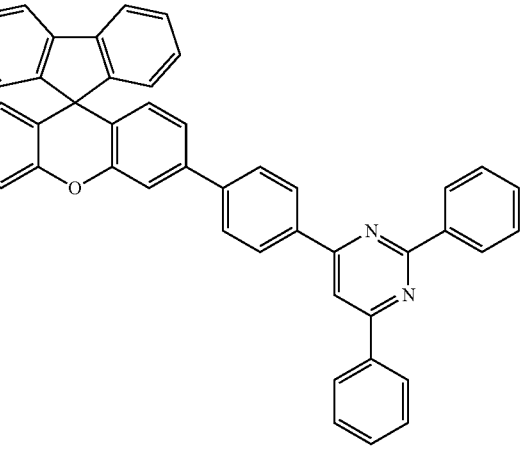

141
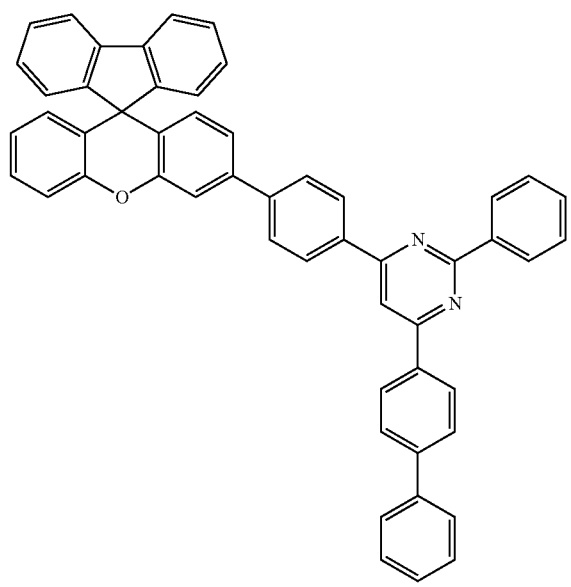
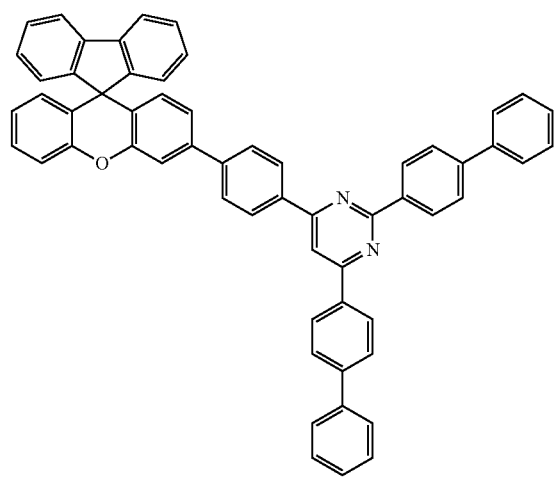
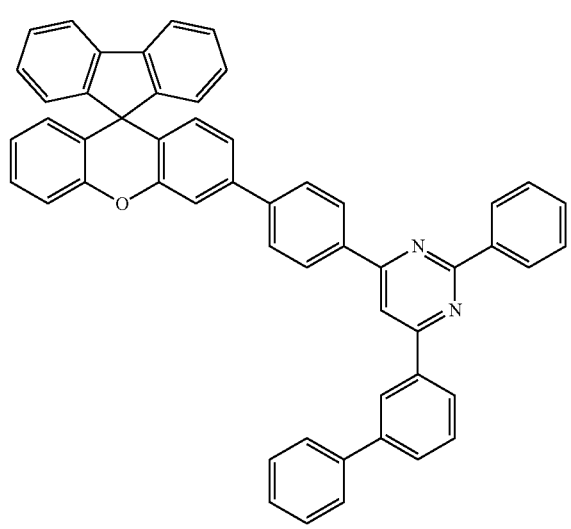
142
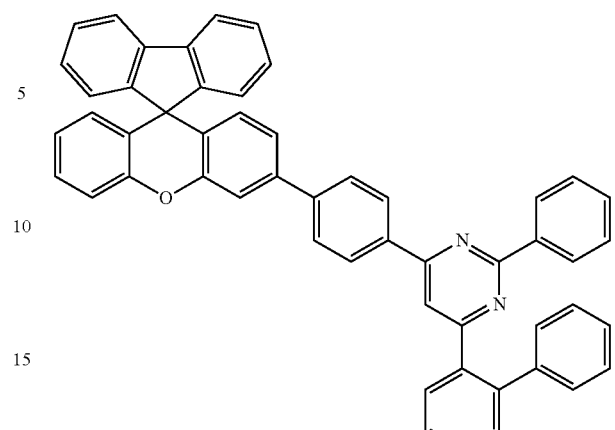
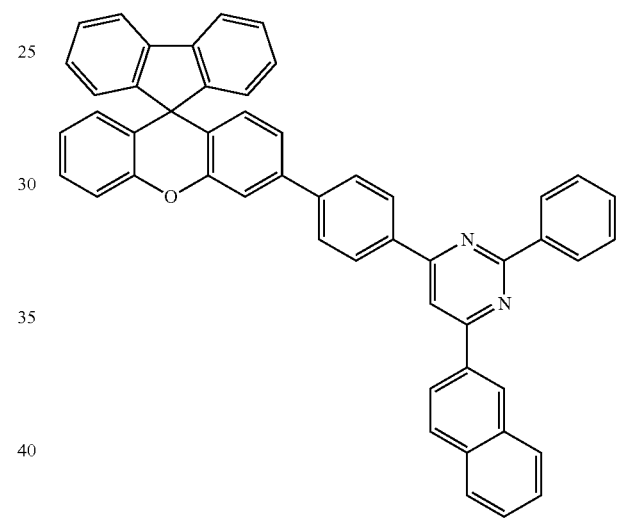
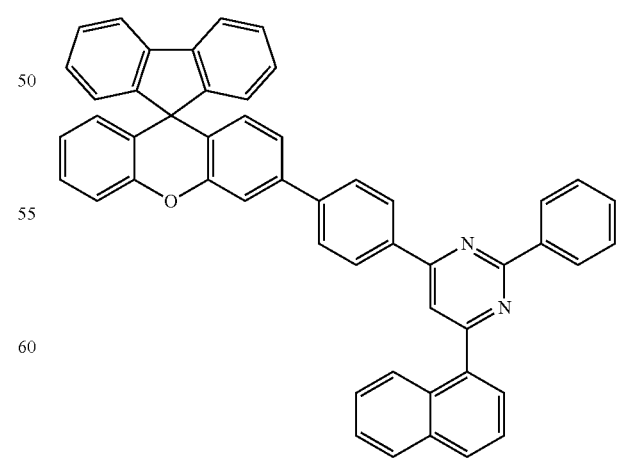

143
-continued
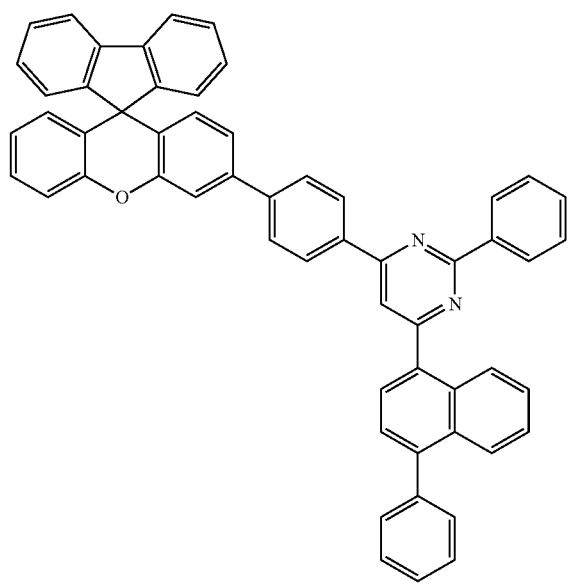
144
-continued
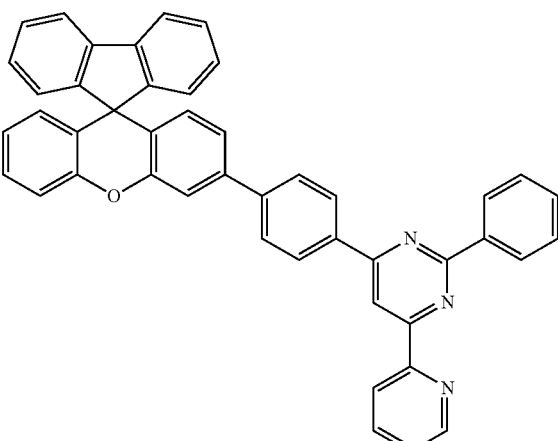
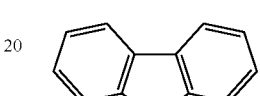
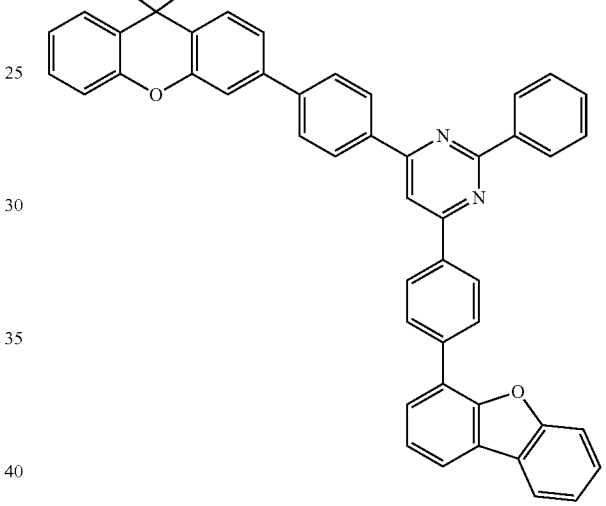
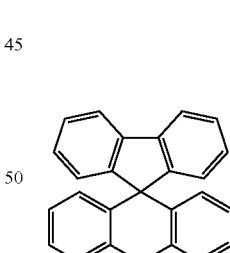
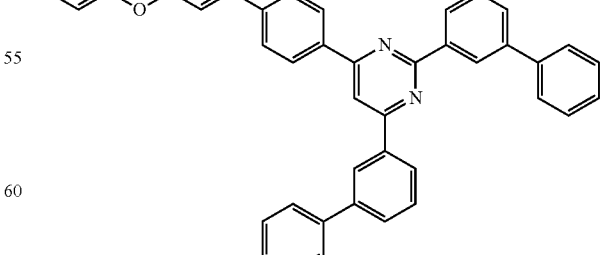

145
-continued
146
-continued
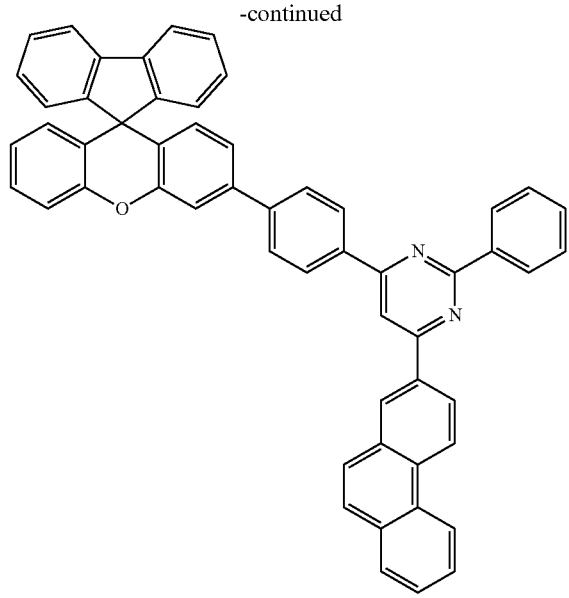
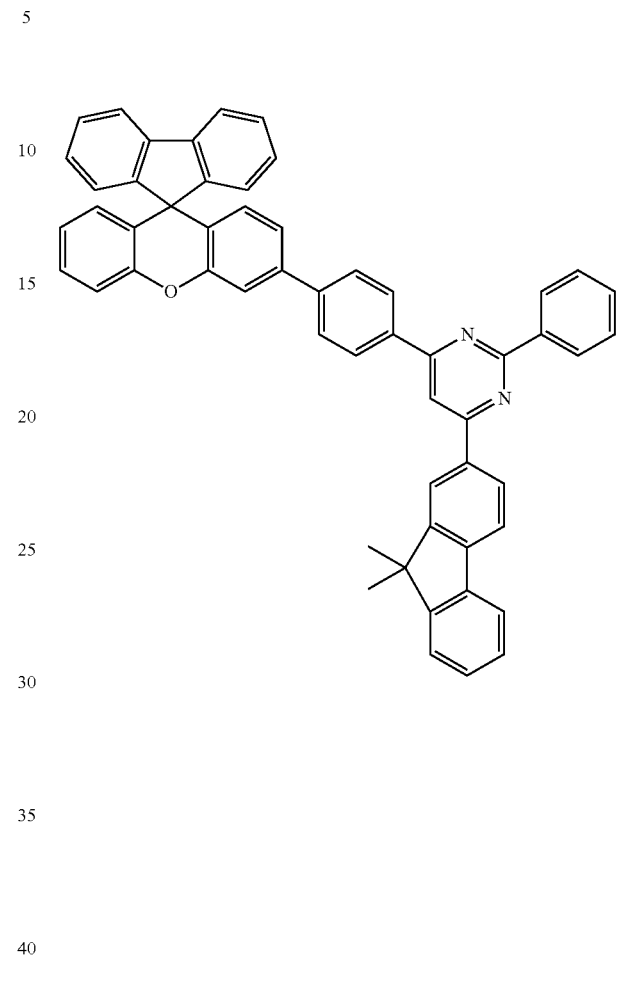
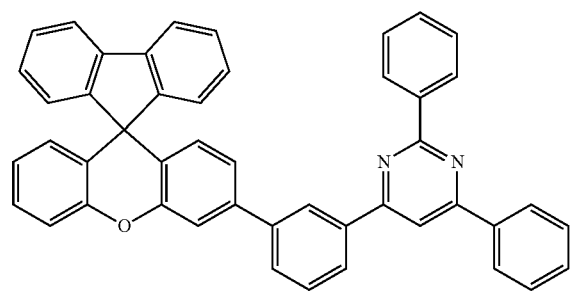

-continued
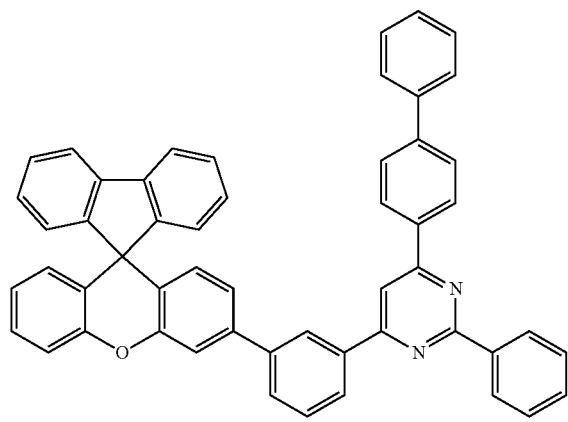
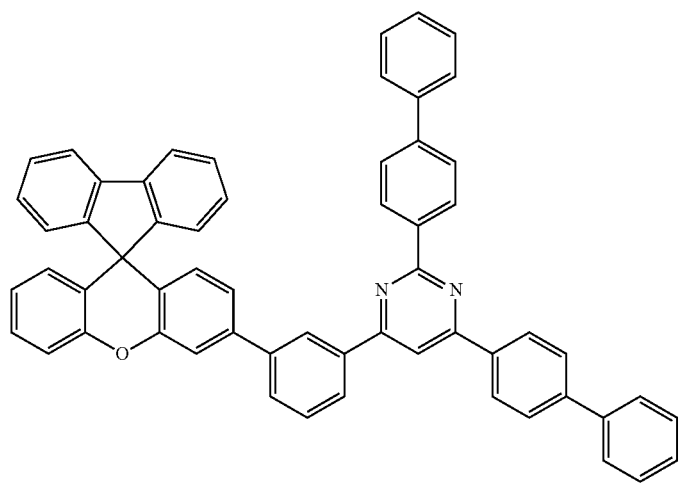
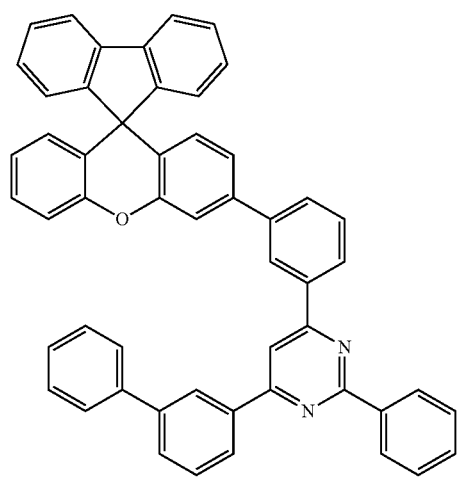
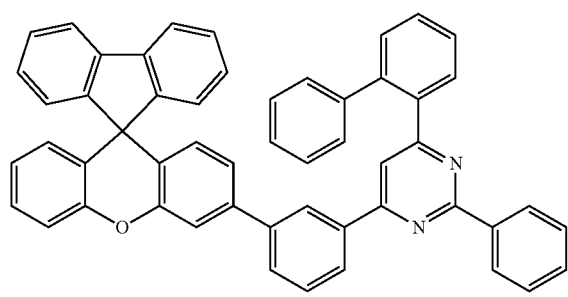

-continued
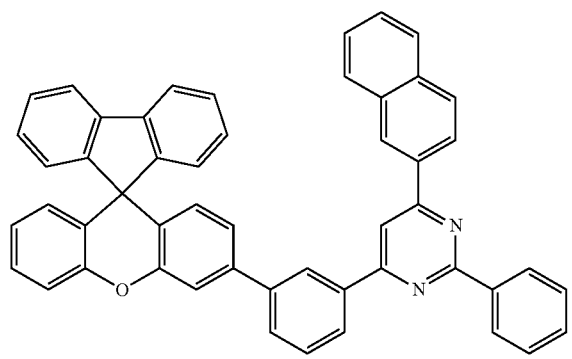
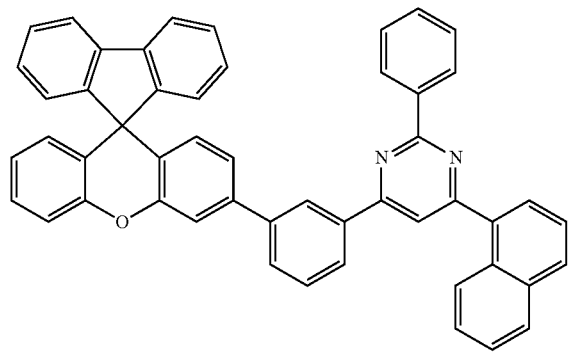
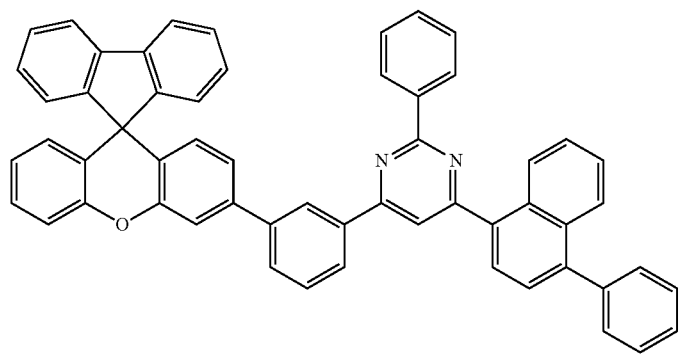
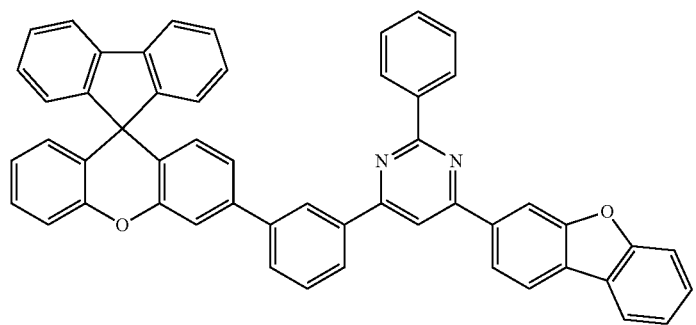

-continued
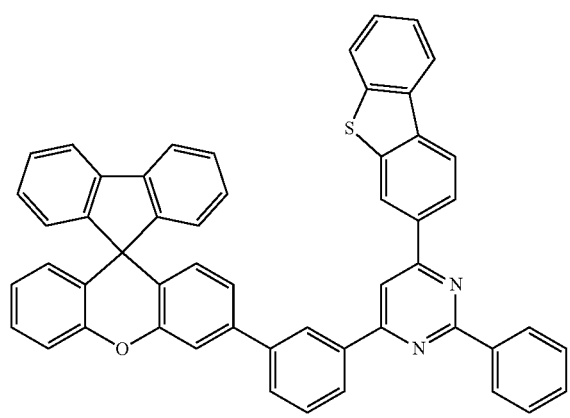
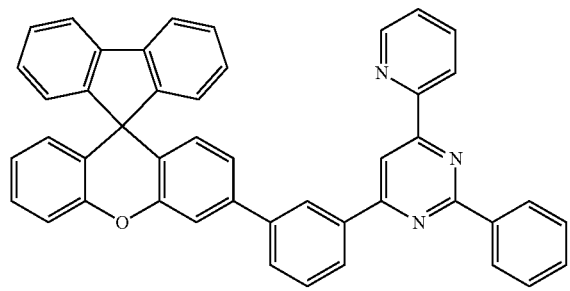
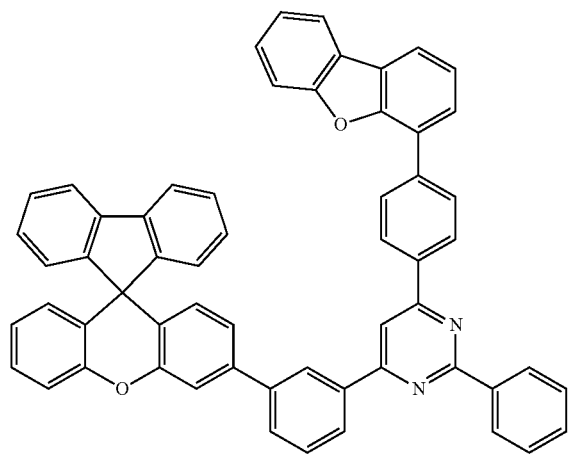
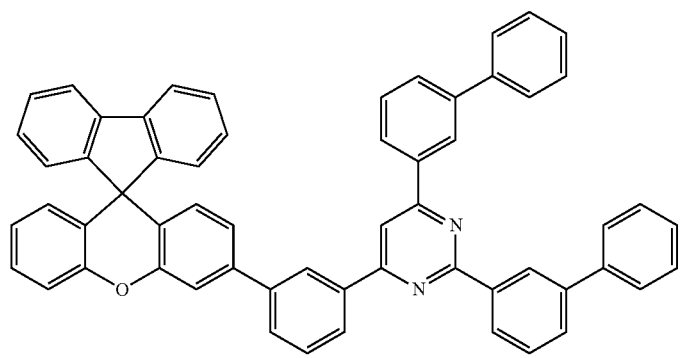

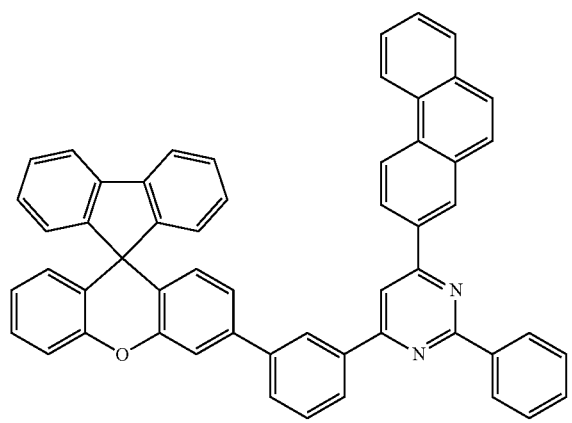
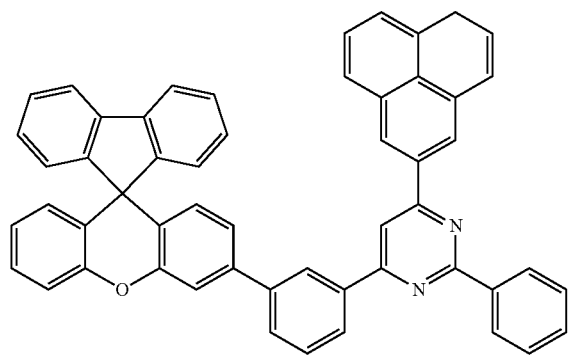
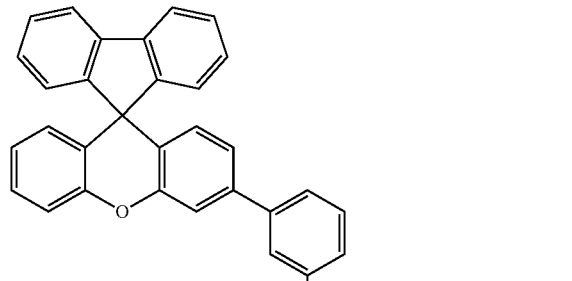
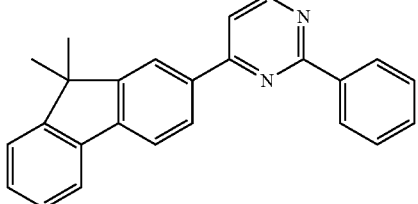
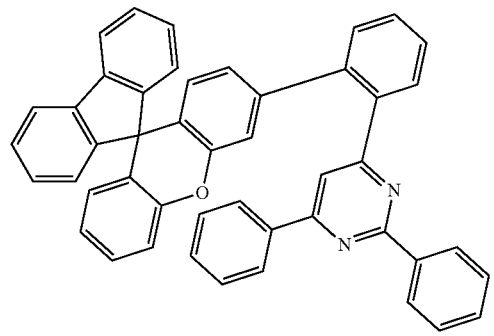

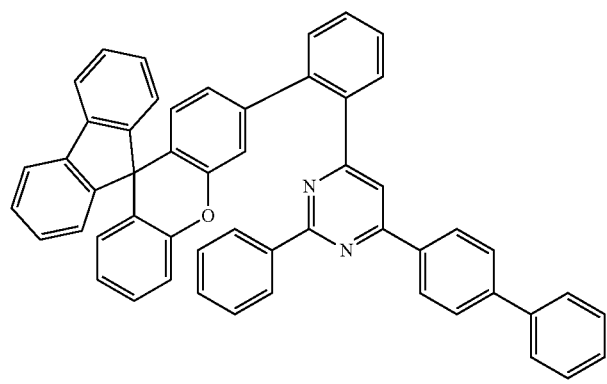
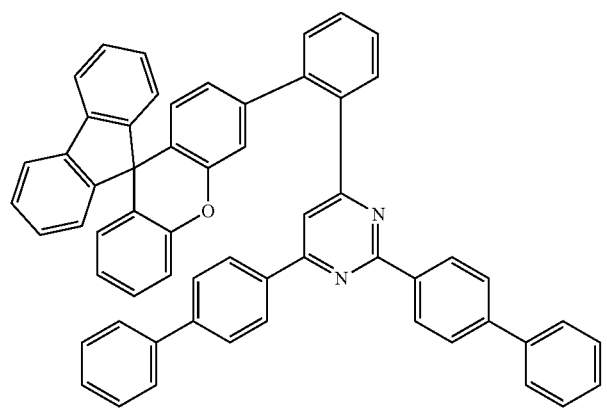
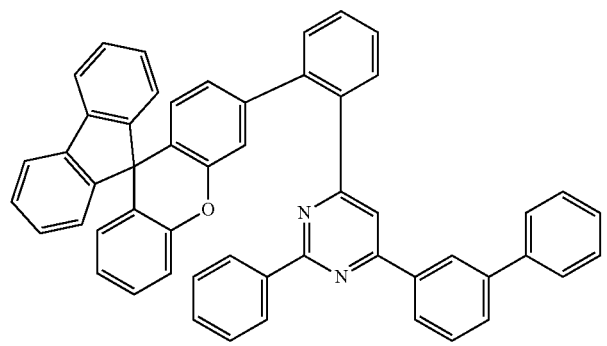
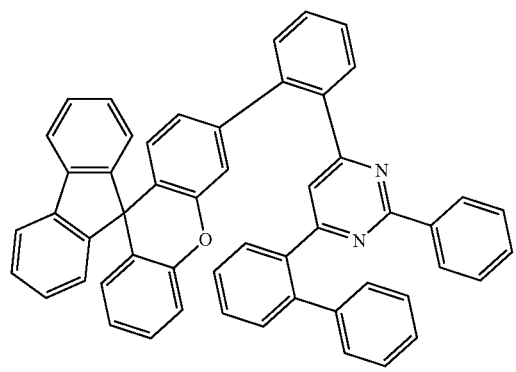

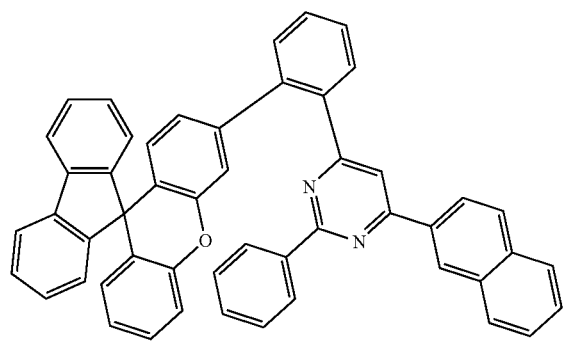
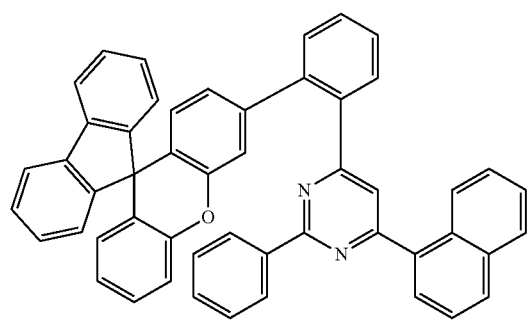
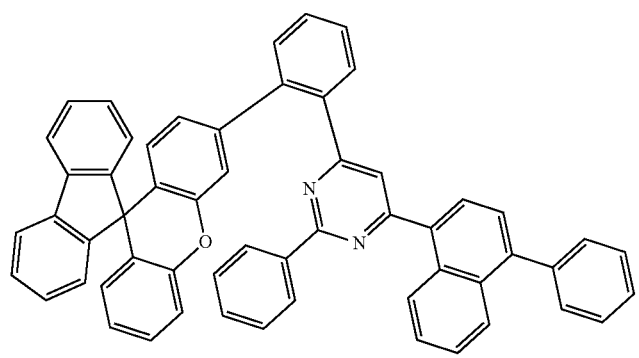
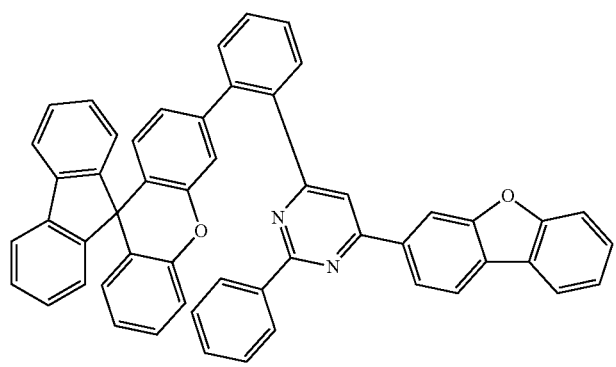

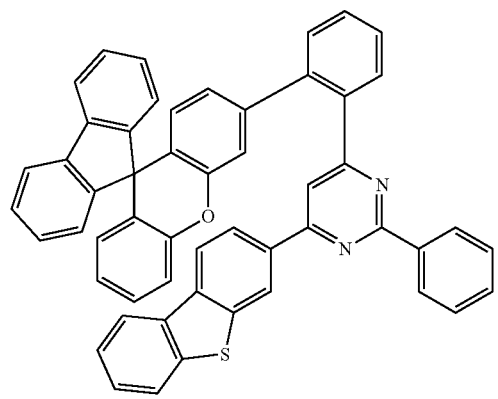
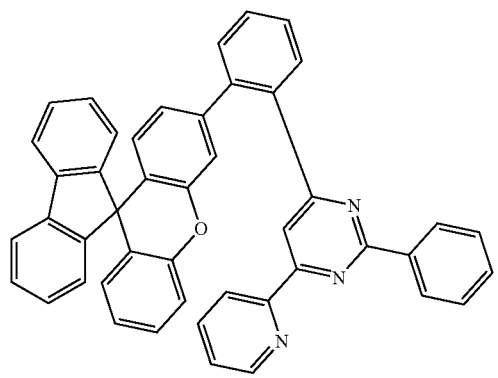
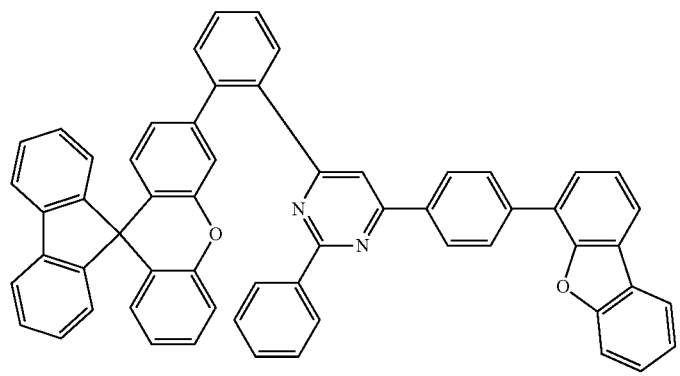
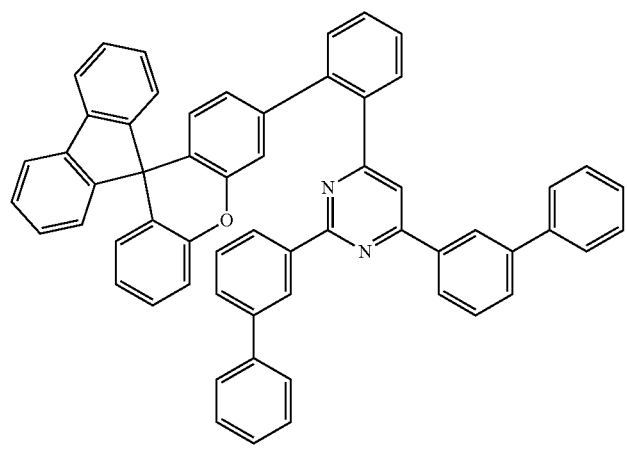

-continued
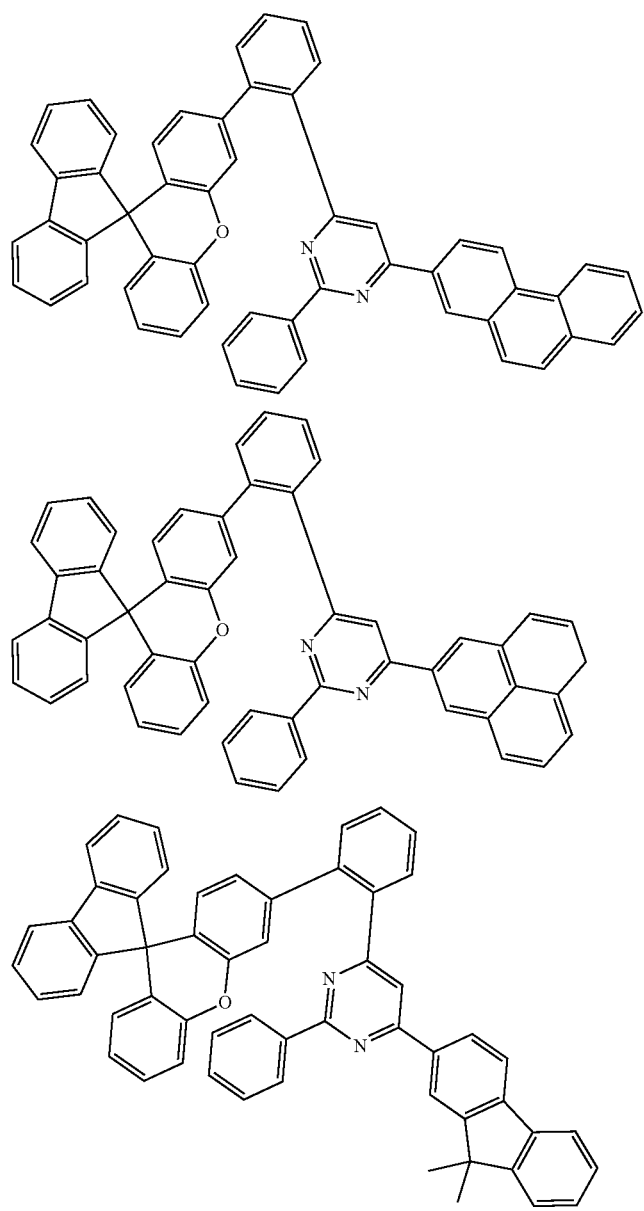
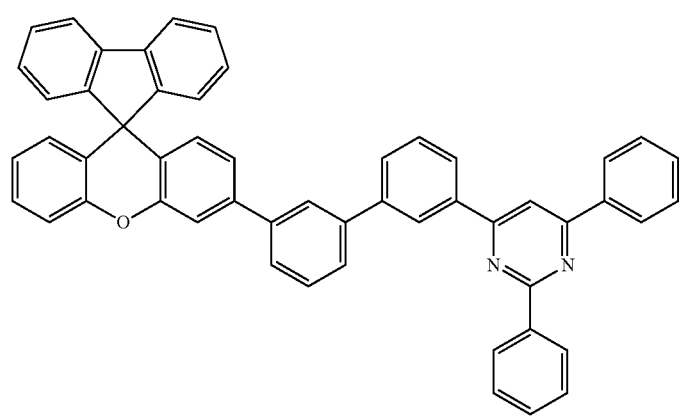

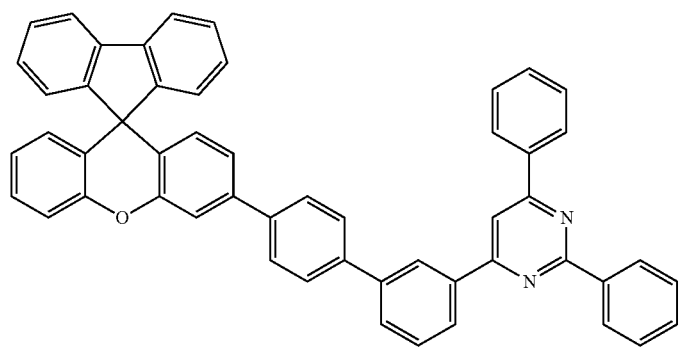
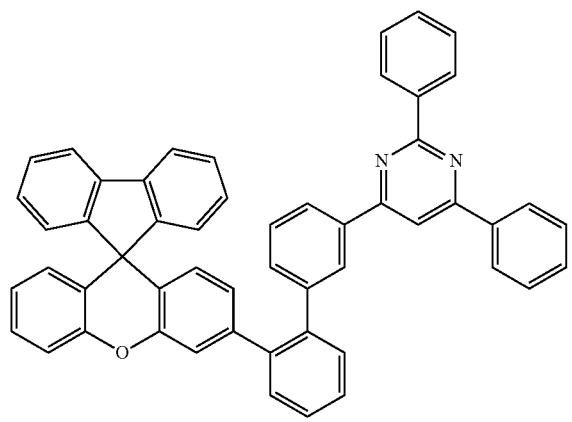
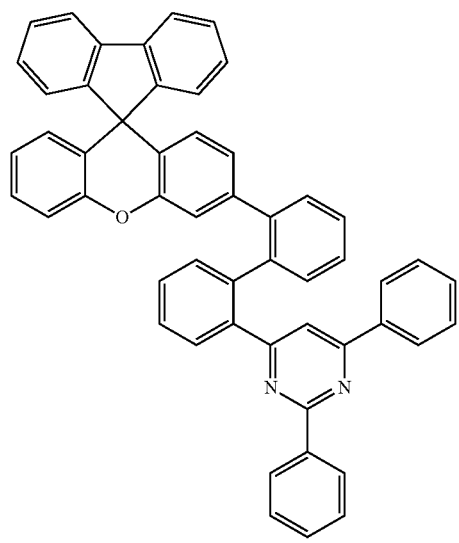

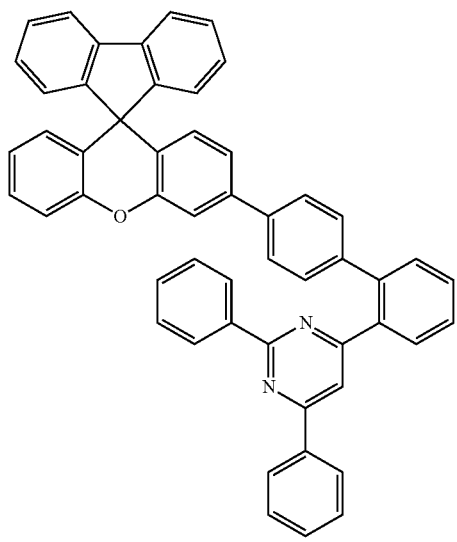
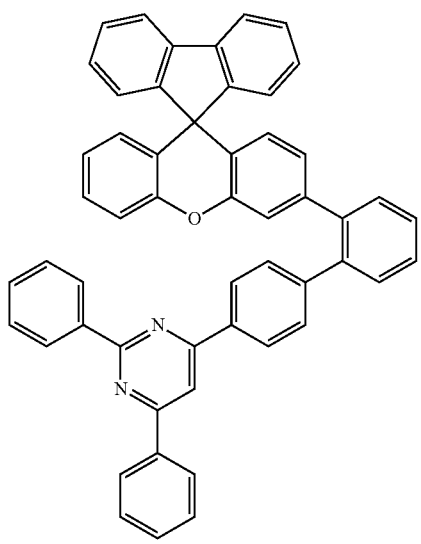
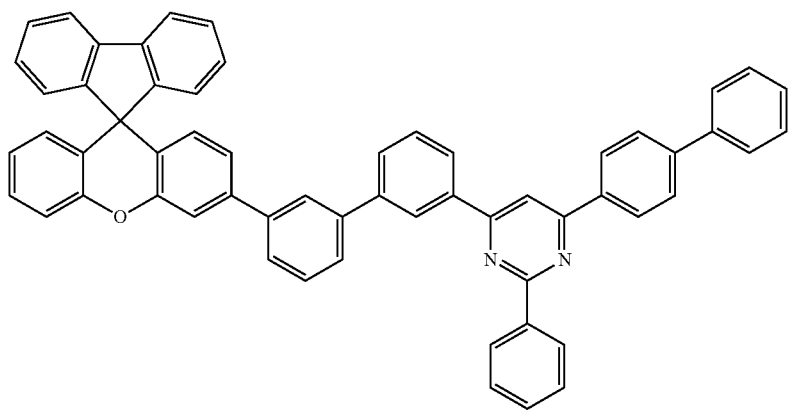

-continued
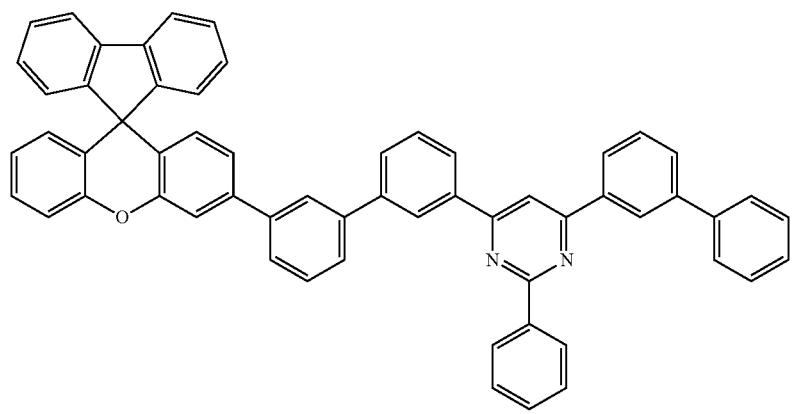
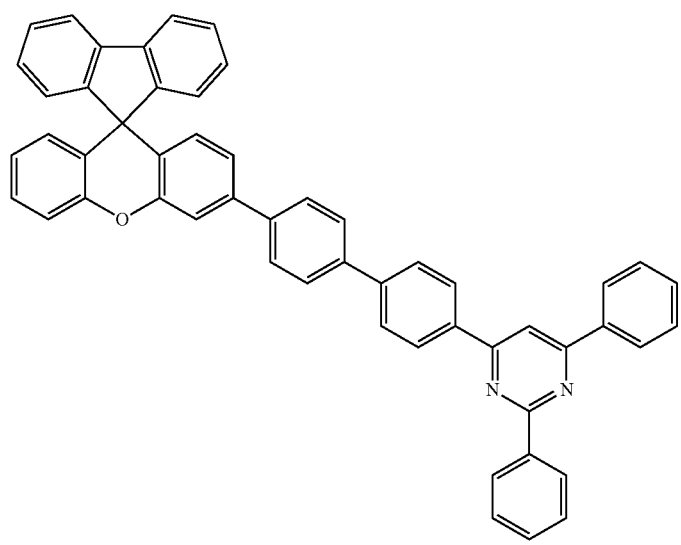
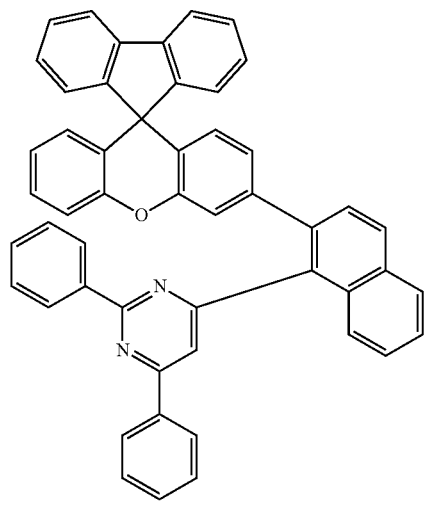

-continued
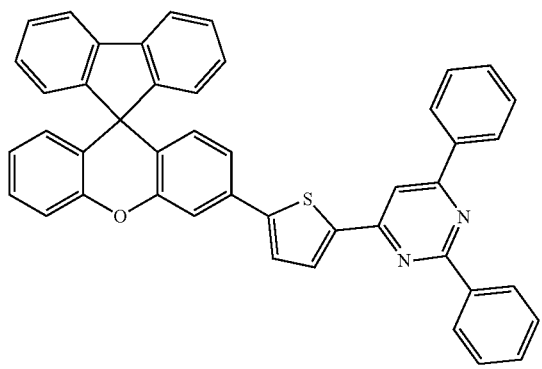
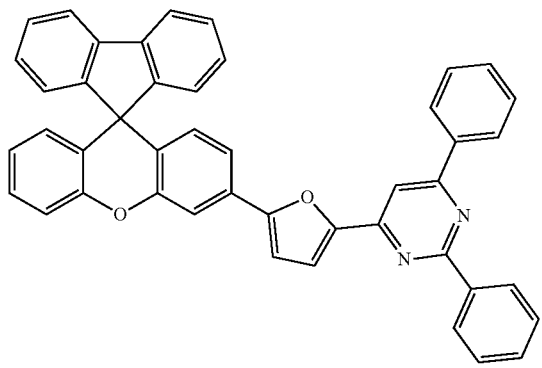
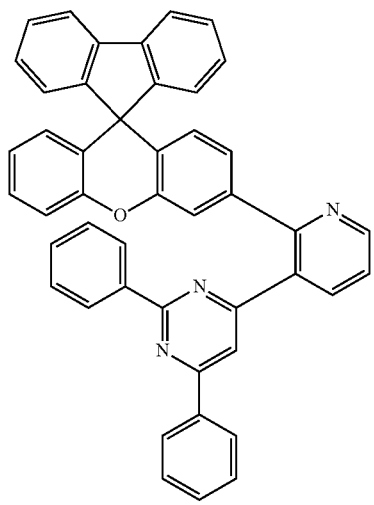
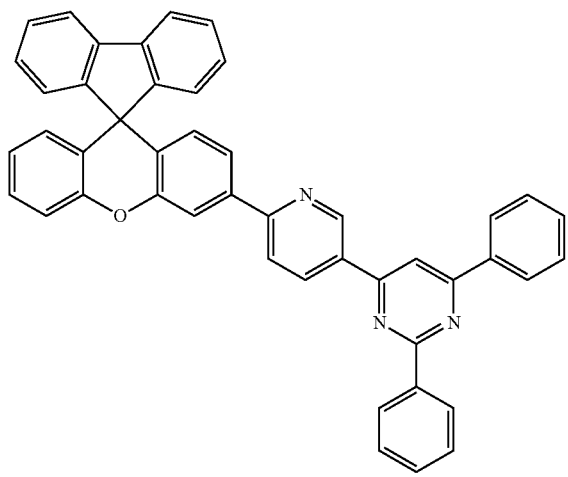

-continued
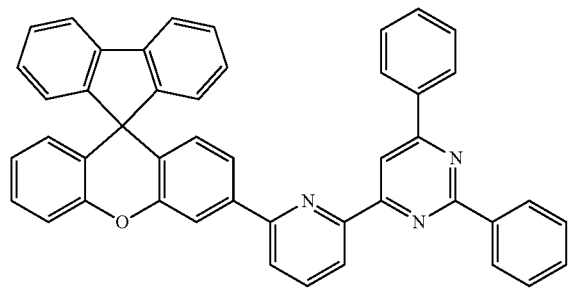
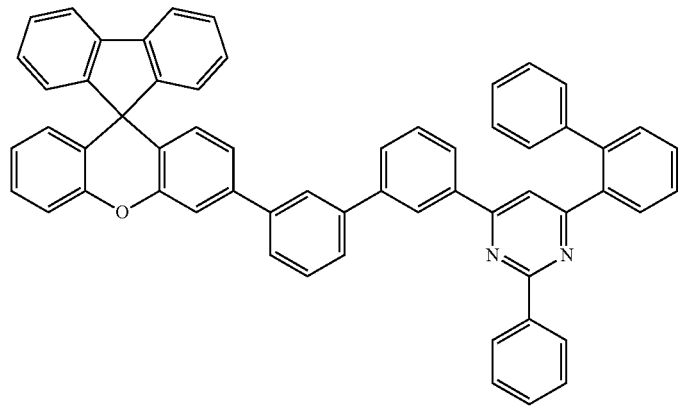
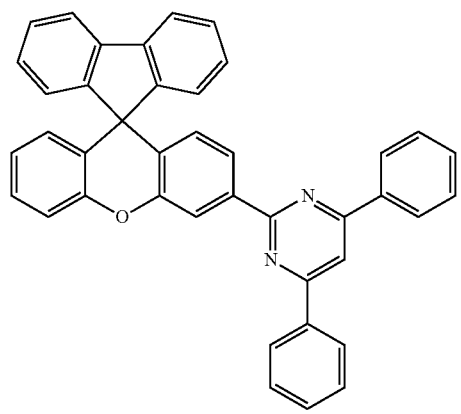
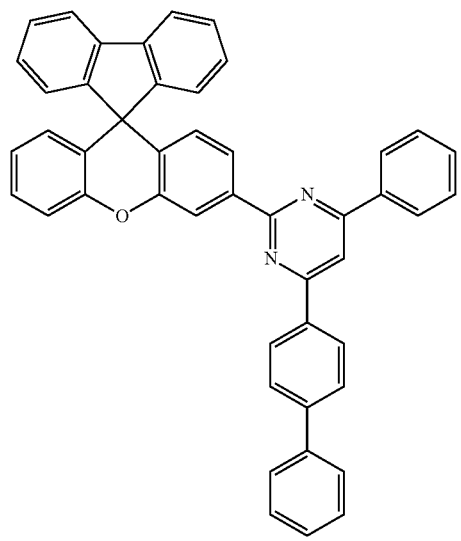

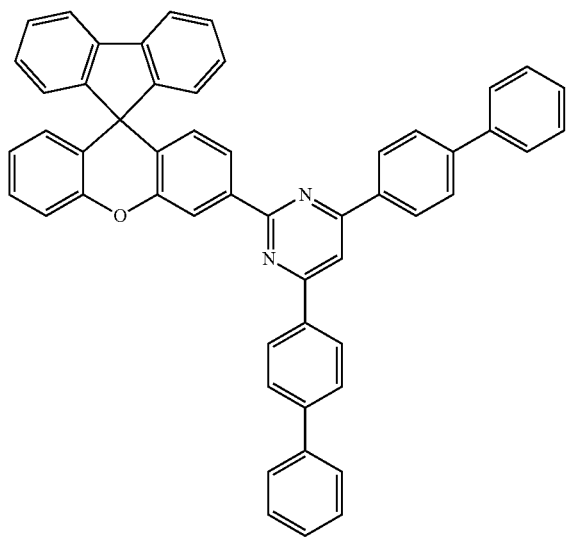
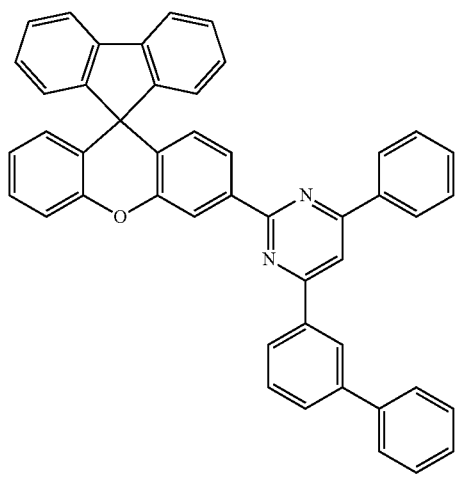
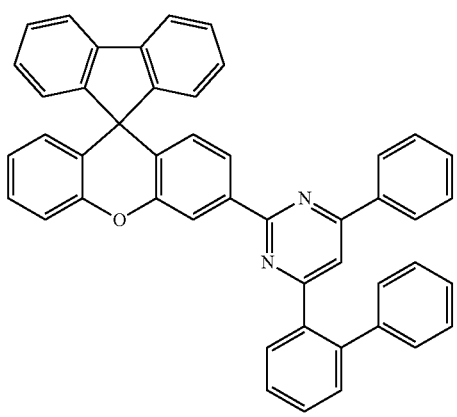

-continued
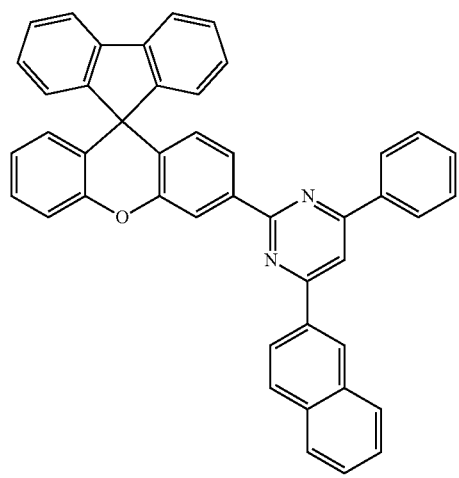
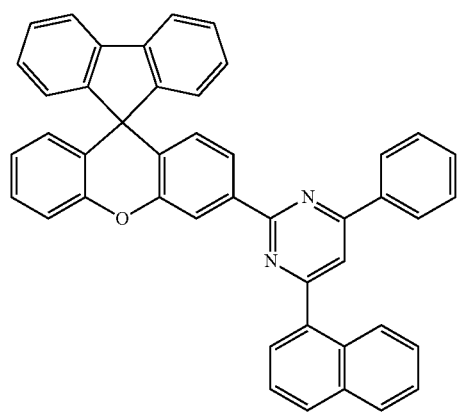
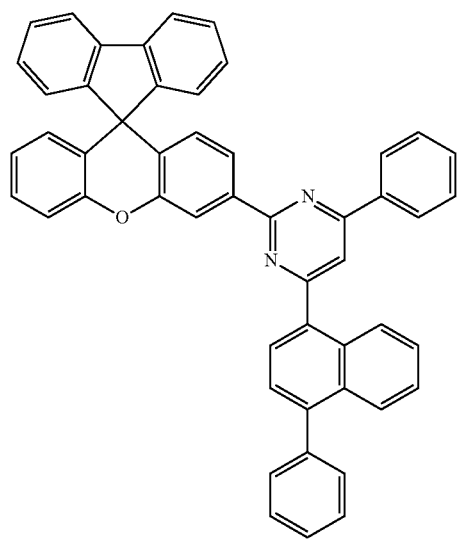

-continued
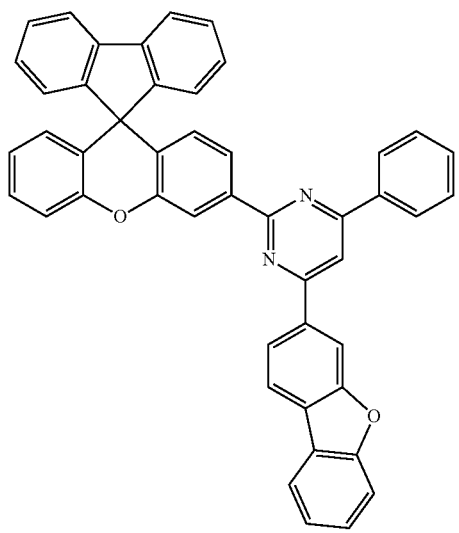
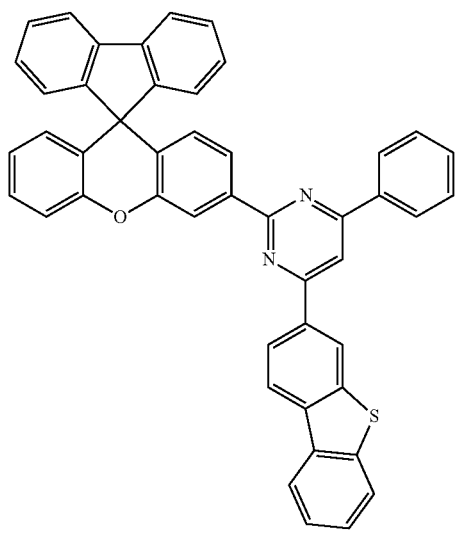
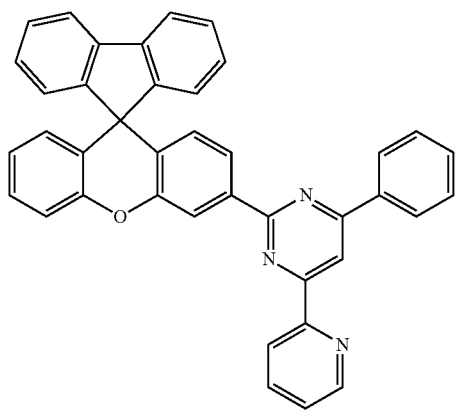

-continued
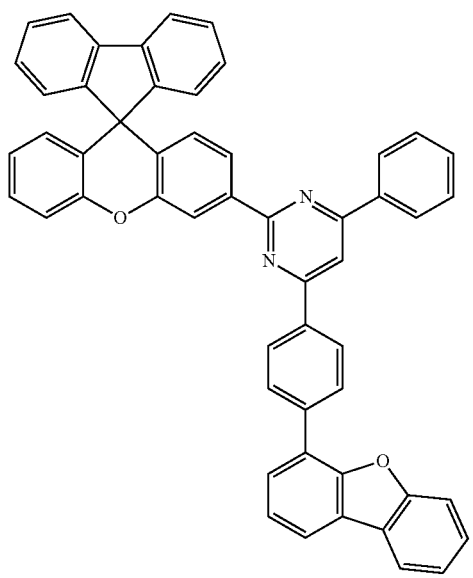
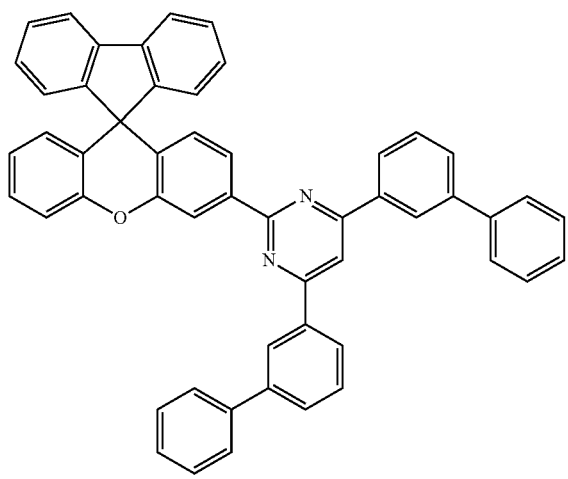
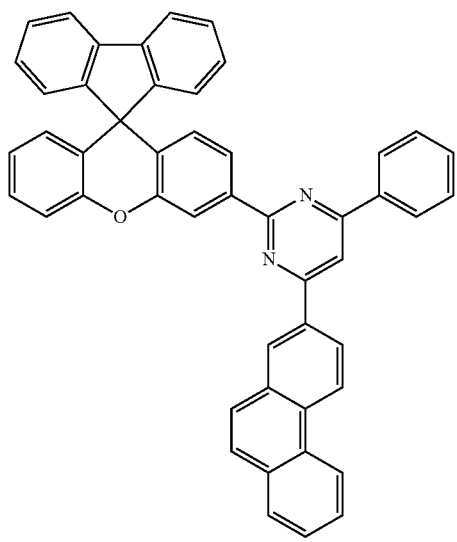

-continued
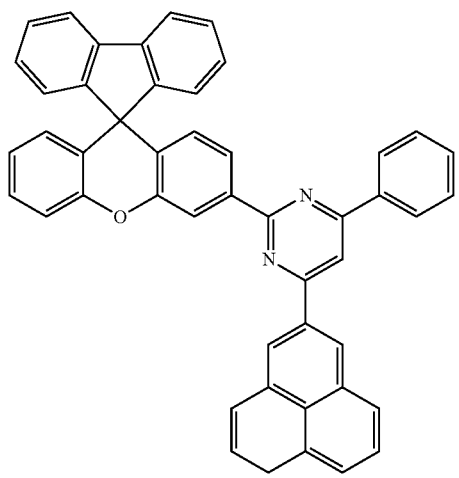
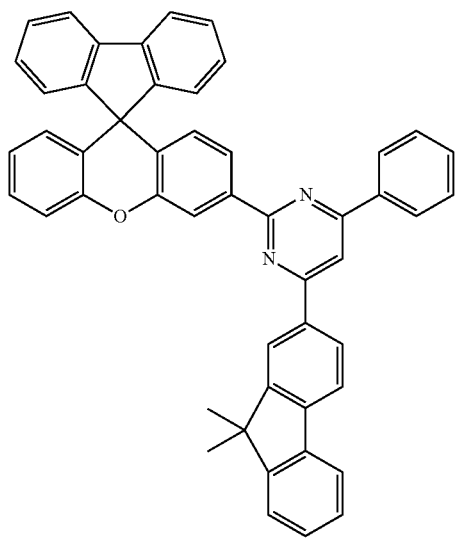
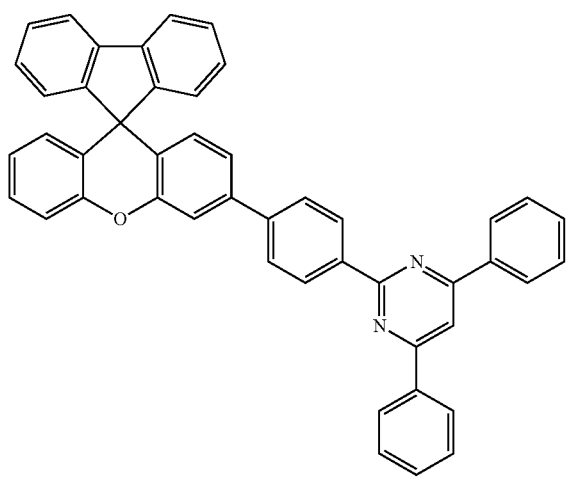

-continued
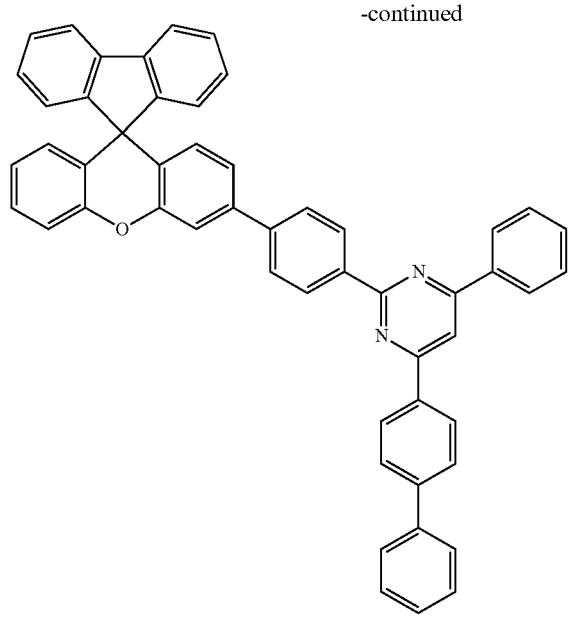
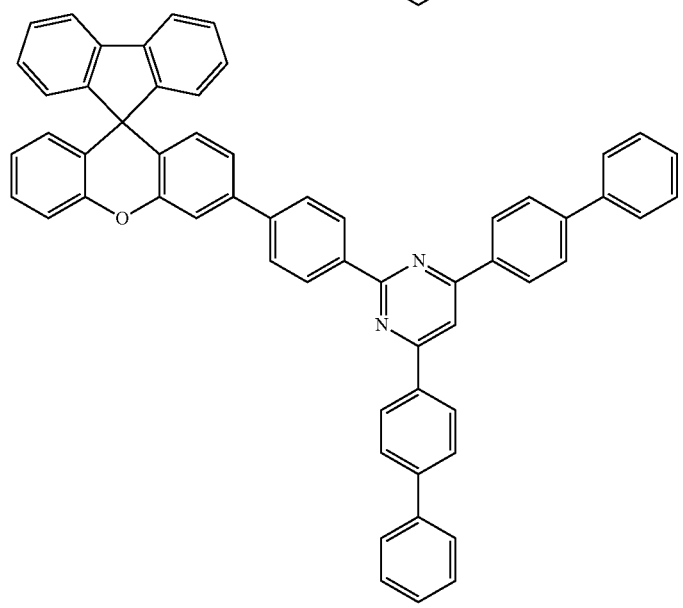
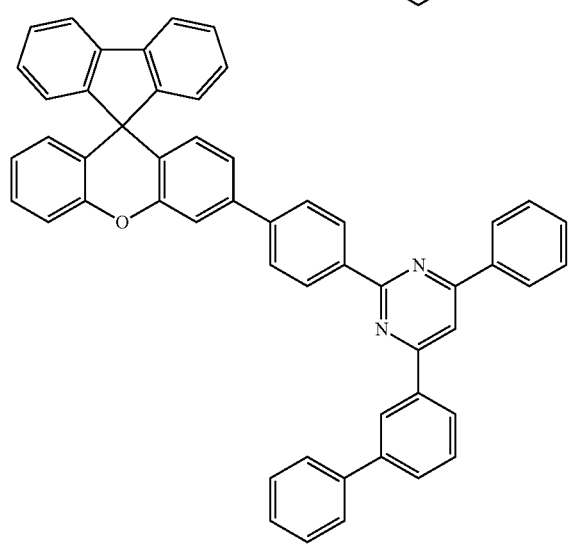

-continued
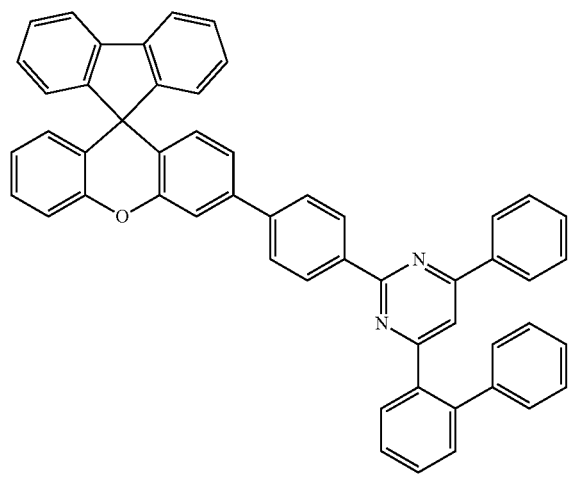
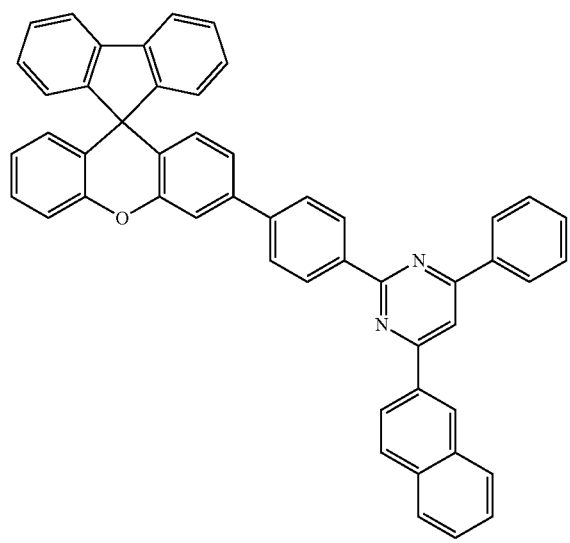
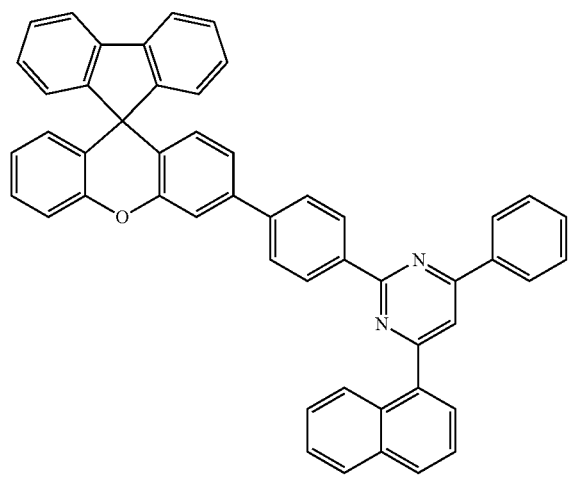

-continued
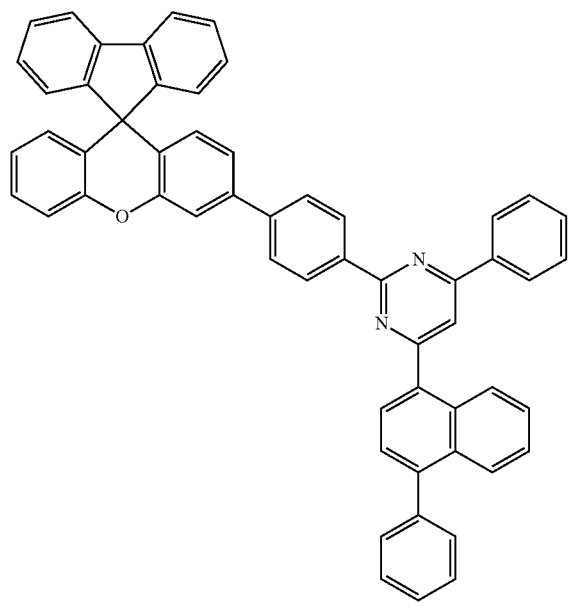
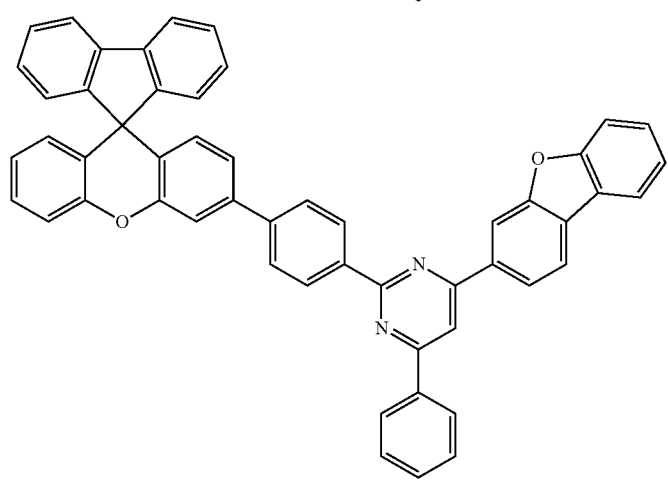
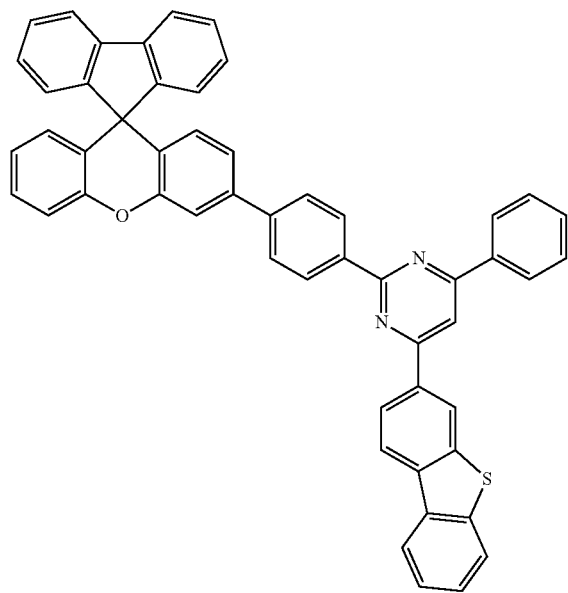

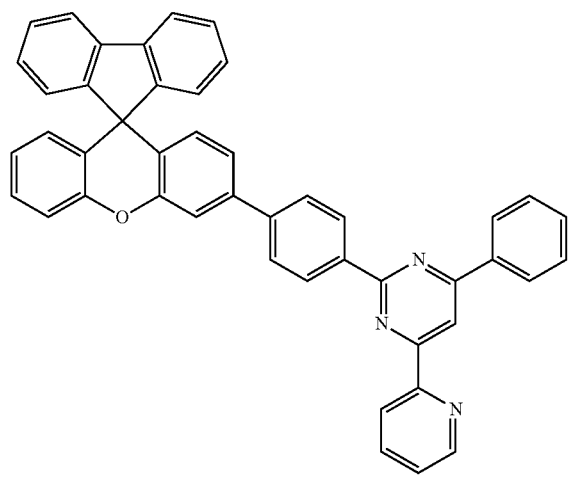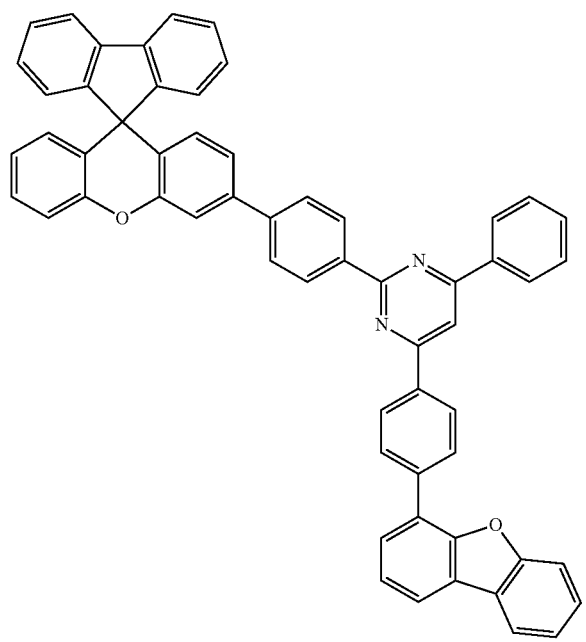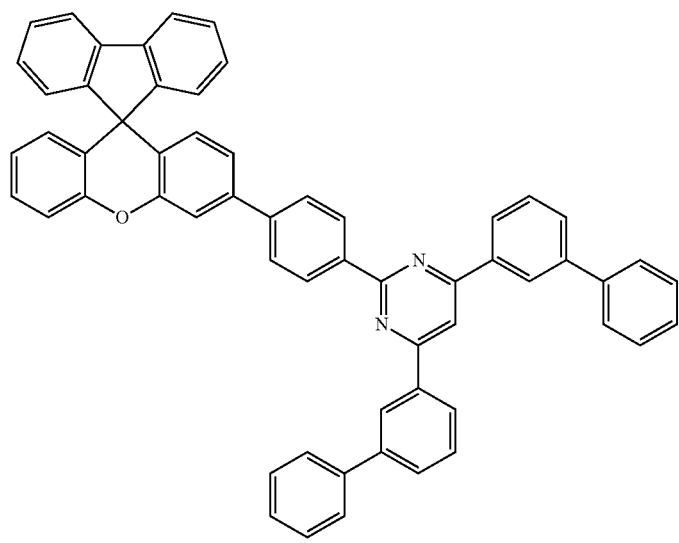

-continued
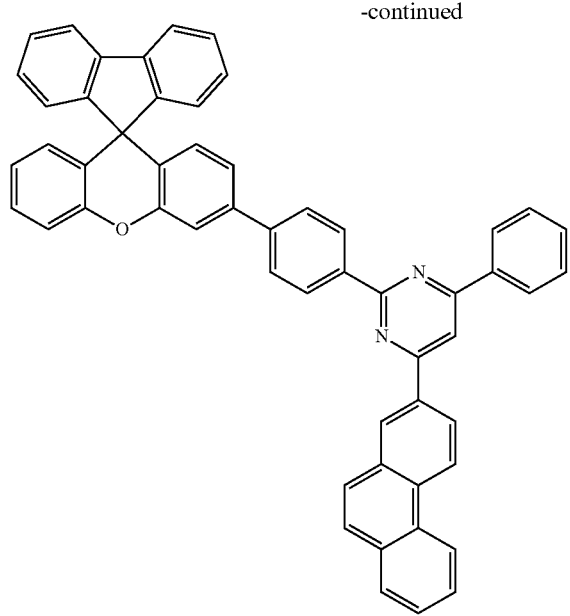
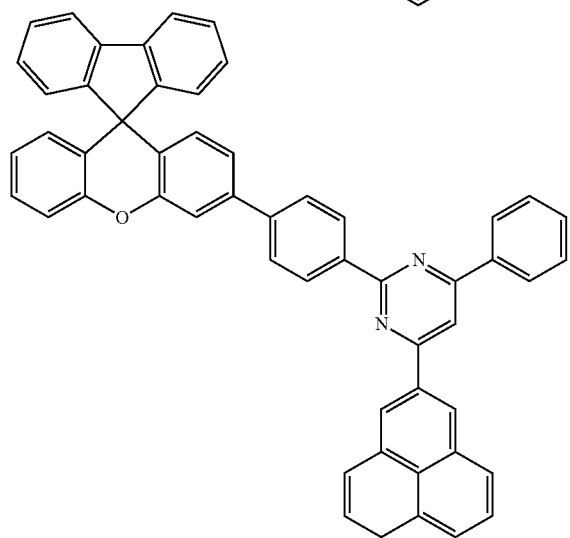
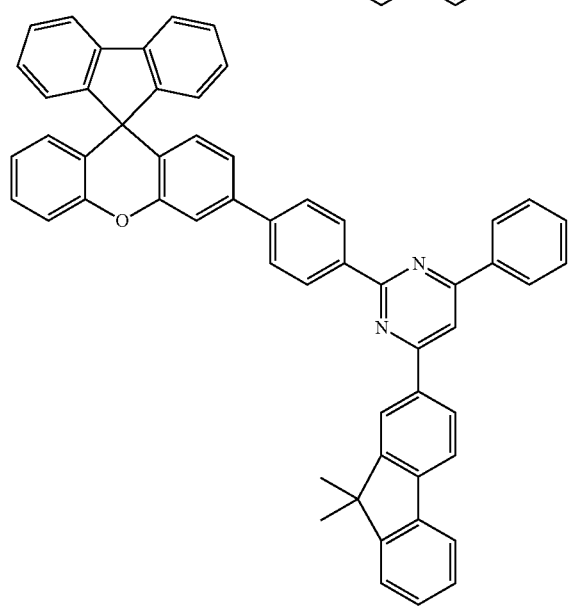

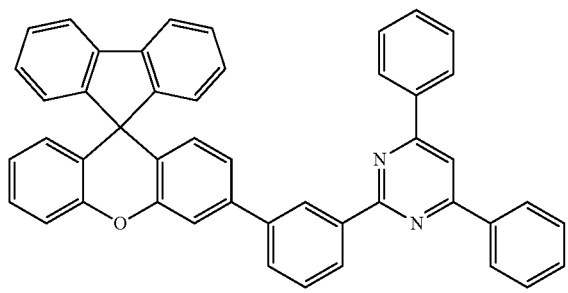
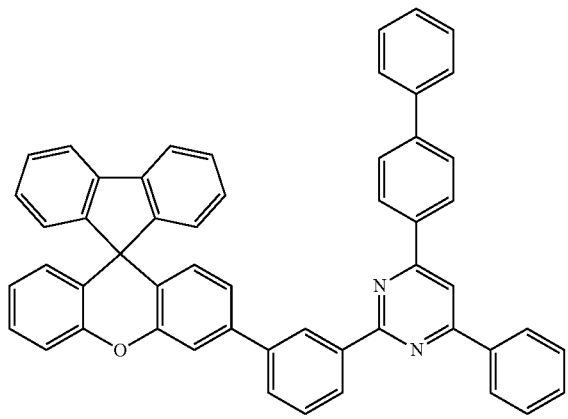
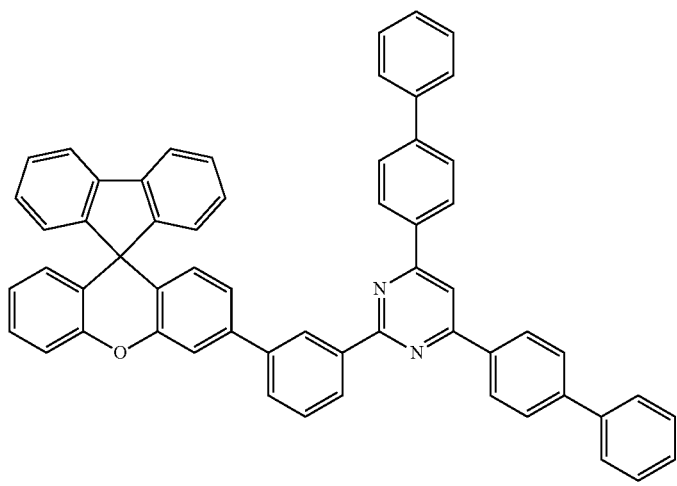
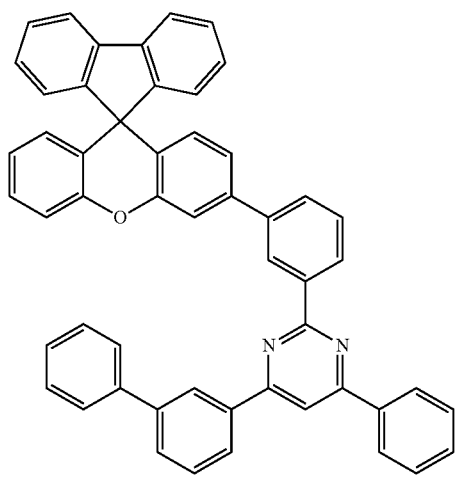

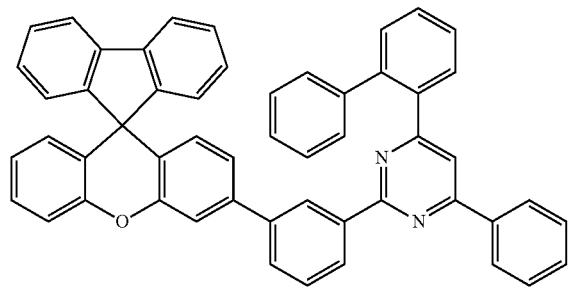
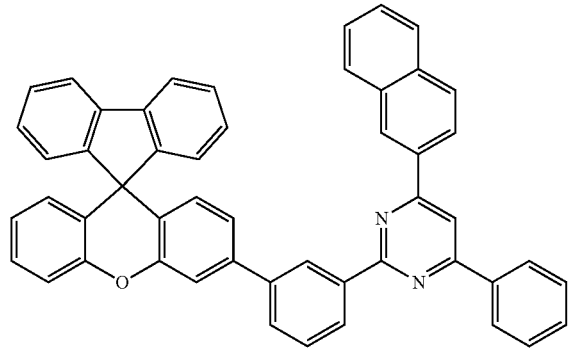
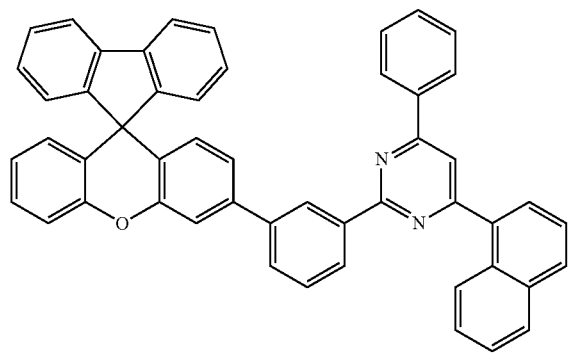
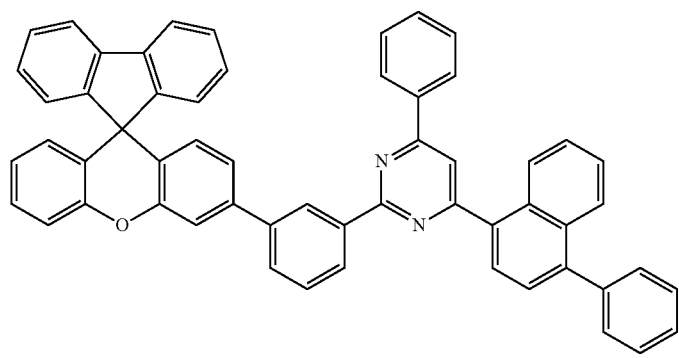
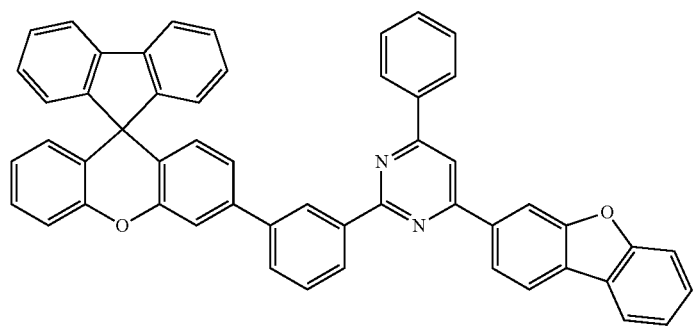

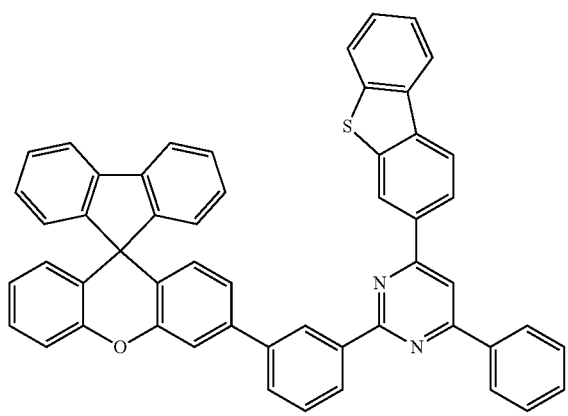
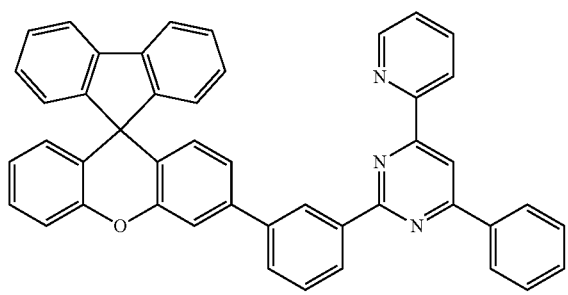
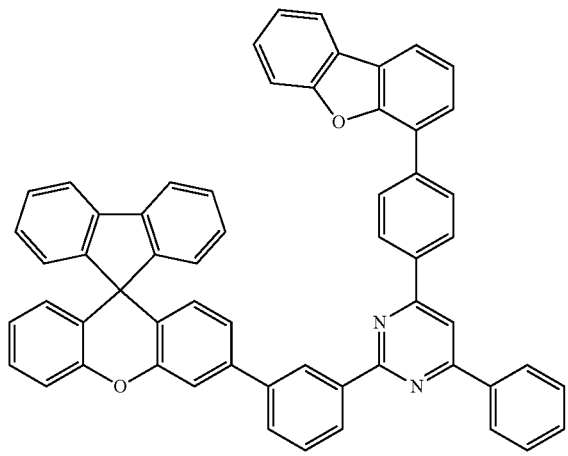
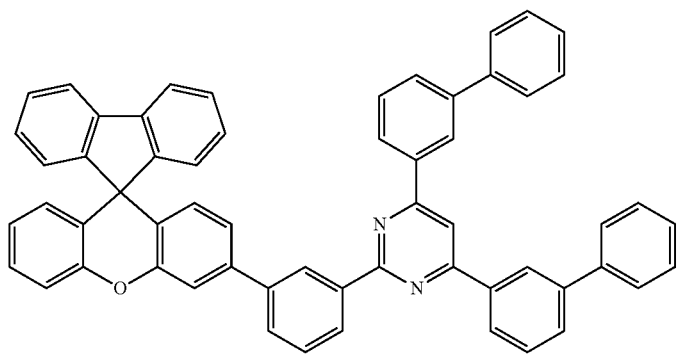

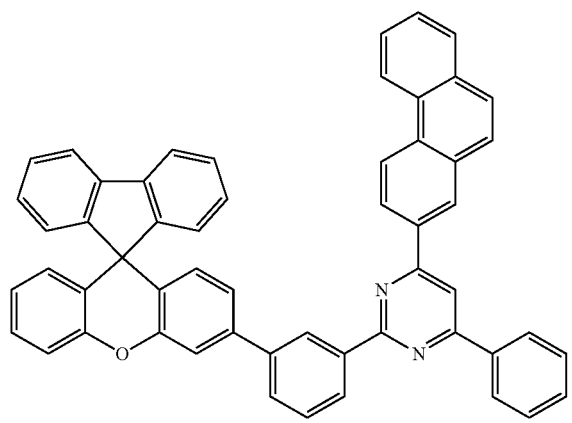
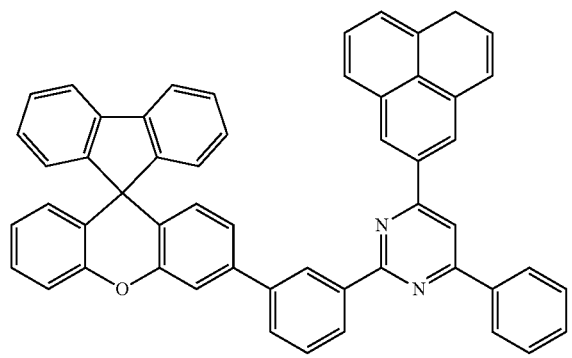
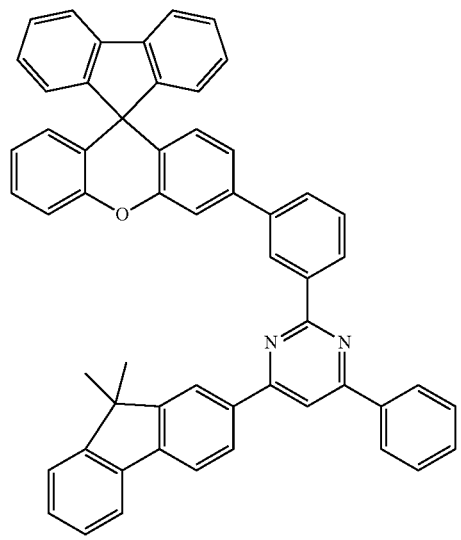
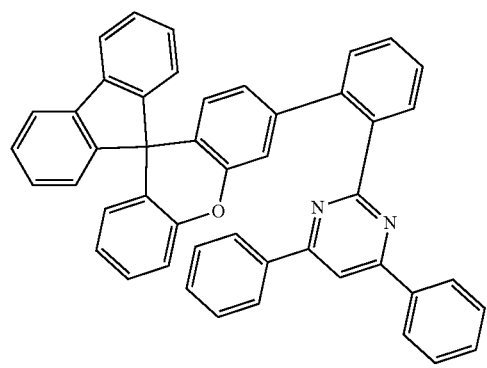

-continued
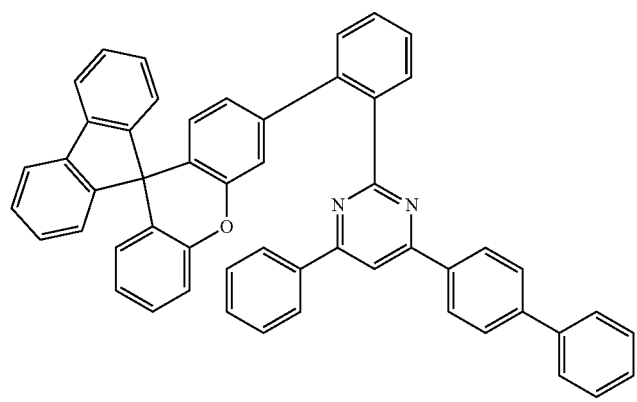
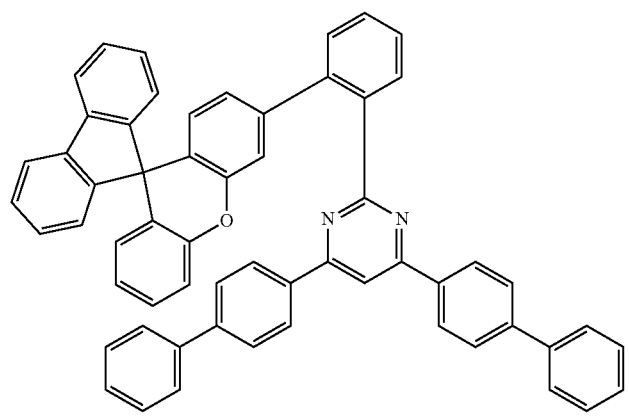
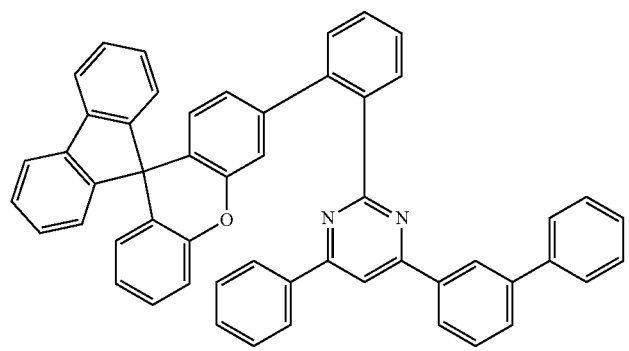
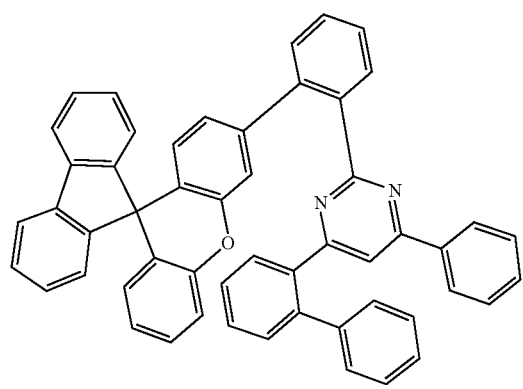

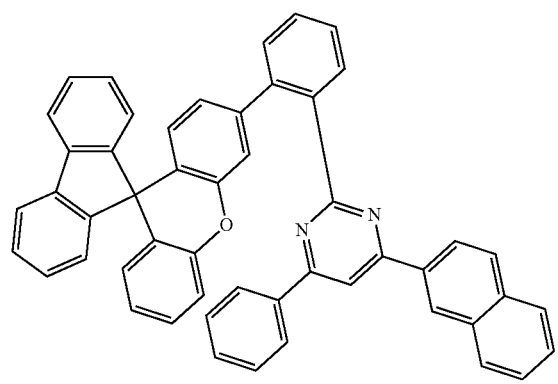
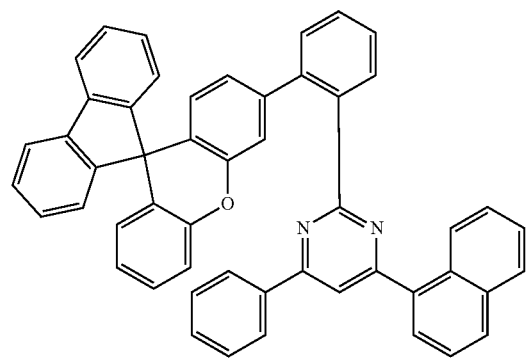
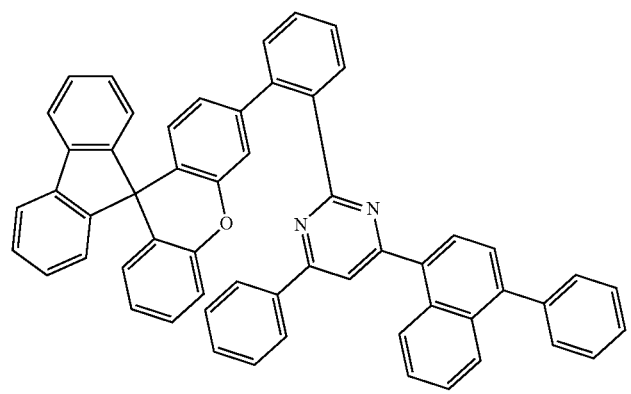
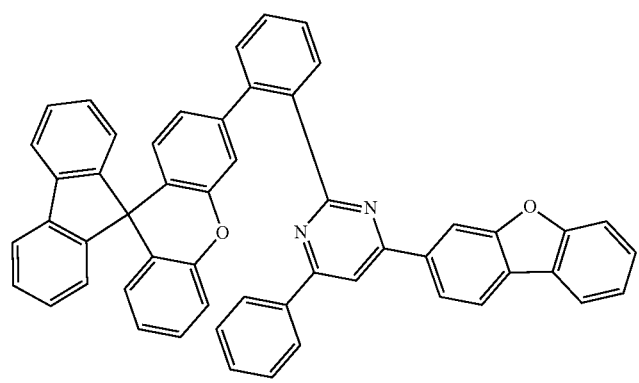

-continued
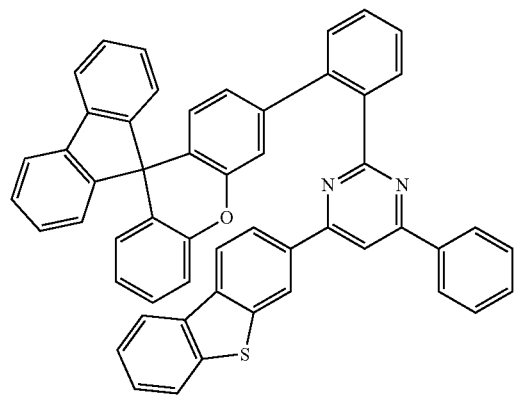
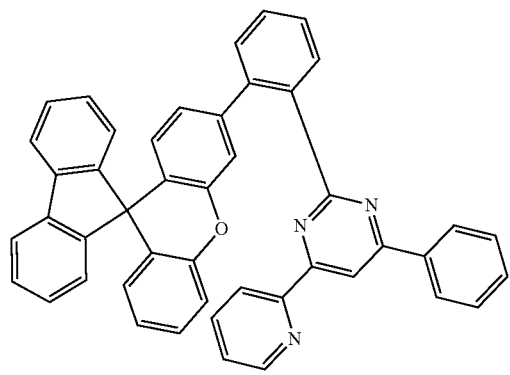
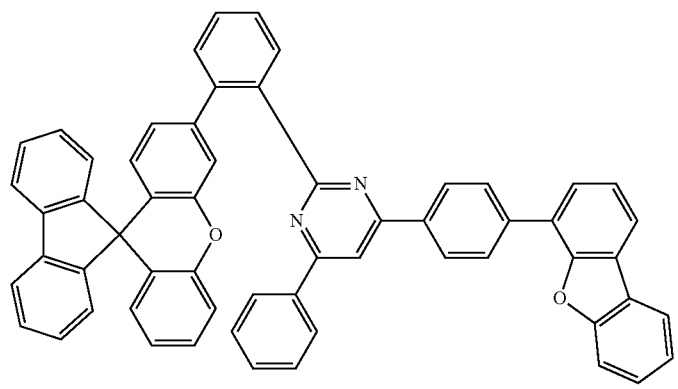
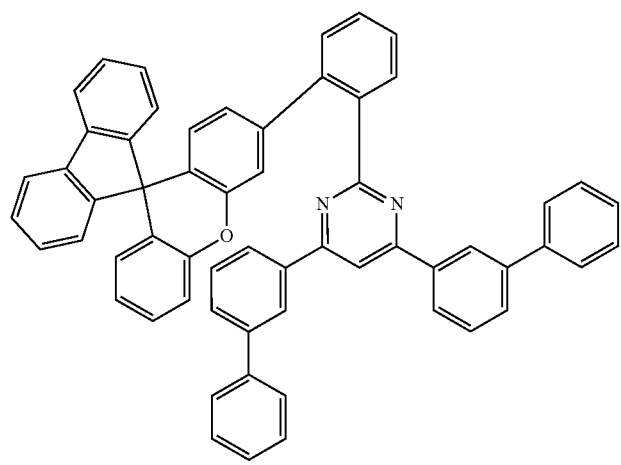

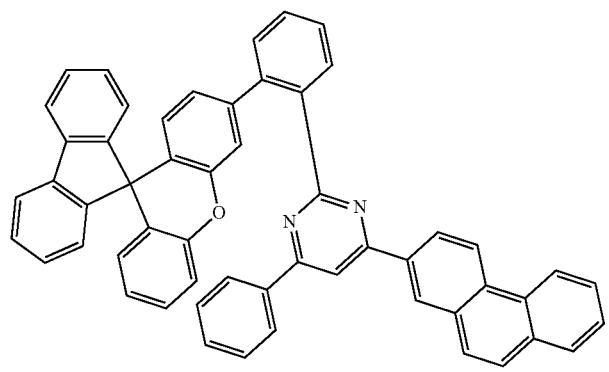
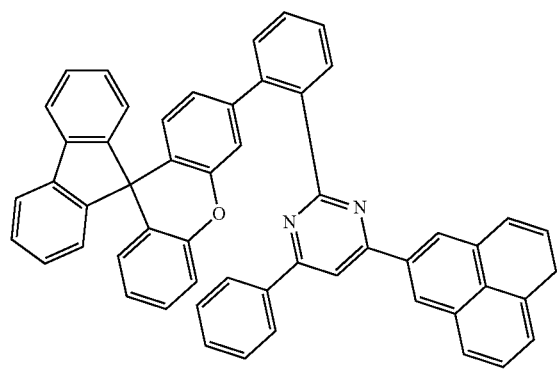
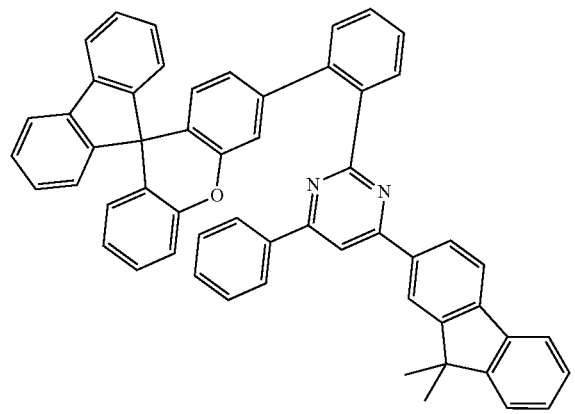
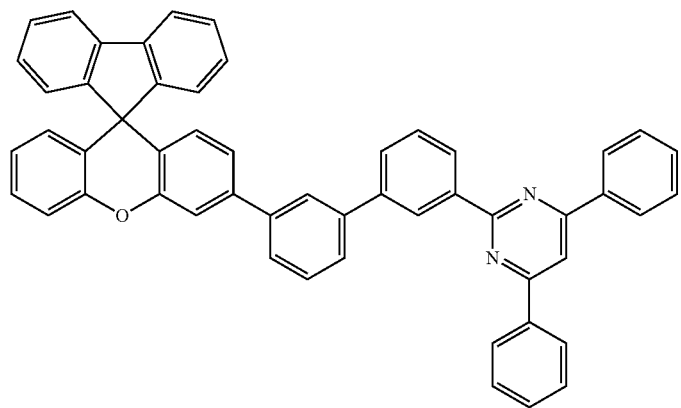

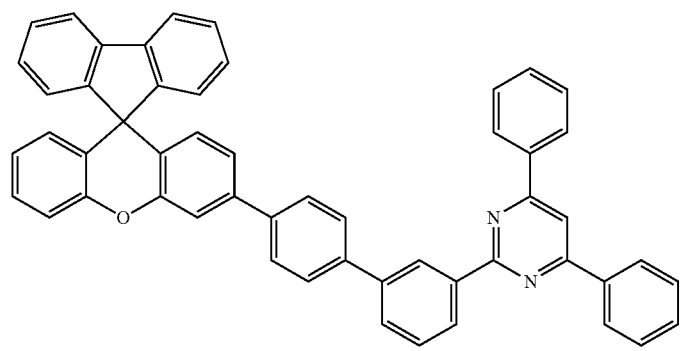
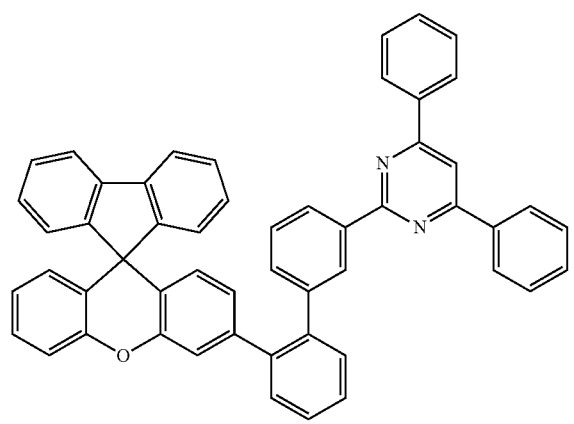
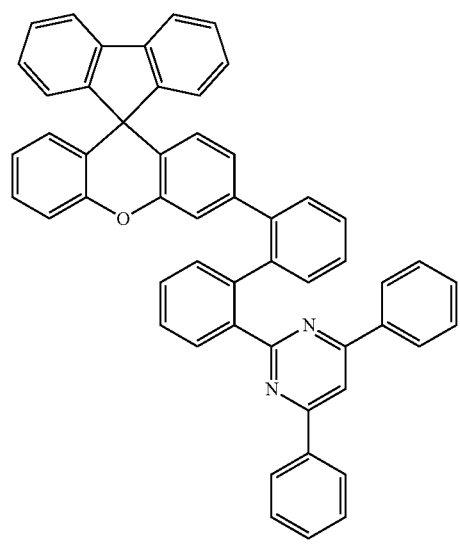

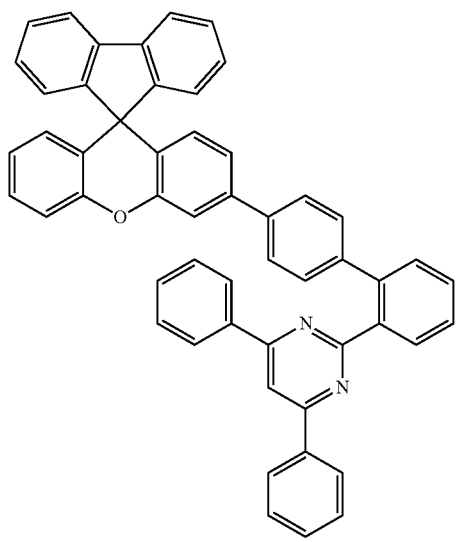
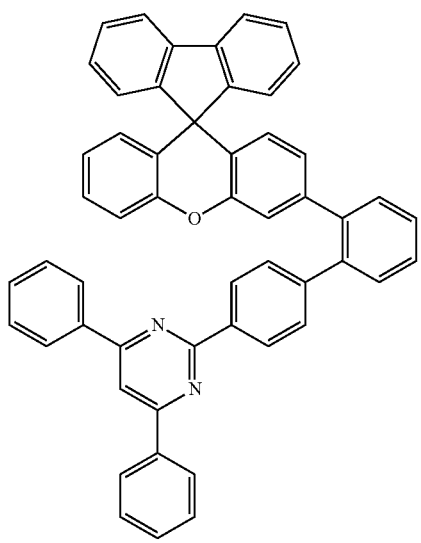
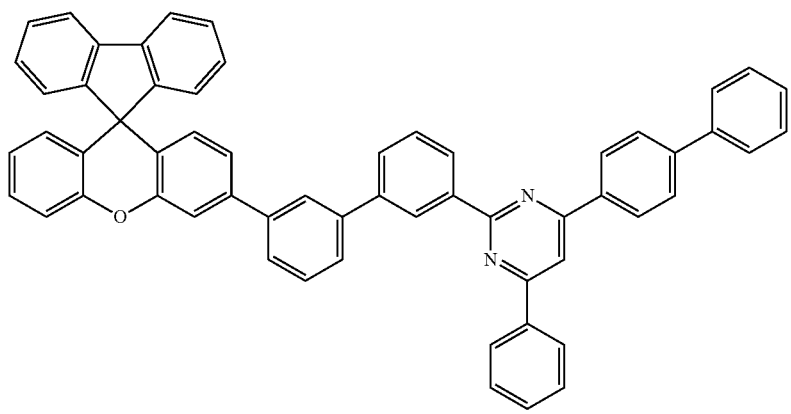

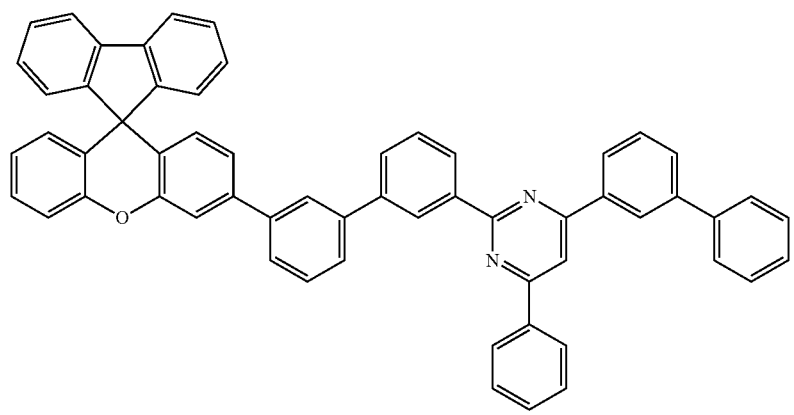
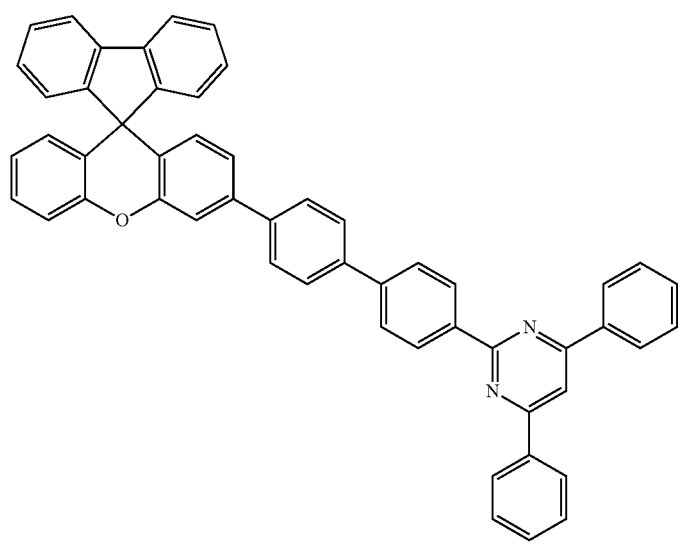
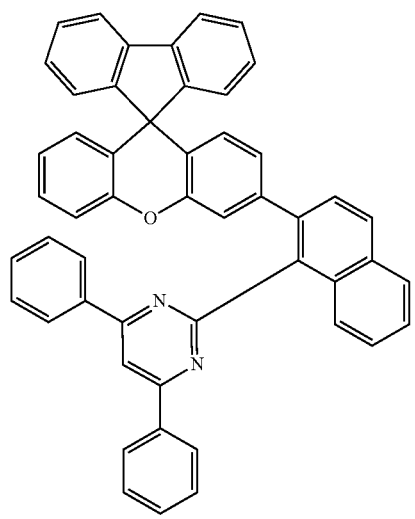

-continued
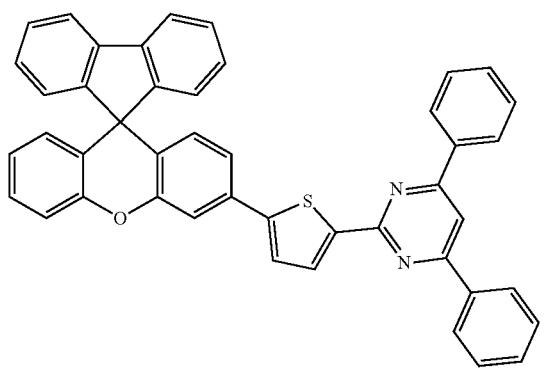
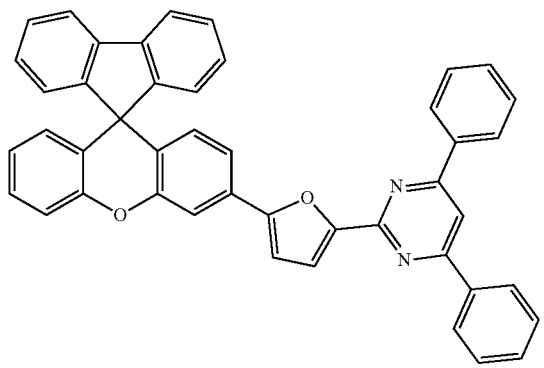
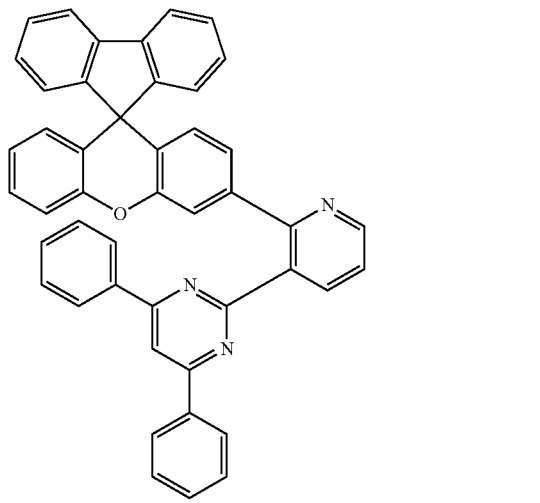
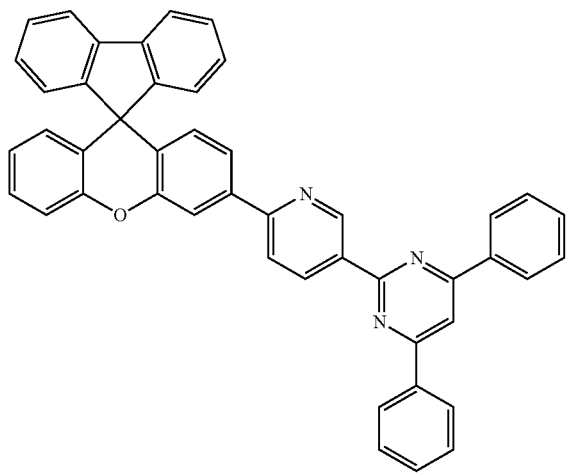

-continued
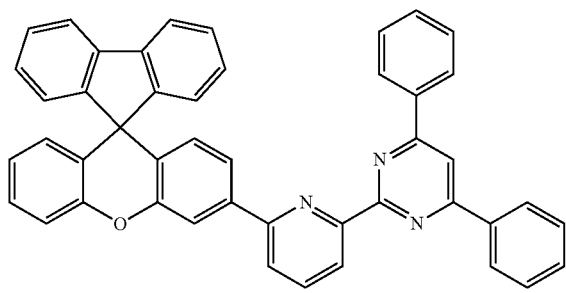
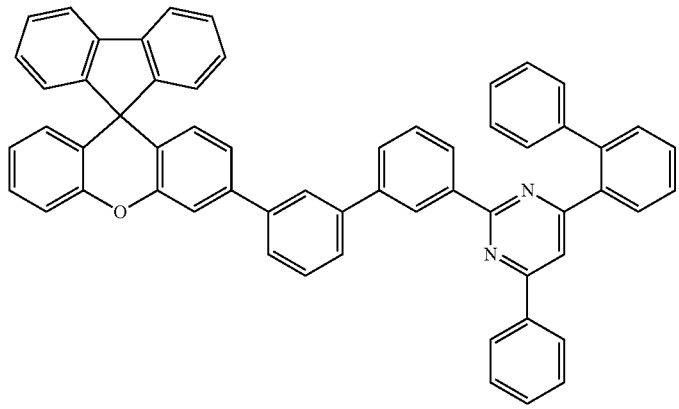
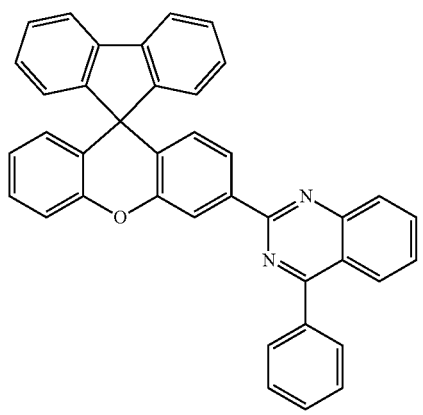
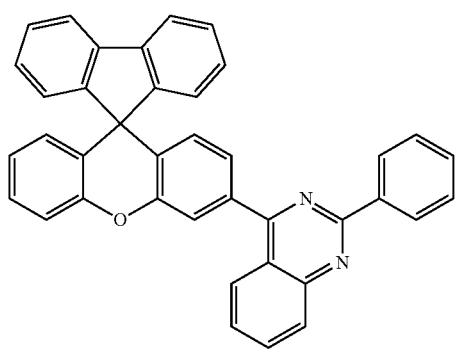

-continued
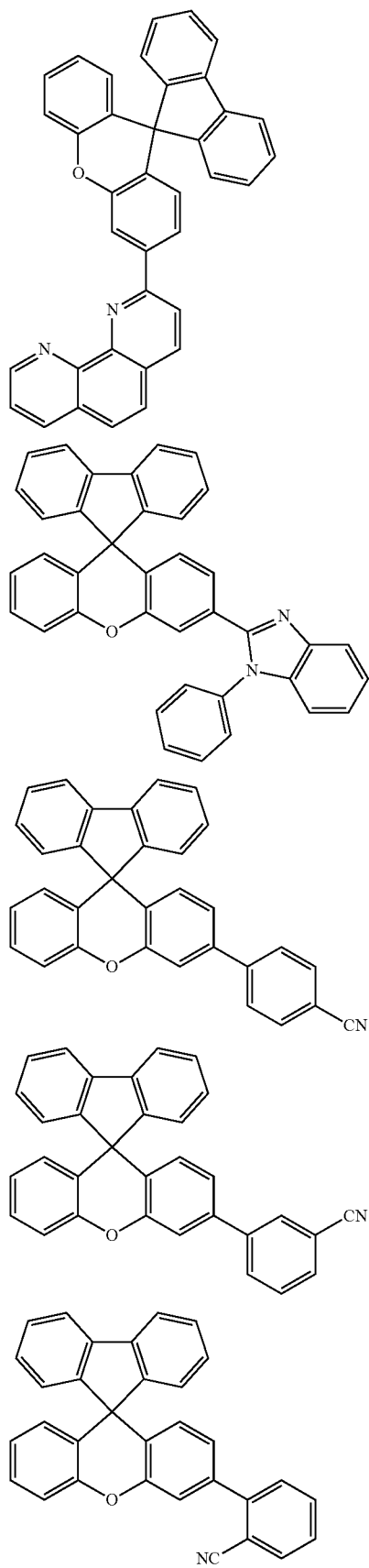

-continued
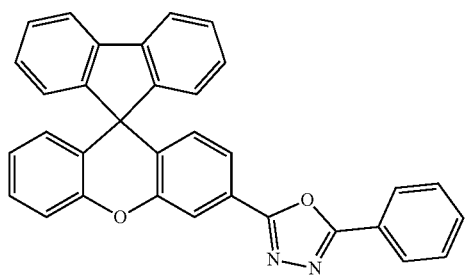
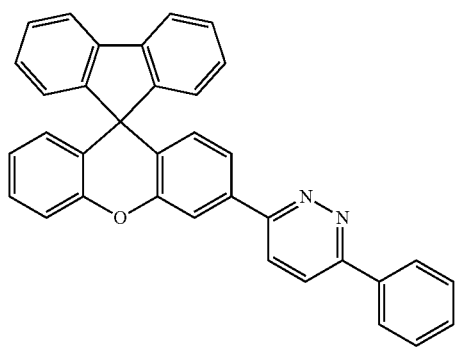
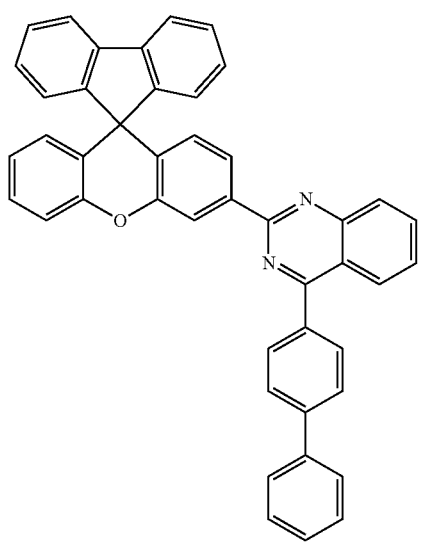
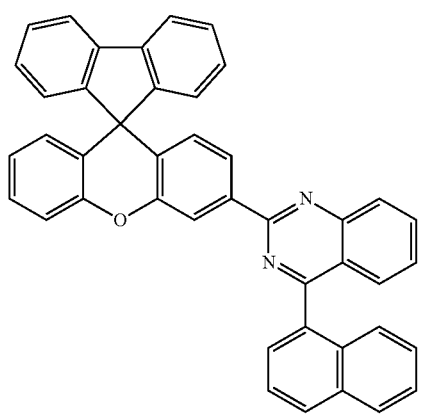

-continued
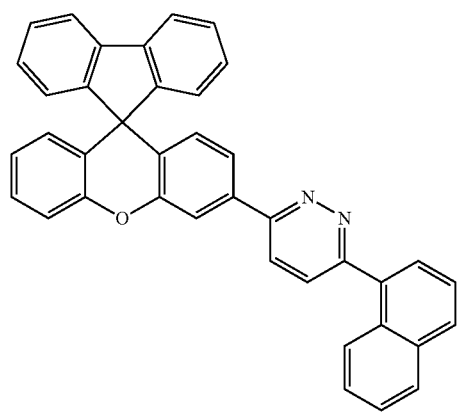
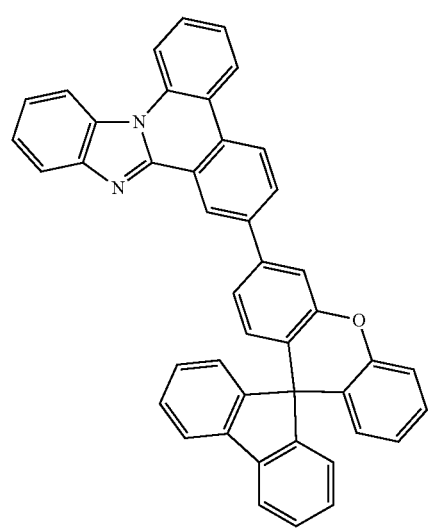
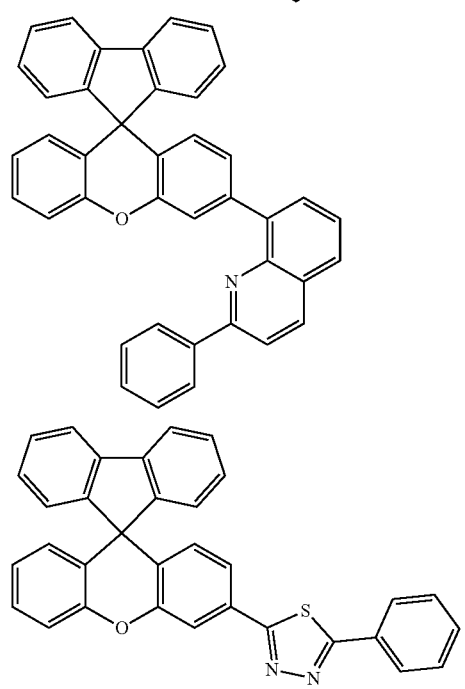

-continued
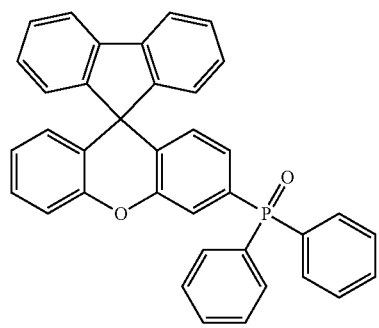
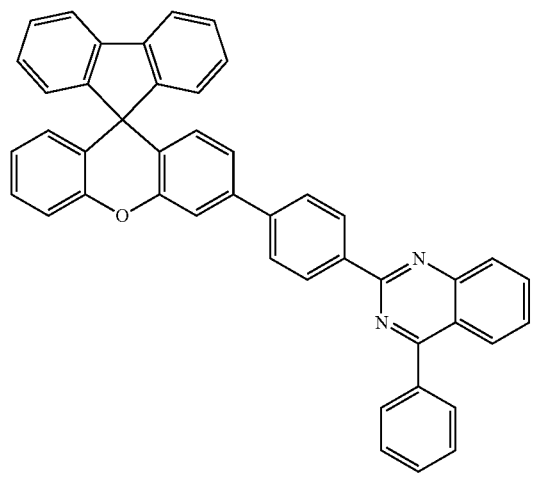
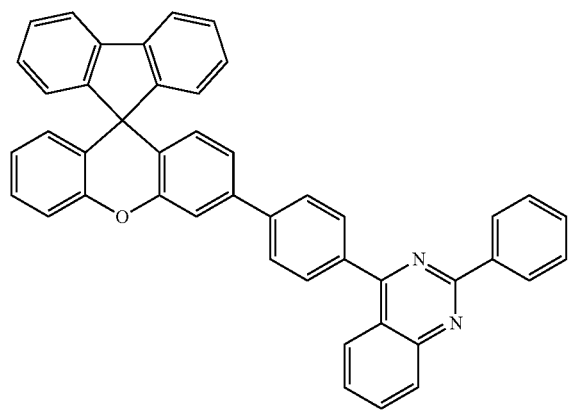
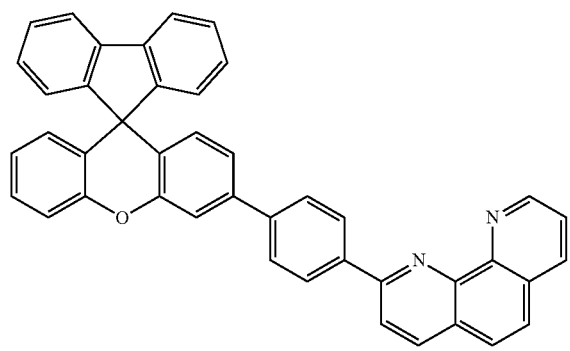

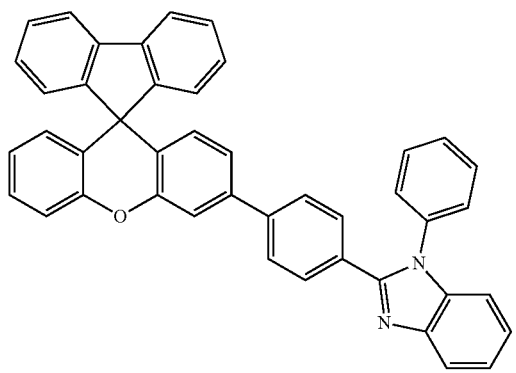
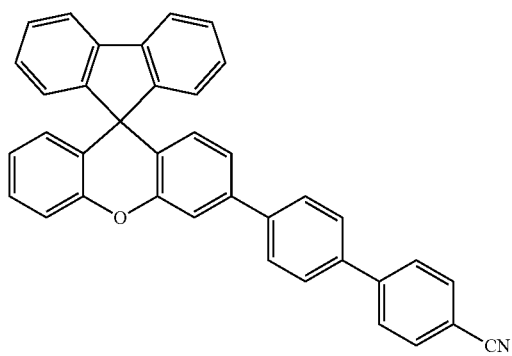
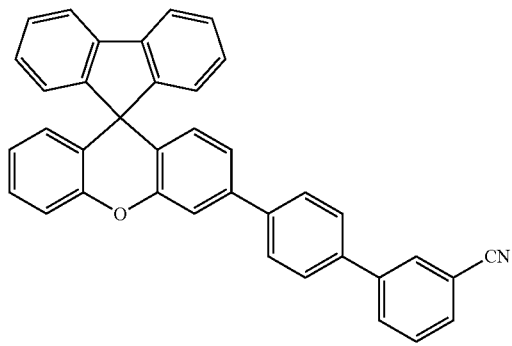
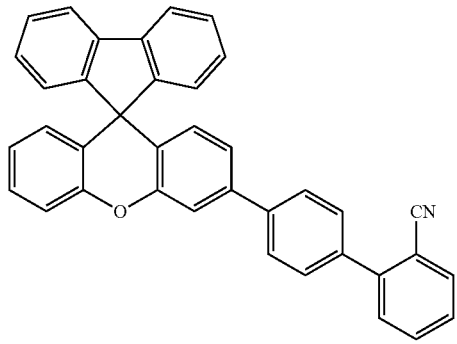

-continued
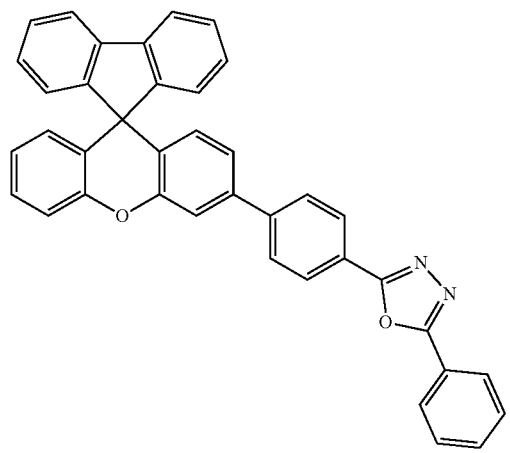
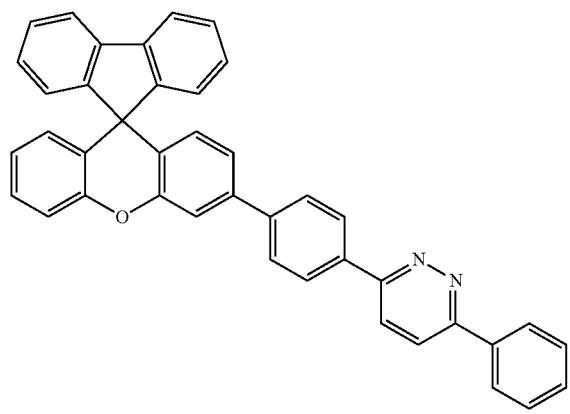
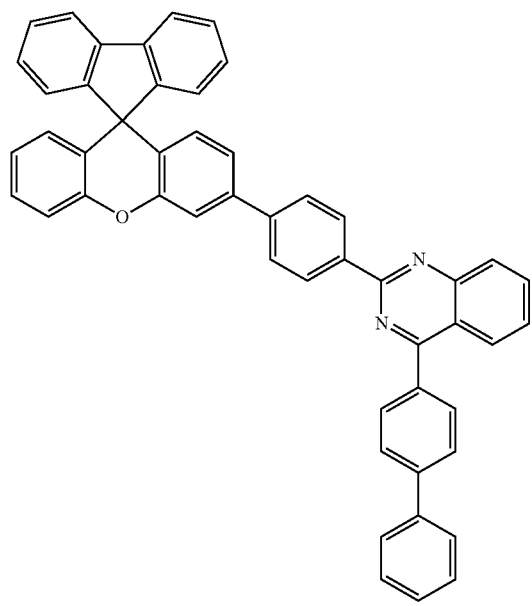

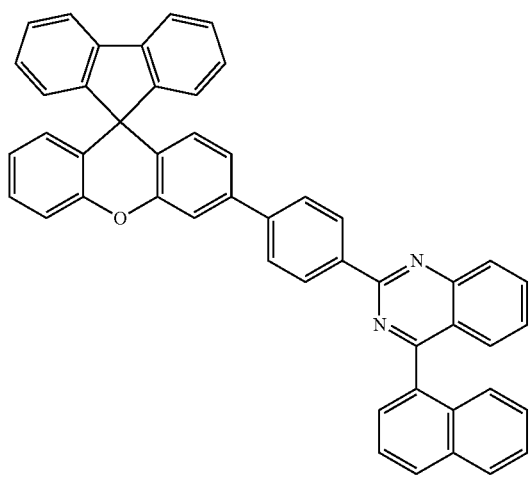
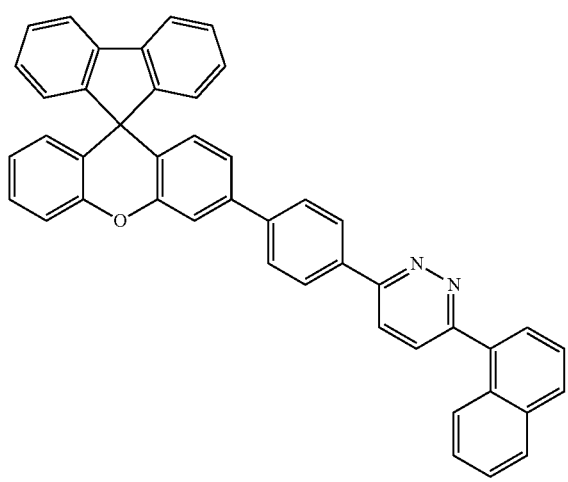
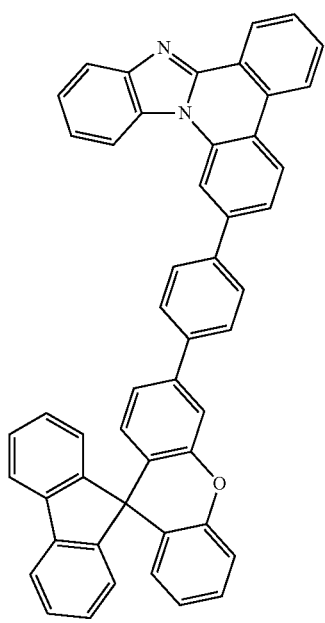

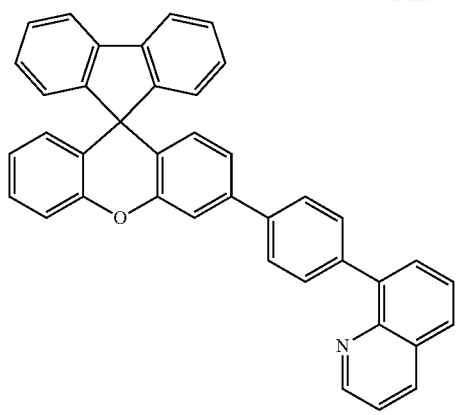
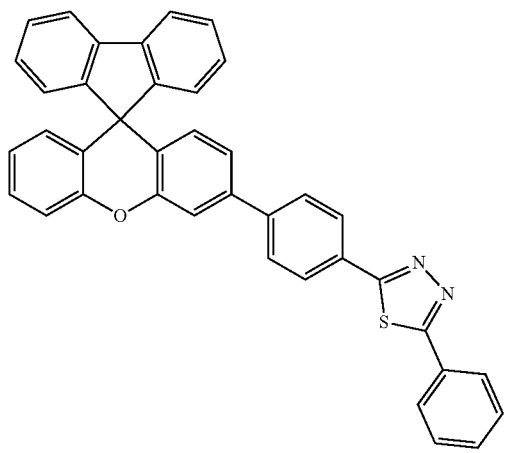
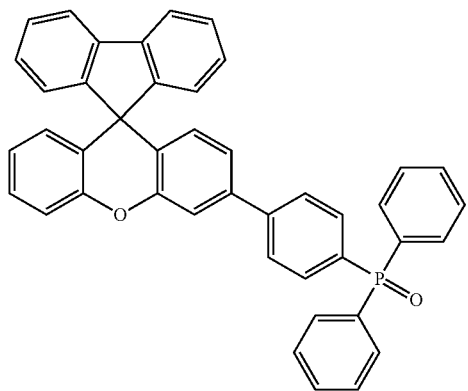
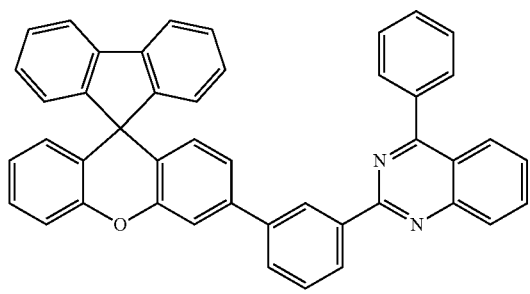

-continued
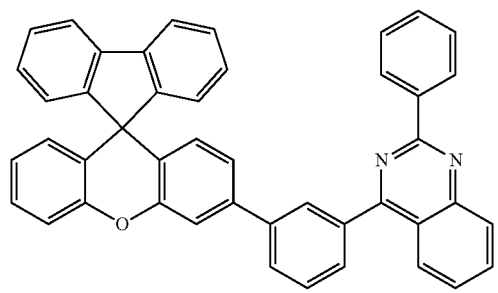
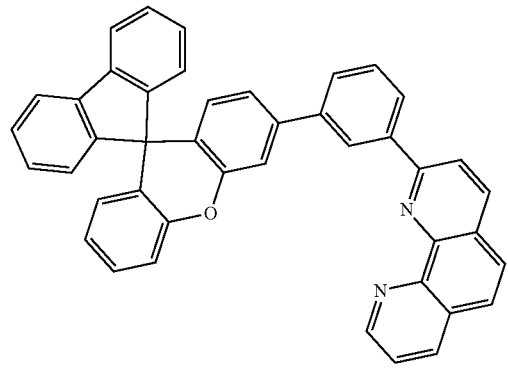
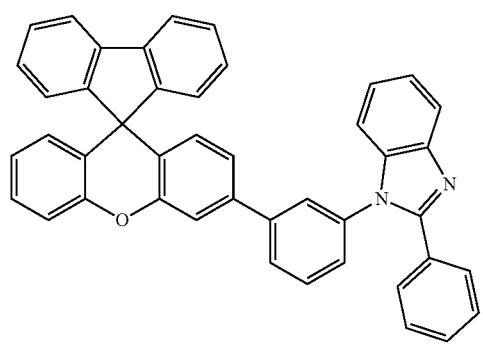
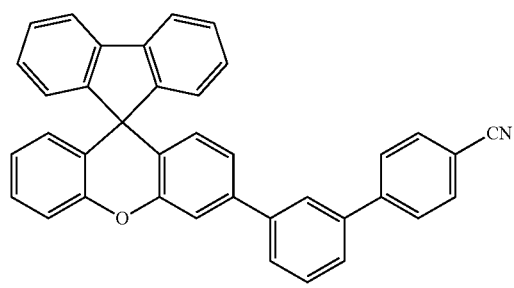
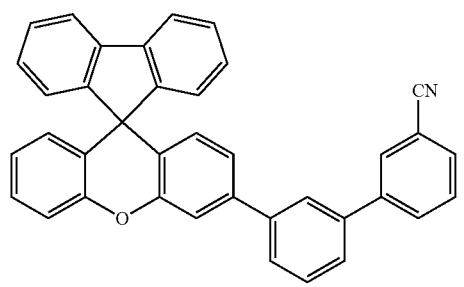

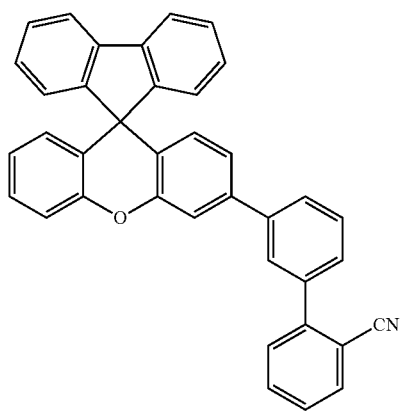
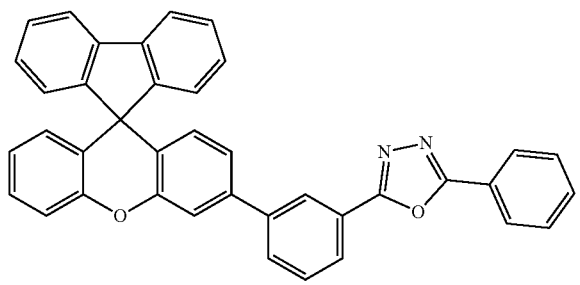
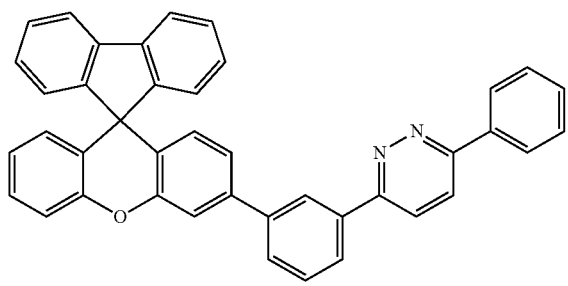
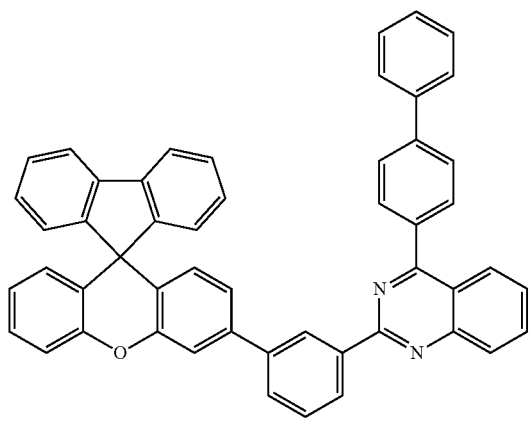
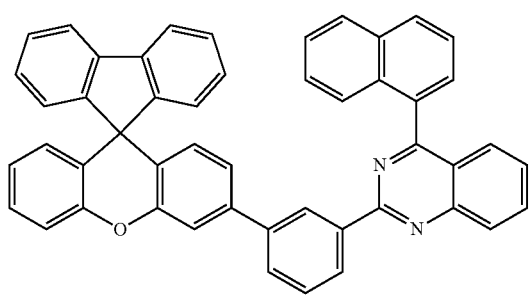

-continued
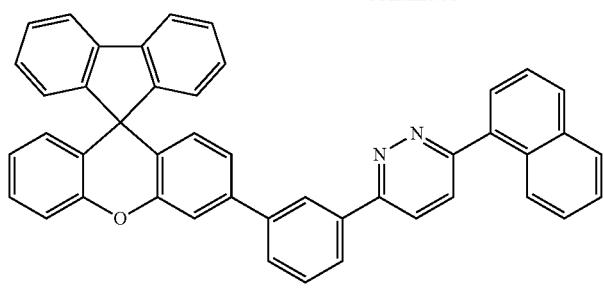
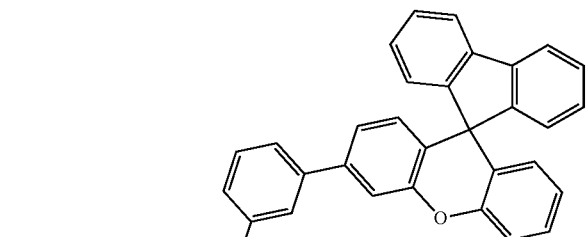
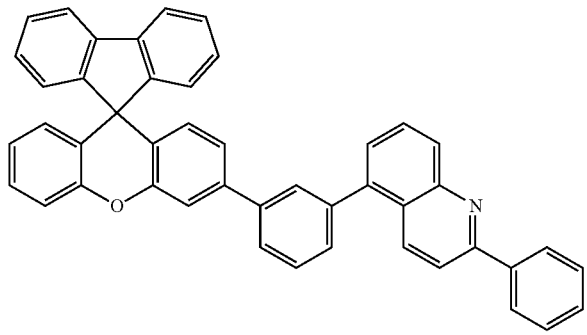
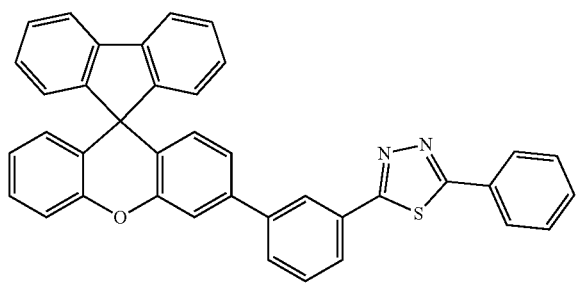
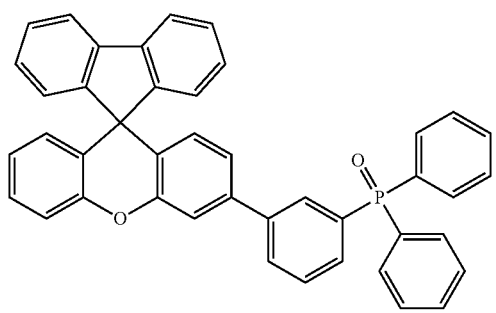

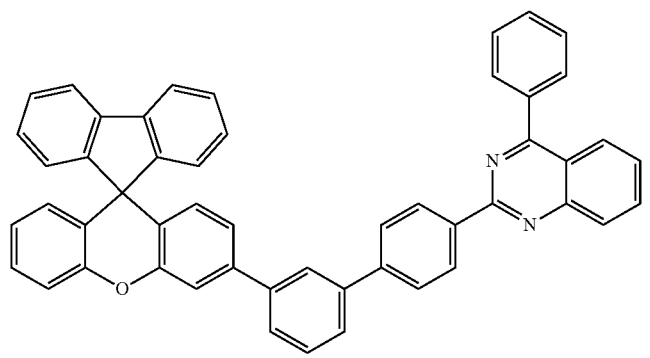
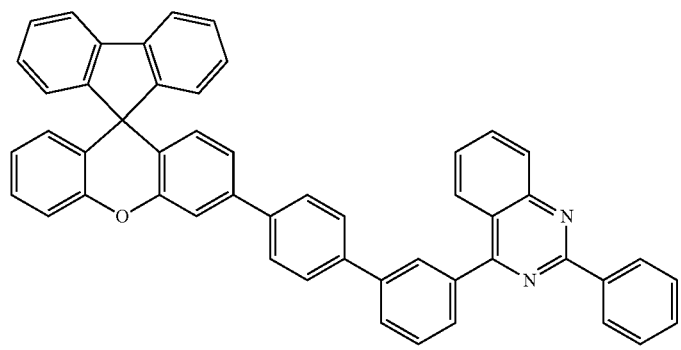
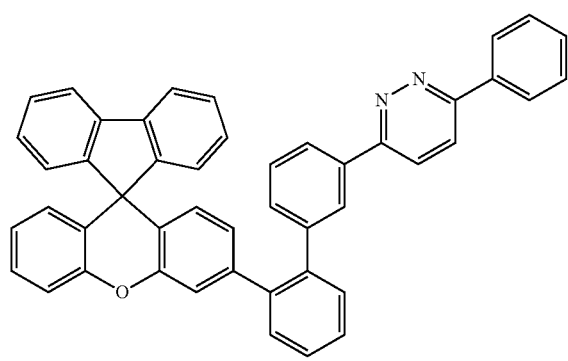
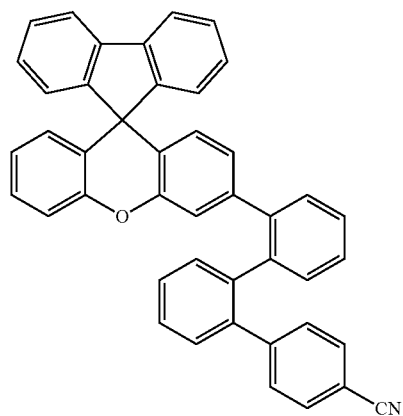

-continued
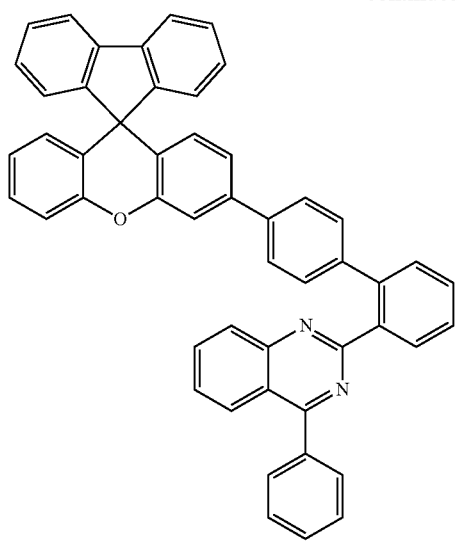
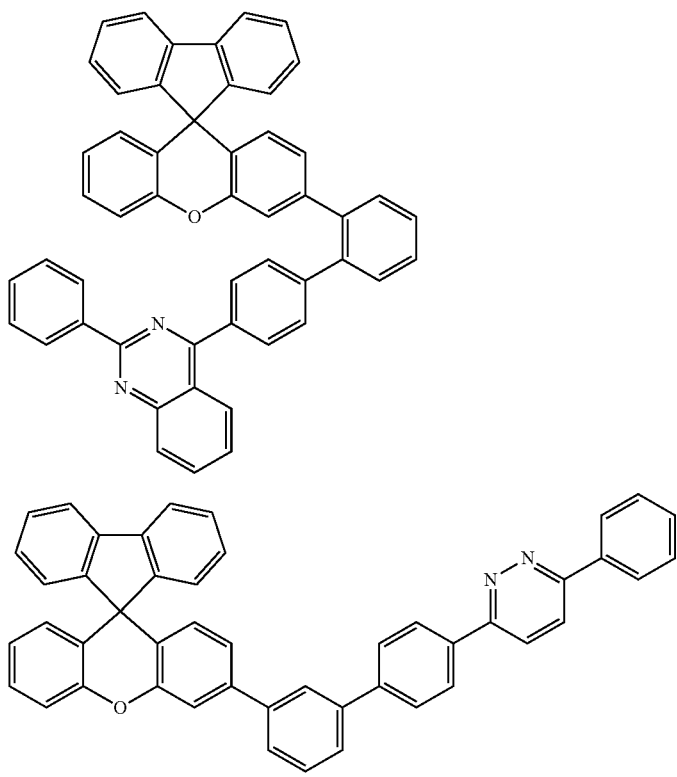
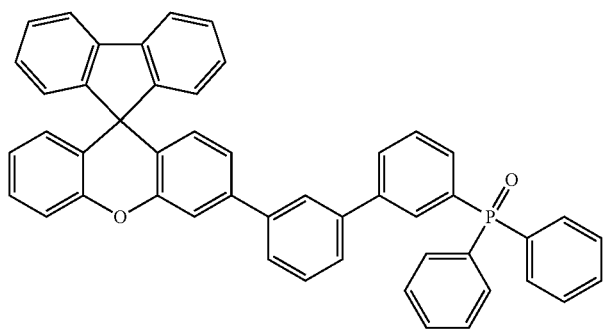

-continued
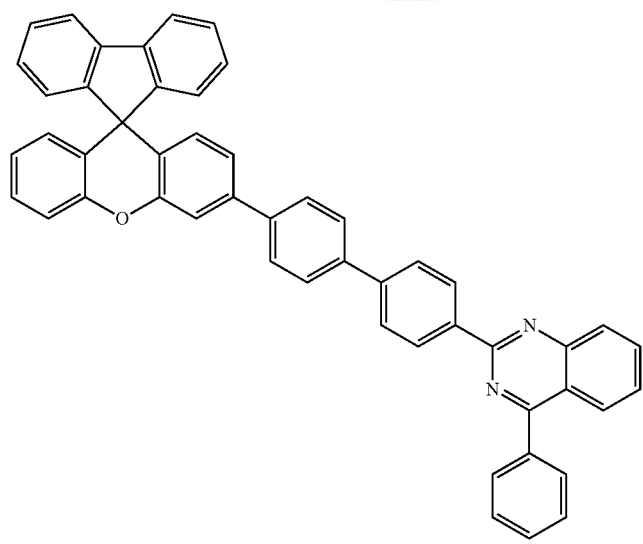
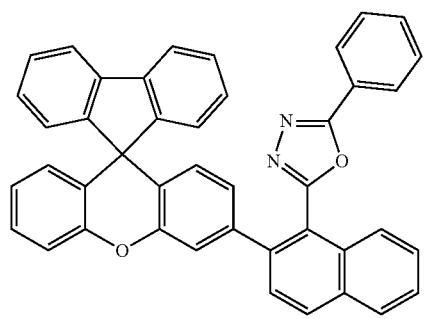
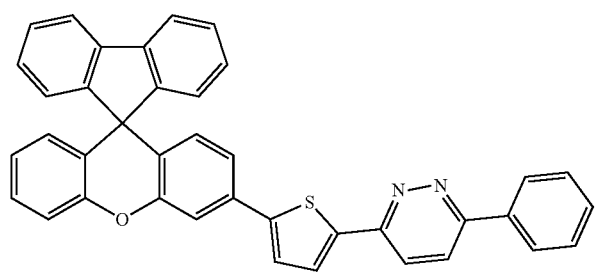
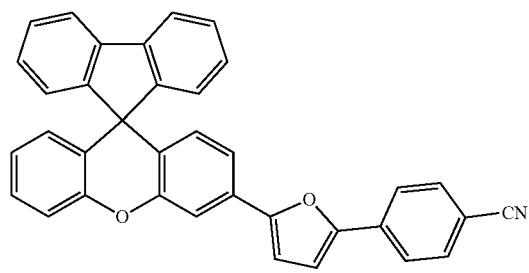

-continued
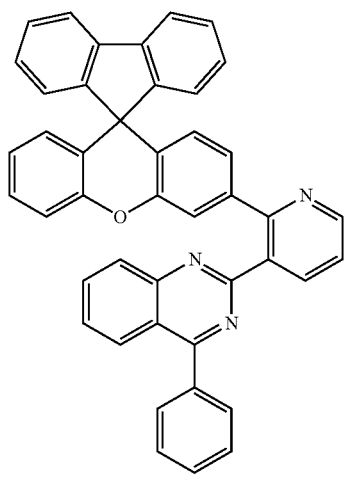
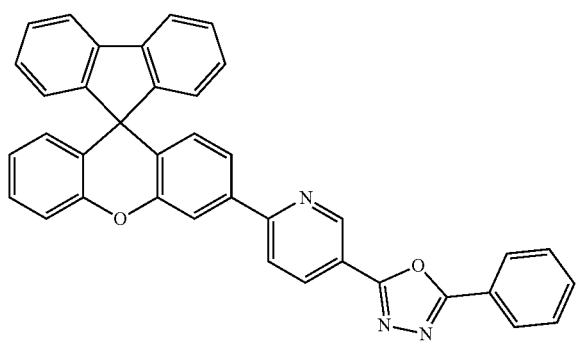
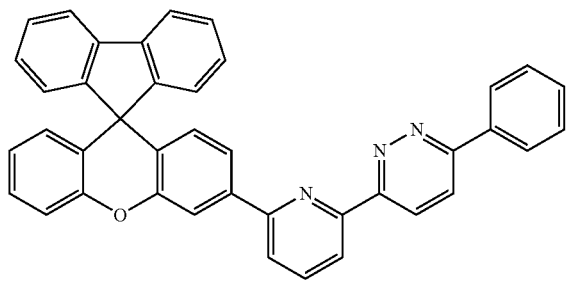
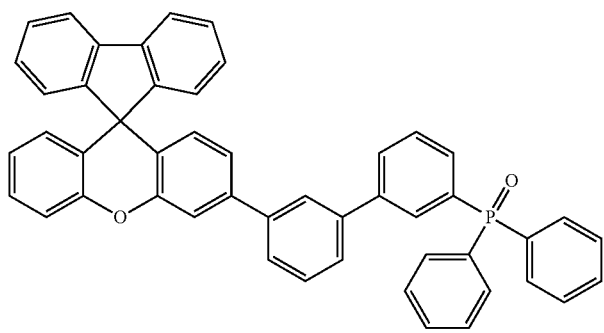

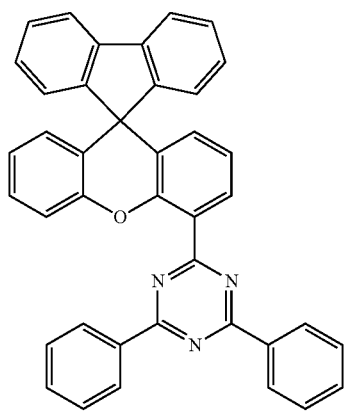
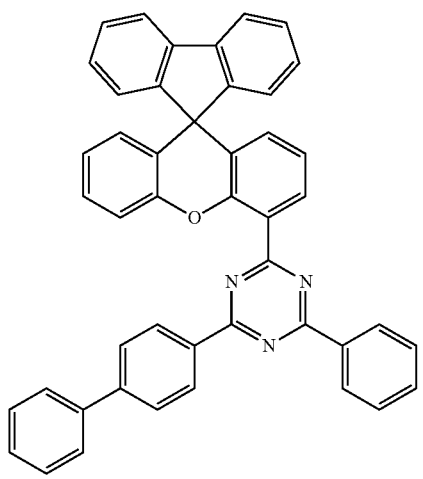
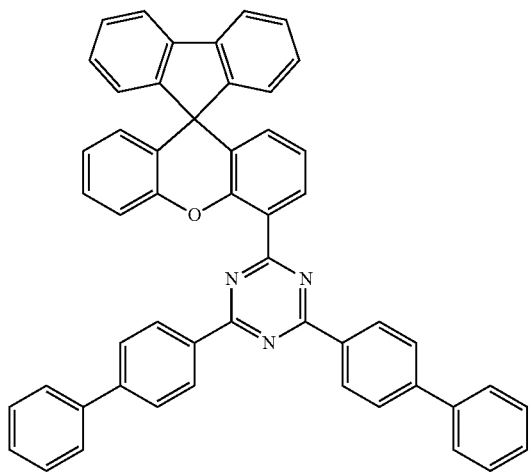

-continued
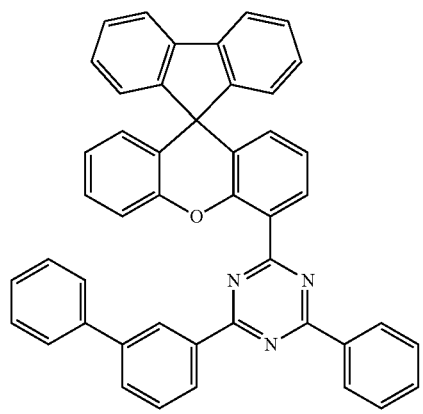
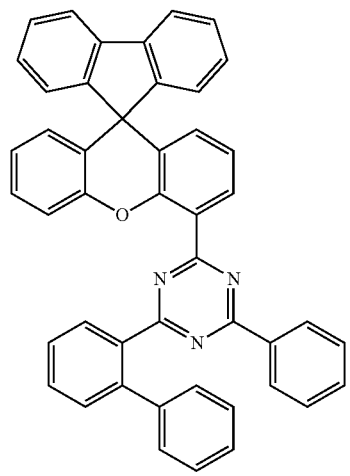
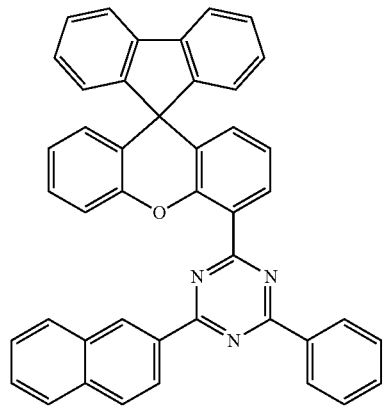

-continued
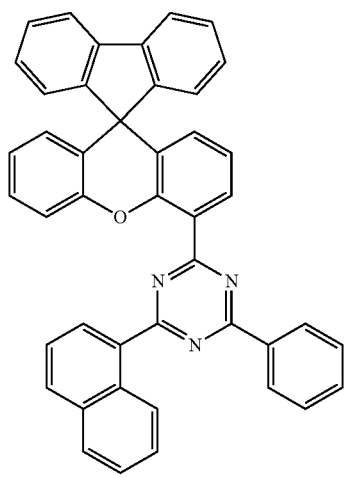
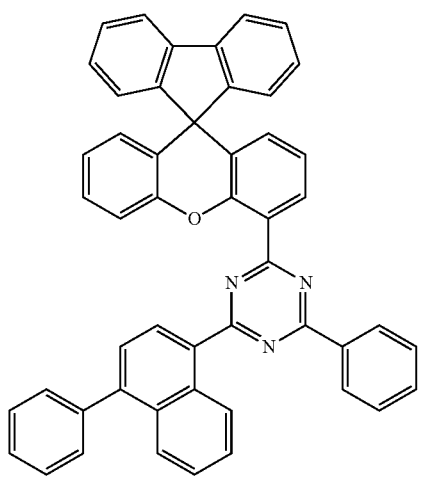
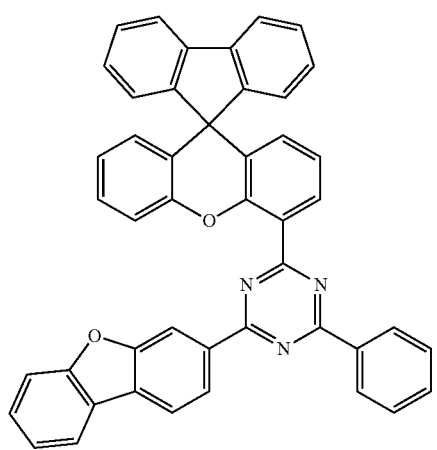

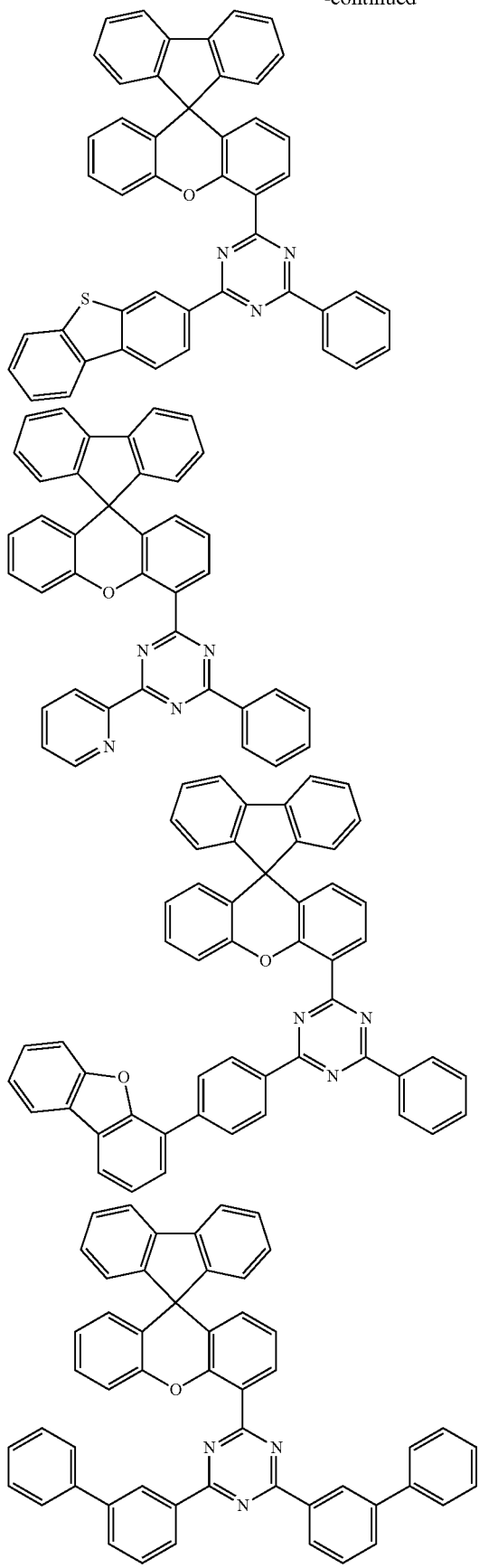

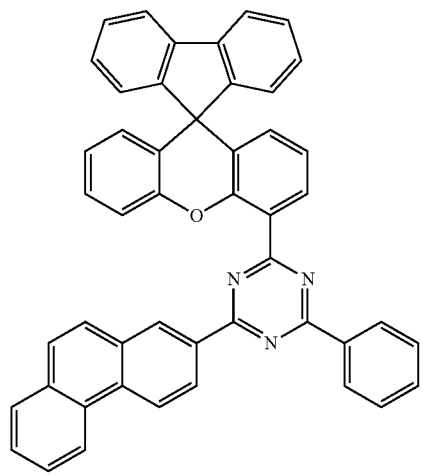
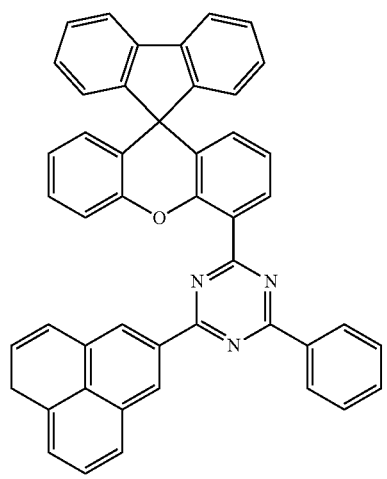
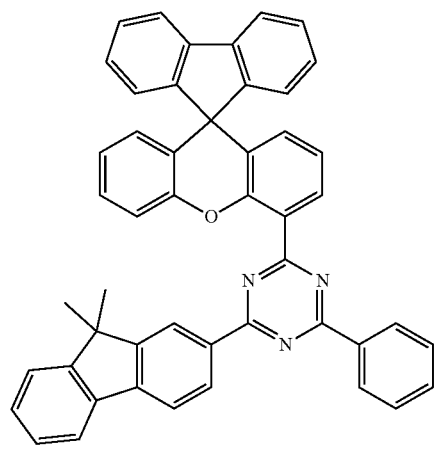

259
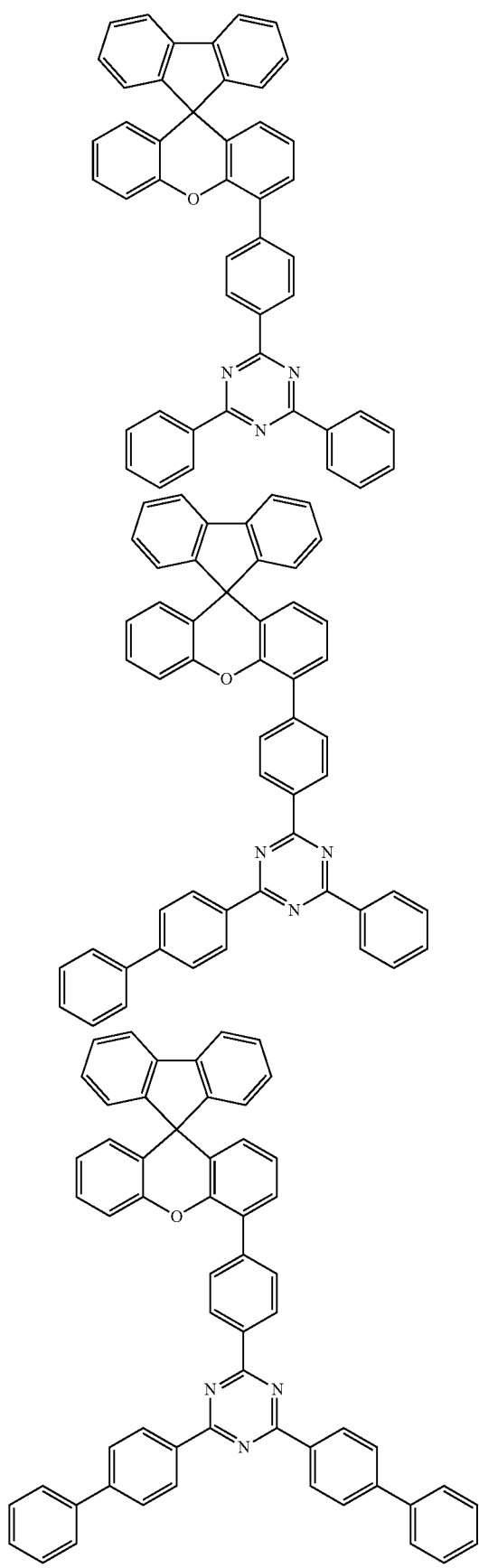
260
-continued
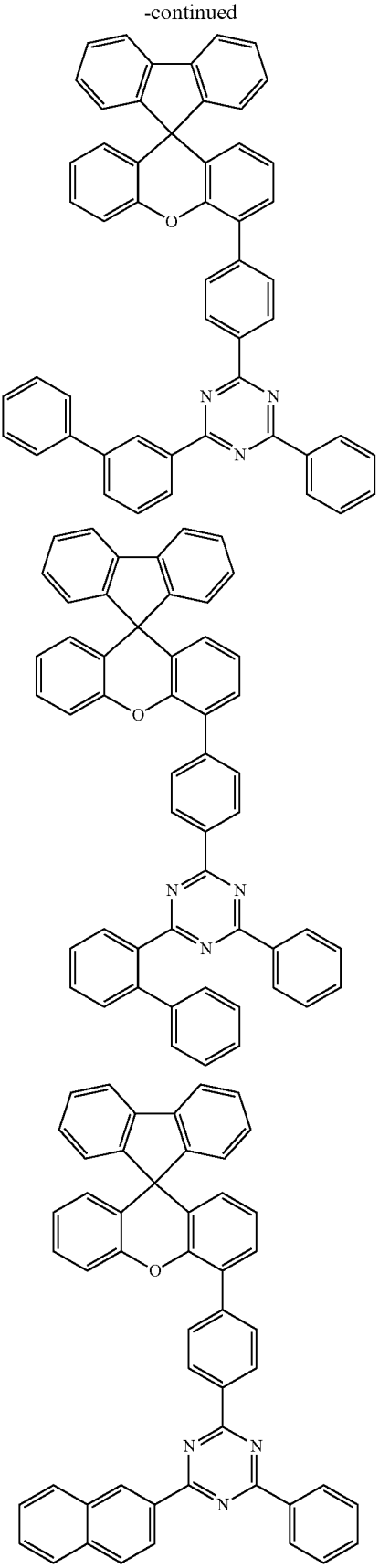

261
-continued
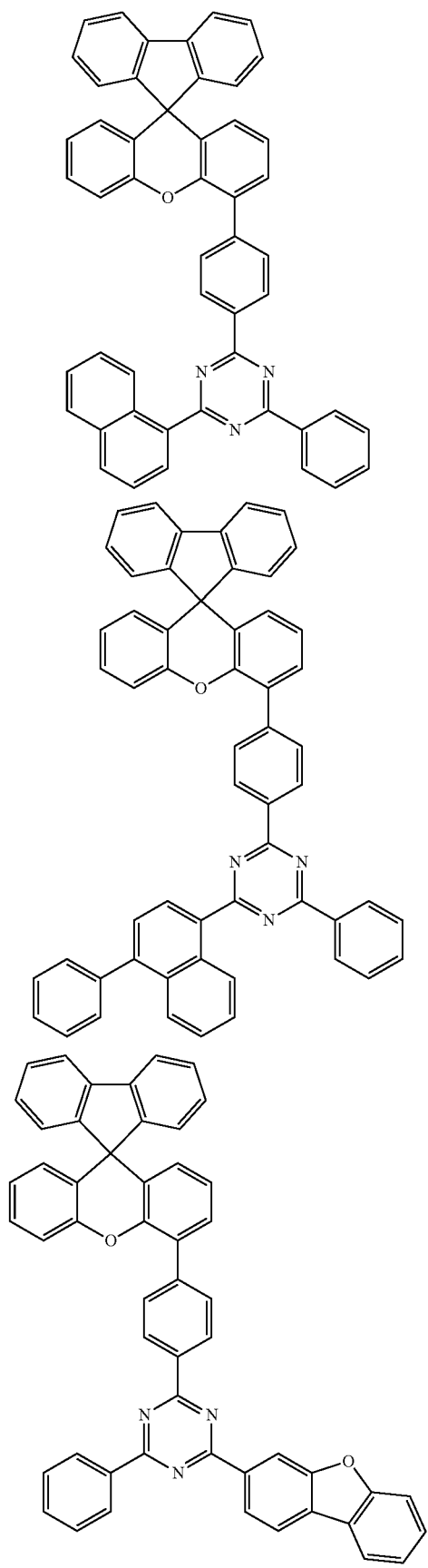
262
-continued
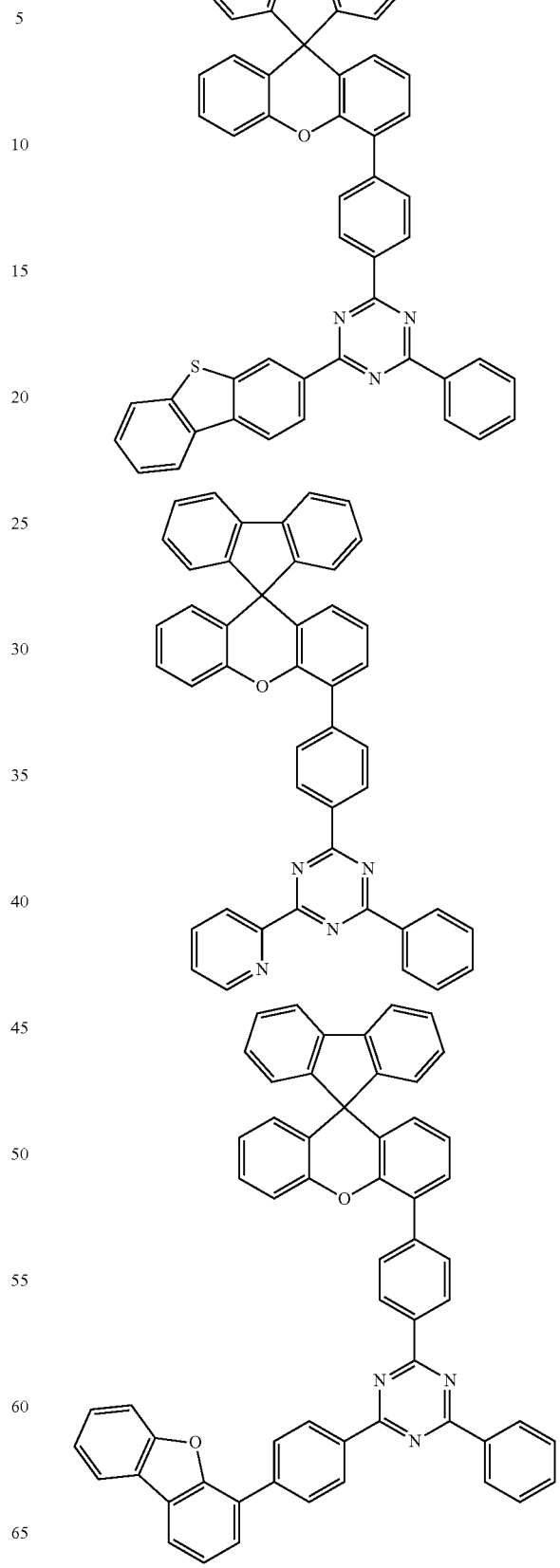

263
-continued
264
-continued
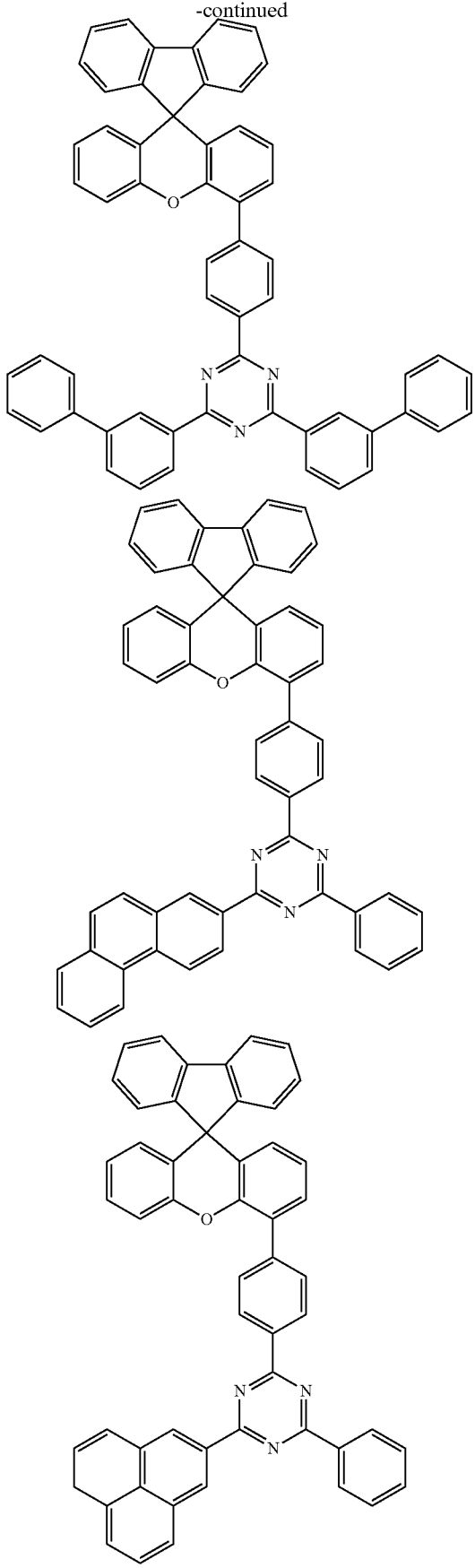

265
-continued
266
-continued
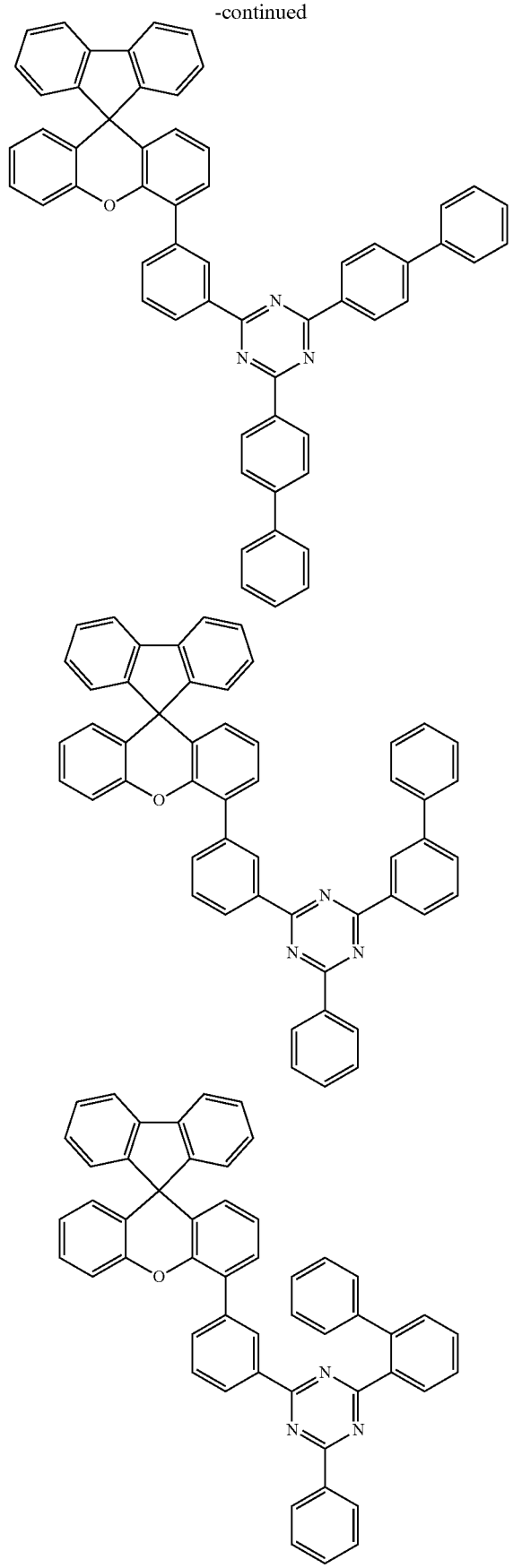
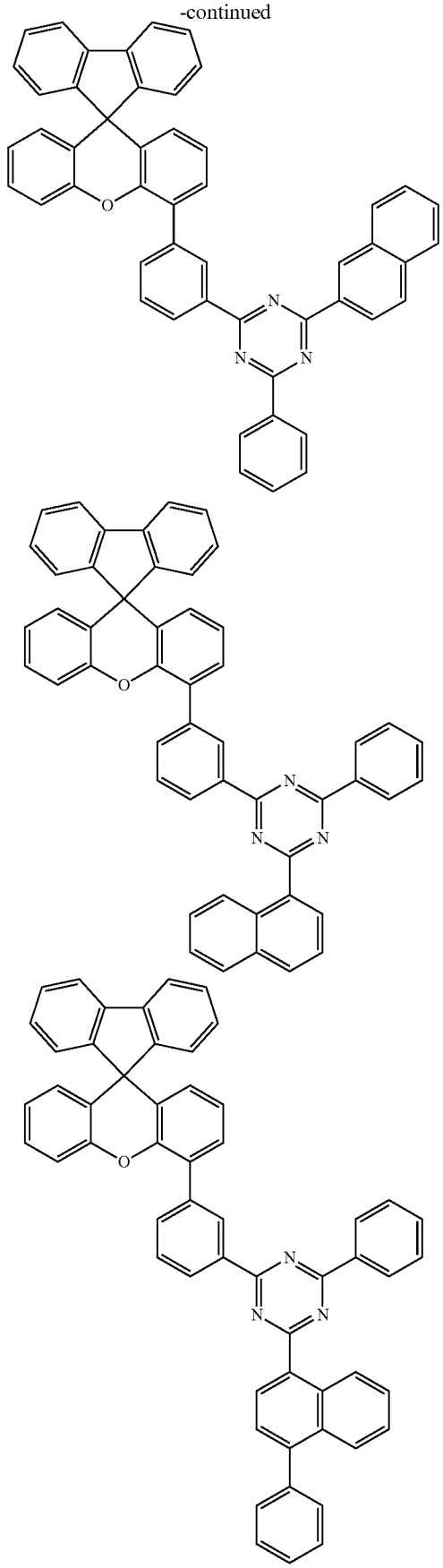

267
-continued
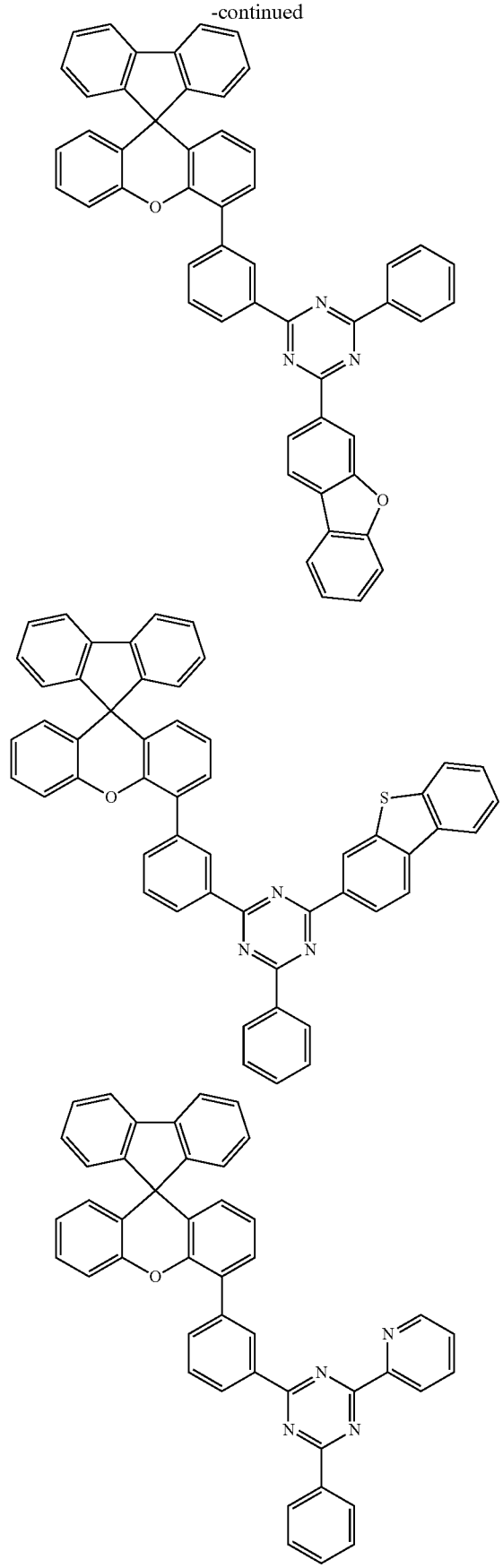
268
-continued
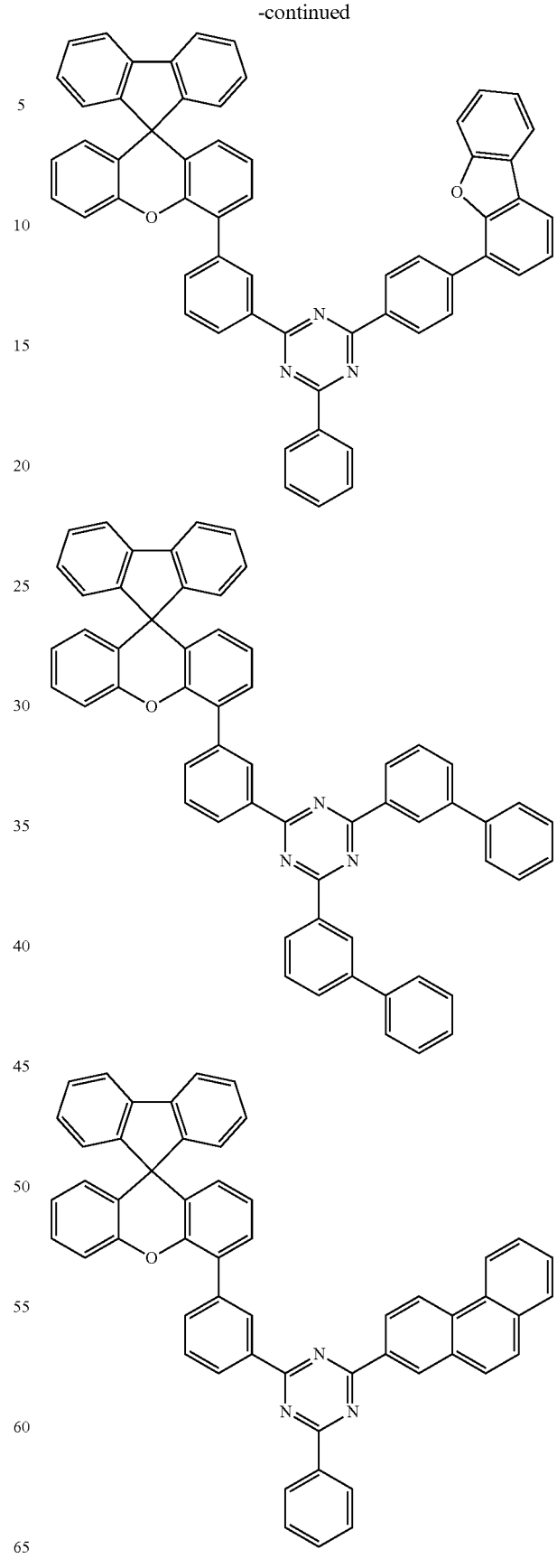

269
-continued
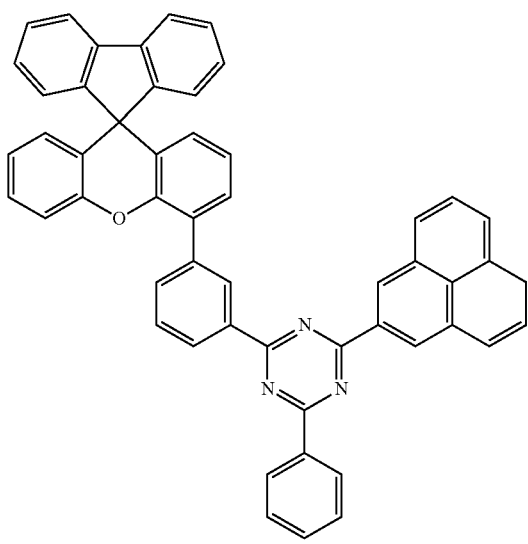
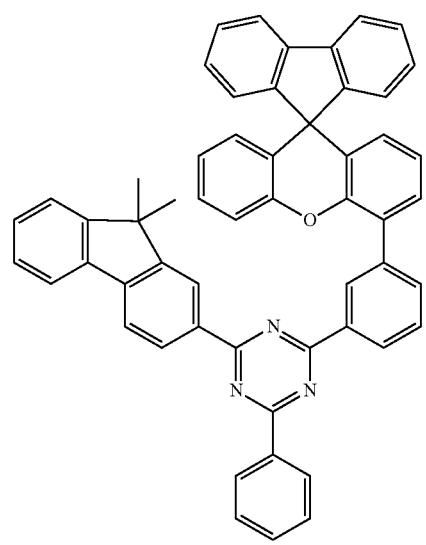
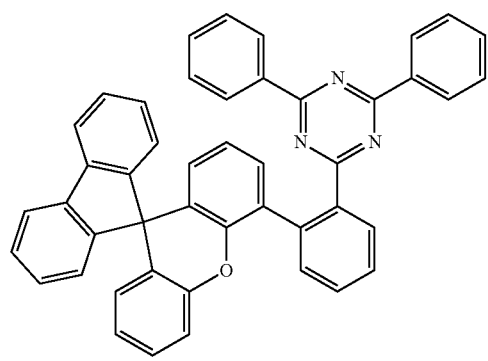
270
-continued
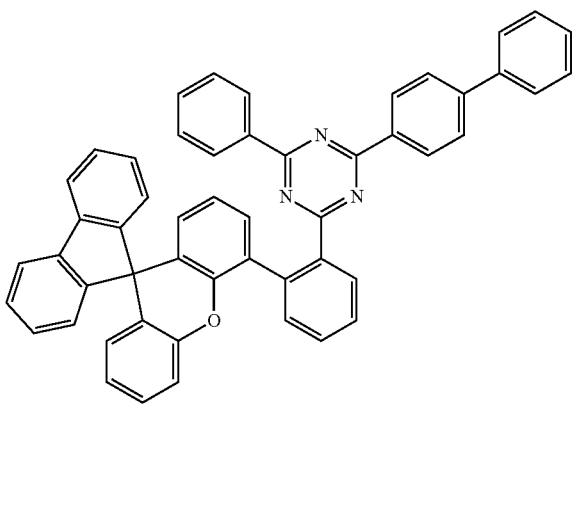
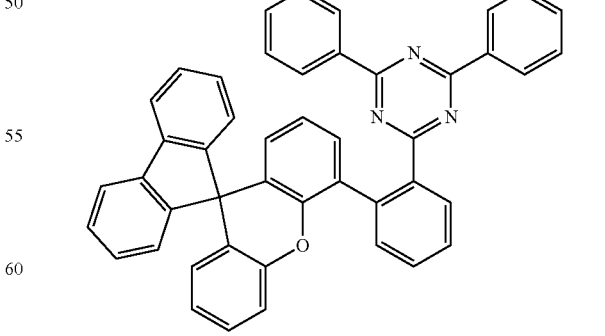

271
-continued
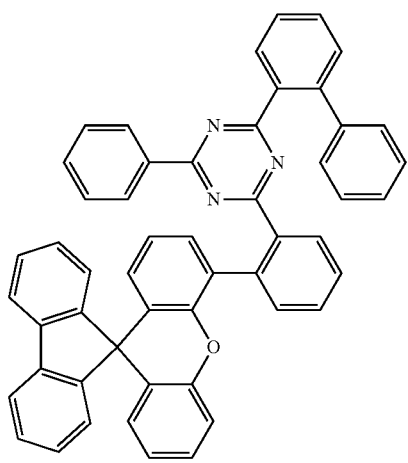
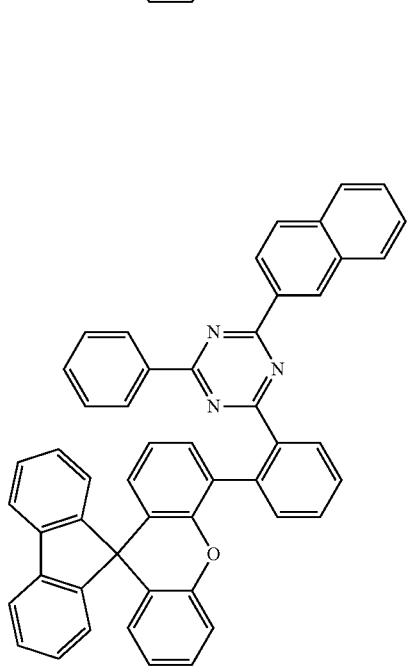
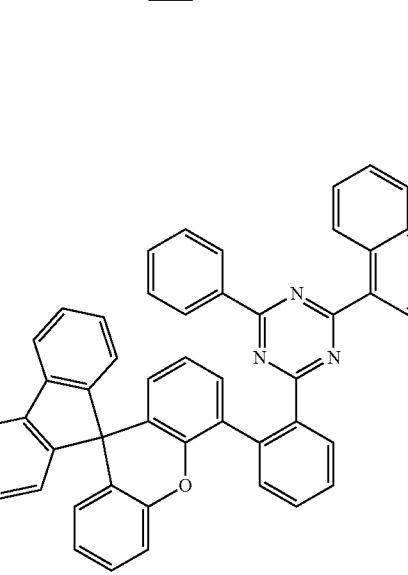
272
-continued
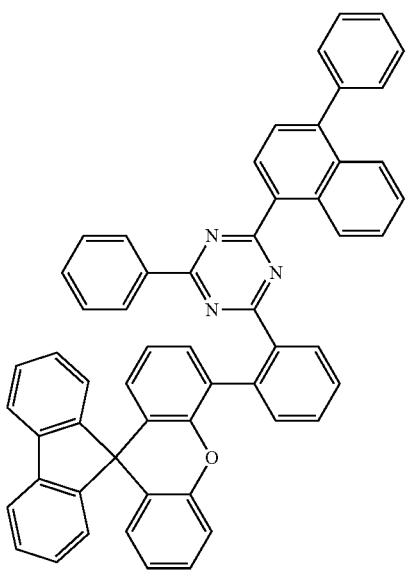
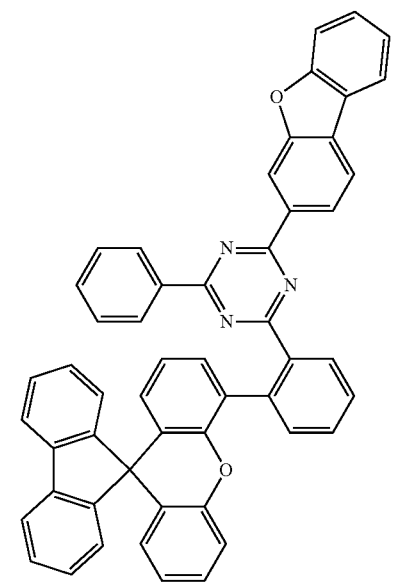
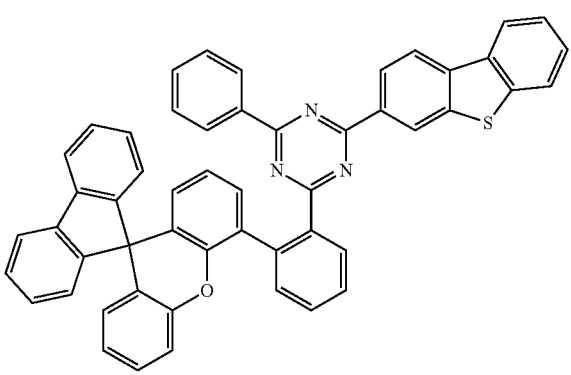

273
-continued
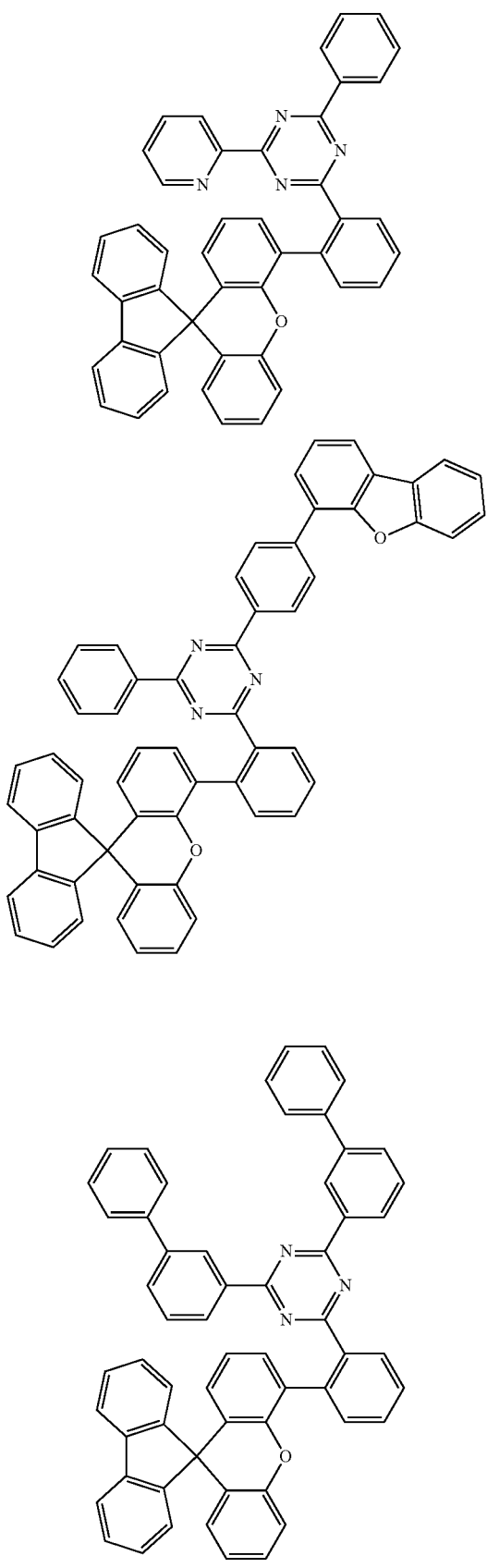
274
-continued
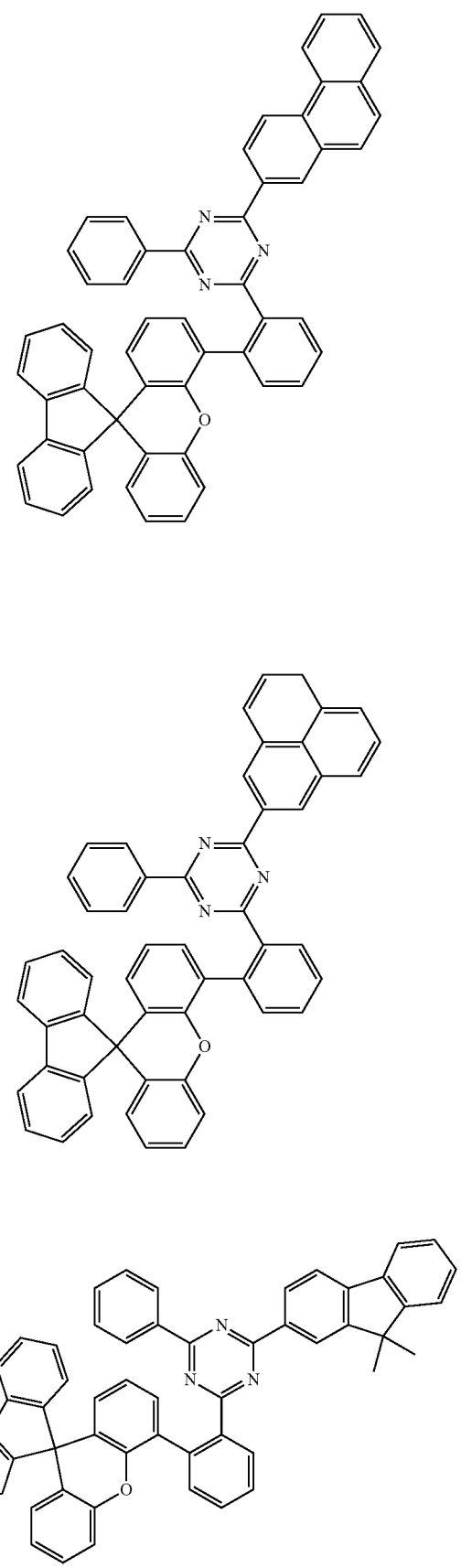

275
-continued
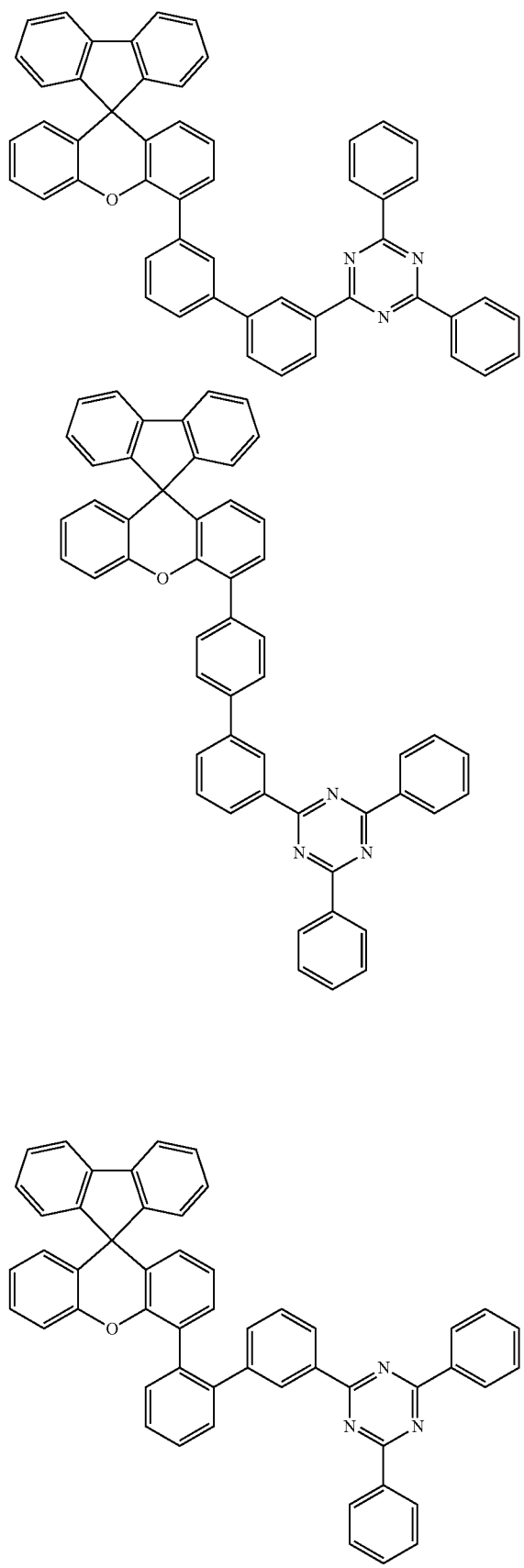
276
-continued
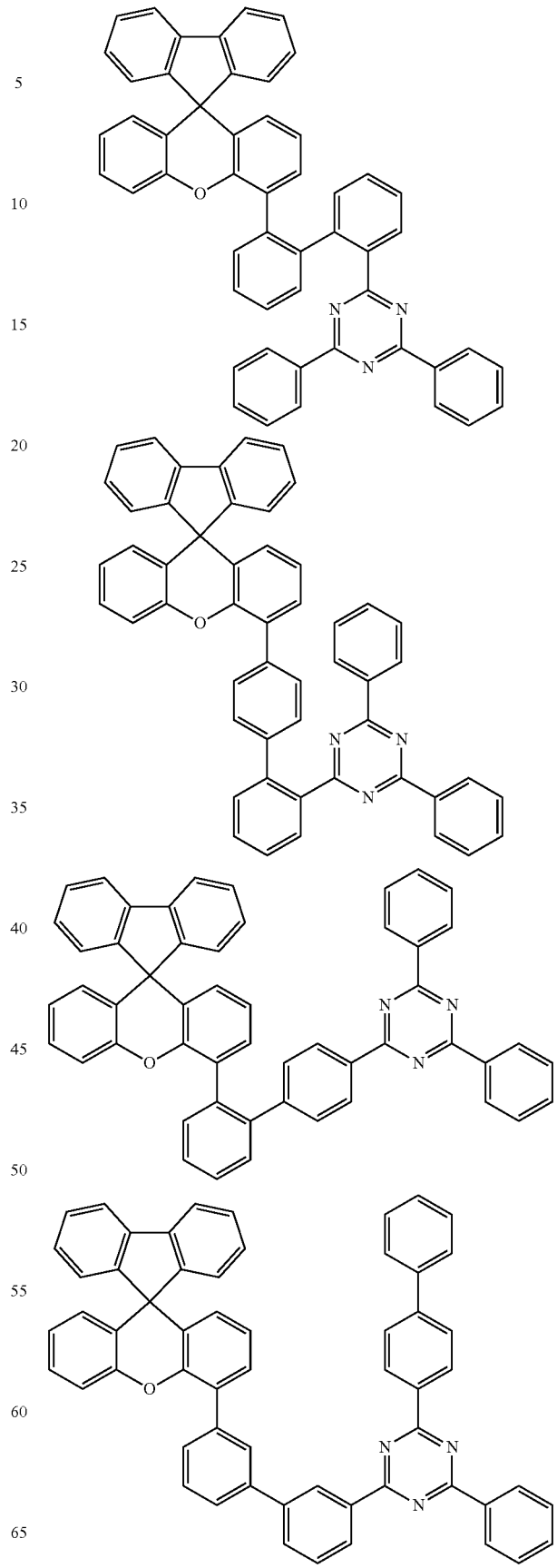

277
-continued
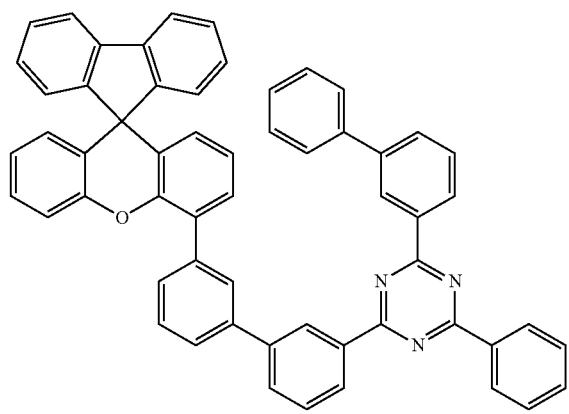
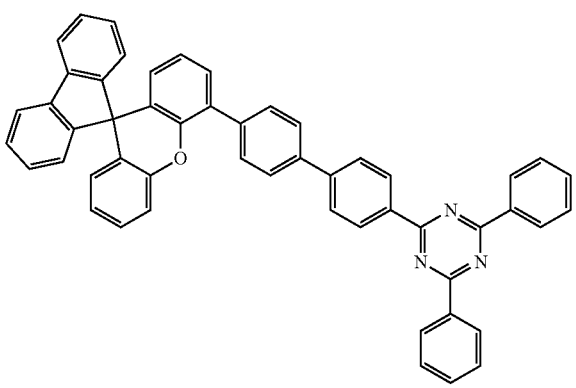
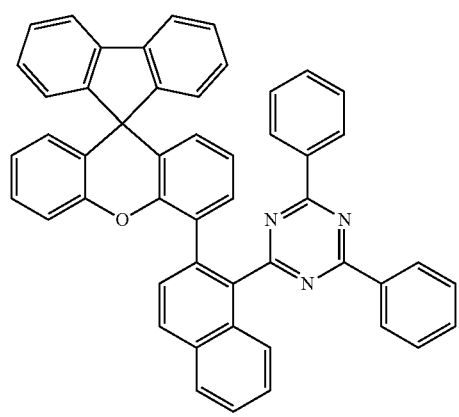
278
-continued
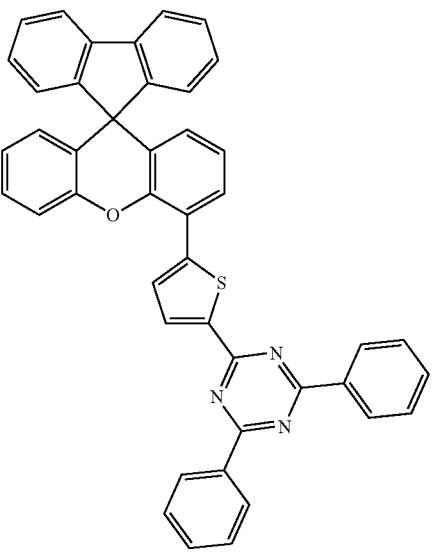
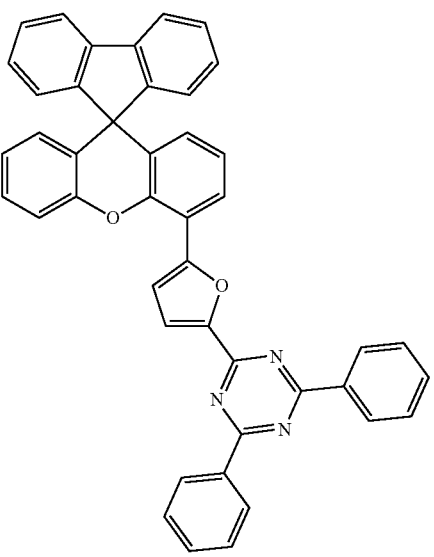
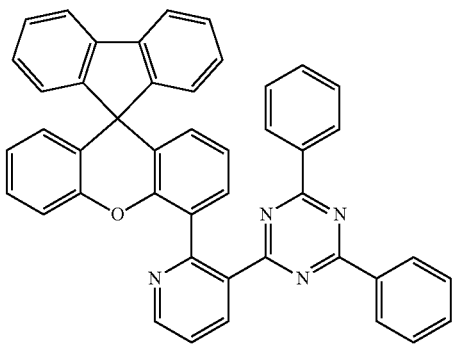

279
-continued
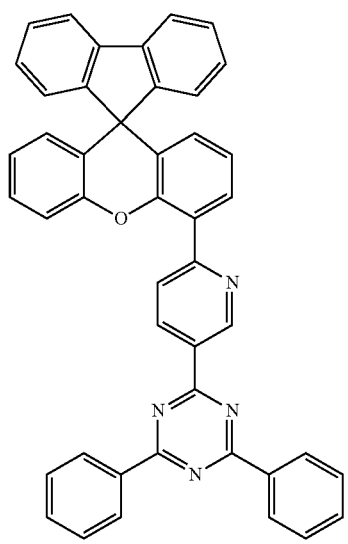
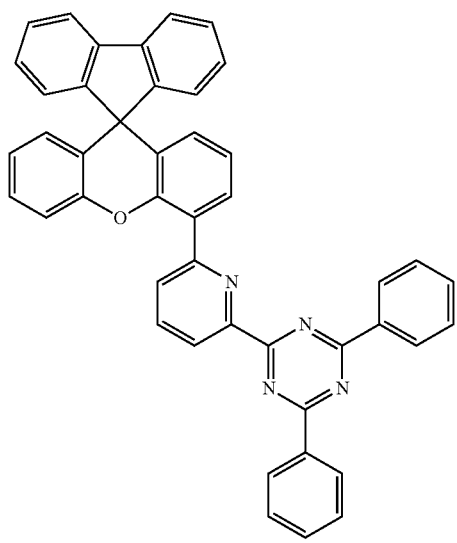
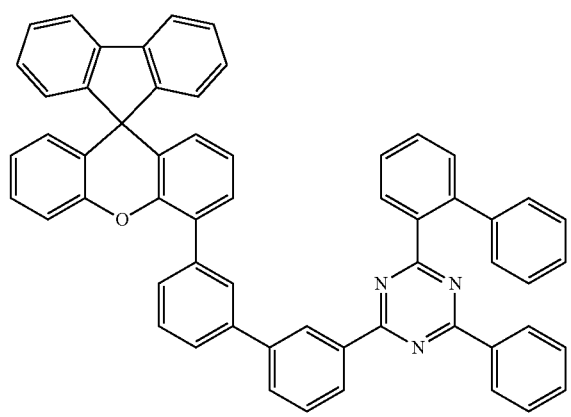
280
-continued
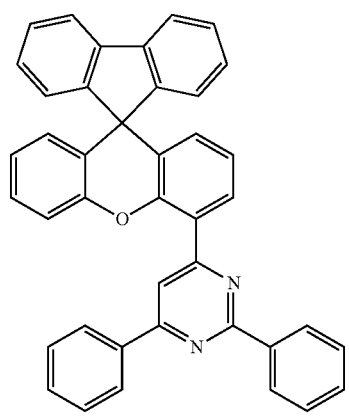
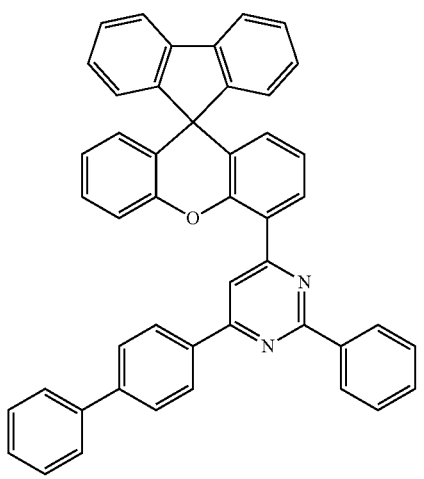
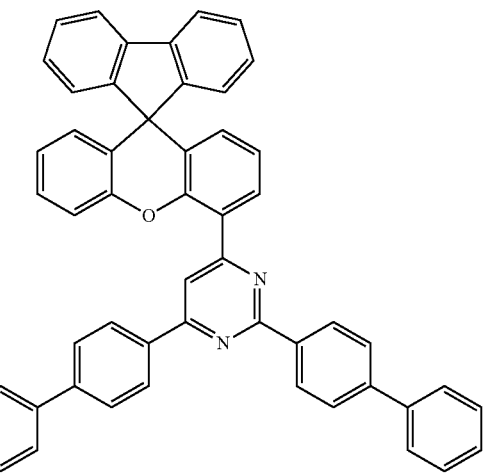

281
-continued
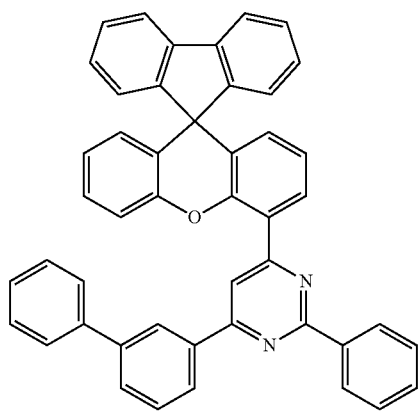
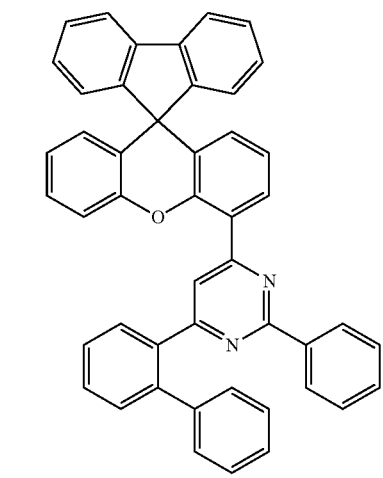
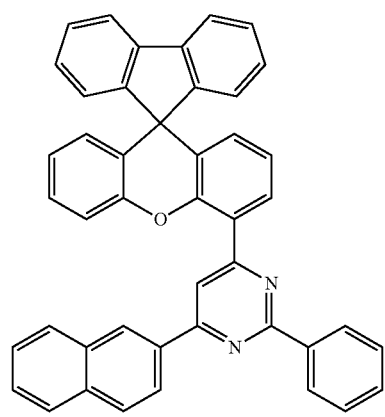
282
-continued
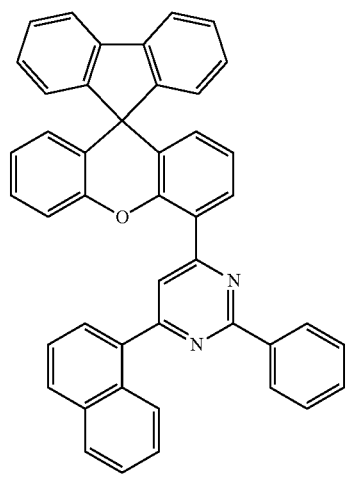
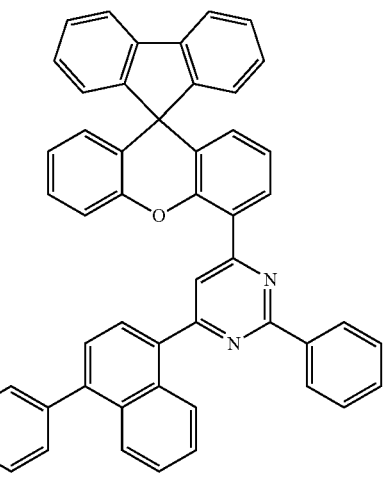
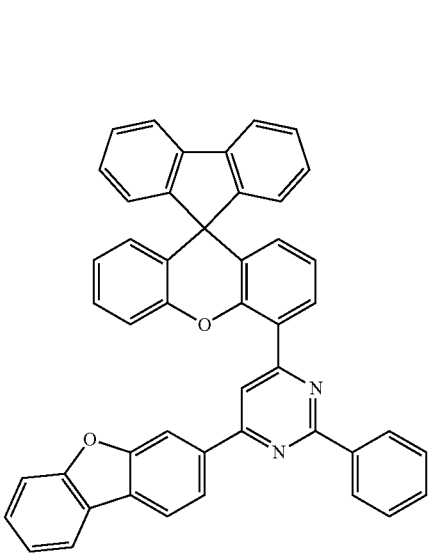

283
-continued
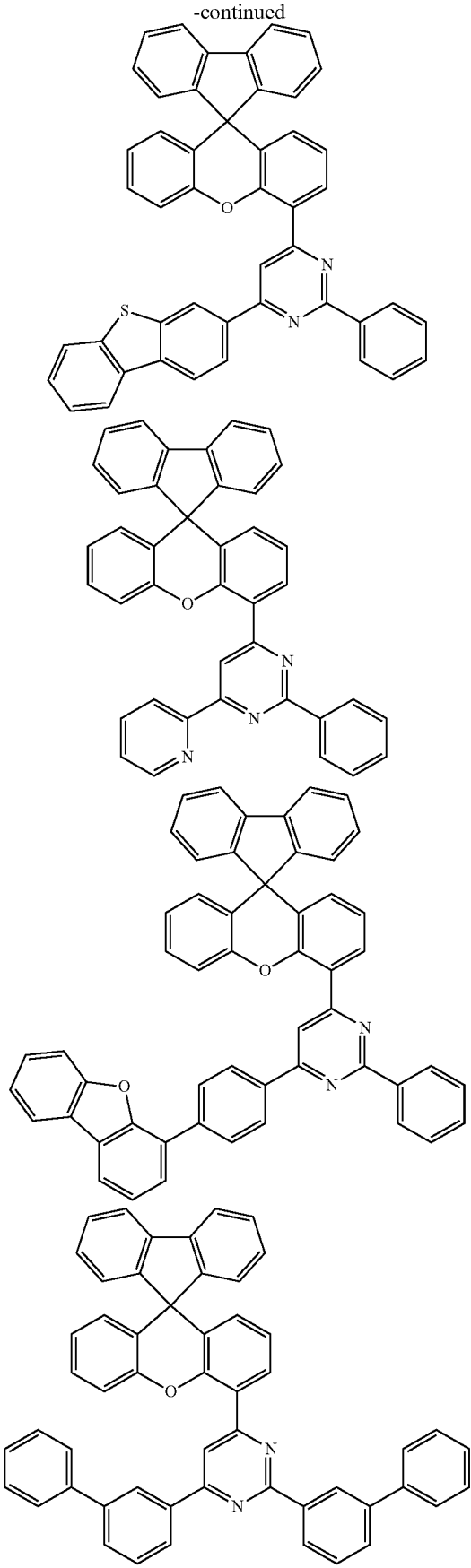
284
-continued
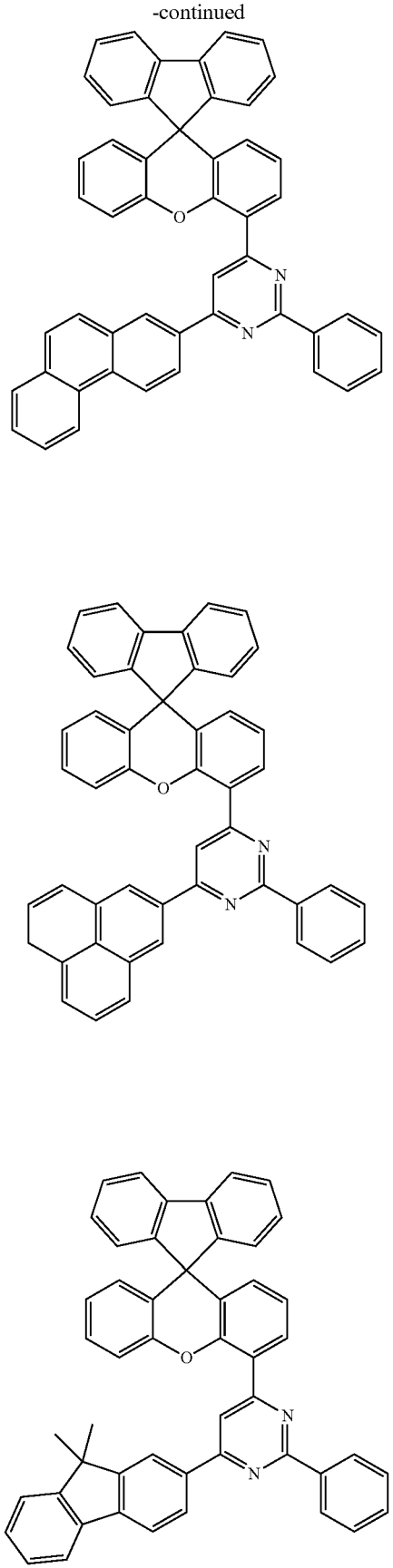

285
-continued
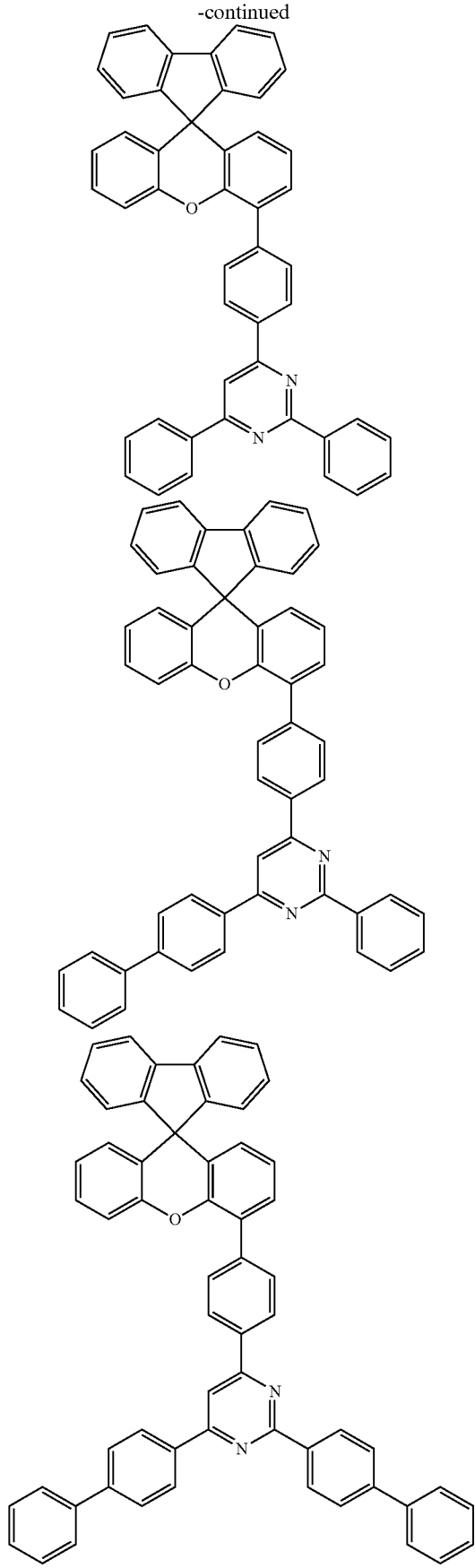
286
-continued
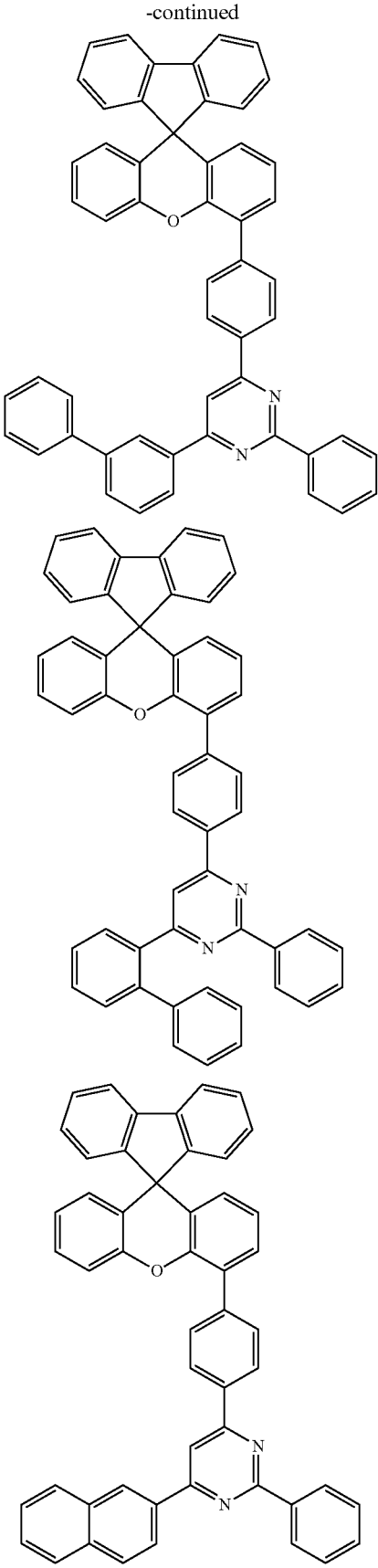

287
-continued
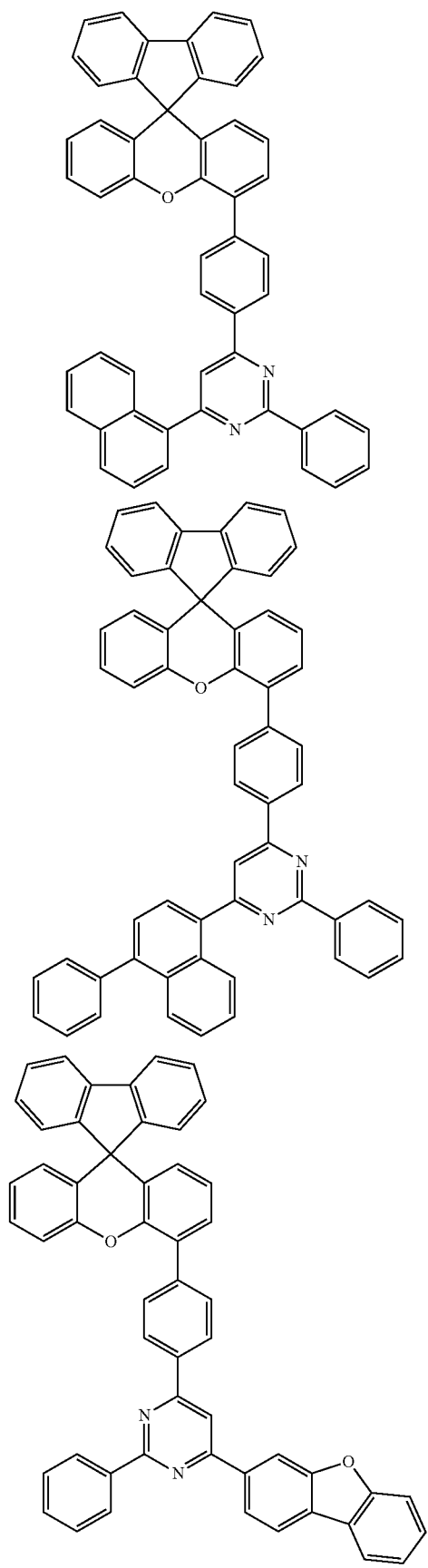
288
-continued
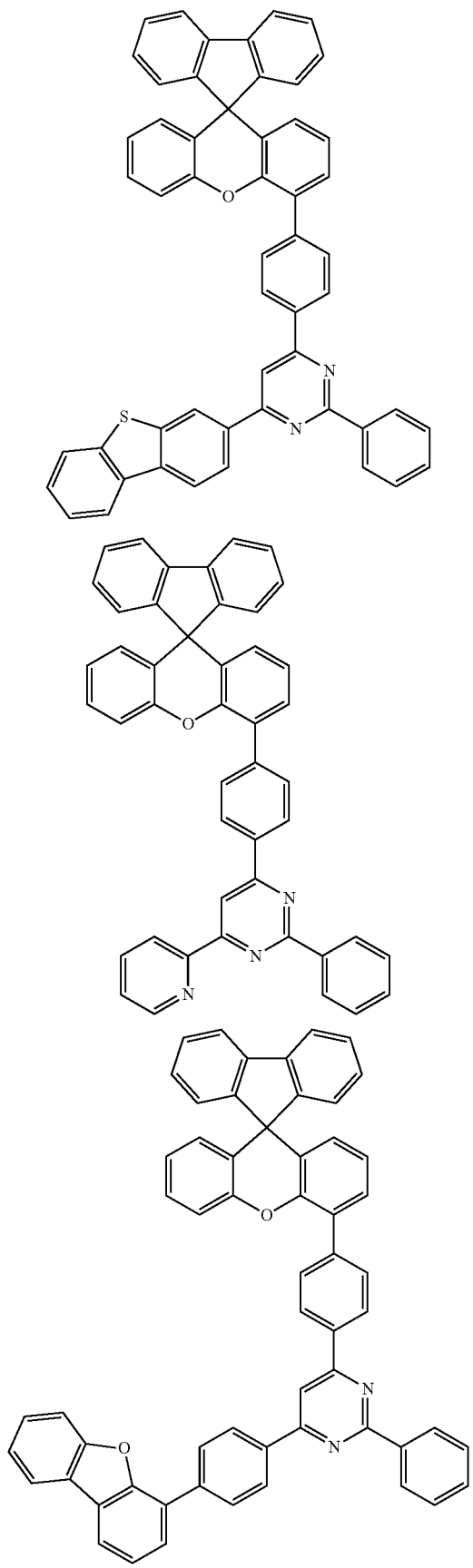

289
-continued
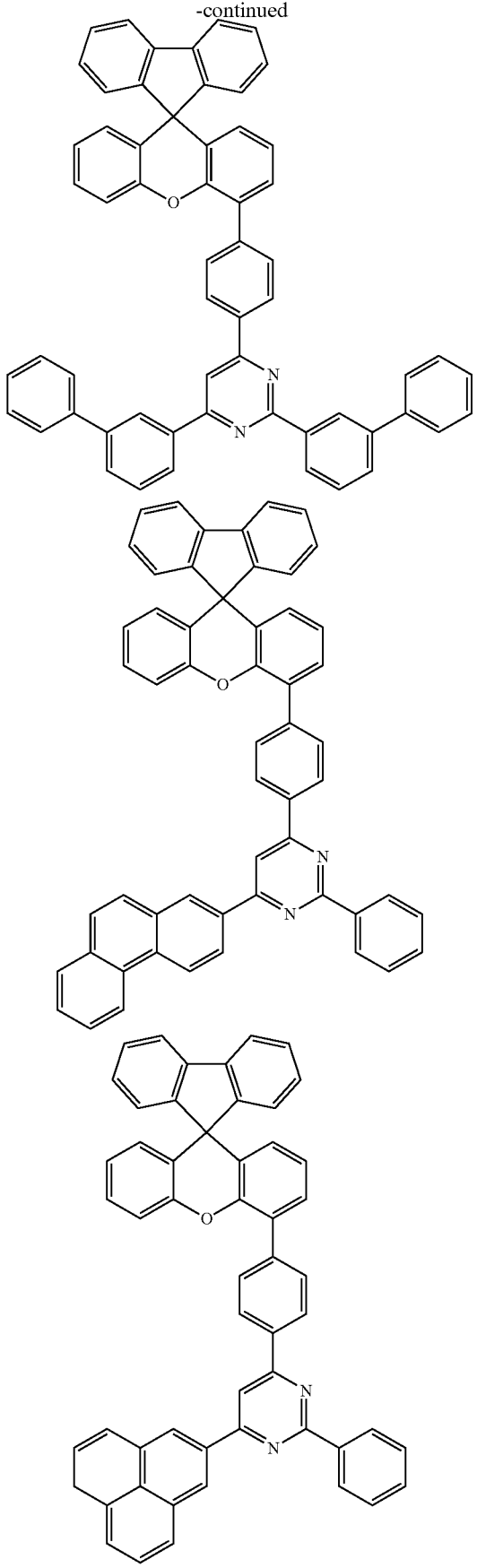
290
-continued
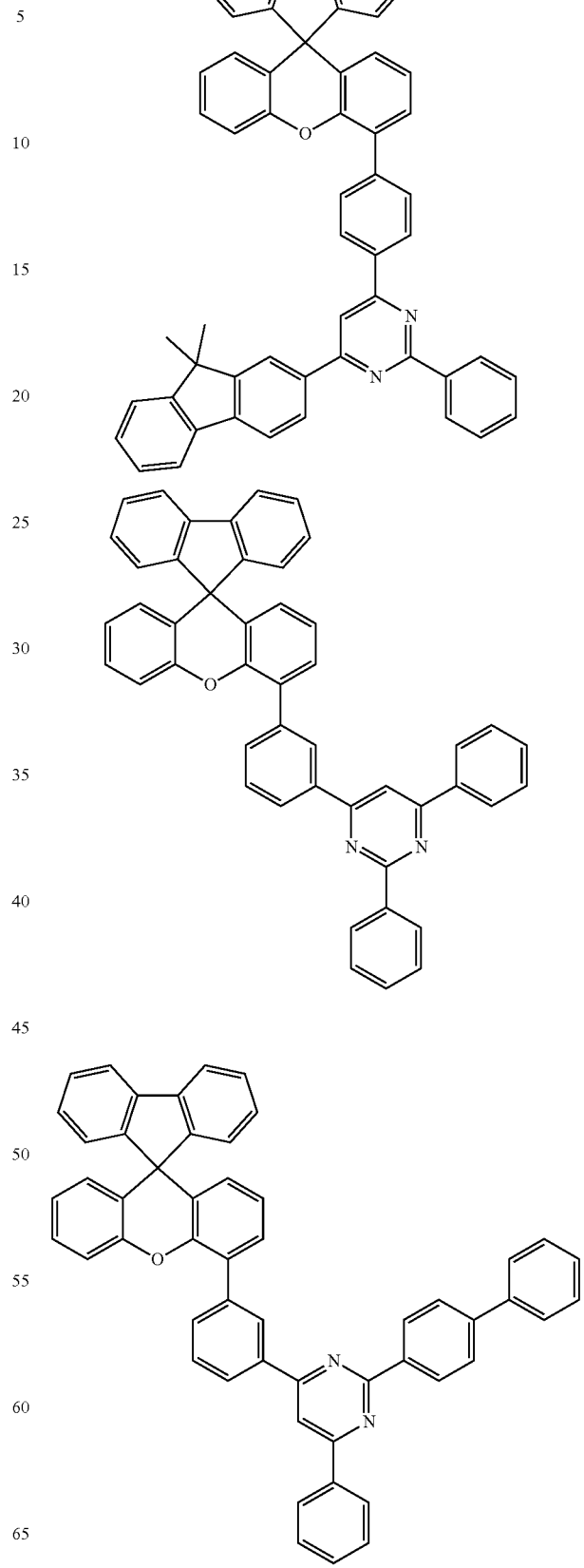

291
-continued
292
-continued
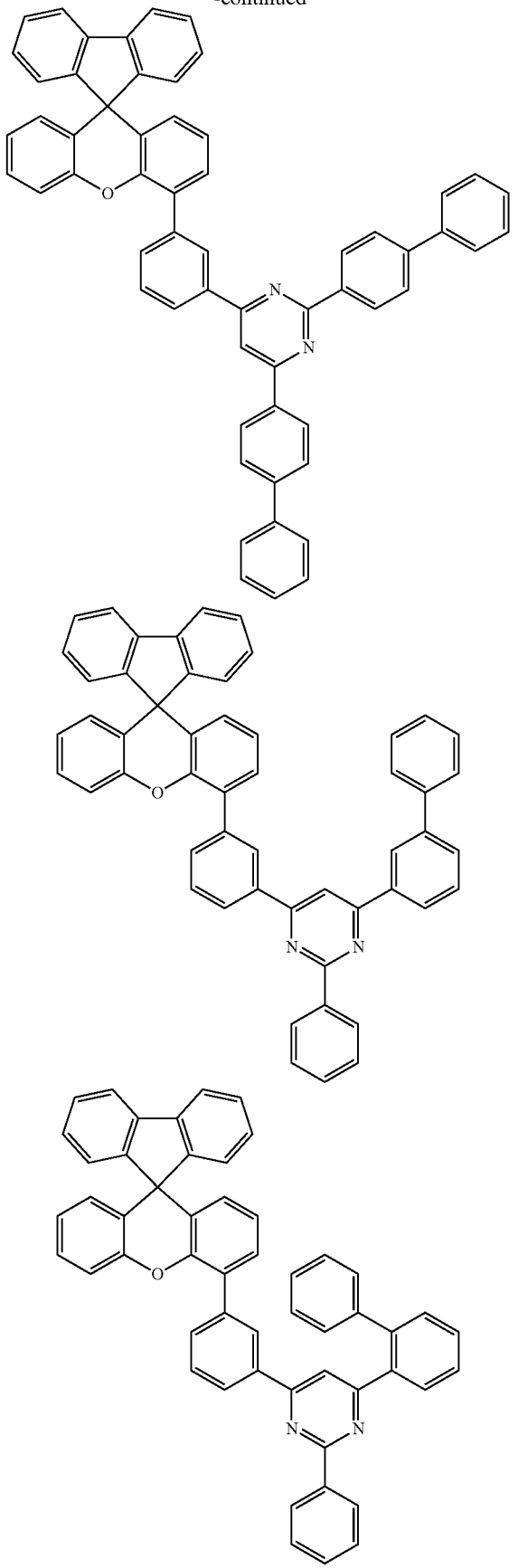
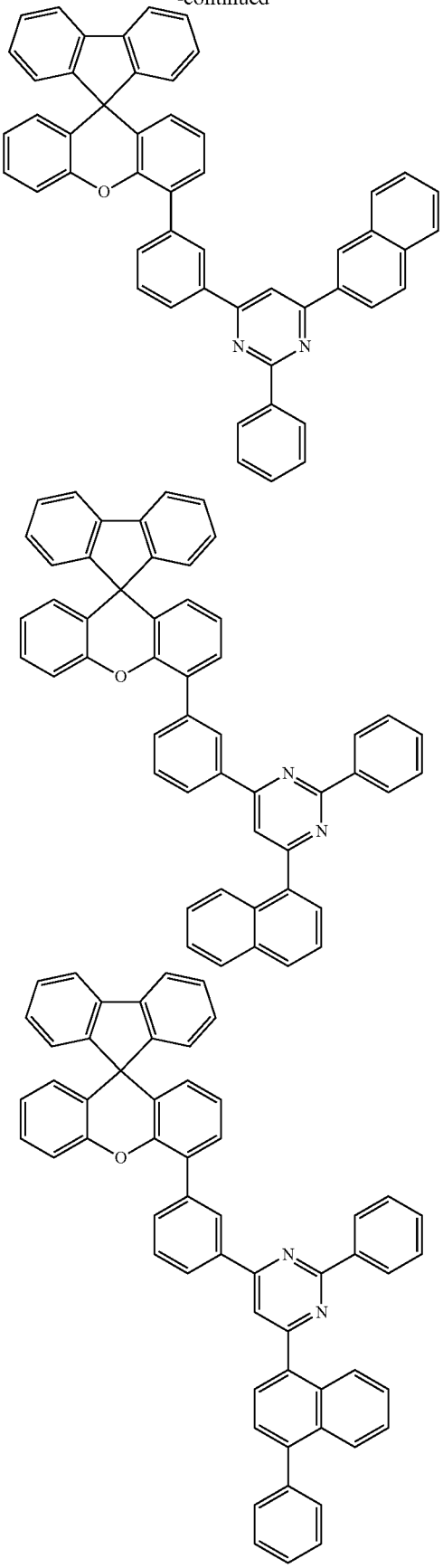

293
-continued
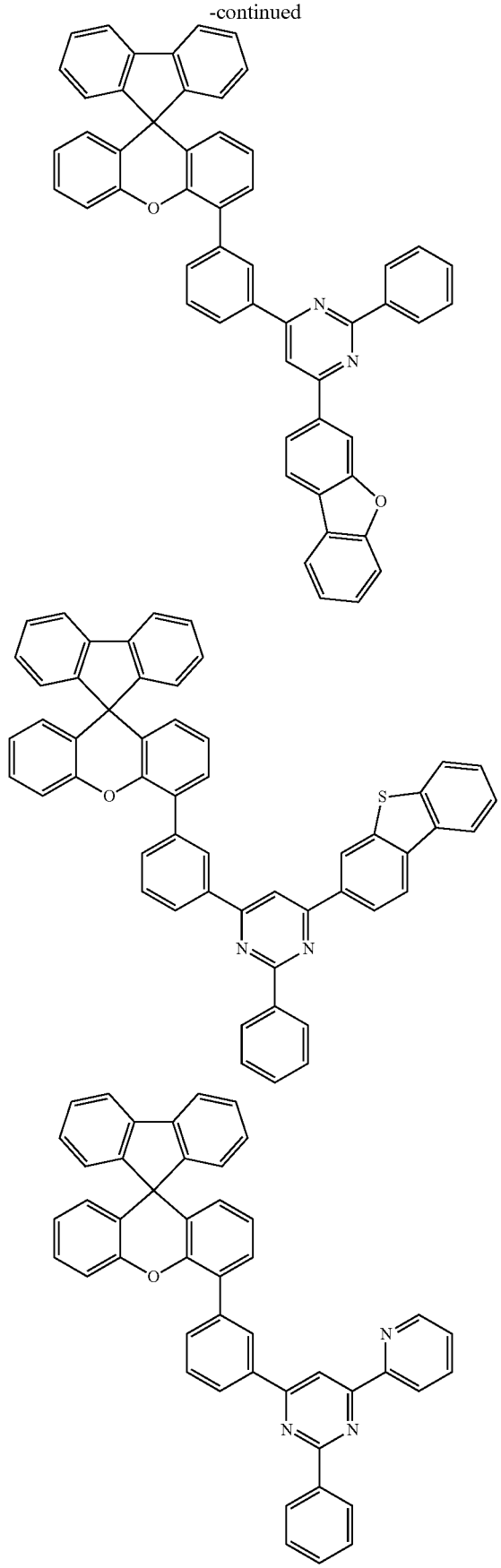
294
-continued
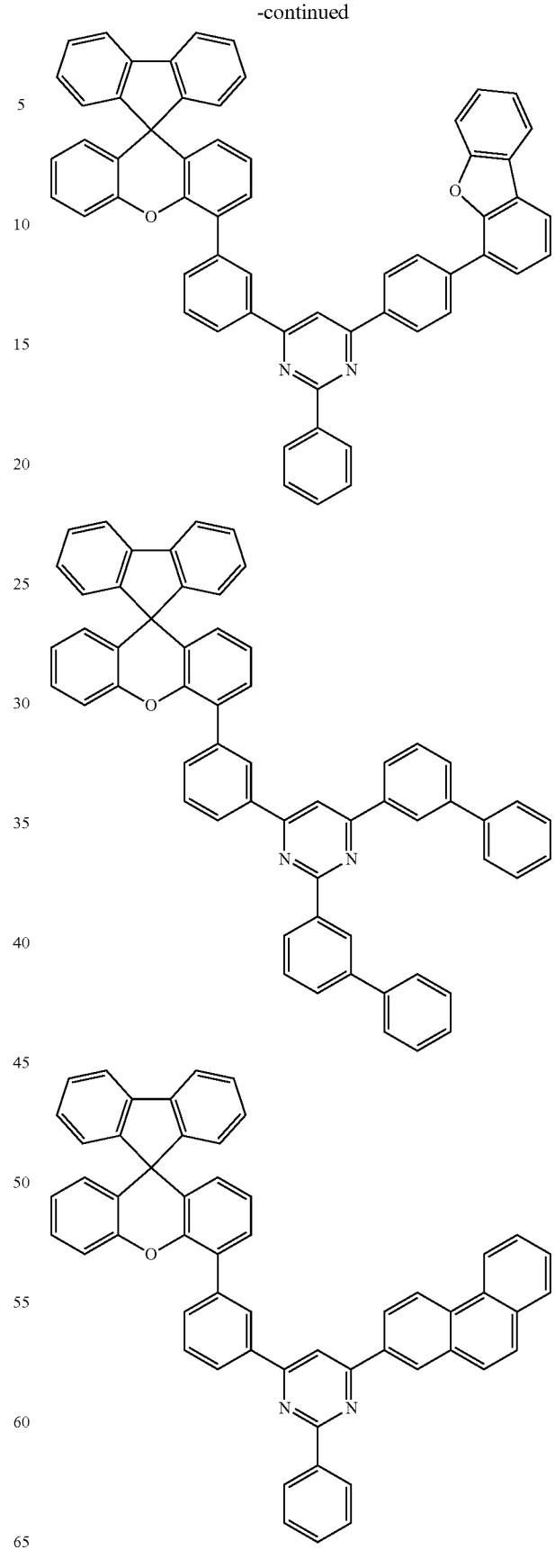

295
-continued
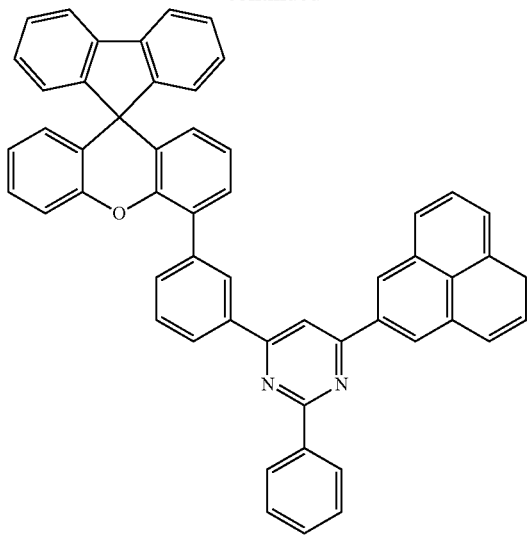
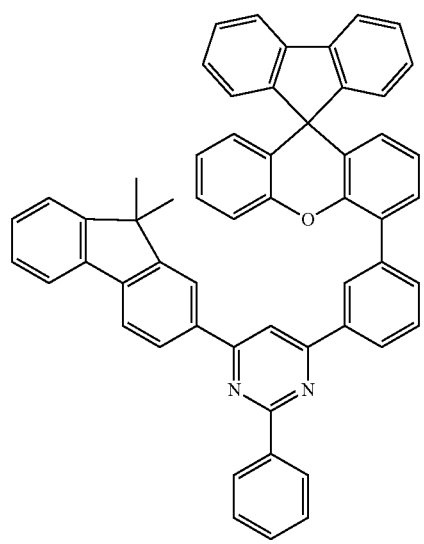
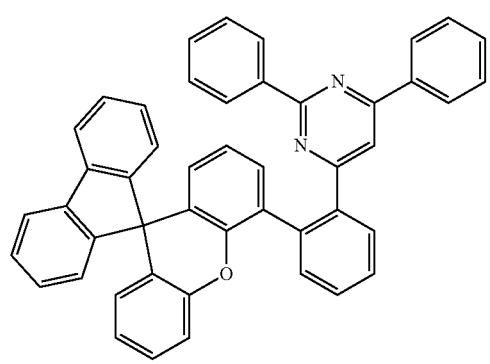
296
-continued
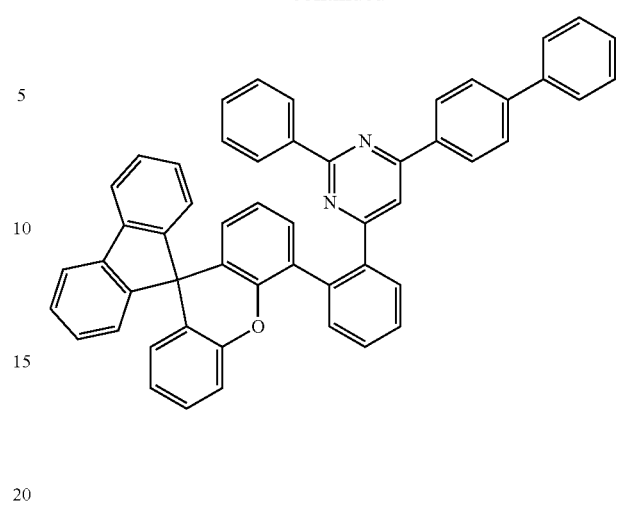
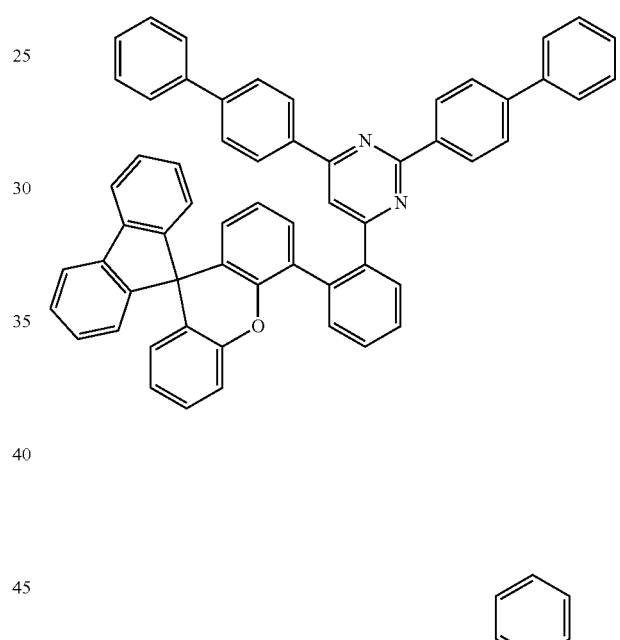
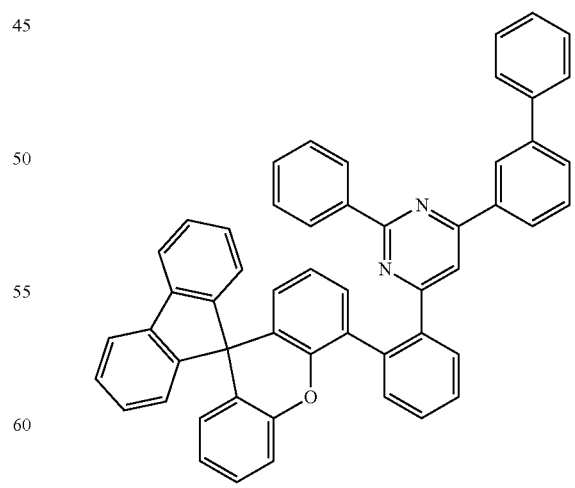

297
-continued
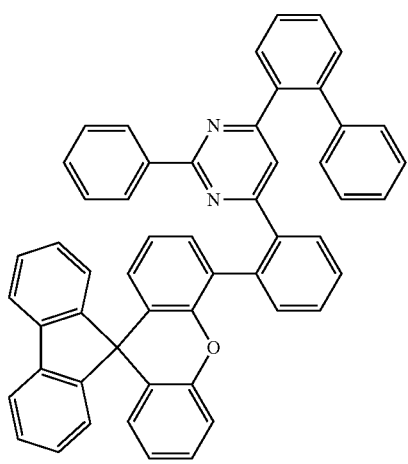
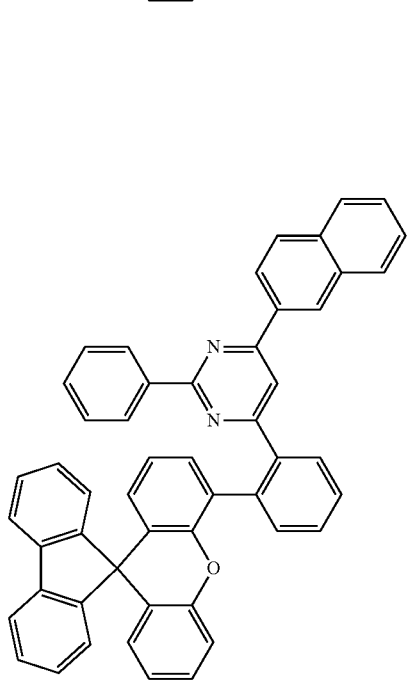
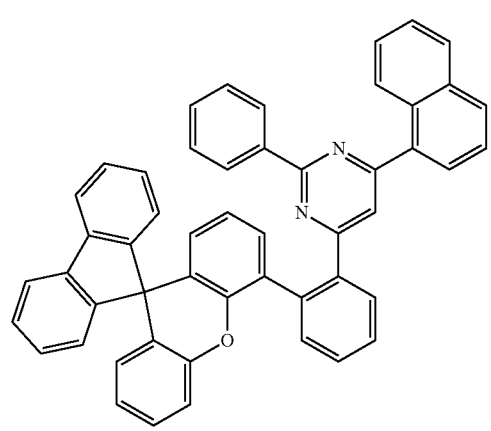
298
-continued
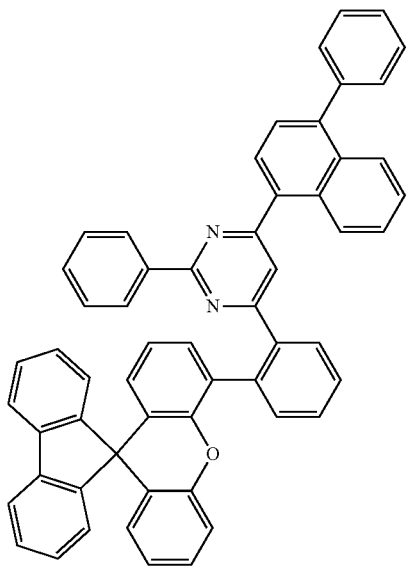
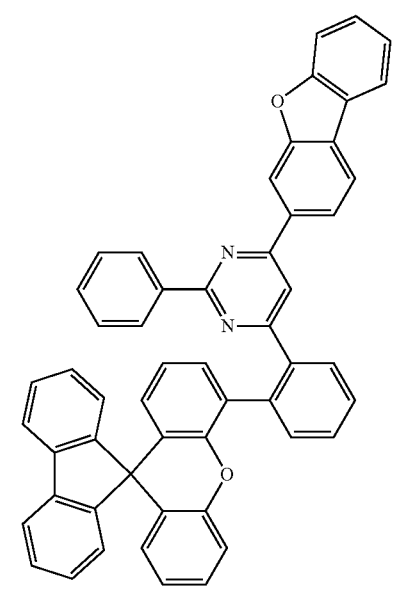
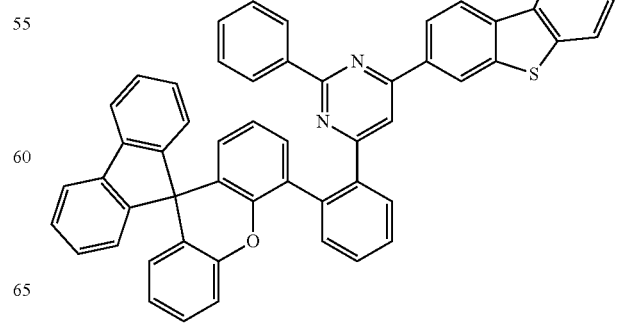

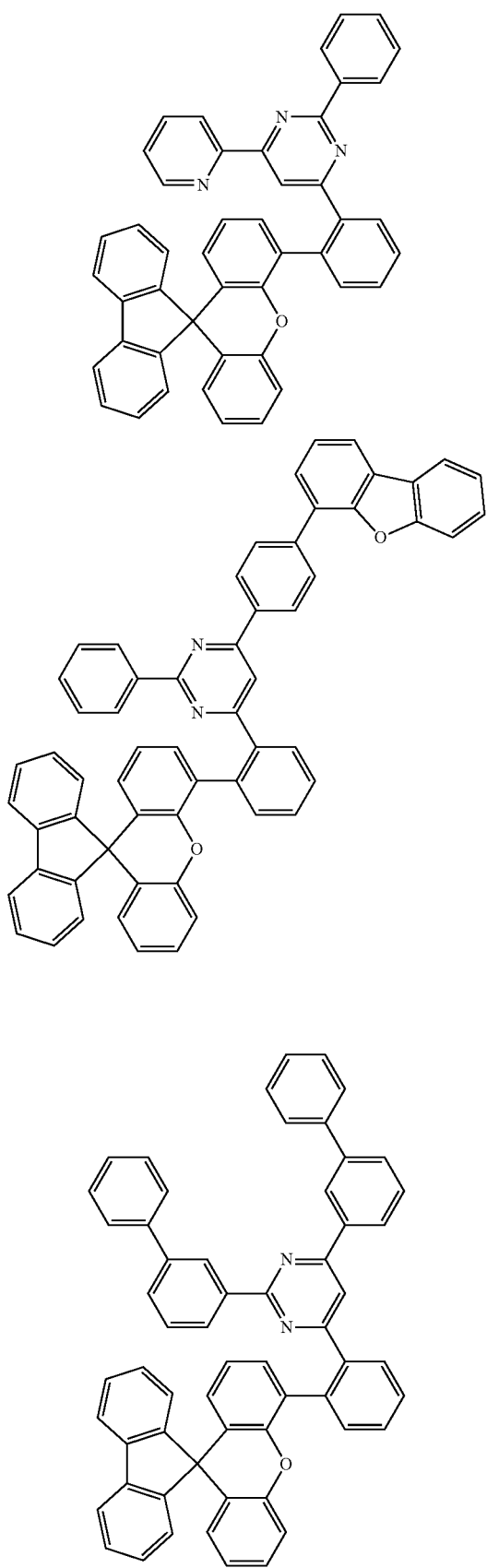 [SMILES: c1ccc(-c2nc(-c3ccccn3)nc(-c3ccccc3-c3cccc4c3Oc3ccccc3C43c4ccccc4-c4ccccc43)n2)cc1 ; c1ccc(-c2nc(-c3ccc(-c4cccc5c4oc4ccccc45)cc3)nc(-c3ccccc3-c3cccc4c3Oc3ccccc3C43c4ccccc4-c4ccccc43)n2)cc1 ; c1ccc(-c2cccc(-c3nc(-c4cccc(-c5ccccc5)c4)nc(-c4ccccc4-c4cccc5c4Oc4ccccc4C54c5ccccc5-c5ccccc54)n3)c2)cc1]

301
-continued
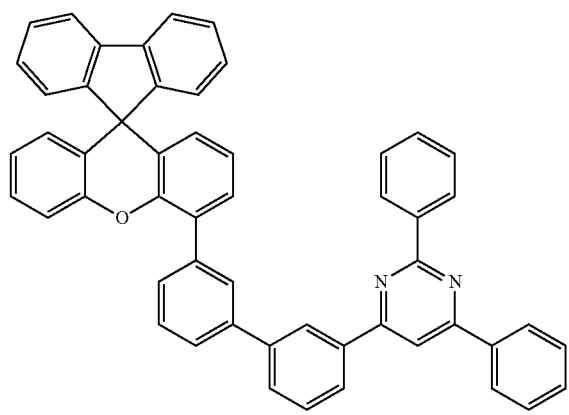
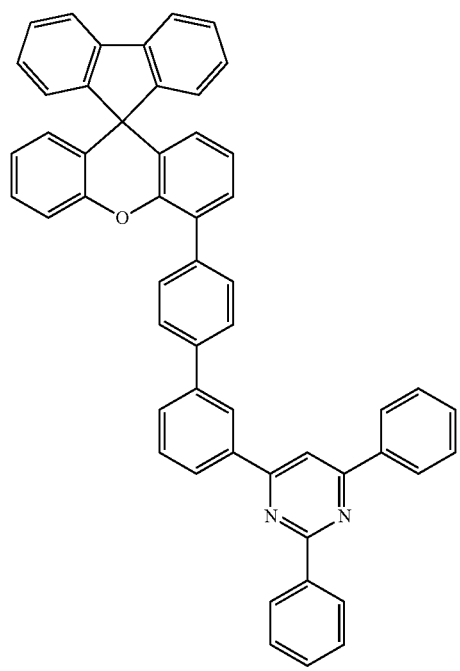
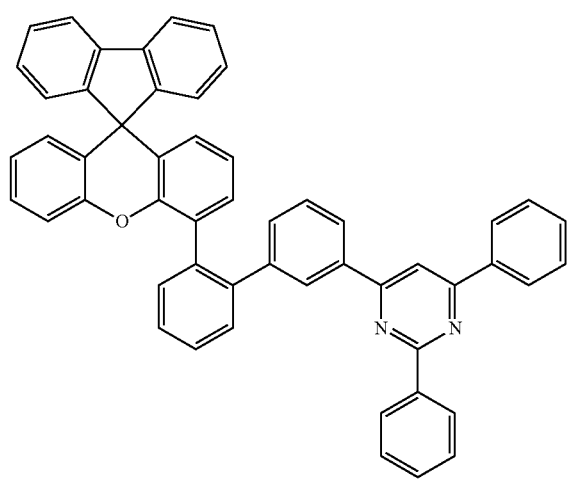
302
-continued
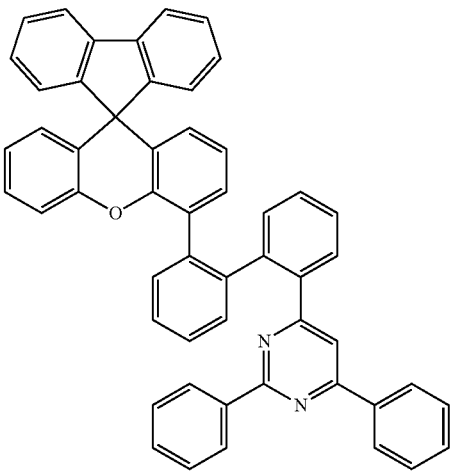
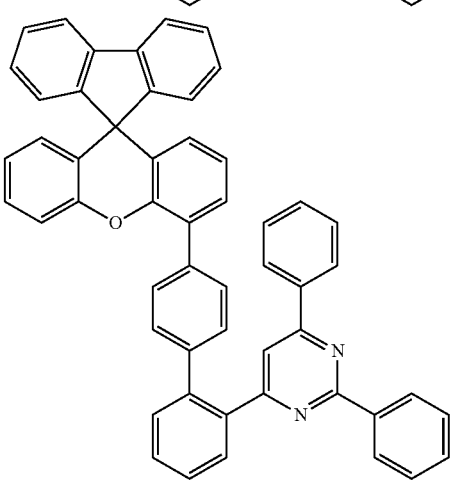
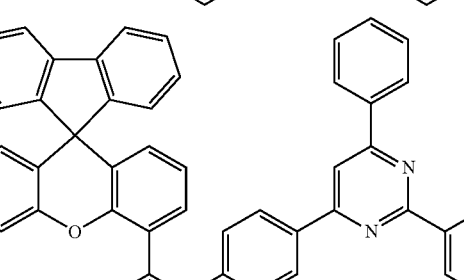
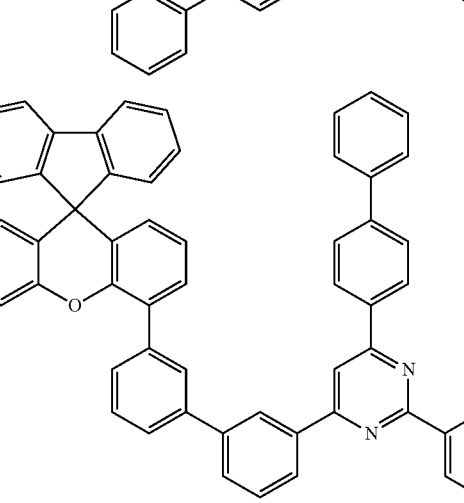

303
-continued
304
-continued
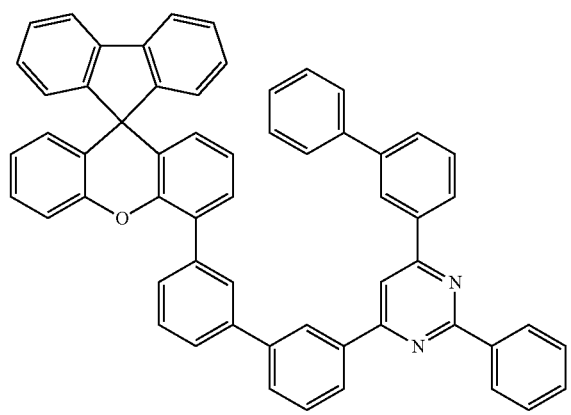
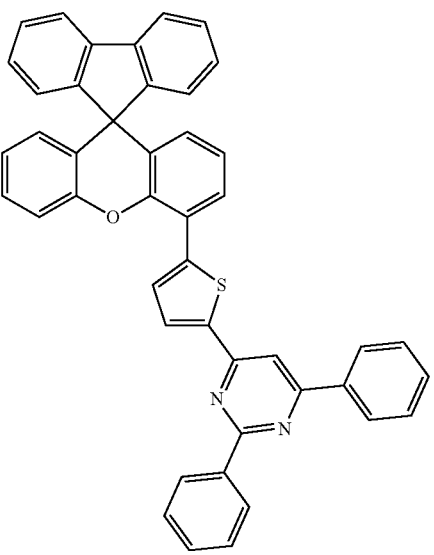
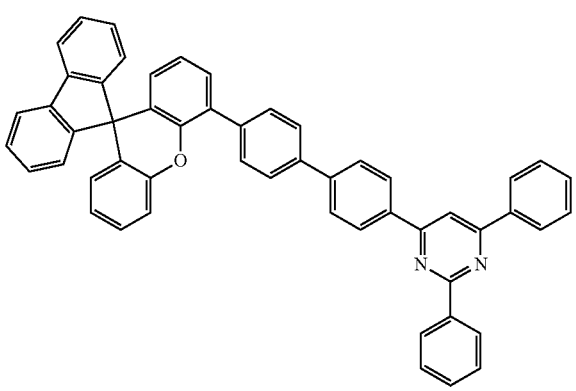
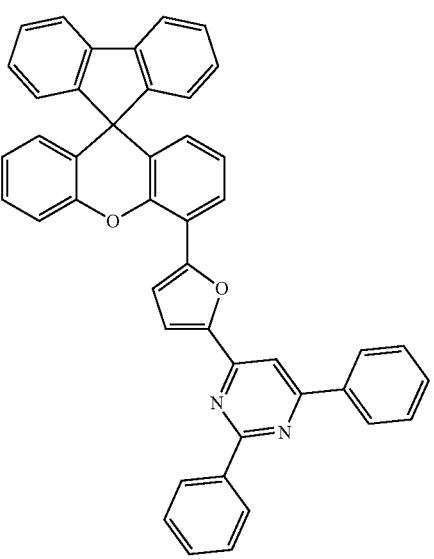
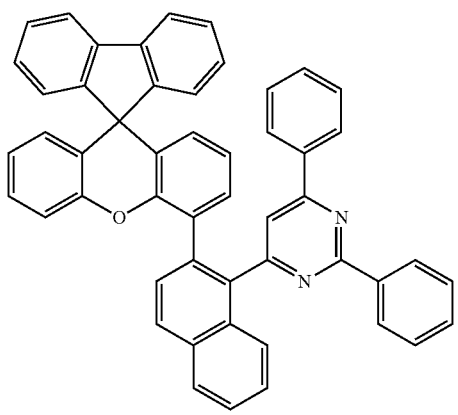
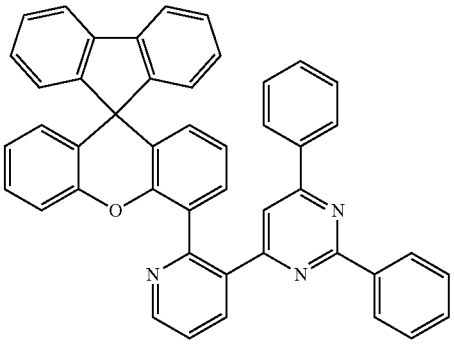

305
-continued
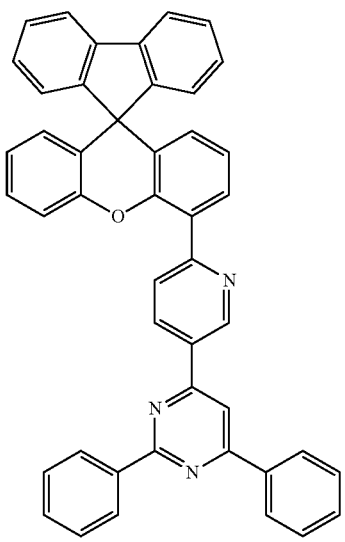
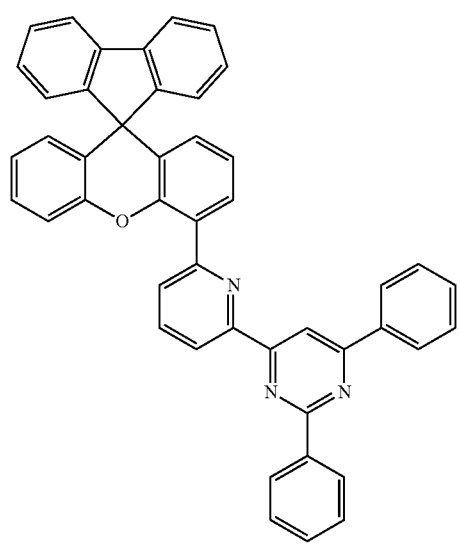
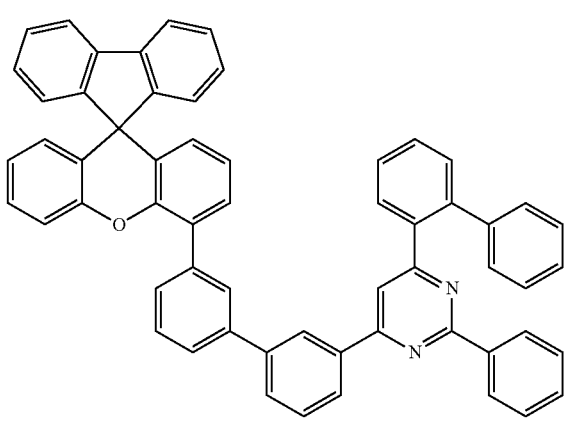
306
-continued
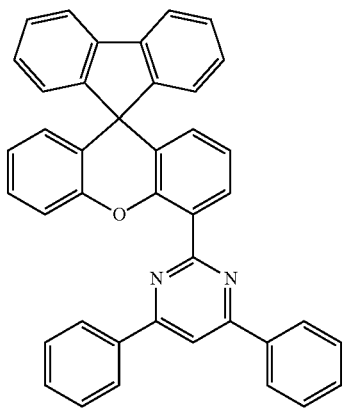
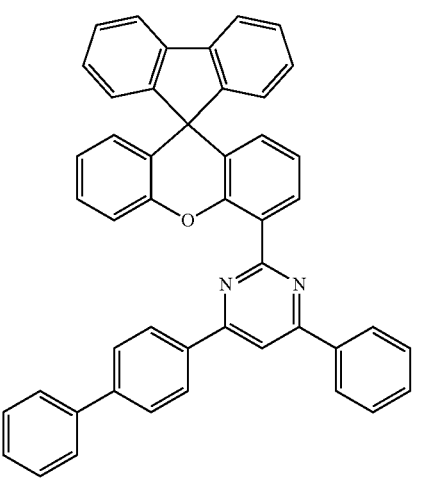
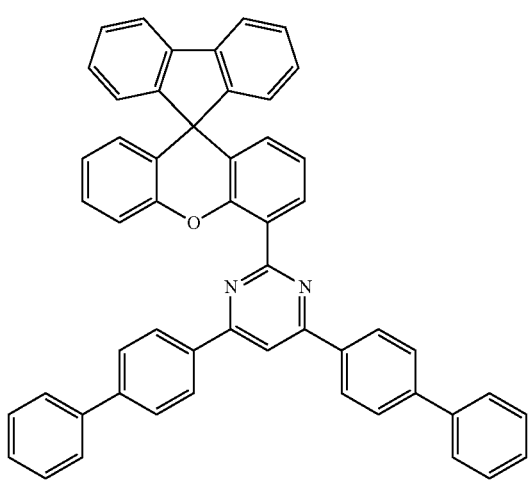

307
-continued
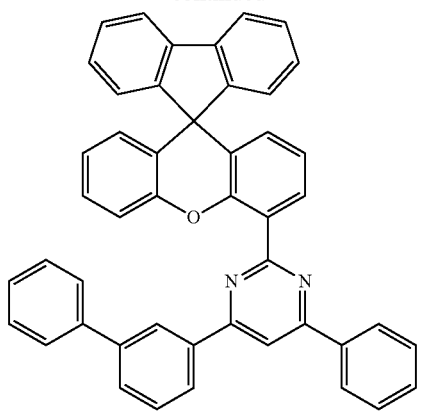
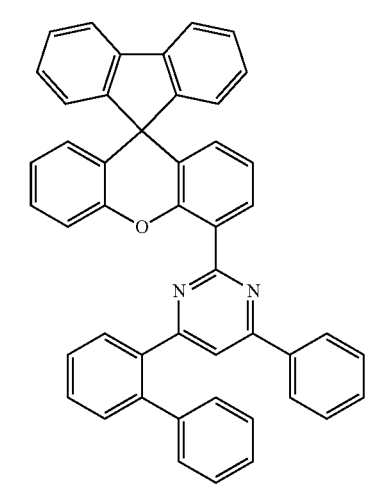
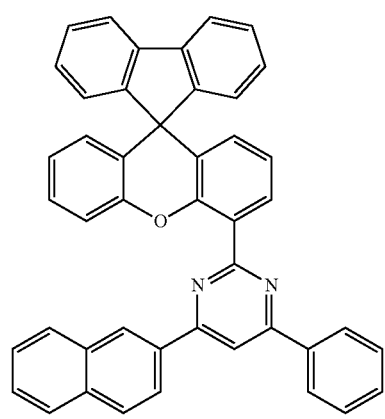
308
-continued
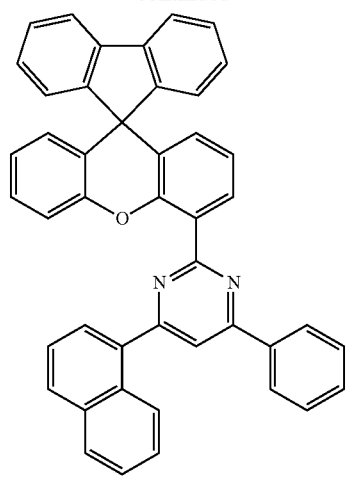
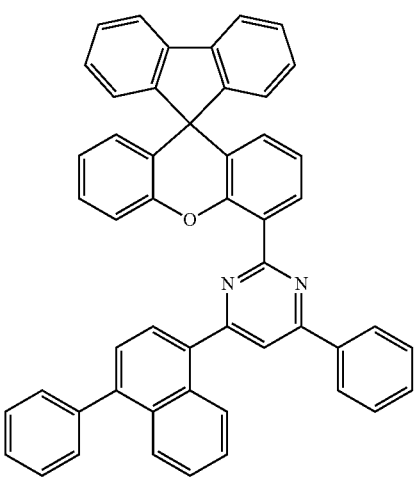
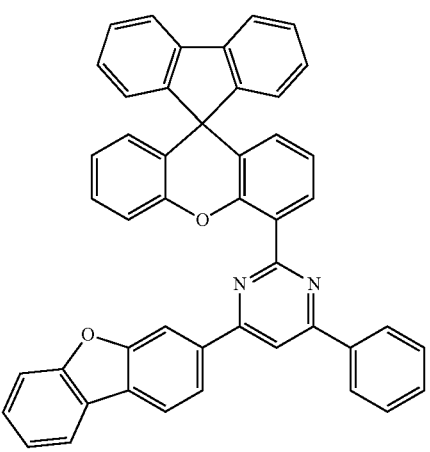

309
-continued
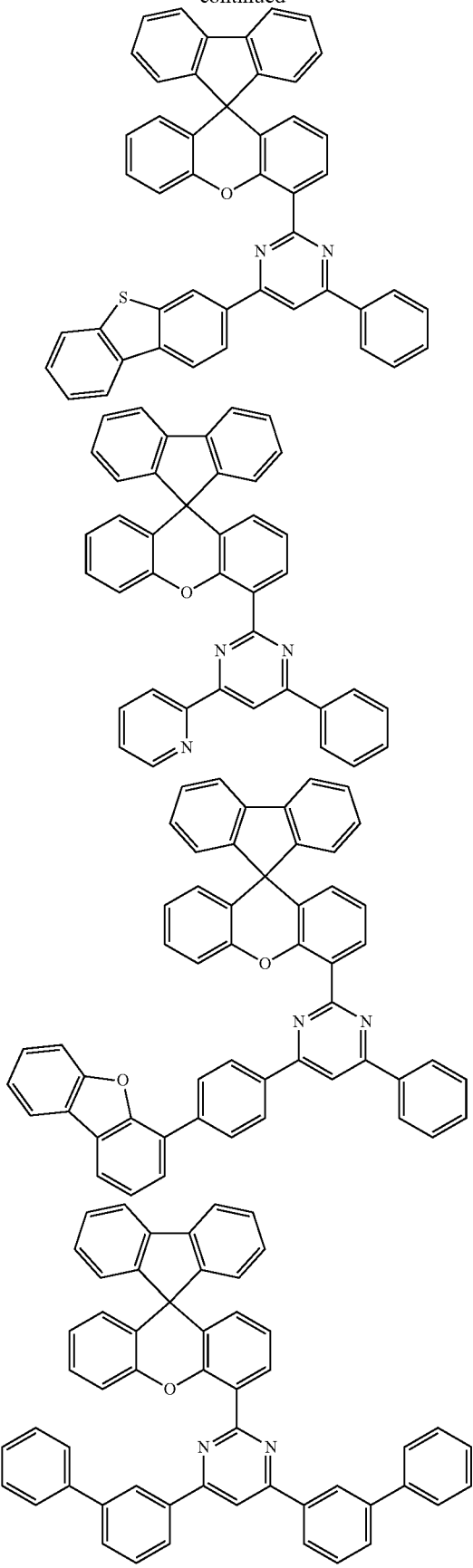
310
-continued
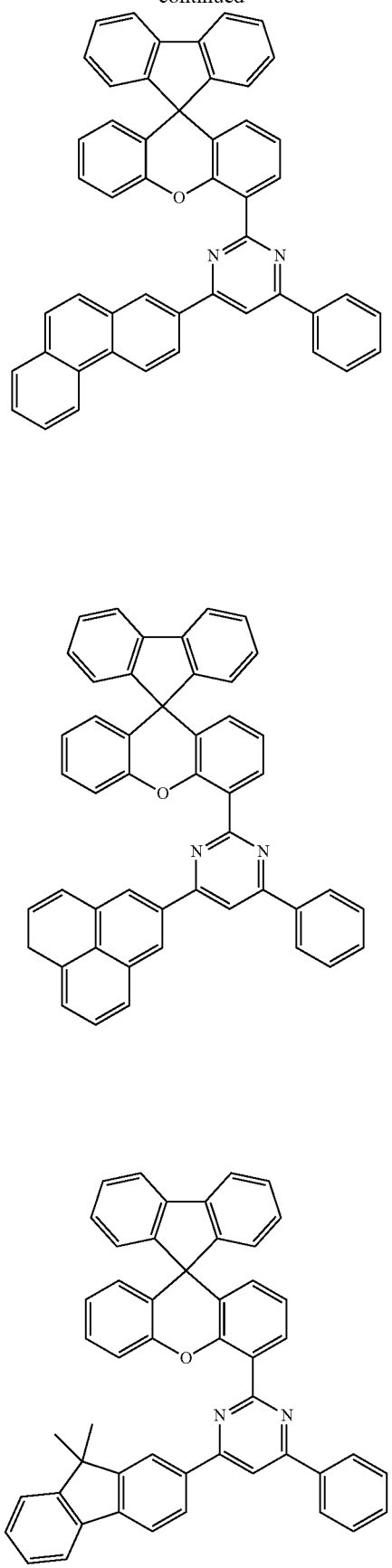

311
-continued
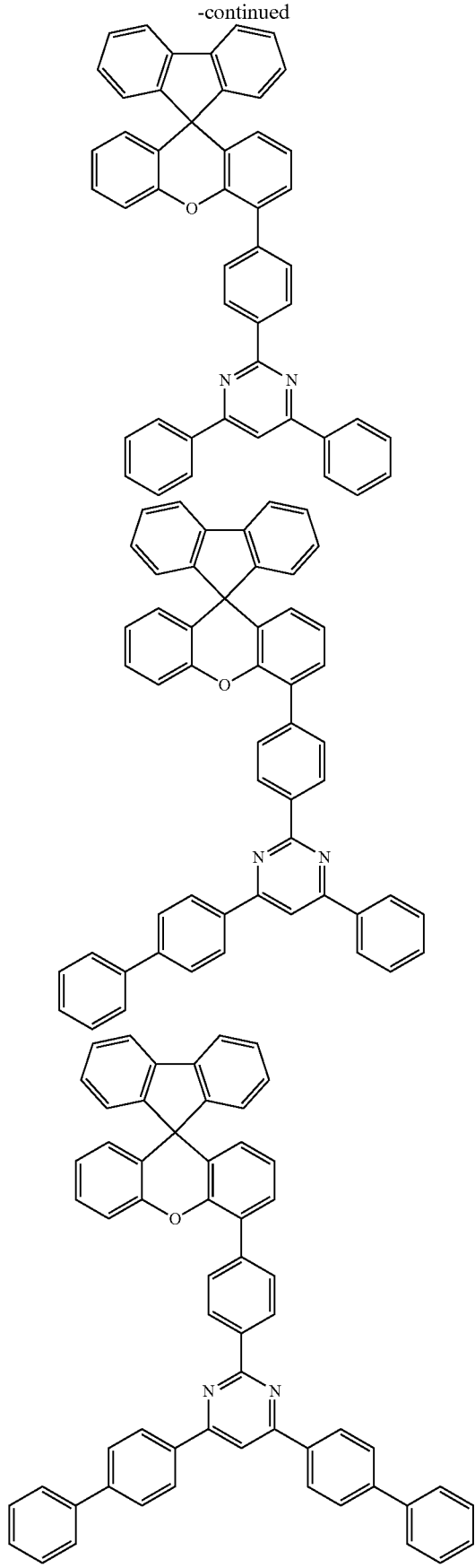
312
-continued
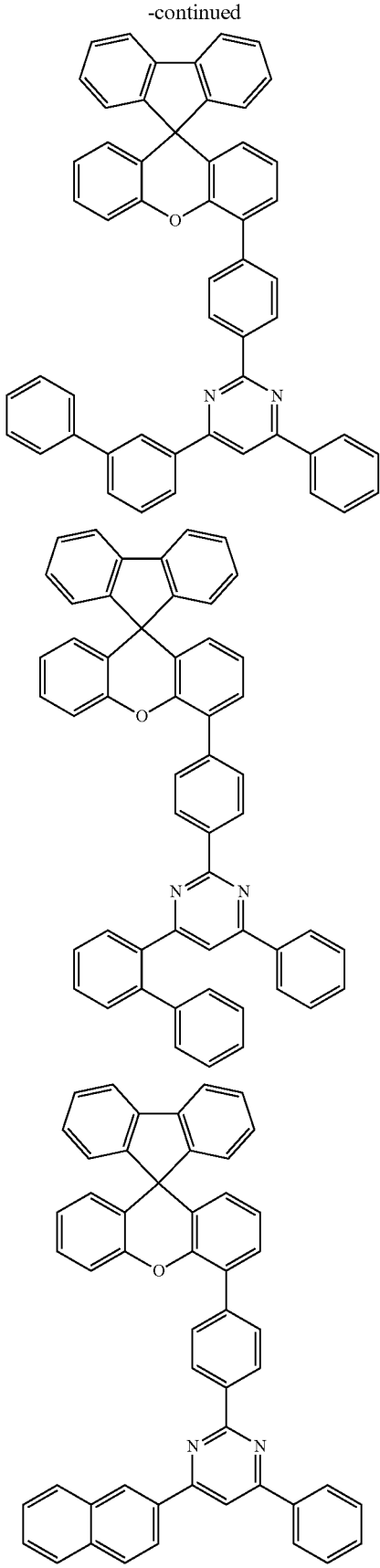

313
-continued
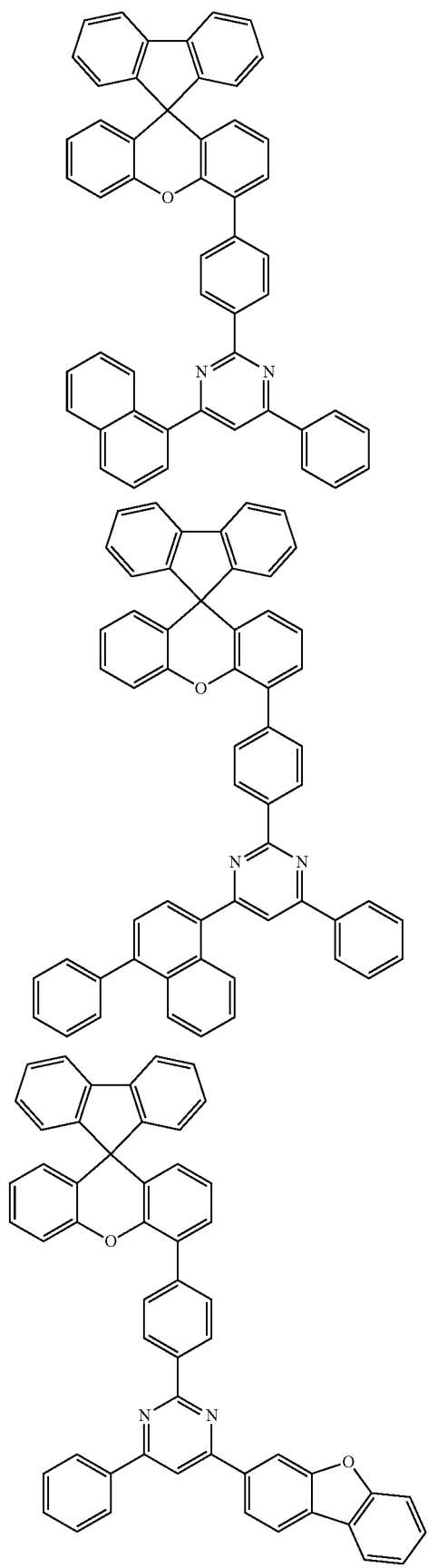
314
-continued
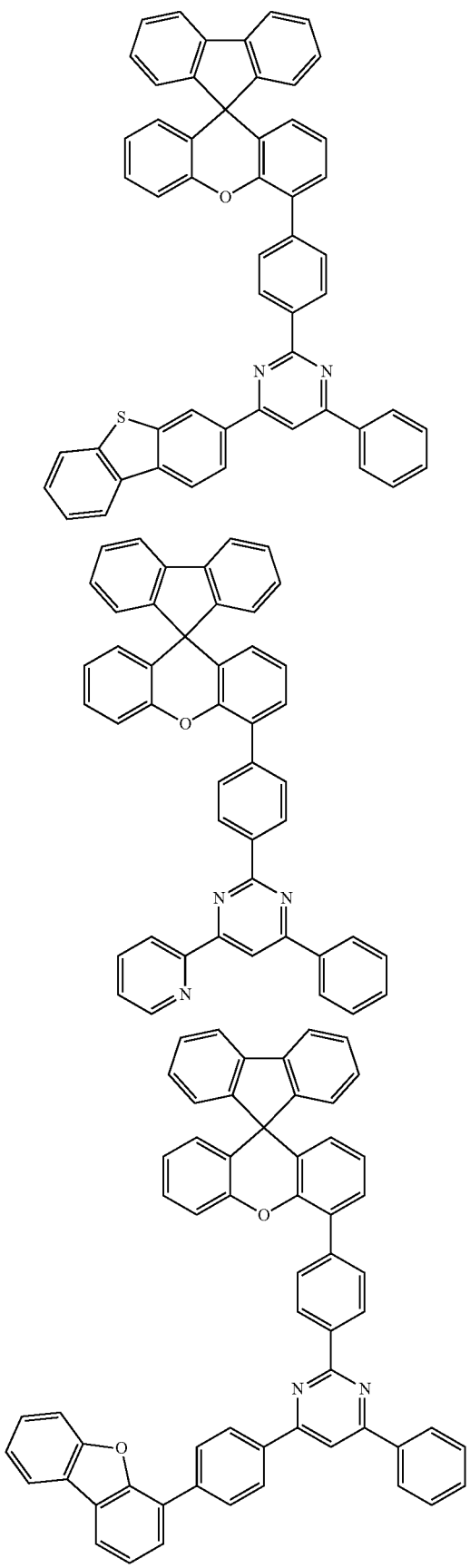

315
-continued
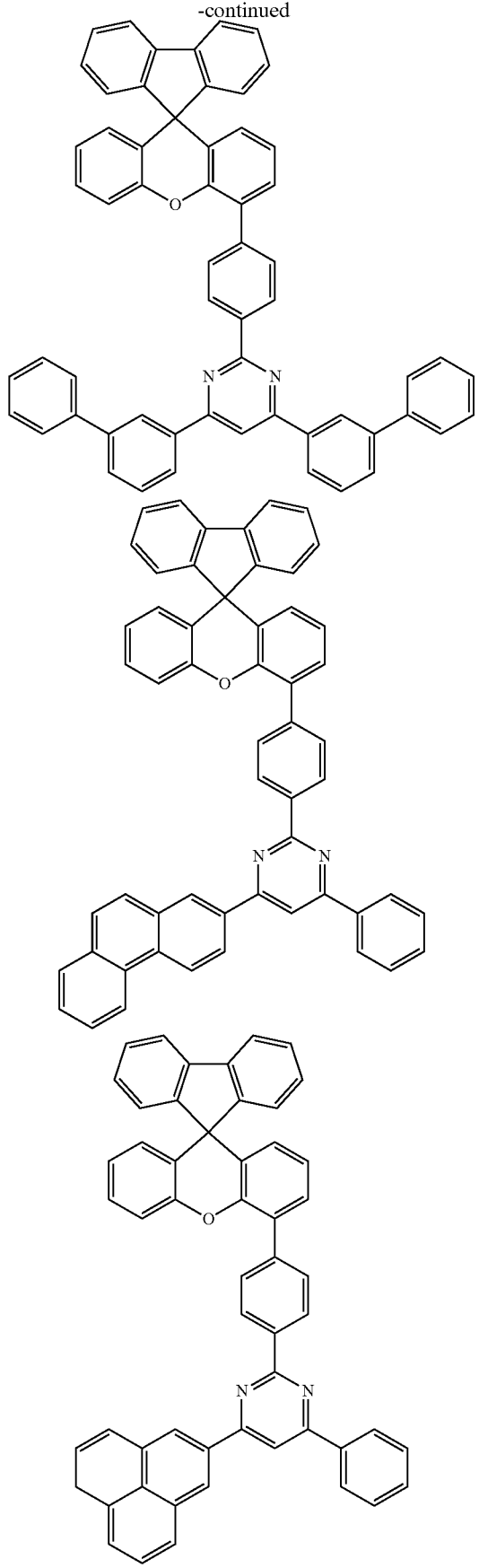
316
-continued
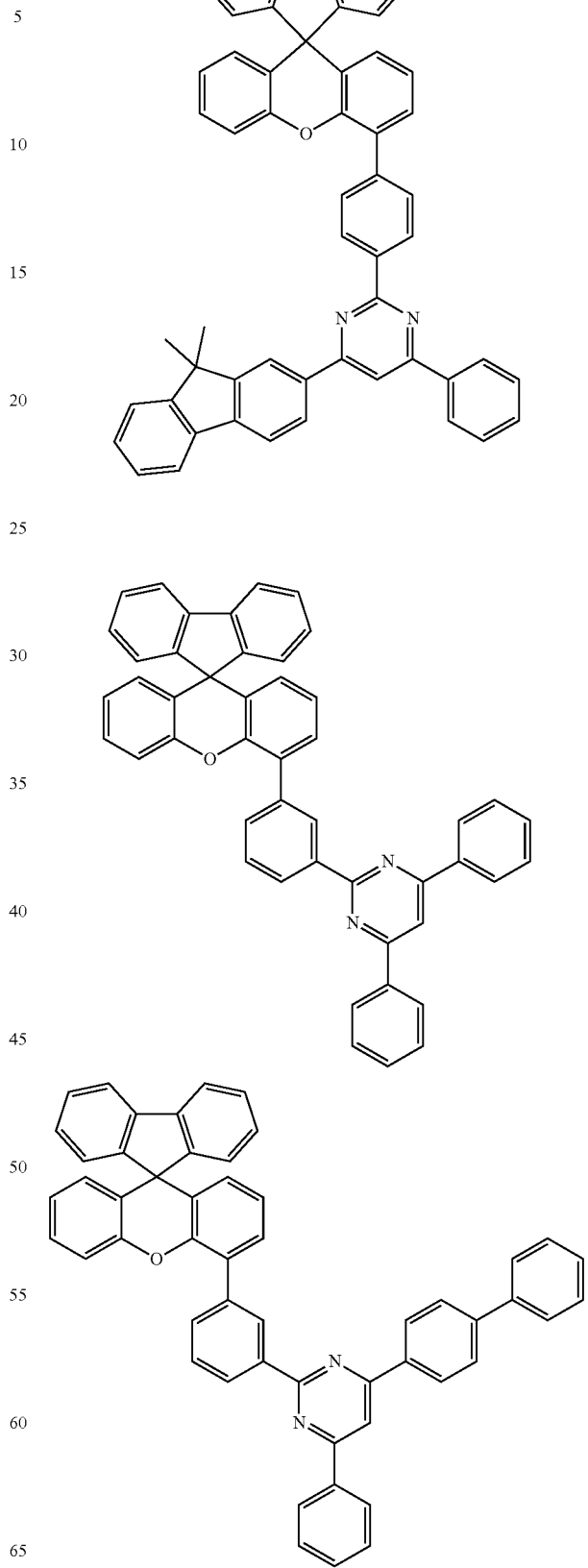

317
-continued
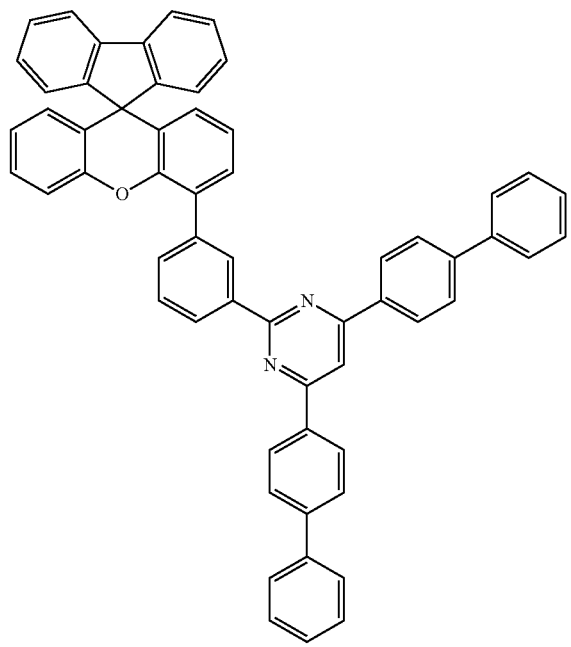
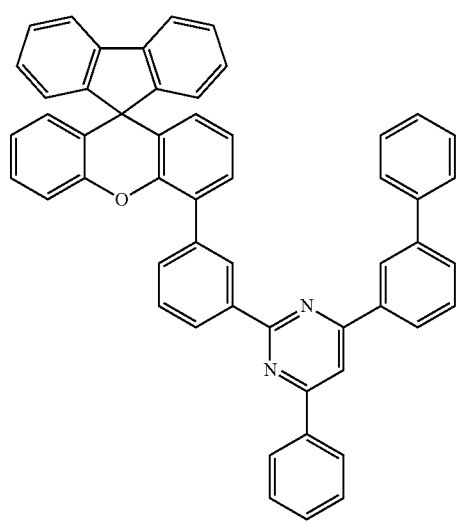
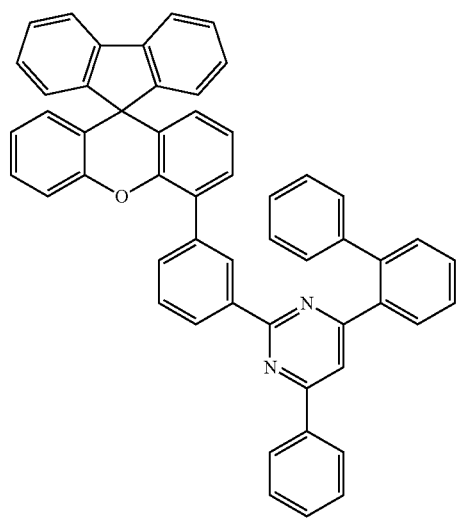
318
-continued
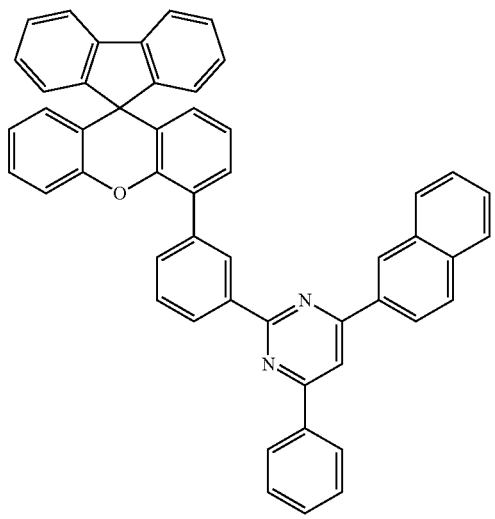
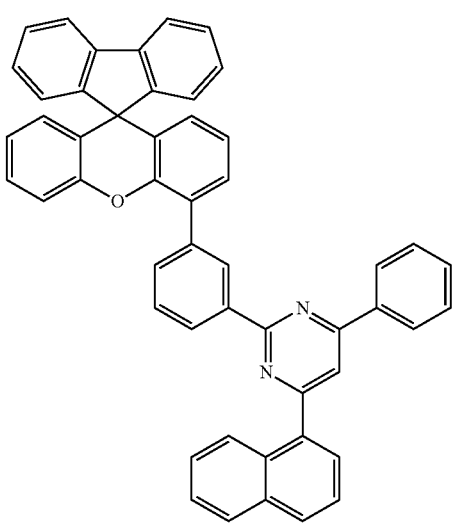
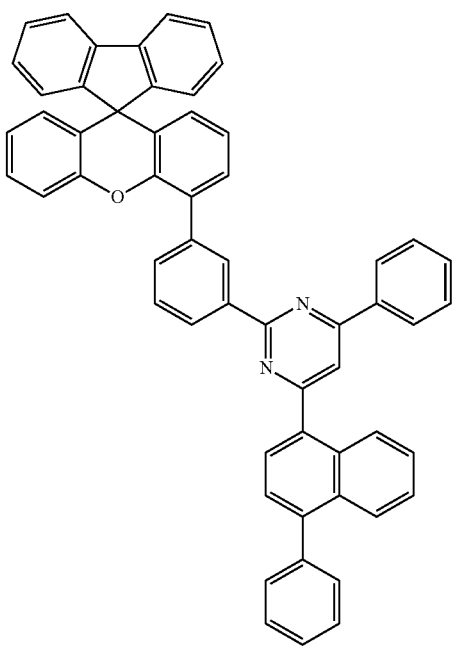

319
-continued
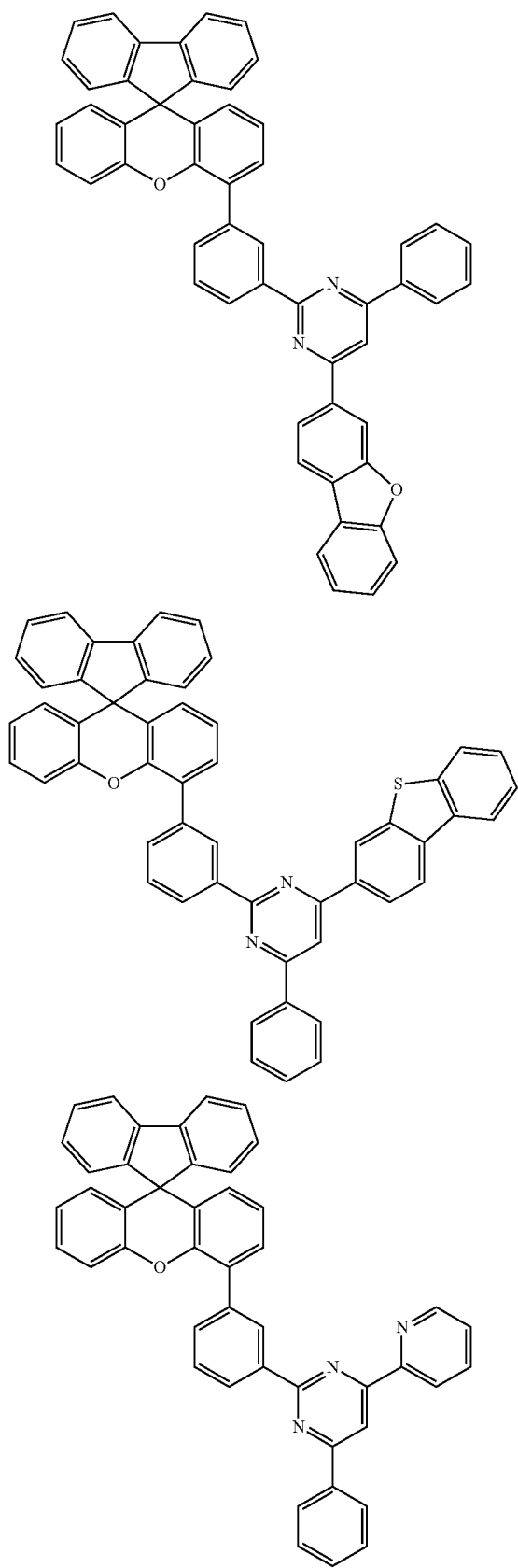
320
-continued
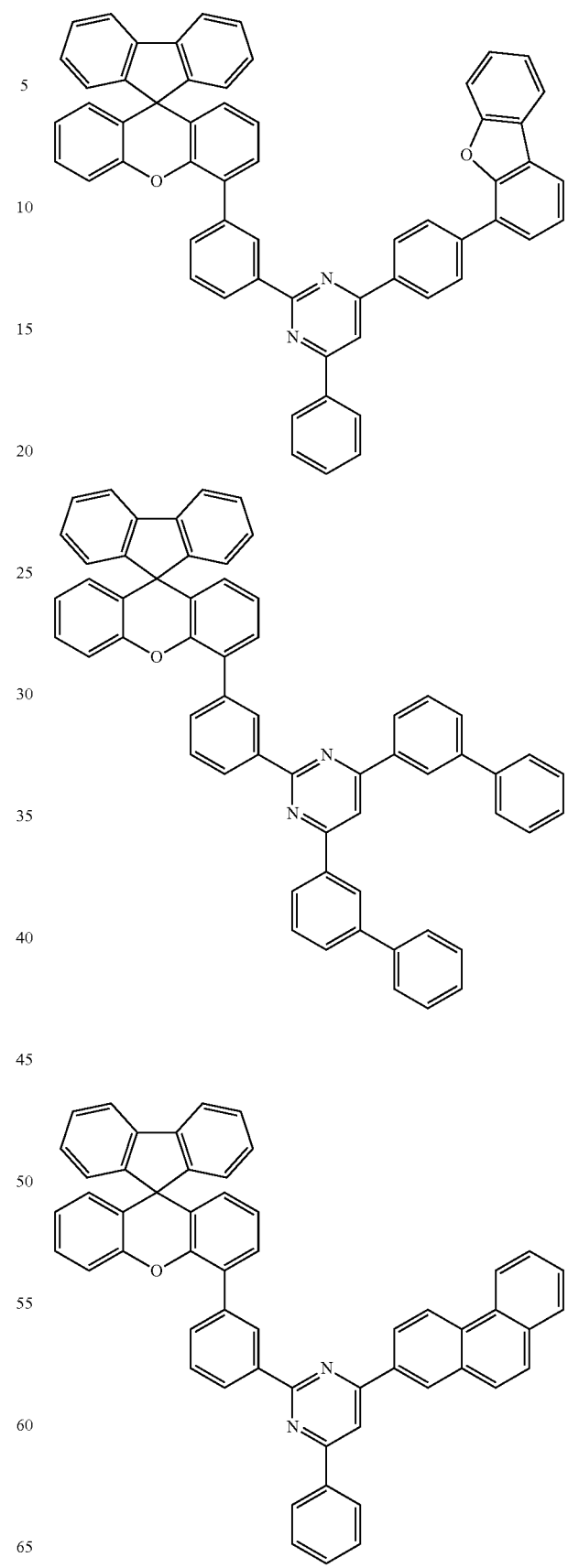

321
-continued
322
-continued
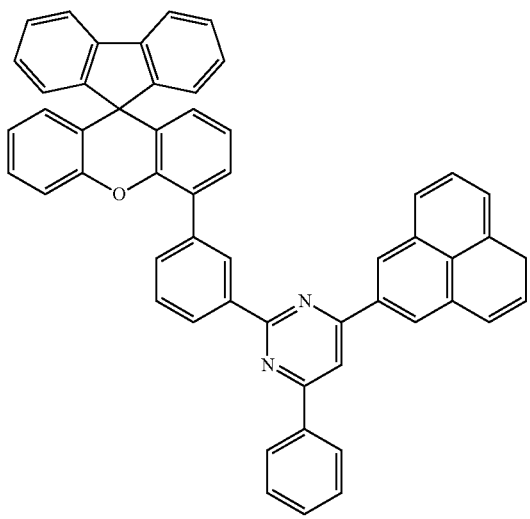
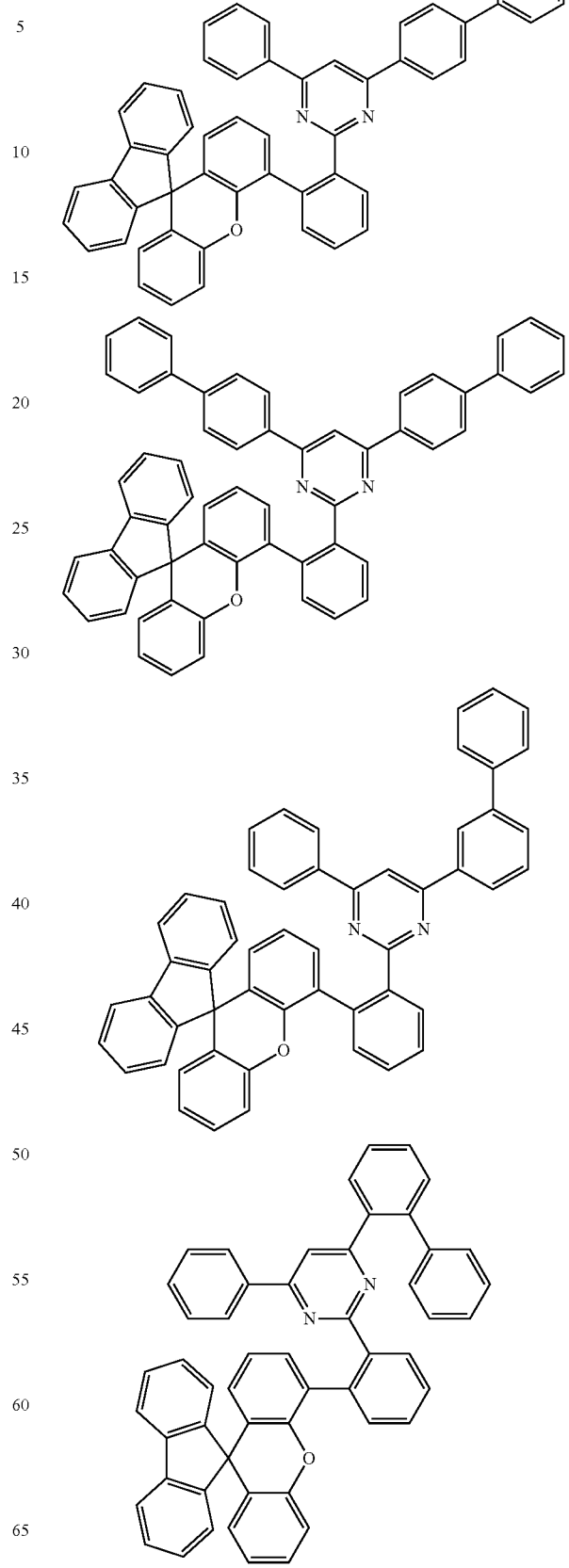

323
-continued
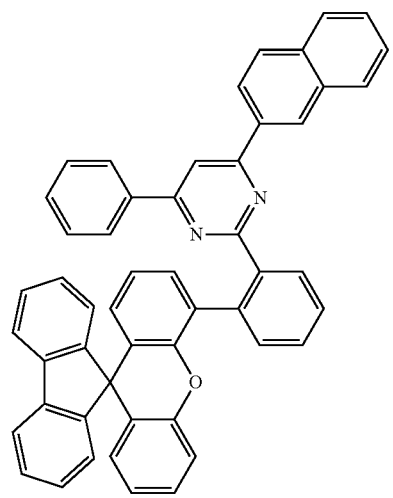
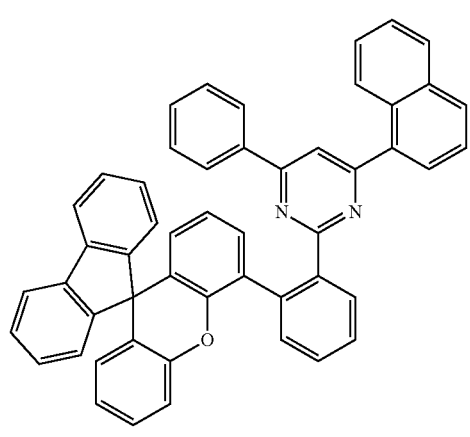
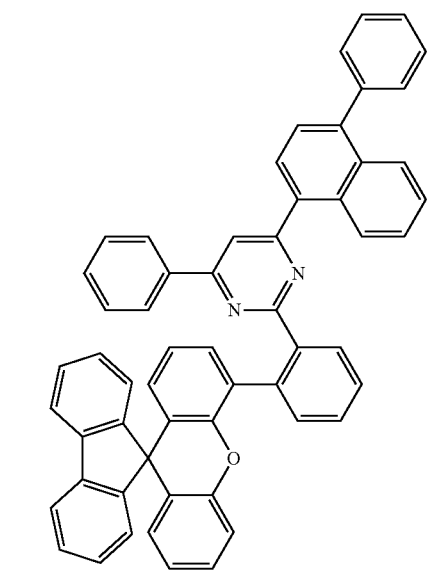
324
-continued
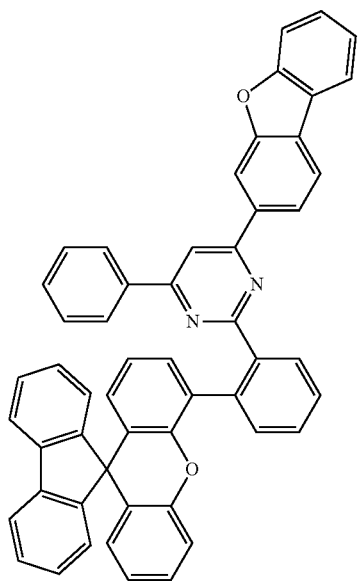
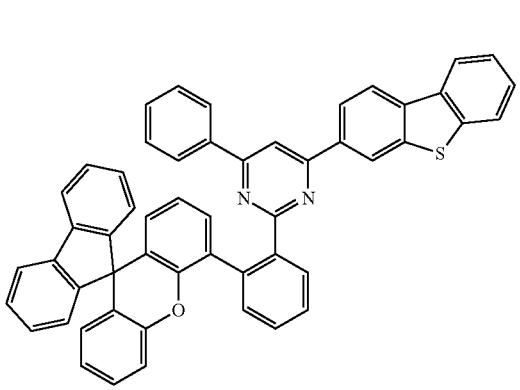
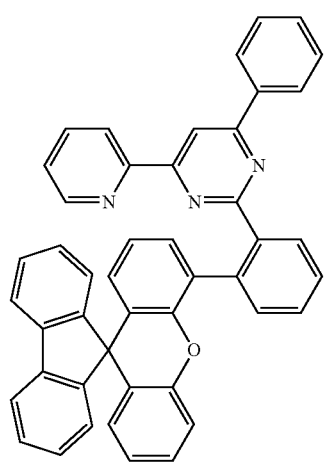

325
-continued
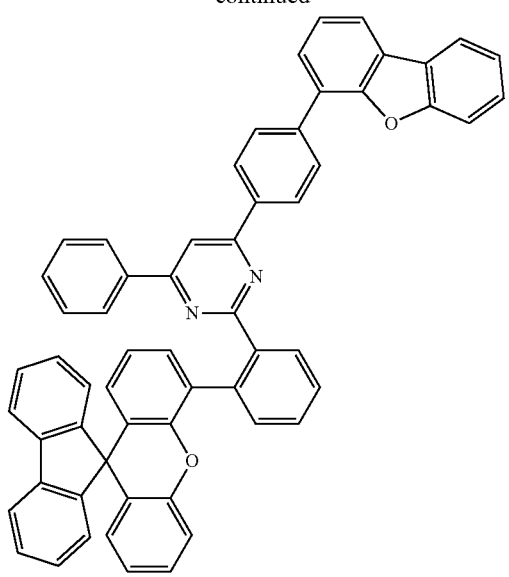
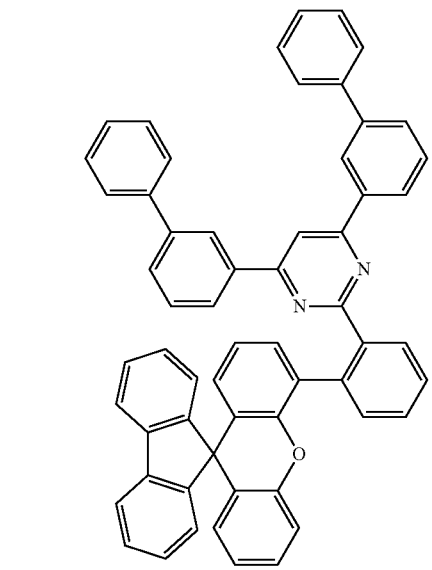
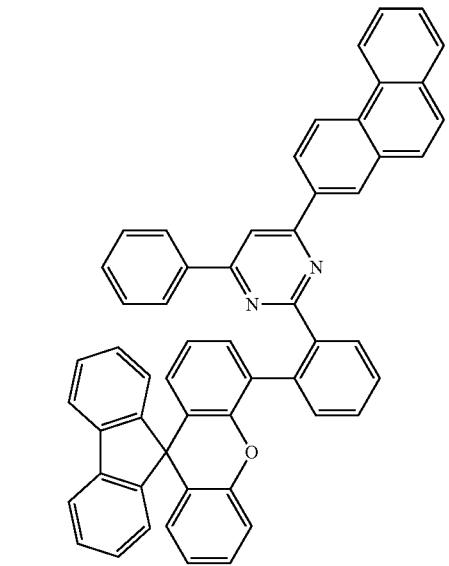
326
-continued
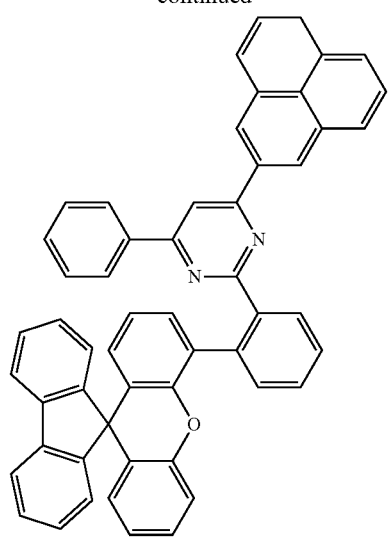
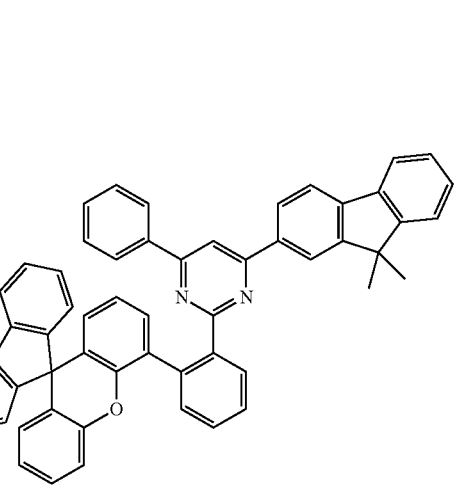
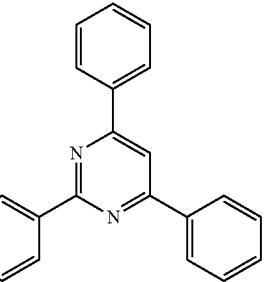

327
-continued
328
-continued
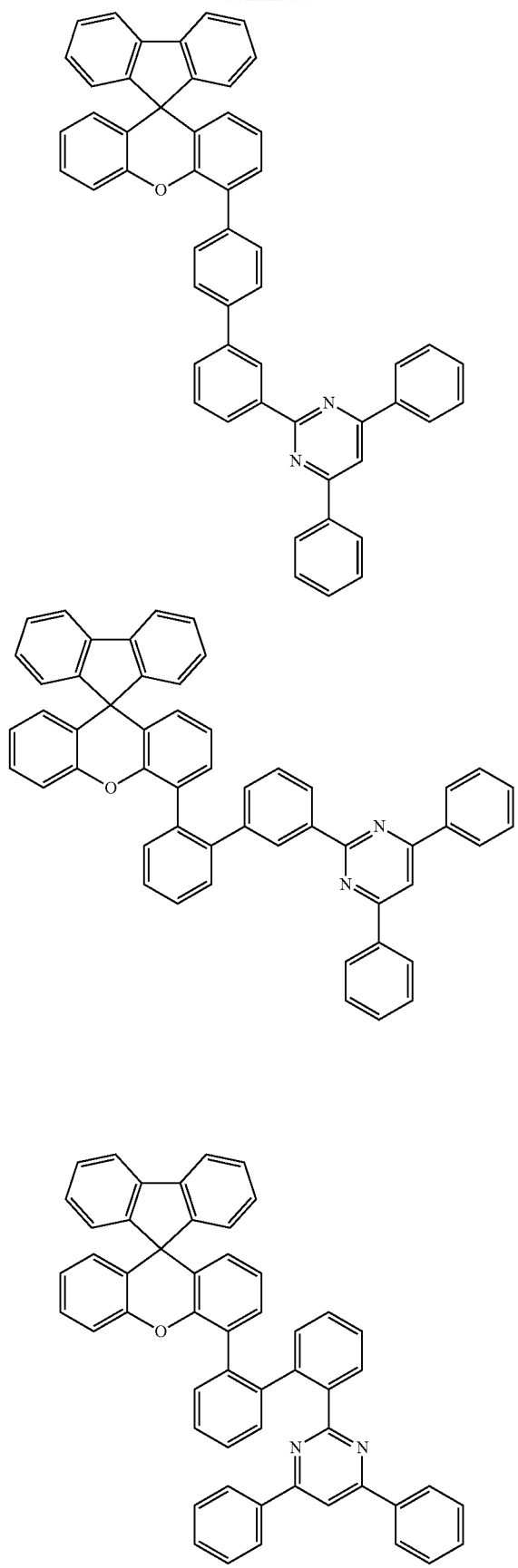
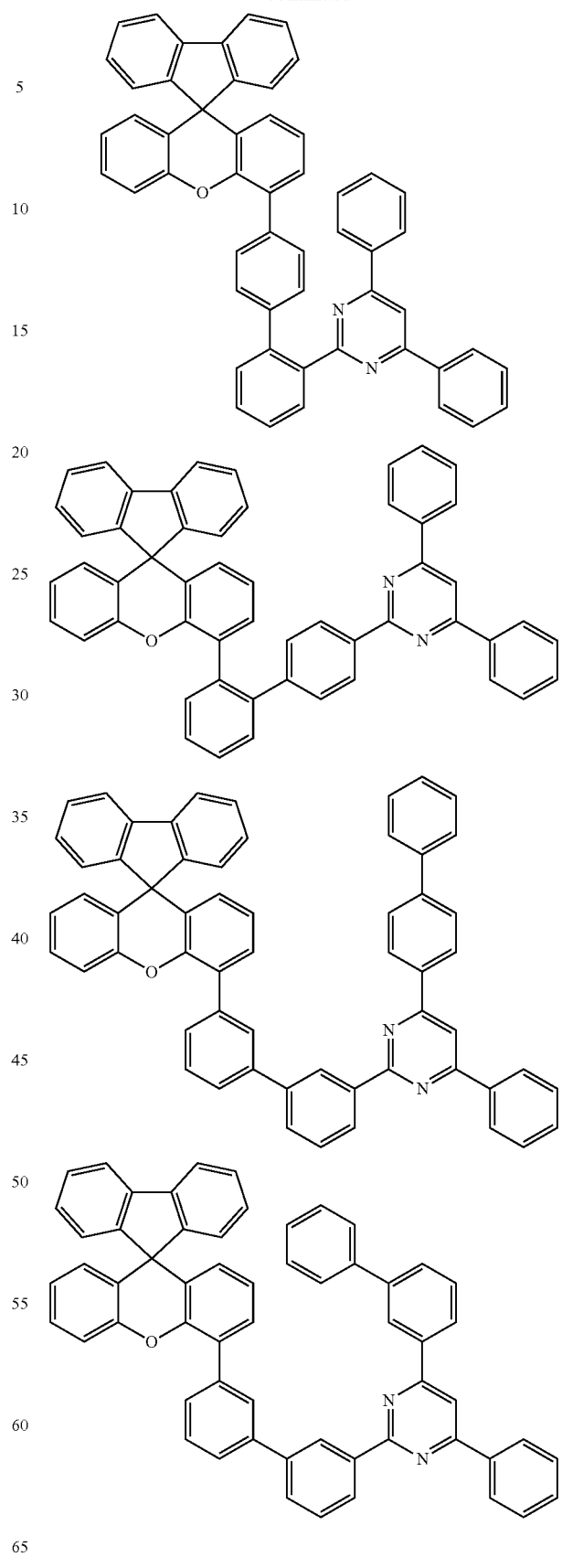

329
-continued
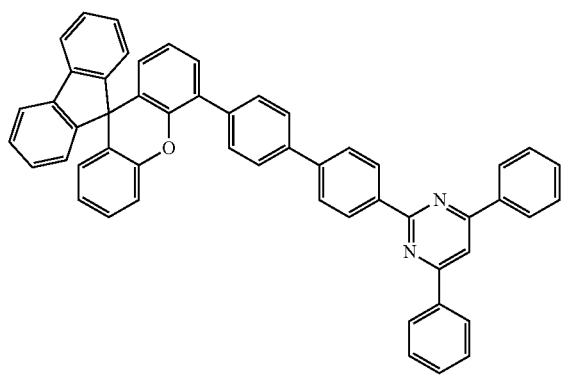
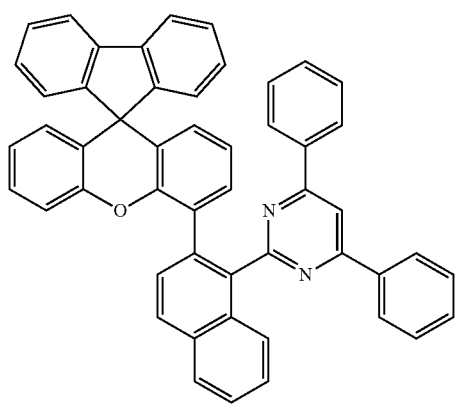
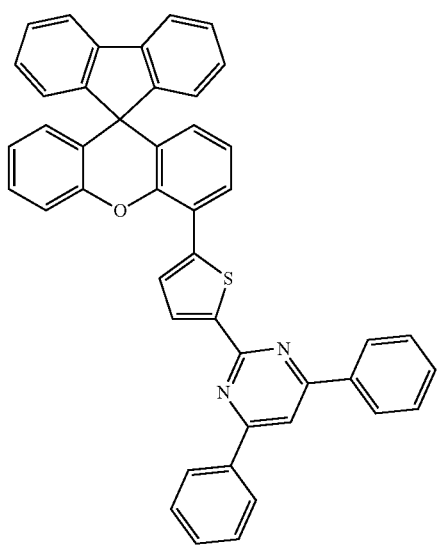
330
-continued
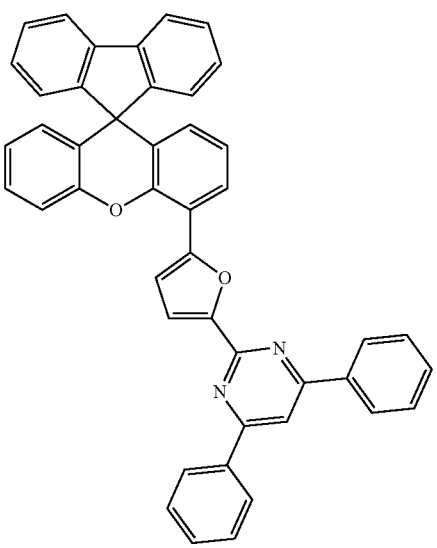
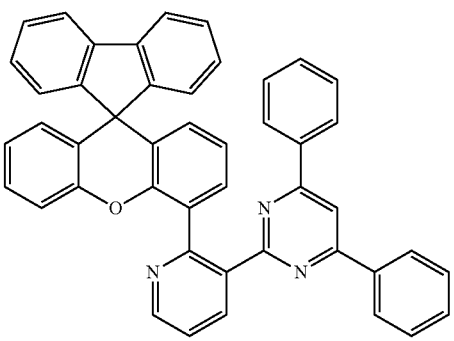
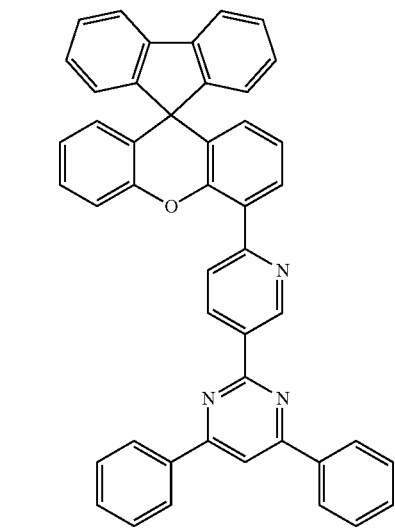

331
-continued
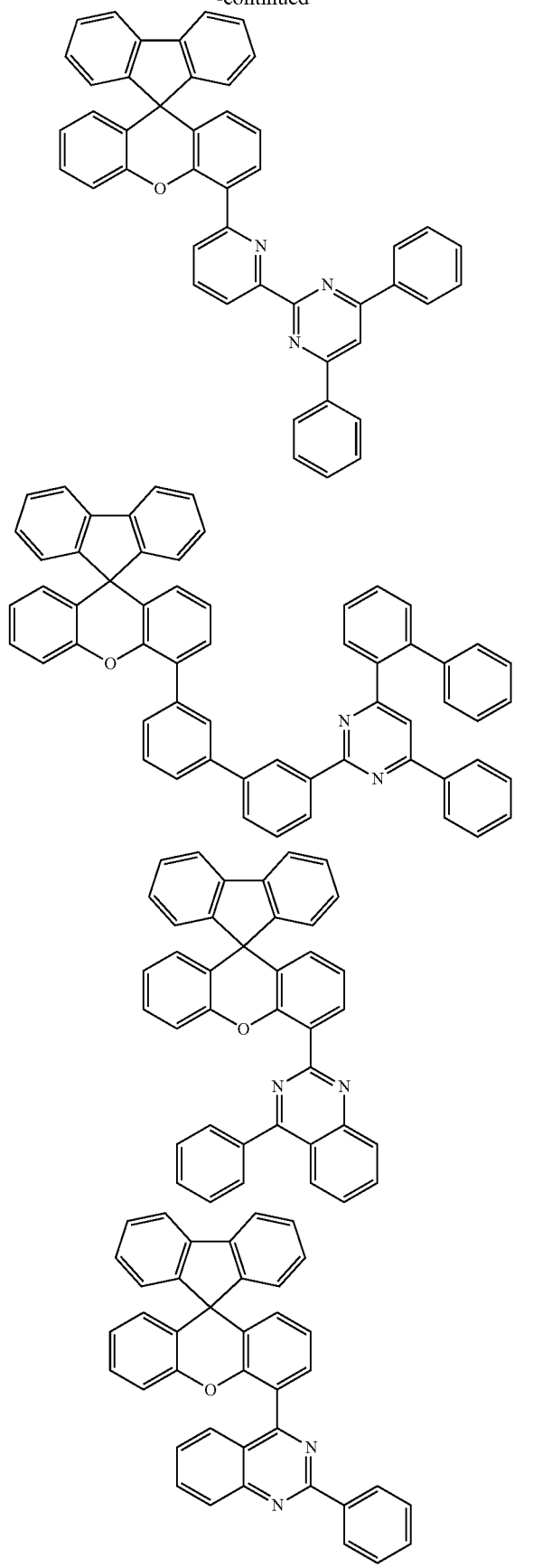
332
-continued
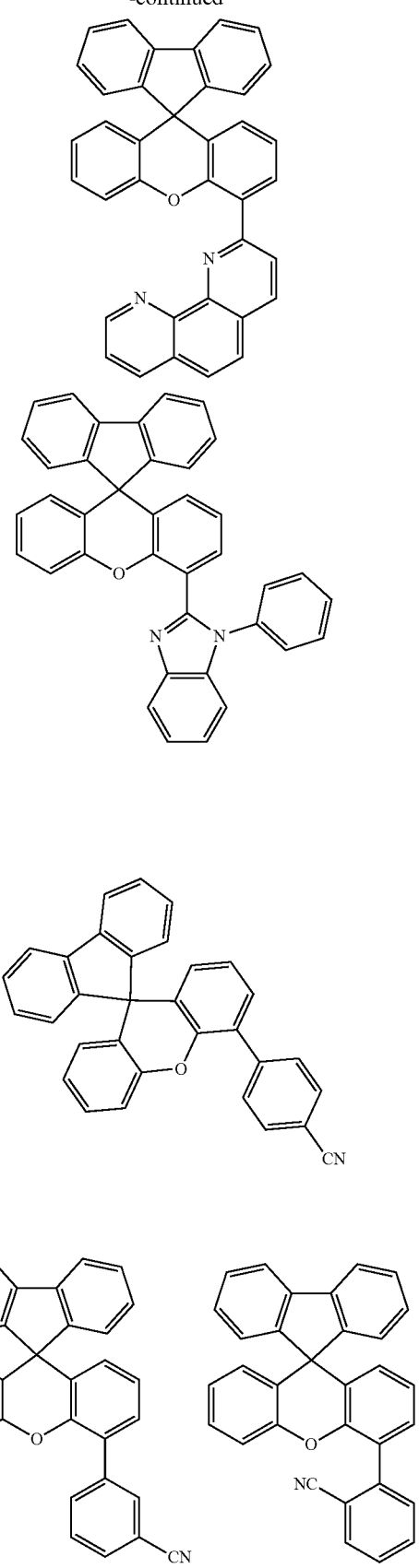

333
-continued
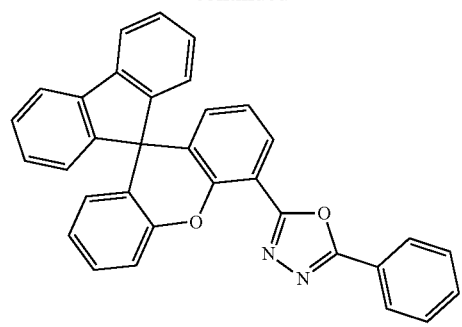
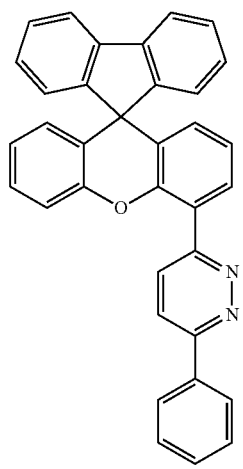
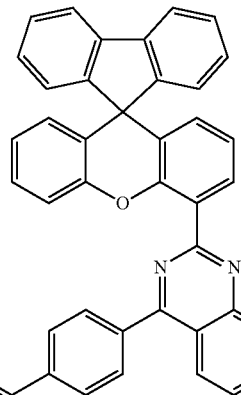
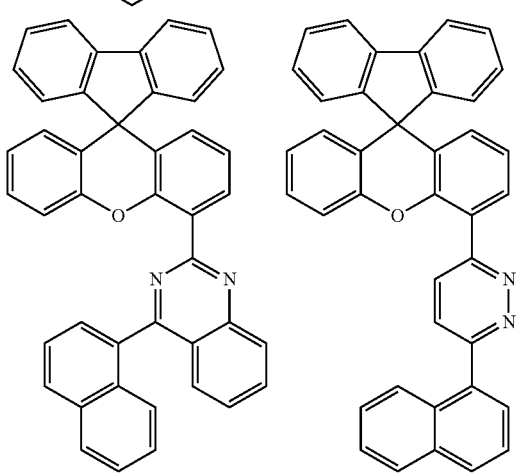
334
-continued
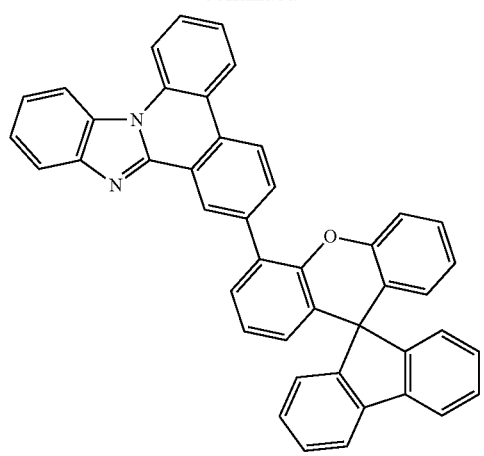
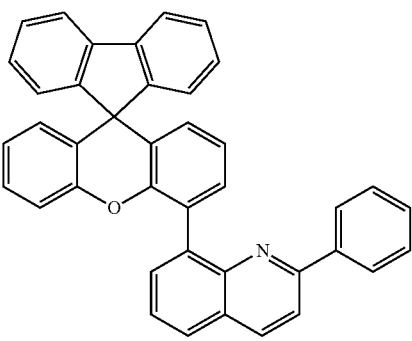
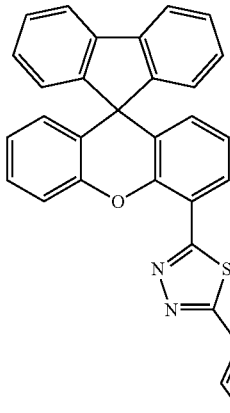
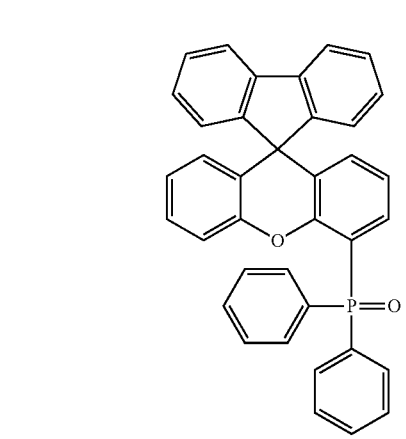

335
-continued
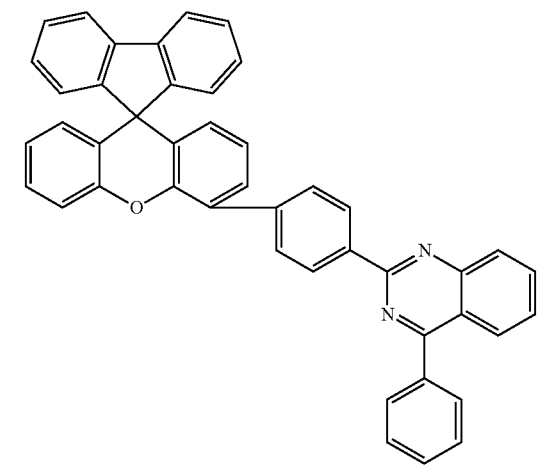
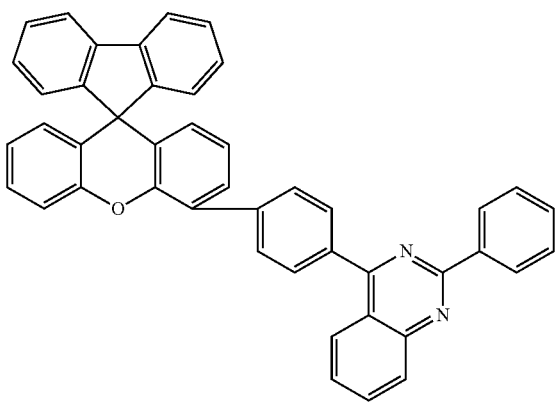
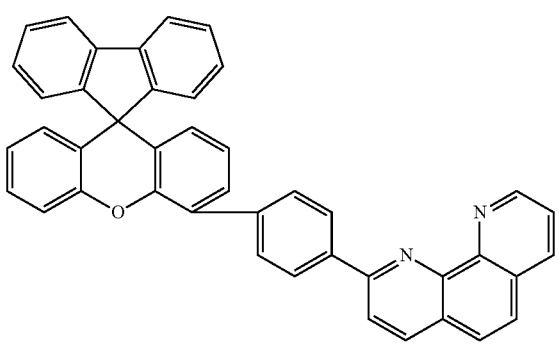
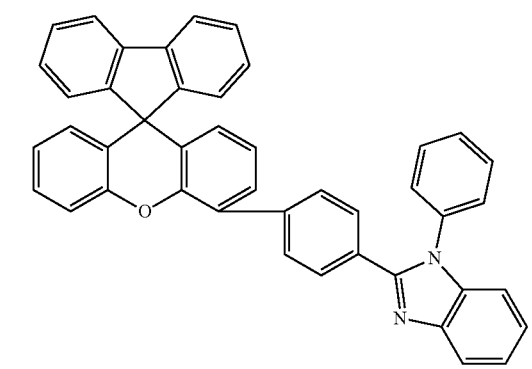
336
-continued
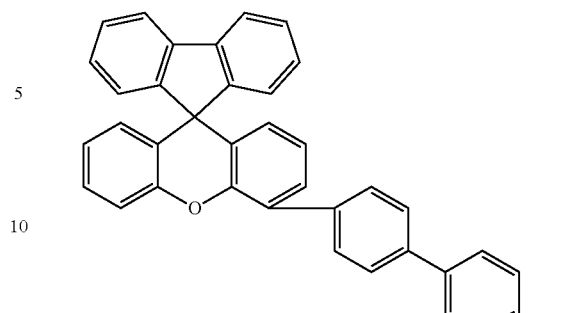
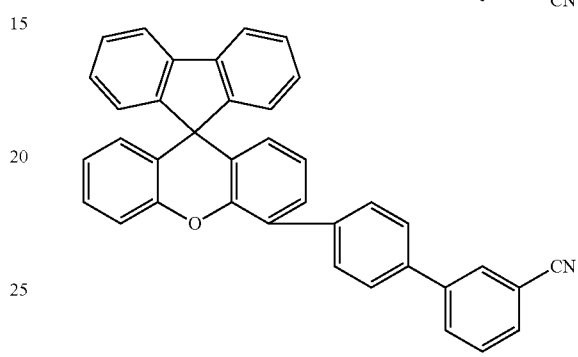
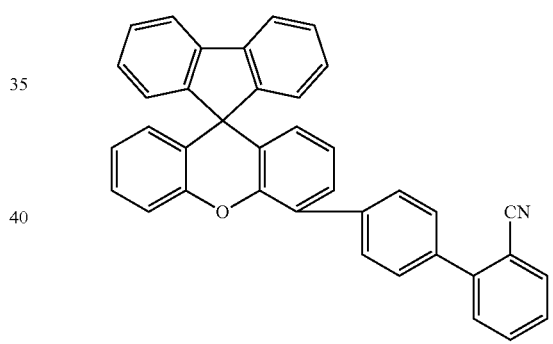
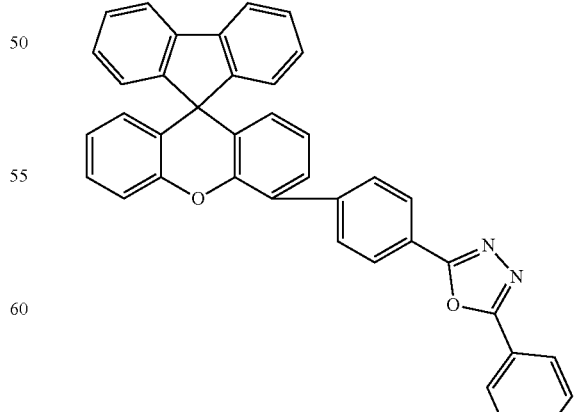

337
-continued
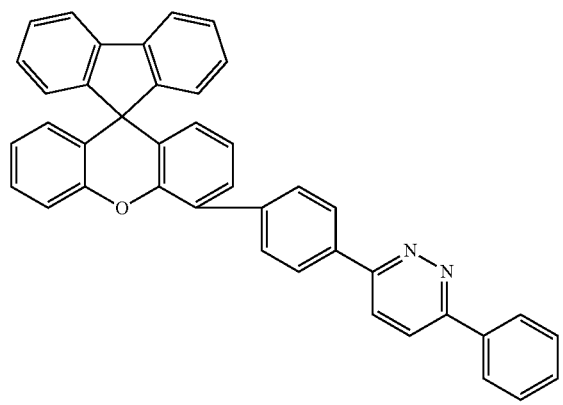
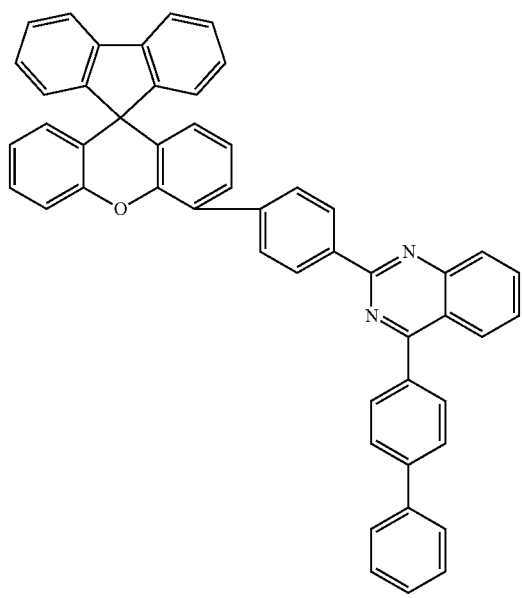
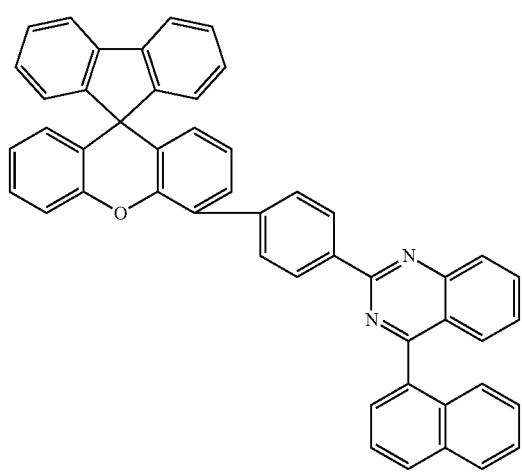
338
-continued
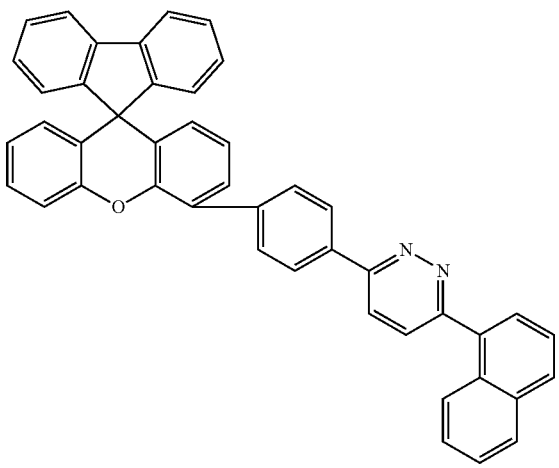
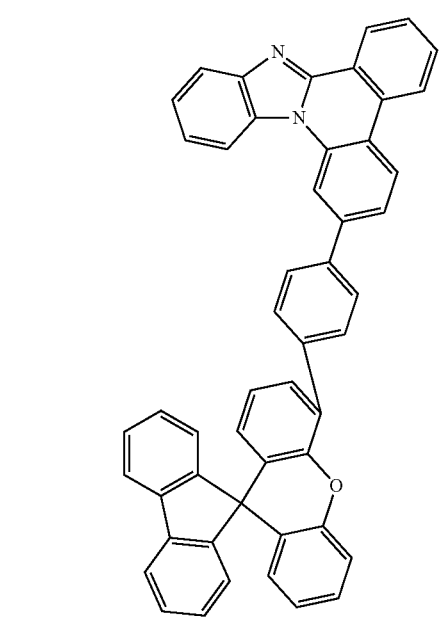
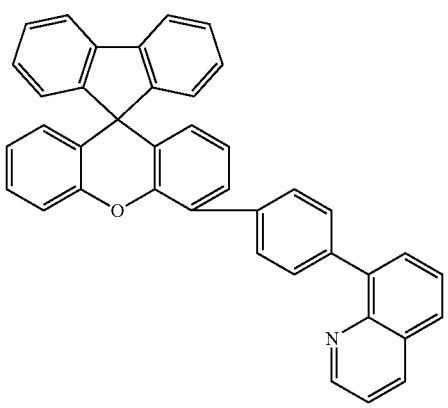

339
-continued
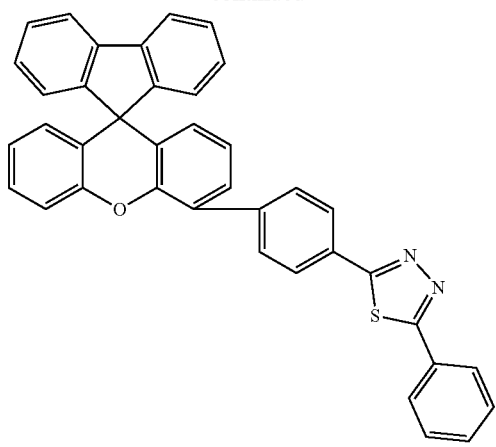
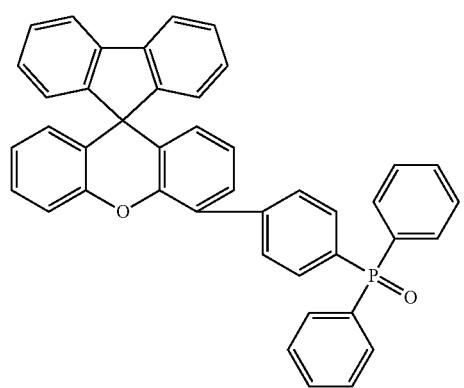
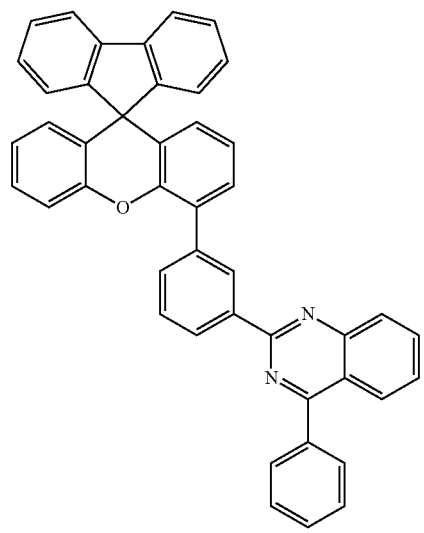
340
-continued
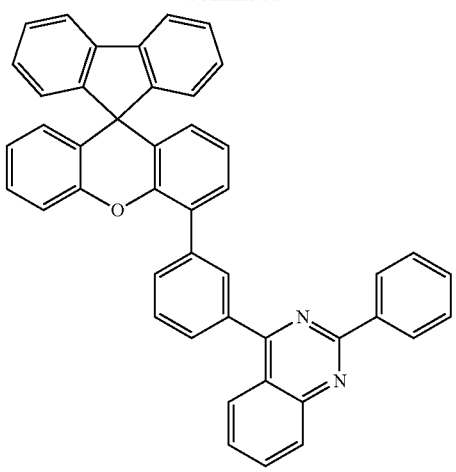
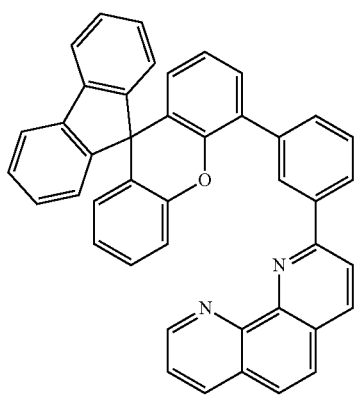
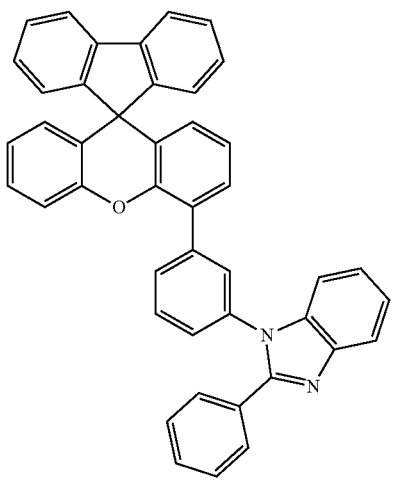
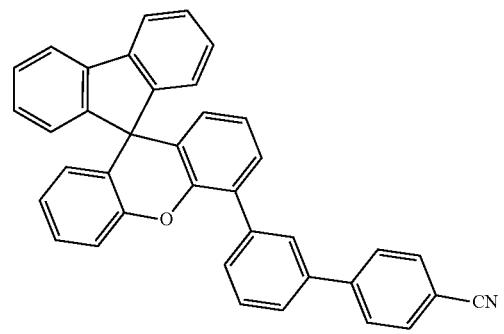

341
-continued
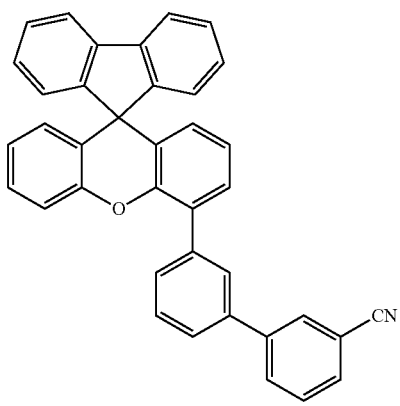
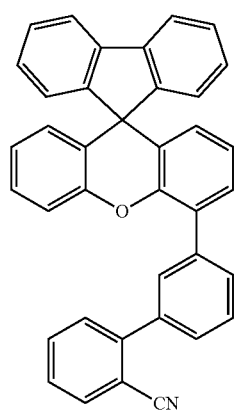
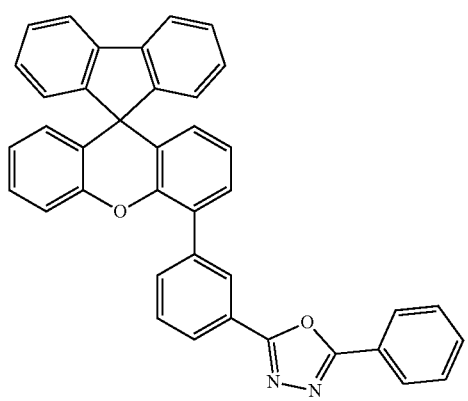
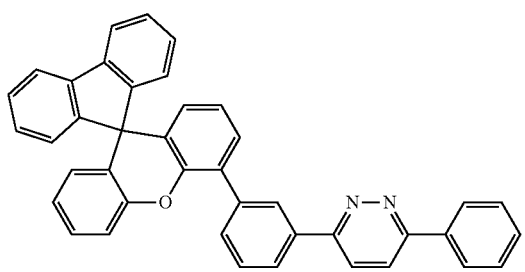
342
-continued
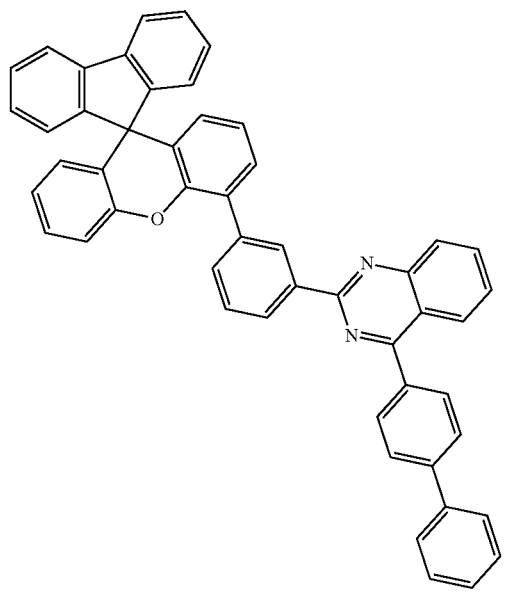
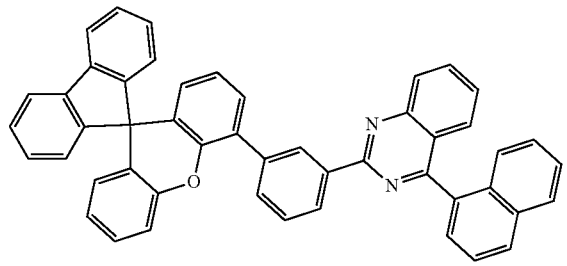
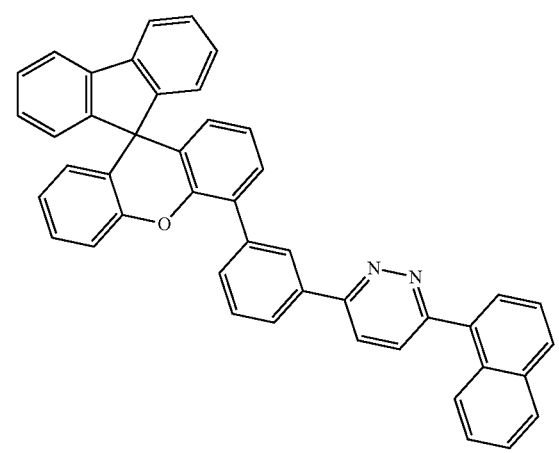

343
-continued
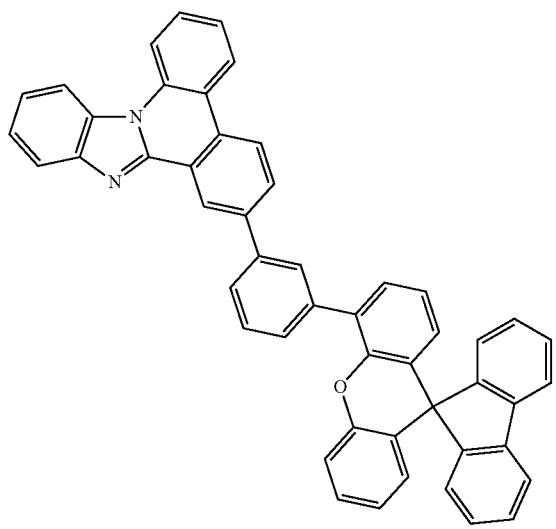
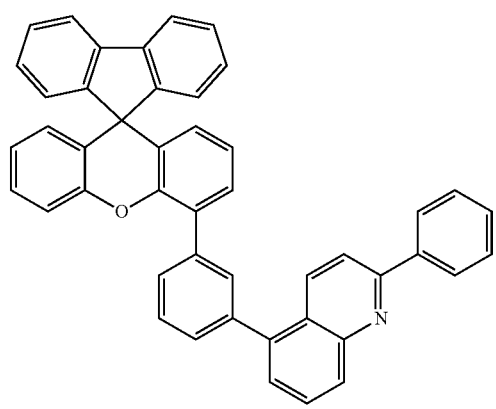
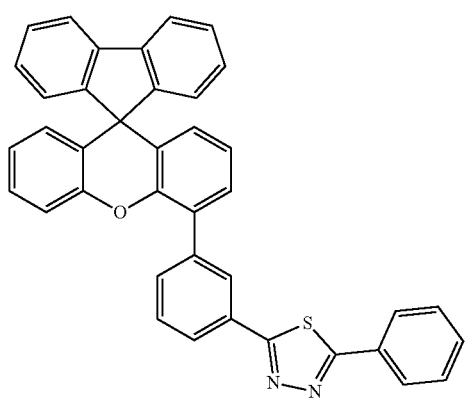
344
-continued
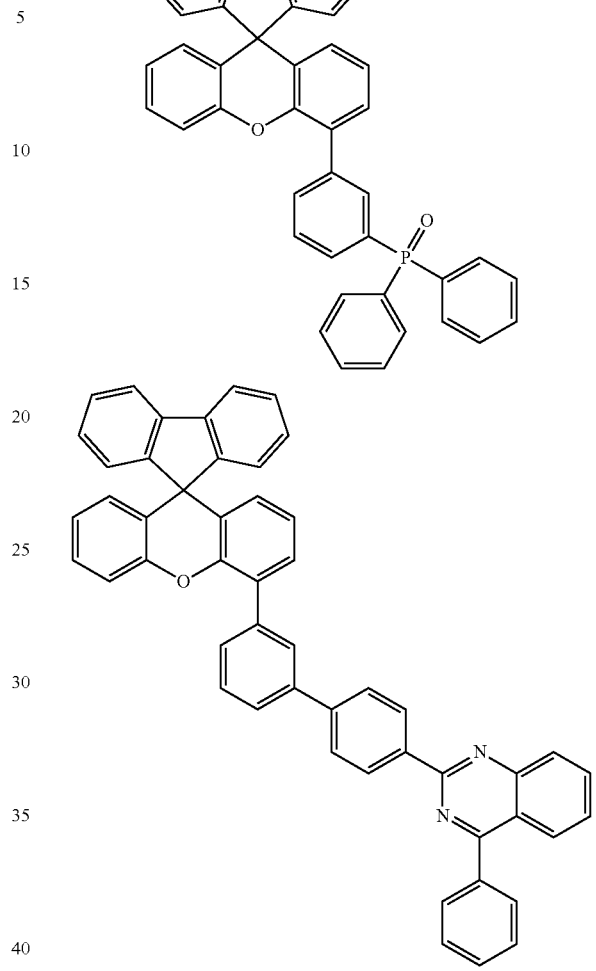
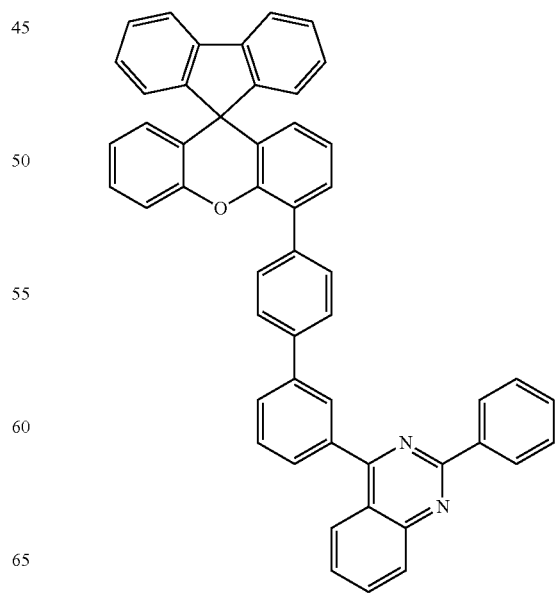

345
-continued
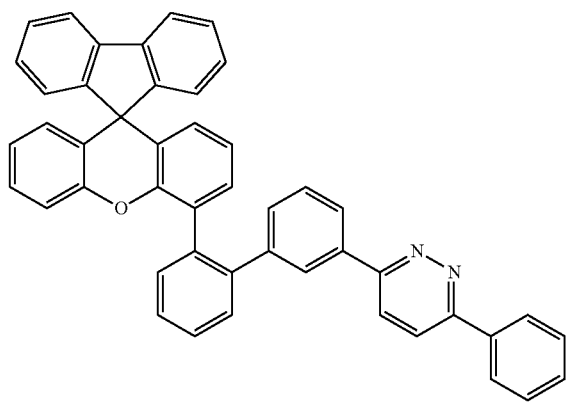
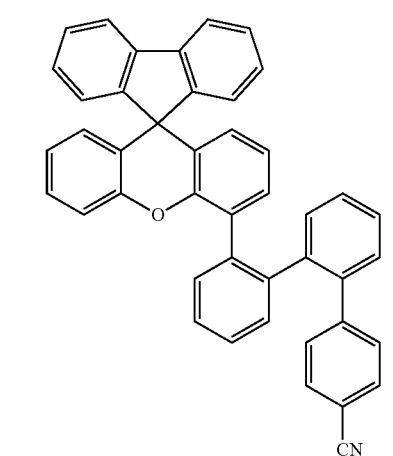
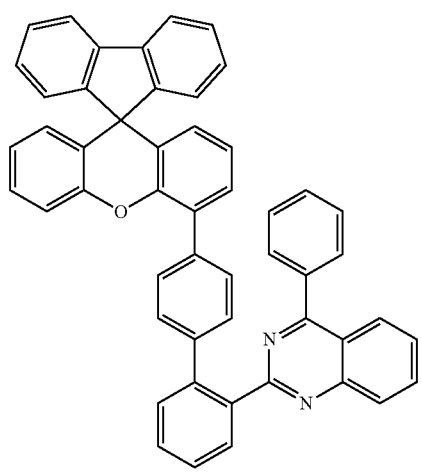
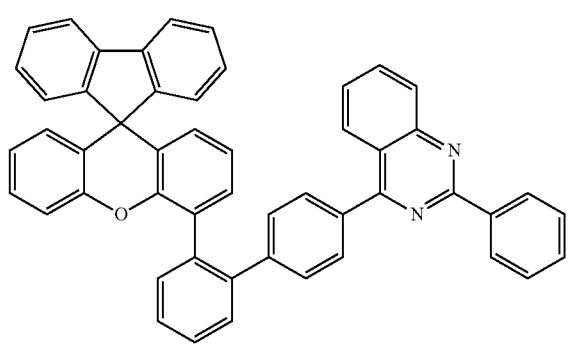
346
-continued
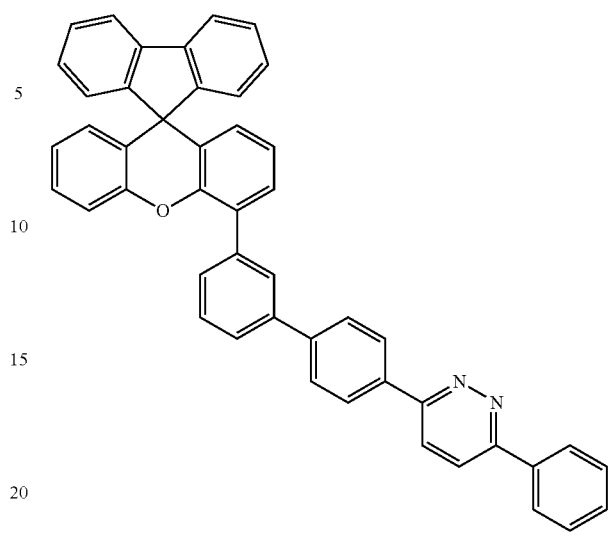
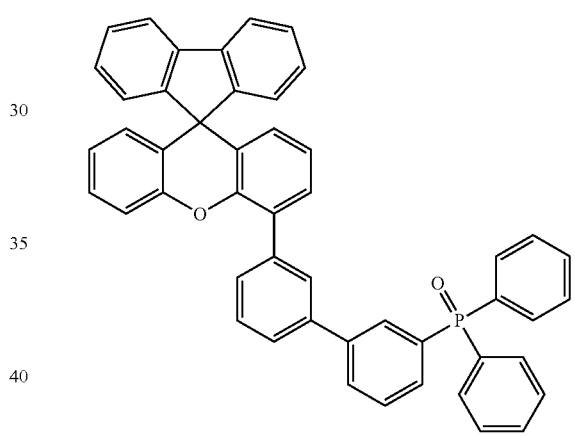
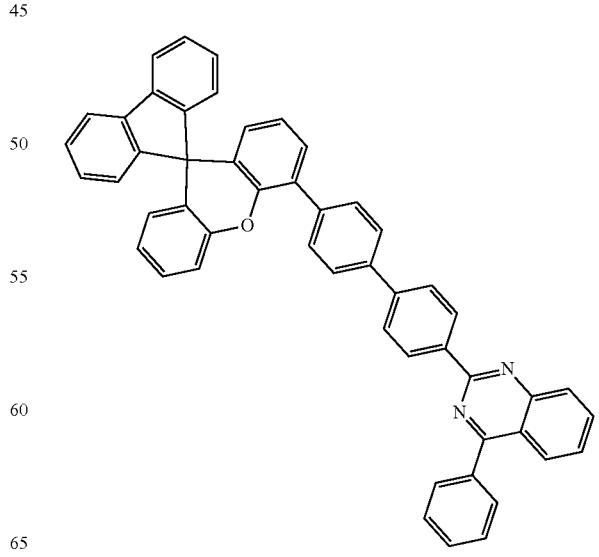

347
-continued
348
-continued
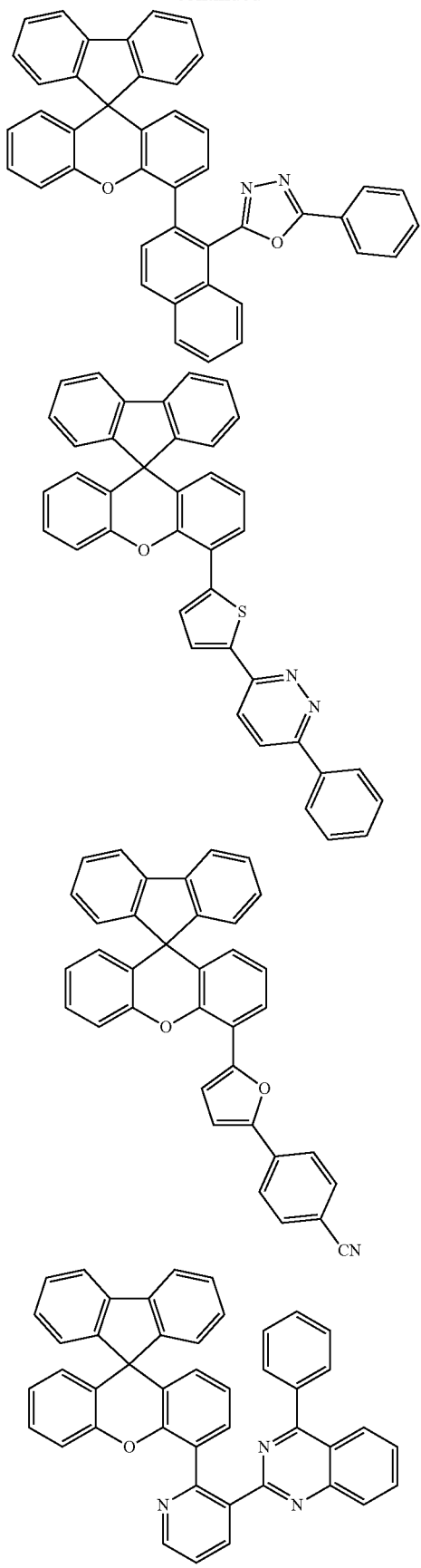
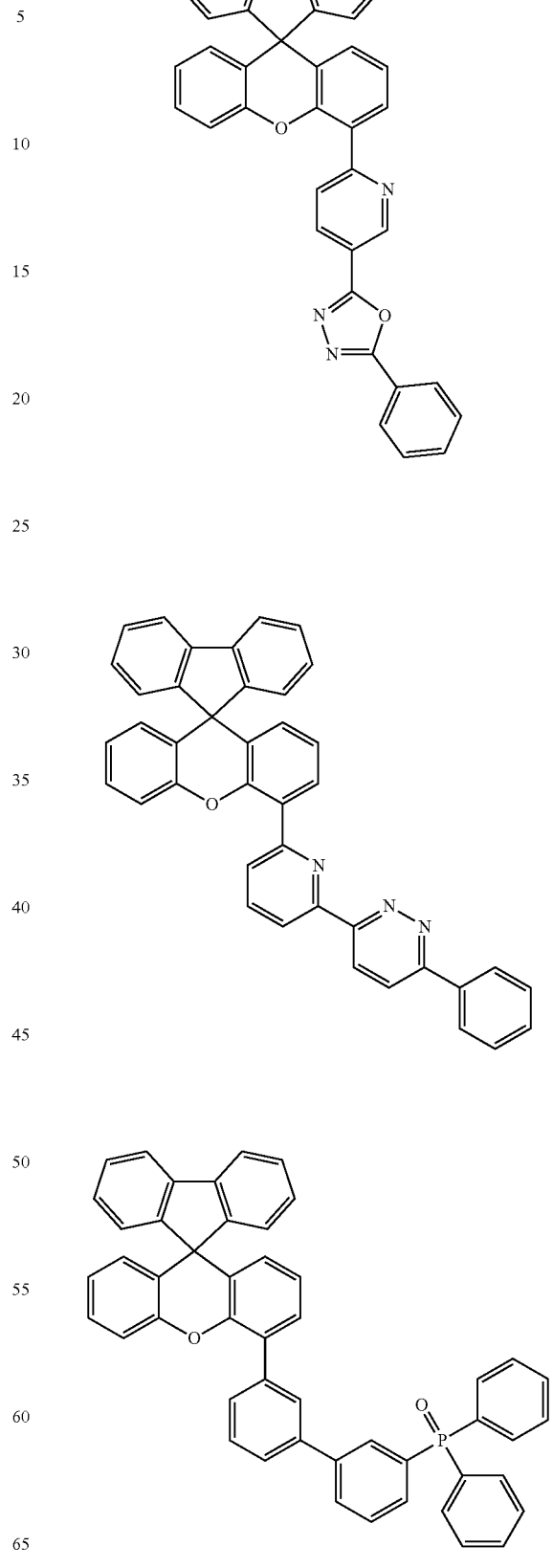

349
-continued
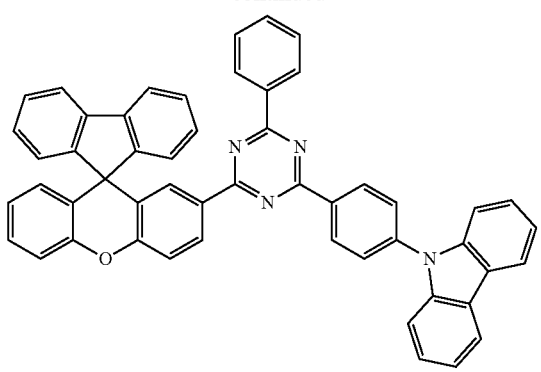
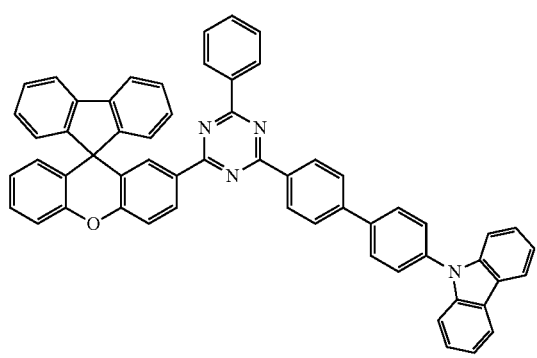
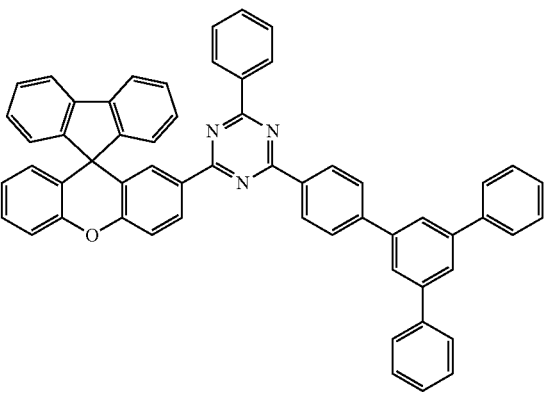
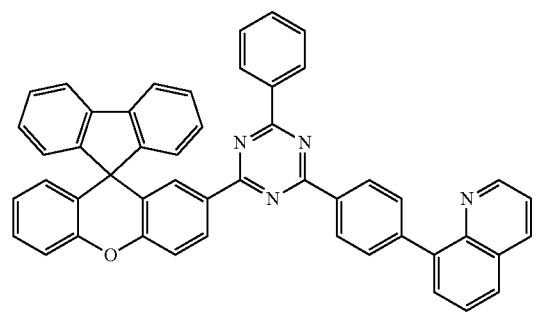
350
-continued
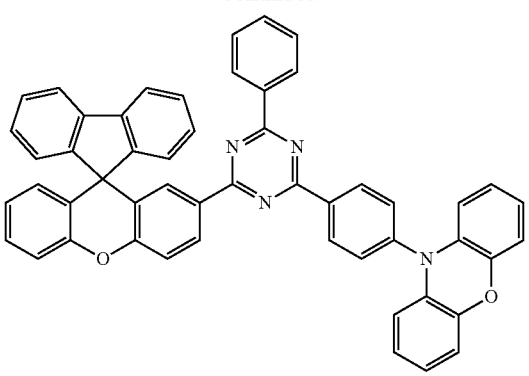
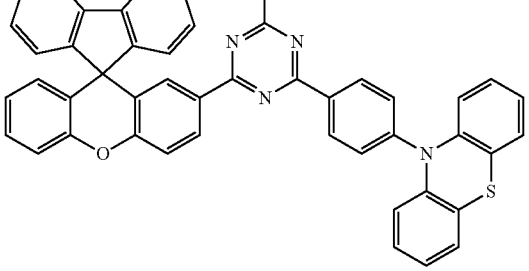
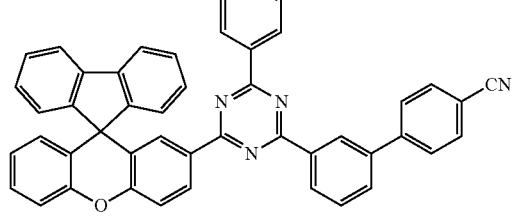
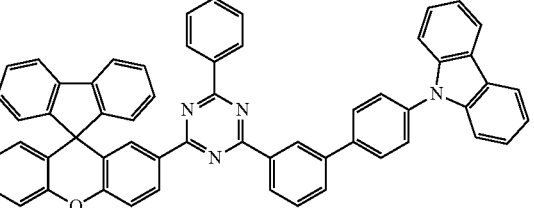
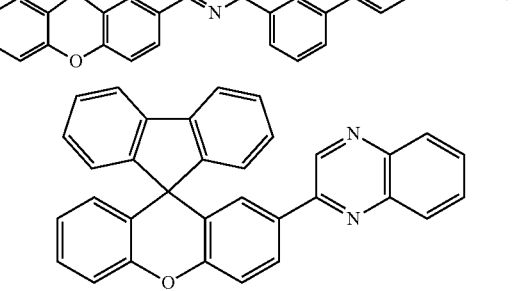

351
-continued
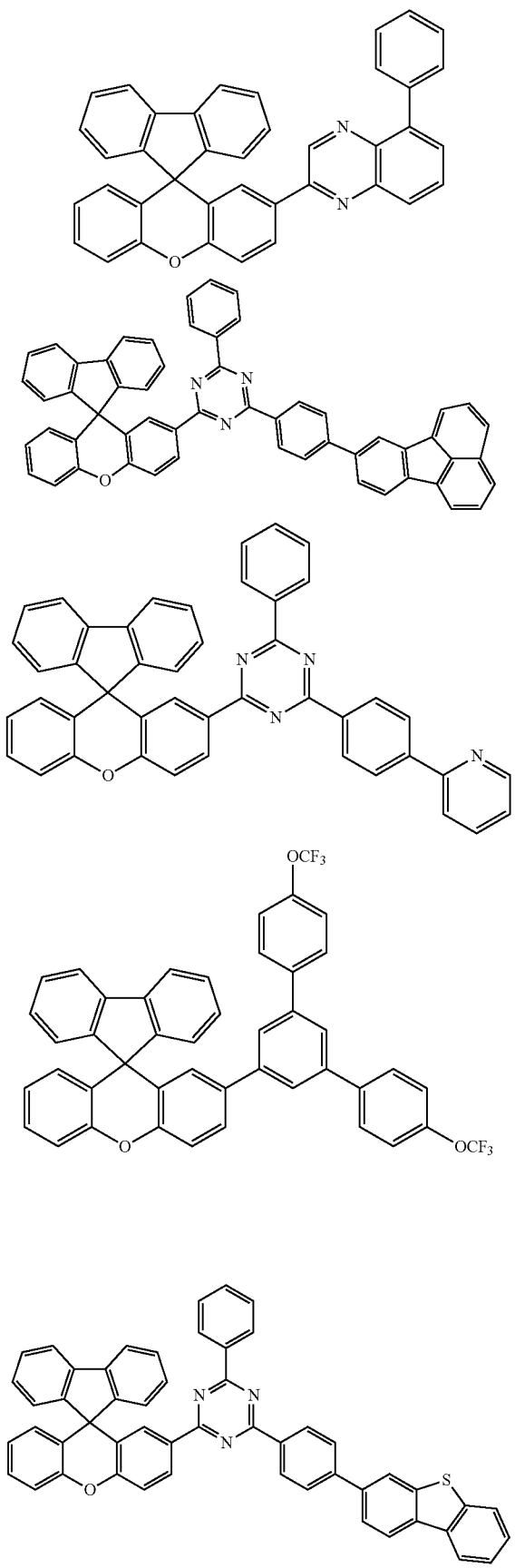
352
-continued
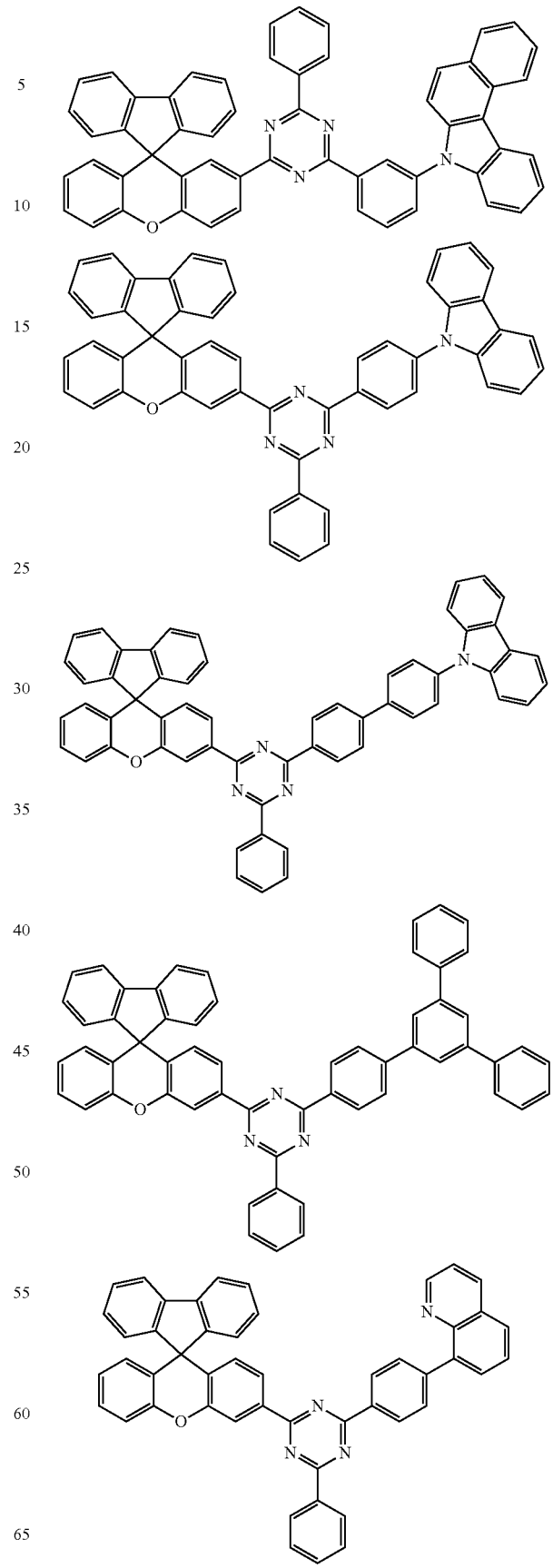

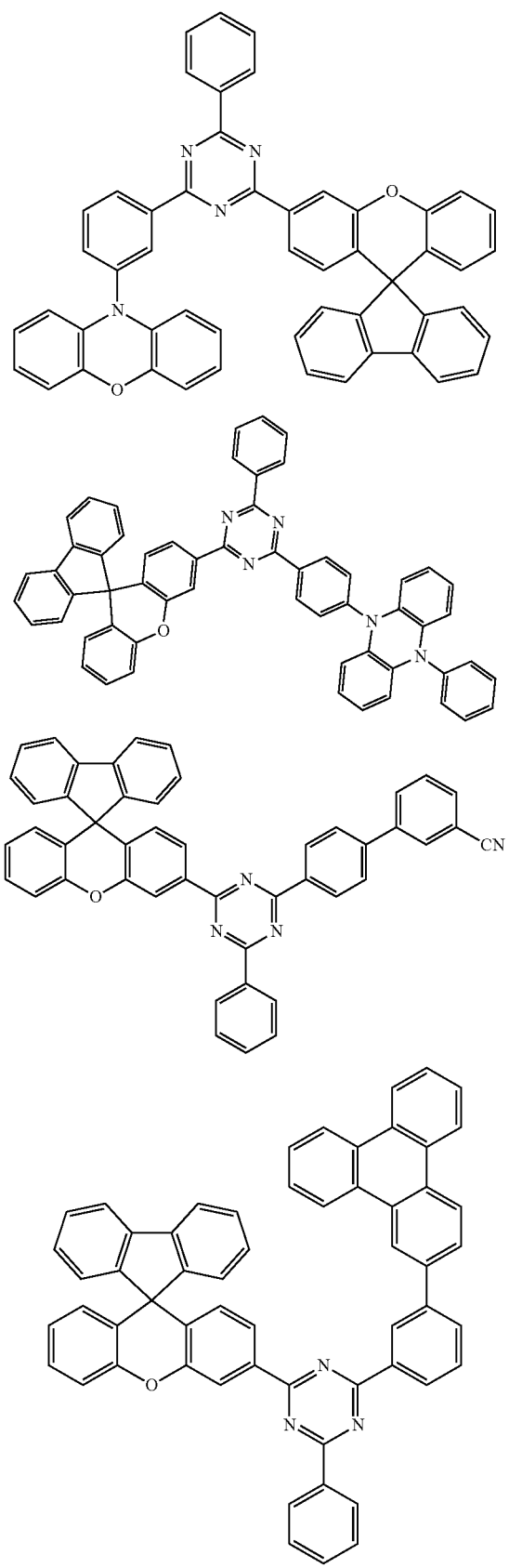
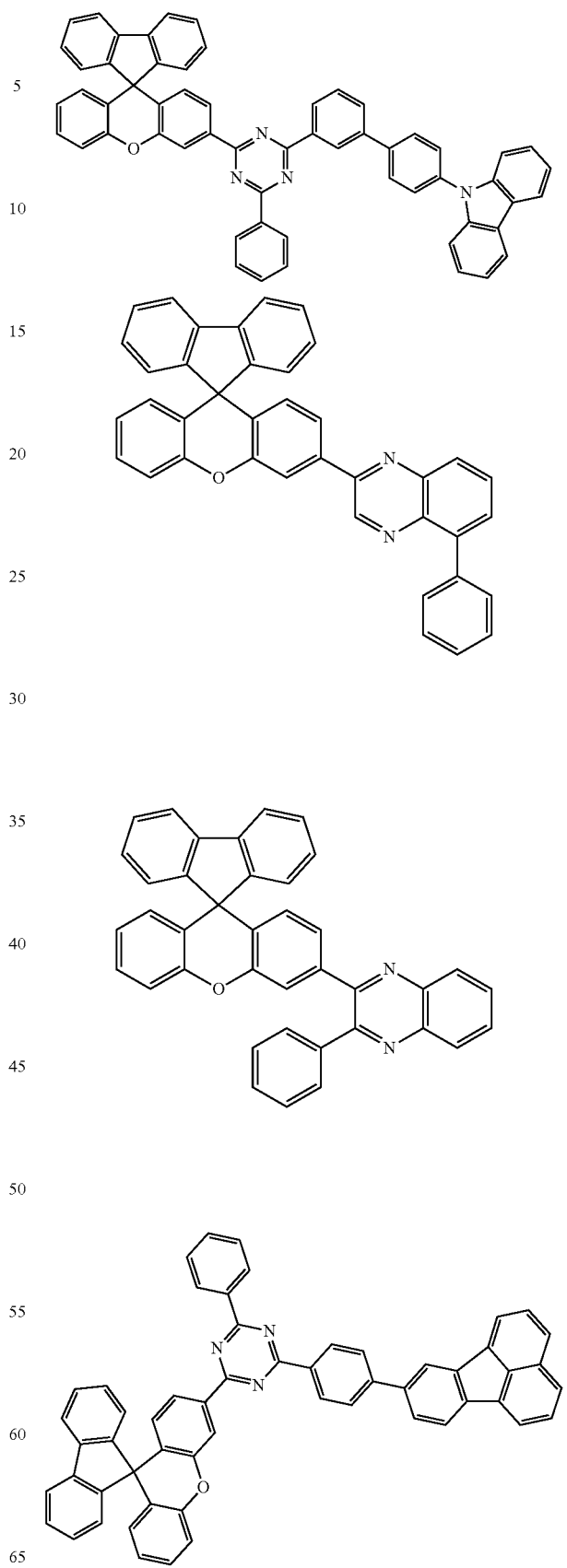

355
-continued
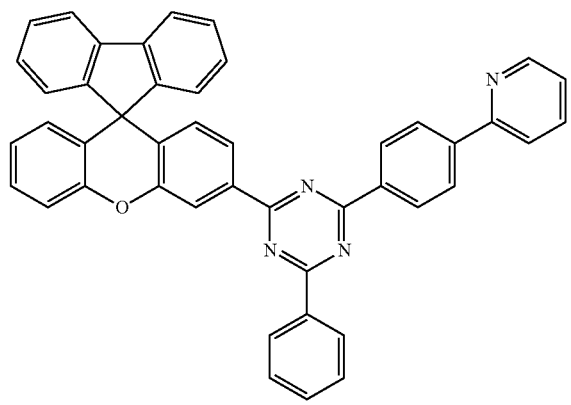
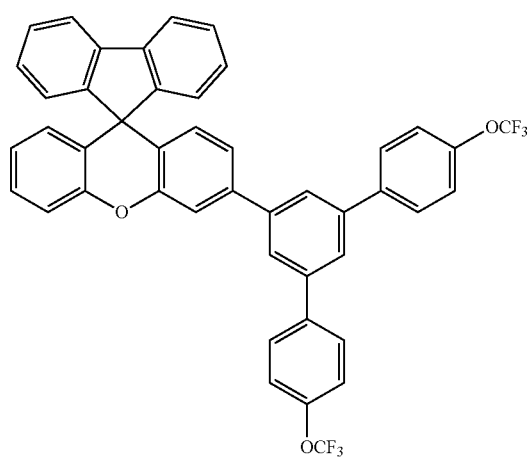
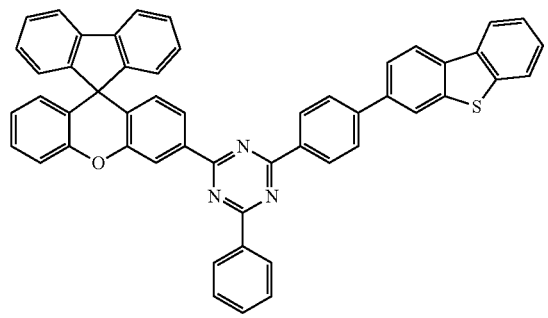
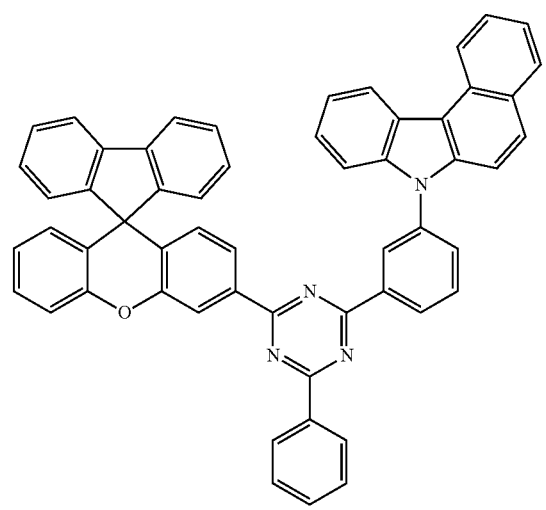
356
-continued
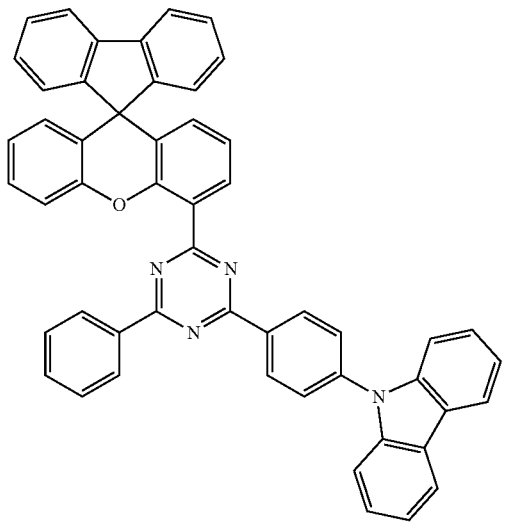
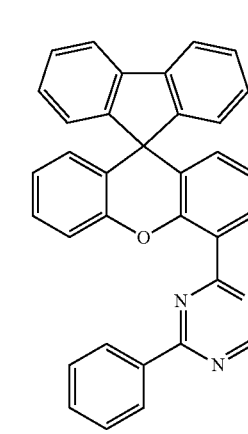
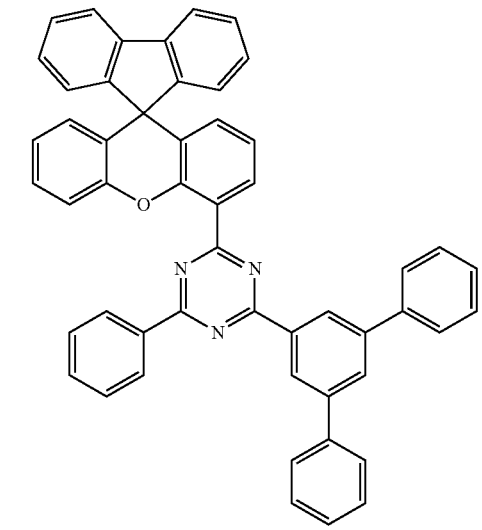

357
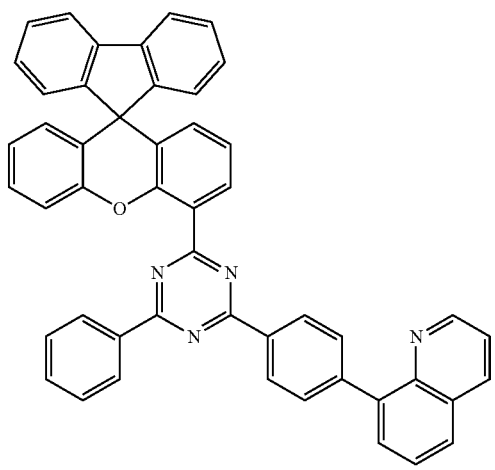
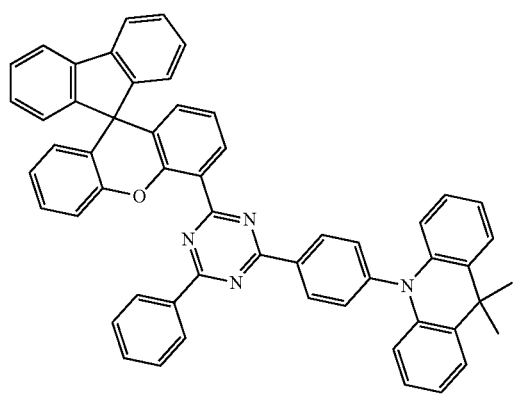
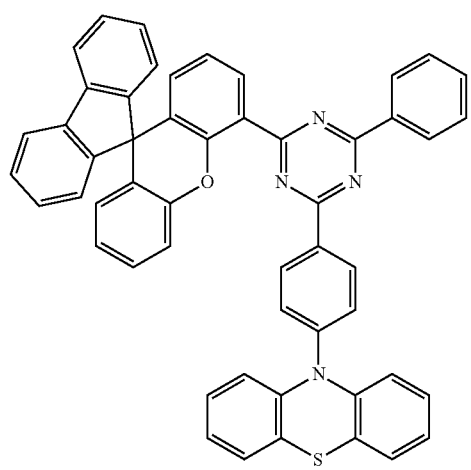
358
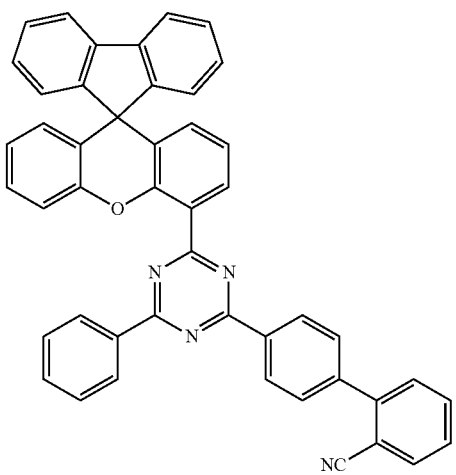
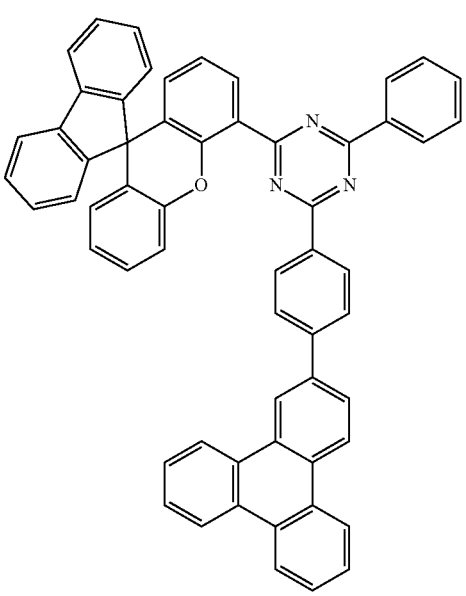
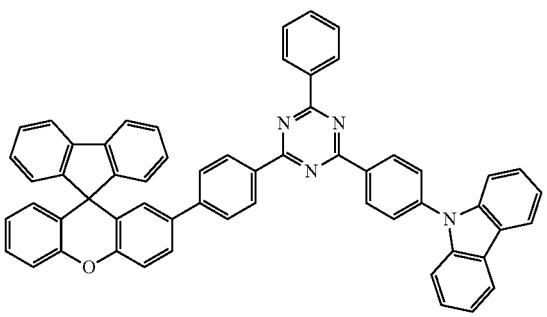

359
-continued
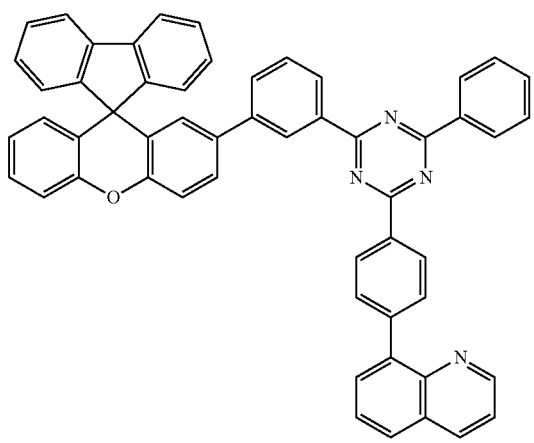
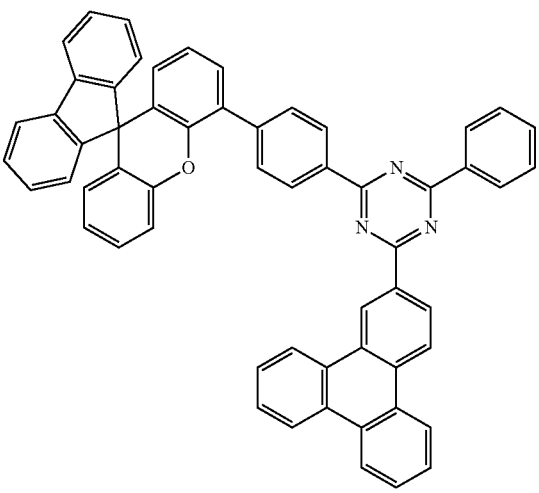
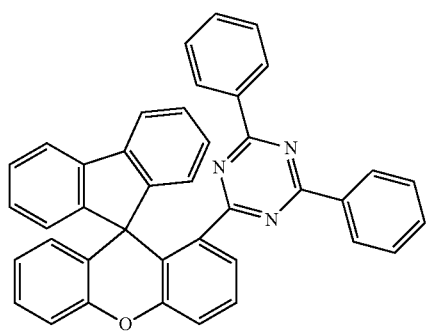
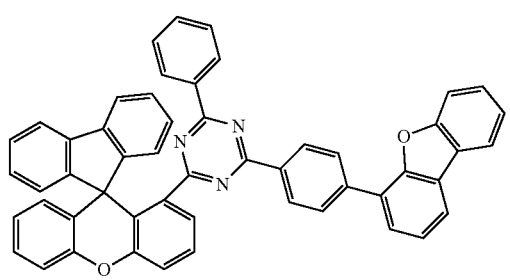
360
-continued
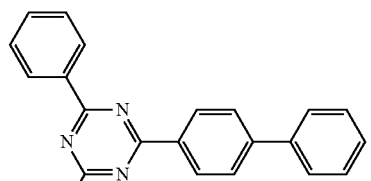
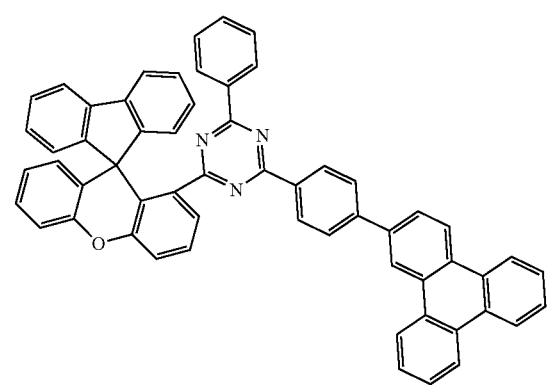
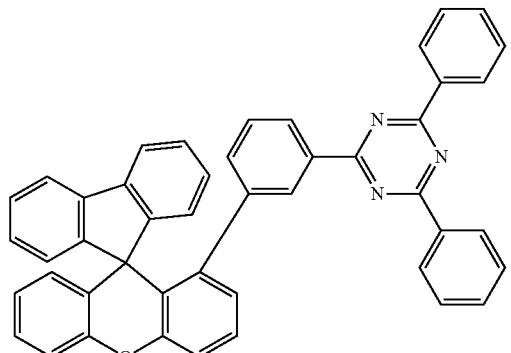
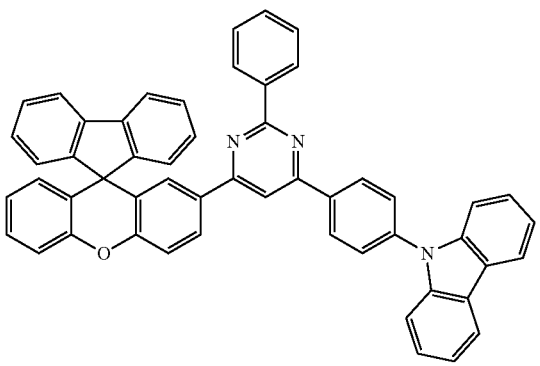

361
-continued
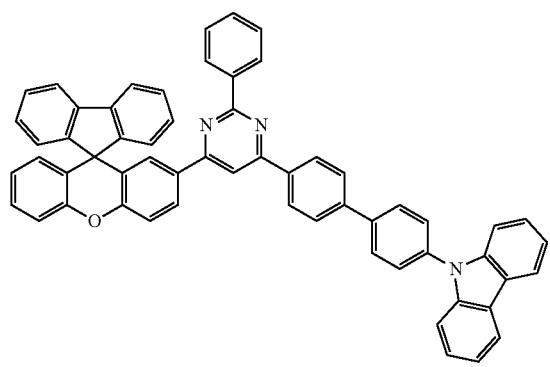
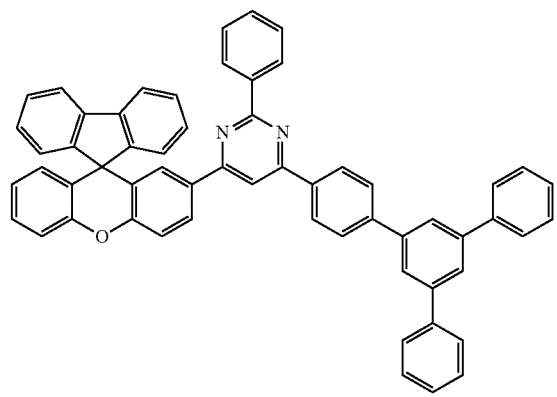
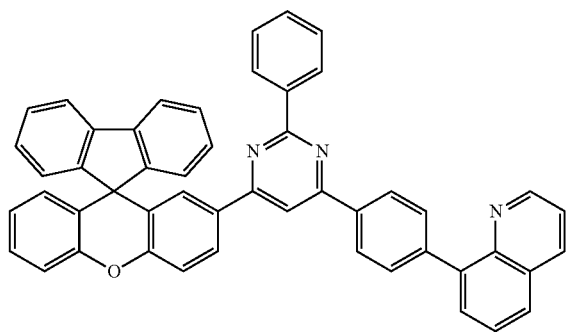
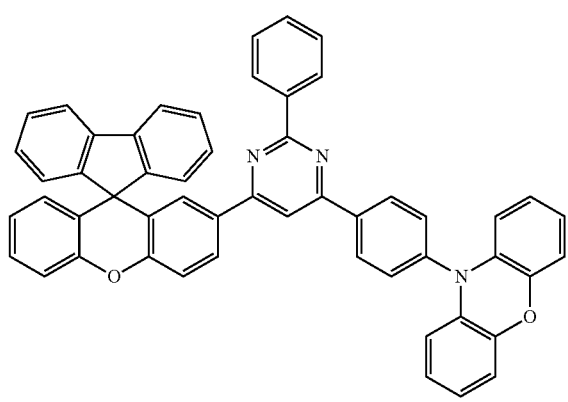
362
-continued
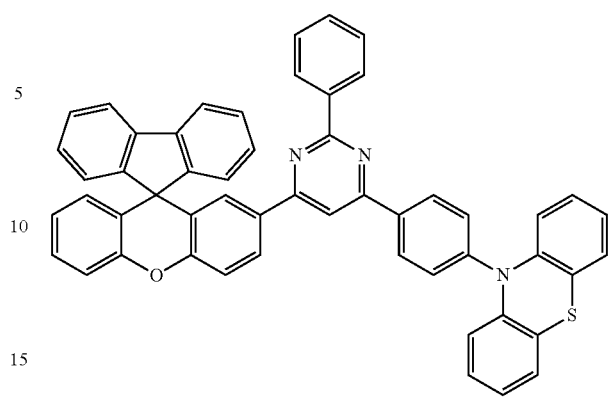
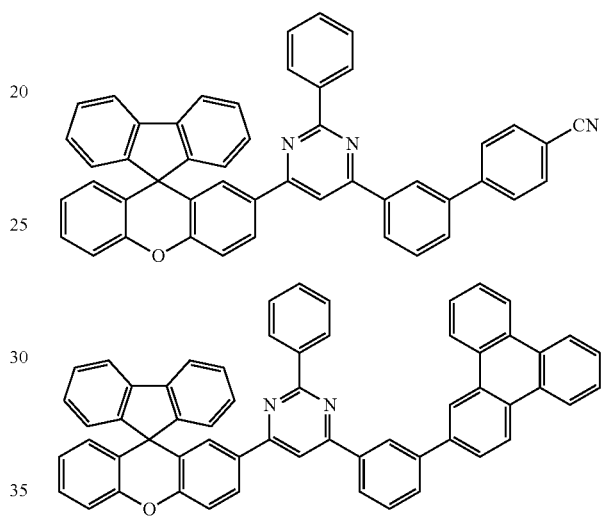
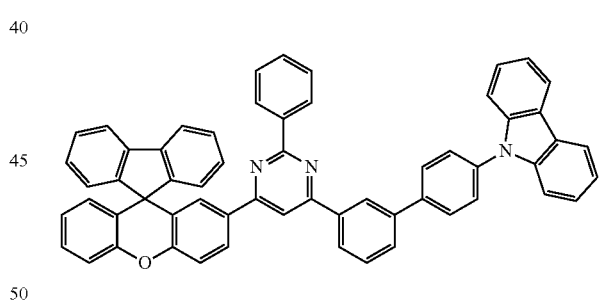
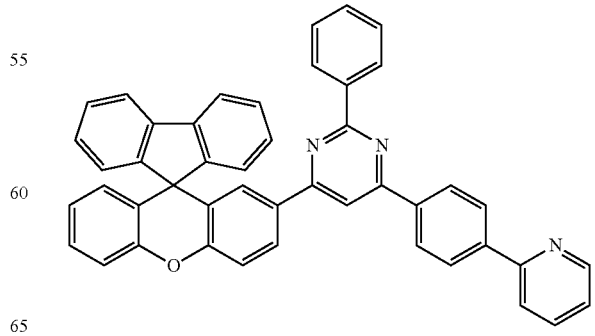

363
-continued
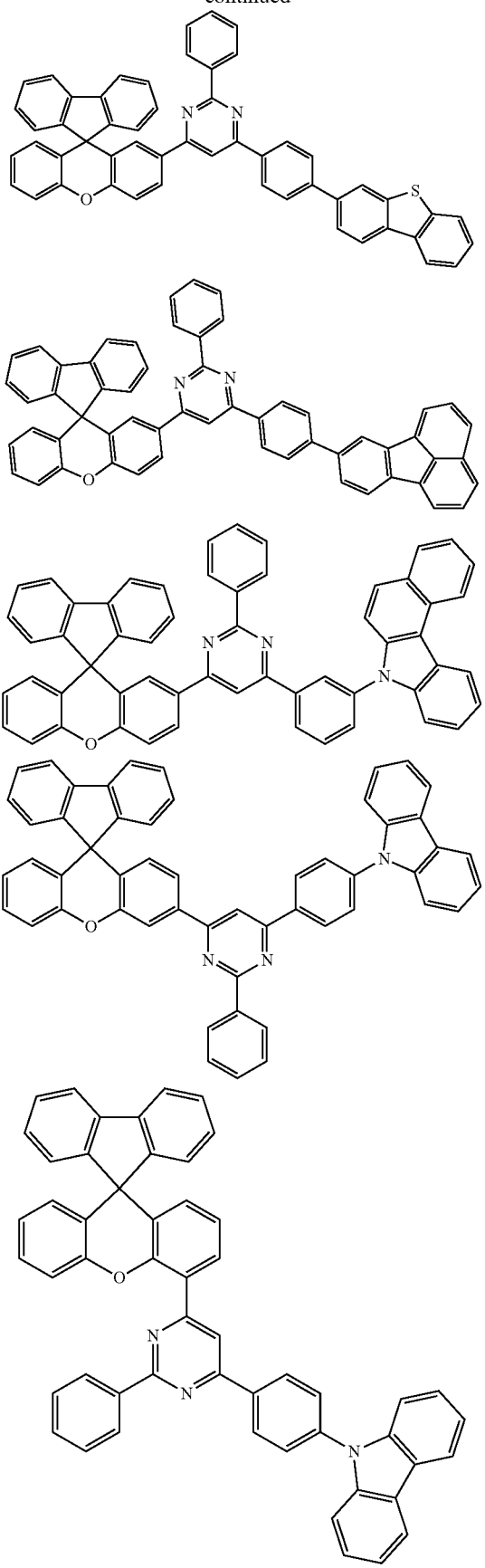
364
-continued
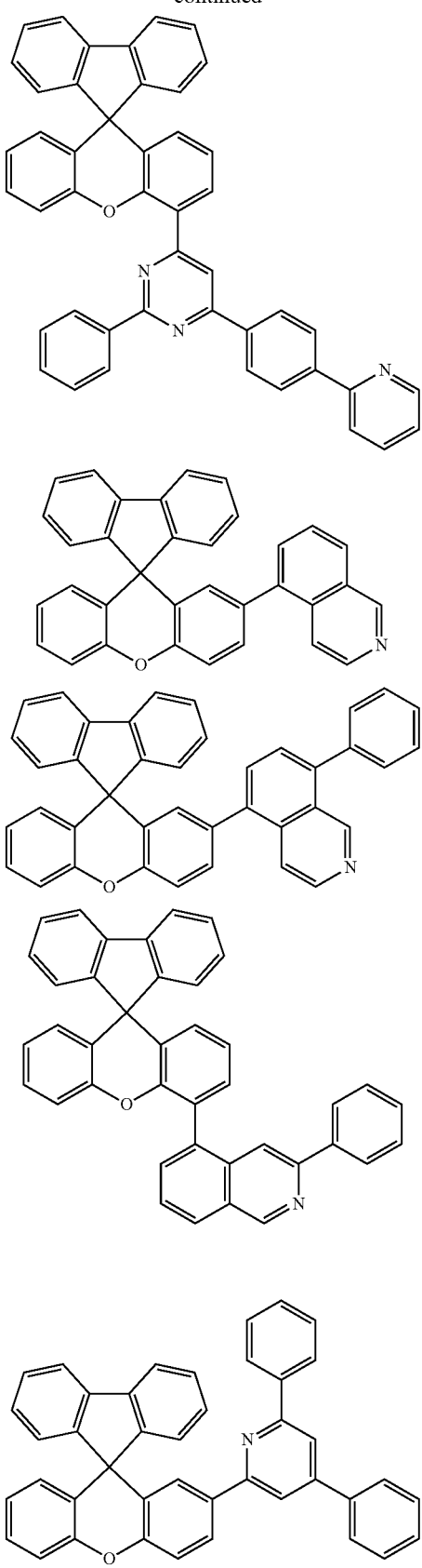

-continued

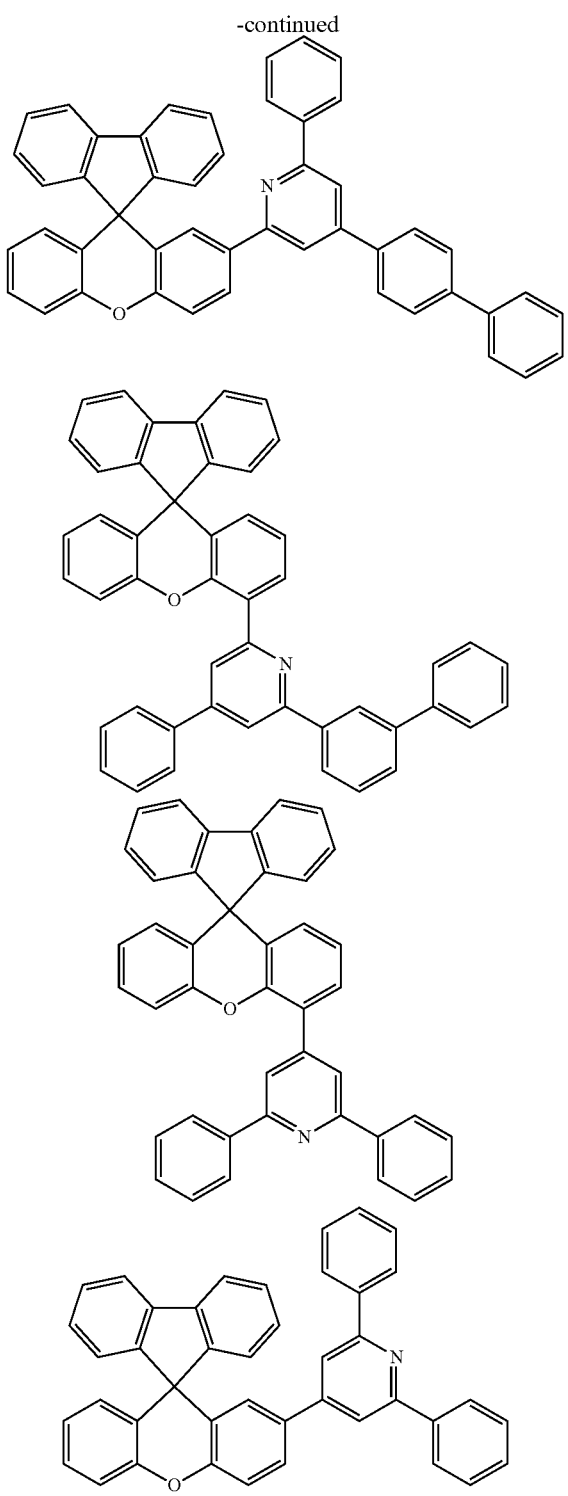

One embodiment of the present specification provides an organic light emitting device comprising a first electrode; a second electrode provided opposite to the first electrode; and one or more organic material layers provided between the first electrode and the second electrode, wherein one or more layers of the organic material layers comprise the hetero-cyclic compound described above.

According to one embodiment of the present specification, the organic material layer of the organic light emitting device of the present specification may be formed in a single layer structure, but may be formed in a multilayer structure in which two or more organic material layers are laminated. For example, the organic light emitting device of the present disclosure may have a structure comprising a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and may include less or more numbers of organic material layers.

For example, structures of an organic light emitting device of the present specification may be as illustrated in FIG. 1 and FIG. 2, but are not limited thereto.

FIG. 1 illustrates a structure of an organic light emitting device (10) in which a first electrode (30), a light emitting layer (40) and a second electrode (50) are consecutively laminated on a substrate (20). FIG. 1 is an exemplary structure of an organic light emitting device according to one embodiment of the present specification, and other organic material layers may be further included.

FIG. 2 illustrates a structure of an organic light emitting device (11) in which a first electrode (30), a hole injection layer (60), a hole transfer layer (70), a light emitting layer (40), an electron transfer layer (80), an electron injection layer (90) and a second electrode (50) are consecutively laminated on a substrate (20). FIG. 2 is an exemplary structure of an organic light emitting device according to an embodiment of the present specification, and other organic material layers may be further included.

FIG. 3 illustrates a structure of an organic light emitting device (13) in which a first electrode (30), a hole injection layer (60), a hole transfer layer (70), a light emitting layer (40), an electron control layer (100), an electron transfer layer (80), an electron injection layer (90) and a second electrode (50) are consecutively laminated on a substrate (20). FIG. 3 is an exemplary structure of an organic light emitting device according to an embodiment of the present specification, and other organic material layers may be further included.

According to one embodiment of the present specification, the organic material layer comprises an electron injection layer, an electron transfer layer or a layer carrying out electron injection and electron transfer at the same time, and the electron injection layer, the electron transfer layer or the layer carrying out electron injection and electron transfer at the same time comprises the hetero-cyclic compound represented by Chemical Formula 1.

In one embodiment of the present specification, when using the hetero-cyclic compound represented by Chemical Formula 1 in the organic material layer capable of carrying out electron injection and electron transfer at the same time, an n-type dopant used in the art may be mixed thereto.

In one embodiment of the present specification, when an n-type dopant is further comprised in the electron transfer layer, the electron injection layer or the layer carrying out electron injection and electron transfer at the same time in addition to the compound of Chemical Formula 1, a weight ratio of the compound of Chemical Formula 1 and the n-type dopant may be from 1:100 to 100:1. The weight ratio may be specifically from 1:10 to 10:1. The weight ratio may be more specifically 1:1.

In one embodiment of the present specification, the n-type dopant may be a metal complex and the like, and may use an alkali metal such as Li, Na, K, Rb, Cs or Fr; an alkali-earth metal such as Be, Mg, Ca, Sr, Ba or Ra; a rare-earth metal such as La, Ce, Pr, Nd, Sm, Eu, Tb, Th, Dy, Ho, Er, Em, Gd, Yb, Lu, Y or Mn; or a metal compound including one or more metals of the above-mentioned metals, however, the n-type dopant is not limited thereto, and those known in the art may be used. According to one embodiment, the electron transfer layer, the electron injection layer or the layer carrying out electron injection and electron transfer at the same time including the compound of Chemical Formula 1 may further include LiQ.

According to one embodiment of the present specification, the organic material layer comprises a hole blocking layer, and the hole blocking layer comprises the hetero-cyclic compound represented by Chemical Formula 1.

According to one embodiment of the present specification, the organic material layer comprises an electron control layer, and the electron control layer comprises the hetero-cyclic compound represented by Chemical Formula 1.

According to one embodiment of the present specification, the organic material layer may further comprise one or more layers selected from the group consisting of a hole injection layer, a hole transfer layer, a light emitting layer, an electron transfer layer and an electron injection layer.

The organic light emitting device of the present specification may be manufactured using materials and methods known in the art, except that one or more layers of the organic material layers comprise the hetero-cyclic compound of the present specification, that is, the hetero-cyclic compound represented by Chemical Formula 1.

When the organic light emitting device comprises a plurality of organic material layers, the organic material layers may be formed with materials the same as or different from each other.

For example, the organic light emitting device of the present specification may be manufactured by consecutively laminating a first electrode, an organic material layer and a second electrode on a substrate. Herein, the organic light emitting device may be manufactured by forming a first electrode on a substrate by depositing a metal, a metal oxide having conductivity, or an alloy thereof using a physical vapor deposition (PVD) method such as sputtering or e-beam evaporation, and forming an organic material layer comprising a hole injection layer, a hole transfer layer, a light emitting layer and an electron transfer layer thereon, and then depositing a material capable of being used as a second electrode thereon. In addition to such a method, the organic light emitting device may also be manufactured by consecutively depositing a second electrode material, an organic material layer and a first electrode material on a substrate. In addition, the hetero-cyclic compound represented by Chemical Formula 1 may be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole series compounds; dimerized styryl compounds; BAlq; 10-hydroxybenzo quinoline-metal compounds; benzoxazole, benzthiazole and benzimidazole series compounds; poly(p-phenylenevinylene) (PPV) series polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, but the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including Alq₃; organic radical compounds; hydroxyflavone-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The hole blocking layer is a layer blocking holes from reaching a cathode and generally, may be formed under the same condition as the hole injection layer. Specifically, oxadiazole derivatives, triazole derivatives, phenanthroline derivatives, BCP, aluminum complexes and the like are included, however, the hole blocking layer is not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification may be a top-emission type, a bottom-emission type or a dual-emission type depending on the materials used.

According to one embodiment of the present specification, the hetero-cyclic compound represented by Chemical Formula 1 may be included in organic solar cells or organic transistors in addition to organic light emitting devices.

Hereinafter, the present specification will be described in detail with reference to examples. However, the examples according to the present specification may be modified to various other forms, and the scope of the present specification is not to be construed as being limited to the examples described below. Examples of the present specification are provided in order to more completely describe the present specification to those having average knowledge in the art.

Preparation Example 1. Synthesis of Chemical Formula E1

[Chemical Formula E1]

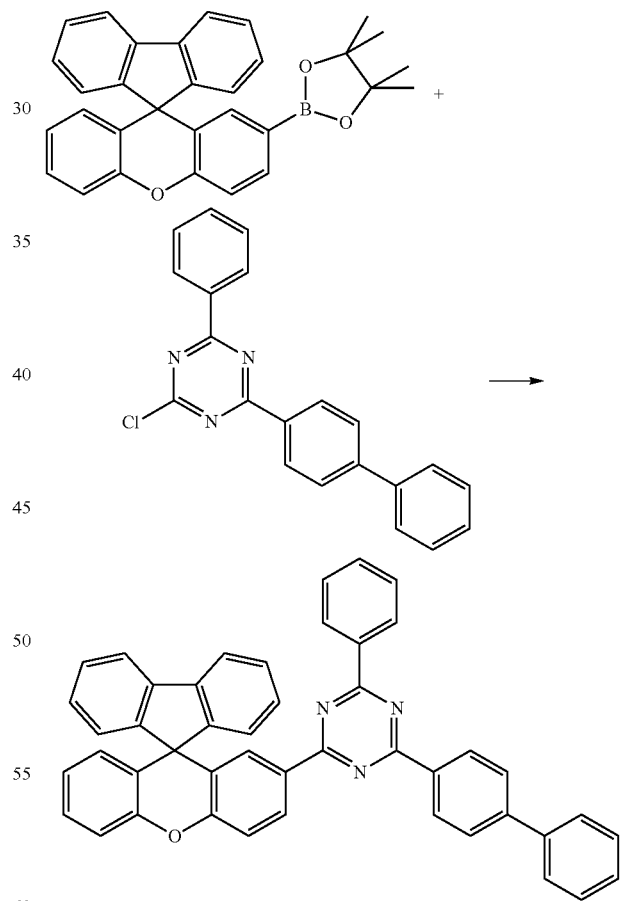

After completely dissolving the compounds 4,4,5,5-tetramethyl-2-(spiro[fluorene-9,9'-xanthen]-2'-yl)-1,3,2-dioxaborolane (10.0 g, 21.8 mmol) and 2-([1,1'-biphenyl]-4-yl)-4-chloro-6-phenyl-1,3,4-triazine (7.5 g, 21.8 mmol) in tetrahydrofuran (100 ml), potassium carbonate (9.0 g, 65.4 mmol) dissolved in 50 ml of water was added thereto, and after adding tetrakis(triphenylphosphine)palladium (756 mg, 0.65 mmol) thereto, the result was heated and stirred for 8 hours. After lowering the temperature to room temperature and terminating the reaction, the potassium carbonate solution was removed to filter white solids. The filtered white solids were washed twice each with tetrahydrofuran and ethyl acetate to prepare the compound of Chemical Formula E1 (12.6 g, yield 90%).

MS[M+H]$^+$=640

Preparation Example 2. Synthesis of Chemical Formula E2

[Chemical Formula E2]

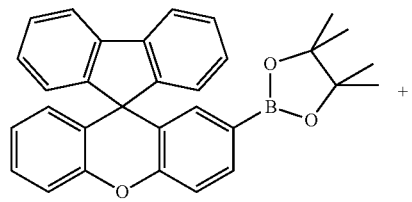

+

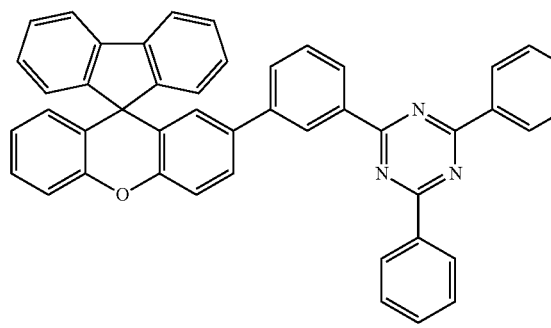

→

The compound of Chemical Formula E2 was prepared in the same manner as in Preparation Example 1, except that 2-(3-bromophenyl)-4,6-diphenyl-1,3,5-triazine was used instead of the compound 2-([1,1'-biphenyl]-4-yl)-4-chloro-6-phenyl-1,3,4-triazine.

MS[M+H]$^+$=640

Preparation Example 3. Synthesis of Chemical Formula E3

[Chemical Formula E3]

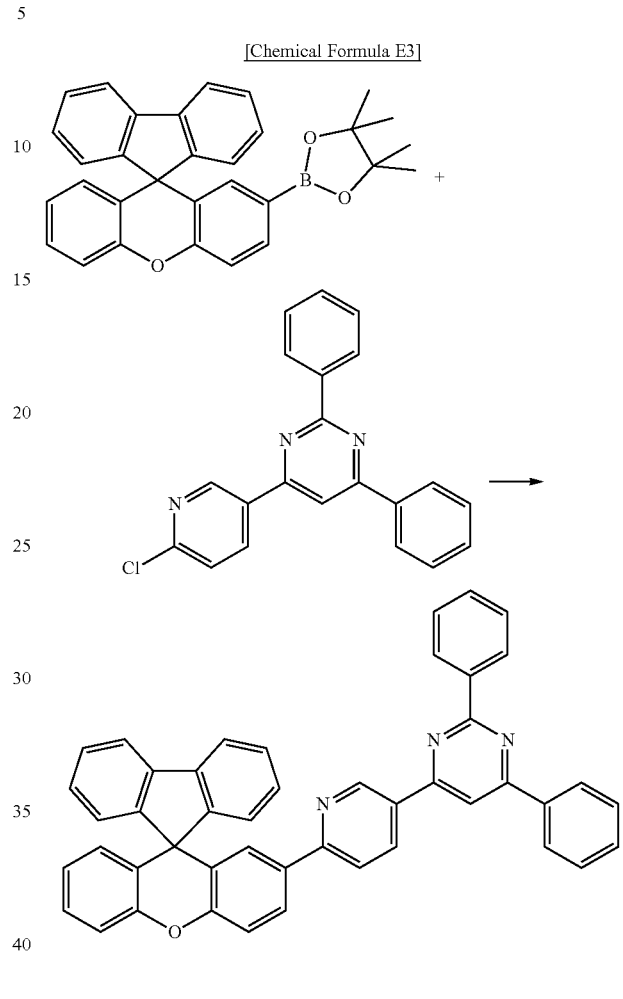

The compound of Chemical Formula E3 was prepared in the same manner as in Preparation Example 1, except that 4-(6-chloropyridin-3-yl)-2,6-diphenylpyrimidine was used instead of the compound 2-([1,1'-biphenyl]-4-yl)-4-chloro-6-phenyl-1,3,4-triazine.

MS[M+H]$^+$=640

Preparation Example 4. Synthesis of Chemical Formula E4

[Chemical Formula E4]

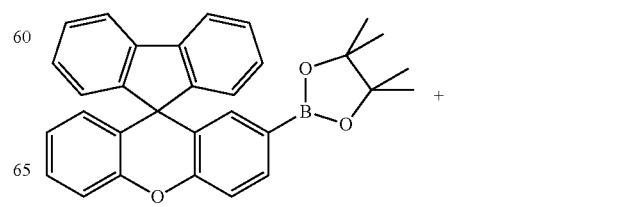

+

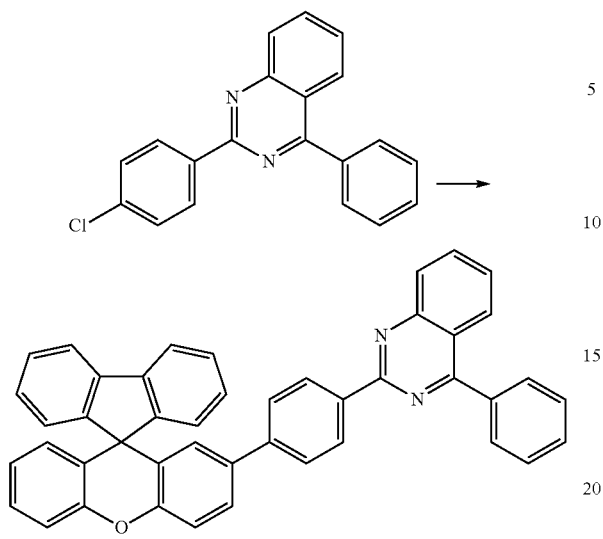

The compound of Chemical Formula E4 was prepared in the same manner as in Preparation Example 1, except that 2-(4-chlorophenyl)-4-phenylquinazoline was used instead of the compound 2-([1,1'-biphenyl]-4-yl)-4-chloro-6-phenyl-1,3,4-triazine.

MS[M+H]$^+$=613

Preparation Example 5. Synthesis of Chemical Formula E5

[Chemical Formula E5]

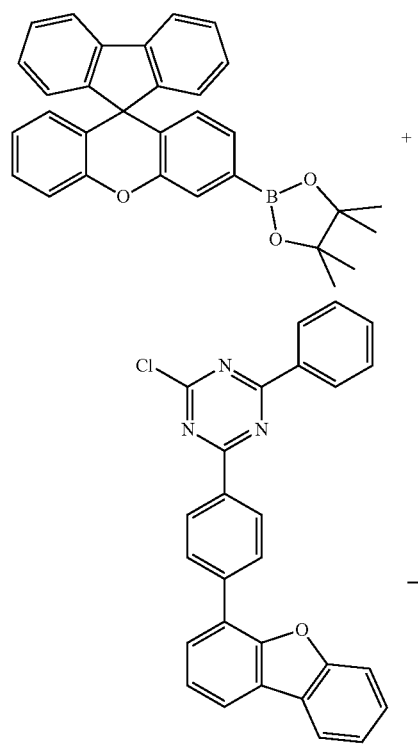

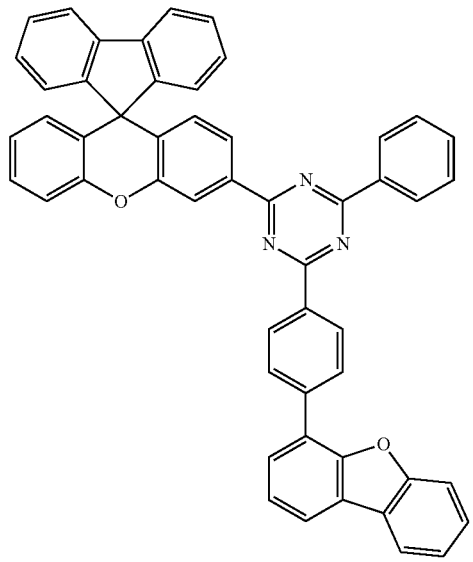

The compound of Chemical Formula E5 was prepared in the same manner as in Preparation Example 1, except that 4,4,5,5-tetramethyl-2-(spiro[fluorene-9,9'-xanthen]-3'-yl)-1,3,2-dioxaborolane was used instead of the compound 4,4,5,5-tetramethyl-2-(spiro[fluorene-9,9'-xanthen]-2'-yl)-1,3,2-dioxaborolane, and 2-chloro-4-(4-(dibenzo[b,d]furan-4-yl)phenyl)-6-phenyl-1,3,5-triazine was used instead of the compound 2-([1,1'-biphenyl]-4-yl)-4-chloro-6-phenyl-1,3,4-triazine.

MS[M+H]$^+$=730)

Preparation Example 6. Synthesis of Chemical Formula E6

[Chemical Formula E6]

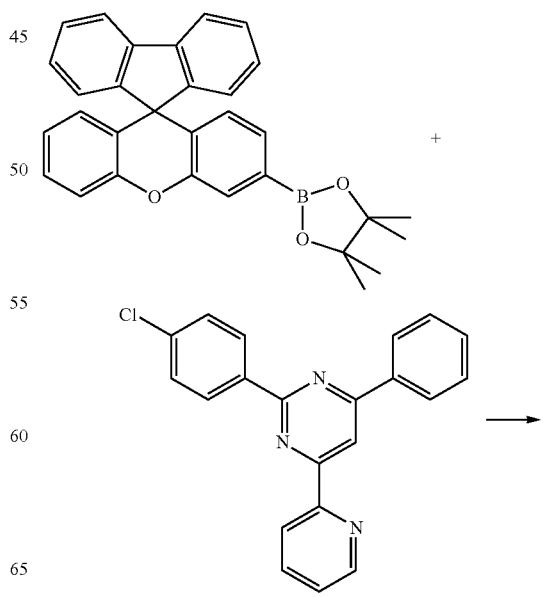

-continued

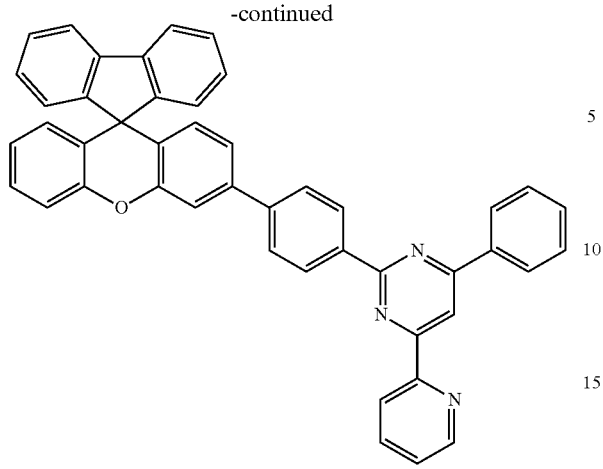

The compound of Chemical Formula E6 was prepared in the same manner as in Preparation Example 5, except that 2-(4-chlorophenyl)-4-phenyl-6-(pyridin-2-yl)pyrimidine was used instead of the compound 2-chloro-4-(4-(dibenzo[b,d]furan-4-yl)phenyl)-6-phenyl-1,3,5-triazine.
MS[M+H]$^+$=640

Preparation Example 7. Synthesis of Chemical Formula E7

[Chemical Formula E7]

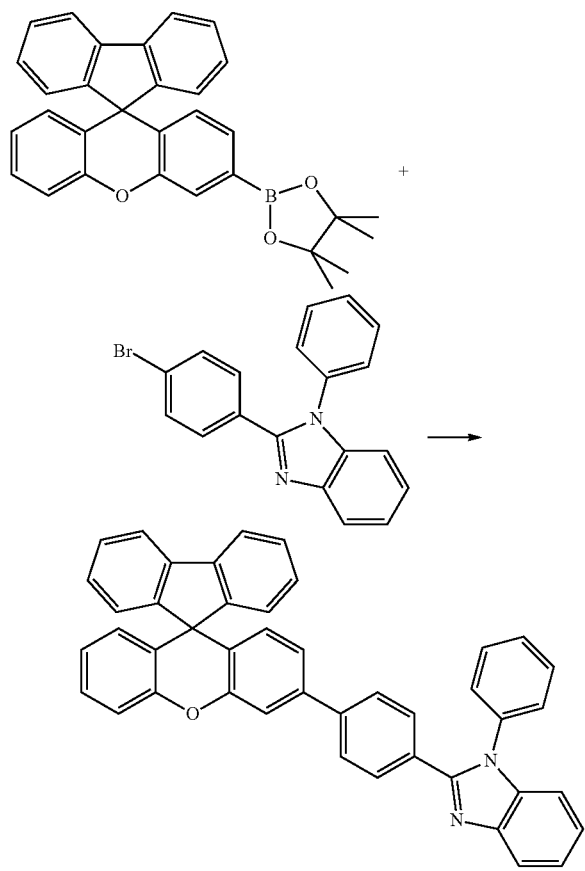

The compound of Chemical Formula E7 was prepared in the same manner as in Preparation Example 5, except that 2-(4-bromophenyl)-1-phenyl-1H-benzo[d]imidazole was used instead of the compound 2-chloro-4-(4-(dibenzo[b,d]furan-4-yl)phenyl)-6-phenyl-1,3,5-triazine.
MS[M+H]$^+$=601

Preparation Example 8. Synthesis of Chemical Formula E8

[Chemical Formula E8]

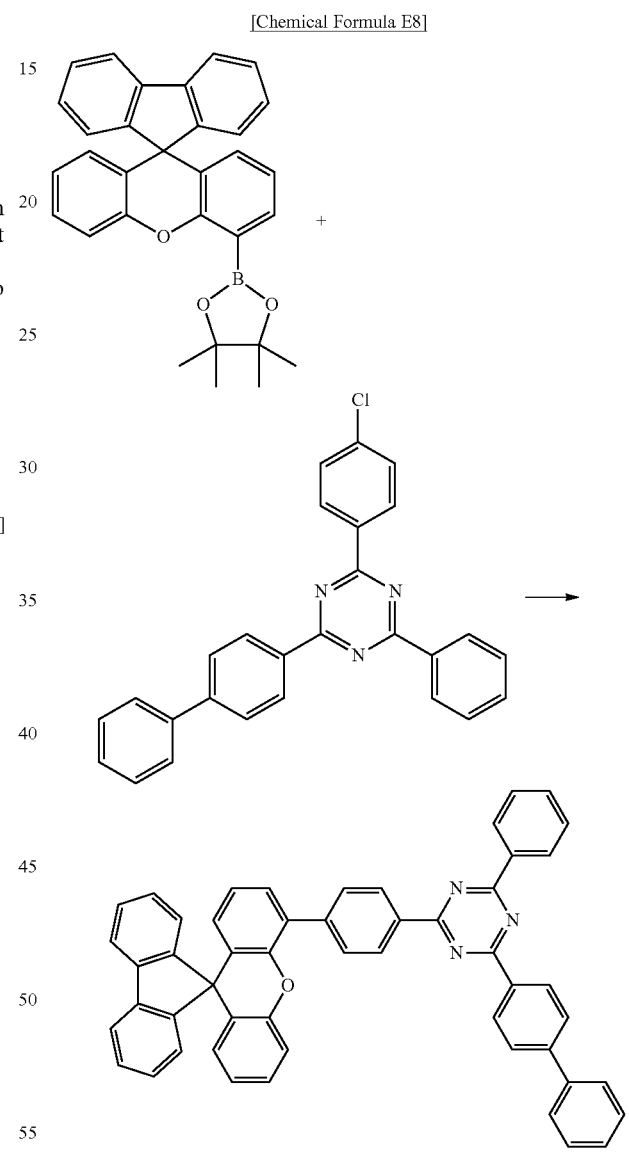

The compound of Chemical Formula E8 was prepared in the same manner as in Preparation Example 1, except that 4,4,5,5-tetramethyl-2-(spiro[fluorene-9,9'-xanthen]-4'-yl)-1,3,2-dioxaborolane was used instead of the compound 4,4,5,5-tetramethyl-2-(spiro[fluorene-9,9'-xanthen]-2'-yl)-1,3,2-dioxaborolane, and 2-([1,1'-biphenyl]-4-yl)-4-(4-chlorophenyl)-6-phenyl-1,3,5-triazine was used instead of the compound 2-([1,1'-biphenyl]-4-yl)-4-chloro-6-phenyl-1,3,4-triazine.
MS[M+H]$^+$=716

Preparation Example 9. Synthesis of Chemical Formula E9

[Chemical Formula E9]

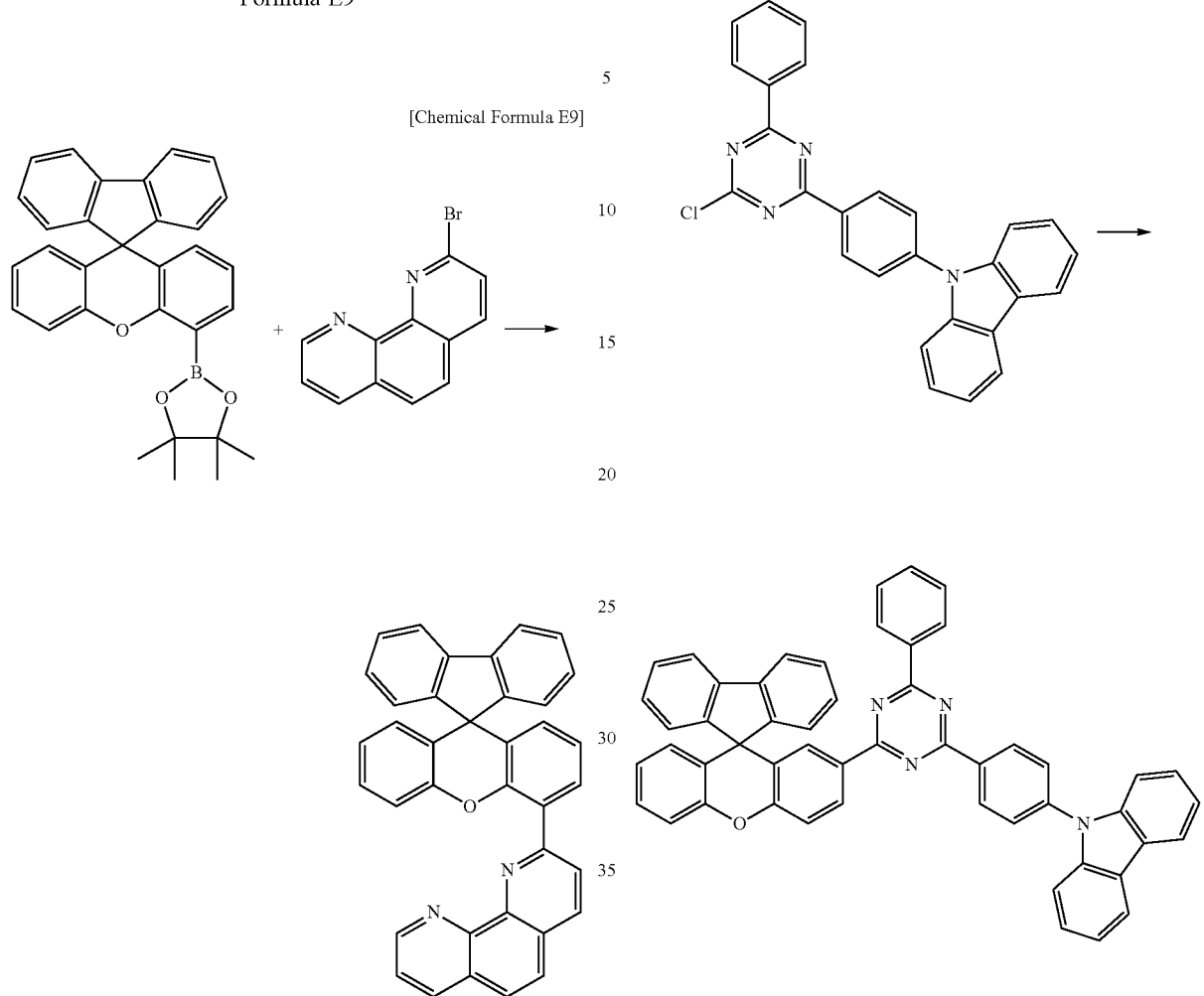

The compound of Chemical Formula E9 was prepared in the same manner as in Preparation Example 8, except that 2-bromo-1,10-phenanthroline was used instead of the compound 2-([1,1'-biphenyl]-4-yl)-4-(4-chlorophenyl)-6-phenyl-1,3,5-triazine.

MS[M+H]$^+$=511

Preparation Example 10. Synthesis of Chemical Formula E10

[Chemical Formula E10]

The compound of Chemical Formula E10 was prepared in the same manner as in Preparation Example 1, except that 9-(4-(4-chloro-6-phenyl-1,3,5-triazin-2-yl)phenyl)-9H-carbazole was used instead of the compound 2-([1,1'-biphenyl]-4-yl)-4-chloro-6-phenyl-1,3,4-triazine.

MS[M+H]$^+$=729

Preparation Example 11. Synthesis of Chemical Formula E11

[Chemical Formula E11]

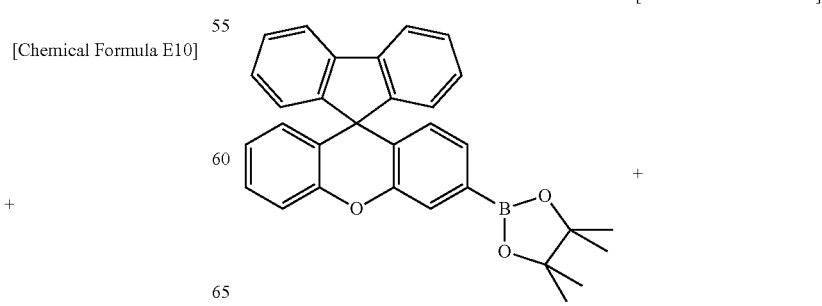

-continued

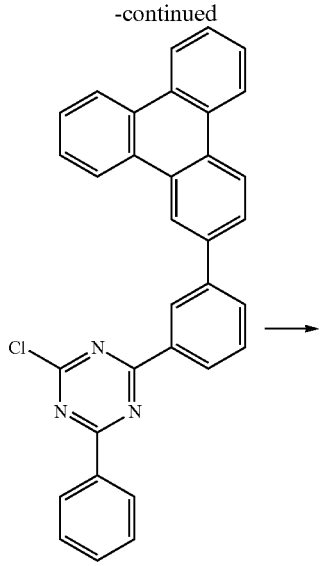

Preparation Example 12. Synthesis of Chemical Formula E12

[Chemical Formula E12]

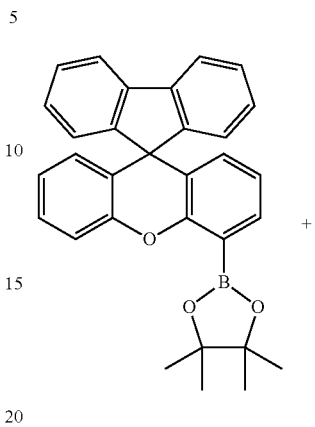

+

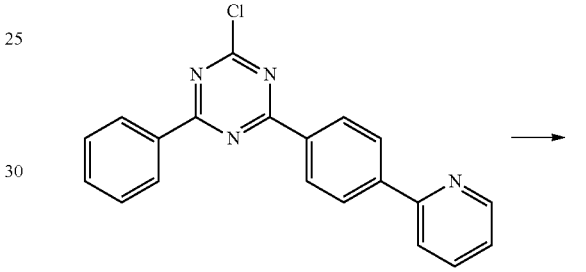

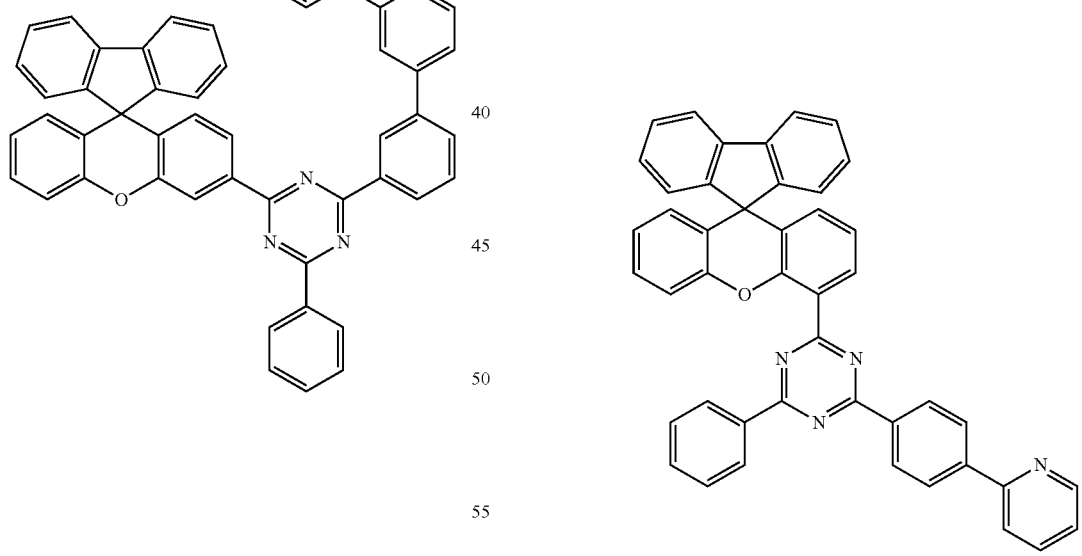

The compound of Chemical Formula E11 was prepared in the same manner as in Preparation Example 5, except that 2-chloro-4-phenyl-6-(3-(triphenylen-2-yl)phenyl)-1,3,5-triazine was used instead of the compound 2-chloro-4-(4-(dibenzo[b,d]furan-4-yl)phenyl)-6-phenyl-1,3,5-triazine.

MS[M+H]$^+$=790

The compound of Chemical Formula E12 was prepared in the same manner as in Preparation Example 8, except that 2-chloro-4-phenyl-6-(4-(pyridin-2-yl)phenyl)-1,3,5-triazine was used instead of the compound 2-([1,1'-biphenyl]-4-yl)-4-(4-chlorophenyl)-6-phenyl-1,3,5-triazine.

MS[M+H]$^+$=641

Preparation Example 13. Synthesis of Chemical Formula E13

[Chemical Formula E13]

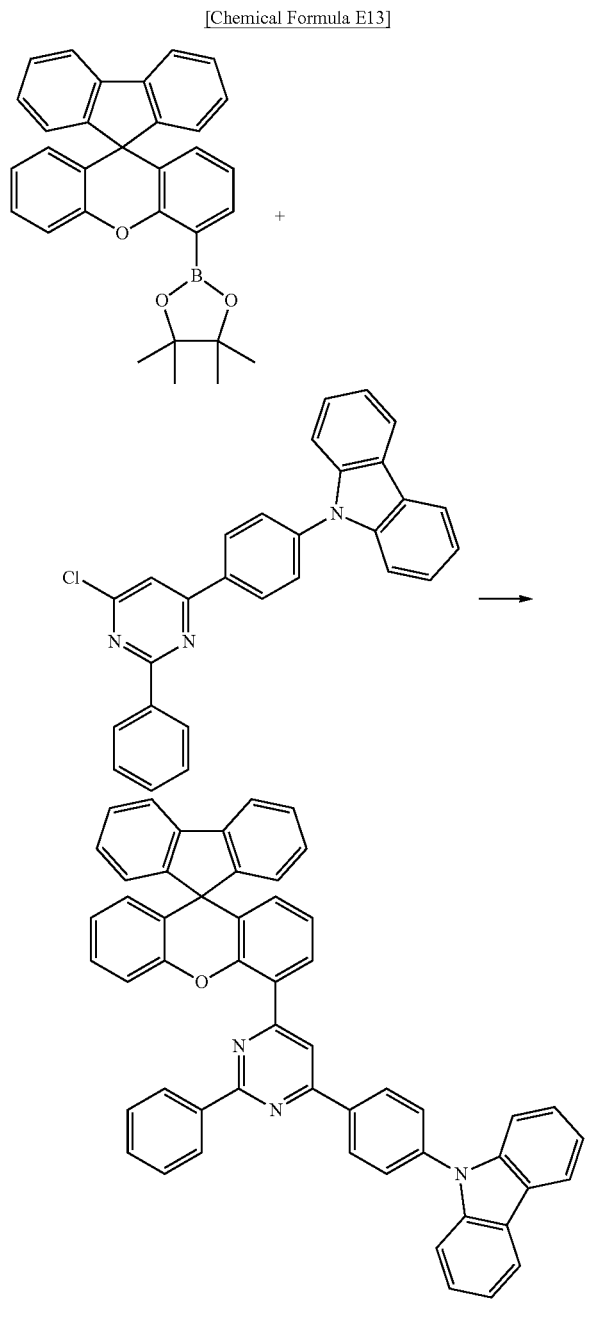

The compound of Chemical Formula E13 was prepared in the same manner as in Preparation Example 8, except that 9-(4-(6-chloro-2-phenylpyridin-4-yl)phenyl)-9H-carbazole was used instead of the compound 2-([1,1'-biphenyl]-4-yl)-4-(4-chlorophenyl)-6-phenyl-1,3,5-triazine.

MS[M+H]$^+$=728

Preparation Example 14. Synthesis of Chemical Formula E14

[Chemical Formula E14]

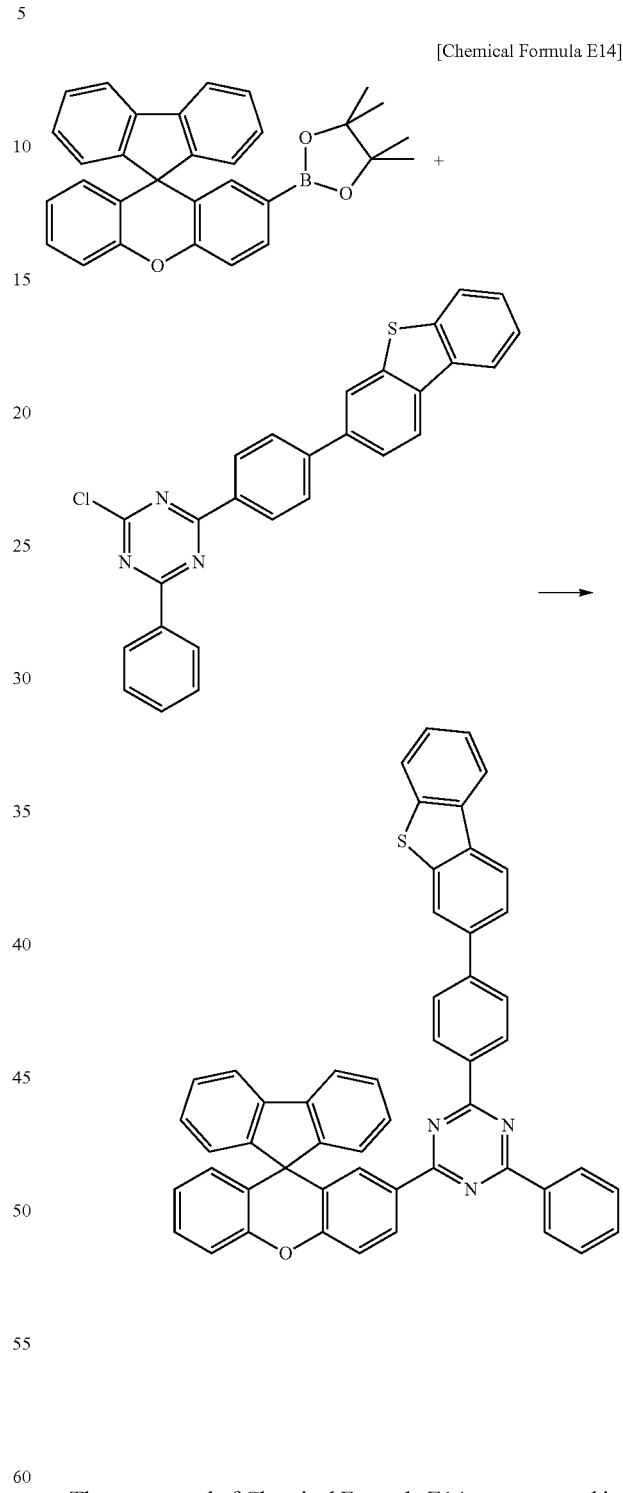

The compound of Chemical Formula E14 was prepared in the same manner as in Preparation Example 1, except that 2-chloro-4-(4-(dibenzo[b,d]thiophen-3-yl)phenyl)-6-phenyl-1,3,5-triazine was used instead of the compound 2-([1,1'-biphenyl]-4-yl)-4-chloro-6-phenyl-1,3,4-triazine.

MS[M+H]$^+$=746

Preparation Example 15. Synthesis of Chemical Formula E15

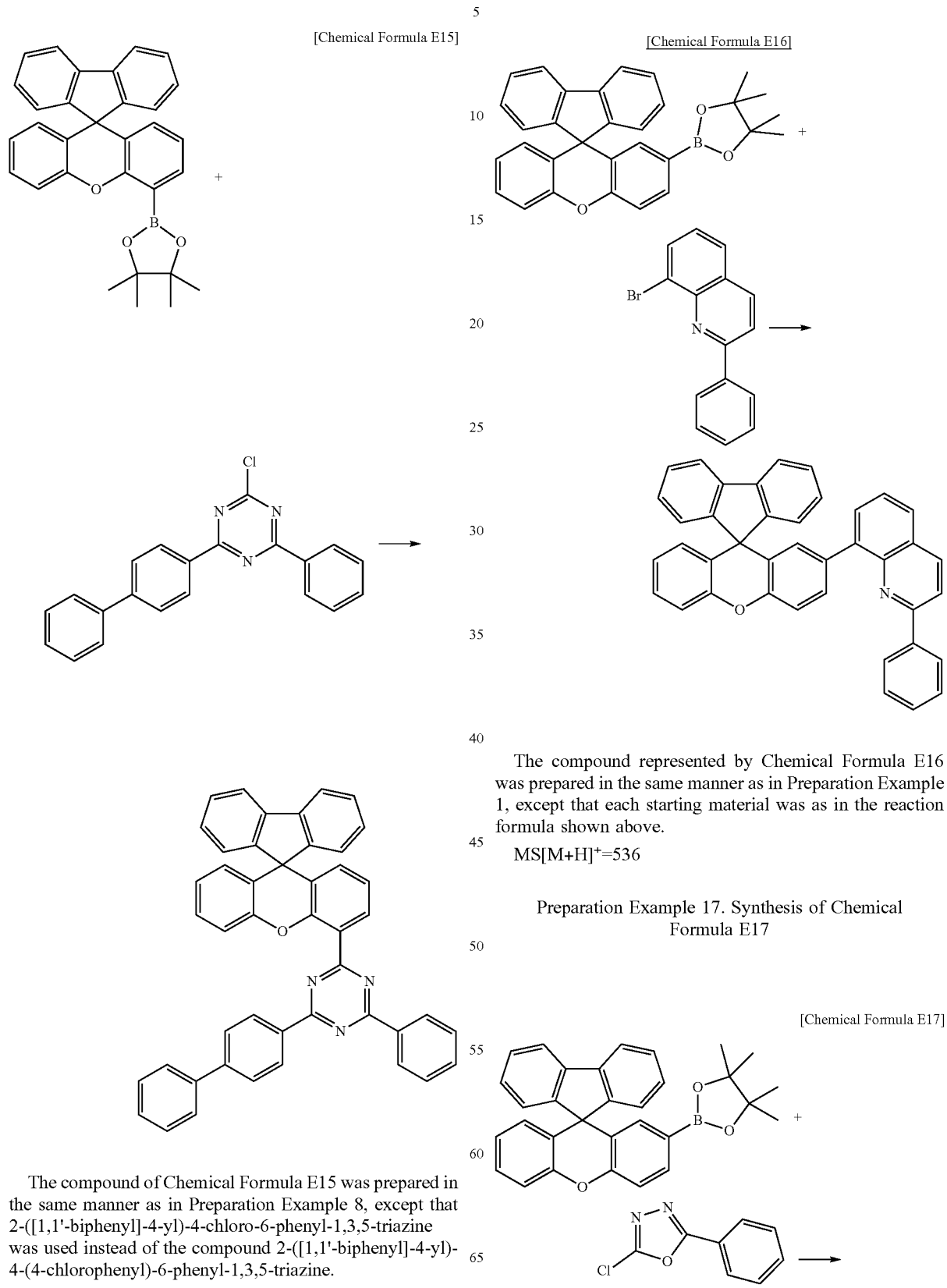

[Chemical Formula E15]

The compound of Chemical Formula E15 was prepared in the same manner as in Preparation Example 8, except that 2-([1,1'-biphenyl]-4-yl)-4-chloro-6-phenyl-1,3,5-triazine was used instead of the compound 2-([1,1'-biphenyl]-4-yl)-4-(4-chlorophenyl)-6-phenyl-1,3,5-triazine.

MS[M+H]$^+$=640

Preparation Example 16. Synthesis of Chemical Formula E16

[Chemical Formula E16]

The compound represented by Chemical Formula E16 was prepared in the same manner as in Preparation Example 1, except that each starting material was as in the reaction formula shown above.

MS[M+H]$^+$=536

Preparation Example 17. Synthesis of Chemical Formula E17

[Chemical Formula E17]

-continued

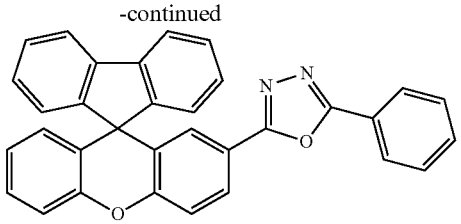

The compound represented by Chemical Formula E17 was prepared in the same manner as in Preparation Example 1, except that each starting material was as in the reaction formula shown above.

MS[M+H]$^+$=477

Preparation Example 18. Synthesis of Chemical Formula E18

[Chemical Formula E18]

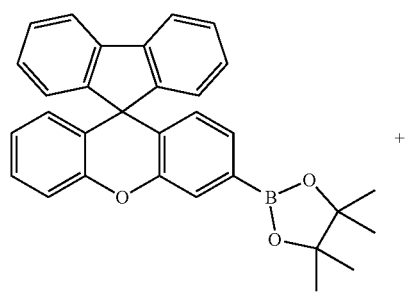

+

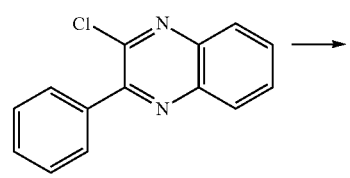

→

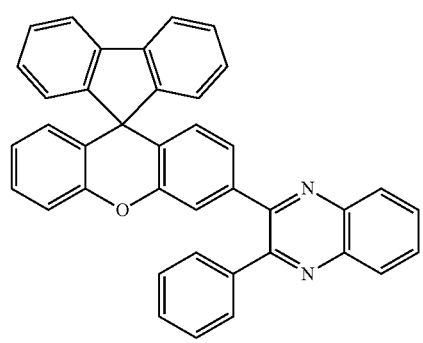

The compound represented by Chemical Formula E18 was prepared in the same manner as in Preparation Example 1, except that each starting material was as in the reaction formula shown above.

MS[M+H]$^+$=537

Preparation Example 19. Synthesis of Chemical Formula E19

[Chemical Formula E19]

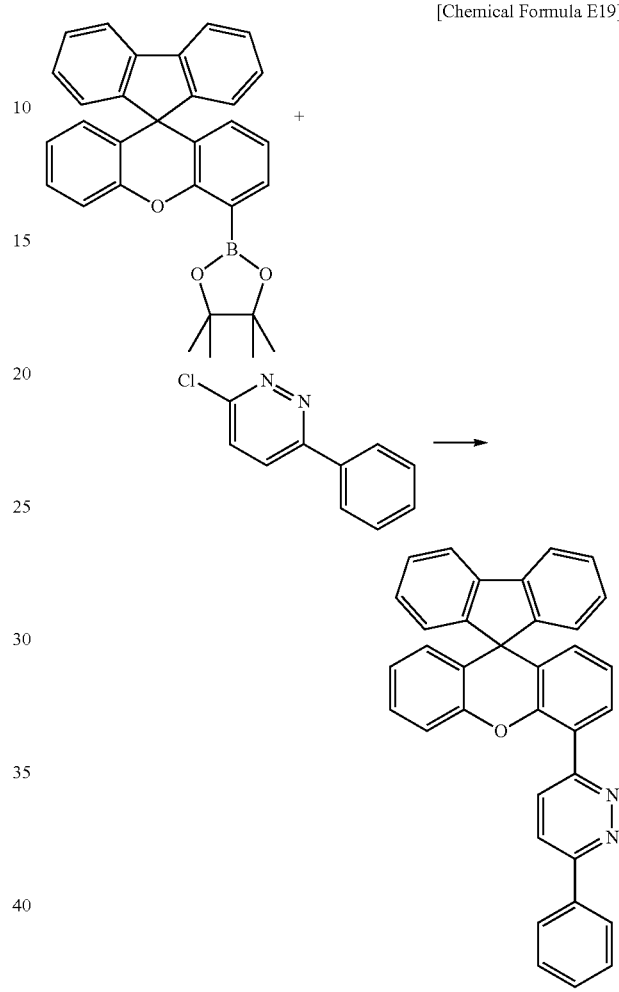

The compound represented by Chemical Formula E19 was prepared in the same manner as in Preparation Example 1, except that each starting material was as in the reaction formula shown above.

MS[M+H]$^+$=487

Preparation Example 20. Synthesis of Chemical Formula E20

[Chemical Formula E20]

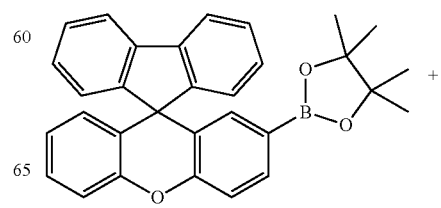

+

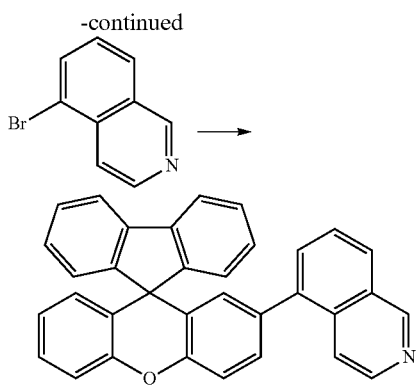

The compound represented by Chemical Formula E20 was prepared in the same manner as in Preparation Example 1, except that each starting material was as in the reaction formula shown above.
MS[M+H]$^+$=460

Preparation Example 21. Synthesis of Chemical Formula E21

[Chemical Formula E21]

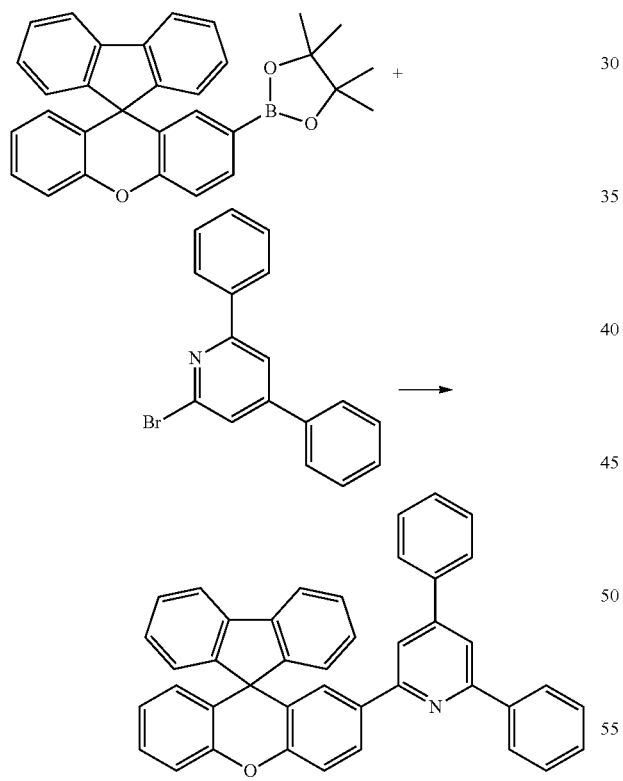

The compound represented by Chemical Formula E21 was prepared in the same manner as in Preparation Example 1, except that each starting material was as in the reaction formula shown above.
MS[M+H]$^+$=562

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing the following compound [HI-A] to a thickness of 600 Å. A hole transfer layer was formed on the hole injection layer by vacuum depositing hexaazatriphenylene (HAT) of the following chemical formula to a thickness of 50 Å and the following compound [HT-A] (600 Å) in consecutive order.

Subsequently, a light emitting layer was formed on the hole transfer layer to a film thickness of 200 Å by vacuum depositing the following compounds [BH] and [BD] in a weight ratio of 25:1.

On the light emitting layer, an electron injection and transfer layer was formed to a thickness of 350 Å by vacuum depositing the compound of [Chemical Formula E1] and the following lithiumquinolate [LiQ] compound in a weight ratio of 1:1. A cathode was formed on the electron injection and transfer layer by depositing lithium fluoride (LiF) to a thickness of 10 Å and aluminum to a thickness of 1,000 Å in consecutive order.

An organic light emitting device was manufactured by maintaining, in the above-mentioned processes, the deposition rates of the organic materials at 0.4 Å/sec to 0.9 Å/sec, the deposition rates of the lithium fluoride and the aluminum of the cathode at 0.3 Å/sec and 2 Å/sec, respectively, and the degree of vacuum during the deposition at 2×10$^{-7}$ torr to 5×10$^{-8}$ torr.

[HAT]

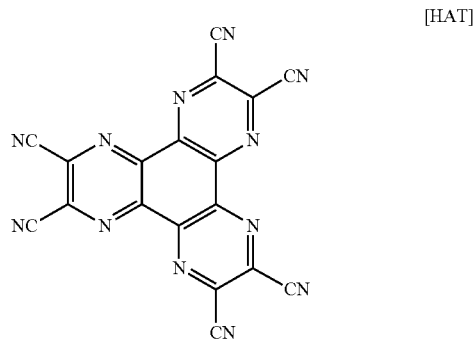

-continued
[HI-A]
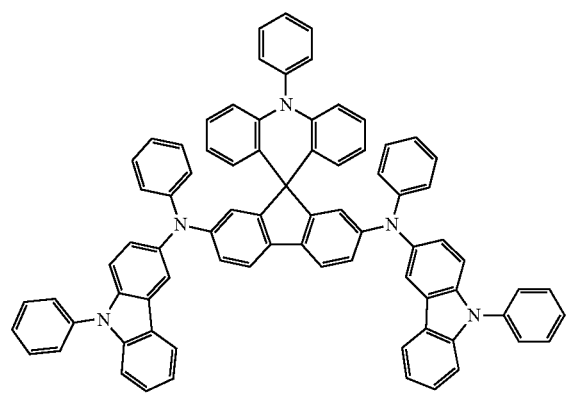
[HT-A]
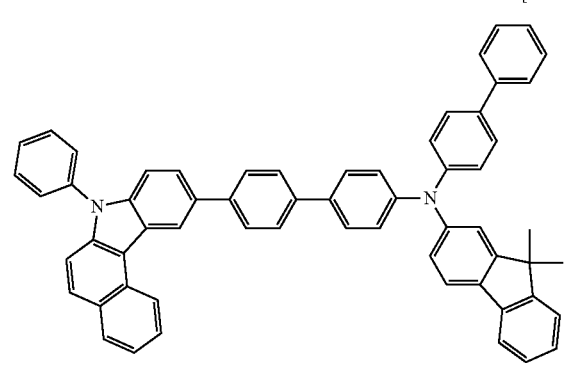
[LiQ]
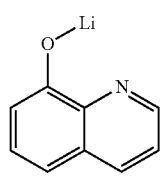
[BH]
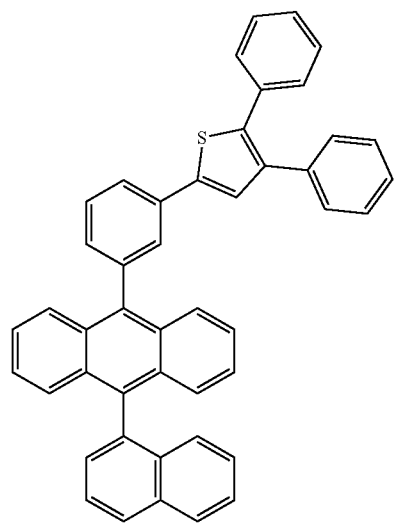
-continued
[BD]
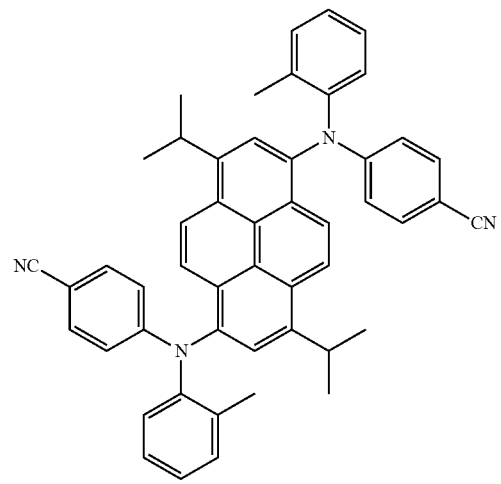
[ET-1-A]
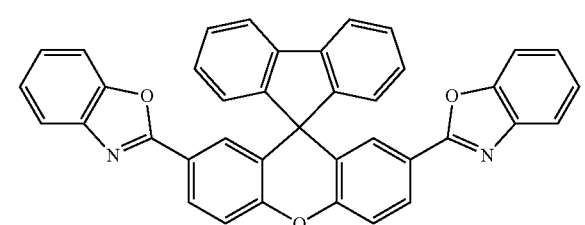
[ET-1-B]
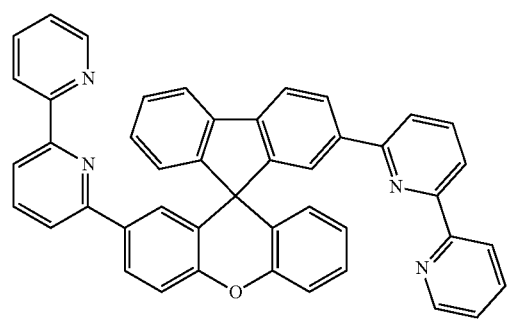
[ET-1-C]
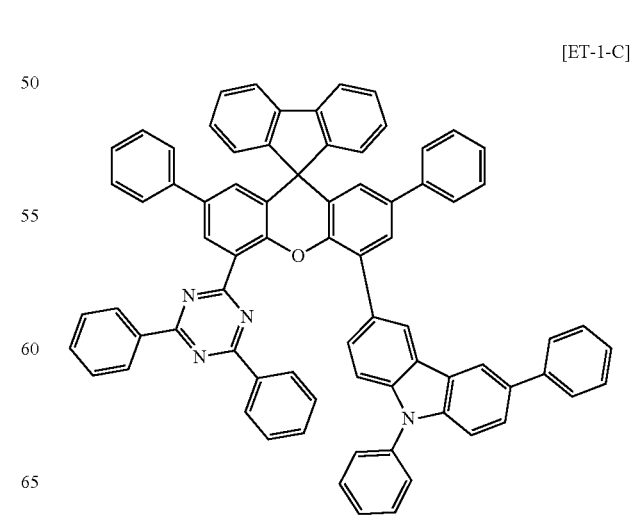

[ET-1-D]

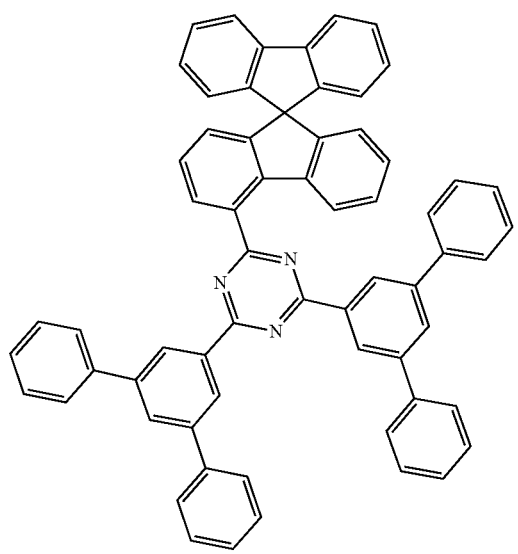

[ET-1-E]

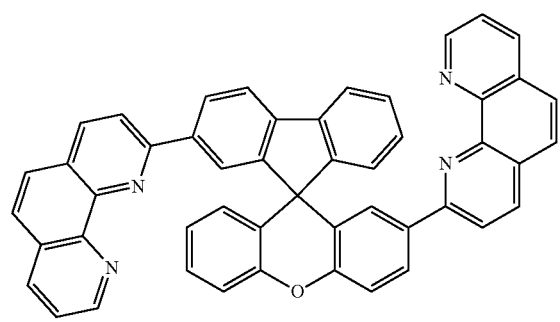

[ET-1-F]

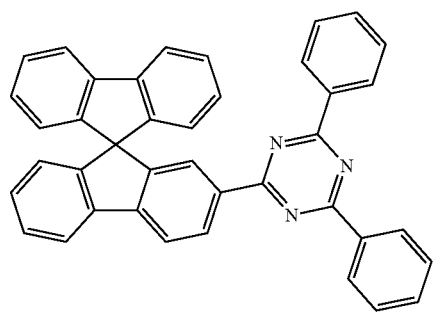

[ET-1-G]

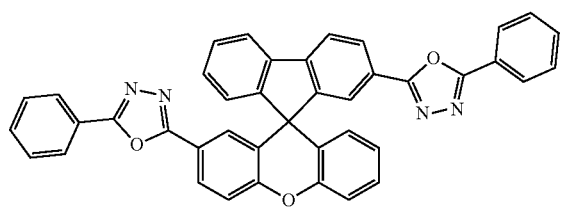

[ET-1-H]

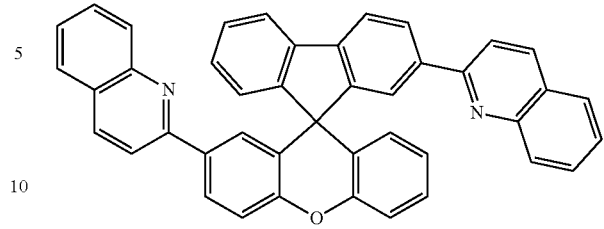

[ET-1-I]

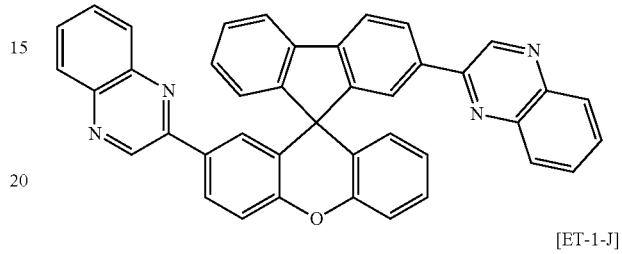

[ET-1-J]

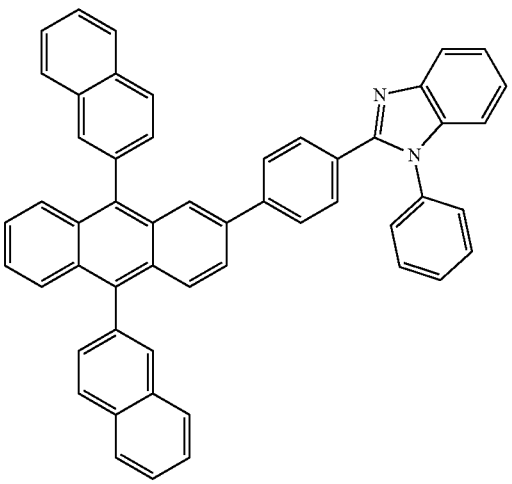

[ET-1-K]

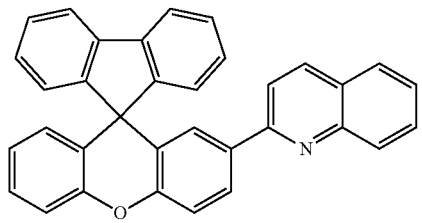

Example 1-2

An organic light emitting device was manufactured in the same manner as in Example 1-1 except that the compound of Chemical Formula E2 was used instead of the compound of Chemical Formula E1.

Example 1-3

An organic light emitting device was manufactured in the same manner as in Example 1-1 except that the compound of Chemical Formula E3 was used instead of the compound of Chemical Formula E1.

Example 1-4

An organic light emitting device was manufactured in the same manner as in Example 1-1 except that the compound of Chemical Formula E4 was used instead of the compound of Chemical Formula E1.

Example 1-5

An organic light emitting device was manufactured in the same manner as in Example 1-1 except that the compound of Chemical Formula E5 was used instead of the compound of Chemical Formula E1.

Example 1-6

An organic light emitting device was manufactured in the same manner as in Example 1-1 except that the compound of Chemical Formula E6 was used instead of the compound of Chemical Formula E1.

Example 1-7

An organic light emitting device was manufactured in the same manner as in Example 1-1 except that the compound of Chemical Formula E7 was used instead of the compound of Chemical Formula E1.

Example 1-8

An organic light emitting device was manufactured in the same manner as in Example 1-1 except that the compound of Chemical Formula E8 was used instead of the compound of Chemical Formula E1.

Example 1-9

An organic light emitting device was manufactured in the same manner as in Example 1-1 except that the compound of Chemical Formula E9 was used instead of the compound of Chemical Formula E1.

Example 1-10

An organic light emitting device was manufactured in the same manner as in Example 1-1 except that the compound of Chemical Formula E10 was used instead of the compound of Chemical Formula E1.

Example 1-11

An organic light emitting device was manufactured in the same manner as in Example 1-1 except that the compound of Chemical Formula E11 was used instead of the compound of Chemical Formula E1.

Example 1-12

An organic light emitting device was manufactured in the same manner as in Example 1-1 except that the compound of Chemical Formula E12 was used instead of the compound of Chemical Formula E1.

Example 1-13

An organic light emitting device was manufactured in the same manner as in Example 1-1 except that the compound of Chemical Formula E13 was used instead of the compound of Chemical Formula E1.

Example 1-14

An organic light emitting device was manufactured in the same manner as in Example 1-1 except that the compound of Chemical Formula E14 was used instead of the compound of Chemical Formula E1.

Example 1-15

An organic light emitting device was manufactured in the same manner as in Example 1-1 except that the compound of Chemical Formula Ely was used instead of the compound of Chemical Formula E1.

Example 1-16

An organic light emitting device was manufactured in the same manner as in Example 1-1 except that the compound of Chemical Formula E16 was used instead of the compound of Chemical Formula E1.

Example 1-17

An organic light emitting device was manufactured in the same manner as in Example 1-1 except that the compound of Chemical Formula E11 was used instead of the compound of Chemical Formula E1.

Example 1-18

An organic light emitting device was manufactured in the same manner as in Example 1-1 except that the compound of Chemical Formula E18 was used instead of the compound of Chemical Formula E1.

Example 1-19

An organic light emitting device was manufactured in the same manner as in Example 1-1 except that the compound of Chemical Formula E19 was used instead of the compound of Chemical Formula E1.

Example 1-20

An organic light emitting device was manufactured in the same manner as in Example 1-1 except that the compound of Chemical Formula E20 was used instead of the compound of Chemical Formula E1.

Example 1-21

An organic light emitting device was manufactured in the same manner as in Example 1-1 except that the compound of Chemical Formula E21 was used instead of the compound of Chemical Formula E1.

Comparative Example 1-1

An organic light emitting device was manufactured in the same manner as in Example 1-1 except that the compound of Chemical Formula ET-1-A was used instead of the compound of Chemical Formula E1.

Comparative Example 1-2

An organic light emitting device was manufactured in the same manner as in Example 1-1 except that the compound of Chemical Formula ET-1-B was used instead of the compound of Chemical Formula E1.

Comparative Example 1-3

An organic light emitting device was manufactured in the same manner as in Example 1-1 except that the compound of Chemical Formula ET-1-C was used instead of the compound of Chemical Formula E1.

Comparative Example 1-4

An organic light emitting device was manufactured in the same manner as in Example 1-1 except that the compound of Chemical Formula ET-1-D was used instead of the compound of Chemical Formula E1.

Comparative Example 1-5

An organic light emitting device was manufactured in the same manner as in Example 1-1 except that the compound of Chemical Formula ET-1-E was used instead of the compound of Chemical Formula E1.

Comparative Example 1-6

An organic light emitting device was manufactured in the same manner as in Example 1-1 except that the compound of Chemical Formula ET-1-F was used instead of the compound of Chemical Formula E1.

Comparative Example 1-7

An organic light emitting device was manufactured in the same manner as in Example 1-1 except that the compound of Chemical Formula ET-1-G was used instead of the compound of Chemical Formula E1.

Comparative Example 1-8

An organic light emitting device was manufactured in the same manner as in Example 1-1 except that the compound of Chemical Formula ET-1-H was used instead of the compound of Chemical Formula E1.

Comparative Example 1-9

An organic light emitting device was manufactured in the same manner as in Example 1-1 except that the compound of Chemical Formula ET-1-I was used instead of the compound of Chemical Formula E1.

Comparative Example 1-10

An organic light emitting device was manufactured in the same manner as in Example 1-1 except that the compound of Chemical Formula ET-1-J was used instead of the compound of Chemical Formula E1.

Comparative Example 1-11

An organic light emitting device was manufactured in the same manner as in Example 1-1 except that the compound of Chemical Formula ET-1-K was used instead of the compound of Chemical Formula E1.

For the organic light emitting devices manufactured using the methods of Examples 1-1 to 1-21 and Comparative Examples 1-1 to 1-11 described above, a driving voltage and light emission efficiency were measured at current density of 10 mA/cm$^2$, and time taken for the luminance decreasing to 90% compared to its initial luminance ($T_H$) was measured at current density of 20 mA/cm$^2$. The results are shown in the following Table 1.

TABLE 1

| | Chemical Formula | Voltage (V@10 mA/cm$^2$) | Efficiency (cd/A@10 mA/cm$^2$) | Color Coordinate (x, y) | Lifespan (h) $T_{90}$ at 20 mA/cm$^2$ |
|---|---|---|---|---|---|
| Example 1-1 | E1 | 4.27 | 5.67 | (0.142, 0.097) | 160 |
| Example 1-2 | E2 | 4.36 | 5.23 | (0.142, 0.096) | 170 |
| Example 1-3 | E3 | 4.31 | 5.31 | (0.142, 0.096) | 151 |
| Example 1-4 | E4 | 4.40 | 5.07 | (0.142, 0.096) | 201 |
| Example 1-5 | E5 | 4.26 | 5.30 | (0.142, 0.096) | 149 |
| Example 1-6 | E6 | 4.37 | 5.23 | (0.142, 0.097) | 153 |
| Example 1-7 | E7 | 4.27 | 5.39 | (0.142, 0.096) | 140 |
| Example 1-8 | E8 | 4.2 | 5.48 | (0.142, 0.099) | 135 |
| Example 1-9 | E9 | 4.39 | 5.02 | (0.142, 0.096) | 148 |
| Example 1-10 | E10 | 4.28 | 5.41 | (0.142, 0.098) | 159 |
| Example 1-11 | E11 | 4.31 | 5.38 | (0.142, 0.096) | 150 |
| Example 1-12 | E12 | 4.2 | 5.33 | (0.142, 0.097) | 142 |
| Example 1-13 | E13 | 4.21 | 5.35 | (0.142, 0.096) | 140 |
| Example 1-14 | E14 | 4.51 | 5.01 | (0.142, 0.097) | 176 |
| Example 1-15 | E15 | 4.30 | 5.27 | (0.142, 0.097) | 167 |
| Example 1-16 | E16 | 4.38 | 4.99 | (0.142, 0.097) | 125 |
| Example 1-17 | E17 | 4.39 | 4.98 | (0.142, 0.097) | 126 |
| Example 1-18 | E18 | 4.36 | 4.95 | (0.142, 0.096) | 130 |
| Example 1-19 | E19 | 4.29 | 5.30 | (0.142, 0.096) | 180 |
| Example 1-20 | E20 | 4.40 | 4.96 | (0.142, 0.097) | 122 |
| Example 1-21 | E21 | 4.38 | 4.98 | (0.142, 0.096) | 124 |
| Comparative Example 1-1 | ET-1-A | 4.72 | 3.91 | (0.142, 0.098) | 90 |
| Comparative Example 1-2 | ET-1-B | 4.84 | 4.01 | (0.142, 0.102) | 87 |
| Comparative Example 1-3 | ET-1-C | 4.91 | 3.99 | (0.142, 0.096) | 91 |
| Comparative Example 1-4 | ET-1-D | 4.67 | 4.10 | (0.142, 0.096) | 67 |
| Comparative Example 1-5 | ET-1-E | 5.01 | 3.61 | (0.142, 0.096) | 75 |
| Comparative Example 1-6 | ET-1-F | 5.10 | 3.52 | (0.142, 0.096) | 92 |
| Comparative Example 1-7 | ET-1-G | 5.33 | 3.21 | (0.142, 0.096) | 60 |
| Comparative Example 1-8 | ET-1-H | 5.45 | 3.20 | (0.142, 0.096) | 55 |

TABLE 1-continued

|  | Chemical Formula | Voltage (V@10 mA/cm$^2$) | Efficiency (cd/A@10 mA/cm$^2$) | Color Coordinate (x, y) | Lifespan (h) T$_{90}$ at 20 mA/cm$^2$ |
|---|---|---|---|---|---|
| Comparative Example 1-9 | ET-1-I | 5.55 | 3.10 | (0.142, 0.096) | 62 |
| Comparative Example 1-10 | ET-1-J | 5.43 | 3.33 | (0.142, 0.096) | 78 |
| Comparative Example 1-11 | ET-1-K | 5.00 | 3.60 | (0.142, 0.097) | 98 |

From the results of Table 1, it was identified that the hetero-cyclic compound represented by Chemical Formula 1 according to one embodiment of the present specification was able to be used in an organic material layer capable of carrying out electron injection and electron transfer at the same time of an organic light emitting device.

Specifically, when comparing Examples 1-1 to 1-21 with Comparative Examples 1-1, 1-2, 1-3, 1-5, 1-7, 1-8 and 1-9, it was identified that the compound in which only one heteroaryl group substitutes in the spiro fluorene xanthen skeleton as in Chemical Formula 1 had excellent properties in terms of driving voltage, efficiency and lifespan in an organic light emitting device compared to the compound having two or more substituents in the spiro fluorene xanthen skeleton.

When referring to FIG. 10 and FIG. 11 showing 3D structures of Compounds E9 and E18 according to one embodiment of the present specification, it was identified that the molecules of the compounds had a horizontal structure, and when referring to FIG. 12 and FIG. 13 showing 3D structures of Compounds ET-1-E and ET-1-I, the A axis and the B axis were almost perpendicular to each other in each compound identifying that the molecule was very out of a horizontal structure.

As a result, when comparing FIG. 10 and FIG. 11 showing 3D structures of Compounds E9 and E18 according to one embodiment of the present specification and FIG. 12 and FIG. 13 showing 3D structures of Compounds ET-1-E and ET-1-I, it was seen that the hetero-cyclic compound according to one embodiment of the present specification had a more horizontal structure due to a difference in orientation in the molecular 3D structure. Accordingly, the compound in which only one heteroaryl group substitutes in the spiro fluorene xanthen skeleton as in Chemical Formula 1 of Examples 1-1 to 1-21 had a strong tendency toward a horizontal structure of the molecule compared to the compound having two or more substituents in the Spiro fluorene xanthen resulting in an increase in the electron mobility, and effects of low driving voltage, high efficiency and long lifespan are obtained in an organic light emitting device.

In addition, when comparing Examples 1-1 to 1-21 with Comparative Examples 1-4 and 1-6, it was identified that the structure of Chemical Formula 1 comprising spiro fluorene xanthen exhibited excellent properties in an organic light emitting device compared to the structure comprising a spiro fluorene group.

Furthermore, when comparing Examples 1-16 and 1-20 with Comparative Example 1-11, it was identified that the structure of Chemical Formula 1 comprising spiro fluorene xanthen exhibited excellent properties in an organic light emitting device compared to the structure comprising N of isoquinoline in a different position in the spiro fluorene xanthen.

The hetero-cyclic compound represented by Chemical Formula 1 according to one embodiment of the present specification is capable of having excellent properties by having excellent thermal stability, a deep HOMO level of 6.0 eV or higher, high triplet energy (ET) and hole stability.

Particularly, in Examples 1-1, 1-2, 1-5, 1-8, 1-11, 1-12, 1-14 and 1-15, that is, when Ar1 is a triazine group or a pyrimidine group in Chemical Formula 1, electron mobility was high with deep HOMO energy of 6.1 eV or higher, and excellent properties may be exhibited in terms of driving voltage, efficiency and lifespan when in an organic light emitting device. Specifically, in Examples 1-1, 1-2, 1-5, 1-8, 1-11, 1-12, 1-14 and 1-15, it was identified that significantly superior properties were obtained in terms of driving voltage, efficiency and lifespan compared to Example 1-21 in which Ar1 is a pyridine group (one N).

In one embodiment of the present specification, when using the hetero-cyclic compound represented by Chemical Formula 1 in an organic material layer carrying out electron injection and electron transfer at the same time, an n-type dopant used in the art may be mixed thereto.

Accordingly, the hetero-cyclic compound represented by Chemical Formula 1 according to one embodiment of the present specification has low driving voltage and high efficiency, and is capable of enhancing device stability by hole stability of the compound.

Example 2-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner.

On the transparent ITO electrode prepared as above, a hole injection layer was formed by thermal vacuum depositing the following compound [HI-A] to a thickness of 600 Å. A hole transfer layer was formed on the hole injection layer by vacuum depositing hexaazatriphenylene (HAT) of the following chemical formula to a thickness of 50 Å and the following compound [HT-A] (600 Å) in consecutive order.

Subsequently, a light emitting layer was formed on the hole transfer layer to a film thickness of 200 Å by vacuum depositing the following compounds [BH] and [BD] in a weight ratio of 25:1.

On the light emitting layer, an electron control layer was formed to a thickness of 200 Å by vacuum depositing [Chemical Formula E1]. On the electron control layer, an electron injection and transfer layer was formed to a thickness of 150 Å by vacuum depositing the following compound [ET-1-J] and the following lithiumquinolate [LiQ] compound in a weight ratio of 1:1. A cathode was formed on the electron injection and transfer layer by depositing lithium fluoride (LiF) to a thickness of 10 Å and aluminum to a thickness of 1,000 Å in consecutive order.

An organic light emitting device was manufactured by maintaining, in the above-mentioned processes, the deposition rates of the organic materials at 0.4 Å/sec to 0.9 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-8}$ torr.

[HAT]
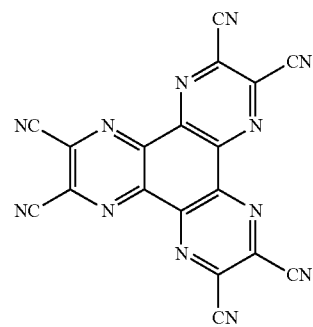
[HI-A]
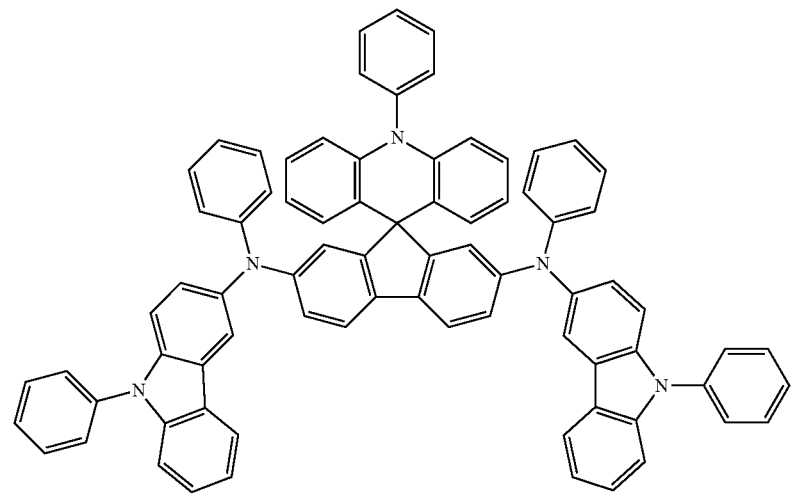
[HT-A]
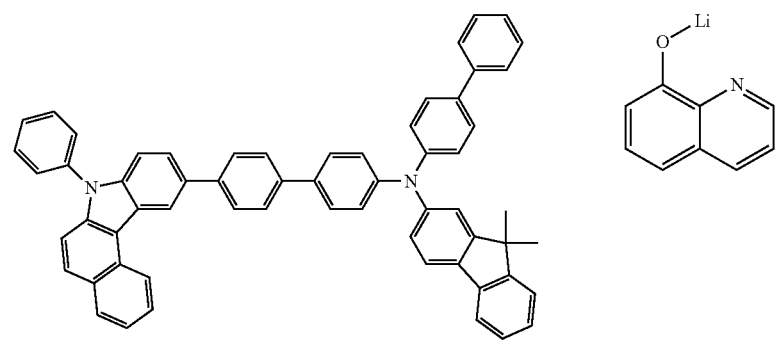
[LiQ]

-continued
401 [BH]
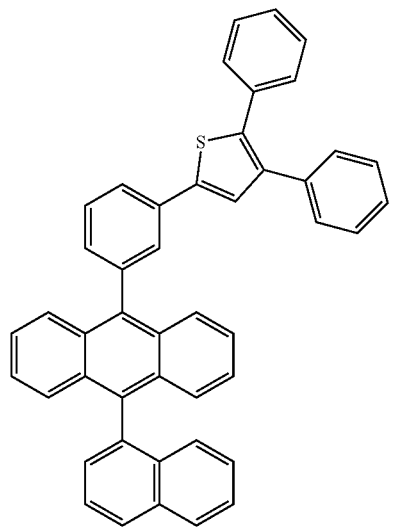
402 [BD]
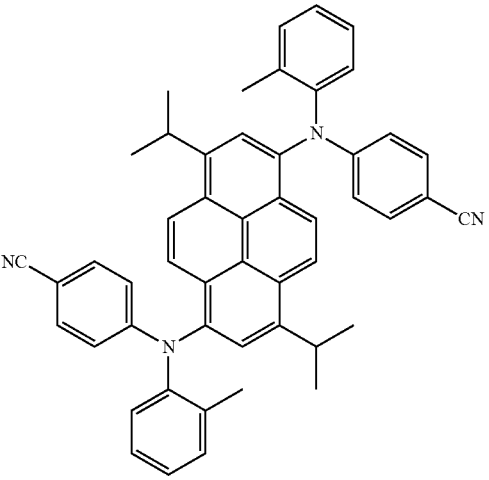
[ET-1-A]
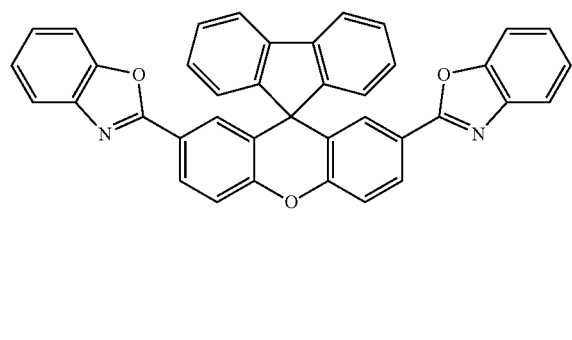
[ET-1-B]
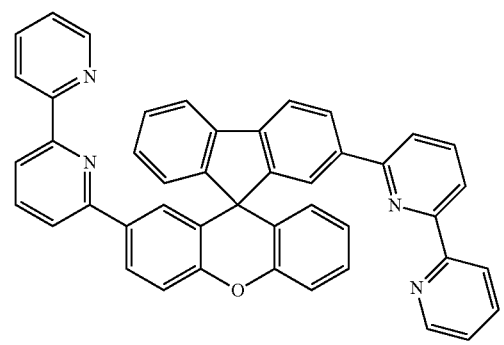
[ET-1-C]
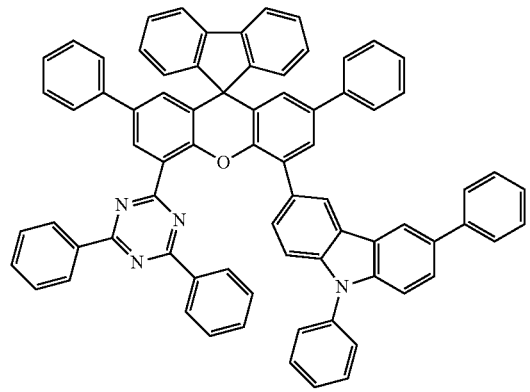
[ET-1-D]
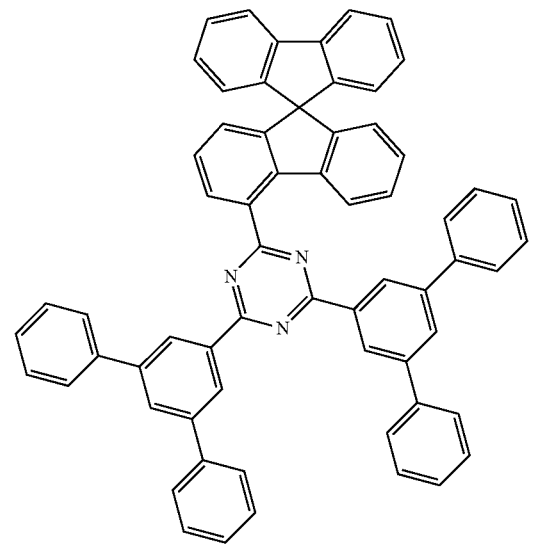

-continued

[ET-1-E]

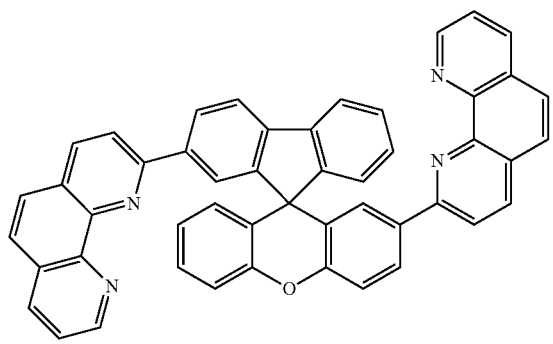

[ET-1-F]

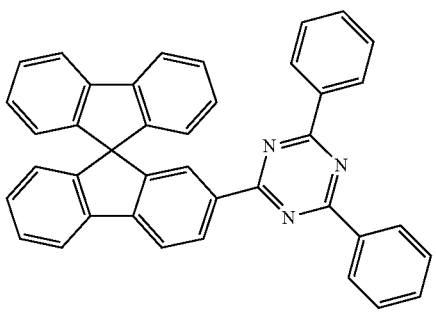

[ET-1-G]

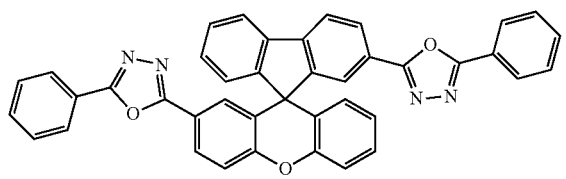

[ET-1-H]

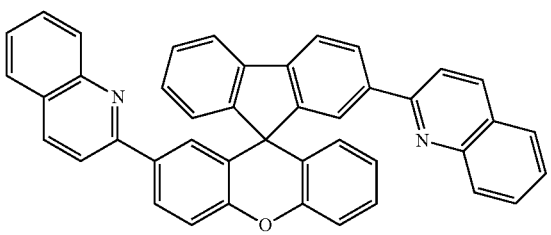

[ET-1-I]

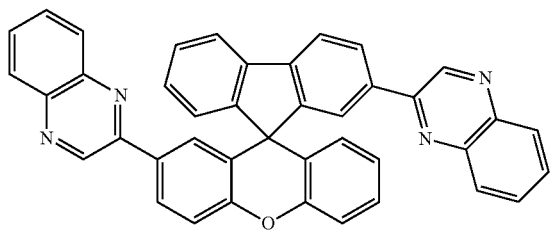

[ET-1-J]

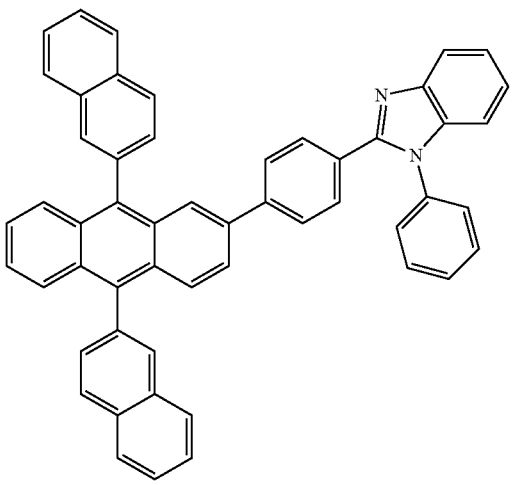

[ET-1-K]

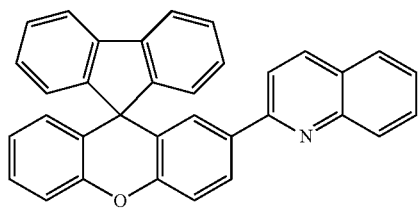

Example 2-2

An organic light emitting device was manufactured in the same manner as in Example 2-1 except that the compound of Chemical Formula E2 was used instead of the compound of Chemical Formula E1.

Example 2-3

An organic light emitting device was manufactured in the same manner as in Example 2-1 except that the compound of Chemical Formula E3 was used instead of the compound of Chemical Formula E1.

Example 2-4

An organic light emitting device was manufactured in the same manner as in Example 2-1 except that the compound of Chemical Formula E4 was used instead of the compound of Chemical Formula E1.

Example 2-5

An organic light emitting device was manufactured in the same manner as in Example 2-1 except that the compound of Chemical Formula E5 was used instead of the compound of Chemical Formula E1.

Example 2-6

An organic light emitting device was manufactured in the same manner as in Example 2-1 except that the compound of Chemical Formula E6 was used instead of the compound of Chemical Formula E1.

Example 2-7

An organic light emitting device was manufactured in the same manner as in Example 2-1 except that the compound of Chemical Formula E7 was used instead of the compound of Chemical Formula E1.

Example 2-8

An organic light emitting device was manufactured in the same manner as in Example 2-1 except that the compound of Chemical Formula E8 was used instead of the compound of Chemical Formula E1.

Example 2-9

An organic light emitting device was manufactured in the same manner as in Example 2-1 except that the compound of Chemical Formula E9 was used instead of the compound of Chemical Formula E1.

Example 2-10

An organic light emitting device was manufactured in the same manner as in Example 2-1 except that the compound of Chemical Formula E10 was used instead of the compound of Chemical Formula E1.

Example 2-11

An organic light emitting device was manufactured in the same manner as in Example 2-1 except that the compound of Chemical Formula E11 was used instead of the compound of Chemical Formula E1.

Example 2-12

An organic light emitting device was manufactured in the same manner as in Example 2-1 except that the compound of Chemical Formula E12 was used instead of the compound of Chemical Formula E1.

Example 2-13

An organic light emitting device was manufactured in the same manner as in Example 2-1 except that the compound of Chemical Formula E13 was used instead of the compound of Chemical Formula E1.

Example 2-14

An organic light emitting device was manufactured in the same manner as in Example 2-1 except that the compound of Chemical Formula E14 was used instead of the compound of Chemical Formula E1.

Example 2-15

An organic light emitting device was manufactured in the same manner as in Example 2-1 except that the compound of Chemical Formula Ely was used instead of the compound of Chemical Formula E1.

Example 2-16

An organic light emitting device was manufactured in the same manner as in Example 2-1 except that the compound of Chemical Formula E16 was used instead of the compound of Chemical Formula E1.

Example 2-17

An organic light emitting device was manufactured in the same manner as in Example 2-1 except that the compound of Chemical Formula E11 was used instead of the compound of Chemical Formula E1.

Example 2-18

An organic light emitting device was manufactured in the same manner as in Example 2-1 except that the compound of Chemical Formula E18 was used instead of the compound of Chemical Formula E1.

Example 2-19

An organic light emitting device was manufactured in the same manner as in Example 2-1 except that the compound of Chemical Formula E19 was used instead of the compound of Chemical Formula E1.

Example 2-20

An organic light emitting device was manufactured in the same manner as in Example 2-1 except that the compound of Chemical Formula E20 was used instead of the compound of Chemical Formula E1.

Example 2-21

An organic light emitting device was manufactured in the same manner as in Example 2-1 except that the compound of Chemical Formula E21 was used instead of the compound of Chemical Formula E1.

Comparative Example 2-1

An organic light emitting device was manufactured in the same manner as in Example 2-1 except that the compound of Chemical Formula ET-1-A was used instead of the compound of Chemical Formula E1.

Comparative Example 2-2

An organic light emitting device was manufactured in the same manner as in Example 2-1 except that the compound of Chemical Formula ET-1-B was used instead of the compound of Chemical Formula E1.

Comparative Example 2-3

An organic light emitting device was manufactured in the same manner as in Example 2-1 except that the compound of Chemical Formula ET-1-C was used instead of the compound of Chemical Formula E1.

Comparative Example 2-4

An organic light emitting device was manufactured in the same manner as in Example 2-1 except that the compound of Chemical Formula ET-1-D was used instead of the compound of Chemical Formula E1.

Comparative Example 2-5

An organic light emitting device was manufactured in the same manner as in Example 2-1 except that the compound of Chemical Formula ET-1-E was used instead of the compound of Chemical Formula E1.

Comparative Example 2-6

An organic light emitting device was manufactured in the same manner as in Example 2-1 except that the compound of Chemical Formula ET-1-F was used instead of the compound of Chemical Formula E1.

Comparative Example 2-7

An organic light emitting device was manufactured in the same manner as in Example 2-1 except that the compound of Chemical Formula ET-1-G was used instead of the compound of Chemical Formula E1.

Comparative Example 2-8

An organic light emitting device was manufactured in the same manner as in Example 2-1 except that the compound of Chemical Formula ET-1-H was used instead of the compound of Chemical Formula E1.

Comparative Example 2-9

An organic light emitting device was manufactured in the same manner as in Example 2-1 except that the compound of Chemical Formula ET-1-I was used instead of the compound of Chemical Formula E1.

Comparative Example 2-10

An organic light emitting device was manufactured in the same manner as in Example 2-1 except that the compound of Chemical Formula ET-1-J was used instead of the compound of Chemical Formula E1.

Comparative Example 2-11

An organic light emitting device was manufactured in the same manner as in Example 2-1 except that the compound of Chemical Formula ET-1-K was used instead of the compound of Chemical Formula E1.

For the organic light emitting devices manufactured using the methods of Examples 2-1 to 2-21 and Comparative Examples 2-1 to 2-11 described above, a driving voltage and light emission efficiency were measured at current density of 10 mA/cm$^2$, and time taken for the luminance decreasing to 90% compared to its initial luminance ($T_H$) was measured at current density of 20 mA/cm$^2$. The results are shown in the following Table 2.

TABLE 2

| | Chemical Formula | Voltage (V@10 mA/cm$^2$) | Efficiency (cd/A@10 mA/cm$^2$) | Color Coordinate (x, y) | Lifespan (h) $T_{90}$ at 20 mA/cm$^2$ |
|---|---|---|---|---|---|
| Example 2-1 | E1 | 4.20 | 5.60 | (0.142, 0.097) | 230 |
| Example 2-2 | E2 | 4.19 | 5.69 | (0.142, 0.096) | 222 |
| Example 2-3 | E3 | 4.26 | 5.58 | (0.142, 0.096) | 260 |
| Example 2-4 | E4 | 4.30 | 5.09 | (0.142, 0.096) | 159 |
| Example 2-5 | E5 | 4.24 | 5.50 | (0.142, 0.096) | 232 |
| Example 2-6 | E6 | 4.29 | 5.47 | (0.142, 0.097) | 244 |
| Example 2-7 | E7 | 4.44 | 5.07 | (0.142, 0.096) | 150 |
| Example 2-8 | E8 | 4.18 | 5.68 | (0.142, 0.099) | 211 |
| Example 2-9 | E9 | 4.32 | 5.00 | (0.142, 0.096) | 149 |
| Example 2-10 | E10 | 4.27 | 5.51 | (0.142, 0.098) | 219 |
| Example 2-11 | E11 | 4.29 | 5.48 | (0.142, 0.097) | 217 |
| Example 2-12 | E12 | 4.18 | 5.53 | (0.142, 0.096) | 251 |
| Example 2-13 | E13 | 4.20 | 5.57 | (0.142, 0.097) | 220 |
| Example 2-14 | E14 | 4.30 | 5.47 | (0.142, 0.097) | 246 |
| Example 2-15 | E15 | 4.16 | 5.70 | (0.142, 0.097) | 219 |
| Example 2-16 | E16 | 4.36 | 4.98 | (0.142, 0.097) | 146 |
| Example 2-17 | E17 | 4.34 | 4.98 | (0.142, 0.097) | 130 |
| Example 2-18 | E18 | 4.36 | 4.96 | (0.142, 0.096) | 132 |
| Example 2-19 | E19 | 4.24 | 5.50 | (0.142, 0.096) | 249 |
| Example 2-20 | E20 | 4.38 | 4.96 | (0.142, 0.096) | 144 |
| Example 2-21 | E21 | 4.37 | 4.95 | (0.142, 0.096) | 133 |
| Comparative Example 2-1 | ET-1-A | 4.80 | 3.89 | (0.142, 0.098) | 80 |
| Comparative Example 2-2 | ET-1-B | 4.87 | 4.00 | (0.142, 0.102) | 76 |
| Comparative Example 2-3 | ET-1-C | 4.98 | 3.81 | (0.142, 0.096) | 82 |
| Comparative Example 2-4 | ET-1-D | 4.73 | 4.07 | (0.142, 0.096) | 57 |
| Comparative Example 2-5 | ET-1-E | 5.02 | 3.58 | (0.142, 0.096) | 69 |
| Comparative Example 2-6 | ET-1-F | 5.11 | 3.44 | (0.142, 0.096) | 72 |
| Comparative Example 2-7 | ET-1-G | 5.42 | 3.07 | (0.142, 0.096) | 54 |
| Comparative Example 2-8 | ET-1-H | 5.46 | 3.11 | (0.142, 0.096) | 50 |
| Comparative Example 2-9 | ET-1-I | 5.57 | 3.06 | (0.142, 0.096) | 55 |

TABLE 2-continued

| | Chemical Formula | Voltage (V@10 mA/cm$^2$) | Efficiency (cd/A@10 mA/cm$^2$) | Color Coordinate (x, y) | Lifespan (h) T$_{90}$ at 20 mA/cm$^2$ |
|---|---|---|---|---|---|
| Comparative Example 2-10 | ET-1-J | 5.47 | 3.99 | (0.142, 0.096) | 78 |
| Comparative Example 2-11 | ET-1-K | 5.00 | 4.14 | (0.142, 0.097) | 95 |

From the results of Table 2, it was identified that the hetero-cyclic compound represented by Chemical Formula 1 according to one embodiment of the present specification was able to be used in an electron control layer of an organic light emitting device.

Specifically, when comparing Examples 2-1 to 2-21 with Comparative Examples 2-1, 2-2, 2-3, 2-5, 2-7, 2-8 and 2-9, it was identified that the compound in which only one heteroaryl group substitutes in the spiro fluorene xanthen skeleton as in Chemical Formula 1 had excellent properties in terms of driving voltage, efficiency and lifespan in an organic light emitting device compared to the compound having two or more substituents in the spiro fluorene xanthen skeleton.

When referring to FIG. 10 and FIG. 11 showing 3D structures of Compounds E9 and E18 according to one embodiment of the present specification, it was identified that the molecules of the compounds had a horizontal structure, and when referring to FIG. 12 and FIG. 13 showing 3D structures of Compounds ET-1-E and ET-1-I, the A axis and the B axis were almost perpendicular to each other in each compound identifying that the molecule was very out of a horizontal structure.

As a result, when comparing FIG. 10 and FIG. 11 showing 3D structures of Compounds E9 and E18 according to one embodiment of the present specification and FIG. 12 and FIG. 13 showing 3D structures of Compounds ET-1-E and ET-1-I, it was seen that the hetero-cyclic compound according to one embodiment of the present specification had a more horizontal structure due to a difference in orientation in the molecular 3D structure. Accordingly, the compound in which only one heteroaryl group substitutes in the spiro fluorene xanthen skeleton as in Chemical Formula 1 of Examples 2-1 to 2-21 had a strong tendency toward a horizontal structure of the molecule compared to the compound having two or more substituents in the spiro fluorene xanthen resulting in an increase in the electron mobility, and effects of low driving voltage, high efficiency and long lifespan are obtained in an organic light emitting device.

In addition, when comparing Examples 2-1 to 2-21 with Comparative Examples 2-4 and 2-6, it was identified that the structure of Chemical Formula 1 comprising spiro fluorene xanthen exhibited excellent properties in an organic light emitting device compared to the structure comprising a spiro fluorene group.

Furthermore, when comparing Examples 2-16 and 2-20 with Comparative Example 2-11, it was identified that the structure of Chemical Formula 1 comprising spiro fluorene xanthen exhibited excellent properties in an organic light emitting device compared to the structure comprising N of isoquinoline in a different position in the spiro fluorene xanthen.

The hetero-cyclic compound represented by Chemical Formula 1 according to one embodiment of the present specification is capable of having excellent properties by having excellent thermal stability, a deep HOMO level of 6.0 eV or higher, high triplet energy (ET) and hole stability.

Particularly, in Examples 2-1, 2-2, 2-5, 2-8, 2-11, 2-12, 2-14 and 2-15, that is, when Ar1 is a triazine group or a pyrimidine group in Chemical Formula 1, a role of, particularly, a hole blocking layer (electron control layer) was smoothly carried out with deep HOMO energy of 6.1 eV or higher, and electron mobility was high, and excellent properties may be exhibited in terms of driving voltage, efficiency and lifespan when used in an organic light emitting device. Specifically, in Examples 2-1, 2-2, 2-5, 2-8, 2-11, 2-12, 2-14 and 2-15, it was identified that significantly superior properties were obtained in terms of driving voltage, efficiency and lifespan compared to Example 2-21 in which Ar1 is a pyridine group (one N).

In one embodiment of the present specification, the hetero-cyclic compound represented by Chemical Formula 1 is capable of being used in an electron control layer.

Accordingly, the hetero-cyclic compound represented by Chemical Formula 1 according to one embodiment of the present specification has low driving voltage and high efficiency, and is capable of enhancing device stability by hole stability of the compound.

Example 3

HOMO energy and LUMO energy values of compounds represented by the following Chemical Formula E1 and Chemical Formula E2 corresponding to the hetero-cyclic compound represented by Chemical Formula 1 according to one embodiment of the present specification are shown in the following Table 3.

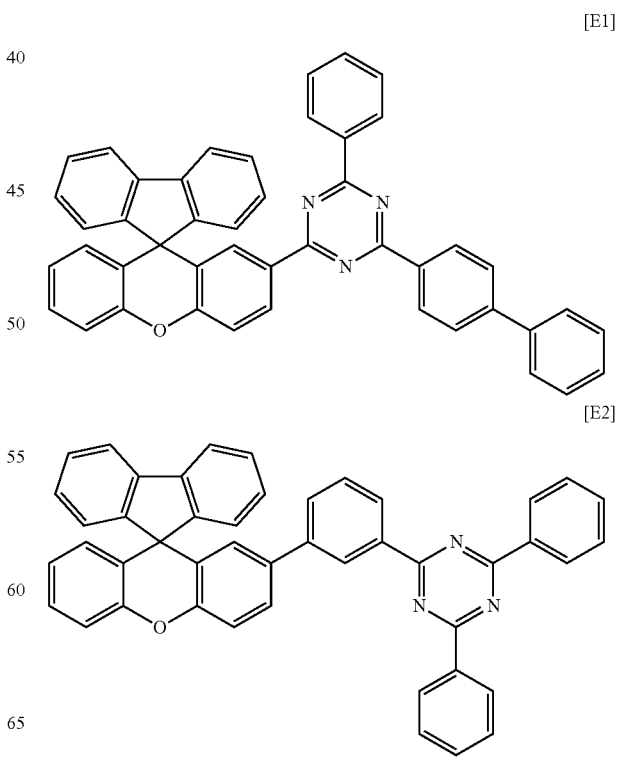

-continued

[ET-1-J]

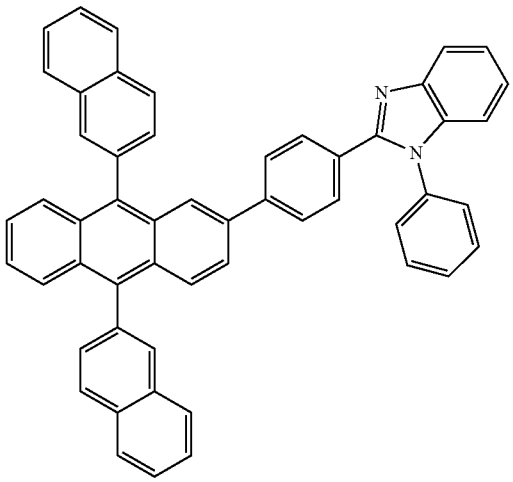

In the examples of the present specification, the HOMO level was measured using a photoelectron spectrometer (manufactured by RIKEN KEIKI Co., Ltd.: AC3) under atmospheric air.

In the examples of the present specification, the LUMO level was calculated as a wavelength value measured through photoluminescence (PL).

TABLE 3

| Chemical Formula | HOMO (eV) | LUMO (eV) |
| --- | --- | --- |
| E1 | 6.20 | 2.70 |
| E2 | 6.16 | 2.92 |
| ET-1-J | 5.70 | 2.87 |

The invention claimed is:
1. A hetero-cyclic compound represented by the following Chemical Formula 1:

[Chemical Formula 1]

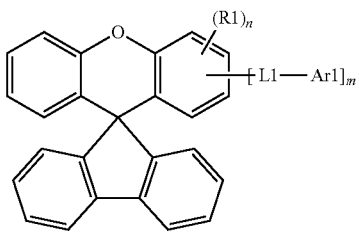

wherein, in Chemical Formula 1,
R1 is deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group;

L1 is a direct bond; a substituted or unsubstituted arylene group; or a substituted or unsubstituted heteroarylene group;

Ar1 is a structure represented by the following Chemical Formulae 4 to 8, 10 and 11;

m is an integer of 1 to 4;

n is an integer of 0;

1≤n+m≤4;

when m is each 2 or greater, each of L1-Ar1 is the same as or different from each other,

[Chemical Formula 4]

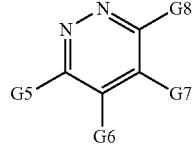

in Chemical Formula 4,
any one of G5 to G8 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 5]

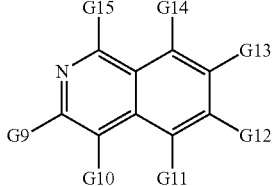

in Chemical Formula 5,
any one of G9 to G15 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 6]

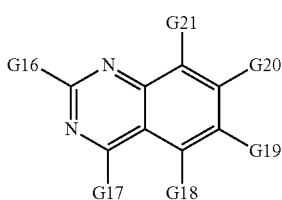

in Chemical Formula 6,
any one of G16 to G21 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 7]

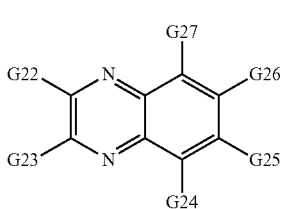

in Chemical Formula 7,
any one of G22 to G27 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 8]

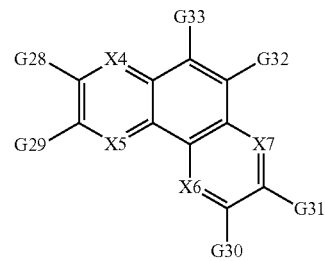

in Chemical Formula 8,
X4 is N or CR14, X5 is N or CR15, X6 is N or CR16 and X7 is N or CR17;
at least one of X4 to X7 is N; and
any one of G28 to G33 and R14 to R17 is a site bonding to L1 of Chemical Formula 1, and the rest are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 10]

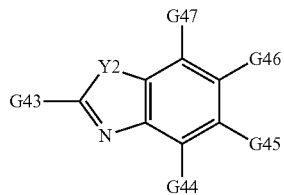

in Chemical Formula 10,
Y2 is O, or S; and
any one of G43 to G47 is a site bonding to L1 of Chemical Formula 1, and the rest and Q4 to Q6 are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted ring,

[Chemical Formula 11]

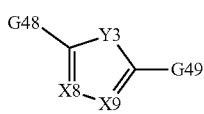

in Chemical Formula 11,
Y3 is O, S or NQ7;
X8 is N or CR18 and X9 is N or CR19; and
any one of G48, G49, R18 and R19 is a site bonding to L1 of Chemical Formula 1, and the rest and Q7 are the same as or different from each other and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,
with the proviso that when R1, L1 and/or Ar1 contain a carbazolyl group, the carbazolyl group is not substituted with a nitrile group.

2. The hetero-cyclic compound of claim 1, wherein Chemical Formula 1 is represented by any one of the following Chemical Formulae 1-1 to 1-4:

[Chemical Formula 1-1]

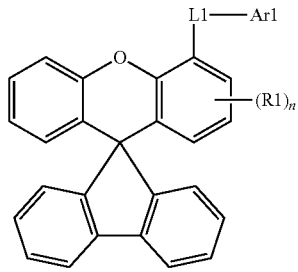

[Chemical Formula 1-2]

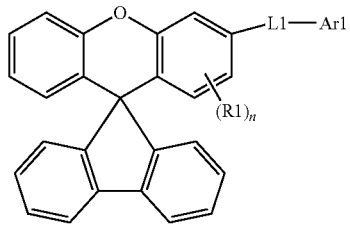

[Chemical Formula 1-3]

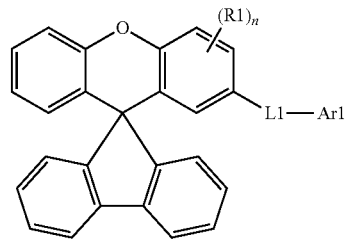

[Chemical Formula 1-4]

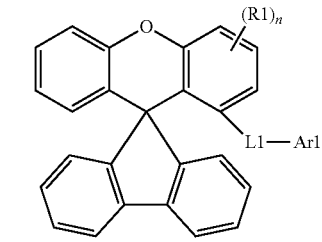

wherein, in Chemical Formulae 1-1 to 1-4,
definitions of L1, Ar1, R1 and n are the same as in Chemical Formula 1.

3. The hetero-cyclic compound of claim 1, wherein Chemical Formula 1 is selected as any one of the following compounds:

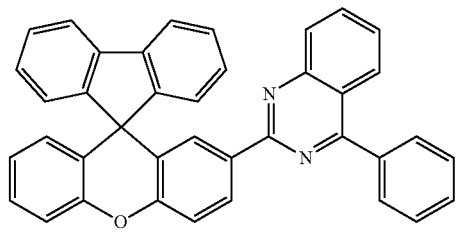

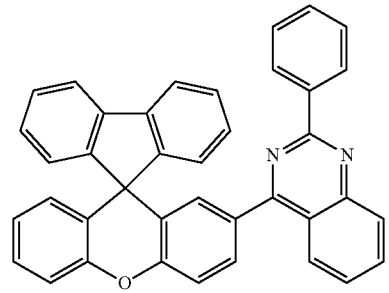

417
-continued
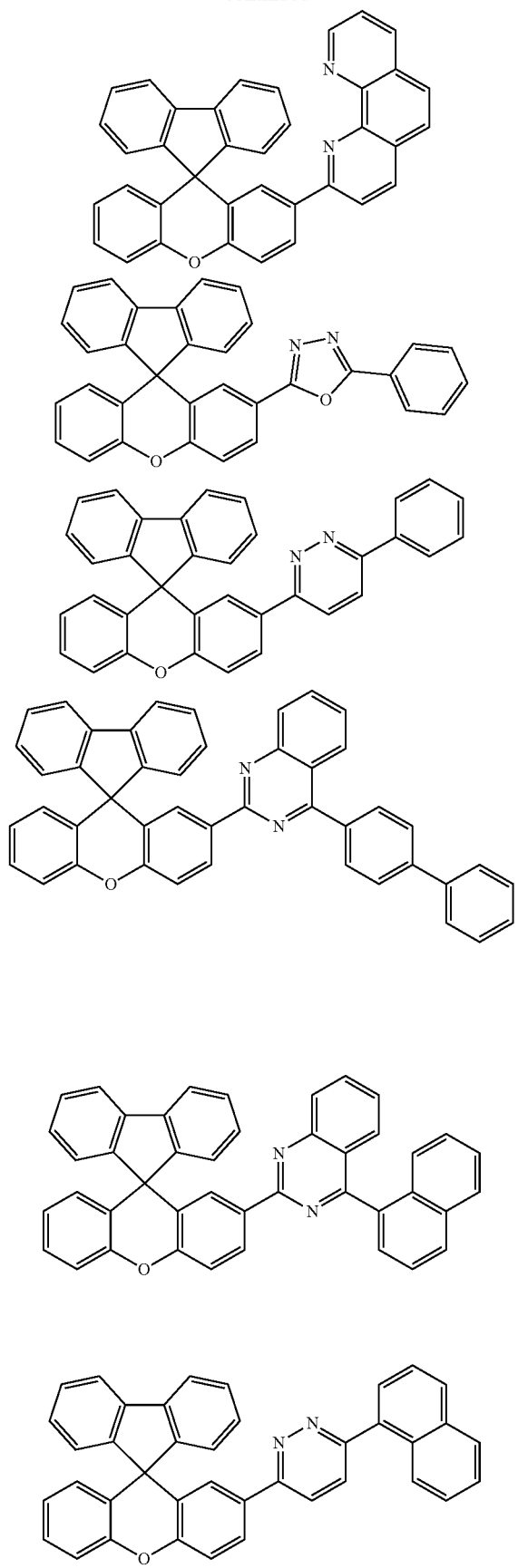
418
-continued
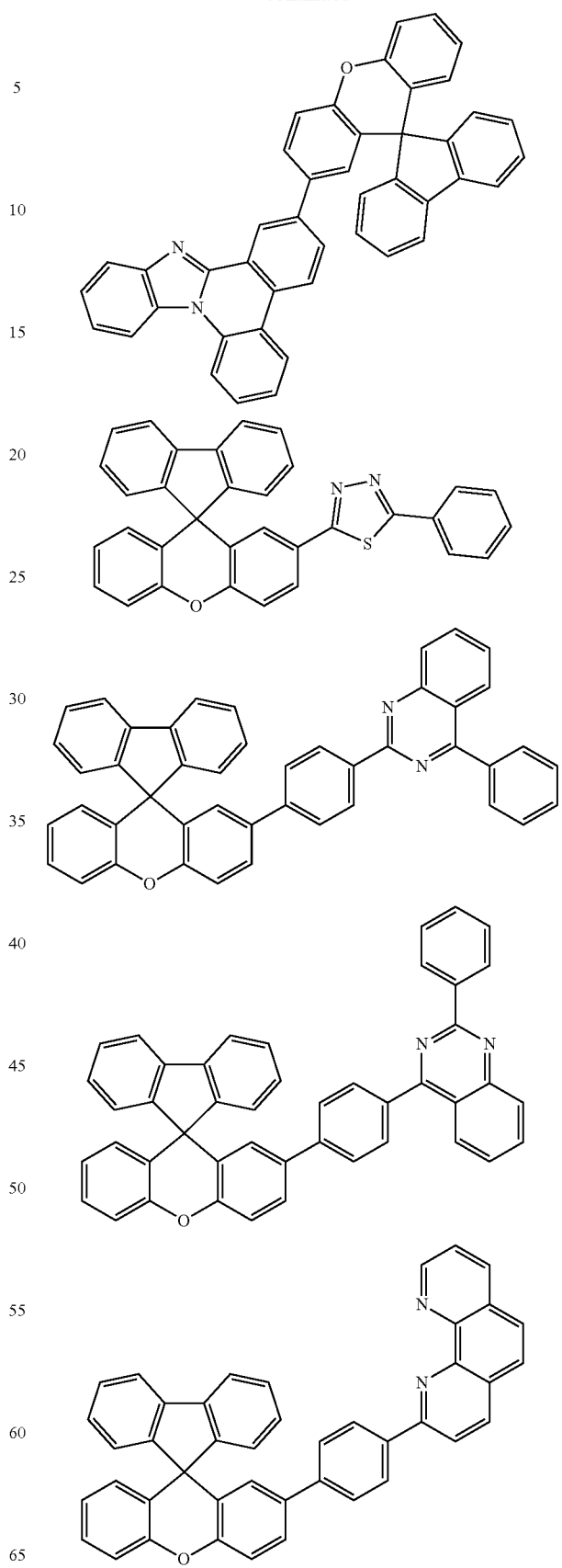

419
-continued
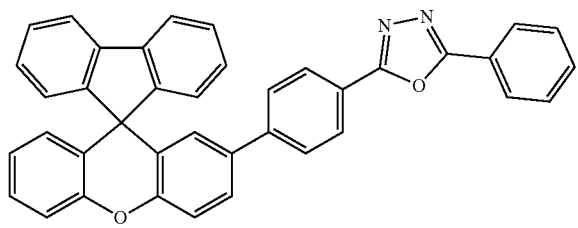
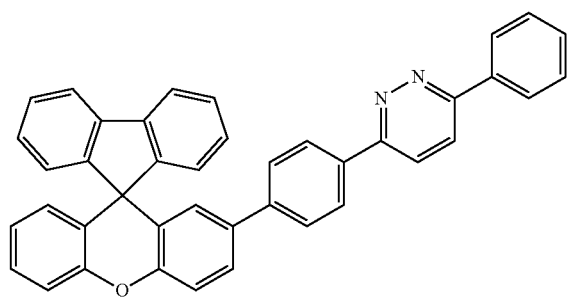
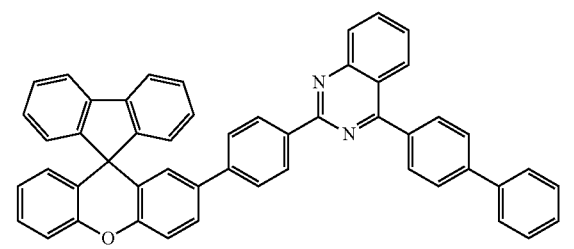
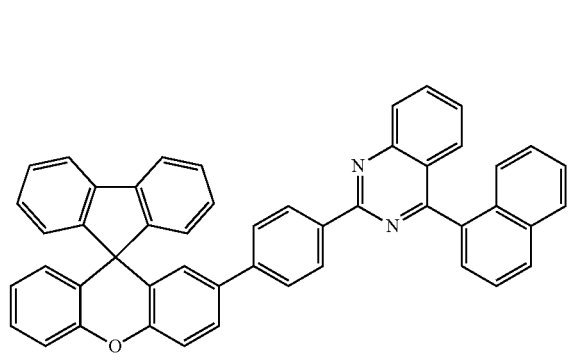
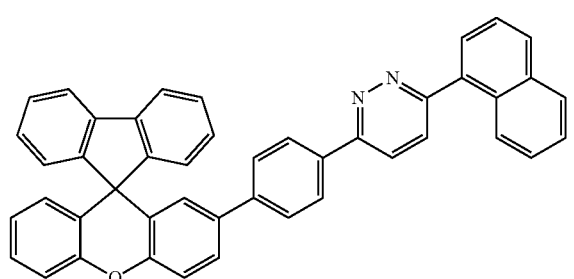
420
-continued
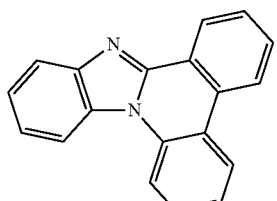
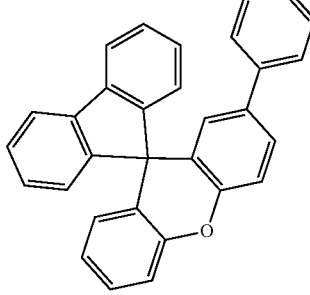
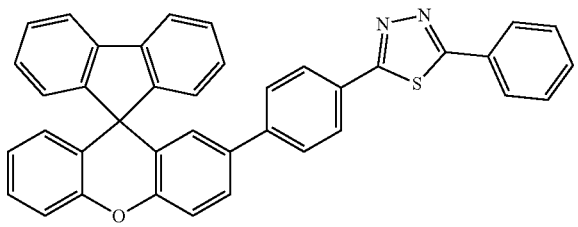
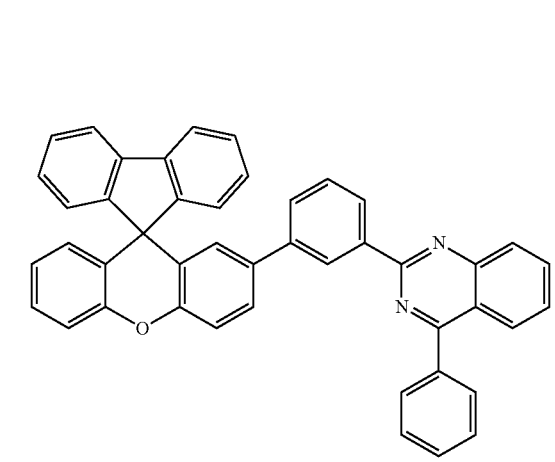
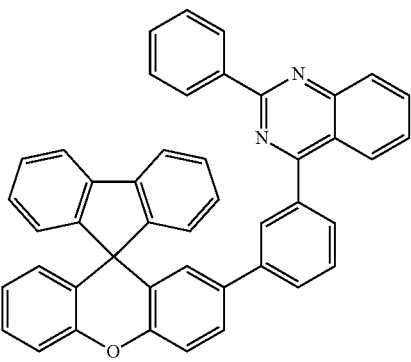

421
-continued
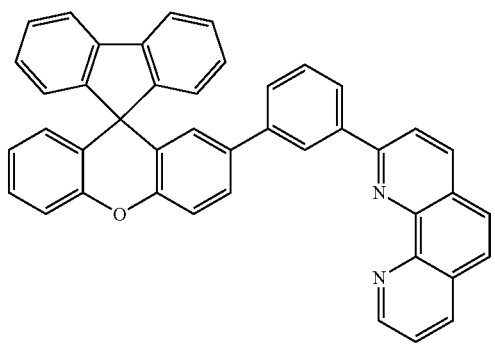
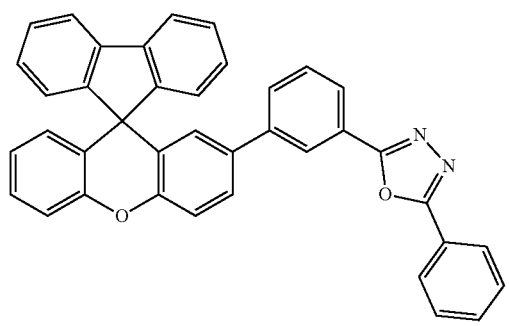
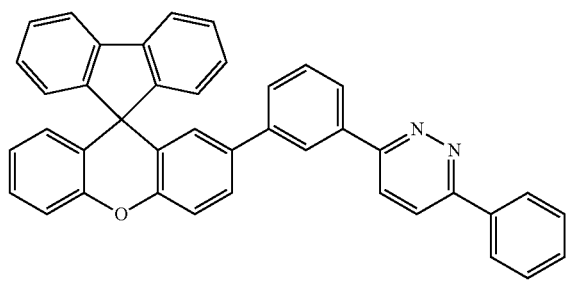
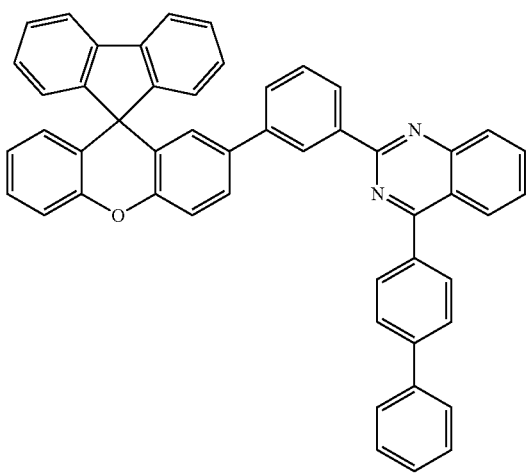
422
-continued
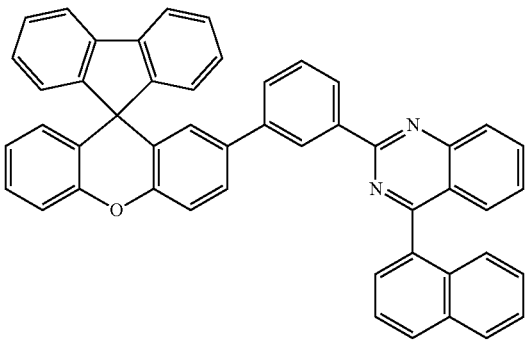
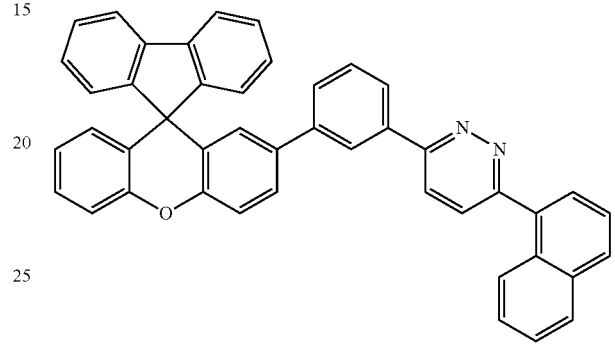
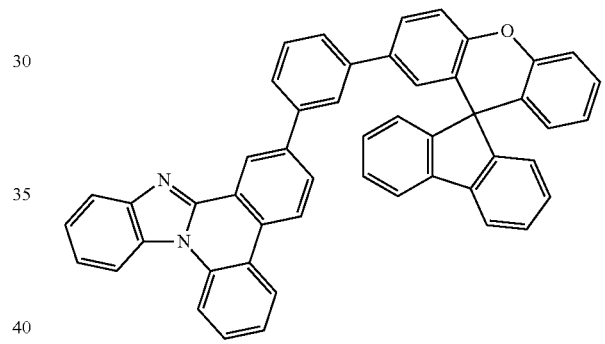
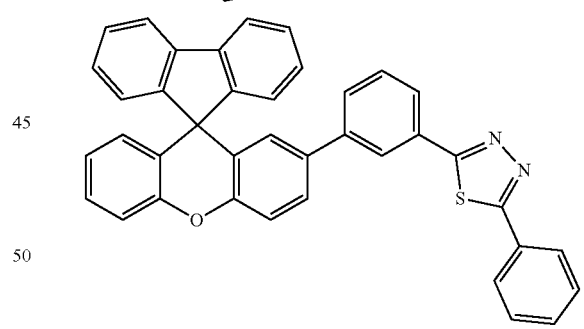
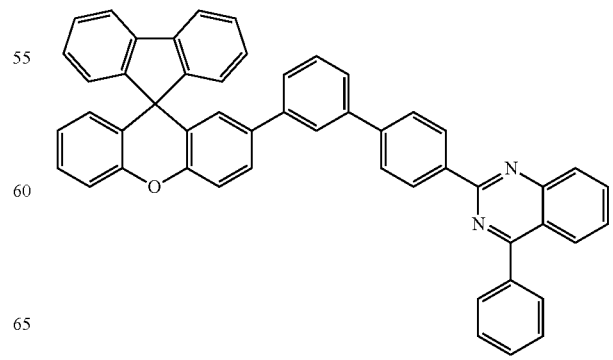

423
-continued
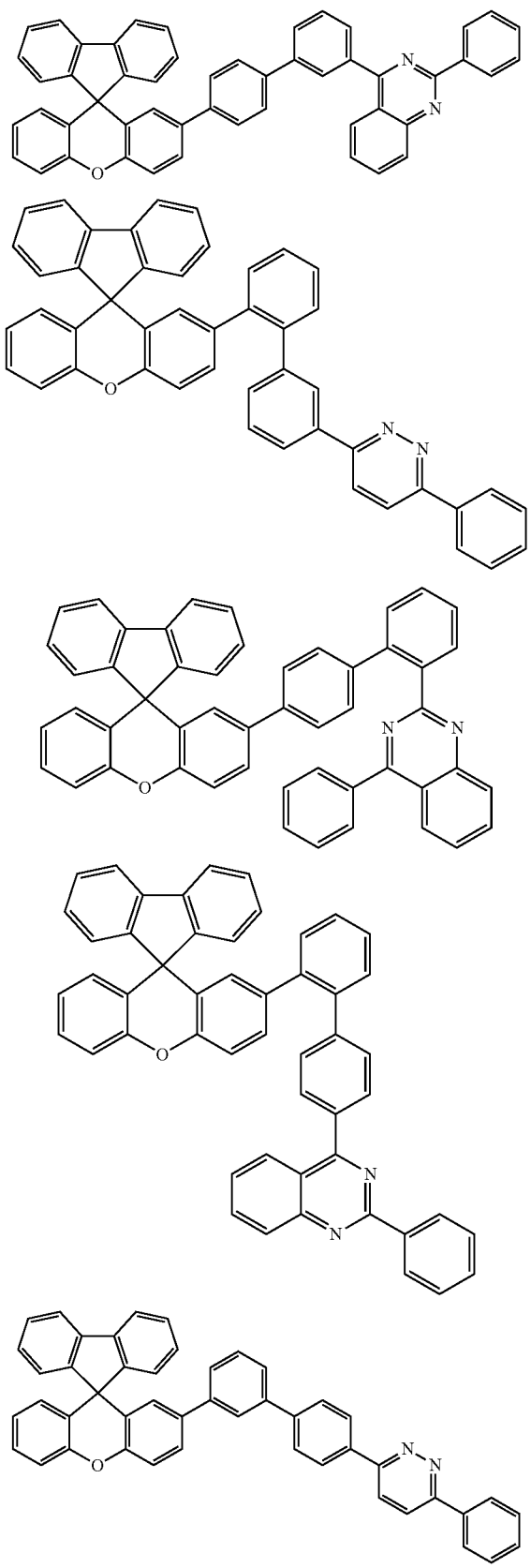
424
-continued
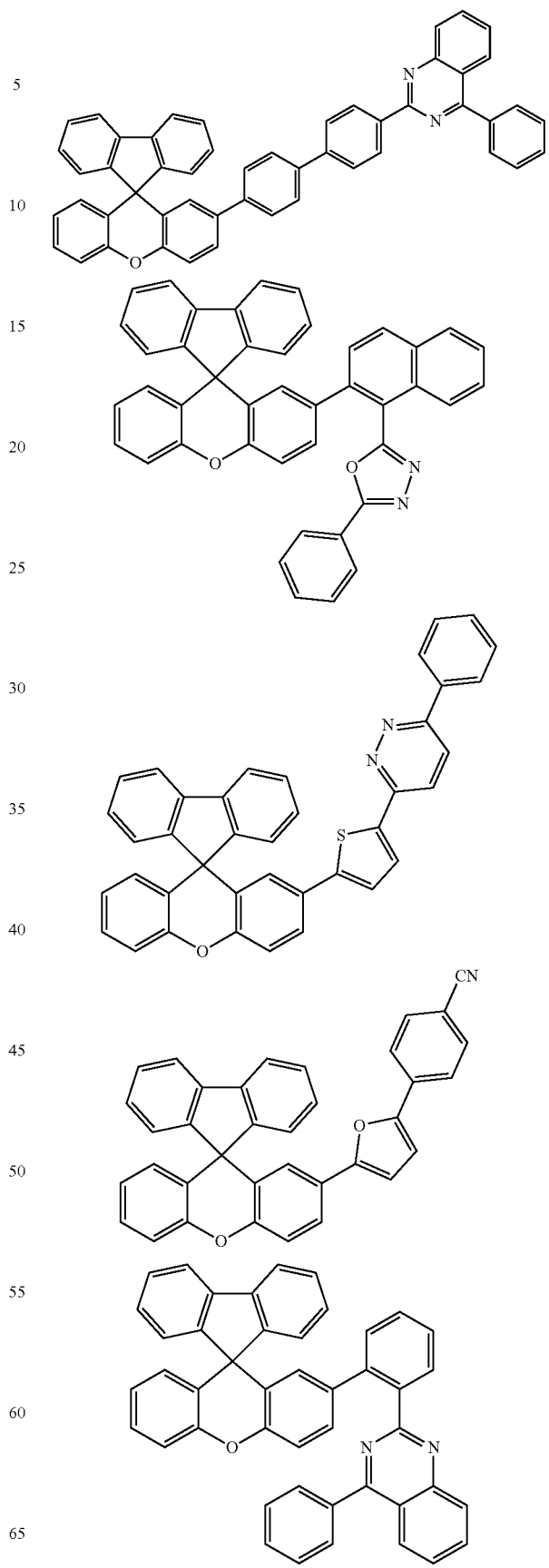

425
-continued
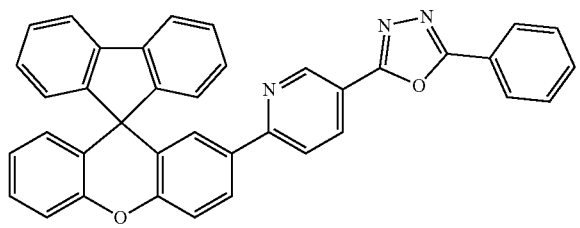
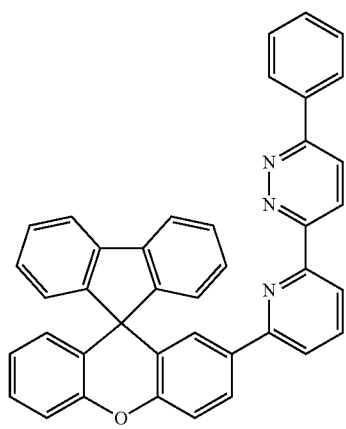
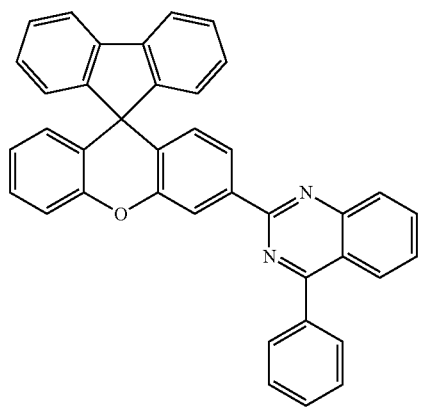
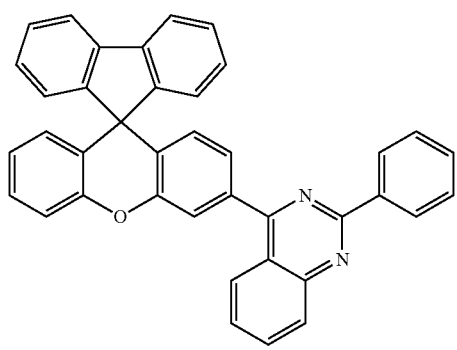
426
-continued
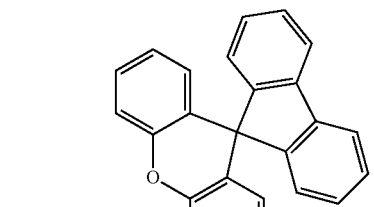
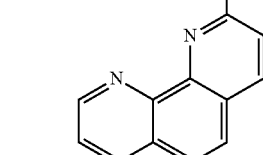
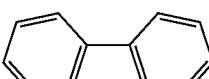
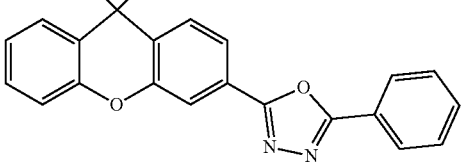
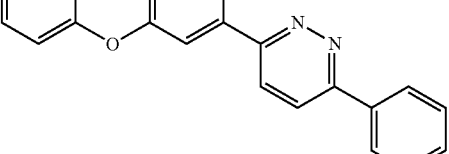
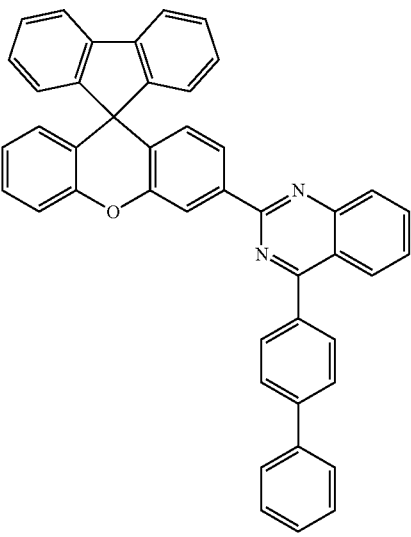

427
-continued
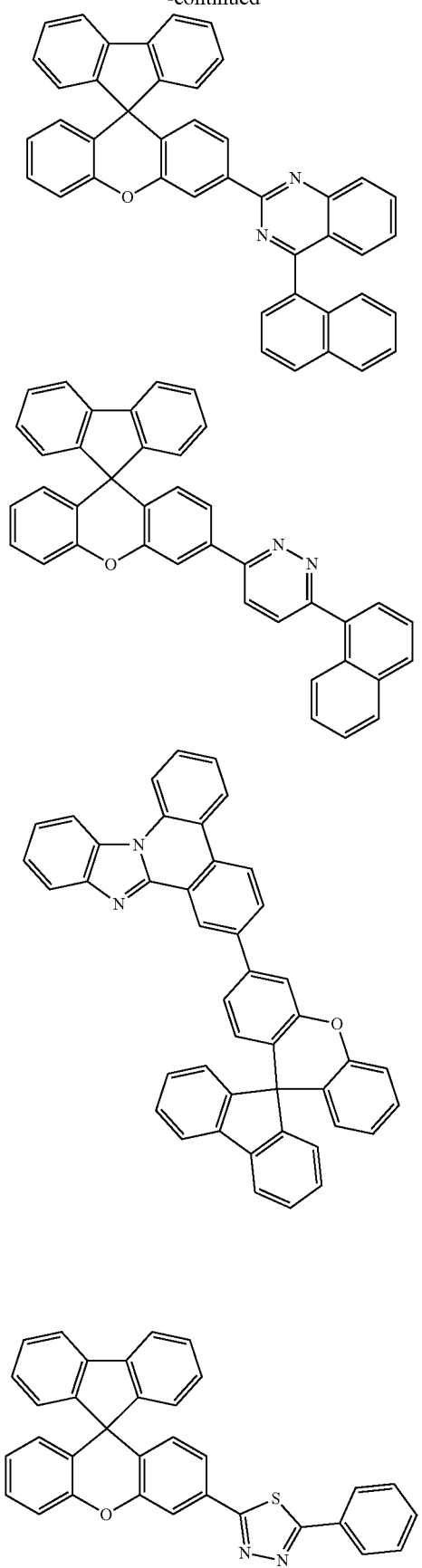
428
-continued
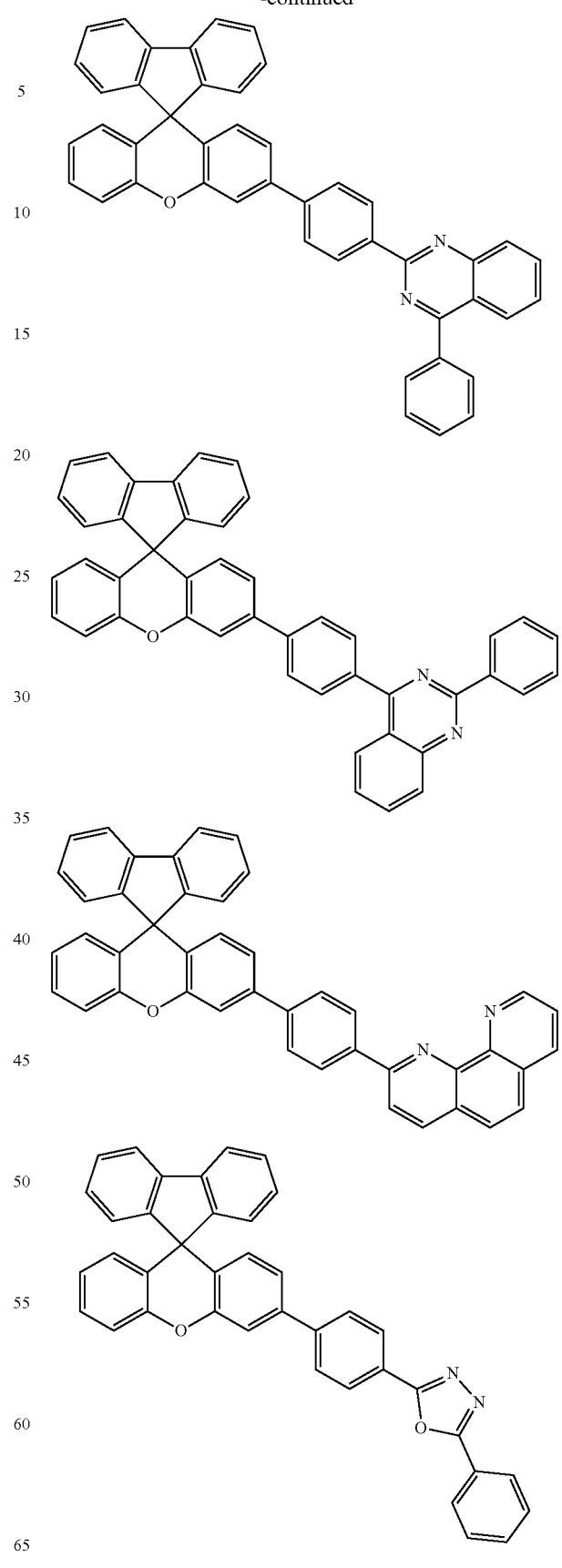

429
-continued
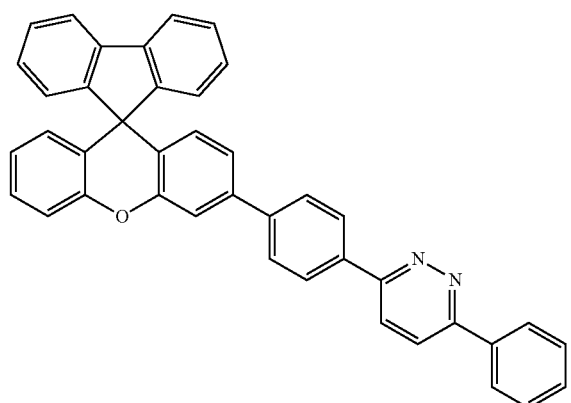
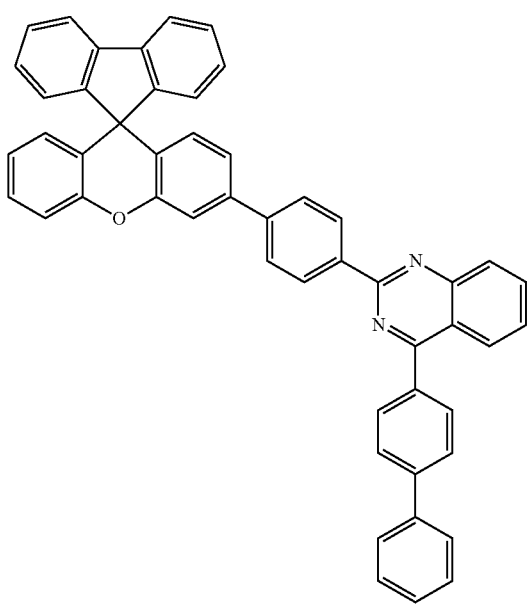
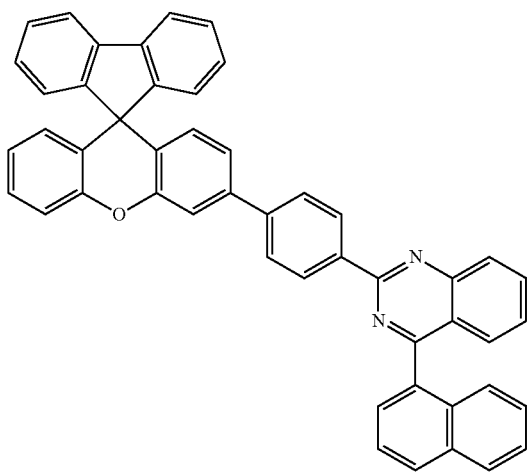
430
-continued
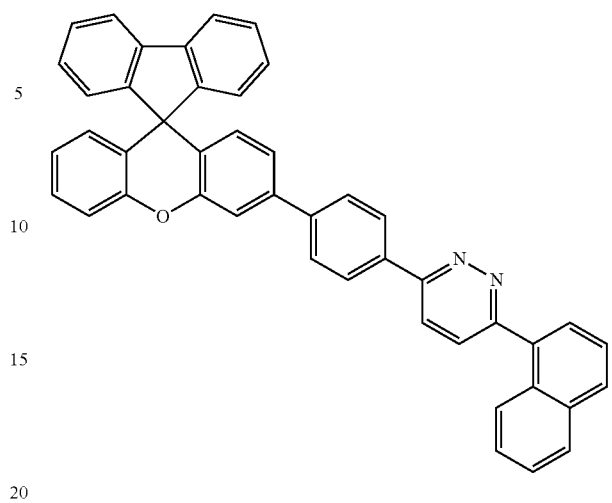
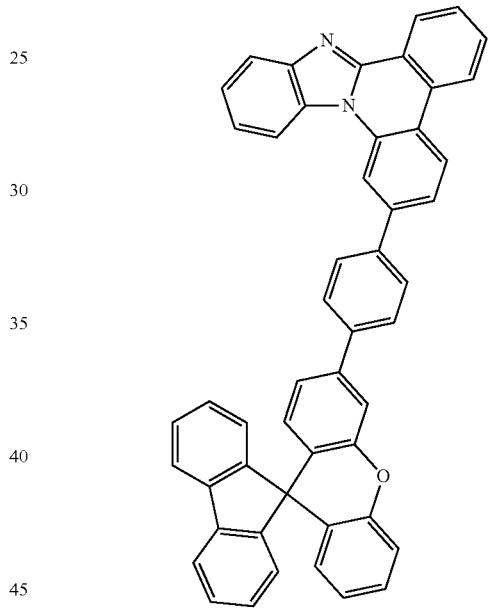
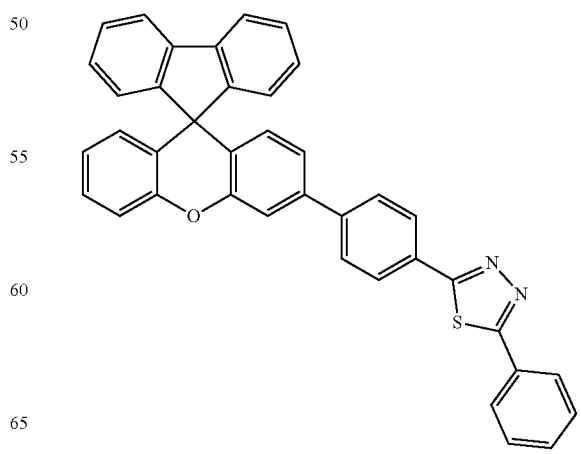

431
-continued
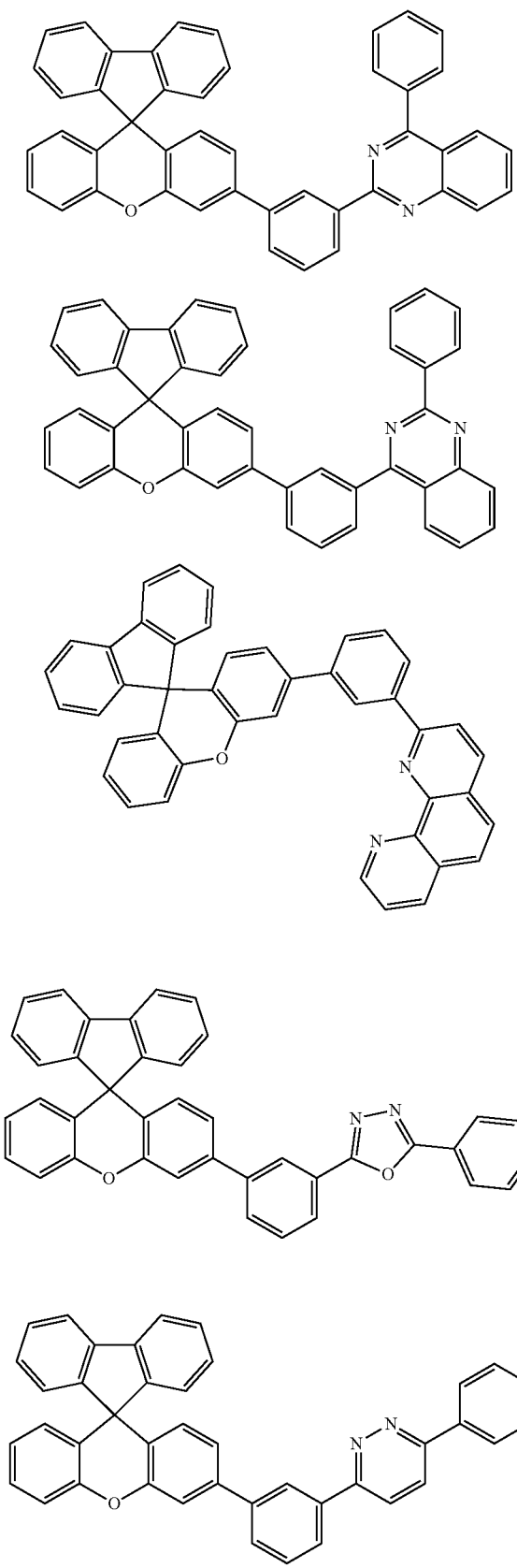
432
-continued
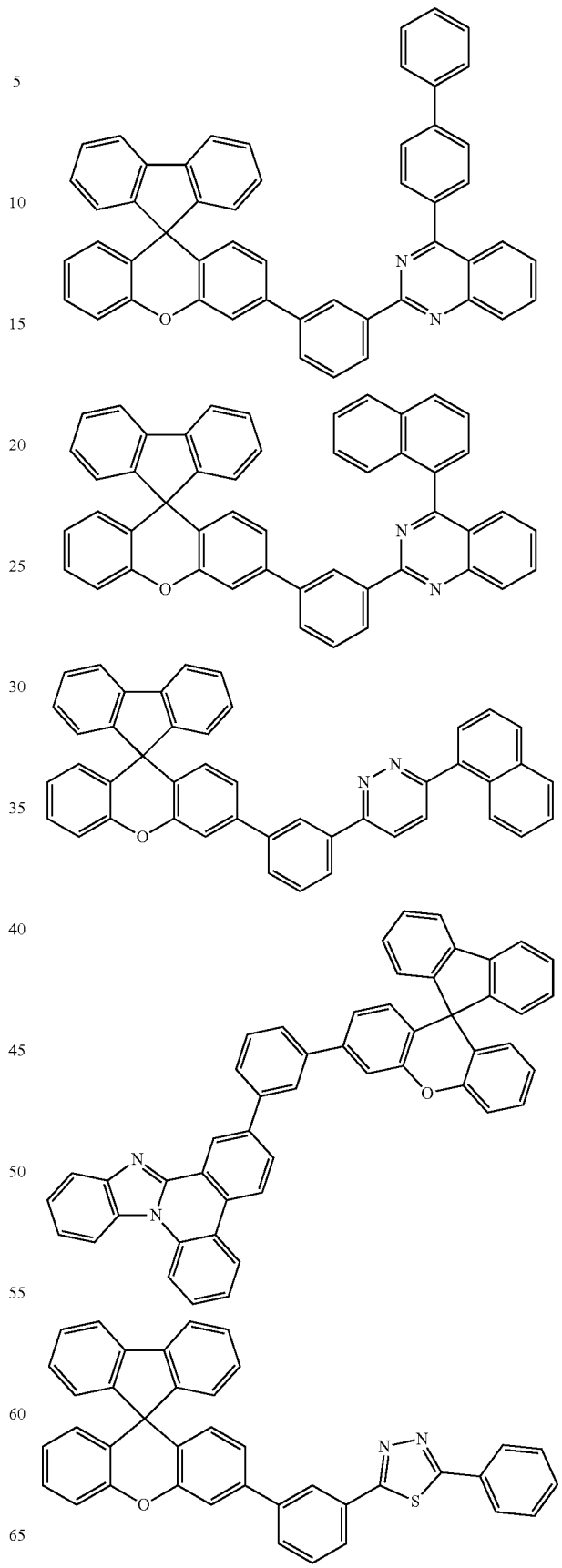

433
-continued
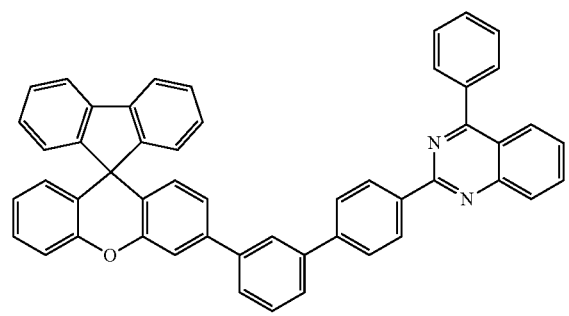
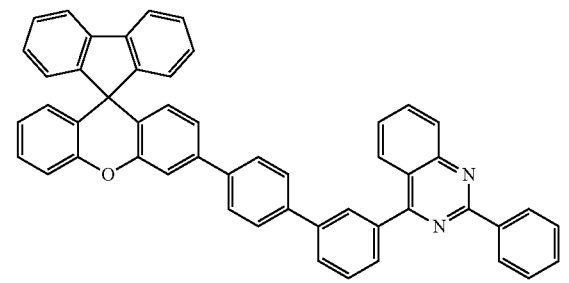
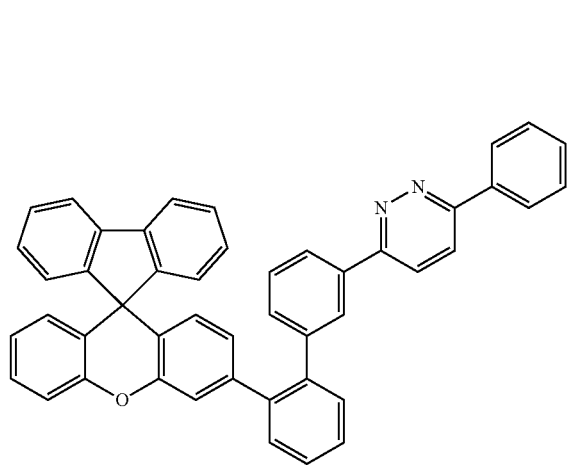
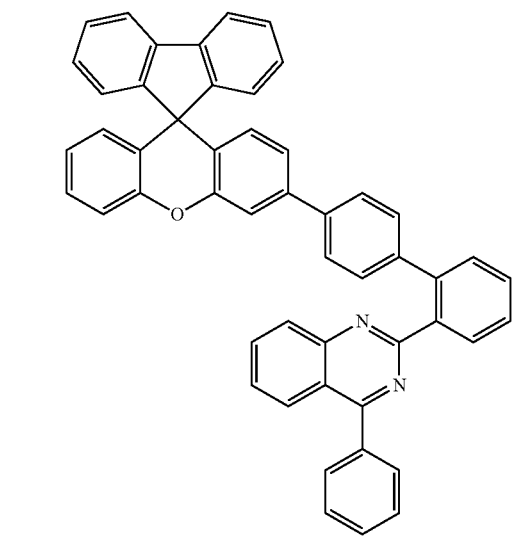
434
-continued
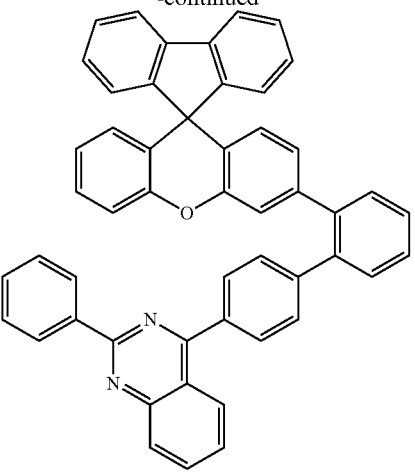
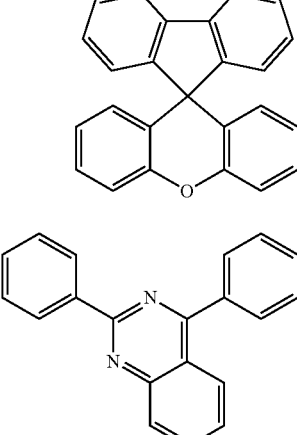
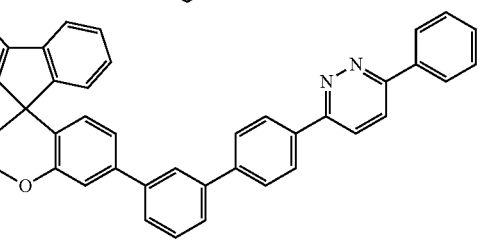
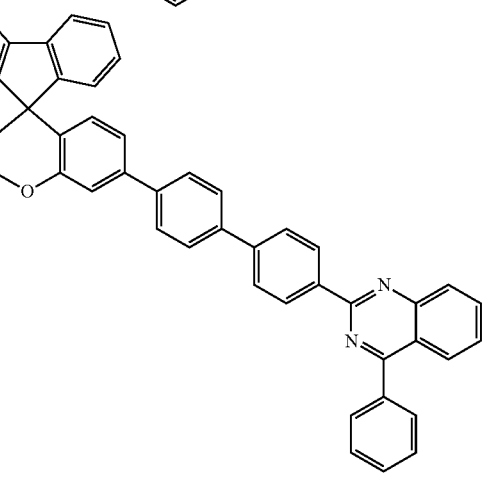
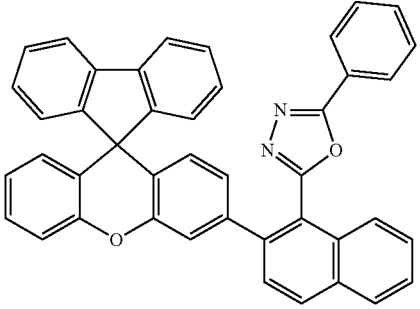
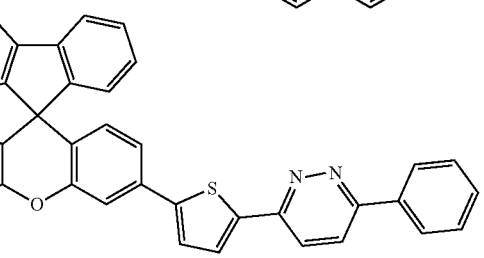

435
-continued
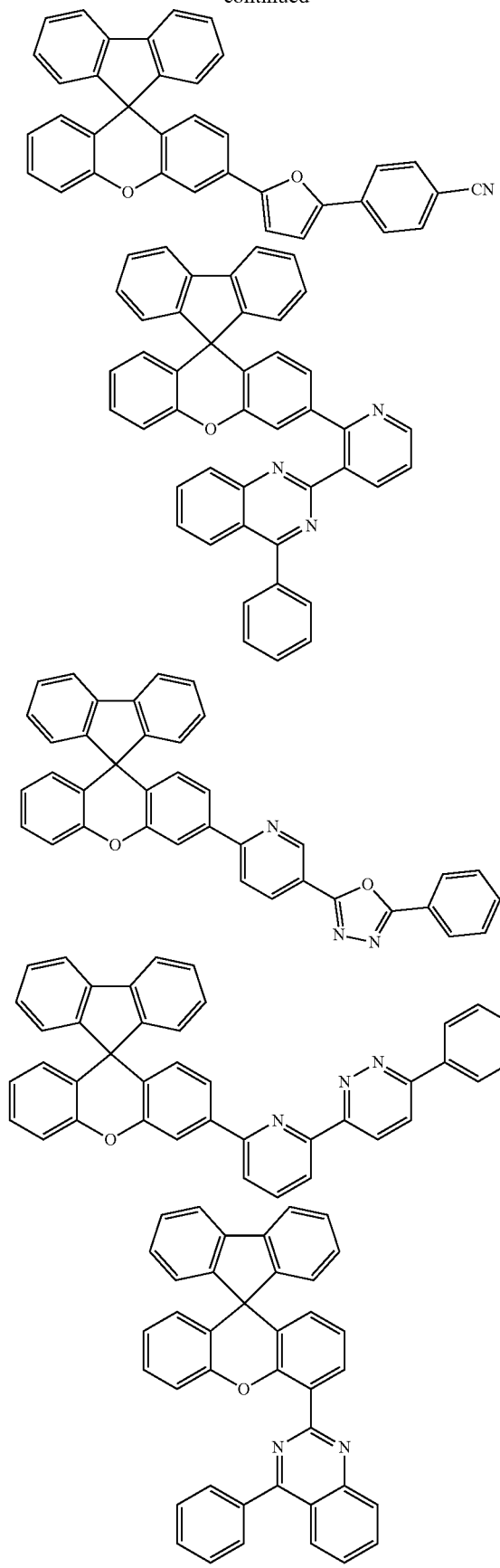
436
-continued
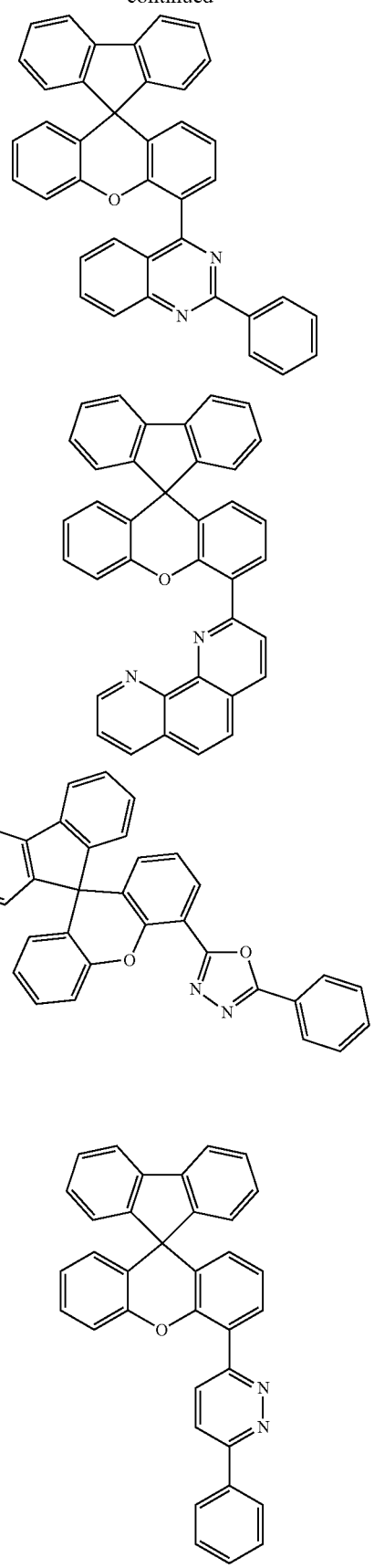

437
-continued
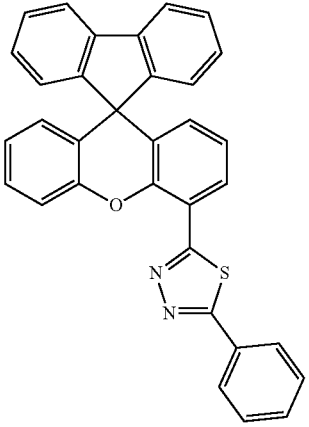
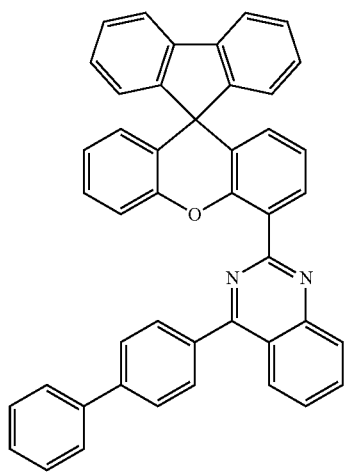
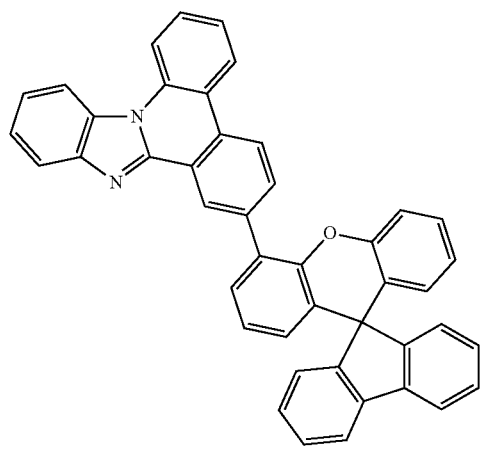
438
-continued
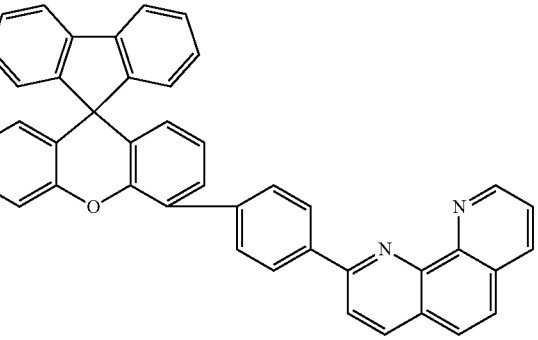
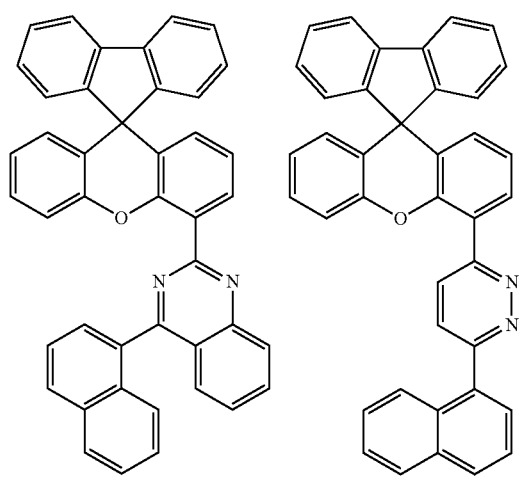

439
-continued
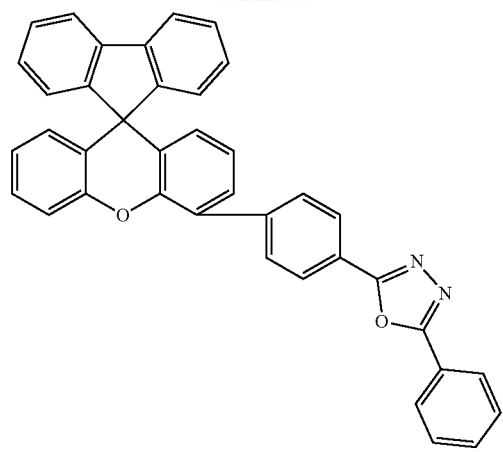
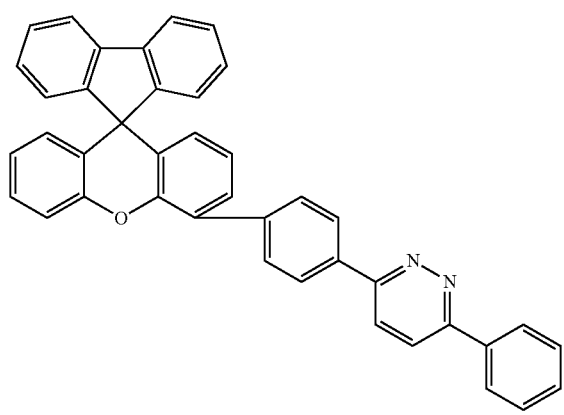
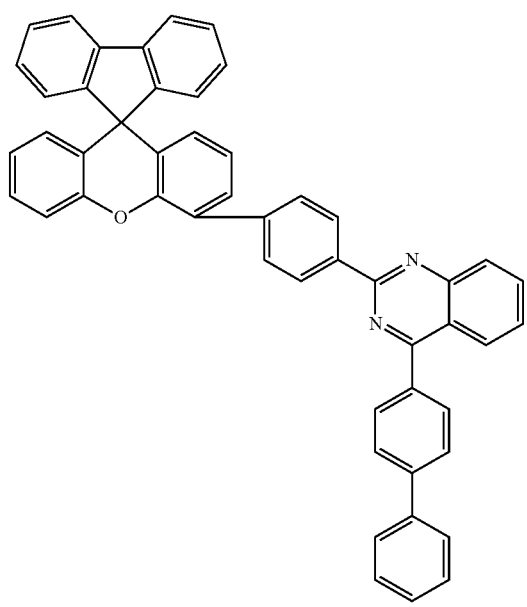
440
-continued
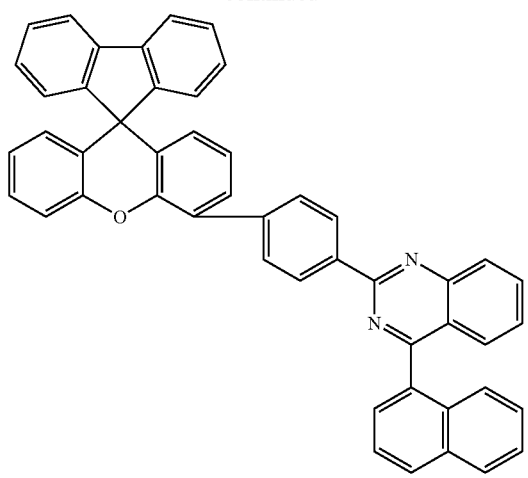
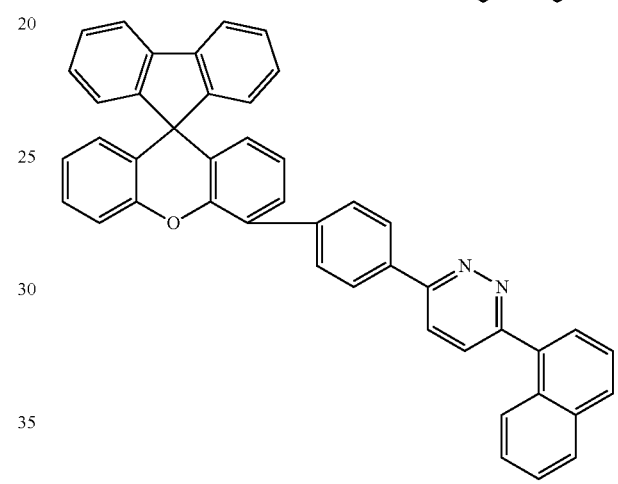
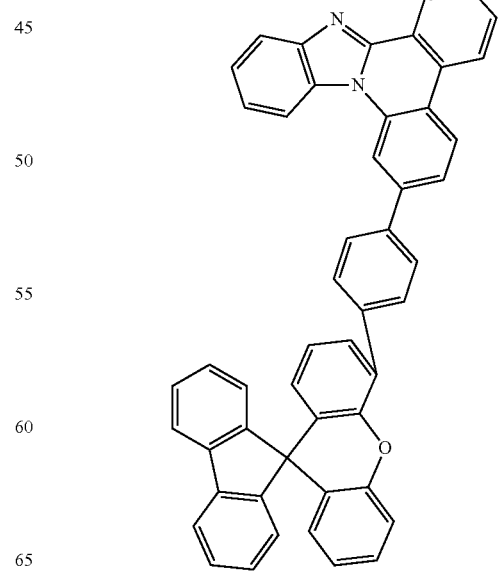

441
-continued
442
-continued
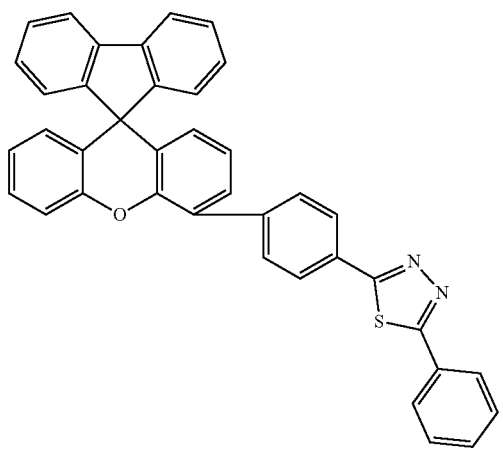
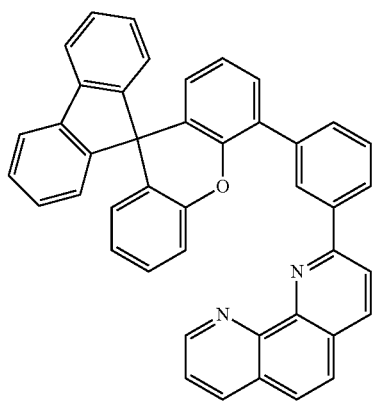
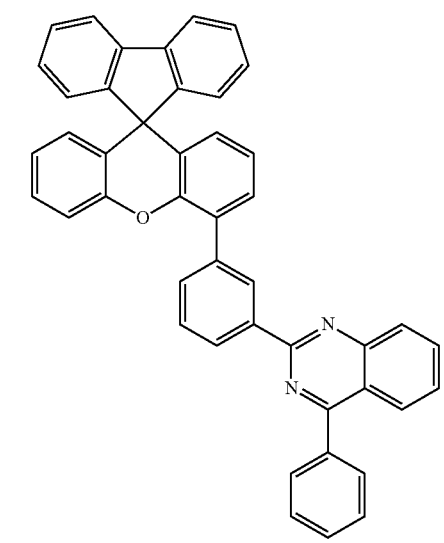
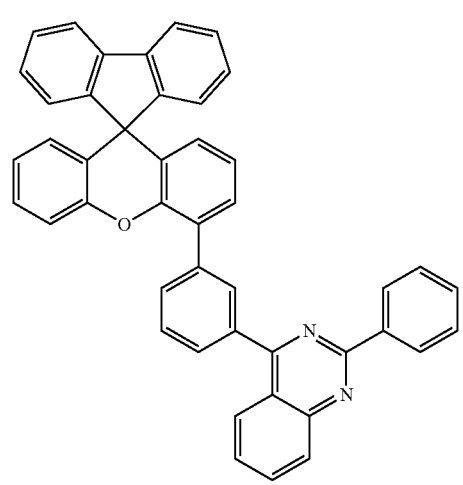
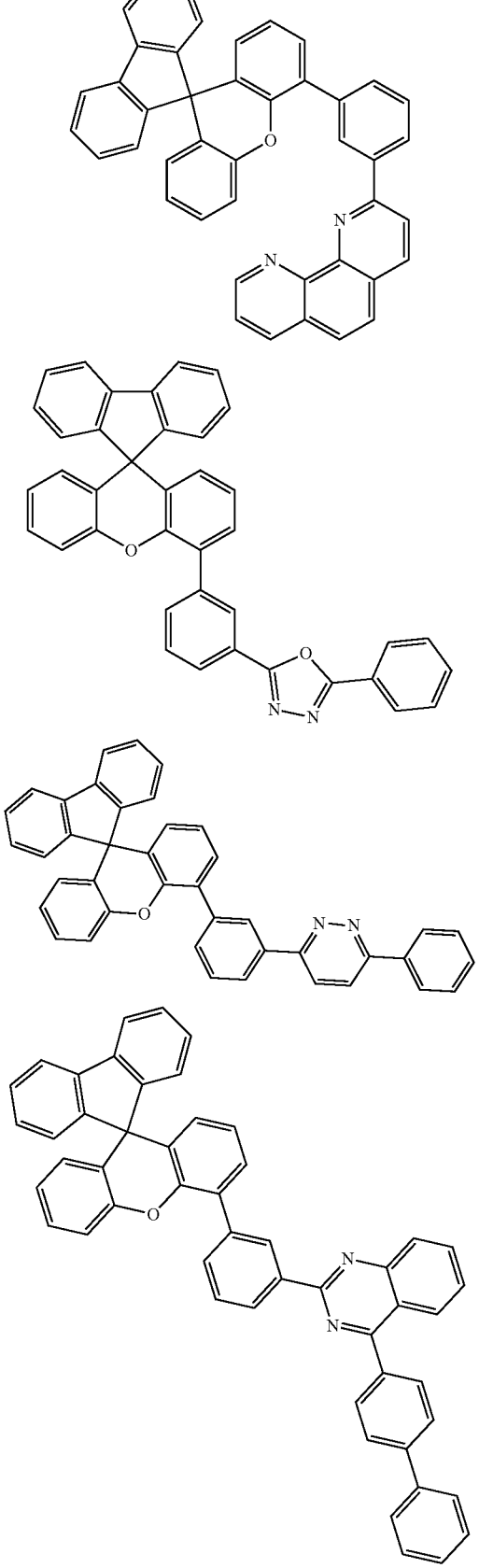

443
-continued
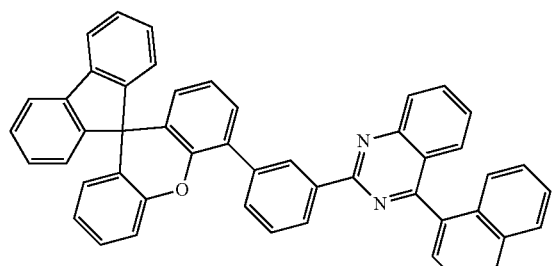
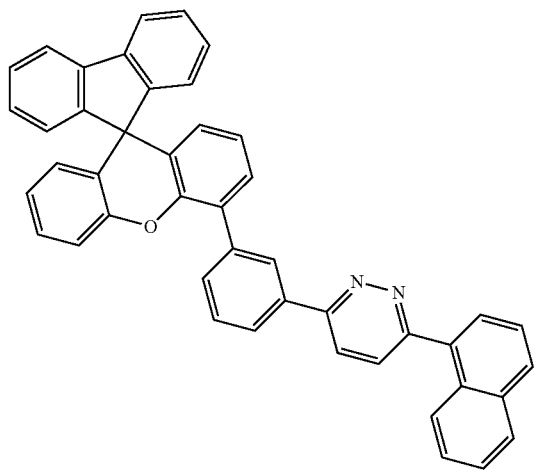
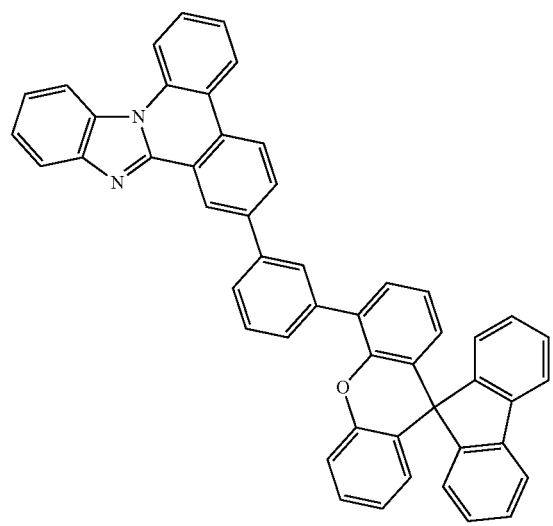
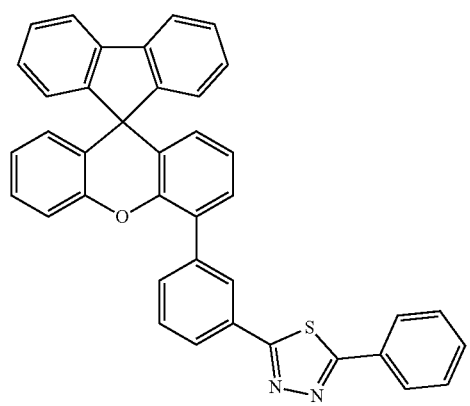
444
-continued
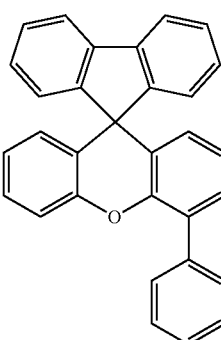
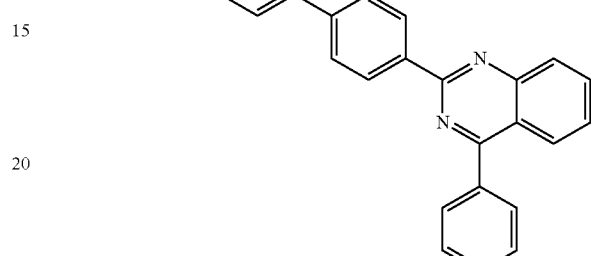
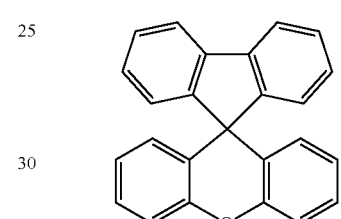
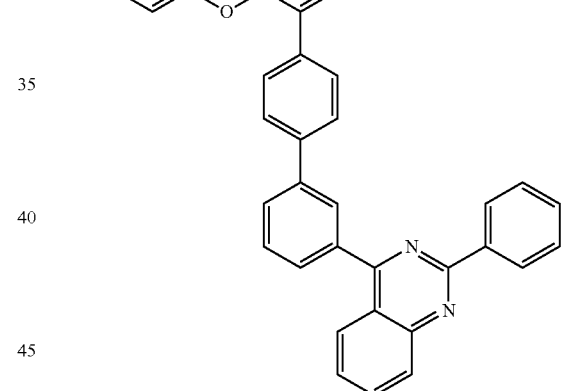
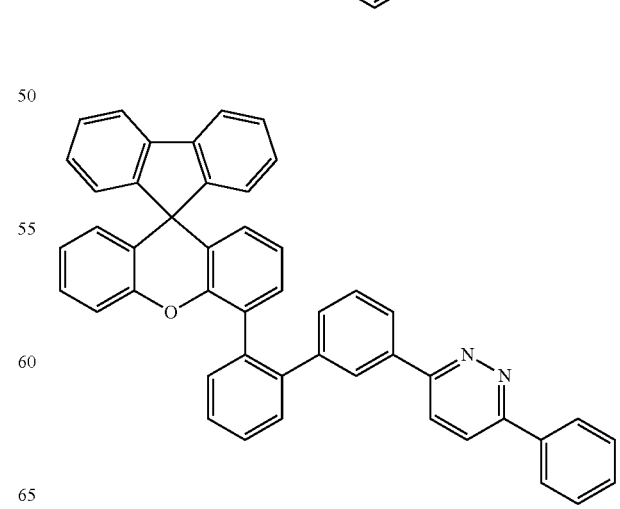

445
-continued
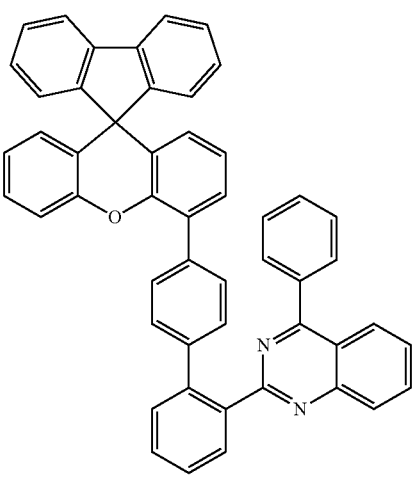
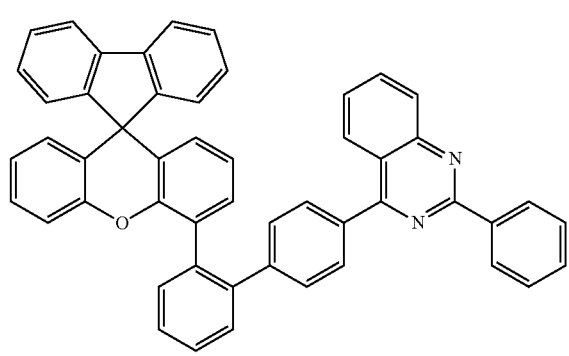
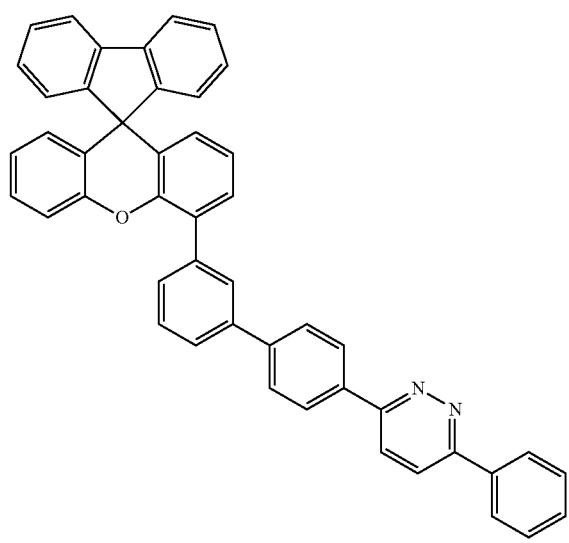
446
-continued
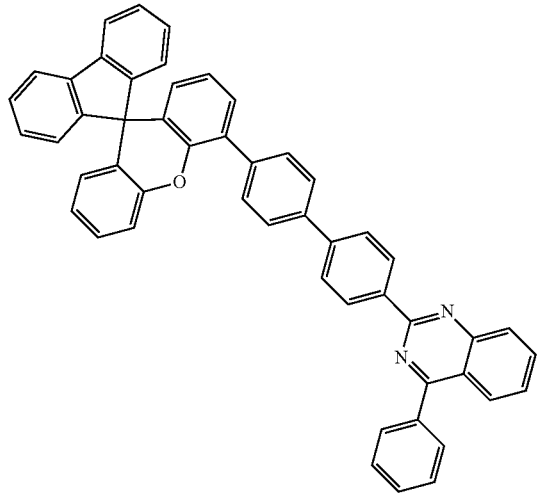
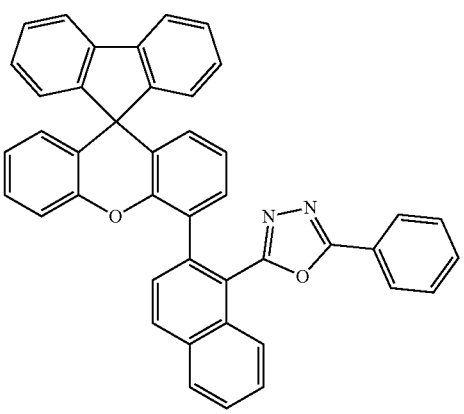
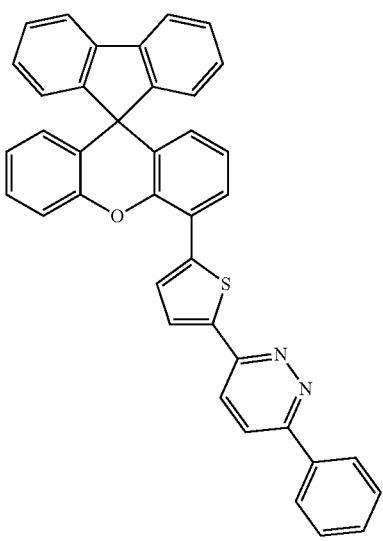

447
-continued
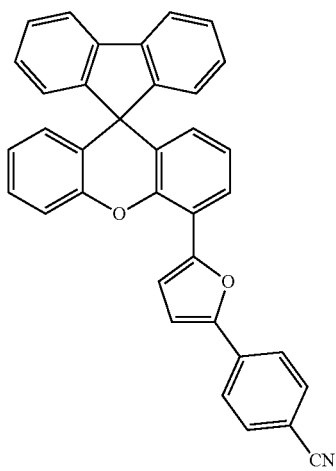
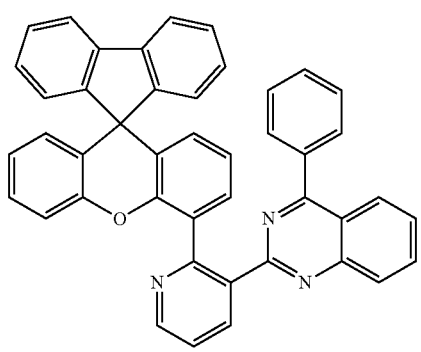
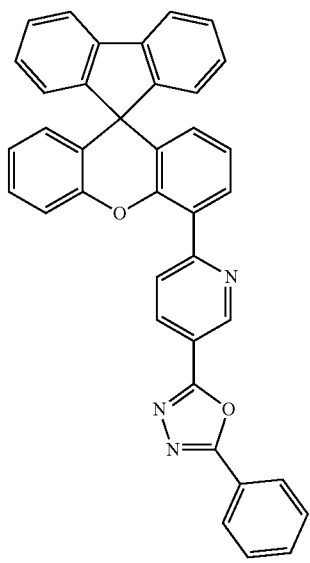
448
-continued
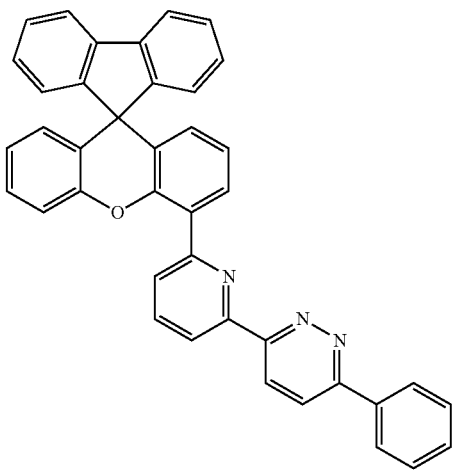
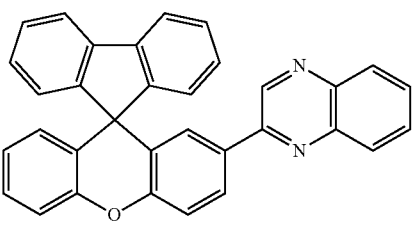
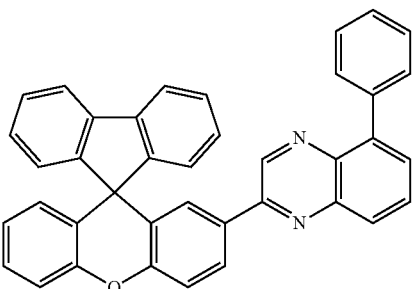
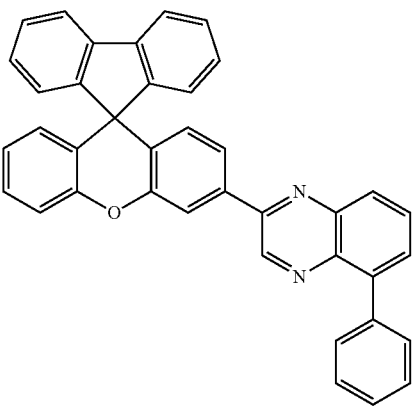

449
-continued

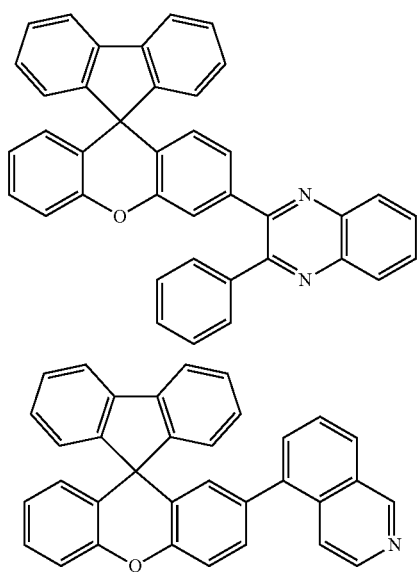

450
-continued

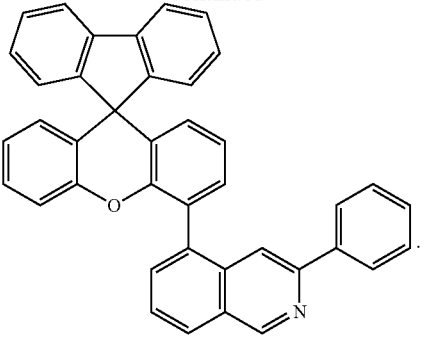

4. An organic light emitting device comprising:
a first electrode;
a second electrode provided opposite to the first electrode; and
one or more organic material layers provided between the first electrode and the second electrode, wherein the one or more organic material layers comprise the hetero-cyclic compound of claim 1.

5. The organic light emitting device of claim 4, wherein the one or more organic material layers comprise an electron injection layer, an electron transfer layer or a layer carrying out electron injection and electron transfer at the same time, and the electron injection layer, the electron transfer layer or the layer carrying out electron injection and electron transfer at the same time comprises the hetero-cyclic compound.

6. The organic light emitting device of claim 4, wherein the one or more organic material layers comprise a hole blocking layer, and the hole blocking layer comprises the hetero-cyclic compound.

7. The organic light emitting device of claim 4, wherein the one or more organic material layers comprise an electron control layer, and the electron control layer comprises the hetero-cyclic compound.

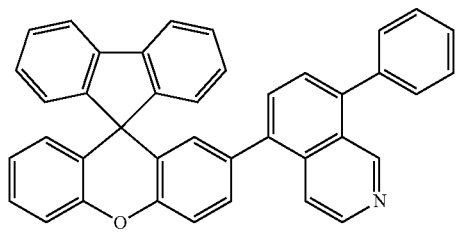

* * * * *